United States Patent
Cacace et al.

(10) Patent No.: US 11,291,659 B2
(45) Date of Patent: *Apr. 5, 2022

(54) P38 KINASE INHIBITORS REDUCE DUX4 AND DOWNSTREAM GENE EXPRESSION FOR THE TREATMENT OF FSHD

(71) Applicant: Fulcrum Therapeutics, Inc., Cambridge, MA (US)

(72) Inventors: Angela Marie Cacace, Haddam Neck, CT (US); Luis Gustavo Alejandro Rojas Soto, Cambridge, MA (US); Lorin A. Thompson, III, Cohasset, MA (US); Owen Brendan Wallace, Brookline, MA (US); Lucienne V. Ronco, Wellesley, MA (US); Ning Shen, Cambridge, MA (US); Alan Scott Robertson, Cambridge, MA (US); Aaron Nakwon Chang, Lexington, MA (US)

(73) Assignee: Fulcrum Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/748,217

(22) Filed: Jan. 21, 2020

(65) Prior Publication Data
US 2020/0383963 A1    Dec. 10, 2020

Related U.S. Application Data

(63) Continuation of application No. 16/195,361, filed on Nov. 19, 2018, now Pat. No. 10,537,560, which is a (Continued)

(51) Int. Cl.
*A61K 31/455*    (2006.01)
*A61K 31/4418*    (2006.01)
(Continued)

(52) U.S. Cl.
CPC ........ *A61K 31/4418* (2013.01); *A61K 31/416* (2013.01); *A61K 31/437* (2013.01);
(Continued)

(58) Field of Classification Search
CPC ................ A61K 31/416; A61K 31/437; A61K 31/4418; A61K 31/4439; A61K 31/454;
(Continued)

(56) References Cited

U.S. PATENT DOCUMENTS 4,522,811 A    6/1985  Eppstein et al.
5,670,527 A    9/1997  Adams et al.
(Continued)

FOREIGN PATENT DOCUMENTS

DE    10255040 A1    6/2004
EP    1247810 A1    10/2002
(Continued)

OTHER PUBLICATIONS

U.S. Appl. No. 16/753,664, filed Apr. 3, 2020, Pending, US 2020-0332291 A1.
(Continued)

*Primary Examiner* — Savitha M Rao
(74) *Attorney, Agent, or Firm* — Goodwin Procter LLP

(57) ABSTRACT

The disclosure relates to methods and compositions including p38 kinase inhibitors and agents that regulate expression of DUX4 and downstream genes including but not restricted to ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A. Methods useful for treating a disease associated with abnormal DUX4 and downstream gene expression (e.g., Fascioscapulohumeral muscular dystrophy) are disclosed.

15 Claims, 25 Drawing Sheets

Specification includes a Sequence Listing.

Related U.S. Application Data continuation of application No. PCT/US2018/054642, filed on Oct. 5, 2018.

(60) Provisional application No. 62/682,563, filed on Jun. 8, 2018, provisional application No. 62/682,565, filed on Jun. 8, 2018, provisional application No. 62/568,673, filed on Oct. 5, 2017, provisional application No. 62/568,754, filed on Oct. 5, 2017.

(51) Int. Cl.

| | | |
|---|---|---|
| *A61K 45/06* | (2006.01) | |
| *A61K 31/4439* | (2006.01) | |
| *A61K 31/519* | (2006.01) | |
| *A61K 31/437* | (2006.01) | |
| *A61K 31/496* | (2006.01) | |
| *A61K 31/5377* | (2006.01) | |
| *A61K 31/53* | (2006.01) | |
| *A61K 31/416* | (2006.01) | |
| *A61K 31/454* | (2006.01) | |
| *A61K 31/513* | (2006.01) | |
| *A61K 31/506* | (2006.01) | |
| *A61P 21/00* | (2006.01) | |
| *C12Q 1/6827* | (2018.01) | |
| *C12Q 1/686* | (2018.01) | |
| *A61K 9/00* | (2006.01) | |
| *C12Q 1/6883* | (2018.01) | |

(52) U.S. Cl.
CPC ........ *A61K 31/4439* (2013.01); *A61K 31/454* (2013.01); *A61K 31/496* (2013.01); *A61K 31/506* (2013.01); *A61K 31/513* (2013.01); *A61K 31/519* (2013.01); *A61K 31/53* (2013.01); *A61K 31/5377* (2013.01); *A61P 21/00* (2018.01); *C12Q 1/686* (2013.01); *C12Q 1/6827* (2013.01); *C12Q 1/6883* (2013.01); *A61K 9/0019* (2013.01); *A61K 9/0053* (2013.01); *A61K 9/0073* (2013.01); *C12Q 2600/106* (2013.01); *C12Q 2600/156* (2013.01)

(58) Field of Classification Search
CPC .. A61K 31/496; A61K 31/506; A61K 31/513; A61K 31/519; A61K 31/53; A61K 31/5377; A61K 9/0019; A61K 9/0053; A61K 9/0073; A61P 21/00; C12Q 1/6827; C12Q 1/686; C12Q 1/6883; C12Q 2600/106; C12Q 2600/156
See application file for complete search history.

(56) References Cited

U.S. PATENT DOCUMENTS

| | | |
|---|---|---|
| 5,716,955 A | 2/1998 | Adams et al. |
| 6,096,753 A | 8/2000 | Spohr et al. |
| 6,147,080 A | 11/2000 | Bemis et al. |
| 6,218,537 B1 | 4/2001 | Adams et al. |
| 6,319,921 B1 | 11/2001 | Cirillo et al. |
| 6,340,685 B1 | 1/2002 | Mavunkel et al. |
| 6,369,068 B1 | 4/2002 | Adams et al. |
| 6,448,257 B1 | 9/2002 | Mavunkel et al. |
| 6,476,031 B1 | 11/2002 | Chakravarty et al. |
| 6,589,954 B1 | 7/2003 | Mavunkel et al. |
| 6,696,566 B2 | 2/2004 | Chen et al. |
| 6,867,209 B1 | 3/2005 | Mavunkel et al. |
| 7,115,746 B2 | 10/2006 | Snoonian et al. |
| 7,125,898 B2 | 10/2006 | Aston et al. |
| 7,160,883 B2 | 1/2007 | Dyckman et al. |
| 7,276,527 B2 | 10/2007 | Ohkawa et al. |
| 7,314,881 B2 | 1/2008 | Adams et al. |
| 7,323,472 B2 | 1/2008 | Adams et al. |
| 7,462,616 B2 | 12/2008 | Dyckman et al. |
| 7,473,784 B2 | 1/2009 | Liu et al. |
| 7,521,447 B2 | 4/2009 | Munson et al. |
| 7,582,652 B2 | 9/2009 | Bonjouklian et al. |
| 7,759,337 B2 | 7/2010 | Tasker et al. |
| 7,759,343 B2 | 7/2010 | Dyckman et al. |
| 8,003,657 B2 | 8/2011 | Stieber et al. |
| 8,044,083 B2 | 10/2011 | Groneberg et al. |
| 8,058,282 B2 | 11/2011 | Adams et al. |
| 8,202,899 B2 | 6/2012 | Munson et al. |
| 8,314,131 B2 | 11/2012 | Pettus et al. |
| 8,367,671 B2 | 2/2013 | Tasker et al. |
| 8,420,649 B2 | 4/2013 | Pettus et al. |
| 8,450,314 B2 | 5/2013 | Beswick et al. |
| 8,497,269 B2 | 7/2013 | Tasker et al. |
| 8,513,289 B2 | 8/2013 | Koyama et al. |
| 8,557,797 B2 | 10/2013 | Finch et al. |
| 8,633,312 B2 | 1/2014 | Laufer et al. |
| 8,772,481 B2 | 7/2014 | Tasker et al. |
| 8,846,931 B2 | 9/2014 | Hoelzemann et al. |
| 8,916,708 B2 | 12/2014 | Woo et al. |
| 9,051,318 B2 | 6/2015 | Dorsch et al. |
| 9,427,439 B1 | 8/2016 | Alam |
| 10,342,786 B2 | 7/2019 | Cacace et al. |
| 10,537,560 B2 | 1/2020 | Cacace et al. |
| 10,973,805 B2 | 4/2021 | Efremov et al. |
| 2002/0115671 A1 | 8/2002 | Goehring et al. |
| 2002/0137747 A1 | 9/2002 | Moriarty et al. |
| 2003/0229081 A1 | 12/2003 | Maduskuie |
| 2003/0236193 A1 | 12/2003 | Oliner et al. |
| 2004/0033222 A1 | 2/2004 | Wood et al. |
| 2004/0067996 A1 | 4/2004 | Sheppeck |
| 2004/0077682 A1 | 4/2004 | Dombroski et al. |
| 2004/0087615 A1 | 5/2004 | Dombroski et al. |
| 2004/0092547 A1 | 5/2004 | Dombroski et al. |
| 2004/0097493 A1 | 5/2004 | Chen et al. |
| 2004/0157846 A1 | 8/2004 | Chen et al. |
| 2004/0157877 A1 | 8/2004 | Dombroski et al. |
| 2004/0176325 A1 | 9/2004 | Munson et al. |
| 2004/0192653 A1 | 9/2004 | Munson et al. |
| 2004/0209886 A1 | 10/2004 | Salvati et al. |
| 2004/0209903 A1 | 10/2004 | Dewdney et al. |
| 2004/0209904 A1 | 10/2004 | Dunn et al. |
| 2004/0242602 A1 | 12/2004 | Gungor et al. |
| 2005/0020587 A1 | 1/2005 | Bailey et al. |
| 2005/0020626 A1 | 1/2005 | Mathias |
| 2005/0026952 A1 | 2/2005 | Mathias |
| 2005/0043306 A1 | 2/2005 | Leftheris et al. |
| 2005/0107408 A1 | 5/2005 | Goldstein |
| 2005/0176775 A1 | 8/2005 | Devadas et al. |
| 2005/0176965 A1 | 8/2005 | Chen et al. |
| 2005/0277681 A1 | 12/2005 | Hanney et al. |
| 2005/0288299 A1 | 12/2005 | Mavunkel et al. |
| 2006/0019928 A1 | 1/2006 | Lin et al. |
| 2006/0035922 A1 | 2/2006 | Mathias et al. |
| 2006/0052390 A1 | 3/2006 | Schreiner et al. |
| 2006/0058296 A1 | 3/2006 | Higgins et al. |
| 2006/0079461 A1 | 4/2006 | Brewer et al. |
| 2006/0111416 A1 | 5/2006 | Lane et al. |
| 2006/0217401 A1 | 9/2006 | Boehm et al. |
| 2006/0235020 A1 | 10/2006 | Kim et al. |
| 2008/0146590 A1 | 6/2008 | Gabriel et al. |
| 2008/0207684 A1 | 8/2008 | Gabriel et al. |
| 2008/0275052 A1 | 11/2008 | Dhar et al. |
| 2009/0041722 A1 | 2/2009 | Liu et al. |
| 2009/0042856 A1 | 2/2009 | Yamazaki et al. |
| 2009/0312331 A1 | 12/2009 | Kim et al. |
| 2010/0093734 A1 | 4/2010 | Boman et al. |
| 2011/0117055 A1 | 5/2011 | MacDonald et al. |
| 2011/0166154 A1 | 7/2011 | Slamon et al. |
| 2011/0250197 A1 | 10/2011 | Sattigeri et al. |
| 2012/0108594 A1 | 5/2012 | Kim et al. |
| 2012/0157500 A1 | 6/2012 | Tao |
| 2014/0069419 A1 | 3/2014 | Ghidini |
| 2014/0296208 A1 | 10/2014 | Baker et al. |
| 2015/0087636 A1 | 3/2015 | Sverdrup |
| 2015/0225373 A1 | 8/2015 | Fyfe et al. |
| 2015/0232449 A1 | 8/2015 | Juhl et al. |

(56) References Cited

U.S. PATENT DOCUMENTS

| | | |
|---|---|---|
| 2016/0016934 A1 | 1/2016 | Fyfe |
| 2016/0166587 A1 | 6/2016 | Simpson et al. |
| 2016/0220550 A1 | 8/2016 | Sprecher et al. |
| 2017/0073343 A1 | 3/2017 | Galatsis et al. |
| 2020/0332291 A1 | 10/2020 | Cacace et al. |

FOREIGN PATENT DOCUMENTS

| | | |
|---|---|---|
| EP | 1538201 A1 | 6/2005 |
| EP | 1574501 A1 | 9/2005 |
| EP | 1577291 A1 | 9/2005 |
| EP | 1577292 A1 | 9/2005 |
| EP | 1609789 A1 | 12/2005 |
| EP | 2036905 A1 | 3/2009 |
| EP | 2044957 A1 | 4/2009 |
| EP | 2123255 A1 | 11/2009 |
| EP | 3381472 A1 | 10/2018 |
| JP | 2009-263234 A | 11/2009 |
| WO | 96/21452 A1 | 7/1996 |
| WO | 96/40143 A1 | 12/1996 |
| WO | 97/025046 A1 | 7/1997 |
| WO | 97/25047 A1 | 7/1997 |
| WO | 97/25048 A1 | 7/1997 |
| WO | 97/32583 A1 | 9/1997 |
| WO | 97/33883 A1 | 9/1997 |
| WO | 97/34137 A2 | 9/1997 |
| WO | 97/35855 A1 | 10/1997 |
| WO | 97/35856 A1 | 10/1997 |
| WO | 98/07425 A1 | 2/1998 |
| WO | 98/027098 A1 | 6/1998 |
| WO | 98/28292 A1 | 7/1998 |
| WO | 98/047892 A1 | 10/1998 |
| WO | 98/56377 A1 | 12/1998 |
| WO | 98/57966 A1 | 12/1998 |
| WO | 99/00357 A1 | 1/1999 |
| WO | 99/01130 A1 | 1/1999 |
| WO | 99/01136 A1 | 1/1999 |
| WO | 99/20624 A1 | 4/1999 |
| WO | 99/21859 A1 | 5/1999 |
| WO | 99/42592 A1 | 8/1999 |
| WO | 99/057101 A1 | 11/1999 |
| WO | 99/58502 A1 | 11/1999 |
| WO | 99/61426 A1 | 12/1999 |
| WO | 99/61437 A1 | 12/1999 |
| WO | 99/64400 A1 | 12/1999 |
| WO | 00/010563 A1 | 3/2000 |
| WO | 00/012497 A2 | 3/2000 |
| WO | 00/017175 A1 | 3/2000 |
| WO | 00/019824 A1 | 4/2000 |
| WO | 00/025791 A1 | 5/2000 |
| WO | 00/031063 A1 | 6/2000 |
| WO | 2000/43384 A1 | 7/2000 |
| WO | 00/059904 A2 | 10/2000 |
| WO | 00/071535 A1 | 11/2000 |
| WO | 01/004115 A2 | 1/2001 |
| WO | 01/019322 A2 | 3/2001 |
| WO | 01/021591 A1 | 3/2001 |
| WO | 01/029041 A1 | 4/2001 |
| WO | 01/029042 A1 | 4/2001 |
| WO | 01/037837 A1 | 5/2001 |
| WO | 01/038313 A1 | 5/2001 |
| WO | 01/038314 A1 | 5/2001 |
| WO | 01/047897 A1 | 7/2001 |
| WO | 01/064676 A2 | 9/2001 |
| WO | 01/064679 A1 | 9/2001 |
| WO | 01/038312 A2 | 11/2001 |
| WO | 02/007772 A2 | 1/2002 |
| WO | 02/016359 A1 | 2/2002 |
| WO | 02/018379 A2 | 3/2002 |
| WO | 02/018380 A1 | 3/2002 |
| WO | 02/032862 A2 | 4/2002 |
| WO | 02/040486 A2 | 5/2002 |
| WO | 02/042292 A2 | 5/2002 |
| WO | 02/044168 A2 | 6/2002 |
| WO | 02/045752 A2 | 6/2002 |
| WO | 02/046158 A2 | 6/2002 |
| WO | 02/058695 A1 | 8/2002 |
| WO | 02/059083 A2 | 8/2002 |
| WO | 02/060869 A2 | 8/2002 |
| WO | 02/064594 A2 | 8/2002 |
| WO | 02/069892 A2 | 9/2002 |
| WO | 02/072576 A1 | 9/2002 |
| WO | 02/072579 A1 | 9/2002 |
| WO | 02/076396 A2 | 10/2002 |
| WO | 02/076463 A1 | 10/2002 |
| WO | 02/076954 A1 | 10/2002 |
| WO | 02/076984 A1 | 10/2002 |
| WO | 02/076985 A1 | 10/2002 |
| WO | 02/085405 A2 | 10/2002 |
| WO | 02/090360 A1 | 11/2002 |
| WO | 02/092087 A1 | 11/2002 |
| WO | 02/094833 A1 | 11/2002 |
| WO | 02/100405 A1 | 12/2002 |
| WO | 03/000682 A1 | 1/2003 |
| WO | 03/002544 A1 | 1/2003 |
| WO | 03/005999 A2 | 1/2003 |
| WO | 03/015828 A1 | 2/2003 |
| WO | 03/020715 A1 | 3/2003 |
| WO | 03/026568 A2 | 4/2003 |
| WO | 03/032894 A2 | 4/2003 |
| WO | 03/032970 A1 | 4/2003 |
| WO | 03/032971 A1 | 4/2003 |
| WO | 03/032972 A1 | 4/2003 |
| WO | 03/032980 A1 | 4/2003 |
| WO | 03/032986 A1 | 4/2003 |
| WO | 03/032987 A1 | 4/2003 |
| WO | 03/033482 A1 | 4/2003 |
| WO | 03/033483 A1 | 4/2003 |
| WO | 03/039534 A1 | 5/2003 |
| WO | 03/041644 A2 | 5/2003 |
| WO | 03/048340 A2 | 6/2003 |
| WO | 03/049742 A1 | 6/2003 |
| WO | 03/057197 A1 | 7/2003 |
| WO | 03/059293 A2 | 7/2003 |
| WO | 03/064417 A1 | 8/2003 |
| WO | 03/064418 A1 | 8/2003 |
| WO | 03/064419 A1 | 8/2003 |
| WO | 03/068223 A1 | 8/2003 |
| WO | 03/068747 A1 | 8/2003 |
| WO | 03/074530 A1 | 9/2003 |
| WO | 03/077919 A1 | 9/2003 |
| WO | 03/082208 A2 | 10/2003 |
| WO | 03/082871 A1 | 10/2003 |
| WO | 03/084503 A2 | 10/2003 |
| WO | 03/084539 A2 | 10/2003 |
| WO | 03/087096 A1 | 10/2003 |
| WO | 03/087394 A1 | 10/2003 |
| WO | 03/088972 A1 | 10/2003 |
| WO | 03/090912 A1 | 11/2003 |
| WO | 03/091229 A1 | 11/2003 |
| WO | 03/092588 A2 | 11/2003 |
| WO | 03/093248 A1 | 11/2003 |
| WO | 03/097615 A1 | 11/2003 |
| WO | 03/099206 A2 | 12/2003 |
| WO | 03/099820 A1 | 12/2003 |
| WO | 03/103590 A2 | 12/2003 |
| WO | 2004/004725 A2 | 1/2004 |
| WO | 2004/010929 A2 | 2/2004 |
| WO | 2004/010995 A1 | 2/2004 |
| WO | 2004/014387 A1 | 2/2004 |
| WO | 2004/014870 A1 | 2/2004 |
| WO | 2004/014900 A1 | 2/2004 |
| WO | 2004/014907 A1 | 2/2004 |
| WO | 2004/019873 A2 | 3/2004 |
| WO | 2004/020438 A2 | 3/2004 |
| WO | 2004/020440 A1 | 3/2004 |
| WO | 2004/021979 A2 | 3/2004 |
| WO | 2004/021988 A2 | 3/2004 |
| WO | 2004/022712 A2 | 3/2004 |
| WO | 2004/024699 A1 | 3/2004 |
| WO | 2004/026871 A1 | 4/2004 |
| WO | 2004/029040 A1 | 4/2004 |
| WO | 2004/032874 A2 | 4/2004 |
| WO | 2004/041277 A1 | 5/2004 |

(56) References Cited

FOREIGN PATENT DOCUMENTS

| | | |
|---|---|---|
| WO | 2004/048373 A1 | 6/2004 |
| WO | 2004/053107 A2 | 6/2004 |
| WO | 2004/069793 A2 | 8/2004 |
| WO | 2004/072038 A1 | 8/2004 |
| WO | 2004/072072 A1 | 8/2004 |
| WO | 2004/073628 A2 | 9/2004 |
| WO | 2004/076450 A1 | 9/2004 |
| WO | 2004/089874 A1 | 10/2004 |
| WO | 2004/089875 A1 | 10/2004 |
| WO | 2004/089876 A1 | 10/2004 |
| WO | 2004/098518 A2 | 11/2004 |
| WO | 2004/098528 A2 | 11/2004 |
| WO | 2004/099156 A1 | 11/2004 |
| WO | 2004/100874 A2 | 11/2004 |
| WO | 2004/100946 A1 | 11/2004 |
| WO | 2004/108675 A1 | 12/2004 |
| WO | 2005/005380 A2 | 1/2005 |
| WO | 2005/005606 A2 | 1/2005 |
| WO | 2005/009367 A2 | 2/2005 |
| WO | 2005/009965 A1 | 2/2005 |
| WO | 2005/009966 A1 | 2/2005 |
| WO | 2005/009973 A1 | 2/2005 |
| WO | 2005/012875 A2 | 2/2005 |
| WO | 2005/014550 A1 | 2/2005 |
| WO | 2005/018557 A2 | 3/2005 |
| WO | 2005/018624 A2 | 3/2005 |
| WO | 2005/023201 A2 | 3/2005 |
| WO | 2005/023761 A2 | 3/2005 |
| WO | 2005/025572 A1 | 3/2005 |
| WO | 2005/032481 A2 | 4/2005 |
| WO | 2005/032551 A1 | 4/2005 |
| WO | 2005/033072 A2 | 4/2005 |
| WO | 2005/042537 A1 | 5/2005 |
| WO | 2005/058308 A2 | 6/2005 |
| WO | 2005/060967 A1 | 7/2005 |
| WO | 2005/063715 A1 | 7/2005 |
| WO | 2005/065691 A1 | 7/2005 |
| WO | 2005/073189 A1 | 8/2005 |
| WO | 2005/073217 A1 | 8/2005 |
| WO | 2005/073219 A1 | 8/2005 |
| WO | 2005/073232 A1 | 8/2005 |
| WO | 2005/075425 A2 | 8/2005 |
| WO | 2005/075478 A1 | 8/2005 |
| WO | 2005/077945 A2 | 8/2005 |
| WO | 2005/080380 A1 | 9/2005 |
| WO | 2005/082862 A2 | 9/2005 |
| WO | 2005/085206 A1 | 9/2005 |
| WO | 2005/085248 A1 | 9/2005 |
| WO | 2005/090288 A1 | 9/2005 |
| WO | 2005/091891 A2 | 10/2005 |
| WO | 2005/105091 A1 | 11/2005 |
| WO | 2005/110455 A2 | 11/2005 |
| WO | 2006/009741 A1 | 1/2006 |
| WO | 2006/015775 A2 | 2/2006 |
| WO | 2006/020904 A1 | 2/2006 |
| WO | 2006/026196 A2 | 3/2006 |
| WO | 2006/039718 A2 | 4/2006 |
| WO | 2006/040056 A1 | 4/2006 |
| WO | 2006/044860 A2 | 4/2006 |
| WO | 2006/048266 A2 | 5/2006 |
| WO | 2006/051373 A1 | 5/2006 |
| WO | 2006/051375 A1 | 5/2006 |
| WO | 2006/055302 A2 | 5/2006 |
| WO | 2006/055404 A2 | 5/2006 |
| WO | 2006/058023 A2 | 6/2006 |
| WO | 2006/060108 A1 | 6/2006 |
| WO | 2006/063856 A1 | 6/2006 |
| WO | 2006/067165 A2 | 6/2006 |
| WO | 2006/067168 A1 | 6/2006 |
| WO | 2006/067175 A1 | 6/2006 |
| WO | 2006/070927 A1 | 7/2006 |
| WO | 2006/084017 A2 | 8/2006 |
| WO | 2006/089798 A1 | 8/2006 |
| WO | 2006/094187 A2 | 9/2006 |
| WO | 2006/104889 A2 | 10/2006 |
| WO | 2006/104915 A2 | 10/2006 |
| WO | 2006/110173 A2 | 10/2006 |
| WO | 2006/122230 A1 | 11/2006 |
| WO | 2006/127678 A2 | 11/2006 |
| WO | 2006/134382 A1 | 12/2006 |
| WO | 2007/005863 A1 | 1/2007 |
| WO | 2007/016358 A1 | 2/2007 |
| WO | 2007/016392 A2 | 2/2007 |
| WO | 2007/021710 A1 | 2/2007 |
| WO | 2007/023105 A1 | 3/2007 |
| WO | 2007/023110 A2 | 3/2007 |
| WO | 2007/023111 A2 | 3/2007 |
| WO | 2007/023114 A1 | 3/2007 |
| WO | 2007/023115 A2 | 3/2007 |
| WO | 2007/024754 A1 | 3/2007 |
| WO | 2007/034325 A1 | 3/2007 |
| WO | 2007/038444 A2 | 4/2007 |
| WO | 2007/045989 A1 | 4/2007 |
| WO | 2007/052124 A1 | 5/2007 |
| WO | 2007/053346 A1 | 5/2007 |
| WO | 2007/053394 A1 | 5/2007 |
| WO | 2007/056016 A2 | 5/2007 |
| WO | 2007/059500 A2 | 5/2007 |
| WO | 2007/072163 A2 | 6/2007 |
| WO | 2007/075896 A2 | 7/2007 |
| WO | 2007/084391 A2 | 7/2007 |
| WO | 2007/089646 A1 | 8/2007 |
| WO | 2007/091152 A1 | 8/2007 |
| WO | 2007/091176 A1 | 8/2007 |
| WO | 2007/096151 A2 | 8/2007 |
| WO | 2007/103468 A2 | 9/2007 |
| WO | 2007/103839 A2 | 9/2007 |
| WO | 2007/107828 A2 | 9/2007 |
| WO | 2007/115670 A1 | 10/2007 |
| WO | 2007/124181 A2 | 11/2007 |
| WO | 2007/126871 A1 | 11/2007 |
| WO | 2007/144390 A1 | 12/2007 |
| WO | 2007/146712 A2 | 12/2007 |
| WO | 2007/147103 A2 | 12/2007 |
| WO | 2007/147104 A2 | 12/2007 |
| WO | 2007/147109 A2 | 12/2007 |
| WO | 2008/001929 A1 | 1/2008 |
| WO | 2008/001930 A1 | 1/2008 |
| WO | 2008/011032 A1 | 1/2008 |
| WO | 2008/013823 A2 | 1/2008 |
| WO | 2008/021388 A1 | 2/2008 |
| WO | 2008/024391 A1 | 2/2008 |
| WO | 2008/041095 A1 | 4/2008 |
| WO | 2008/045393 A2 | 4/2008 |
| WO | 2008/048540 A2 | 4/2008 |
| WO | 2008/049842 A2 | 5/2008 |
| WO | 2008/071664 A1 | 6/2008 |
| WO | 2008/071665 A1 | 6/2008 |
| WO | 2008/072079 A2 | 6/2008 |
| WO | 2008/076265 A1 | 6/2008 |
| WO | 2008/079857 A1 | 7/2008 |
| WO | 2008/089034 A2 | 7/2008 |
| WO | 2008/098096 A1 | 8/2008 |
| WO | 2008/099615 A1 | 8/2008 |
| WO | 2008/103276 A2 | 8/2008 |
| WO | 2008/105808 A2 | 9/2008 |
| WO | 2008/135819 A1 | 11/2008 |
| WO | 2008/136948 A1 | 11/2008 |
| WO | 2008/137176 A1 | 11/2008 |
| WO | 2009/011871 A2 | 1/2009 |
| WO | 2009/011880 A2 | 1/2009 |
| WO | 2009/015000 A1 | 1/2009 |
| WO | 2009/015169 A1 | 1/2009 |
| WO | 2009/034432 A2 | 3/2009 |
| WO | 2009/038784 A1 | 3/2009 |
| WO | 2009/069032 A2 | 6/2009 |
| WO | 2009/074518 A1 | 6/2009 |
| WO | 2009/074519 A1 | 6/2009 |
| WO | 2009/078992 A1 | 6/2009 |
| WO | 2009/094556 A2 | 7/2009 |
| WO | 2009/103336 A1 | 8/2009 |
| WO | 2009/117156 A1 | 9/2009 |
| WO | 2009/152072 A1 | 12/2009 |
| WO | 2009/155388 A1 | 12/2009 |

(56) References Cited

FOREIGN PATENT DOCUMENTS

| | | |
|---|---|---|
| WO | 2009/155389 A1 | 12/2009 |
| WO | 2009/158446 A2 | 12/2009 |
| WO | 2009/158450 A1 | 12/2009 |
| WO | 2010/004517 A1 | 1/2010 |
| WO | 2010/007552 A1 | 1/2010 |
| WO | 2010/007561 A1 | 1/2010 |
| WO | 2010/025201 A1 | 3/2010 |
| WO | 2010/025202 A1 | 3/2010 |
| WO | 2010/038428 A1 | 4/2010 |
| WO | 2010/040843 A2 | 4/2010 |
| WO | 2010/042646 A1 | 4/2010 |
| WO | 2010/042649 A2 | 4/2010 |
| WO | 2010/083246 A1 | 7/2010 |
| WO | 2010/089391 A1 | 8/2010 |
| WO | 2010/093889 A2 | 8/2010 |
| WO | 2010/093890 A2 | 8/2010 |
| WO | 2010/120963 A1 | 10/2010 |
| WO | 2010/129208 A1 | 11/2010 |
| WO | 2011/050192 A1 | 4/2011 |
| WO | 2011/083387 A1 | 7/2011 |
| WO | 2011/119848 A1 | 9/2011 |
| WO | 2011/119863 A1 | 9/2011 |
| WO | 2011/154738 A1 | 12/2011 |
| WO | 2012/000595 A1 | 1/2012 |
| WO | 2012/003912 A1 | 1/2012 |
| WO | 2012/031057 A1 | 3/2012 |
| WO | 2012/074761 A1 | 6/2012 |
| WO | 2012/074933 A1 | 6/2012 |
| WO | 2012/119690 A1 | 9/2012 |
| WO | 2012/154814 A1 | 11/2012 |
| WO | 2012/168359 A1 | 12/2012 |
| WO | 2013/007708 A1 | 1/2013 |
| WO | 2013/070460 A1 | 5/2013 |
| WO | 2013/083206 A1 | 6/2013 |
| WO | 2013/083604 A1 | 6/2013 |
| WO | 2013/083606 A1 | 6/2013 |
| WO | 2013/086002 A1 | 6/2013 |
| WO | 2013/106643 A2 | 7/2013 |
| WO | 2013/130573 A1 | 9/2013 |
| WO | 2013/139809 A1 | 9/2013 |
| WO | 2013/174780 A1 | 11/2013 |
| WO | 2014/014706 A1 | 1/2014 |
| WO | 2014/027209 A1 | 2/2014 |
| WO | 2014/033446 A1 | 3/2014 |
| WO | 2014/033447 A2 | 3/2014 |
| WO | 2014/033448 A1 | 3/2014 |
| WO | 2014/033449 A1 | 3/2014 |
| WO | 2014/076484 A1 | 5/2014 |
| WO | 2014/083026 A1 | 6/2014 |
| WO | 2014/134313 A1 | 9/2014 |
| WO | 2014/140582 A1 | 9/2014 |
| WO | 2014/155135 A1 | 10/2014 |
| WO | 2014/181213 A1 | 11/2014 |
| WO | 2014/194956 A1 | 12/2014 |
| WO | 2014/195400 A1 | 12/2014 |
| WO | 2014/195402 A1 | 12/2014 |
| WO | 2015/004089 A1 | 1/2015 |
| WO | 2015/006752 A1 | 1/2015 |
| WO | 2015/006753 A2 | 1/2015 |
| WO | 2015/091889 A1 | 6/2015 |
| WO | 2015/092423 A1 | 6/2015 |
| WO | 2015/121444 A1 | 8/2015 |
| WO | 2015/121660 A1 | 8/2015 |
| WO | 2015/191986 A1 | 12/2015 |
| WO | 2015/191996 A1 | 12/2015 |
| WO | 2016/007616 A1 | 1/2016 |
| WO | 2016/049677 A1 | 4/2016 |
| WO | 2016/051186 A1 | 4/2016 |
| WO | 2016/051187 A1 | 4/2016 |
| WO | 2016/051188 A1 | 4/2016 |
| WO | 2016/066687 A1 | 5/2016 |
| WO | 2016/114655 A1 | 7/2016 |
| WO | 2016/115490 A1 | 7/2016 |
| WO | WO2016114655 * 7/2016 ........... A61K 31/365 |
| WO | 2016/124793 A1 | 8/2016 |
| WO | 2016/128456 A1 | 8/2016 |
| WO | 2016/142310 A1 | 9/2016 |
| WO | 2016/159301 A1 | 10/2016 |
| WO | 2016/166239 A1 | 10/2016 |
| WO | 2016/198698 A2 | 12/2016 |
| WO | 2017/075013 A1 | 5/2017 |
| WO | 2017/093208 A1 | 6/2017 |
| WO | 2017/108736 A1 | 6/2017 |
| WO | 2017/110093 A1 | 6/2017 |
| WO | 2017/117182 A1 | 7/2017 |
| WO | 2017/134053 A1 | 8/2017 |
| WO | 2017/136480 A1 | 8/2017 |
| WO | 2017/211830 A1 | 12/2017 |
| WO | 2018/007788 A1 | 1/2018 |
| WO | 2018/148797 A1 | 8/2018 |
| WO | 2019/103926 A1 | 5/2019 |
| WO | 2020/106876 A2 | 5/2020 |

OTHER PUBLICATIONS

U.S. Appl. No. 16/166,031, filed Oct. 19, 2018, Patented, U.S. Pat. No. 10,342,786.

U.S. Appl. No. 16/195,361, filed Nov. 19, 2018, Patented, U.S. Pat. No. 10,537,560.

Ali, Nermin, et al. "Ebselen inhibits p38 mitogen-activated protein kinasemediated endothelial cell death by hydrogen peroxide." European journal of pharmacology 485.1-3 (2004): 127-135.

Aouadi, M. et al., "Role of MAPKs in development and differentiation: lessons from knockout mice," Biochimie. 88(9):1091-1098 (2006).

Ariey-Bonnet, Jeremy, et al. "In silica molecular target prediction unveils mebendazole as a potent MAPK14 inhibitor" bioRxiv (2020).

Aston, N. M. et al., p38a Mitogen-Activated Protein Kinase Inhibitors: Optimization of a Series of.

Barbour, A. M. et al., "Safety, tolerability, pharmacokinetics and pharmacodynamics of losmapimod following a single intravenous or oral dose in healthy volunteers," Br J Clin Pharmacol, 76(1):99-106 (2012).

Biphenylamides to Give a Molecule Suitable for Clinical Progression, J. Med. Chem. 52(20):6257-6269 (2009).

Bosnakovski, D. et al., "High-throughput screening identifies inhibitors of DUX4-induced myoblast toxicity," Skeletal Muscle, 4(4) (2014), 11 pages; Retrieved from http://www.skeletalmusclejournal.com/contenU1/1/1.

Boudou, T. et al., "A Microfabricated Platform to Measure and Manipulate the Mechanics of Engineered Cardiac Microtissues," Tissue Engineering: Part A, 18(9,10):910-616 (2012).

Campbell, Amy E., et al. "BET bromodomain inhibitors and agonists of the beta-2 adrenergic receptor identified in screens for compounds that inhibit DUX4 expression in FSHD muscle cells." Skeletal muscle 7.1 (2017): 1-18. Published online Sep. 4, 2017.

Cuadrado, A & Nebreda, AR., "Mechanisms and functions of p3 8 MAPK signalling," Biochem J., 429(3):403-417 (2010).

Cuenda, A & Rousseau, S., "p38 MAP-Kinases pathway regulation, function and role in human diseases," Biochimica et Biophysica Acta 1773:1358-1375 (2007).

Dalkilic, I. & Kunkel, L. M., "Muscular dystrophies: genes to pathogenesis," Current Opinion in Genetics & Development, 13:231-238 (2003).

Dandapat, A et al., "Expression of the Human FSHD-Linked DUX4 Gene Induces Neurogenesis During Differentiation of Murine Embryonic Stem Cells," Stem Cells and Development, 22(17):2440 2448 (2013).

Ehrlich, M. & Lacey, M., "Deciphering transcription dysregulation in FSH muscular dystrophy," Journal of Human Genetics, 57(8):477-484 (2012).

Esvelt, K. M. et al., "Orthogonal Cas9 Proteins for RNA-Guided Gene Regulation and Editing," Nat Methods, 10(11):1116-1121 (2013).

GenBank Accession No. NC_000019.10, Mar. 26, 2018.
GenBank Accession No. NG_034189.2, Dec. 24, 2018.
GenBank Accession No. NM_001126063.2, Jun. 23, 2018.

(56) References Cited

OTHER PUBLICATIONS

GenBank Accession No. NM_001143832.1, Jun. 24, 2018.
GenBank Accession No. NM_001293798.2, Dec. 23, 2018.
GenBank Accession No. NM_001315.2, Dec. 23, 2018.
GenBank Accession No. NM_002751.6, Aug. 19, 2018.
GenBank Accession No. NM_023014.1, Jun. 23, 2018.
GenBank Accession No. NM_144614.3, Jun. 23, 2018.
GenBank Accession No. NM_152677.2, Dec. 23, 2018.
GenBank Accession No. NP_001119535.1, Dec. 23, 2018.
GenBank Accession No. NP_001 137304.1, Jun. 24, 2018.
GenBank Accession No. NP_001280727.1, Dec. 23, 2018.
GenBank Accession No. NP_001306.1, Dec. 23, 2018.
GenBank Accession No. NP_002742.3, Nov. 23, 2018.
GenBank Accession No. NP_075390.1, Jun. 23, 2018.
GenBank Accession No. NP_620155.1, Jul. 1, 2018.
GenBank Accession No. NP_653215.2, Jun. 23, 2018.
GenBank Accession No. NP_689890.1, Dec. 23, 2018.
GenBankAccession No. NC_000001.11, Mar. 26, 2018.
GenBankAccession No. NC_000002.12, Mar. 26, 2018.
GenBankAccession No. NC_000006.12, Mar. 26, 2018.
GenBankAccession No. NM_138800.2, Jul. 1, 2018.
Geng, L. N. et al., "DUX4 Activates Germline Genes, Retroelements, and Immune Mediators: Implications for Facioscapulohumeral Dystrophy," Developmental Cell, 22(1):38-51 (2012).
Hammaker, D., and G. S. Firestein. Go upstream, young man: lessons learned from the p38 saga. Annals of the rheumatic diseases 69.Suppl 1 (2010): i77-i82.
Himeda, C. L. et al., "CRISPR/dCas9-mediated Transcriptional Inhibition Ameliorates the Epigenetic Dysregulation of D4Z4 and Represses DUX4-fl in FSH Muscular Dystrophy," Molecular Therapy, 24(3):527-533 (2016).
Himeda, C. L. et al., "Facioscapulohumeral Muscular Dystrophy As a Model for Epigenetic Regulation and Disease," Antioxidants & Redox Signaling, 22(16):1463-1482 (2015).
Himeda, C. L. et al., "Myogenic enhancers regulate expression of the Facioscapulohumeral muscular dystrophy associated DUX4 gene," Mol. Cell. Biol., 34(11): 1942-1955 (2014).
Homma, S. et al., "Expression of FSHD-related DUX4-FL alters proteostasis and induces TDP-43 aggregation," Annals of Clinical and Translational Neurology, 2(2):151-166 (2015).
http://dx.doi.org/10.1155/2014/352371.
https://www.fishersci.com/shop/products/eo-I 428-tocris-2/2908I 0. Accessed Apr. 26, 2019.
International Search Report and Written Opinion dated Jan. 25, 2019 for International Application No. PCT/US2018/054638, 16 pages.
International Search Report and Written Opinion dated Jan. 30, 2019 for International Application No. PCT/US2018/054642, 11 pages.
Ishizawa, T. et al., Substituent Effects of Benzopyran-4-(N-Cyano)-Carboxamidine Potassium Channel.
Keranen, Tiina, et al. "Anti-inflammatory effects of 132-receptor agonists salbutamol and terbutaline are mediated by MKP-1." PLoS One 11.2 (2016): e0148144.
Keren, A. et al., "The p38 MAPK signaling pathway: A major regulator of skeletal muscle development," Molecular and Cellular Endocrinology, 252:224-230 (2006).
Kim, D. et al., "TopHat2: accurate alignment of transcriptomes in the presence of insertions, deletions and gene fusions," Genome Biology, 14:R36, (2013), 13 pages; Retrieved from http://qenomebioloqv.com/2013/14/4/R36.
Kimmel, A. R., "Identification and Characterization of Specific Clones: Strategy for Confirming the Validity of Presumptive Clones," Methods in Enzymology, 152:507-511 (1987).
Krementsov, D. N. et al., "The Emerging Role of p38 Mitogen-Activated Protein Kinase in Multiple Sclerosis and Its Models," Molecular and Cellular Biology, 33(19):3728-3734 (2013).
Kyriakis, J. M. & Avruch, J., "Mammalian Mitogen-Activated Protein Kinase Signal Transduction Pathways Activated by Stress and Inflammation," Physiological Review, 81(2):807-869 (2001).

Lemmers, R. J. F., et al., "Digenic Inheritance of an SMCHDJ Mutation and an FSHD—Permissive D4Z4 Allele Causes Facioscapulohumeral Muscular Dystrophy Type 2" Nat Genet 2012, 44, 1370-1376.
Lemmers, R. J. L. F., et al., "A Unifying Genetic Model for Facioscapulohumeral Muscular Dystrophy" Science 2010, 329, 1650-1653.
Lima, Gabriel Ferreira, et al. "Inosine, an endogenous purine nucleoside, avoids early stages of atherosclerosis development associated to eNOS activation and p38 MAPK/NF-kB inhibition in rats." European journal of pharmacology 882 (2020): 173289.
Mamchaoui, K. et al., "Immortalized pathological human myoblasts: towards a universal tool for the study of neuromuscular disorders," Skeletal Muscle, 1:34 (2011), 11 pages; Retrieved from http://www.skeletalmusclejournal.com/content/1/1/31.
Martin, E. D. et al., "p38 MAPK in cardioprotection—are we there yet?," British Journal of Pharmacology, 172:2101-2113 (2015).
Masson, D., et al., "Increased HDL Cholesterol and ApoA-I in Humans and Mice Treated With a Novel SR-BI Inhibitor" Arterioscler Thromb Vase Biol 2009, 29, 2054-2060.
McElroy, Pallavi B., et al. "Post-translational activation of glutamate cysteine ligase with dimercaprol: A novel mechanism of inhibiting neuroinflammation in-vitro" Journal of Biological Chemistry 292.13 (2017): 5532-5545.
Openers for Selectivity to Guinea Pig Trachealis, Bioorganic & Medicinal Chemistry Letters, 4(16):1995-1998 (1994).
Ozbek, Emin, et al. "Atorvastatin prevents gentamicin-induced renal damage in rats through the inhibition of p38-MAPK and NF-kB pathways." Renal failure 31.5 (2009): 382-392.
PatentPack™ readout generated and downloaded from WO 2018/007788, Apr. 26, 2019.
Perdiguero, E. et al., "Genetic analysis of p38 MAP kinases in myogenesis: fundamental role of p38a in abrogating myoblast proliferation," The EMBO Journal, 26(5):1245-1256 (2007).
Pi, Rongbiao, et al. "Minocycline prevents glutamate-induced apoptosis of cerebellar granule neurons by differential regulation of p38 and Akt pathways."
Rautio, J. et al., "Prodrugs: design and clinical applications," Nature Reviews of Drug Discovery, 7:255-270 (2008).
Rickard, A. M. et al., "Endogenous DUX4 expression in FSHD myotubes is sufficient to cause cell death and disrupts RNA splicing and cell migration pathways," Human Molecular Genetics, 24(20):5901-5914 (2015).
Sakellariou, P. et al., "Neuromuscular electrical stimulation promotes development in mice of mature human muscle from immortalized human myoblasts," Skeletal Muscle, 6:4 (2016), 14 pages; doi: 10.1186/s13395-016-0078-6.
Shadle, S. C. et al., "DUX4-induced dsRNA and MYC mRNA stabilization activate apoptotic pathways in human cell models of Facioscapulohumeral dystrophy," PLoS Genetics (2017), 25 pages; Retrieved from https://doi.orq/10.1371/journal.oaen.1006658.
Statland, J.M. & Tawil, R., "Facioscapulohumeral Muscular Dystrophy," Neural Clin., 32(3):721-ix (2014), 10 pages; doi: 10.1016/j.ncl.2014.04.003.
Stone, Albert A., and Timothy C. Chambers. "Microtubule inhibitors elicit differential effects on MAP kinase (JNK, ERK, and p38) signaling pathways in human KB-3 carcinoma cells." Experimental cell research 254.1 (2000): 110-119.
Tawil, R. et al., "Facioscapulohumeral dystrophy: the path to consensus on pathophysiology," Skeletal Muscle, 4:12 (2014), 15 pages; doi:10.1186/2044-5040-4-12.
Third party observations in European Patent Application 18792812. 2. Filed on Mar. 30, 2021.
Third party observations in European Patent Application 18797227. 8. Filed on Mar. 12, 2021.
Third party submission under 37 CFR 1.290 in U.S. Appl. No. 16/753,664, filed Apr. 22, 2021.
Third party submission under 37 CFR 1.290 in U.S. Appl. No. 16/753,664, filed Dec. 4, 2020.
Thorley, M. et al., "Skeletal muscle characteristics are preserved in hTERT/cdk4 human myogenic cell lines," Skeletal Muscle, 6:43 (2016), 12 pages; doi: 10 1186/s13395-016-0115-5.

(56) References Cited

OTHER PUBLICATIONS

Van Der Maarel, S. M. et al., "Facioscapulohumeral muscular dystrophy," Biochimica et Biophysica Acta, 1772:186-194 (2007).

Viemann, D. et al., "Transcriptional profiling of IKK2/NF-KB- and p38 MAPkinase-dependent gene expression in TNF-a-stimulated primary human endothelial cells," Blood, 103(9):3365-3373 (2004).

Wahl, G. M. et al., "Molecular Hybridization of Immobilized Nucleic Acids: Theoretical Concepts and Practical Considerations," Methods in Enzymology, 152:399-407 (1987).

Wallace, L. M. et al., "DUX4, a Candidate Gene for Facioscapulohumeral Muscular Dystrophy, Causes p53-Dependent Myopathy In Vivo," Ann Neural, 69(3):540-552 (2011).

Welsh, S. et al., "Antitumor activity and pharmacodynamic properties of PX-478, an inhibitor of hypoxia-inducible factor-1a," Molecular Cancer Therapeutics, 3(3):233 244 (2004).

Whitmarsh, A. J., "A central role for p38 MAPK in the early transcriptional response to stress," BMC Biology, 8:47 (2010), 3 pages; doi: 10 1186/17 41-7007-8-47.

Wissing, E. R. et al., "P38a MAPK underlies muscular dystrophy and myofiber death through a Bax-dependent mechanism," Human Molecular Genetics, 23(20):5452-5463 (2014).

Yang, T., et al., "Functional Roles ofp38 Mitogen-Activated Protein Kinase in Macrophage-Mediated Inflammatory Responses" Mediat Injlamm 2014, Article ID 352371, 13 pages.

Yao, Z. et al., "DUX4-induced gene expression is the major molecular signature in FSHD skeletal muscle," Human Molecular Genetics, 23(20):5342-5352 (2014).

Yong, H.-Y. et al., "The p38 MAPK inhibitors for the treatment of inflammatory diseases and cancer," Expert Opin Investig Drugs, 18(12):1893-1905 (2009).

Zarubin, T. & Han, J., "Activation and signaling of the p38 MAP kinase pathway," Cell Research, 15(1):11-18 (2005).

Zhang, Y. et al., "Comparison of non-canonical PAMs for CRISPR/Cas9-mediated DNA cleavage in human cells," Scientific Reports, 4:5405 (2005), 5 pages; doi: 10.1038/srep05405.

Down et al., "The discloveery and initial optimisation of pyrrole-2-carboxamides as inhibitors of p38α MAP kinase," Bioorganic & Medicinal Chemistry letters 20:3936-3940 (2010).

\* cited by examiner

FIG. 6C
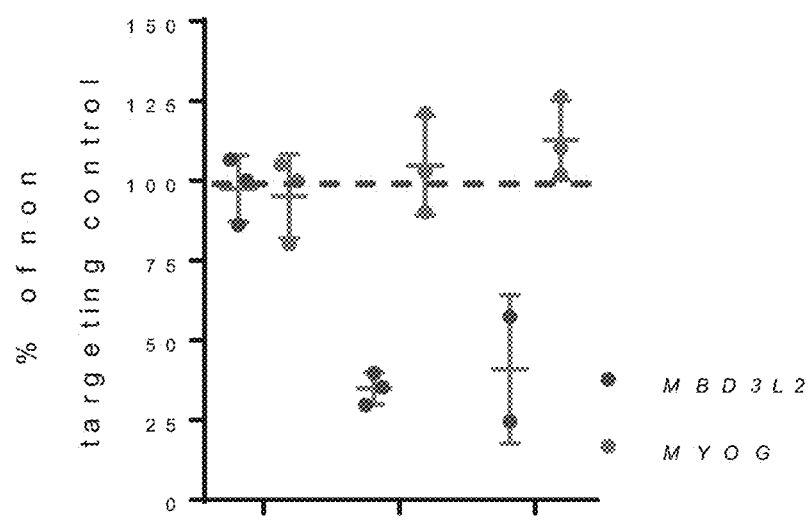
FIG. 7
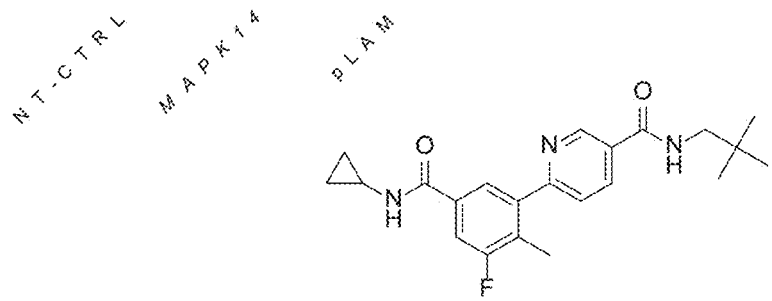
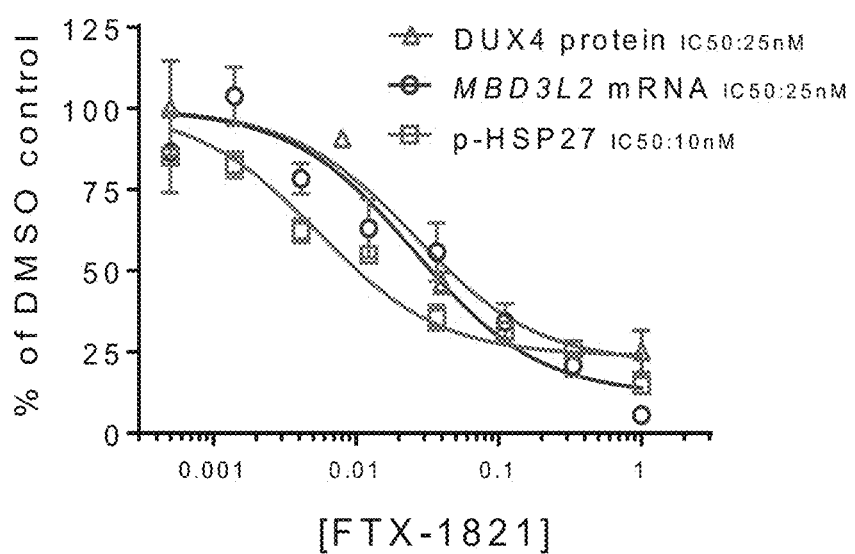

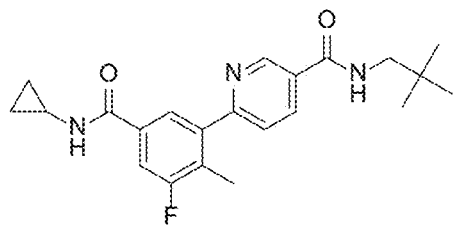
FTX-1821
Quantification of nuclei in MHC+ myotubes after FTX-1821
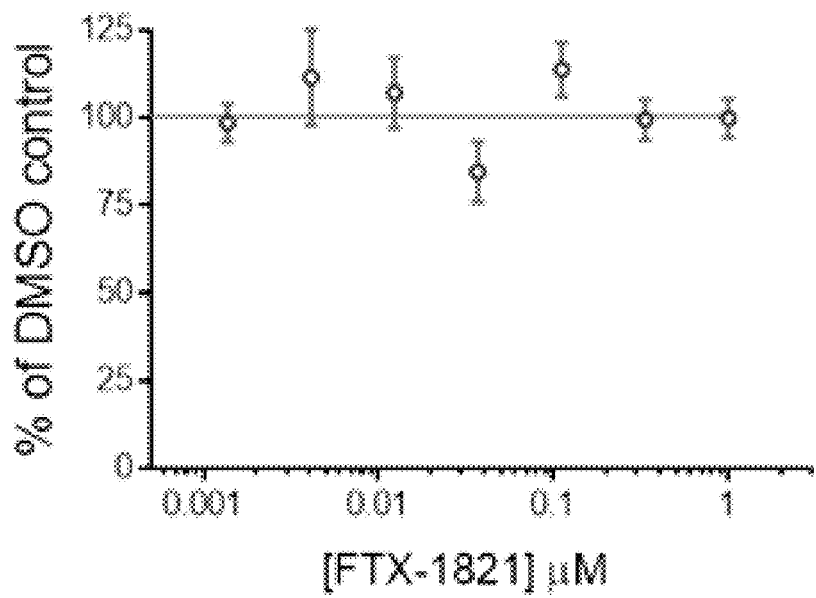
FIG. 8B

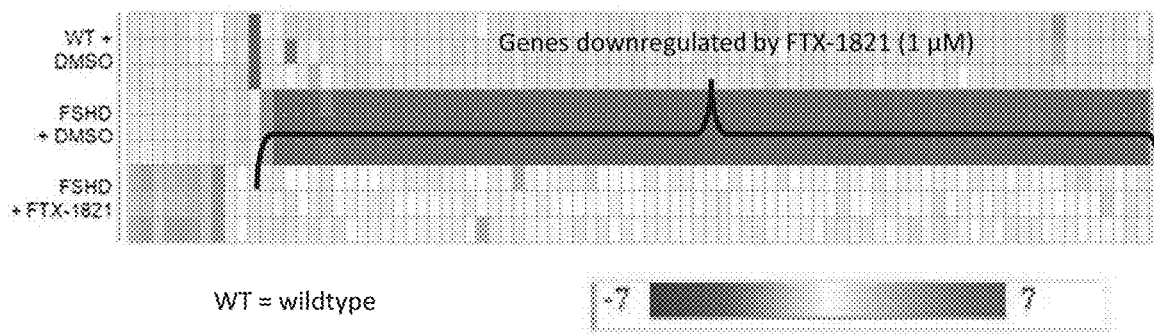

Genes downregulated by FTX-1821:

| | | | | | |
|---|---|---|---|---|---|
| ZSCAN4 | TRIM51BP | MBD3L3 | UBTFL5 | AP001043.1 | ABRA |
| PRAMEF20 | KHDC1P1 | KDM4F | HNRNPCL3 | MBD3L5 | WIPF3 |
| PRAMEF6 | RFPL4A | DUXA | ZIM3 | TRIM51CP | UBTFL1 |
| PRAMEF17 | ZSCAN5DP | TPRX1 | TRIM53BP | TRIM53CP | POU5F1B |
| PRAMEF1 | PRAMEF9 | PRAMEF13 | TRIM53AP | CILP | UBTFL2 |
| ZNF705E | KLF17 | TRIM43 | DPPA3 | SLC2A3 | FAM151A |
| LEUTX | RFPL2 | MBD3L2 | MBD3L2B | TRIM49 | TRIM60 |
| PRAMEF15 | CCNA1 | PRAMEF11 | USP29 | ZNF705G | PRAMEF28P |
| ZNF705A | PRAMEF2 | PRAMEF14 | ZNF296 | TRIM43CP | KLF18 |
| PRAMEF12 | HNRNPCL1 | KHDC1L | F2RL1 | TRIM48 | SNAI1P1 |
| SLC34A2 | DUXB | PRAMEF19 | FREM2 | UBTFL6 | HUNK |
| HNRNPCL2 | HSPA6 | PRAMEF4 | PRAMEF8 | PRAMEF33 | P2RX1 |
| PRAMEF18 | TRIM43B | KDM4E | TRIM51 | C1DP2 | TPRX2P |
| TRIM49C | TC2N | TRIM49B | IGFN1 | DPYSL5 | FAM9C |
| | | | | | GJA5 |
| | | | | | IMPG2 |

FIG. 10A

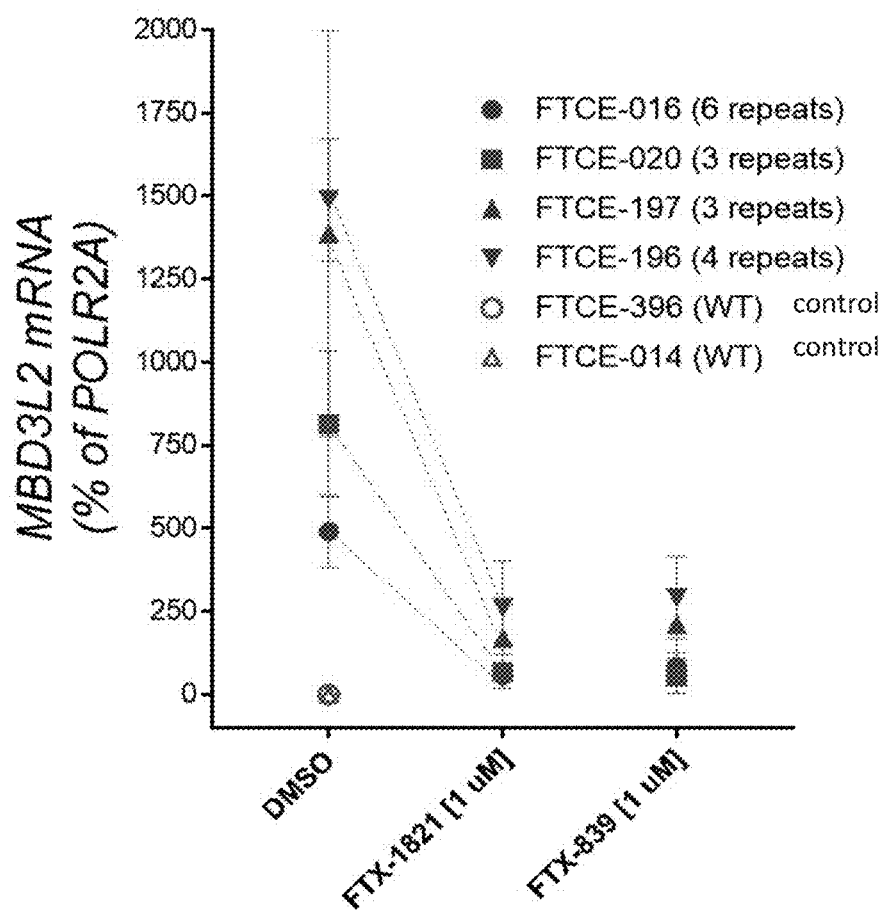
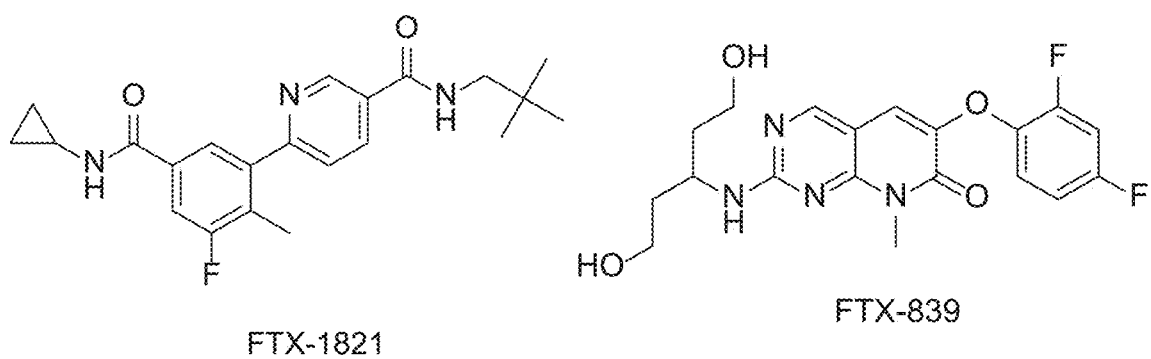
FIG. 11

Table 1.

| DRUG_NAME | Formatted ID | IC50 *MBD3L2* (nM) |
|---|---|---|
| TAK-715 | FTX000500 | 48 |
| VX-702 | FTX000638 | 41 |
| R1487 | FTX000830 | 6 |
| Pamapimod | FTX000839 | 10 |
| AS1940477 | FTX001341 | 20 |
| Losmapimod | FTX001821 | 30 |
| LY2228820 | FTX002865 | 10 |
| SCIO-469 | FTX004078 | 25 |
| Doramapimod | FTX004385 | 42 |
| BMS-582949 | FTX005041 | 68 |
| PH-797804 | FTX005042 | 10 |
| Pexmetinib | FTX005043 | 5 |

FIG. 12A

Table 2.

| CTID # | ID | p/i | Cell type | Repeat # | Control/FSHD |
|---|---|---|---|---|---|
| CTID-001 | FTCE-204 | primary | Fibroblast | 39 | Control |
| CTID-002 | FTCE-425 | primary | Myoblast | 5.5 | FSHD |
| CTID-003 | FTCE-423 | primary | Myoblast | 3 | FSHD |
| CTID-004 | FTCE-396 | primary | Myoblast | NA | Control |
| CTID-005 | FTCE-422 | primary | Myoblast | 2 | FSHD |
| CTID-006 | FTCE-424 | primary | Myoblast | 4.5 | FSHD |
| CTID-007 | FTCE-426 | primary | Myoblast | 4.5 | FSHD |
| CTID-008 | FTCE-428 | primary | Myoblast | SMCHD1 | FSHD2 |
| CTID-009 | FTCE-197 | primary | Myoblast | 2 | FSHD |
| CTID-010 | FTCE-196 | primary | Myoblast | 3 | FSHD |
| CTID-011 | FTCE-429 | primary | Myoblast | SMCHD1 | FSHD2 |
| CTID-012 | FTCE-421 | primary | Myoblast | 7 | FSHD |
| CTID-013 | FTCE-205 | primary | Myoblast | 12 | Control |
| CTID-014 | FTCE-427 | primary | Myoblast | SMCHD1 | FSHD2 |
| CTID-015 | FTCE-16 | immortalized | Myoblast | 6.5 | FSHD |
| C6 CONTROL | FTCE-20 | immortalized | Myoblast | 3 | FSHD |
| WT CONTROL | FTCE-14 | immortalized | Myoblast | NA | Control |
| A4 CONTROL | FTCE-13 | immortalized | Myoblast | NA | Control |

FIG. 13

The Dux4 dependent mRNA program is elevated in muscles of FSHD vs. control xenografted mice

P38 KINASE INHIBITORS REDUCE DUX4 AND DOWNSTREAM GENE EXPRESSION FOR THE TREATMENT OF FSHD

RELATED APPLICATIONS

This application is a continuation application of U.S. application Ser. No. 16/195,361, filed on Nov. 19, 2018, which is a continuation application of International Application No. PCT/US2018/054642, filed on Oct. 5, 2018, which claims priority to U.S. Provisional Application No. 62/568,673, filed on Oct. 5, 2017; U.S. Provisional Application No. 62/568,754, filed on Oct. 5, 2017; U.S. Provisional Application No. 62/682,563, filed on Jun. 8, 2018; and U.S. Provisional Application No. 62/682,565, filed on Jun. 8, 2018; all of which are incorporated by reference herein in their entireties.

INCORPORATION OF SEQUENCE LISTING

The contents of the text file named "FULC-02602US_ST25," which was created on Oct. 17, 2018, and is 3 KB in size, are hereby incorporated by reference in their entirety.

FIELD OF THE INVENTION

The present invention relates to methods of inhibiting p38 kinase for reduction of DUX4 expression levels and/or downstream gene and protein expression and the treatment of diseases associated with DUX4.

BACKGROUND OF THE INVENTION

The muscular dystrophies (MD) are a group of more than 30 different genetic diseases characterized by progressive weakness and degeneration of the skeletal muscles that control movement. Some forms of MD occur in infancy or childhood, while others may not appear until middle age or older. The various MD diseases differ in terms of the distribution and extent of muscle weakness (some forms of MD also affect cardiac muscle), age of onset, rate of progression, and pattern of inheritance.

Facioscapulohumeral muscular dystrophy (FSHD) is the third most common form of muscular dystrophy and affects approximately 1 in 15,000 people worldwide. FSHD is caused by genetic mutations resulting in the epigenetic derepression of the DUX4 gene, which makes this disease unique among muscular dystrophies. FSHD's primary manifestations are weakness and wasting of muscles of the face, shoulder girdle, upper arms, and trunk, and impacts lower extremities in more severe cases.

Genetic mutations associated with FSHD lead to a partial decompaction of the D4Z4 chromatin structure and a resulting failure to repress DUX4, a transcription factor encoded by the D4Z4 unit, in skeletal muscle. FSHD1, representing about 95% of FSHD cases reported, is associated with deletions of macrosatellite D4Z4 repeats in the subtelomeric region of chromosome 4q35, leaving 1-10 D4Z4 repeats (reviewed in Tawil et. al., 2014). FSHD2 is caused by mutations in Structural Maintenance of Chromosomes Flexible Hinge Domain Containing 1 gene (SMCHD1) on chromosome 18 (reviewed in van der Maarel et. al., 2007). Both FSHD1 and FSHD2 mutations lead to loss of repression at the 4q35 D4Z4 repeat array, allowing aberrant transcription in muscle of a full-length form of Double homeobox 4, DUX4, mRNA (DUX4-fl), which encodes the double homeobox 4 (DUX4) transcription factor (Tawil et. al., 2014). DUX4-fl RNA isoforms found associated with FSHD vary only in the 3' untranslated region and have no identified functional distinction.

There is currently no approved treatment that can halt or reverse the effects of FSHD, although nonsteroidal anti-inflammatory drug are often prescribed to improve comfort and mobility. Clearly, therefore, there is a need in the art for new methods for reducing the expression levels of DUX4, e.g., DUX4-fl mRNA and/or DUX4 protein, e.g., to treat FSHD and other diseases. The present invention meets this need.

SUMMARY OF THE INVENTION

In one aspect, a method for treating a disorder responsive to p38 kinase inhibition is provided. The method includes administering to a subject in need thereof, an effective amount of a p38 kinase inhibitor of Formula V':

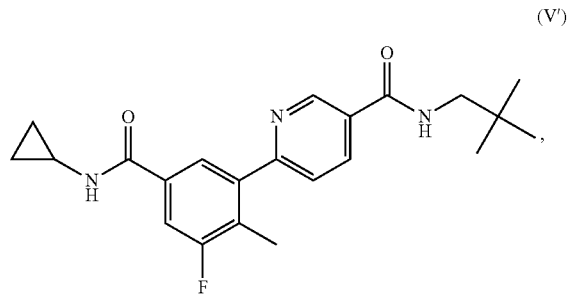 [SMILES: Cc1c(F)cc(C(=O)NC2CC2)cc1-c1ccc(C(=O)NCC(C)(C)C)cn1]

or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In another aspect, a method for treating facioscapulohumeral muscular dystrophy (FSHD) is provided. The method includes administering to a subject in need thereof, an effective amount of a p38 kinase inhibitor of Formula V', or a stereoisomer thereof, an isotopically-enriched compound thereof, a prodrug thereof, a solvate thereof, or a pharmaceutically acceptable salt thereof.

In one aspect, a method for treating a disorder responsive to p38 kinase inhibition is provided. The method includes administering to a subject in need thereof, an effective amount of a p38 kinase inhibitor selected from one or more of the following Formulae I'-XXIX':

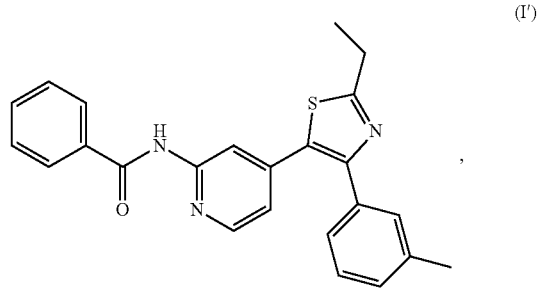

(II')
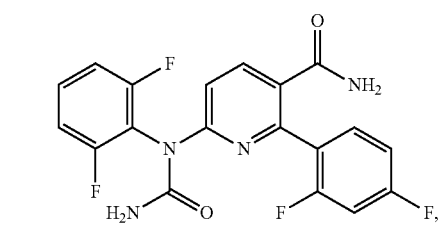
(III'a)
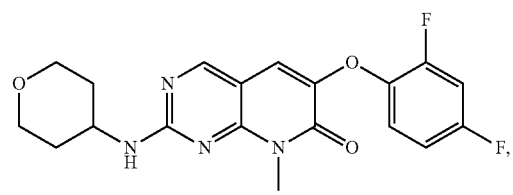
(III'b)
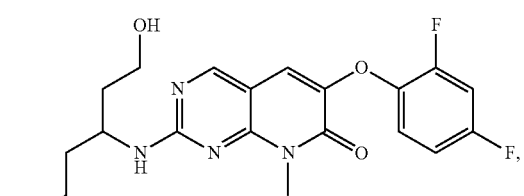
(IV')
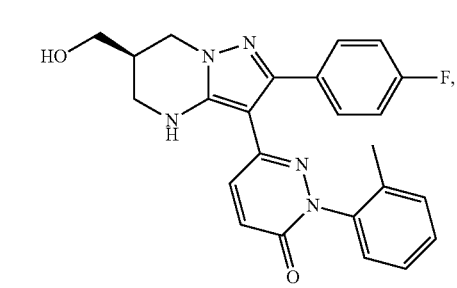
(V')
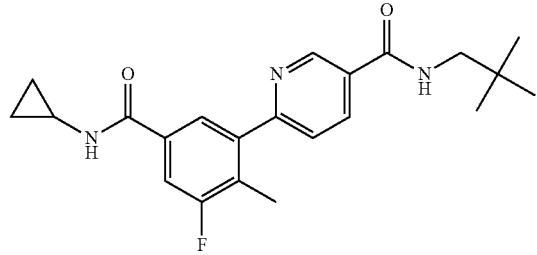
(VI')
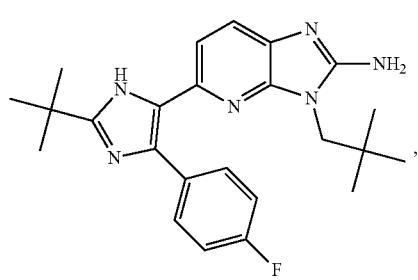
(VII')
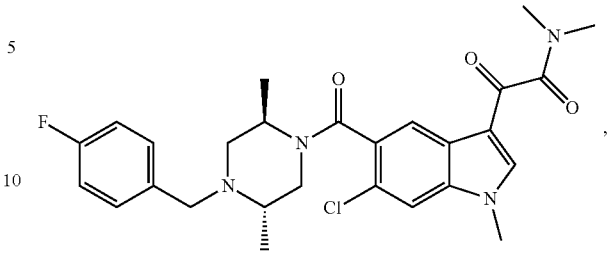
(VIII')
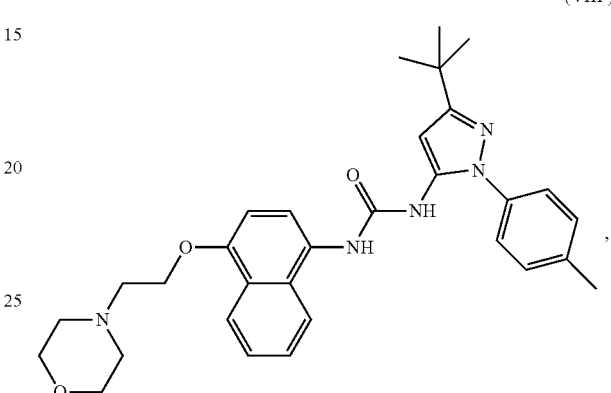
(IX')
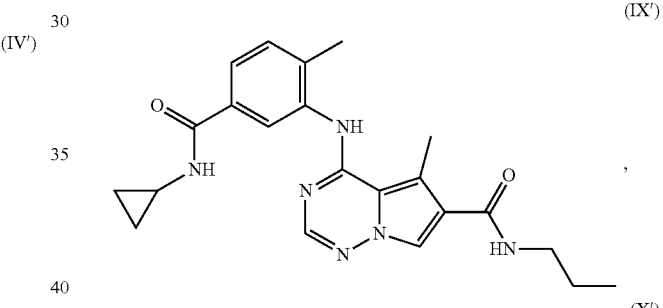
(X')
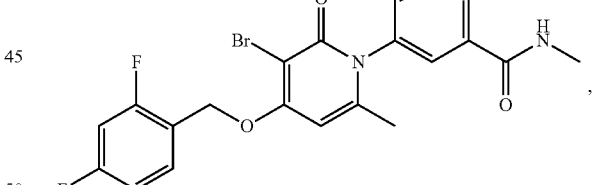
(XI')
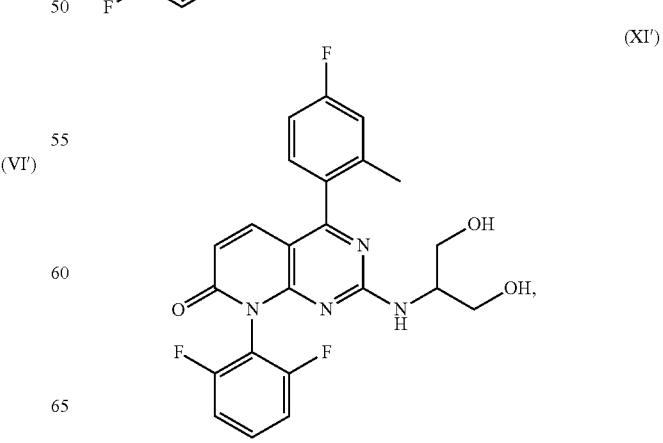

(XII')
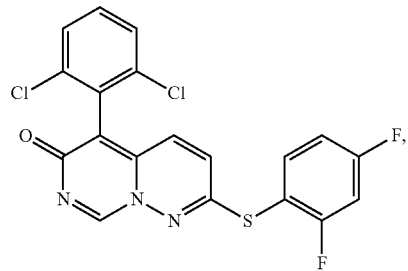
(XIII')
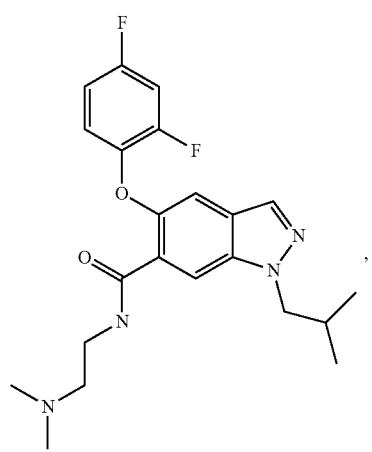
(XIV')
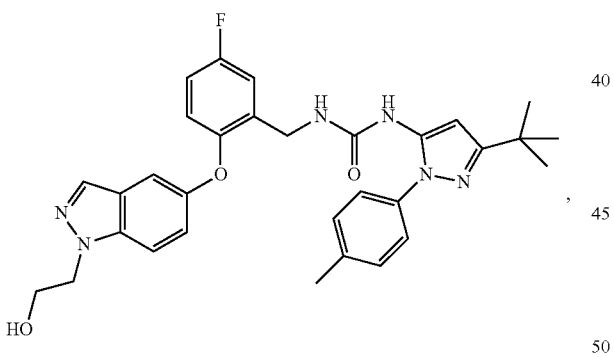
(XV')
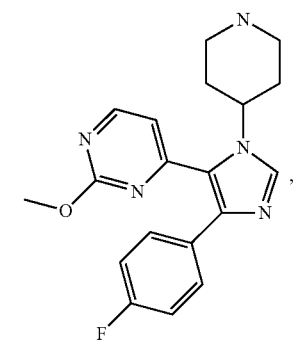
(XVI')
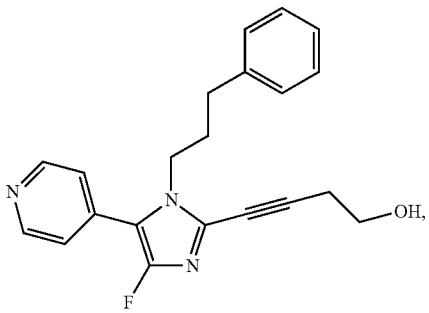
(XVII')
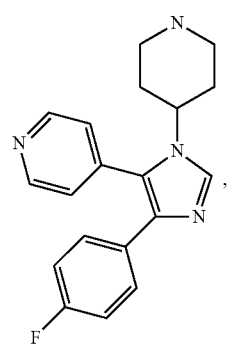
(XVIII')
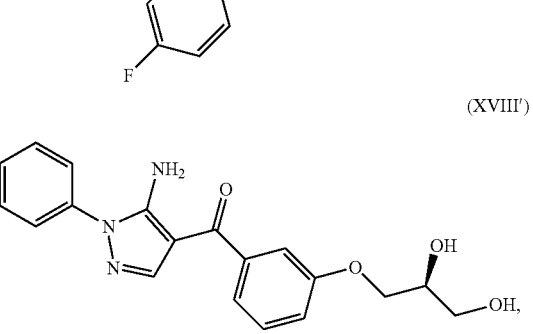
(XIX')
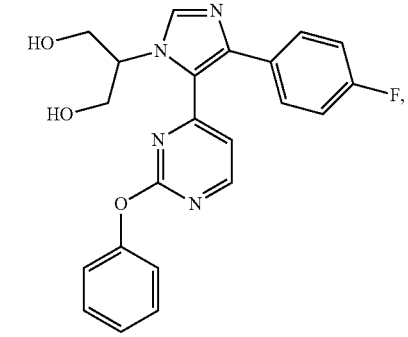
(XX')
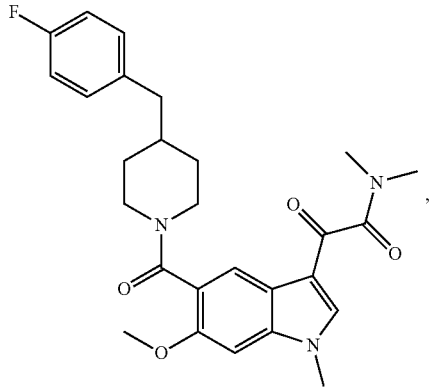

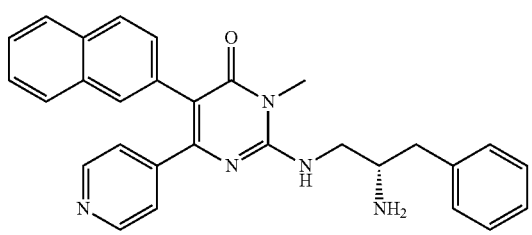
(XXI')

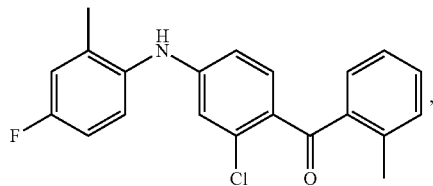
(XXII')

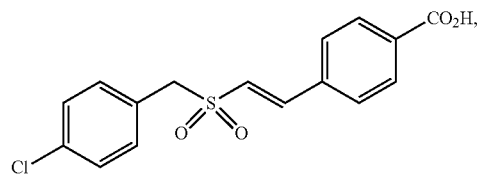
(XXIII')

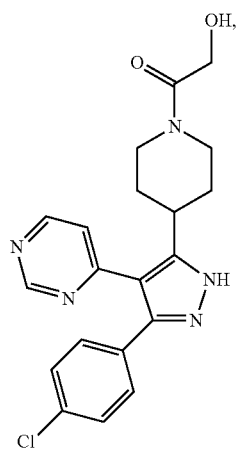
(XXIV')

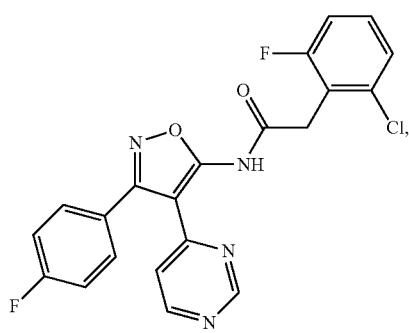
(XXV')

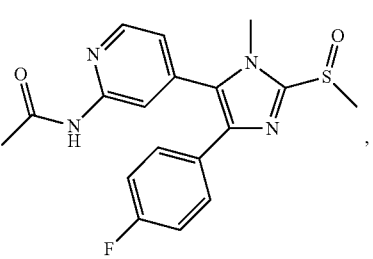
(XXVI')

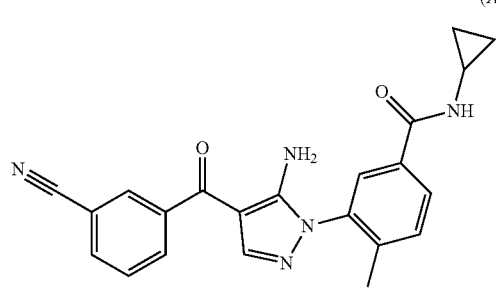
(XXVII')

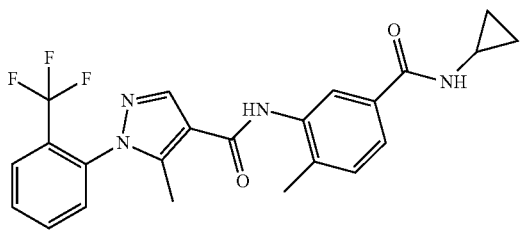
(XXVIII'), and

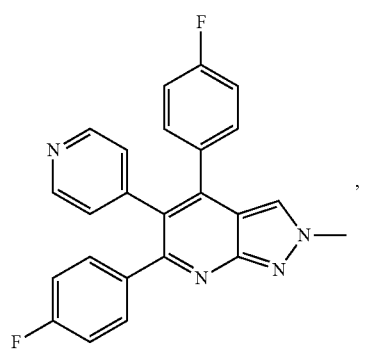
(XXIX')

or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In another aspect, a method for treating facioscapulohumeral muscular dystrophy (FSHD) is provided. The method includes administering to a subject in need thereof, an effective amount of a p38 kinase inhibitor selected from one or more of Formulae I'-XXIX', or a stereoisomer thereof, an isotopically-enriched compound thereof, a prodrug thereof, a solvate thereof, or a pharmaceutically acceptable salt thereof.

In one aspect, a method for treating a disorder responsive to p38 kinase inhibition is provided. The method includes administering to a subject in need thereof, an effective amount of a p38 kinase inhibitor selected from one or more of Formulae I-XIII (of Genuses I-XIII described herein), or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In another aspect, a method for treating facioscapulohumeral muscular dystrophy (FSHD) is provided. The method includes administering to a subject in need thereof, an effective amount of a p38 kinase inhibitor selected from one or more of Formulae I-XIII (of Genuses I-XIII described herein), or a stereoisomer thereof, an isotopically-enriched compound thereof, a prodrug thereof, a solvate thereof, or a pharmaceutically acceptable salt thereof.

In one aspect, a method for treating a disorder responsive to p38 kinase inhibition is provided. The method includes administering to a subject in need thereof, an effective amount of a p38 kinase inhibitor, or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In several embodiments, a method for treating facioscapulohumeral muscular dystrophy (FSHD) is provided. The method includes administering to a subject in need thereof, an effective amount of a p38 kinase inhibitor described herein, or a stereoisomer thereof, an isotopically-enriched compound thereof, a prodrug thereof, a solvate thereof, or a pharmaceutically acceptable salt thereof.

BRIEF DESCRIPTION OF THE DRAWINGS

FIG. 1A includes micrographs of FSHD myotubes stained using an antibody that binds DUX4 protein and/or DAPI (to detect nuclei). Mature FSHD myotubes showed actin striations in culture (not shown) and expressed DUX4 protein in discrete sets of nuclei contained within a differentiated myotube (FIG. 1A). FIG. 1B is a graph showing relative expression of DUX4 mRNA in FSHD myotubes and myotubes from an isogenic wild type (healthy) control.

FIG. 3A is a graph showing grouped plate quality control data comparing MBD3L2 expression in FSHD myotubes treated with DMSO control or 1 µM DUX4-targeted ASOs, and healthy normal isogenic wild-type myotubes (WT). FIG. 3B is a graph showing dose-dependent reduction of MBD3L2 mRNA expression in FSHD myotubes treated with different dilutions of the DUX4-targeted ASO (FTX-2). FIG. 3C shows plate-based assay statistics comparing MBD3L2 signal in FSHD myotubes treated with DMSO to DUX4-targeted ASOs or wild type myotubes treated with DMSO.

FIG. 5A is a graph showing that dose-dependent reduction in DUX4-fl mRNA (filled circles) and MBD3L2 mRNA (open circles). FIG. 5B shows micrographs of FSHD myotubes treated with either DMSO or Pamapimod.

FIGS. 6A-6C are graphs showing mRNA levels of MAPK14 (FIG. 6A) and MBD3L2 (FIG. 6B and FIG. 6C) in FSHD myotubes treated with siRNAs targeting p38a MAPK14 (siMAPK14 85 and siMAPK14 86; FIG. 6A and FIG. 6B) or treated with p38a kinase (MAPK14 and DUX4 pLAM) Cas9/sgRNA RNPs (FIG. 6C), as compared to non-targeting control (NT CTRL). In FIG. 6C, for each treatment, the results shown left to right correspond to MBD3L2 and MYOG, respectively.

FIG. 7 is a graph showing expression levels of DUX4 protein, MBD3L2 mRNA, and p-HSP27 protein in FSHD myotubes following treatment with increasing dosages of FIX-1821 (structure shown), as a percentage of DMSO control treatment levels. Bars represent standard deviation.

FIGS. 8A and 8B show the effect of FTX-1821 on myotube formation. FIG. 8A provides representative images of morphology of immortalized FSHD myotubes obtained after treatment with vehicle (DMSO) or the indicated concentrations of FTX-1821, and staining with antibodies against MHC and DAPI (nuclear stain). FIG. 8B is a graph showing quantification of nuclei in myotubes, as defined by MHC staining, after treatment with FIX-1821 at concentrations tested. Bars represent standard deviation of three replicates.

FIG. 9A provides micrographs of FSHD myotubes stained for active caspase-3 (as a marker of apoptosis) or DAPI. Apoptosis was detected in a sporadic manner in a subset of myotubes in culture as shown by white circles in the left panel and in the magnified region to the right. FIG. 9B is a graph showing quantification of active caspase-3 signal in FSHD myotubes treated with the indicated concentrations of FTX 1821.

FIGS. 10A and 10B illustrate the identification of genes downregulated in FSHD myotubes by FTX-1821. FIG. 10A is a heatmap, which illustrates differentially expressed genes identified by RNA-seq profiling. Three replicates for each condition were analyzed by RNA-seq and genes were clustered by the direction and intensity of change as indicated. The color bar indicates the normalized changes observed, e.g., genes that were downregulated by FTX-1821 are enriched in samples treated with only DMSO. Down-regulated genes are listed in FIG. 10A.

FIG. 10B is a graph showing the normalized expression level reads of the DUX4 target genes that were downregulated upon treatment with FTX-1821 in wild type cells treated with vehicle control DMSO, FSHD cells treated with DMSO, or FSHD cells treated with FTX-1821.

FIG. 11 is a graph showing mRNA expression levels by qRT-PCR of the DUX4 target gene, MBD3L2 (normalized to POLR2A), in myotubes derived from four distinct FSHD patient myoblast lines, FTCE-016, -020, -197, -196 and two wild type (WT) control lines, following the indicated treatment with DMSO vehicle control, FTX-1821 or FTX-839.

FIGS. 12A and 12B provide information on various p38 kinase inhibitors. FIG. 12A is a table of data summarizing pharmacology for the indicated p38α and β inhibitors, including $IC_{50}$ for reducing MBD3L2 expression in FSHD cells. Comparable MBD3L2 $IC_{50}$ values are shown, indicating inhibition of DUX4 downstream gene expression in FSHD myotubes across a broad structural panel of p38α and β inhibitors reported to have similar enzyme potencies. These data indicate that p38 inhibition result in DUX4 target gene, MBD3L2, reduction $IC_{50}$ values in the range of ~6-68 nM. FIG. 12B provides the compound structures of the p38 kinase inhibitors listed in FIG. 12A.

FIG. 13 is a table of various cell lines utilized in "clinical trial in a dish," which shows diversity of genotypes, and includes both primary and immortalized lines, as well as FSHD1 and FSHD2 patient lines.

DETAILED DESCRIPTION OF THE INVENTION

Figure 1A:
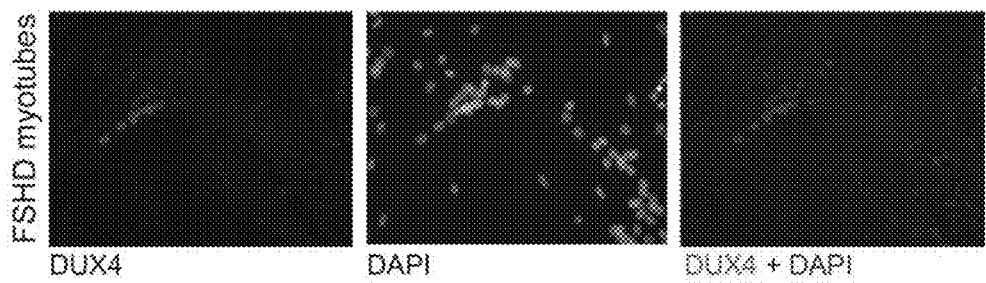
FIGS. 1A and 1B show expression of DUX4 protein and RNA in FSHD myotubes.
Figure 1B:
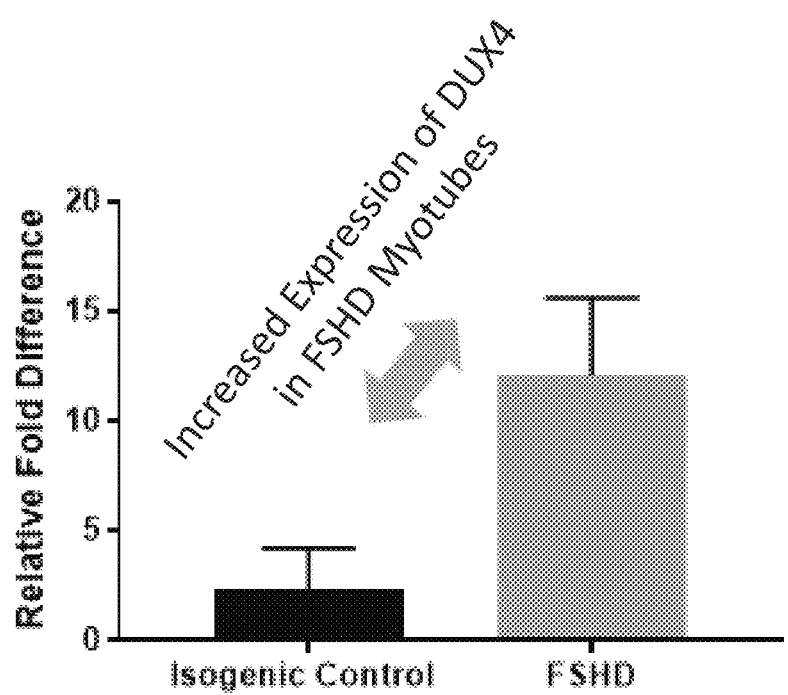

The present invention is based, in part, on the discovery that inhibition of p38 kinase, e.g., p38-α, results in reduced expression of DUX4 and downstream genes regulated by DUX4. Accordingly, the invention includes methods and compositions related to using an inhibitor of p38, e.g., p38-α, (alone or in combination with another agent) to reduce the expression and/or activity levels of DUX4 and/or any of its downstream target genes, e.g., in the treatment or prevention of diseases associated with aberrant DUX4 expression, such as FSHD, a type of muscular dystrophy.

The muscular dystrophies are a diverse group of genetic diseases that cause progressive weakness of the body's muscles. Some types of muscular dystrophy will present symptoms in early childhood, while other types will appear in adulthood. Different muscle groups also may be affected depending on the type of muscular dystrophy. See, e.g., Isin Dalkilic and Louis M Kunkel. Nearly 30 genes are known to give rise to various forms of muscular dystrophy, which differ in age of onset, severity, and muscle groups affected. The number of genes identified increases each year, adding to our understanding as well as revealing the overall complexity of the pathogenesis of these diseases.

For example, two common muscular dystrophies—Duchenne Muscular Dystrophy (DMD) and Facioscapulohumeral dystrophy (FSHD)—are considered to be unique diseases with some shared characteristics. Similarities between DMD and FSHD include that both are genetic diseases and symptoms include muscle loss with muscle weakness leading to disability (therefore both DMD and FSHD are grouped in the large category of muscular dystrophies, which means muscle degeneration). However, DMD and FSHD have very different etiology and disease diagnosis (dystrophin loss in DMD vs expression of DUX4-myotoxin in FSHD). For example, in DMD, mutations in the DMD gene (>2000 known) result in dysfunctional or missing dystrophin. In FSHD, the disease is due to overexpression of the DUX4 gene in muscle tissue; it is not due to point mutations in the gene (DUX4 protein is expressed when the number of D4Z4 repeats in the DUX4 gene is between 1 and 8, or when repression is lost at the D4Z4 by mutations in other silencing machinery). Other differences include that only skeletal muscle is involved in FSHD, whereas both skeletal and cardiac muscle are affected in DMD; the diaphragm is involved in DMD but not FSHD; generally there is childhood onset in DMD but adult/adolescent onset in FSHD; and onset with ambulatory involvement in DMD but onset with face and proximal arm/shoulders in FSHD. Another important distinction is that there is response to steroids in DMD but not in FSHD. In addition, the approved treatment for DMD (Exondys-51 in the US; Ataluren in the EU) will not have any effect in FSHD. Finally, only males are affected in DMD while there is equal involvement of both sexes in FSHD.

FSHD also has an unusual pathology, and it is unique among muscular dystrophies in that its development requires both genetic and epigenetic conditions. The genetic condition is the presence of a complete DUX4 gene. The DUX4 gene is a retrogene normally expressed in germ line and early embryonic cells, but it is repressed by D4Z4 repeat-induced silencing in adult tissues (Ehrlich and Lacey, 2012). Each D4Z4 element contains a promoter and the DUX4 ORF, but lacks a polyadenylation signal (PAS), resulting in rapid DUX4 mRNA degradation. In contrast, transcripts initiated in the distal D4Z4 unit on a 4qA permissive allele extend outside of the repeat array and reach a PAS in the flanking pLAM sequence (reviewed in Tawil et al., 2014; Himeda et al., 2015). The resulting poly-A tail stabilizes the DUX4 mRNAs and allows for their translation into a protein that is not normally expressed in healthy muscle and is toxic to skeletal muscle function. Two enhancers, DUX4 myogenic enhancer 1 (DME1) and DME2, which activate DUX4-fl expression in skeletal myocytes, have been described to regulate DUX4-fl expression in FSHD (Himeda et al., 2014).

FSHD1, FSHD2 and stages in early development as well as germline formation stages appear to confer a transcriptionally permissive conformation to D4Z4 chromatin. This is evidenced by changes in histone modification, partial but variable hypomethylation of D4Z4 in FSHD1, and more extensive hypomethylation in FSHD2 (Himeda et al., 2015). However, D4Z4 hypomethylation does not suffice for the disease, since there is an absence of muscular dystrophy symptoms in patients with ICF (immunodeficiency, centromeric region instability and facial anomalies), a rare, unrelated DNA hypomethylation-associated disease in which D4Z4 is strongly hypomethylated (OMIM Entry— #614069).

DUX4 is a homeobox transcription factor protein, and expression of DUX4 in muscle induces a transcriptional program leading to expression of downstream genes and protein products that are not normally expressed in skeletal muscle. For example, DUX4 expression results in the induction of several germline genes in FSHD skeletal muscles and in transfected cells (Yao et al, 2014; Ehrlich and Lacey, 2012). Many of these novel transcripts are expressed in FSHD muscle cells but not in control muscle cells (Yao et al., 2014; Homma et al., 2015; Shadle et al., 2017; Bosnakovski et al., 2014). Since some of the downstream target genes of DUX4 encode transcription factors, DUX4 pathological activation leads to a large gene expression deregulation cascade in muscle, which causes the disease (Yao et al., 2014; Homma et al., 2015; Shadle et al., 2017; Bosnakovski et al., 2014).

Endogenous (in the FSHD myofiber) and forced DUX4 expression in muscle cells is toxic, leads to apoptosis and oxidative stress, and interferes with myogenesis and sarcomere function (Rickard et al., 2015; Homma et al., 2015; Bosnokovski et al., 2014; Tawil et al., 2014; Himeda et al., 2015). Clinical heterogeneity in both disease progression and age of onset can be accounted for, in part, by epigenetic instability leading to progressive changes in DUX4 transcription. The role of DNA hypomethylation and permissive DUX4 transcription is exemplified by the high clinical severity observed in patients who inherited combined FSHD1 and 2 defects (reviewed in Tawil et al., 2014; van der Maarel et al., 2007). Clinical heterogeneity is also explained by differences in the severity of D4Z4 repeat shortening, with more severe phenotype and younger age at onset in patients with shorter repeats (1-3) compared to patients with less severely contracted repeats (4-7).

DUX4 is now recognized as the cause of the pathology of FSHD, since activation of its target genes is the main molecular signature in FSHD muscle (Reviewed in Tawil et al., 2014; Himeda et al., 2015). Major downstream target genes are members of highly homologous gene families that are clustered spatially on chromosomes, including PRAMEF (preferentially expressed in melanoma), TRIM (tripartite motif-containing), MBDL (methyl-CpG binding protein-like), ZSCAN (zinc finger and SCAN domain containing) and RFPL (ret-finger protein-like) families (Geng et al., 2012; Yao et al., 2014; Shadle et al., 2017; Ehrlich and Lacey, 2012; Tawil et al., 2014; van der Maarel et al., 2007). Discrimination between FSHD and control skeletal muscle can be made using ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, ZNF280A etc. (described in but not limited to Yao et al., 2014; Shadle et al., 2017; Ehrlich and Lacey, 2012).

Annotated chemical probes were screened to identify disease-modifying small molecule drug targets that reduce DUX4 expression in FSHD myotubes. These screens identified multiple chemical scaffolds that inhibit p38 mitogen-activated protein kinase alpha (MAPK14 or p38-$\alpha$). As described in the accompanying Examples, it has been shown that knockdown of the MAPK14 gene using small interfering RNA (siRNA) technology or CRISPR-mediated genome editing with specific guide RNA's (gRNAs) that selectively target the alpha isoform of p38 kinase also reduces DUX4 and DUX4-related downstream gene expression in FSHD myotubes. It was also found that selective p38$\alpha$ and $\beta$ kinase inhibitors specifically reduced DUX4 and its downstream genes in FSHD myotubes, thereby impacting the core pathophysiology of the FSHD disease process (data exemplified herein). The same experiments revealed that p38$\alpha$ and $\beta$ kinase inhibitors do not impact myogenin or the expression of other myogenic factors, nor do they impact proliferation of myoblasts or differentiation of myoblasts exhibited by myogenic fusion in FSHD myotubes. These p38 kinase inhibitor small molecules reduce the expression of DUX4 and related downstream genes, thereby impacting pathophysiology of the FSHD disease process, including reducing apoptotic cell death. p38-mediated DUX4 reduction would be expected to impact downstream inflammatory, fatty infiltration and fibrotic processes in FSHD.

Members of the p38 MAPK family, composed of $\alpha$, $\beta$, $\gamma$ and $\delta$, isoforms are encoded by separate genes that play a critical role in cellular responses needed for adaptation to stress and survival (reviewed in Whitmarsh 2010; Martin et al., 2014; Krementsov et al., 2013). In many inflammatory diseases, including cardiovascular and other chronic diseases, these same p38 MAPK stress-induced signals can trigger maladaptive responses that aggravate, rather than alleviate, the disease (reviewed in Whitmarsh 2010; Martin et al., 2014). Indeed, in skeletal muscle, a variety of cellular stresses including chronic exercise, insulin exposure and altered endocrine states, myoblast differentiation into myocytes, reactive oxygen species, as well as apoptosis, have all been shown to induce the p38 kinase pathway (Keren, et. al., 2006; Zarubin et al., 2006). In fact, the p38 kinase pathway can be activated by a number of external stimuli, including pro-inflammatory cytokines and cellular stress, leading to activation of the dual-specificity MAPK kinases MKK3 and MKK6. Activation of MKK3 and MKK6, which in turn phosphorylate p38 in its activation loop, trigger downstream phosphorylation events. These include phosphorylation of HSP27, MAPKAPK2 (MK2) and a variety of transcription factors culminating in transcriptional changes in the nucleus. A modest number of p38-regulated transcripts and a large number of downstream effectors of p38 kinase have been identified (described in Cuenda et al., 2007 and Kyriakis et. al., 2001, Viemann et al. 2004).

Several compounds from different chemical scaffolds that inhibit the p38$\alpha$ MAPK signaling pathway have entered clinical trials in diverse (non-neuromuscular) indications, including rheumatoid arthritis, chronic obstructive pulmonary disease, pain, cardiovascular diseases, and cancer. Inhibition of p38$\alpha$ and $\beta$ in clinical trials has proven to be safe but not efficacious in any of these indications. In vitro and in vivo pharmacology suggest that p38$\alpha$ target engagement in these clinical studies was robust, as demonstrated by measuring reduction in phosphorylation of HSP27 (an indirect target) and pMK2 (a direct target).

p38$\alpha$ MAPK is known to play critical roles in skeletal muscle biology, specifically in abrogating proliferating myoblasts to differentiation and subsequently fusion to form multi-nucleated myotubes. Treatment of muscular dystrophy patients that are constitutively undergoing processes of degeneration and regeneration with p38$\alpha$ inhibitors would not be obvious. Complete knockout (KO) of p38$\alpha$ is embryonically lethal. Embryonic rescue allows for survival of pups to a few days postnatal and isolation of satellite cells to study Myogenic precursors lacking p38$\alpha$. Myoblasts completely lacking p38$\alpha$ express significantly less critical differentiation genes and show severe deficits in fusion. Histology of P2 pups show significantly increased cycling satellite cells and a left-shifted fiber distribution. (Perdiguero et. al, 2007). Importantly, KO of p38$\alpha$ in mature muscle (cre driven by Myl1 promoter) shows no deficiencies in early time points, but mice deficient in p38$\alpha$ at 6 months of age show significantly greater regeneration and type I fibers, as well as a smaller fiber distribution compared to controls (Wissing et. al, 2014). These data suggest that inhibition of p38$\alpha$ would trigger skeletal muscle regeneration in diseases deficient in regeneration in addition to FSHD by a mechanism independent of regulation of DUX4 expression.

In skeletal muscle, p38 has been shown to regulate gene expression during myogenesis. p38γ has been shown to be required for myogenesis using both specific gene knock out and conditional knock out approaches (Cuenda et. al., 2007; Kern et. al., 2006; Aouadi et. al., 2006). In the adult, selective inhibitors of p38α and β avoid p38γ-related impact to myogenesis.

The present disclosure finds that p38 is activated during myogenesis, and that inhibition of p38α and β by molecules exemplified herein, including FTX-839, FTX-1821, etc., profoundly reduces DUX4 expression and its downstream gene program in FSHD myotubes (data exemplified herein). Without wishing to be bound by theory, p38α appears to directly regulate DUX4 expression by impacting the activity of critical myogenic enhancers required for pathologic DUX4 expression at the level of the mutated D4Z4 locus with shorter repeats (FSHD1) or SMCHD1 mutations (FSHD2) or when repression is lost by other mechanisms in the muscle of FSHD patients. This is a differentiated mechanism from the previous clinical studies, which targeted functions of p38 in the cytoplasm and failed to show efficacy in numerous diseases, including rheumatoid arthritis, pain, depression, chronic obstructive pulmonary disease, and cardiovascular disease. Inhibitors of p38 have never been explored clinically for FSHD.

Definitions

As used in this specification and the appended claims, the singular forms "a," "an" and "the" include plural references unless the content clearly dictates otherwise.

As used in this specification, the term "and/or" is used in this disclosure to either "and" or "or" unless indicated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" refers herein to introducing an agent or composition into a subject or contacting an agent or composition with a cell and/or tissue.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Certain compounds of the present invention may exist in stereoisomeric forms (e.g. they may contain one or more asymmetric carbon atoms or may exhibit cis-trans isomerism). Some compounds may include more than one asymmetric carbon atoms. "Stereoisomer" refers to a compound that differ in orientation (R/S) about one or more asymmetric carbon atom(s), or differs in orientation (cis:trans) about a double bond. The term stereoisomer may also encompass atropisomers, which arise from hindered rotation about a single bond, e.g., in compounds having a substituted biphenyl moiety. An "enantiomer" is a compound that is a mirror image of another compound, i.e., all asymmetric carbon atoms of an enantiomer exist in opposite orientation (R/S) with respect to the other compound. A "diastereomer" is a compound that is not a mirror image of another compound, but includes one or more asymmetric carbon atoms existing in opposite orientation (R/S) with respect to the other compound. The embodiments of the present invention may include mixtures of stereoisomers, or may include a single stereoisomer. Single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

"Isotopically-enriched" refers to a compound wherein one or more atoms is enriched with an isotope beyond its natural abundance. For example, the natural abundance of deuterium is 0.015%. One of ordinary skill in the art recognizes that in all chemical compounds with a H atom, the H atom actually represents a mixture of H and D, with about 0.015% being D. An isoptically-enriched compound may have one or more specific chemical sites wherein the H/D ratio is greater than 0.015%. An isotopically-enriched compound may be referred to as isotopically-labeled.

"Solvate" refers to an aggregate of a compound with one or more solvent molecules—a complex of variable stoichiometry formed by a solute and the solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. All such solvates are included within the scope of the present invention. For example, the solvent in any solvate described herein may include water.

"Prodrug" refers to a compound that may be converted under physiological conditions or by solvolysis to the specified compound or to a pharmaceutically acceptable salt of such compound.

"Pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base. For example, salts of the present invention include, but are not limited to: sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, iso-butyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitro-menzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. For example, salts of the present invention include, but are not limited to: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Parnoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. For example, salts of the present invention include, but are not limited to: hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. For example, salts of the present invention include, but are not limited to: alkali metal salts: sodium salt, potassium salt and the like; alkaline earth metal salt: calcium salt, magnesium salt, barium salt, and the like; aluminum salt and the like. As a suitable example of a salt with an organic base, for example, there are salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. As a suitable example of a salt with an inorganic acid, for example, there are salts with hydrochloric acid, hydrobromic acid, nitric acid, sulfuric acid, phosphoric acid and the like. As a suitable example of a salt with an organic acid, for example, there are salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. As a suitable example of a salt with a basic amino acid, for example, there are salts with alginine, lysine, ornithine and the like. As a suitable example of a salt with an acidic amino acid, for example, there are salts with aspartic acid, glutamic acid and the like.

Methods of Use

In several embodiments, a method for treating a disorder responsive to p38 kinase inhibition is provided. The method may include administering to a subject in need thereof, an effective amount of a p38 kinase inhibitor selected from one or more of the following Formulae I'-XXIX':

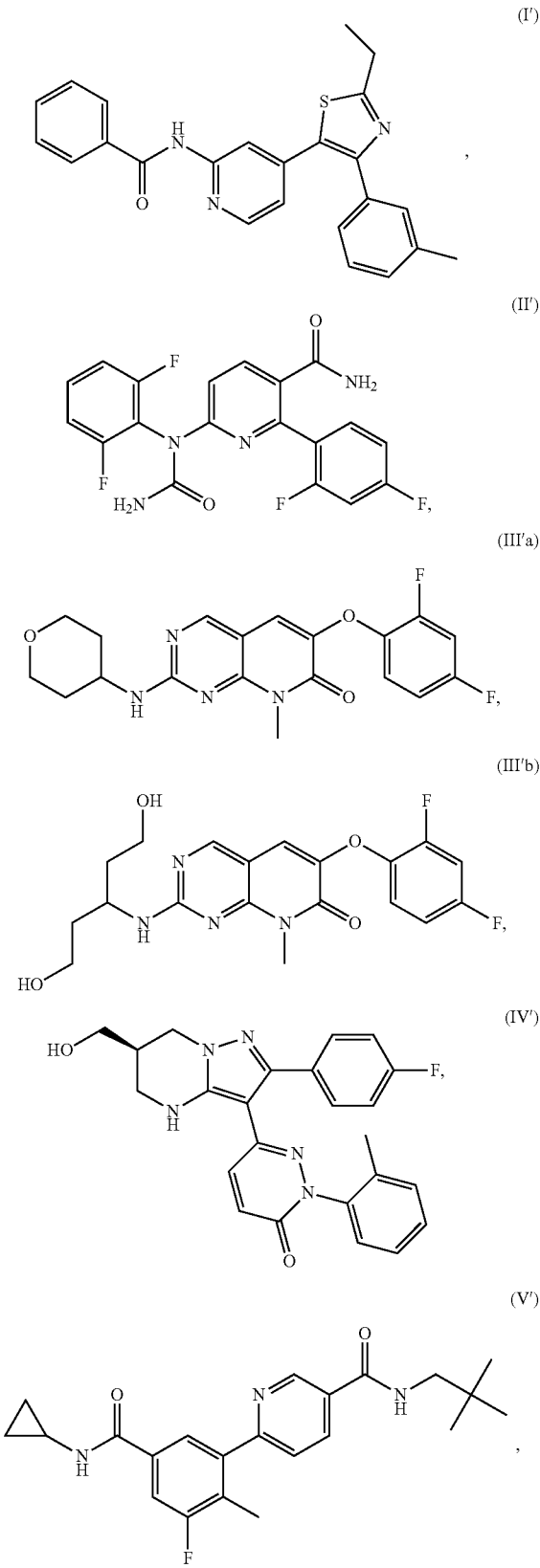

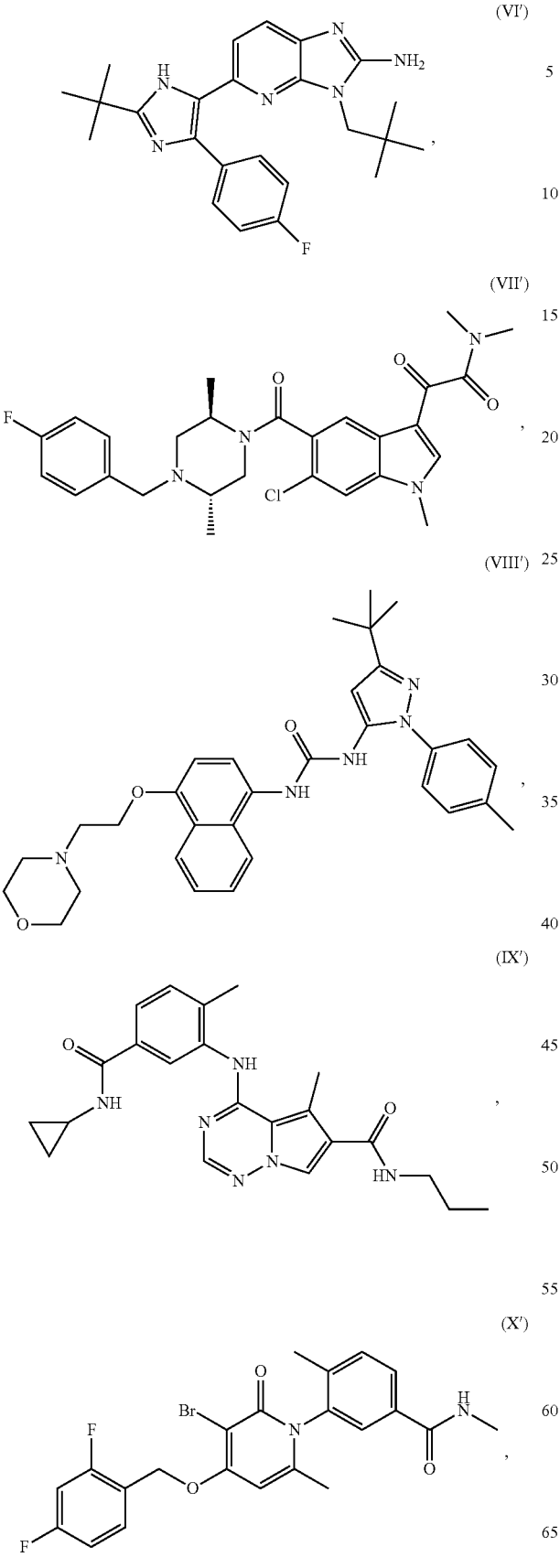
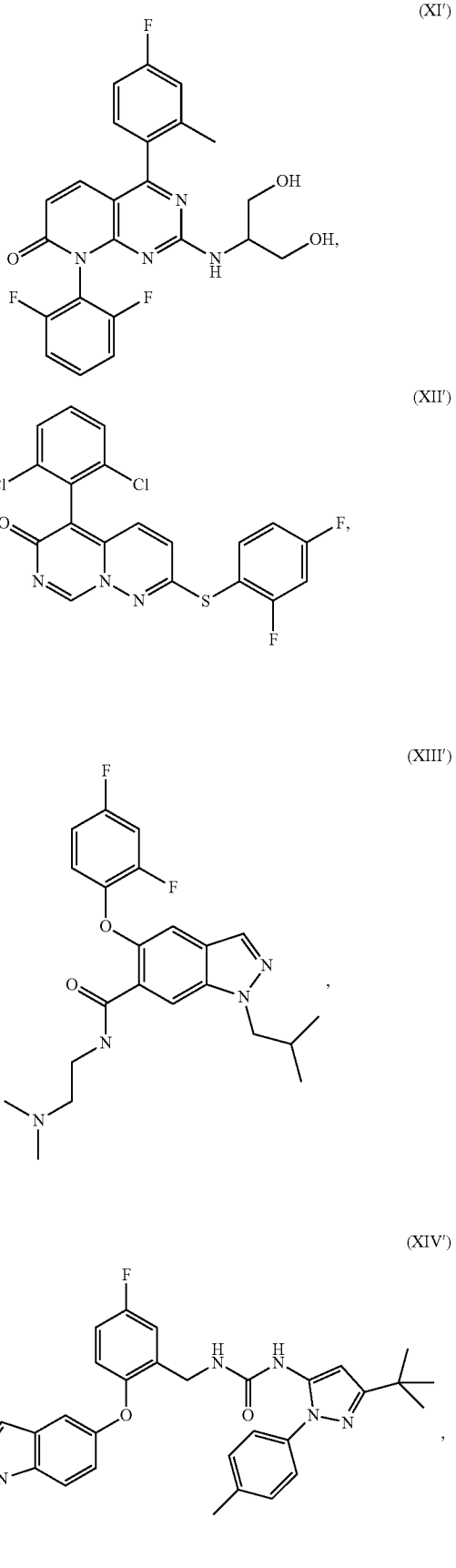

-continued
(XV')
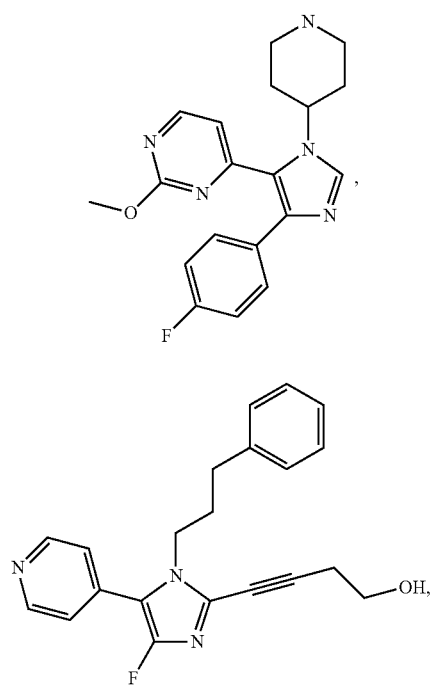
(XVI')
(XVII')
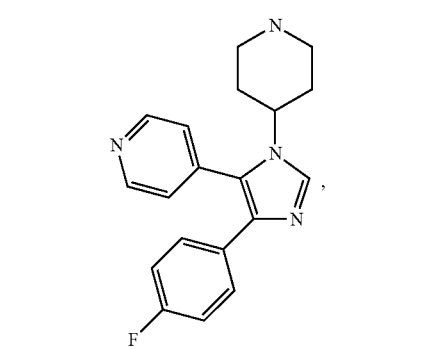
(XVIII')
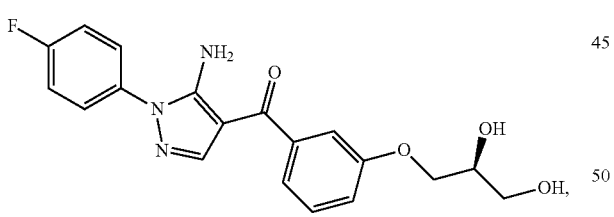
(XIX')
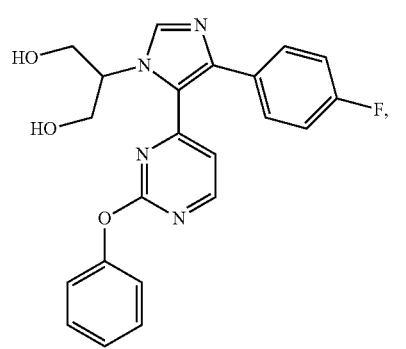
-continued
(XX')
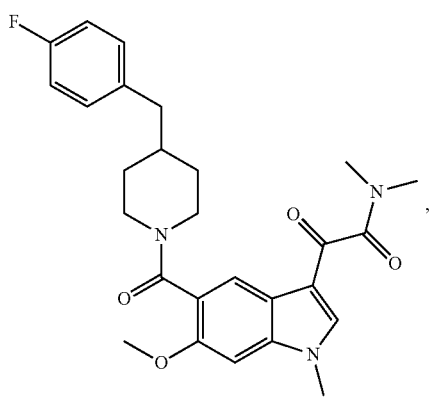
(XXI')
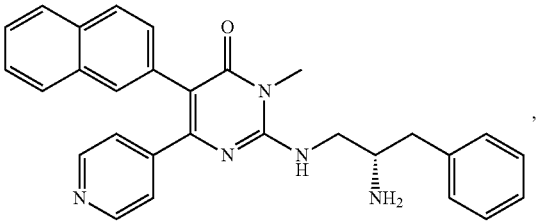
(XXII')
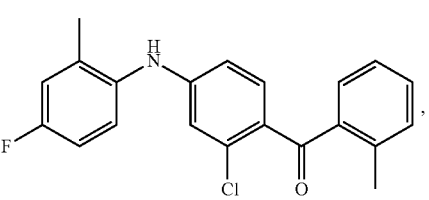
(XXIII')
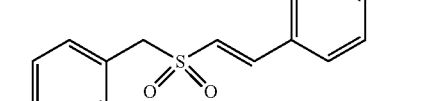
(XXIV')
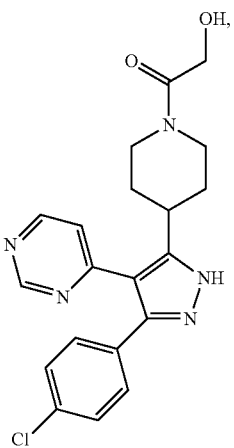

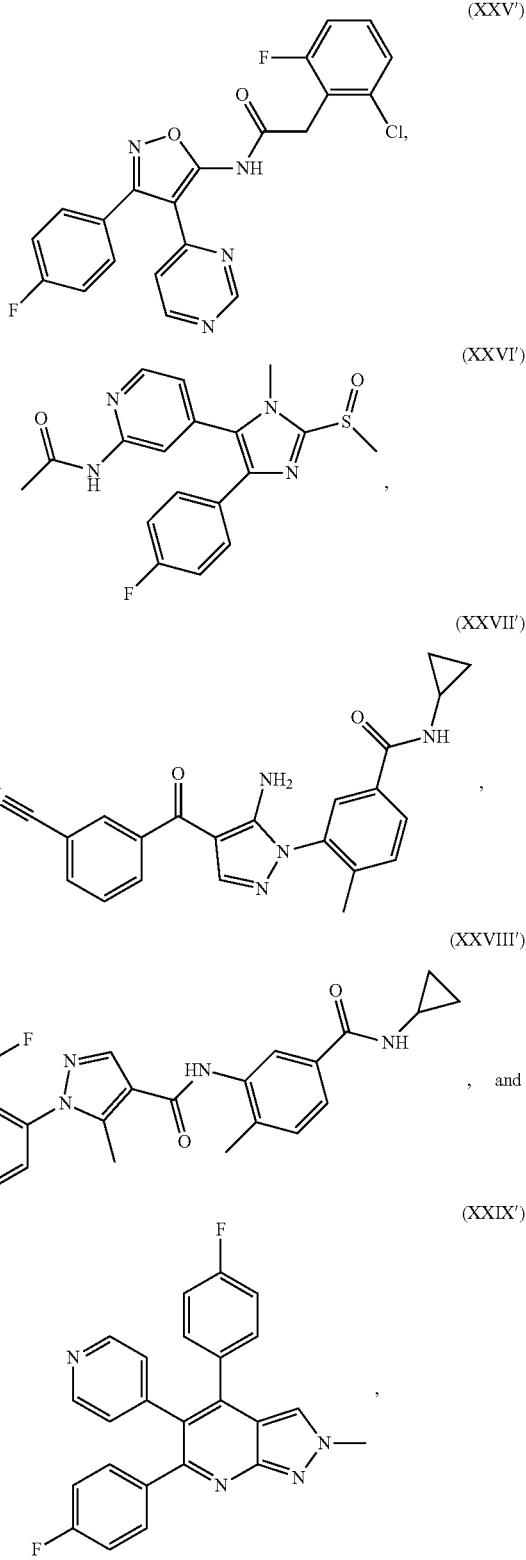

or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In some embodiments, the p38 kinase inhibitor is a compound selected from Formulae I'-XXIX', or a stereoisomer thereof, an isotopically-enriched compound thereof, a prodrug thereof, a solvate thereof, or a pharmaceutically acceptable salt thereof.

In some embodiments, the p38 kinase inhibitor is selected from Formulae I', II', III'a, III'b, and IV'-XIV', or a stereoisomer thereof, an isotopically-enriched compound thereof, a prodrug thereof, a solvate thereof, or a pharmaceutically acceptable salt thereof.

In some embodiments, the p38 kinase inhibitor is selected from Formulae I', II', IV'-VIII', and X'-XIII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula I', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula II', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula IIIa', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula IIIb', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula IV', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula V', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula VI', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula VII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula VIII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula IX', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula X', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XI', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XIII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XIV', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XV', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XVI', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XVII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XVIII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XIX', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XX', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXI', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXIII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXIV', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXV', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXVI', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXVII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXVIII', or a stereoisomer thereof, an isotopically-enriched compound thereof, a prodrug thereof, a solvate thereof, or a pharmaceutically acceptable salt thereof.

In one embodiment, the p38 kinase inhibitor is a compound of Formula XXIX', or a stereoisomer thereof, an isotopically-enriched compound thereof, a prodrug thereof, a solvate thereof, or a pharmaceutically acceptable salt thereof.

In many embodiments, the cells are muscle cells. In some embodiments, the cells are terminally-differentiated muscle cells.

In some embodiments, the cells include one or more mutations in a Structural Maintenance Of Chromosomes Flexible Hinge Domain Containing 1 (SMCHD1) gene. In some embodiments, the cells may include at least one non-deleted 4qA allele.

In many embodiments, the cells may include an increased expression level of a DUX4 polypeptide, or a polypeptide encoded by one or more downstream target genes, as compared to the expression level of a DUX4 polypeptide, or a polypeptide encoded by one or more downstream target genes in a control cell.

In many embodiments, the DUX4 is a DUX4 full length (DUX4-fl).

In some embodiments, the cells may be associated with FSHD.

In some embodiments, the disorder is associated with DUX4 gene expression.

In some embodiments, the disorder is associated with DUX4 gene expression and the DUX4 gene expression may result from the subject having less than 10 D4Z4 repeats in the subtelomeric region of chromosome 4q35. In some embodiments, the cells may include a deletion of one or more macrosatellite D4Z4 repeats in the subtelomeric region of chromosome 4q35. In other embodiments, the cells may include less than 7 macrosatellite D4Z4 repeats in the subtelomeric region of chromosome 4q35.

In some embodiments, the cells may include a dysregulated D4Z4 array at chromosome 4q35 prior to administration of the p38 kinase inhibitor. In one embodiment, the cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the cells are muscle cells and the cells may include a dysregulated D4Z4 array at chromosome 4q35 prior to administration of the p38 kinase inhibitor. In one embodiment, the muscles cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

In one embodiment, the disorder is ICF (immunodeficiency, centromeric region instability and facial anomalies).

In one embodiment, the disorder is amyotrophic lateral sclerosis (ALS).

In one embodiment, the disorder is inclusion body myopathy (IBM).

In one embodiment, the disorder is cancer. The cancer may be selected from Ewing's sarcoma, soft tissue sarcoma, rhabdomyosarcoma, and adult and pediatric B-cell acute lymphoblastic leukemia.

In some embodiments, the disorder may be selected from one or more of: FSHD1, FSHD2, ICF, ALS, IBM, Ewing's sarcoma, soft tissue sarcoma, rhabdomyosarcoma, and adult and pediatric B-cell acute lymphoblastic leukemia.

In one embodiment, the subject is identified as having FSHD based upon the presence of a transcriptionally active DUX4. In another embodiment, the subject is identified as having FSHD based upon the presence of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in muscle. In another embodiment, the subject is identified as having FSHD based upon the presence of increased expression levels of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A relative to a healthy control. In another embodiment, the subject is identified as having FSHD based upon the presence of a transcriptionally active DUX4 and the presence of downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject prior to the administration of the p38 kinase inhibitor. The method may further include determining that the subject is in need of treatment if the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A is/are elevated relative to a healthy control.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the cells of the subject before and after the administration of the p38 kinase inhibitor. The method may include comparing the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject before and after the administration of the p38 kinase inhibitor. The method may include determining the effectiveness of treatment by the comparing of the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A before and after the administration of the p38 kinase inhibitor, wherein a decrease in the expression level(s) is indicative of effective treatment.

In some embodiments, the p38 kinase inhibitor reduces one or more downstream genes selected from ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In one embodiment, the p38 kinase inhibitor reduces MBD3L2.

In one embodiment, the p38 kinase inhibitor reduces ZSCAN4.

In one embodiment, the p38 kinase inhibitor reduces LEUTX.

In one embodiment, the p38 kinase inhibitor reduces PRAMEF2.

In one embodiment, the p38 kinase inhibitor reduces TRIM43.

In one embodiment, the p38 kinase inhibitor reduces KHDC1L.

In one embodiment, a transcriptional modulator of DUX4 and downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A are inhibited by p38 kinase.

In some embodiments, the administering may be combined with clinical management involving physical therapy, aerobic exercise, respiratory function therapy, orthopedic interventions.

In some embodiments, the administering includes administering of the p38 kinase inhibitor with another pharmaceutical agent.

In some embodiments, the administering includes administering of the p38 kinase inhibitor with another pharmaceutical agent for the treatment of FSHD.

In some embodiments, the administering causes a decrease in muscle degeneration.

In some embodiments, the administering causes a reduction in apoptosis of muscle cells in the subject. In one embodiment, the muscles cells are terminally differentiated.

In several embodiments, a method for treating facioscapulohumeral muscular dystrophy (FSHD) is provided. The method may include administering to a subject in need thereof, an effective amount of a p38 kinase inhibitor selected from one or more of Formulae I'-XXIX', or a stereoisomer thereof, an isotopically-enriched compound thereof, a prodrug thereof, a solvate thereof, or a pharmaceutically acceptable salt thereof.

In some embodiments, the p38 kinase inhibitor is selected from Formulae I'-XXIX', or a stereoisomer thereof, an isotopically-enriched compound thereof, a prodrug thereof, a solvate thereof, or a pharmaceutically acceptable salt thereof.

In some embodiments, the p38 kinase inhibitor is selected from Formulae I', II', III'a, III'b, and IV'-XIV', or a stereoisomer thereof, an isotopically-enriched compound thereof, a prodrug thereof, a solvate thereof, or a pharmaceutically acceptable salt thereof.

In some embodiments, the p38 kinase inhibitor is selected from Formulae I', II', IV'-VIII', and X'-XIII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula I', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula II', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula IIIa', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula IIIb', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula IV', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula V', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula VI', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula VII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula VIII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula IX', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula X', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XI', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XIII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XIV', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XV', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XVI', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XVII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XVIII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XIX', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XX', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXI', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXIII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXIV', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXV', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXVI', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXVII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXVIII', or a stereoisomer thereof, an isotopically-enriched compound thereof, a prodrug thereof, a solvate thereof, or a pharmaceutically acceptable salt thereof.

In one embodiment, the p38 kinase inhibitor may include a compound of Formula XXIX', or a stereoisomer thereof, an isotopically-enriched compound thereof, a prodrug thereof, a solvate thereof, or a pharmaceutically acceptable salt thereof.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

In several embodiments, a method for treating a disorder responsive to p38 kinase inhibition is provided. The method may include administering to a subject in need thereof, an effective amount of a p38 kinase inhibitor of Formula V':

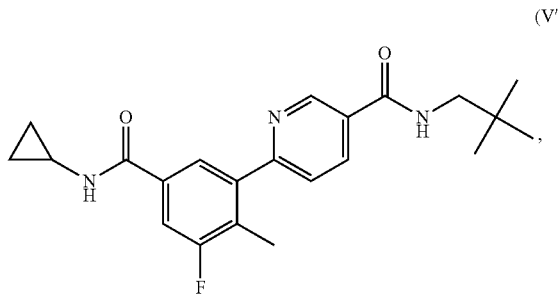

(V')

or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In many embodiments, the cells are muscle cells. In some embodiments, the cells are terminally-differentiated muscle cells.

In some embodiments, the cells include one or more mutations in a Structural Maintenance Of Chromosomes Flexible Hinge Domain Containing 1 (SMCHD1) gene. In some embodiments, the cells may include at least one non-deleted 4qA allele.

In many embodiments, the cells may include an increased expression level of a DUX4 polypeptide, or a polypeptide encoded by one or more downstream target genes, as compared to the expression level of a DUX4 polypeptide, or a polypeptide encoded by one or more downstream target genes in a control cell.

In many embodiments, the DUX4 is a DUX4 full length (DUX4-fl).

In some embodiments, the cells may be associated with FSHD.

In some embodiments, the disorder is associated with DUX4 gene expression.

In some embodiments, the disorder is associated with DUX4 gene expression and the DUX4 gene expression may result from the subject having less than 10 D4Z4 repeats in the subtelomeric region of chromosome 4q35. In some embodiments, the cells may include a deletion of one or more macrosatellite D4Z4 repeats in the subtelomeric region of chromosome 4q35. In other embodiments, the cells may include less than 7 macrosatellite D4Z4 repeats in the subtelomeric region of chromosome 4q35.

In some embodiments, the cells may include a dysregulated D4Z4 array at chromosome 4q35 prior to administration of the p38 kinase inhibitor. In one embodiment, the cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the cells are muscle cells and the cells may include a dysregulated D4Z4 array at chromosome 4q35 prior to administration of the p38 kinase inhibitor. In one embodiment, the muscles cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

In one embodiment, the disorder is ICF.
In one embodiment, the disorder is ALS.
In one embodiment, the disorder is IBM.
In one embodiment, the disorder is cancer. The cancer may be selected from Ewing's sarcoma, soft tissue sarcoma, rhabdomyosarcoma, and adult and pediatric B-cell acute lymphoblastic leukemia.

In some embodiments, the disorder may be selected from one or more of: FSHD1, FSHD2, ICF, ALS, IBM, Ewing's sarcoma, soft tissue sarcoma, rhabdomyosarcoma, and adult and pediatric B-cell acute lymphoblastic leukemia.

In one embodiment, the subject is identified as having FSHD based upon the presence of a transcriptionally active DUX4. In another embodiment, the subject is identified as having FSHD based upon the presence of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in muscle. In another embodiment, the subject is identified as having FSHD based upon the presence of increased expression levels of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A relative to a healthy control. In another embodiment, the subject is identified as having FSHD based upon the presence of a transcriptionally active DUX4 and the presence of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject prior to the administration of the p38 kinase inhibitor. The method may further include determining that the subject is in need of treatment if the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6. PRAMEF15, and ZNF280A is/are elevated relative to a healthy control.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the cells of the subject before and after the administration of the p38 kinase inhibitor. The method may include comparing the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject before and after the administration of the p38 kinase inhibitor. The method may include determining the effectiveness of treatment by the comparing of the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A before and after the administration of the p38 kinase inhibitor, wherein a decrease in the expression level(s) is indicative of effective treatment.

In some embodiments, the p38 kinase inhibitor reduces one or more downstream genes selected from ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In one embodiment, the p38 kinase inhibitor reduces MBD3L2.

In one embodiment, the p38 kinase inhibitor reduces ZSCAN4.

In one embodiment, the p38 kinase inhibitor reduces LEUTX.

In one embodiment, the p38 kinase inhibitor reduces PRAMEF2.

In one embodiment, the p38 kinase inhibitor reduces TRIM43.

In one embodiment, the p38 kinase inhibitor reduces KHDC1L.

In one embodiment, a transcriptional modulator of DUX4 and downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A are inhibited by p38 kinase.

In some embodiments, the administering may be combined with clinical management involving physical therapy, aerobic exercise, respiratory function therapy, orthopedic interventions.

In some embodiments, the administering includes administering of the p38 kinase inhibitor with another pharmaceutical agent.

In some embodiments, the administering includes administering of the p38 kinase inhibitor with another pharmaceutical agent for the treatment of FSHD.

In some embodiments, the administering causes a decrease in muscle degeneration.

In some embodiments, the administering causes a reduction in apoptosis of muscle cells in the subject. In one embodiment, the muscles cells are terminally differentiated.

In several embodiments, a method for treating facioscapulohumeral muscular dystrophy (FSHD) is provided. The method may include administering to a subject in need thereof, an effective amount of a p38 kinase inhibitor of Formula V':

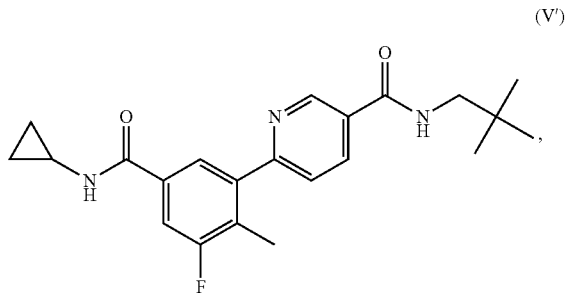 [SMILES: Cc1c(F)cc(C(=O)NC2CC2)cc1-c1ccc(C(=O)NCC(C)(C)C)cn1]

or a stereoisomer thereof, an isotopically-enriched compound thereof, a prodrug thereof, a solvate thereof, or a pharmaceutically acceptable salt thereof.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

In several embodiments, a method for treating a disorder responsive to p38 kinase inhibition is provided. The method may include administering to a subject in need thereof, an effective amount of a p38 kinase inhibitor selected from one or more of Formulae I-XIII (of Genuses I-XIII described below), or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 kinase inhibitor may reduce DUX4 expression levels and/or the expression of one or more downstream genes in cells of the subject.

In many embodiments, the cells are muscle cells. In some embodiments, the cells are terminally-differentiated muscle cells.

In some embodiments, the cells include one or more mutations in a Structural Maintenance Of Chromosomes Flexible Hinge Domain Containing 1 (SMCHD1) gene. In some embodiments, the cells may include at least one non-deleted 4qA allele.

In many embodiments, the cells may include an increased expression level of a DUX4 polypeptide, or a polypeptide encoded by one or more downstream target genes, as compared to the expression level of a DUX4 polypeptide, or a polypeptide encoded by one or more downstream target genes in a control cell.

In many embodiments, the DUX4 is a DUX4 full length (DUX4-fl).

In some embodiments, the cells may be associated with FSHD.

In some embodiments, the disorder is associated with DUX4 gene expression.

In some embodiments, the disorder is associated with DUX4 gene expression and the DUX4 gene expression may result from the subject having less than 10 D4Z4 repeats in the subtelomeric region of chromosome 4q35. In some embodiments, the cells may include a deletion of one or more macrosatellite D4Z4 repeats in the subtelomeric region of chromosome 4q35. In other embodiments, the cells may include less than 7 macrosatellite D4Z4 repeats in the subtelomeric region of chromosome 4q35.

In some embodiments, the cells may include a dysregulated D4Z4 array at chromosome 4q35 prior to administration of the p38 kinase inhibitor. In one embodiment, the cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the cells are muscle cells and the cells may include a dysregulated D4Z4 array at chromosome 4q35 prior to administration of the p38 kinase inhibitor. In one embodiment, the muscles cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

In one embodiment, the disorder is ICF.

In one embodiment, the disorder is ALS.

In one embodiment, the disorder is IBM.

In one embodiment, the disorder is cancer. The cancer may be selected from Ewing's sarcoma, soft tissue sarcoma, rhabdomyosarcoma, and adult and pediatric B-cell acute lymphoblastic leukemia.

In some embodiments, the disorder may be selected from one or more of: FSHD1, FSHD2, ICF, ALS, IBM, Ewing's sarcoma, soft tissue sarcoma, rhabdomyosarcoma, and adult and pediatric B-cell acute lymphoblastic leukemia.

In one embodiment, the subject is identified as having FSHD based upon the presence of a transcriptionally active DUX4. In another embodiment, the subject is identified as having FSHD based upon the presence of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in muscle. In another embodiment, the subject is identified as having FSHD based upon the presence of increased expression levels of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A relative to a healthy control. In another embodiment, the subject is identified as having FSHD based upon the presence of a transcriptionally active DUX4 and the presence of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject prior to the administration of the p38 kinase inhibitor. The method may further include determining that the subject is in need of treatment if the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A is/are elevated relative to a healthy control.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the cells of the subject before and after the administration of the p38 kinase inhibitor. The method may include comparing the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject before and after the administration of the p38 kinase inhibitor. The method may include determining the effectiveness of treatment by the comparing of the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A before and after the administration of the p38 kinase inhibitor, wherein a decrease in the expression level(s) is indicative of effective treatment.

In some embodiments, the p38 kinase inhibitor reduces one or more downstream genes selected from ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In one embodiment, the p38 kinase inhibitor reduces MBD3L2.

In one embodiment, the p38 kinase inhibitor reduces ZSCAN4.

In one embodiment, the p38 kinase inhibitor reduces LEUTX.

In one embodiment, the p38 kinase inhibitor reduces PRAMEF2.

In one embodiment, the p38 kinase inhibitor reduces TRIM43.

In one embodiment, the p38 kinase inhibitor reduces KHDC1L.

In one embodiment, a transcriptional modulator of DUX4 and downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A are inhibited by p38 kinase.

In some embodiments, the administering may be combined with clinical management involving physical therapy, aerobic exercise, respiratory function therapy, orthopedic interventions.

In some embodiments, the administering includes administering of the p38 kinase inhibitor with another pharmaceutical agent.

In some embodiments, the administering includes administering of the p38 kinase inhibitor with another pharmaceutical agent for the treatment of FSHD.

In some embodiments, the administering causes a decrease in muscle degeneration.

In some embodiments, the administering causes a reduction in apoptosis of muscle cells in the subject. In one embodiment, the muscles cells are terminally differentiated.

In several embodiments, a method for treating facioscapulohumeral muscular dystrophy (FSHD) is provided. The method may include administering to a subject in need thereof, an effective amount of a p38 kinase inhibitor selected from one or more of Formulae I-XIII (of Genuses I-XIII described below), or a stereoisomer thereof, an isotopically-enriched compound thereof, a prodrug thereof, a solvate thereof, or a pharmaceutically acceptable salt thereof.

In some embodiments, the p38 kinase inhibitor is selected from one or more of Genuses I-XIII characterized by Formulae I-XIII. Each chemical identifier, e.g., $R^1$, $R^2$, X, Z, and the like, is unique to the Genus under which it is described. Likewise, each definition of any such chemical identifiers or chemical nomenclature terms, e.g., aryl, heteroaryl, alkynyl, and the like, are unique to the Genus under which it is described. If any such chemical nomenclature term is not specifically defined for a particular Genus, the term shall be construed to involve the definition understood by a person of ordinary skill in the art.

In one embodiment, the p38 kinase inhibitor is selected from Genus I, II, III, IV, V, VI, VII, VIII, IX, X, XI, XII, and XIII, or any combination thereof. For example, the p38 kinase inhibitor may be selected from Genus I, II and III. For example, the p38 kinase inhibitor may be selected from Genus III and V.

In one embodiment, the p38 kinase inhibitor is selected from Genus I.

In one embodiment, the p38 kinase inhibitor is selected from Genus 11.

In one embodiment, the p38 kinase inhibitor is selected from Genus III.

In one embodiment, the p38 kinase inhibitor is selected from Genus IV.

In one embodiment, the p38 kinase inhibitor is selected from Genus V.

In one embodiment, the p38 kinase inhibitor is selected from Genus VI.

In one embodiment, the p38 kinase inhibitor is selected from Genus VII.

In one embodiment, the p38 kinase inhibitor is selected from Genus VIII.

In one embodiment, the p38 kinase inhibitor is selected from Genus IX.

In one embodiment, the p38 kinase inhibitor is selected from Genus X.

In one embodiment, the p38 kinase inhibitor is selected from Genus XI.

In one embodiment, the p38 kinase inhibitor is selected from Genus XII.

In one embodiment, the p38 kinase inhibitor is selected from Genus XIII.

In one embodiment, the p38 kinase inhibitor is selected from Genus I, II, III, V, VI, VII, VIII, X, XI, XII, and XIII.

Genus I Description

Compounds of Genus I can be prepared according to the disclosure of U.S. Pat. No. 7,276,527, which is herein incorporated herein by reference in its entirety.

Genus I is characterized by optionally N-oxidized compounds of Formula (I):

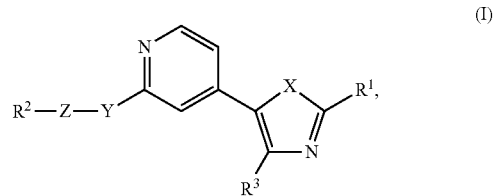

or stereoisomers thereof, isotopically-enriched compounds thereof, prodrugs thereof, solvates thereof, and pharmaceutically acceptable salts thereof;
wherein:
$R^1$ is selected from:
  (i) hydrogen,
  (ii) a group selected from $C_{1-6}$ alkyl, $C_{2-6}$ alkenyl, $C_{2-6}$ alkynyl, $C_{3-6}$ cycloalkyl, $C_{6-14}$ aryl, and $C_{7-16}$ aralkyl group,
    wherein the $C_{1-6}$ alkyl, $C_{2-6}$ alkenyl, $C_{2-6}$ alkynyl, $C_{3-6}$ cycloalkyl, $C_{6-14}$ aryl, or $C_{7-16}$ aralkyl is optionally substituted with one or more substituents selected from a Substituent Group A,
  (iii) —(C=O)—$R^5$, —(C=O)—$OR^5$, —(C=O)—$NR^5R^6$, —(C=S)—$NHR^5$, or —$SO^2$—$R^7$
  wherein:
    $R^5$ hydrogen, $C_{1-6}$ alkyl, $C_{2-6}$ alkenyl, $C_{2-6}$ alkynyl, $C_{3-6}$ cycloalkyl, $C_{6-14}$ aryl, or $C_{7-16}$ aralkyl,
      wherein the $C_{1-6}$ alkyl, $C_{2-6}$ alkenyl, $C_{2-6}$ alkynyl, $C_{3-6}$ cycloalkyl, $C_{6-14}$ aryl, or $C_{7-16}$ aralkyl is optionally substituted with one or more substituents selected from the Substituent Group A,
    $R^6$ is hydrogen or $C_{1-6}$ alkyl,
    $R^7$ is $C_{1-6}$ alkyl, $C_{2-6}$ alkenyl, $C_{2-6}$ alkynyl, $C_{3-6}$ cycloalkyl, a $C_{6-14}$ aryl, or $C_{7-16}$ aralkyl,
      wherein the $C_{1-6}$ alkyl, $C_{2-6}$ alkenyl, $C_{2-6}$ alkynyl, $C_{3-6}$ cycloalkyl, $C_{6-14}$ aryl, or $C_{7-16}$ aralkyl is optionally substituted with one or more substituents selected from the Substituent Group A, or
  (iv) an amino group optionally substituted with substituents selected from:
    (a) $C_{1-6}$ alkyl, $C_{2-6}$ alkenyl, $C_{2-6}$ alkynyl, $C_{3-6}$ cycloalkyl, $C_{6-14}$ aryl, or $C_{7-16}$ aralkyl,
      wherein the $C_{1-6}$ alkyl, $C_{2-6}$ alkenyl, $C_{2-6}$ alkynyl, $C_{3-6}$ cycloalkyl, $C_{6-14}$ aryl, and a $C_{7-16}$ aralkyl is optionally substituted with one or more substituents selected from the Substituent Group A,
    (b) —(C=O)—$R^5$, —(C=O)—$OR^5$, —(C=O)—$NR^5R^6$, —(C=S)—$NHR^5$, or —$SO^2$—$R^7$, and
    (c) $C_{1-6}$ alkylidene optionally substituted with one or more substituents selected from the Substituent Group A
$R^2$ is a $C_{6-14}$ monocyclic or fused polycyclic aryl optionally substituted with one or more substituents selected from the Substituent Group A;
$R^3$ is hydrogen or $C_{6-14}$ aryl, wherein the $C_{6-14}$ aryl is optionally substituted with one more substituents selected from the Substituent Group A;
X is —S—, S(O)—, or $S(O)_2$—;
Y is a bond, —O—, —S—, S(O)—, $S(O)_2$—, or $NR^4$, wherein $R^4$ is:
  (a) hydrogen,
  (b) $C_{1-6}$ alkyl, $C_{2-6}$ alkenyl, $C_{2-6}$ alkynyl, $C_{3-6}$ cycloalkyl, $C_{6-14}$ aryl, or $C_{7-16}$ aralkyl, wherein the $C_{1-6}$ alkyl, $C_{2-6}$ alkenyl, $C_{2-6}$ alkynyl, $C_{3-6}$ cycloalkyl, $C_{6-14}$ aryl, and $C_{7-16}$ aralkyl is optionally substituted with one or more substituents selected from the Substituent Group A, or (c) —(C=O)—$R^5$, —(C=O)—$OR^5$, —(C=O)—$NR^5R^6$, —(C=S)—$NHR^5$, or —$SO^2$—$R^7$;

Z is a bond, $C_{1-15}$ alkylene, $C_{2-16}$ alkenylene, or $C_{2-16}$ alkynylene, wherein the $C_{1-15}$ alkylene, $C_{2-16}$ alkenylene, or $C_{2-16}$ alkynylene is optionally substituted with one or more substituents selected from the Substituent Group A; and a substituent of the Substituent Group A is selected from: oxo, halogen, $C_{1-3}$ alkylenedioxy, nitro, cyano, optionally halogenated $C_{1-6}$ alkyl, optionally halogenated $C_{2-6}$ alkenyl, carboxy $C_{2-6}$ alkenyl, optionally halogenated $C_{2-6}$ alkynyl, optionally halogenated $C_{3-6}$ cycloalkyl, $C_{6-14}$ aryl, optionally halogenated $C_{1-8}$ alkoxy, $C_{1-6}$ alkoxycarbonyl-$C_{1-6}$ alkoxy, hydroxy, $C_{6-14}$ aryloxy, $C_{7-16}$ aralkyloxy, mercapto, optionally halogenated $C_{1-6}$ alkylthio, $C_{6-14}$ arylthio, $C_{7-16}$aralkylthio, amino, mono-$C_{1-6}$ alkylamino, mono-$C_{6-14}$ arylamino, di-$C_{1-6}$alkylamino, di-$C_{6-14}$ arylamino, formyl, carboxy, $C_{1-6}$ alkyl-carbonyl, $C_{3-6}$cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, carbamoyl, thiocarbamoyl, mono-$C_{1-6}$ alkyl-carbamoyl, di-$C_{1-6}$ alkyl-carbamoyl, $C_{6-14}$aryl-carbamoyl, $C_{1-6}$ alkylsulfonyl, $C_{6-14}$ arylsulfonyl, $C_{1-6}$ alkylsulfinyl, $C_{6-14}$arylsulfinyl, formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino, $C_{6-14}$ arylsulfonylamino, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, sulfo, sulfamoyl, sulfinamoyl and sulfenamoyl.

In some embodiments, the p38 kinase inhibitor from Genus I is selected from the following:

(F) N-[5-[2-benzoylamino-4-pyridyl)-4-(3,5-dimethylphenyl)-1,3-thiazol-2-yl]acetamide;

N-[5-(2-benzylamino-4-pyridyl)-4-(3,5-dimethylphenyl)-1,3-thiazol-2-yl]acetamide;

N-[4-[4-(4-methoxyphenyl)-2-methyl-1,3-thiazol-5-yl]-2-pyridyl]benzamide;

N-[4-[2-(4-fluorophenyl)-4-(3-methylphenyl)-1,3-thiazol-5-yl]-2-pyridyl]phenylacetamide;

N-[4-[2-ethyl-4-(3-methylphenyl)-1,3-thiazol-5-yl]-2-pyridyl]phenylacetamide;

N-[4-[4-(3-methylphenyl)-2-propyl-1,3-thiazol-5-yl]-2-pyridyl]phenylacetamide;

N-[4-[2-butyl-4-(3-methylphenyl)-1,3-thiazol-5-yl]-2-pyridyl]phenylacetamide;

N-[4-[4-(3-methylphenyl)-2-(4-methylthiophenyl)-1,3-thiazol-5-yl]-2-pyridyl]phenylacetamide;

N-[4-[2-ethyl-4-(3-methylphenyl)-1,3-thiazol-5-yl]-2-pyridyl]benzamide;

N-[4-[2-ethyl-4-(3-methylphenyl)-1,3-thiazol-5-yl]-2-pyridyl]-3-phenylpropionamide;

N-[4-[2-ethyl-4-(3-methylphenyl)-1,3-thiazol-5-yl]-2-pyridyl]-3-(4-methoxyphenyl)propionamide;

N-[4-[2-ethyl-4-(3-methylphenyl)-1,3-thiazol-5-yl]-2-pyridyl]-4-phenylbutyramide;

N-[4-[4-(3-methylphenyl)-2-propyl-1,3-thiazol-5-yl]-2-pyridyl]benzamide;

N-[4-[4-(3-methylphenyl)-2-propyl-1,3-thiazol-5-yl]-2-pyridyl]-3-phenylpropionamide;

N-[4-[2-butyl-4-(3-methylphenyl)-1,3-thiazol-5-yl]-2-pyridyl]benzamide;

N-[4-[2-butyl-4-(3-methylphenyl)-1,3-thiazol-5-yl]-2-pyridyl]-3-phenylpropionamide;

N-[4-[2-(4-fluorophenyl)-4-(3-methylphenyl)-1,3-thiazol-5-yl]-2-pyridyl]benzamide;

N-[4-[2-(4-fluorophenyl)-4-(3-methylphenyl)-1,3-thiazol-5-yl]-2-pyridyl]-3-phenylpropionamide;

N-[4-[4-(3-methylphenyl)-2-(4-methylthiophenyl)-1,3-thiazol-5-yl]-2-pyridyl]benzamide;

N-[4-[4-(3-methylphenyl)-2-(4-methylthiophenyl)-1,3-thiazol-5-yl]-2-pyridyl]-3-phenylpropionamide;

N-benzyl-N-[4-[2-ethyl-4-(3-methylphenyl)-1,3-thiazol-5-yl]-2-pyridyl]amine;

N-[4-[2-ethyl-4-(3-methylphenyl)-1,3-thiazol-5-yl]-2-pyridyl]-N-(2-phenylethyl)amine;

N-[4-[2-ethyl-4-(3-methylphenyl)-1,3-thiazol-5-yl]-2-pyridyl]-N-(3-phenylpropyl)amine;

N-benzyl-N-[4-[4-(3-methylphenyl)-2-propyl-1,3-thiazol-5-yl]-2-pyridyl]amine;

N-[4-(4-(3-methylphenyl)-2-propyl-1,3-thiazol-5-yl]-2-pyridyl]-N-(2-phenylethyl)amine;

N-[4-[4-(3-methylphenyl)-2-propyl-1,3-thiazol-5-yl]-2-pyridyl]-N-(3-phenylpropyl)amine;

N-benzyl-N-[4-[2-butyl-4-(3-methylphenyl)-1,3-thiazol-5-yl]-2-pyridyl]amine;

N-(4-[2-butyl-4-(3-methylphenyl)-1,3-thiazol-5-yl]-2-pyridyl]-N-(2-phenylethyl)amine;

N-[4-[2-butyl-4-(3-methylphenyl)-1,3-thiazol-5-yl]-2-pyridyl]-N-(3-phenylpropyl)amine;

N-benzyl-N-[4-[4-(3-methylphenyl)-2-(4-methylthiophenyl)-1,3-thiazol-5-yl]-2-pyridyl]amine;

N-[4-[4-(3-methylphenyl)-2-(4-methylthiophenyl)-1,3-thiazol-5-yl]-2-pyridyl]-N-(2-phenylethyl)amine N-[4-[4-(3-methylphenyl)-2-(4-methylthiophenyl)-1,3-thiazol-5-yl]-2-pyridyl]-N-(3-phenylpropyl)amine;

N-[4-[4-(3-methylphenyl)-2-(4-methylsulfonylphenyl)-1,3-thiazol-5-yl]-2-pyridyl]benzamide N-[4-[4-(3-methylphenyl)-2-(4-methylsulfonylphenyl)-1,3-thiazol-5-yl]-2-pyridyl]phenylacetamide N-[4-[4-(3-methylphenyl)-2-(4-methylsulfonylphenyl)-1,3-thiazol-5-yl]-2-pyridyl]-3-phenylpropionamide N-benzyl-N-[4-[4-(3-methylphenyl)-2-(4-methylsulfonylphenyl)-1,3-thiazol-5-yl]-2-pyridyl]amine;

N-[4-[4-(3-methylphenyl)-2-(4-methylsulfonylphenyl)-1,3-thiazol-5-yl]-2-pyridyl]-N-(3-phenylpropyl)amine;

N-[4-[4-(3-methylphenyl)-2-(4-methylsulfonylphenyl)-1,3-thiazol-5-yl]-2-pyridyl]-N-(2-phenylethyl)amine;

N-(4-fluorobenzyl)-N-[4-[4-(3-methylphenyl)-2-(4-methylsulfonylphenyl)-1,3-thiazol-5-yl]-2-pyridyl]amine;

(E) [4-(3,5-dimethylphenyl)-5-(2-phenylmethyloxy-4-pyridyl)-1,3-thiazol-2-yl]amine;

N-[4-[2-benzoylamino-4-(4-methoxyphenyl)-1,3-thiazol-5-yl]-2-pyridyl]benzamide;

N-[4-(4-methoxyphenyl)-5-[2-[(3-pyridylcarbonylamino)]-4-pyridyl]-1,3-thiazol-2-yl]nicotinamide;

N-[4-[2-amino-4-(4-methoxyphenyl)-1,3-thiazol-5-yl]-2-pyridyl]benzamide;

N-[4-[2-amino-4-(3,5-dimethylphenyl)-1,3-thiazol-5-yl]-2-pyridyl]benzamide;

N-[4-[2-amino-4-(3,5-dimethylphenyl)-1,3-thiazol-5-yl]-2-pyridyl]benzylamine;

N-[4-[2-amino-4-(3,5-dimethylphenyl)-1,3-thiazol-5-yl]-2-pyridyl]benzamide; hydrochloride;

N-[4-[2-amino-4-(3,5-dimethylphenyl)-1,3-thiazol-5-yl]-2-pyridyl]benzylamine dihydrochloride; and N-(4-(2-ethyl-4-(3-methylphenyl)-1,3-thiazol-5-yl]-2-pyridyl]benzamide ("TAK-715"), Formula (I').

In one embodiment, the p38 kinase inhibitor is N-(4-(2-ethyl-4-(3-methylphenyl)-1,3-thiazol-5-yl]-2-pyridyl]benzamide ("TAK-715"), Formula (I').

Genus I Definitions

In the aforementioned Formula, $R^1$ represents a hydrogen atom, a hydrocarbon group optionally having substituents, a heterocyclic group optionally having substituents, an amino group optionally having substituents or acyl group.

As "acyl group" represented by $R^1$, for example, there are an acyl group represented by the Formula: —(C=O)—$R^5$, —(C=O)—$OR^5$, —(C=O)—$NR^5R^6$, —(C=S)—$NHR^5$ or —$SO_2$—$R^7$ (wherein $R^5$ represents a hydrogen atom, a hydrocarbon group optionally having substituents or a heterocyclic group optionally having substituents, $R^6$ represents a hydrogen atom or a $C_{1-6}$alkyl, $R^7$ represents a hydrocarbon group optionally having substituents or a heterocyclic group optionally having substituents) and the like.

In the aforementioned Formula, as "hydrocarbon group" of "hydrocarbon group optionally having substituents", for example, there are an acyclic or cyclic hydrocarbon group (for example, alkyl, alkenyl, alkynyl, cycloalkyl, aryl, aralkyl and the like) and the like. Among them, acyclic or cyclic hydrocarbon groups having carbon number of 1 to 16 are preferable.

As "alkyl", for example, $C_{1-6}$ alkyl (for example, methyl, ethyl, propyl, isopropyl, butyl, isobutyl, sec-butyl, tert-butyl, pentyl, hexyl and the like) is preferable and, in particular, $C_{1-3}$ alkyl (for example, methyl, ethyl, propyl and isopropyl) and the like are preferable.

As "alkenyl", for example, $C_{2-6}$ alkenyl (for example, vinyl, allyl, isopropenyl, 1-butenyl, 2-butenyl, 3-butenyl, 2-methyl-2-propenyl, 1-methyl-2-propenyl, 2-methyl-1-propenyl and the like) and the like are preferable.

As "alkynyl", for example, $C_{2-6}$ alkynyl (for example, ethynyl, propargyl, 1-butynyl, 2-butynyl, 3-butynyl, 1-hexynyl and the like) and the like are preferable.

As "cycloalkyl", for example, $C_{3-6}$ cycloalkyl (for example, cyclopropyl, cyclobutyl, cyclopentyl, cyclohexyl and the like) and the like are preferable.

As "aryl", for example, $C_{6-14}$ aryl (for example, phenyl, 1-naphthyl, 2-naphthyl, 2-biphenylyl, 3-biphenylyl, 4-biphenylyl, 2-anthryl and the like) and the like are preferable.

As "aralkyl", for example, $C_{7-16}$ aralkyl (for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like are preferable.

As "substituents" of "hydrocarbon group optionally having substituents" represented by $R^5$, for example, there are oxo, halogen atom (for example, fluorine, chlorine, bromine, iodine and the like), $C_{1-3}$ alkylenedioxy (for example, methylenedioxy, ethylenedioxy and the like), nitro, cyano, optionally halogenated $C_{1-6}$ alkyl, optionally halogenated $C_{2-6}$ alkenyl, carboxy $C_{2-6}$ alkenyl (for example, 2-carboxyethenyl, 2-carboxy-2-methylethenyl and the like), optionally halogenated $C_{2-6}$ alkynyl, optionally halogenated $C_{3-6}$ cycloalkyl, $C_{6-14}$ aryl (for example, phenyl, 1-naphthyl, 2-naphthyl, 2-biphenylyl, 3-biphenylyl, 4-biphenylyl, 2-anthryl and the like), optionally halogenated $C_{1-8}$ alkoxy, $C_{1-6}$ alkoxy-carbonyl-$C_{1-6}$ alkoxy (for example, ethoxycarbonylmethyloxy and the like), hydroxy, $C_{6-14}$ aryloxy (for example, phenyloxy, 1-naphthyloxy, 2-naphthyloxy and the like), $C_{7-16}$aralkyloxy (for example, benzyloxy, phenethyloxy and the like), mercapto, optionally halogenated $C_{1-6}$ alkylthio, $C_{6-14}$ arylthio (for example, phenylthio, 1-naphthylthio, 2-naphthylthio and the like), $C_{7-16}$ aralkylthio (for example, benzylthio, phenethylthio and the like), amino, mono-$C_{1-6}$alkylamino (for example, methylamino, ethylamino and the like), mono-$C_{6-14}$ arylamino (for example, phenylamino, 1-naphthylamino, 2-naphthylamino and the like), di-$C_{1-6}$ alkylamino (for example, dimethylamino, diethylamino, ethylmethylamino and the like), di-$C_{6-14}$arylamino (for example, diphenylamino and the like), formyl, carboxy, $C_{1-6}$alkyl-carbonyl (for example, acetyl, propionyl and the like), $C_{3-6}$ cycloalkyl-carbonyl (for example, cyclopropylcarbonyl, cyclopentylcarbonyl, cyclohexylcarbonyl and the like), $C_{1-6}$ alkoxy-carbonyl (for example, methoxycarbonyl, ethoxycarbonyl, propoxycarbonyl, tert-butoxycarbonyl and the like), $C_{6-14}$ aryl-carbonyl (for example, benzoyl, 1-naphthoyl, 2-naphthoyl and the like), $C_{7-16}$ aralkyl-carbonyl (for example, phenylacetyl, 3-phenylpropionyl and the like), $C_{6-14}$ aryloxy-carbonyl (for example, phenoxycarbonyl and the like), $C_{7-16}$ aralkyloxy-carbonyl (for example, benzyloxycarbonyl, phenethyloxycarbonyl and the like), 5 or 6 membered heterocyclic carbonyl (for example, nicotinoyl, isonicotinoyl, thenoyl, furoyl, morpholinocarbonyl, thiomorpholinocarbonyl, piperazin-1-ylcarbonyl, pyrrolidin-1-ylcarbonyl and the like), carbamoyl, thiocarbamoyl, mono-$C_{1-6}$alkyl-carbamoyl (for example, methylcarbamoyl, ethylcarbamoyl and the like), di-$C_{1-6}$ alkyl-carbamoyl (for example, dimethylcarbamoyl, diethylcarbamoyl, ethylmethylcarbamoyl and the like), $C_{6-14}$ aryl-carbamoyl (for example, phenylcarbamoyl, 1-naphthylcarbamoyl, 2-naphthylcarbamoyl and the like), 5 or 6 membered heterocyclic carbamoyl (for example, 2-pyridylcarbamoyl, 3-pyridylcarbamoyl, 4-pyridylcarbamoyl, 2-thienylcarbamoyl, 3-thienylcarbamoyl and the like), $C_{1-6}$ alkylsulfonyl (for example, methylsulfonyl, ethylsulfonyl and the like), $C_{6-14}$ arylsulfonyl (for example, phenylsulfonyl, 1-naphthylsulfonyl, 2-naphthylsolfonyl and the like), $C_{1-6}$ alkylsulfinyl (for example, methylsulfinyl, ethylsulfinyl and the like), $C_{6-14}$ arylsulfinyl (for example, phenylsulfinyl, 1-naphthylsulfinyl, 2-naphthylsulfinyl and the like), formylamino, $C_{1-6}$ alkyl-carbonylamino (for example, acetylamino and the like), $C_{6-14}$ aryl-carbonylamino (for example, benzoylamino, naphthoylamino and the like), $C_{1-6}$ alkoxy-carbonylamino (for example, methoxycarbonylamino, ethoxycarbonylamino, propoxycarbonylamino, butoxycarbonylamino and the like), $C_{1-6}$alkylsulfonylamino (for example, methylsulfonylamino, ethylsulfonylamino and the like), $C_{6-14}$ arylsulfonylamino (for example, phenylsulfonylamino, 2-naphthylsulfonylamino, 1-naphthylsulfonylamino and the like), $C_{1-6}$ alkyl-carbonyloxy (for example, acetoxy, propionyloxy and the like), $C_{6-14}$ aryl-carbonyloxy (for example, benzoyloxy, naphthylcarbonyloxy and the like), $C_{1-6}$ alkoxy-carbonyloxy (for example, methoxycarbonyloxy, ethoxycarbonyloxy, propoxycarbonyloxy, butoxycarbonyloxy and the like), mono-$C_{1-6}$ alkyl-carbamoyloxy (for example, methylcarbamoyloxy, ethylcarbamoyloxy and the like), di-$C_{1-6}$ alkyl-carbamoyloxy (for example, dimethylcarbamoyloxy, diethylcarbamoyloxy and the like), $C_{6-14}$ aryl-carbamoyloxy (for example, phenylcarbamoyloxy, naphthylcarbamoyloxy and the like), nicotinoyloxy, 5 to 7 membered saturated cyclic amino optionally having substituents, 5 to 10 membered aromatic heterocyclic group (for example, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), sulfo, sulfamoyl, sulfinamoyl, sulfenamoyl and the like.

The "hydrocarbon group" may have 1 to 5, preferably 1 to 3 aforementioned substituents at a substitutable position and, when the number of substituents is 2 or more, respective substituents may be the same or different.

As aforementioned "optionally halogenated $C_{1-6}$ alkyl", for example, there are $C_1$-6 alkyl (for example, methyl, ethyl, propyl, isopropyl, butyl, isobutyl, sec-butyl, tert-butyl, pentyl, hexyl and the like) and the like optionally having 1 to 5, preferably 1 to 3 halogen atoms (for example, fluorine, chlorine, bromine, iodine and the like). Examples thereof are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

As the aforementioned "optionally halogenated $C_{2-6}$ alkenyl", for example, there are $C_{2-6}$ alkenyl (for example, vinyl, propenyl, isopropenyl, 2-buten-1-yl, 4-penten-1-yl, 5-hexen-1-yl) and the like optionally having 1 to 5, preferably 1 to 3 halogen atoms (for example, fluorine, chlorine, bromine, iodine and the like).

As the aforementioned "optionally halogenated $C_{2-6}$ alkynyl", there are $C_{2-6}$alkynyl (for example, 2-butyn-1-yl, 4-pentyn-1-yl, 5-hexyn-1-yl and the like) and the like optionally having 1 to 5, preferably 1 to 3 halogen atoms (for example, fluorine, chlorine, bromine, iodine and the like).

As the aforementioned "optionally halogenated $C_{3-6}$ cycloalkyl", for example, there are $C_{3-6}$ cycloalkyl (for example, cyclopropyl, cyclobutyl, cyclopentyl, cyclohexyl and the like) and the like optionally having 1 to 5, preferably 1 to 3 halogen atoms (for example, fluorine, chlorine, bromine, iodine and the like). Examples thereof are cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

As the aforementioned "optionally halogenated $C_{1-8}$ alkoxyl", for example, there are $C_{1-8}$ alkoxy (for example, methoxy, ethoxy, propoxy, isopropoxy, butoxy, isobutoxy, sec-butoxy, pentyloxy, hexyloxy and the like) and the like optionally having 1 to 5, preferably 1 to 3 halogen atoms (for example, fluorine, chlorine, bromine, iodine and the like). Examples thereof are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

As the aforementioned "optionally halogenated $C_{1-6}$ alkylthio", for example, there are $C_{1-6}$ alkylthio (for example, methylthio, ethylthio, propylthio, isopropylthio, butylthio, sec-butylthio, tert-butylthio and the like) and the like optionally having 1 to 5, preferably 1 to 3 halogen atoms (for example, fluorine, chlorine, bromine, iodine and the like). Examples thereof are methylthio, difluoromethylthio, trifluoromethylthio, ethylthio, propylthio, isopropylthio, butylthio, 4,4,4-trifluorobutylthio, pentylthio, hexylthio and the like.

As "5 to 7 membered saturated cyclic amino" of the aforementioned "5 to 7 membered saturated cyclic amino optionally having substituents", there are 5 to 7 membered saturated cyclic amino optionally containing 1 to 4 heteroatoms of one or two kinds selected from a nitrogen atom, a sulfur atom and an oxygen atom in addition to one nitrogen atom and carbon atoms and examples thereof are pyrolidin-1-yl, piperidino, piperazin-1-yl, morpholino, thiomorpholino, hexahydroazepin-1-yl and the like.

As "substituents" of the "5 to 7 membered saturated cyclic amino optionally having substituents", for example, there are 1 to 3 $C_{1-6}$ alkyl (for example, methyl, ethyl, propyl, isopropyl, butyl, isobutyl, sec-butyl, tert-butyl, pentyl, hexyl and the like), $C_{6-14}$ aryl (for example, phenyl, 1-naphthyl, 2-naphthyl, 2-biphenylyl, 3-biphenylyl, 4-biphenylyl, 2-anthryl and the like), $C_{1-6}$ alkyl-carbonyl (for example, acetyl, propionyl and the like), 5 to 10 membered aromatic heterocyclic group (for example, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), oxo and the like.

As "heterocyclic group" of "heterocyclic group optionally having substituents" represented by $R^5$, for example, there is a monovalent group obtained by removing one arbitrary hydrogen atom from a 5 to 14 membered (monocyclic, bicyclic or tricyclic) heterocycle containing 1 to 4 heteroatoms of one or two kinds selected from a nitrogen atom, a sulfur atom and an oxygen atom in addition to carbon atoms, preferably (i) a 5 to 14 membered (preferably 5 to 10 membered, particularly preferably 5 to 6 membered) aromatic heterocycle, (ii) a 5 to 10 membered (preferably 5 to 6 membered) non-aromatic heterocycle or (iii) a 7 to 10 membered bridged heterocycle.

As the aforementioned "5 to 14 membered (preferably 5 to 10 membered) aromatic heterocycle", there are an aromatic heterocycle such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, and a ring formed by fusing these rings (preferably monocyclic) with 1 or a plurality (preferably 1 to 2) of aromatic rings (for example, benzene ring and the like).

As the aforementioned "5 to 10 membered non-aromatic heterocycle", for example, there are pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole and the like.

As the aforementioned "7 to 10 membered bridged heterocycle", for example, there are quinuclidine, 7-azabicyclo[2.2.1]heptane and the like.

The "heterocyclic group" is preferably a 5 to 14 membered (preferably 5 to 10 membered) (monocyclic or bicyclic) heterocyclic group containing preferably 1 to 4 heteroatoms of one or two kinds selected from a nitrogen atom, a sulfur atom and an oxygen atom in addition to carbon atoms. More particularly, examples thereof are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, and a non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

Among them, for example, a 5 or 6 membered heterocyclic group containing 1 to 3 heteroatoms selected from a nitrogen atom, a sulfur atom and an oxygen atom in addition to carbon atoms is further preferable. More particularly, examples thereof are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

As "substituents" of "heterocyclic group optionally having substituents", for example, there are the same "substituents" as substituents of "hydrocarbon group optionally having substituents" represented by $R^5$.

The "heterocyclic group" may have 1 to 5, preferably 1 to 3 aforementioned substituents at a substitutable position and, when the number of substituents is 2 or more, respective substituents may be the same or different.

As "$C_{1-6}$ alkyl" represented by $R^6$, for example, there are methyl, ethyl, propyl, isopropyl, butyl, isobutyl, sec-butyl, tert-butyl, pentyl, hexyl and the like.

As "hydrocarbon group optionally having substituents" and "heterocyclic group optionally having substituents" represented by $R^7$, for example, there are the aforementioned "hydrocarbon group optionally having substituents" and "heterocyclic group optionally having substituents" represented by $R^5$, respectively.

As "hydrocarbon group optionally having substituents" and "heterocyclic group optionally having substituents" represented by $R^1$, for example, there are the aforementioned "hydrocarbon group optionally having substituents" and "heterocyclic group optionally having substituents" represented by $R^5$, respectively.

As "amino group optionally having substituents" represented by $R^1$, for example, there are (1) an amino group optionally having 1 or 2 substituents and (2) a cyclic amino group optionally having substituents and the like.

As "substituents" of "amino group optionally having 1 or 2 substituents" of the aforementioned (1), for example, there are a hydrocarbon group optionally having substituents, a heterocyclic group optionally having substituents, an acyl group, an alkylidene group optionally having substituents and the like. As these "hydrocarbon group optionally having substituents" and "heterocyclic group optionally having substituents", there are the same "hydrocarbon group optionally having substituents" and "heterocyclic group optionally having substituents" as those represented by $R^5$ described above, respectively. As the "acyl group", there is the same "acyl group" as that by represented by $R^1$ as described above.

As "alkylidene group" of "alkylidene group optionally having substituents", for example, there are a $C_{1-6}$ alkylidene group (for example, methylidene, ethylidene, propylidene and the like) and the like. As "substituents" of "alkylidene group optionally having substituents", there are 1 to 5, preferably 1 to 3 same substituents as "substituents" of "hydrocarbon group optionally having substituents" represented by $R^5$.

When the number of the aforementioned "substituents" of "amino group optionally having 1 or 2 substituents" is 2, respective substituents may be the same or different.

As "cyclic amino group" of "cyclic amino group optionally having substituents" of the aforementioned (2), there are a 5 to 7 membered non-aromatic cyclic amino group optionally containing 1 to 4 heteroatoms of one or two kinds selected from a nitrogen atom, a sulfur atom and an oxygen atom in addition to one nitrogen atom and carbon atoms. More particularly, examples thereof are pyrrolidin-1-yl, piperidino, piperazin-1-yl, morpholino, thiomorpholino, hexahydroazepin-1-yl, imidazolidin-1-yl, 2,3-dihydro-1H-imidazol-1-yl, tetrahydro-1(2H)-pyrimidinyl, 3,6-dihydro-1(2H)-pyrimidinyl, 3,4-dihydro-1(2H)-pyrimidinyl and the like. As "substituents" of "cyclic amino optionally having substituents", there are 1 to 3 same ones as "substituents" of "5 to 7 membered saturated cyclic amino group" which were described in detail as "substituents" of "hydrocarbon group optionally having substituents" represented by $R^5$.

Examples of the 5 to 7 membered non-aromatic cyclic amino group having 1 oxo, there are 2-oxoimidazolidin-1-yl, 2-oxo-2,3-dihydro-1H-imidazol-1-yl, 2-oxotetrahydro-1(2H)-pyrimidinyl, 2-oxo-3,6-dihydro-1(2H)-pyrimidinyl, 2-oxo-3,4-dihydro-1(2H)-pyrimidinyl, 2-oxopyrrolidin-1-yl, 2-oxopiperidino, 2-oxopiperazin-1-yl, 3-oxopiperazin-1-yl, 2-oxo-2,3,4,5,6,7-hexahydroazepin-1-yl and the like.

As $R^1$, an amino group optionally having substituents, an aryl group optionally having substituents and an alkyl group optionally having substituents and the like are preferable.

As further preferable example of the "amino group optionally having substituents" is an amino group optionally having 1 or 2 acyl represented by the Formula: —(C=O)—$R^5$, —(C=O)—O$R^5$, —(C=O)—N$R^5R^6$, —(C=S)—NH$R^5$ or —SO$_2$—$R^7$ [wherein respective symbols represent the same meanings as described above]. Particularly preferable example is an amino group optionally having 1 or 2 acyl represented by the Formula: —C(C=O)—$R^5$ or —(C=O)—N$R^5R^6$[wherein respective symbols represent the same meanings as described above].

As the "aryl group optionally having substituents", for example, there is preferably a $C_{6-14}$ aryl group (preferably a phenyl group and the like) optionally having 1 to 5 substituents selected from $C_{1-6}$ alkylthio, $C_{6-14}$arylthio, $C_{1-6}$ alkylsulfinyl, $C_{6-14}$ arylsulfinyl, $C_{1-6}$ alkylsulfonyl, $C_{6-14}$arylsulfonyl and carboxy.

As the "alkyl group optionally having substituents", for example, a $C_{1-6}$alkyl group (for example, methyl, ethyl, propyl, isopropyl, butyl, isobutyl, sec-butyl, tert-butyl and the like) optionally substituted with 1 to 3 substituents selected from halogen atom, $C_{1-6}$ alkoxy, hydroxy, carboxy and $C_{1-6}$ alkoxy-carbonyl and the like are preferable, and particularly $C_{1-3}$alkyl group such as methyl, ethyl and the like is preferable.

Among them, as $R^1$, (i) $C_{1-6}$ alkyl group (for example, $C_{1-4}$ alkyl group such as methyl, ethyl, propyl, butyl), (ii) a $C_{6-14}$ aryl group (for example, a phenyl group) optionally substituted with substituents selected from $C_{1-6}$ alkylthio (for example, methylthio), $C_{1-6}$ alkylsulfonyl (for example, methylsulfonyl) and halogen atom (for example, chlorine atom, fluorine atom) or (iii) an amino group optionally having 1 or 2 acyl represented by the Formula: —(C=O)—$R^{5'}$ (wherein $R^{5'}$ represents {circle around (1)} a $C_{1-6}$ alkyl group (for example, $C_{1-3}$ alkyl group such as methyl), {circle around (2)} a $C_{6-14}$aryl group (for example, a phenyl group) or {circle around (3)} a 5 to 14 membered heterocyclic group containing 1 to 4 heteroatoms of one or two kinds selected from a nitrogen atom, a sulfur atom and an oxygen atom in addition to carbon atoms (for example, a 5 to 6 membered heterocyclic group containing 1 to 2 heteroatoms selected from a nitrogen atom, a sulfur atom and an oxygen atom in addition to carbon atoms such as pyridyl group) are preferable. As $R^{5'}$ and $R^{5''}$, a phenyl group or a pyridyl group is suitable.

In the aforementioned Formula, R2 represents an aromatic group optionally having substituents.

As "aromatic group" of "aromatic group optionally having substituents" represented by $R^2$, for example, there are an aromatic hydrocarbon group, an aromatic heterocyclic group and the like.

As the "aromatic hydrocarbon group", examples thereof include a $C_{6-14}$ monocyclic or fused polycyclic (bicyclic or tricyclic) aromatic hydrocarbon group, etc. As examples, there are a $C_{6-14}$ aryl group and the like such as phenyl, 1-naphthyl, 2-naphthyl, 2-biphenylyl, 3-biphenylyl, 4-biphenylyl, 2-anthryl and the like and, further preferably, a $C_{6-10}$ aryl group and the like (for example, phenyl, 1-naphthyl, 2-naphthyl and the like, preferably phenyl and the like).

As the "aromatic heterocyclic group", there is a monovalent group obtained by removing one arbitrary hydrogen atom from 5 to 14 membered (preferably 5 to 10 membered) aromatic heterocycle containing 1 to 4 heteroatoms of one or two kinds selected from nitrogen atom, sulfur atom and oxygen atom in addition to carbon atoms.

As the aforementioned "5 to 14 membered (preferably 5 to 10 membered) aromatic heterocycle", for example, there are an aromatic heterocycle such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, and a ring formed by fusing these rings (preferably monocycle) with 1 or a plurality of (preferably 1 or 2) aromatic rings (for example, benzene ring and the like).

As the "aromatic heterocyclic group", there are preferably a 5 to 14 membered (preferably 5 to 10 membered)(monocyclic or bicyclic) aromatic heterocyclic group containing preferably 1 to 4 heteroatoms of one or two kinds selected from a nitrogen atom, a sulfur atom and an oxygen atom in addition to carbon atoms and the like and, more particularly, there are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like.

As "substituents" of "aromatic group optionally having substituents", there are 1 to 5, preferably 1 to 3 same substituents as "substituents" of "hydrocarbon group optionally having substituents" represented by $R^5$. When the number of substituents is 2 or more, respective substituents may be the same or different.

As $R^2$, (1) a $C_{6-14}$ aryl group optionally having substituents and (2) a 5 to 14 membered aromatic heterocyclic group containing 1 to 4 heteroatoms of one or two kinds selected from a nitrogen atom, a sulfur atom and an oxygen atom in addition to carbon atoms are preferable and, among them, (1) a $C_{6-14}$ aryl group (for example, phenyl group, naphthyl group) optionally substituted with halogen atom (for example, chlorine atom, fluorine atom) or $C_{1-6}$ alkoxy (for example, methoxy), (2) a 5 to 14 membered aromatic heterocyclic group containing 1 to 4 heteroatoms of one or two kinds selected from a nitrogen atom, a sulfur atom and an oxygen atom in addition to carbon atoms (for example, a 5 to 6 membered aromatic heterocyclic group containing 1 to 2 heteroatoms selected from a nitrogen atom, a sulfur atom and an oxygen atom in addition to carbon atoms such as pyridyl group, thienyl group) and the like are preferable and, in particular, a phenyl group, a pyridyl group and the like are suitable.

In the aforementioned Formula, $R^3$ represents a hydrogen atom, a pyridyl group optionally having substituents or an aromatic hydrocarbon group optionally having substituents.

As "substituents" of "pyridyl group optionally having substituents" represented by $R^3$, there are the same substituents as "substituents" of "hydrocarbon group optionally having substituents" represented by $R^5$.

The "pyridyl group" may, for example, have 1 to 5, preferably 1 to 3 aforementioned substituents at substitutable positions and, when the number of substituents is 2 or more, respective substituents may be the same or different. In addition, an intracyclic nitrogen atom may be N-oxidized.

As "aromatic hydrocarbon group" of "aromatic hydrocarbon group optionally having substituents" represented by $R^3$, there is the same aromatic hydrocarbon group as "aromatic hydrocarbon group" of "aromatic hydrocarbon group optionally having substituents" represented by $R^2$ and, preferably, there are a $C_{6-14}$ aryl group and the like such as phenyl, 1-naphthyl, 2-naphthyl, 2-biphenylyl, 3-biphenylyl, 4-biphenylyl, 2-anthryl and the like and, further preferably, a $C_{6-10}$ aryl group and the like (for example, phenyl, 1-naphthyl, 2-naphthyl and the like, preferably phenyl and the like) and the like. As "substituents" of "aromatic hydrocarbon group optionally having substituents" represented by $R^3$, there are the same substituents as substituents of "aromatic group optionally having substituents" represented by $R^2$.

As $R^3$, a $C_{6-14}$ aryl group optionally having substituents is preferable and, among them, a $C_{6-14}$ aryl group optionally substituted with 1 or 2 $C_{1-6}$ alkyl (for example, methyl, ethyl and the like) or $C_{1-6}$ alkoxy (for example, methoxy, ethoxy and the like) is preferable and, in particular, a phenyl group optionally substituted with 1 or 2 $C_{1-6}$ alkyl or $C_{1-6}$ alkoxy (for example, 3-methoxyphenyl, 2-methylphenyl, 2,4-dimethylphenyl and the like) is suitable.

In the aforementioned Formula, X represents an oxygen atom or an optionally oxidized sulfur atom.

As "optionally oxidized sulfur atom" represented by X, there are S, SO and $SO_2$.

As X, there is preferably an optionally oxidized sulfur atom. Further preferably, it is S.

In the aforementioned Formula, Y represents a bond, an oxygen atom, an optionally oxidized sulfur atom or the Formula $NR^4$ (wherein $R^4$ represents a hydrogen atom, a hydrocarbon group optionally having substituents or an acyl group).

As "optionally oxidized sulfur atom" represented by Y, there are S, SO and SO2.

As "hydrocarbon group optionally having substituents" represented by R4, for example, there is the same group as "hydrocarbon group optionally having substituents" represented by $R^5$. Among them, a $C_{1-6}$ alkyl group such as methyl, ethyl and the like and, in particular, a $C_{1-3}$ alkyl group such as methyl and the like is preferable.

As "acyl group" represented by $R^4$, there is the same group as "acyl group" represented by $R^1$.

As Y, an oxygen atom, an optionally oxidized sulfur atom, a group represented by the Formula $NR^4$ (wherein $R^4$ represents the same meaning as that described above) and the like are preferable and, among them, an oxygen atom, an optionally oxidized sulfur atom, a group represented by the Formula NR⁴' (R⁴' represents a hydrogen group or a $C_{1-6}$ alkyl group) and the like are preferable and, further, an oxygen atom, S, $SO_2$, NH, $N(CH_3)$ and the like are preferable and, in particular, O or NH is suitable.

In the aforementioned Formula, Z represents a bond or a divalent acyclic hydrocarbon group optionally having substituents.

As "divalent acyclic hydrocarbon group" of "divalent acyclic hydrocarbon group optionally having substituents", for example, there are a $C_{1-15}$alkylene group (for example, methylene, ethylene, propylene, butylene, pentamethylene, hexamethylene, heptamethylene, octamethylene and the like, preferably a $C_{1-6}$ alkylene group and the like), a $C_{2-16}$ alkenylene group (for example, vinylene, propylene, 1-butenylene, 2-butenylene, 1-pentenylene, 2-pentenylene, 3-pentenylene and the like), a $C_{2-16}$ alkynylene group (ethynylene, propynylene, 1-butynylene, 2-butynylene, 1-pentynylene, 2-pentynylene, 3-pentynylene and the like) and the like, preferably, a $C_{1-15}$alkylene group, particularly preferably, a $C_{1-6}$ alkylene group and the like. As "substituents" of "divalent acyclic hydrocarbon group optionally having substituents" represented by Z, for example, there are the same substituents as "substituents" of "hydrocarbon group optionally having substituents" represented by $R^5$.

As Z, a lower alkylene group optionally having $C_{1-3}$ alkyl (for example, methyl), oxo and the like (for example, a $C_{1-6}$ alkylene group such as methylene, ethylene, propylene and the like, in particular, a $C_{1-3}$ alkylene group) is preferable and, among them, a $C_{1-6}$ alkylene group optionally having oxo (for example, a $C_{1-3}$ alkylene group such as methylene, ethylene, propylene, in particular, methylene) is suitable.

More particularly, as Z, $—CH_2—$, $—(CH_2)_2—$, $—(CH_2)_3—$, $—CO—$, $—CH_2CO—$, $—(CH_2)_2CO—$, $—CH(CH_3)—$ and the like are used and, in particular, $—CH_2—$, $—CO—$ and the like are suitable.

A nitrogen atom in Formula (I) may be N-oxidized. For example, a nitrogen atom which is a constituent atom of 4-pyridyl group as a substituent at 5-position of a ring represented by the Formula:

wherein a symbol in the Formula represents the same meaning as that described above, may be N-oxidized. As Formula (I), for example, a compound represented by the Formula:

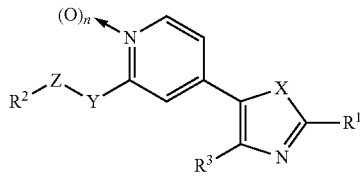

wherein n represents 0 or 1, and other symbols represents the same meanings as those described above, or salts thereof are preferable.

As Formula (I), compounds shown by the following (A) to (F) are preferably used.

(A) Formula (I) wherein $R^1$ is an amino group optionally having substituents, $R^2$ is a $C_{6-14}$ aryl group optionally having substituents, $R^3$ is a $C_{6-14}$ aryl group optionally having substituents, X is a sulfur atom, Y is an oxygen atom or a group represented by the Formula $NR^4$ (wherein $R^4$ represents the same meaning as that described above) or (and) Z is a lower alkylene group optionally having substituents.

(B) Formula (I) wherein $R^1$ is (i) a $C_{1-6}$ alkyl group (for example, a $C_{1-4}$alkyl group such as methyl, ethyl, propyl, butyl and the like), (ii) a $C_{6-14}$ aryl group (for example, a phenyl group) optionally substituted with substituents selected from $C_{1-6}$ alkylthio (for example, methylthio), $C_{1-6}$ alkylsulfonyl (for example, methylsulfonyl) and halogen atom (for example, chlorine atom, fluorine atom), or (iii) an amino group optionally having 1 or 2 acyl represented by the Formula: $—(C=O)—R^{5'}$ [wherein $R^{5'}$ represents {circle around (1)} a $C_{1-6}$alkyl group (for example, $C_{1-3}$ alkyl group such as methyl and the like), {circle around (2)} a $C_{6-14}$ aryl group (for example, a phenyl group) or {circle around (3)} a 5 to 14 membered heterocyclic group containing 1 to 4 heteroatoms of one or two kinds selected from a nitrogen atom, a sulfur atom and an oxygen atom in addition to carbon atoms (for example, a 5 to 6 membered heterocyclic group containing 1 to 2 heteroatoms selected from a nitrogen atom, a sulfur atom and an oxygen atom in addition to carbon atoms such as a pyridyl group);

$R^2$ is a $C_{6-14}$ aryl group (for example, a phenyl group, a naphthyl group) optionally substituents with halogen atom (for example, chlorine atom, fluorine atom) or $C_{1-6}$ alkoxy (for example, methoxy), or a 5 to 14 membered aromatic heterocyclic group containing 1 to 4 heteroatoms of one or two kinds selected from a nitrogen atom, a sulfur atom and an oxygen atom in addition to carbon atoms (for example, a 5 to 6 membered aromatic heterocyclic group containing 1 to 2 heteroatoms selected from a nitrogen atom, a sulfur atom and an oxygen atom in addition to carbon atoms such as a pyridyl group, a thienyl group and the like);

$R^3$ is a $C_{6-14}$ aryl group (particularly, a phenyl group) optionally substituted with 1 or 2 $C_{1-6}$ alkyl (for example, methyl) or $C_{1-6}$ alkoxy (for example, methoxy);

X is a sulfur atom;

Y is an oxygen atom, an optionally oxidized sulfur atom or a group represented by the Formula $NR^{4'}$ ($R^{4'}$ is a hydrogen atom or a $C_{1-6}$ alkyl group) (in particular, an oxygen atom, S, $SO_2$, NH, $N(CH_3)$ and the like);

Z is a $C_{1-6}$ alkylene group (in particular, a $C_{1-3}$ alkylene group) optionally having oxo or $C_{1-6}$ alkyl (for example, $C_{1-3}$ alkyl such as methyl) or a bond.

(C) Formula (I) wherein R1 is an amino group optionally having 1 or 2 acyl represented by the Formula $—(C=O)—R5''$ (wherein R5'' represents {circle around (1)} a C6-14 aryl group (for example, phenyl group) or {circle around (2)} a 5 to 14 membered heterocyclic group containing 1 to 4 heteroatoms of one or two kinds selected from a nitrogen atom, a sulfur atom and an oxygen atom in addition to carbon atoms (for example, a 5 to 6 membered heterocyclic group containing 1 to 2 heteroatoms selected from a nitrogen atom, a sulfur atom and an oxygen atom in addition to carbon atoms such as a pyridyl group);

R2 is a $C_{6-14}$ aryl group (for example, a phenyl group) or a 5 to 14 membered aromatic heterocyclic group containing 1 to 4 heteroatoms of one or two kinds selected from a nitrogen atom, a sulfur atom and an oxygen atom in addition to carbon atoms (for example, a 5 to 6 membered aromatic heterocyclic group containing 1 to 2 heteroatoms selected from a nitrogen atom, a sulfur atom and an oxygen atom in addition to carbon atoms such as a pyridyl group);

R3 is a C6-14 aryl group (in particular, a phenyl group) optionally substituted with 1 or 2 C1-6 alkyl (for example, methyl) or C1-6 alkoxy (for example, methoxy);

X is a sulfur atom;

Y is O, NH or S;

Z is a bond or a C1-6 alkylene group (in particular, a C1-3 alkylene group optionally having oxo, such as methylene, ethylene and the like) optionally having oxo.

Genus II Description

Compounds of Genus II can be prepared according to the disclosure of U.S. Pat. No. 7,115,746, which is herein incorporated herein by reference in its entirety.

Genus II is characterized by compounds of Formula (II):

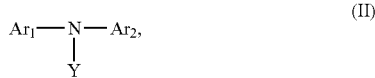

(II)

or stereoisomers thereof, isotopically-enriched compounds thereof, prodrugs thereof, solvates thereof, and pharmaceutically acceptable salts thereof;

wherein:

$Ar_1$ and $Ar_2$ are each independently aryl or heteroaryl optionally fused to a saturated or unsaturated 5-8 membered ring having 0-4 heteroatoms, provided that $Ar_1$ or $Ar_2$ is heteroaryl;

wherein the aryl or heteroaryl is optionally substituted with one or more substituents independently selected from halo; $C_1$-$C_6$ aliphatic optionally substituted with —N(R')$_2$, —OR', —CO$_2$R', —C(O)N(R')$_2$, —OC(O)N(R')$_2$, —NR'CO$_2$R', —NR'C(O)R', —SO$_2$N(R')$_2$, —N=CH—N(R')$_2$, or —OPO$_3$H$_2$; $C_1$-$C_6$ alkoxy optionally substituted with —N(R')$_2$, —OR', —CO$_2$R', —C(O)N(R')$_2$, —OC(O)N(R')$_2$, —NR'CO$_2$R', —NR'C(O)R', —SO$_2$N(R')$_2$, —N=CH—N(R')$_2$, or —OPO$_3$H$_2$; —Ar$_3$; —CF$_3$; —OCF$_3$; —OR'; —SR'; —SO$_2$N(R')$_2$; —OSO$_2$R'; —SCF$_3$; —NO$_2$; —CN; —N(R')$_2$; —CO$_2$R'; —CO$_2$N(R')$_2$; —C(O)N(R')$_2$; —NR'C(O)R'; —NR'CO$_2$R'; —NR'C(O)C(O)R'; —NR'SO$_2$R'; —OC(O)R'; —NR'C(O)R$^2$; —NR'CO$_2$R$^2$; —NR'C(O)C(O)R$^2$; —NR'C(O)N(R')$_2$; —OC(O)N(R')$_2$; —NR'SO$_2$R$^2$; —NR'R$^2$; —N(R$^2$)$_2$; —OC(O)R$^2$; —OPO$_3$H$_2$; and —N=CH—N(R')$_2$;

R' is selected from hydrogen; $C_1$-$C_6$ aliphatic; or a 5-6 membered carbocyclic or heterocyclic ring system optionally substituted with 1 to 3 substituents independently selected from halo, $C_1$-$C_6$ alkoxy, cyano, nitro, amino, hydroxy, and $C_1$-$C_6$ aliphatic;

$R^2$ is a $C_1$-$C_6$ aliphatic optionally substituted with —N(R')$_2$, —OR', —CO$_2$R', —C(O)N(R')$_2$ or —SO$_2$N(R')$_2$; or a carbocyclic or heterocyclic ring system optionally substituted with —N(R')$_2$, —OR', —CO$_2$R', —C(O)N(R')$_2$ or —SO$_2$N(R')$_2$;

$Ar_3$ is an aryl or heteroaryl ring system optionally fused to a saturated or unsaturated 5-8 membered ring having 0-4 heteroatoms, wherein $Ar_3$ is optionally substituted at one or more ring atoms with one or more substituents independently selected from halo; $C_1$-$C_6$ aliphatic optionally substituted with —N(R')$_2$, —OR', —CO$_2$R', —C(O)N(R')$_2$, —OC(O)N(R')$_2$, —NR'CO$_2$R', —NR'C(O)R', —SO$_2$N(R')$_2$, —N=C—N(R')$_2$, or —OPO$_3$H$_2$; $C_1$-$C_6$ alkoxy optionally substituted with —N(R')$_2$, —OR', —CO$_2$R', —C(O)N(R')$_2$, —OC(O)N(R')$_2$, —SO$_2$N(R')$_2$, —NR'CO$_2$R, —NR'C(O)R', —N=C—N(R')$_2$, or —OPO$_3$H$_2$; —CF$_3$; —OCF$_3$; —OR'; —SR'; —SO$_2$N(R')$_2$; —OSO$_2$R'; —SCF$_3$; —NO$_2$; —CN; —N(R')$_2$; —CO$_2$R'; —CO$_2$N(R')$_2$; —C(O)N(R')$_2$; —NR'C(O)R'; —NR'CO$_2$R'; —NR'C(O)C(O)R'; —NR'SO$_2$R'; —NR'C(O)R$^2$; —NR'CO$_2$R$^2$; —NR'C(O)C(O)R$^2$; —NR'C(O)N(R')$_2$; —OC(O)N(R')$_2$; —NR'SO$_2$R$^2$; —NR'R$^2$; —N(R$^2$)$_2$; —OC(O)R$^2$; —OPO$_3$H$_2$; and —N=C—N(R')$_2$; and Y is —C(O)—NH$_2$.

In one embodiment, the p38 kinase inhibitor is 2-(2,4-difluorophenyl)-6-(1-(2,6-difluorophenyl)ureido)nicotinamide ("VX-702"), Formula II'.

Genus II Definitions

As used herein, the following definitions shall apply unless otherwise indicated. The phrase "optionally substituted" is used interchangeably with the phrase "substituted or unsubstituted." Also, combinations of substituents are permissible only if such combinations result in chemically stable compounds. In addition, unless otherwise indicated, functional group radicals are independently selected.

The term "aliphatic" as used herein means straight-chain or branched $C_1$-$C_{12}$ hydrocarbon chain that is completely saturated or that contains one or more units of unsaturation. The term "aliphatic" also includes a monocyclic $C_3$-$C_8$ hydrocarbon or bicyclic $C_8$-$C_{12}$ hydrocarbon that is completely saturated or that contains one or more units of unsaturation, but which is not aromatic (said cyclic hydrocarbon chains are also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms, wherein an alkenyl comprises at least one double bond and an alkynyl comprises at least one triple bond.

The term "chemically stable" or "chemically feasible and stable", as used herein, refers to a compound structure that renders the compound sufficiently stable to allow manufacture and administration to a mammal by methods known in the art. Typically, such compounds are stable at temperature of 40° C. or less, in the absence of moisture or other chemically reactive conditions, for at least a week.

The term "haloalkyl", "haloalkenyl", and "haloalkoxy", means alkyl, alkenyl, or alkoxy, as the case may be, substituted with one or more halogen atoms. The term "halogen" means F, Cl, Br, or I.

The term "heteroatom" means N, O, or S and shall include any oxidized form of nitrogen and sulfur, and the quaternized form of any basic nitrogen.

The term "amine" or "amino" used alone or as part of a larger moiety, refers to a trivalent nitrogen, which may be primary or which may be substituted with 1-2 aliphatic groups.

The term "aryl" used alone or as part of a larger moiety as in "aralkyl", "aralkoxy", or "aryloxyalkyl", refers to monocyclic, bicyclic, and tricyclic carbocyclic ring systems having a total of five to fourteen members, where at least one ring in the system is aromatic and wherein each ring in the system contains 3 to 8 ring members. The term "aryl" may be used interchangeably with the term "aryl ring".

The term "heterocycle", "heterocyclyl", or "heterocyclic" as used herein means non-aromatic, monocyclic, bicyclic, or tricyclic ring systems having five to fourteen ring members in which one or more of the ring members is a heteroatom, wherein each ring in the system contains 3 to 7 ring members.

One having ordinary skill in the art will recognize that the maximum number of heteroatoms in a stable, chemically feasible heterocyclic or heteroaromatic ring is determined by the size of the ring, degree of unsaturation, and valence of the heteroatoms. In general, a heterocyclic or heteroaromatic ring may have one to four heteroatoms so long as the heterocyclic or heteroaromatic ring is chemically feasible and stable.

The term "heteroaryl", used alone or as part of a larger moiety as in "heteroaralkyl" or "heteroarylalkoxy", refers to monocyclic, bicyclic and tricyclic ring systems having a total of five to fourteen ring members, and wherein at least one ring in the system is aromatic, at least one ring in the system contains one or more heteroatoms, and each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroarylalkyl and heteroarylalkoxy and the like) group may contain one or more substituents. Suitable substituents on the unsaturated carbon atom of an aryl, heteroaryl, aralkyl, or heteroaralkyl group are selected from halogen; haloalkyl; —CF$_3$; —R$^4$; —OR$^4$; —SR$^4$; 1,2-methylenedioxy; 1,2-ethylenedioxy; protected OH (such as acyloxy); phenyl (Ph); Ph substituted with R$^4$; —OPh; —OPh substituted with R$^4$; —CH$_2$Ph; —CH$_2$Ph substituted with R$^4$; —CH$_2$CH$_2$(Ph); —CH$_2$CH$_2$(Ph) substituted with R$^4$; —NO$_2$; CN; N(R')$_2$; —NR$^4$C(O)R$^4$; —NR$^4$C(O)N(R$^4$)$_2$; —NR$^4$CO$_2$R$^4$; —NR$^4$NRC(O)R$^4$; —NR$^4$C(O)N(R$^4$)$_2$; —NR$^4$NR$^4$C(O)R$^4$; —NR$^4$NR$^4$C(O)N(R$^4$)$_2$; —NR$^4$NR$^4$CO$_2$R$^4$; —C(O)C(O)R$^4$—C(O)CH$_2$C(O)R'; —CO$_2$R'; —C(O)R'; —C(O)N(R')$_2$; —OC(O)N(R$^4$)$_2$; —SO$_2$R'; —SO$_2$N(R')$_2$; —S(O)R$^4$; —NR$^4$SO$_2$N(R')$_2$; —NR$^4$SO$_2$R$^4$; —C(=S)N(R')$_2$; —C(=NH)—N(R')$_2$; —(CH$_2$)$_y$NHC(O)R$^4$; —(CH$_2$)$_y$R$^4$; —(CH$_2$)$_y$NHC(O)NHR$^4$; —(CH$_2$)$_y$NHC(O)OR$^4$; —(CH$_2$)$_y$NHS(O)R$^4$; —(CH$_2$)$_y$NHSO$_2$R$^4$; or —(CH$_2$)$_y$NHC(O)CH(V—R$^4$)R$^4$; wherein each R$^4$ is independently selected from hydrogen, optionally substituted C$_{1-6}$ aliphatic, an unsubstituted 5-6 membered heteroaryl or heterocyclic ring, phenyl (Ph), —O-Ph, —CH$_2$(Ph); wherein y is 0-6; and V is a linker group. When R$^4$ is C$_{1-6}$ aliphatic, it may be substituted with one or more substituents selected from —NH$_2$, —NH(C$_{1-4}$ aliphatic), —N(C$_{1-4}$ aliphatic)$_2$, —S(O) (C$_{1-4}$ aliphatic), —SO$_2$(C$_{1-4}$ aliphatic), halogen, —(C$_{1-4}$ aliphatic), —OH, —O—(C$_{1-4}$ aliphatic), —NO$_2$, —CN, —CO$_2$H, —CO$_2$ (C$_{1-4}$ aliphatic), —O-(halo C$_{1-4}$ aliphatic), or -halo(C$_{1-4}$ aliphatic); wherein each C$_{1-4}$ aliphatic is unsubstituted.

The term "linker group" or "linker" means an organic moiety that connects two parts of a compound. Linkers are comprised of —O—, —S—, —NR*—, —C(R*)$_2$—, —C(O), or an alkylidene chain. The alkylidene chain is a saturated or unsaturated, straight or branched, C$_{1-6}$ carbon chain which is optionally substituted, and wherein up to two non-adjacent saturated carbons of the chain are optionally replaced by —C(O)—, —C(O)C(O)—, —C(O)NR*—, —C(O)NR*NR*—, NR*NR*—, —NR*C(O)—, —S—, —SO—, —SO$_2$—, —NR*—, —SO$_2$NR*—, or —NR*SO$_2$—; wherein R* is selected from hydrogen or aliphatic. Optional substituents on the alkylidene chain are as described below for an aliphatic group.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR$^5$, =NN(R$^5$)$_2$, =NR$^5$, —OR$^5$, =NNHC(O)R$^5$, =NNHCO$_2$R$^5$, =NNHSO$_2$R$^5$, or =NR$^5$, where each R$^5$ is independently selected from hydrogen or a optionally substituted C$_{1-6}$ aliphatic. When R$^5$ is C$_{1-6}$ aliphatic, it may be substituted with one or more substituents selected from —NH$_2$, —NH (C$_{1-4}$ aliphatic), —N(C$_{1-4}$ aliphatic)$_2$, halogen, —OH, —O—(C$_{1-4}$ aliphatic), —NO$_2$, —CN, —CO$_2$H, —CO$_2$ (C$_{1-4}$ aliphatic), —O-(halo C$_{1-4}$ aliphatic), or (halo C$_{1-4}$ aliphatic); wherein each C$_{1-4}$ aliphatic is unsubstituted.

Substituents on the nitrogen of a non-aromatic heterocyclic ring are selected from —R$^6$, —N(R$^6$)$_2$, —C(O)R$^6$, —CO$_2$R$^6$, —C(O)C(O)R$^6$, —C(O)CH$_2$C(O)R$^6$, —SO$_2$R$^6$, —SO$_2$N(R$^6$)$_2$, —C(=S)N(R')$_2$, —C(=NH)—N(R')$_2$, or —NRSO$_2$R; wherein each R$^6$ is independently selected from hydrogen, an optionally substituted C$_{1-6}$ aliphatic, optionally substituted phenyl (Ph), optionally substituted —O-Ph, optionally substituted —CH$_2$ (Ph), or an unsubstituted 5-6 membered heteroaryl or heterocyclic ring. When R$^6$ is a C$_{1-6}$ aliphatic group or a phenyl ring, it may be substituted with one or more substituents selected from —NH$_2$, —NH(C$_{1-4}$aliphatic), —N(C$_{1-4}$ aliphatic)$_2$, halogen, —(C$_{1-4}$ aliphatic), —OH, —O—(C$_{1-4}$ aliphatic), —NO$_2$, —CN, —CO$_2$H, —CO$_2$(C$_{1-4}$ aliphatic), —O-halo(C$_{1-4}$ aliphatic), or (halo C$_{1-4}$aliphatic); wherein each C$_{1-4}$ aliphatic is unsubstituted.

Genus III Description

Compounds of Genus III can be prepared according to the disclosure of U.S. Pat. No. 6,696,566, which is herein incorporated herein by reference in its entirety.

Genus III is characterized by compounds of Formula III:

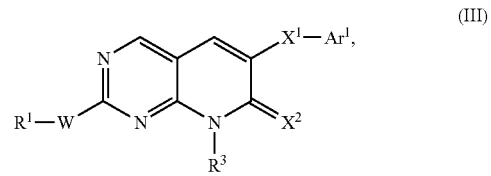

(III)

or stereoisomers thereof, isotopically-enriched compounds thereof, prodrugs thereof, solvates thereof, and pharmaceutically acceptable salts thereof;

wherein:

R$^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, R$^{12}$—SO$_2$-heterocycloamino, —Y$^1$—C(O)—Y$^2$—R$^{11}$, (heterocyclyl)(cycloalkyl)alkyl, or (heterocyclyl)(heteroaryl)alkyl;

wherein:

R$^{12}$ is haloalkyl, aryl, aryalkyl, heteroaryl or heteroaralkyl,

Y$^1$ and Y$^2$ are each independently absent or an alkylene group, and

R$^{11}$ is hydrogen, alkyl, haloalkyl, hydroxy, alkoxy, amino, monoalkylamino or dialkylamino, W is NR$^2$;

X$^1$ is O, NR$^4$, S, or CR$^5$R$^6$, or C=O, wherein:
R⁴ is hydrogen or alkyl, and
R⁵ and R⁶ are each independently hydrogen or alkyl;
X² is O or NR⁷,
wherein R⁷ is hydrogen or alkyl;
Ar¹ is aryl or heteroaryl;
R² is hydrogen alkyl, acyl, alkoxycarbonyl, aryloxycarbonyl, heteroalkylcarbonyl, heteroalkyloxycarbonyl or —R²¹—R²²,
wherein:
R²¹ is alkylene or —C(=O)—, and
R²² is alkyl or alkoxy;
R³ is hydrogen, alkyl, cycloalkyl, cycloalkylalkyl, aryl, aralkyl, haloalkyl, heteroalkyl, cyanoalkyl, alkylene-C(O)—R³¹, amino, monoalkylamino, dialkylamino, or NR³—Y³—R³³,
wherein:
R³¹ is hydrogen, alkyl, hydroxy, alkoxy, amino, monoalkylamino or dialkylamino, and
Y³ is —C(O), —C(O)O—, —C(O)N(R³⁴)—, —S(O)₂—, or —S(O)₂N(R³⁵)—,
wherein:
R³⁴ is hydrogen or alkyl, and
R³³ is hydrogen, alkyl, cycloalkyl, cycloalkylalkyl, heteroalkyl or optionally substituted phenyl) or acyl.

In some embodiments, the p38 kinase inhibitor from Genus III is selected from the following:
2-amino-6-(2-fluorophenoxy)-8-methyl-pyrido[2,3-d]pyrimidin-7(8H)-one;
6-(phenoxy)-8-methyl-2-(tetrahydro-2H-pyran-4-ylamino)pyrido[2,3-d]pyrimidin-7(8H)-one;
6-(3-fluorophenoxy)-8-methyl-2-(tetrahydro-2H-pyran-4-ylamino)pyrido[2,3-d]pyrimidin-7(8H)-one
6-(2,4-difluorophenoxy)-8-methyl-2-(tetrahydro-2H-pyran-4-ylamino)pyrido[2,3-d]pyrimidin-7(8H)-one;
6-(2-fluorobenzyl)-8-methyl-2-(tetrahydro-2H-pyran-4-ylamino)pyrido[2,3-d]pyrimidin-7(8H)-one;
6-[(4-fluorophenyl)thiol-]-2-[(4-hydroxycyclohexyl)amino]-8-methylpyrido[2,3-d]pyrimidin-7(8H)-one;
6-(4-fluorophenoxy)-2-[(4-hydroxycyclohexyl)amino]-8-methylpyrido[2,3-d]pyrimidin-7(8H)-one;
6-(2-fluorobenzyl)-2-[(4-hydroxycyclohexyl)amino]-8-methylpyrido[2,3-d]pyrimidin-7(8H)-one;
6-(2-fluorophenoxy)-2-[(4-methoxycyclohexyl) amino]-8-methylpyrido[2,3-d]pyrimidin-7(8H)-one;
6-(2-fluorophenoxy)-8-methyl-2-{[1-(methyl sulfonyl)piperidin-4-yl]amino}pyrido[2,3-d]pyrimidin-7(8H)-one;
6-(2-fluorophenoxy)-8-(4-fluorophenyl)-2-{[1-(methylsulfonyl)piperidin-4-yl]amino}pyrido[2,3-d]pyrimidin-7(8H)-one;
8-cyclopropyl-6-(2-fluorophenoxy)-2-{[1-(methylsulfonyl)piperidin-4-yl]amino}pyrido[2,3-d]pyrimidin-7(8H)-one;
6-(2-chlorophenoxy)-8-methyl-2-{[1-(methylsulfonyl)piperidin-4-yl]amino}pyrido[2,3-d]pyrimidin-7(8H)-one;
6-(4-chlorophenoxy)-8-methyl-2-{[1-(methylsulfonyl)piperidin-4-yl]amino}pyrido[2,3-d]pyrimidin-7(8H)-one;
2-(cyclopropylamino)-6-(2-fluorophenoxy)-8-methylpyrido[2,3-d]pyrimidin-7(8H)-one;
2-(cyclopentylamino)-6-(4-fluorophenoxy)-8-methylpyrido[2,3-d]pyrimidin-7(8H)-one;
2-(cyclopentylamino)-6-(3-fluorophenoxy)-8-methylpyrido[2,3-d]pyrimidin-7(8H)-one;
2-(butylamino)-6-(2-fluorophenoxy)-8-methylpyrido[2,3-d]pyrimidin-7(8H)-one;
6-(2-fluorophenoxy)-2-[(2-hydroxyethyl) amino]-8methylpyrido[2,3-d]pyrimidin-7(8H)-one;
6-(2-fluorophenoxy)-2-(isobutylamino)-8-methylpyrido[2,3-d]pyrimidin-7(8H)-one;
6-(2-fluorophenoxy)-2-{[(1S)-1-(hydroxy methyl)-2-methylpropyl]amino}-8-methylpyrido[2,3-d]pyrimidin-7(8H)-one;
2-[(2,3-dihydroxypropyl)amino]-6-(2-fluorophenoxy)-8-methylpyrido[2,3-d]pyrimidin-7(8H)-one;
6-(2-fluorophenoxy)-8-methyl-2-[(2-piperidin-1-ylethyl)amino]pyrido[2,3-d]pyrimidin-7(8H)-one;
2-[(cyclohexylmethyl)amino]-6-(2-fluorophenoxy)-8-methylpyrido[2,3-d]pyrimidin-7(8H)-one;
2-[(cyclopropylmethyl)amino]-6-(2-fluoro phenoxy)-8-methylpyrido[2,3-d]pyrimidin-7(8H)-one;
6-(2-fluorophenoxy)-2-[(2-methoxyethyl)amino]-8-methylpyrido[2,3-d]pyrimidin-7(8H)-one;
2-{[3-(dimethylamino)propyl]amino}-6-(2-fluorophenoxy)-8-methylpyrido[2,3-d]pyrimidin-7(8H)-one;
6-(2-fluorophenoxy)-8-methyl-2-{[3-(2-oxopyrrolidin-1-yl)propyl]amino}pyrido[2,3-d]pyrimidin-7(8H)-one;
N-(2-{[6-(2-fluorophenoxy)-8-methyl-7-oxo-7,8-dihydropyrido[2,3-d]pyrimidin-2-yl]amino}ethyl)acetamide;
6-(2-fluorophenoxy)-8-methyl-2-[(2-pyridin-3-ylethyl)amino]pyrido[2,3-d]pyrimidin-7(8H)-one;
ethyl N-[6-(2-fluorophenoxy)-8-methyl-7-oxo-7,8-dihydropyrido[2,3-d]pyrimidin-2-yl]-β-alaninate;
6-(2-fluorophenoxy)-2-[(3-methoxypropyl)amino]-8-methylpyrido[2,3-d]pyrimidin-7(8H)-one;
6-(4-chlorophenoxy)-2-{[(1S)-2-hydroxy-1,2-dimethylpropyl]amino}-8-methylpyrido[2,3-d]pyrimidin-7(8H)-one;
6-(2,4-difluorophenoxy)-2-{[(1S)-2-hydroxy-1,2-dimethylpropyl]amino}-8-methylpyrido[2,3-d]pyrimidin-7(8H)-one;
6-(2-fluorobenzyl)-2-{[(1S)-2-hydroxy-1,2-dimethylpropyl]amino}-8-methylpyrido[2,3-d]pyrimidin-7(8TH-one;
6-(2-fluorophenoxy)-8-methyl-2-[(1-oxidotetrahydro-2H-thiopyran-4-yl)amino]pyrido[2,3-d]pyrimidin-7(8H)-one;
2-[(1,1-dioxidotetrahydro-2H-thiopyran-4-yl)amino]-6-(2-fluorophenoxy)-8-methylpyrido[2,3-d]pyrimidin-7(8H)-one;
6-(2,4-difluorophenoxy)-8-methyl-2-[(1-oxido tetrahydro-2H-thiopyran-4-yl)amino]pyrido[2,3-d]pyrimidin-7(8H)-one;
2-[(1,1-dioxidotetrahydro-2H-thiopyran-4-yl)amino]-6-(2,4-difluorophenoxy)-8-methylpyrido[2,3-d]pyrimidin-7(8H)-one;
6-(2,6-difluorophenoxy)-2-{[1-(hydroxy methyl)butyl]amino}-8-methylpyrido[2,3-d]pyrimidin-7(8H)-one;
6-(2,6-difluorophenoxy)-2-[(2-hydroxy-1,1-dimethylethyl)amino]-8-methylpyrido[2,3-d]pyrimidin-7(8H)-one;
6-(2-fluorophenoxy)-2-{[1-(hydroxymethyl) cyclopentyl]amino}-8-methylpyrido[2,3-d]pyrimidin-7(8H)-one;
6-(2-fluorophenoxy)-2-{[1-(hydroxymethyl)-3-(methylthio)propyl]amino}-8-methylpyrido[2,3-d]pyrimidin-7(8H)-one;
2-(benzylamino)-6-(4-fluorophenoxy)-8-methylpyrido[2,3-d]pyrimidin-7(8H)-one;
2-(benzylamino)-6-(4-fluorobenzyl)-8-methylpyrido[2,3-d]pyrimidin-7(8H)-one;
6-(2-fluorophenoxy)-8-methyl-2-[(1-phenyl propyl)amino]pyrido[2,3-d]pyrimidin-7(8H)-one;
6-(2-fluorophenoxy)-8-methyl-2-[(pyridin-2-ylmethyl)amino]pyrido[2,3-d]pyrimidin-7(8H)-one;
6-(2-fluorophenoxy)-2-[(3-furylmethyl) amino]-8-methylpyrido[2,3-d]pyrimidin-7(8H)-one;
8-methyl-6-phenoxy-2-[(2-phenylethyl) amino]pyrido[2,3-d]pyrimidin-7(8H)-one;

6-(2-chlorophenoxy)-8-methyl-2-[(2-phenyl ethyl)amino]pyrido[2,3-d]pyrimidin-7(8H)-one;
Ethyl 4-{[6-(2,4-difluorophenoxy)-8-methyl-7-oxo-7,8-dihydropyrido[2,3-d]pyrimidin-2-yl]amino}piperidine-1-carboxylate;
8-methyl-2-{[3-(4-methylpiperazin-1-yl)propyl]amino}-6-phenoxypyrido[2,3-d]pyrimidin-7(8H)-one;
6-(2-chlorophenoxy)-8-methyl-2-{[3-(4-methylpiperazin-1-yl)propyl]amino}pyrido[2,3-d]pyrimidin-7(8H)-one;
2-anilino-6-(4-fluorobenzyl)-8-methylpyrido[2,3-d]pyrimidin-7(8H)-one;
6-(4-fluorophenoxy)-2-[(4-fluorophenyl) amino]-8-methylpyrido[2,3-d]pyrimidin-7(8H)-one;
6-(2,6-dichlorophenoxy)-2-[(4-fluorophenyl) amino]-8-methylpyrido[2,3-d]pyrimidin-7(8H)-one;
6-(4-fluorobenzyl)-2-[(4-fluorophenyl)amino]-8-methylpyrido[2,3-d]pyrimidin-7(8H)-one;
2-{[4-(2-hydroxyethyl)phenyl]amino}-8-methyl-6-phenoxypyrido[2,3-d]pyrimidin-7(8H)-one;
6-(2-chlorophenoxy)-2-({4-[2-(diethylamino) ethoxy]phenyl}amino)-8-methylpyrido[2,3-d]pyrimidin-7(8H)-one;
2-({4-[2-(diethylamino)ethoxy]phenyl}amino)-6-(4-fluorophenoxy)-8-methylpyrido[2,3-d]pyrimidin-7(8H)-one;
6-(2-fluorophenoxy)-2-[(3-hydroxypyridin-2-yl)amino]-8-methylpyrido[2,3-d]pyrimidin-7(8H)-one;
6-(2-fluorophenoxy)-8-methyl-2-[(5-methylpyridin-2-yl)amino]pyrido[2,3-d]pyrimidin-7(8H)-one;
2-(benzylthio)-6-(4-fluorophenoxy)pyrido[2,3-d]pyrimidin-7-amine;
6-(2,4-difluorophenoxy)-2-(benzylthio)pyrido[2,3-d]pyrimidin-7(8H)-one;
1-tert-Butyl-3-[6-(2,4-difluoro-phenoxy)-2-(tetrahydropyran-4-ylamino)-pyrido[2,3-d]pyrimidin-7-yl]-urea;
N-[6-(2,4-Difluoro-phenoxy)-2-(tetrahydro-pyran-4-ylamino)-pyrido[2,3-d]pyrimidin-7-yl]-methanesulfonamide;
6-(2,4-difluorophenoxy)-2-{[(1S)-2-fluoro-1,2-dimethylpropyl]amino}-8-methylpyrido[2,3-d]pyrimidin-7(8H)-one;
6-(2,4-Difluoro-phenoxy)-2-{[(1S)-2-hydroxy-1,2-dimethylpropyl]amino}-8-isopropylpyrido[2,3-d]pyrimidin-7(8H)-one;
6-(2,4-difluorophenoxy)-8-methyl-2-(tetrahydro-2H-pyran-4-ylamino)pyrido[2,3-d]pyridin-7(8H)-one;
8-Amino-6-(2,4-difluoro-phenoxy)-2-(tetrahydro-pyran-4-ylamino)-8H-pyrido[2,3-d]pyrimidin-7-one;
6-(2,4-Difluoro-phenoxy)-8-isopropylamino-2-(tetrahydro-pyran-4-ylamino)-8H-pyrido[2,3-d]pyrimidin-7-one;
6-(2,4-Difluoro-phenoxy)-8-[N-methyl-(N-3-methylbutyl)-amino]-2-(tetrahydro-pyran-4-ylamino)-8H-pyrido[2,3-d]pyrimidin-7-one;
6-(2,4-Difluoro-phenoxy)-8-N,N-dimethylamino-2-(tetrahydro-pyran-4-ylamino)-8H-pyrido[2,3-d]pyrimidin-7-one;
6-(2,4-Difluoro-phenylamino)-2-(2-hydroxy-1,1-dimethylethylamino)-8-methyl-8H-pyrido[2,3-d]pyrimidin-7-one;
6-[(2,4-Difluoro-phenyl)-methyl-amino]-8-methyl-2-(tetrahydro-pyran-4-ylamino)-8H-pyrido[2,3-d]pyrimidin-7-one;
6-(2,4-Difluoro-phenoxy)-8-ethyl-2-(tetrahydro-2H-pyran-4-ylamino)pyrido[2,3-d]pyrimidin-7(8H)-one;
6-(2,4-difluorophenoxy)-8-ethyl-2-(3-hydroxy-tetrahydro-pyran-4-ylamino)pyrido[2,3-d]pyrimidin-7(8H)-one;
6-(2,4-Difluoro-phenoxy)-2-(3-hydroxy-1,3-dimethyl-butylamino)-8-methyl-8H-pyrido[2,3-d]pyrimidin-7-one;
6-(2,4-Difluoro-phenoxy)-2-(3-hydroxy-1(S),3-dimethyl-butylamino)-8-methyl-8H-pyrido[2,3-d]pyrimidin-7-one;
6-(2,4-Difluoro-phenoxy)-2-(3-hydroxy-1(R),3-dimethyl-butylamino)-8-methyl-8H-pyrido[2,3-d]pyrimidin-7-one;
6-(2,4-difluorophenoxy)-8-methyl-2-(3-hydroxy-tetrahydro-pyran-4-ylamino)pyrido[2,3-d]pyrimidin-7(8H)-one;
6-(2-fluorophenoxy)-2-[(5-hydroxypyrazol-3-yl)amino]-8-methylpyrido[2,3-d]pyrimidin-7(8H)-one;
6-(2-fluorophenoxy)-2-[(pyridin-2-yl-methyl)amino]-8-methylpyrido[2,3-d]pyrimidin-7(8H)-one;
2-{[(1,5-Dimethyl-1H-pyrazol-4-yl)methyl]amino}-6-(2-fluorophenoxy)-8-methylpyrido[2,3-d]pyrimidin-7(8H)-one;
2-{[(1,3-Dimethyl-1H-pyrazol-4-yl)methyl]amino}-6-(2-fluorophenoxy-8-methylpyrido[2,3-d]pyrimidin-7(8H)-one;
6-(2-fluorophenoxy)-2-{[(3-methyl-isoxazol-5-yl)methyl]amino}-8-methylpyrido[2,3-d]pyrimidin-7(8H)-one;
2-{[1-(Hydroxymethyl)cyclohexyl]amino}-6-(2-methyl-benzyl)-8-methylpyrido[2,3-d]pyrimidin-7(8H)-one;
2-{[1-(Hydroxymethyl)cyclopentyl]amino}-6-(2-methyl-benzyl)-8-methylpyrido[2,3-d]pyrimidin-7(8H)-one;
6-Benzyl-2-{[1-(hydroxymethyl)cyclopentyl]amino}-8-methylpyrido[2,3-d]pyrimidin-7(8H)-one;
N-[6-(2,4-Difluoro-phenoxy)-8-methyl-7-oxo-4a,7,8,8a-tetrahydro-pyrido[2,3d]pyrimidin-2-y]-N-(tetrahydropyran-4-yl)-acetamide;
ethyl 4-{[6-(2-fluorophenoxy)-8-methyl-7-oxo-7,8-dihydropyrido[2,3-d]pyrimidin-2-yl]amino}piperidine-1-carboxylate;
6-(2-fluorophenoxy)-8-methyl-2-{[(1-benzylsulfonyl)piperidinyl-4-yl]amino}pyrido[2,3-d]pyrimidin-7(8H)-one;
6-(2-methyl-4-fluorophenoxy)-8-methyl-2-{[(1-benzylsulfonyl)piperidinyl-4-yl]amino}pyrido[2,3-d]pyrimidin-7(8H)-one;
6-(2,4-difluorophenoxy)-8-methyl-2-(N1-methylsulfonyl)-1,3-diaminopentane) pyrido[2,3-d]pyrimidin-7(8H)-one;
6-(2,4-difluorophenoxy)-8-methyl-2-((tetrahydro-2H-pyran-4-yl)amino)pyrido[2,3-d]pyrimidin-7(8H)-one ("R1487"), Formula III'a; and
6-(2,4-difluorophenoxy)-2-((1,5-dihydroxypentan-3-yl)amino)-8-methylpyrido[2,3-d]pyrimidin-7(8H)-one ("Pamapimod"), Formula III'b.

In one embodiment, the p38 kinase inhibitor is 6-(2,4-difluorophenoxy)-8-methyl-2-((tetrahydro-2H-pyran-4-yl)amino)pyrido[2,3-d]pyrimidin-7(8H)-one ("R1487"), Formula III'a.

In one embodiment, the p38 kinase inhibitor is 6-(2,4-difluorophenoxy)-2-((1,5-dihydroxypentan-3-yl)amino)-8-methylpyrido[2,3-d]pyrimidin-7(8H)-one ("Pamapimod"), Formula III'b.

Genus III Definitions:

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and the like.

"Alkoxy" means a radical —OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" means a radical —SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently with one or more substituents, preferably one, two or three, substituents preferably selected from the group consisting of alkyl, hydroxy, alkoxy, haloalkyl, haloalkoxy, Y—C(O)—R (where Y is absent or an alkylene group and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylamino, heteroalkylsulfonylamino, sulfonamido, methylenedioxy, ethylenedioxy, heterocyclyl or heterocyclylalkyl. More specifically the term aryl includes, but is not limited to, phenyl, chlorophenyl, methoxyphenyl, 2-fluorophenyl, 2,4-difluorophenyl, 1-naphthyl, 2-naphthyl, and the derivatives thereof.

"Aryloxy" means a radical —OR where R is an aryl as defined herein e.g. phenoxy.

"Aryloxycarbonyl" means a radical R—C(=O)— where R is aryloxy, e.g. phenoxycarbonyl.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like.

"Cycloalkylalkyl" means a radical —$R^aR^b$ where $R^a$ is an alkylene group and $R^b$ is cycloalkyl group as defined herein, e.g., cyclohexylmethyl, and the like.

"Substituted cycloalkyl" means a cycloalkyl radical as defined herein with one, two or three (preferably one) ring hydrogen atoms independently replaced by cyano or —Y—C(O)R (where Y is absent or an alkylene group and R is hydrogen, alkyl, haloalkyl, hydroxy, alkoxy, amino, monoalkylamino, dialkylamino, or optionally substituted phenyl).

"Dialkylamino" means a radical —NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$OR^a$, —$N(O)_nR^bR^c$ (where n is 0 or 1 if $R^b$ and $R^c$ are both independently alkyl, cycloalkyl or cycloalkylalkyl, and 0 if not) and —$S(O)_nR^d$ (where n is an integer from 0 to 2), with the understanding that the point of attachment of the heteroalkyl radical is through a carbon atom, wherein $R^a$ is hydrogen, acyl, alkoxycarbonyl, alkyl, cycloalkyl, or cycloalkylalkyl; $R^b$ and $R^c$ are independently of each other hydrogen, acyl, alkoxycarbonyl, alkyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, $R^d$ is hydrogen, alkyl, cycloalkyl, cycloalkylalkyl or optionally substituted phenyl, and when n is 1 or 2, $R^d$ is alkyl, cycloalkyl, cycloalkylalkyl, optionally substituted phenyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylcarbonyl" means the group $R_a$—C(=O)—, where $R_a$ is a heteroalkyl group. Representative examples include acetyloxymethylcarbonyl, aminomethylcarbonyl, 4-acetyloxy-2,2-dimethyl-butan-2-oyl, 2-amino-4-methyl-pentan-2-oyl, and the like.

"Heteroalkyloxy" means the group $R_aO$—, where $R_a$ is a heteroalkyl group. Representative examples include (Me-C(=O)—O—$CH_2$—O—, and the like "Heteroalkyloxycarbonyl" means the group $R_a$—C(=O), where $R_a$ is a heteroalkyloxy group. Representative examples include 1-acetyloxy-methoxycarbonyl (Me-C(=O)—O—$CH_2$—O—C(=O)—) and the like "Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, hydroxy, alkoxy, halo, nitro or cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroaralkyl" means a radical —$R^aR^b$ where $R^a$ is an alkylene group and $R^b$ is a heteroaryl group as defined herein, e.g., pyridin-3-ylmethyl, imidazolylethyl, pyridinylethyl, 3-(benzofuran-2-yl)propyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo (C=O), imino, hydroximino (=NOH), NR'SO$_2$R$^d$ (where R' is hydrogen or alkyl and R$^d$ is alkyl, cycloalkyl, hydroxyalkyl, amino, monoalkylamino or dialkylamino), —X—Y—C(O)R (where X is O or NR', Y is alkylene or absent, R is hydrogen, alkyl, haloalkyl, alkoxy, amino, monoalkylamino, dialkylamino, or optionally substituted phenyl, and R' is H or alkyl), or —S(O)$_n$R (where n is an integer from 0 to 2) such that when n is 0, R is hydrogen, alkyl, cycloalkyl, cycloalkylalkyl optionally substituted phenyl or thienyl, and when n is 1 or 2, R is alkyl, cycloalkyl, cycloalkylalkyl, optionally substituted phenyl, thienyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl or 4-methanesulfonamido-cyclohexyl.

"Heterosubstituted cycloalkyl-alkyl" means a radical R$^a$R$^b$— where R$^a$ is a heterosubstituted cycloalkyl radical and R$^b$ is an alkylene radical.

"Heterocycloamino" means a saturated monovalent cyclic group of 4 to 8 ring atoms, wherein one ring atom is N and the remaining ring atoms are C. Representative examples include piperidine and pyrrolidine.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)R$^a$ (where R$^a$ is alkyl, OR or NR'R" and R is hydrogen, alkyl or haloalkyl, and R' and R" are independently hydrogen or alkyl), or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino, dialkylamino or heteroalkyl. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof.

"Heterocyclylalkyl" means a radical —R$^a$R$^b$ where R$^a$ is an alkylene group and R$^b$ is a heterocyclyl group as defined above, e.g., tetrahydropyran-2-ylmethyl, 2- or 3-piperidinylmethyl, 3-(4-methyl-piperazin-1-yl)propyl and the like.

"(Heterocyclyl)(cycloalkyl)alkyl" means an alkyl radical wherein two hydrogen atoms have been replaced with a heterocyclyl group and a cycloalkyl group.

"(Heterocyclyl)(heteroaryl)alkyl" means an alkyl radical wherein two hydrogen atoms have been replaced with a heterocycyl group and a heteroaryl group. "Heterocyclyl spiro cycloalkyl" means a spiro radical consisting of a cycloalkyl ring and a heterocyclic ring with each ring having 5 to 8 ring atoms and the two rings having only one carbon atom in common, with the understanding that the point of attachment of the heterocyclyl spiro cycloalkyl radical is via the cycloalkyl ring. The spiro radical is formed when two hydrogen atoms from the same carbon atom of the cycloalkyl radical are replaced with a heterocyclyl group as defined herein, and may be optionally substituted with alkyl, hydroxy, hydroxyalkyl, or oxo. Examples include, but are not limited to, for example, 1,4-dioxaspiro[4.5]decan-8-yl, 1,3-diazaspiro[4.5]decan-8-yl, 2,4-dione-1,3-diaza-spiro[4.5]decan-8-yl, 1,5-dioxa-spiro[5.5]undecan-9-yl, (3-hydroxymethyl-3-methyl)-1,5-dioxa-spiro[5.5]undecan-9-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Monoalkylamino" means a radical —NHR where R an alkyl, hydroxyalkyl, cycloalkyl, or cycloalkylalkyl group as defined above, e.g., methylamino, (1-methylethyl)amino, hydroxymethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

Genus IV Description:

Compounds of Genus IV can be prepared according to the disclosure of US 2009/0042856, which is herein incorporated herein by reference in its entirety.

Genus IV is characterized by compounds of Formula IV:

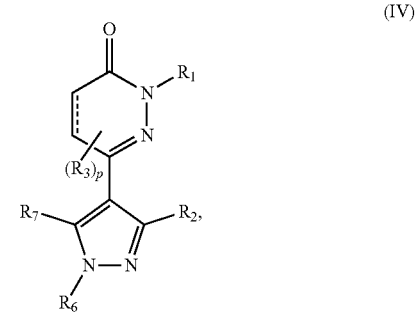

(IV)

or stereoisomers thereof, isotopically-enriched compounds thereof, prodrugs thereof, solvates thereof, and pharmaceutically acceptable salts thereof;

wherein:

R$^1$ is selected from the group consisting of hydrogen, substituted or unsubstituted lower alkyl and substituted or unsubstituted aryl;

R$^2$ is selected from the group consisting of substituted or unsubstituted aryl and substituted or unsubstituted heteroaryl;

$R^3$ is lower alkyl;
p is 0, 1 or 2;
=== is a single or double bond; and
$R^6$ and $R^7$ are taken together to form a group of the Formula:

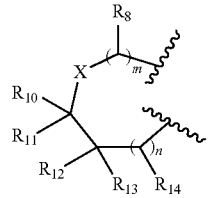

wherein:
$R^8$ is hydrogen, and
X is oxygen or N—$R^9$, in which $R^9$ is hydrogen, substituted or unsubstituted lower alkanoyl or substituted or unsubstituted lower alkyl; or
$R^8$ and $R^9$ may be taken together to form a bond; and
m and n are each independently 0, 1 or 2;
$R^{10}$ and $R^{12}$ are each independently selected from the group consisting of hydrogen, halogen, hydroxy, formyl, cyano, substituted or unsubstituted lower alkyl, substituted or unsubstituted amino, substituted or unsubstituted lower alkoxy, saturated cyclic amino, substituted or unsubstituted carbamoyl, carboxy, substituted or unsubstituted lower alkoxycarbonyl, and substituted or unsubstituted acyloxy, or
$R^9$ and $R^{10}$ may be taken together to form lower alkylene or a bond; and
$R^{11}$, $R^{13}$ and $R^{14}$ are each independently selected from the group consisting of hydrogen, halogen, substituted or unsubstituted lower alkyl, carboxy, and substituted or unsubstituted lower alkoxycarbonyl, or
$R^{10}$ and $R^{11}$ or $R^{12}$ and $R^{13}$ are taken together to form oxo, hydroxyimino, substituted or unsubstituted lower alkylene in which one or more carbon(s) may be replaced by hetero atom(s), or substituted or unsubstituted lower alkylidene, or
$R^{11}$ and $R^{12}$ or $R^{13}$ and $R^{14}$ may be taken together to form a bond; and
provided that when n=1 and $R^{10}$, $R^{11}$, $R^{12}$, $R^{13}$ and $R^{14}$ are simultaneously hydrogen, then $R^9$ is substituted or unsubstituted lower alkyl or substituted or unsubstituted lower alkanoyl.

In one embodiment, the p38 kinase inhibitor from Genus IV is selected from the following:
6-{2-(2,4-Difluorophenyl)-6-[(dimethylamino)methyl]-4,5,6,7-tetrahydropyrazolo[1,5-a]pyrimidin-3-yl}-2-(2-methylphenyl)-3(2H)-pyridazinone;
6-{2-(2,4-Difluorophenyl)-6-[(dimethylamino)methyl]pyrazolo[1,5-a]pyrimidin-3-yl}-2-(2-methylphenyl)-3(2H)-pyridazinone;
6-[L-Ethyl-6-(4-fluorophenyl)-2,3-dihydro-1H-imidazo[1,2-b]pyrazol-7-yl]-2-(2-methylphenyl)-3(2H)-pyridazinone;
6-[2-(4-Fluorophenyl)-6,6-bis(hydroxymethyl)-4,5,6,7-tetrahydropyrazolo[1,5-a]pyrimidin-3-yl]-2-(2-methylphenyl)pyridazin-3(2H)-one;
6-[2-(2,4-Difluorophenyl)-6-(hydroxymethyl)-4,5,6,7-tetrahydropyrazolo[1,5-a]pyrimidin-3-yl)-2-(2-methylphenyl)pyridazin-3(2H)-one;
6-{2-(4-Fluorophenyl)-6-[(4-methylpiperazin-1-yl)methyl]-4,5,6,7-tetrahydropyrazolo[5-a]pyrimidin-3-yl}-2-(2-methylphenyl)pyridazin-3(2H)-one dihydrochloride;
6-{2-(2,4-difluorophenyl)-6-[(dimethylamino)methyl]-4,5,6,7-tetrahydropyrazolo[1,5-a]pyrimidin-3-yl]-2-(2-methylphenyl)-4,5-dihydropyridazin-3(2H)-one;
N-cyclopropyl-2-(4-fluorophenyl)-3-[1-(2-methylphenyl)-6-oxo-1,6-dihydropyridazin-3-yl]-4,5,6,7-tetrahydropyrazolo[1,5-a]pyrimidine-6-carboxamide;
6-[6,6-Difluoro-2-(4-fluorophenyl)-4,5,6,7-tetrahydropyrazolo[1,5-a]pyrimidin-3-yl]-2-(2-methylphenyl)pyridazin-3(2H)-one;
6-{6-[(tert-Butylamino)methyl]-2-(2,4-difluorophenyl)-4,5,6,7-tetrahydropyrazolo[1,5-a]pyrimidin-3-yl}-2-(2-methylphenyl)pyridazin-3(2H)-one;
6-[1-Acetyl-2'-(4-fluorophenyl)-4',5'-dihydrospiro[piperidine-4,6'-pyrazolo[1,5-a]pyrimidin]-3'-yl]-2-(2-methylphenyl)pyridazin-3(2H)-one;
6-[(5S)-2-(4-Fluorophenyl)-5-(hydroxymethyl)-4,5,6,7-tetrahydropyrazolo[1,5-a]pyrimidin-3-yl]-2-(2-methylphenyl)pyridazin-3(2H)-one;
6-[(5S)-2-(4-Fluorophenyl)-5-(hydroxymethyl)-4,5,6,7-tetrahydropyrazolo[1,5-a]pyrimidin-3-yl]-2-(2-methylphenyl)pyridazin-3(2H)-one;
Ethyl 3-(4-fluorophenyl)-2-[1-(2-methylphenyl)-6-oxo-1,6-dihydropyridazin-3-yl]-3-oxopropanoate;
6-(5-Isopropyl-2-phenyl-4,5,6,7-tetrahydropyrazolo[1,5-a]pyrazin-3-yl)-2-(2-methylphenyl)pyridazin-3(2H)-one;
6-[2-(4-Fluorophenyl)-6-(hydroxymethyl)-4,5,6,7-tetrahydropyrazolo[1,5-a]pyrimidin-3-yl]-2-(2-methylphenyl)-3(2H)-pyridazinone;
6-[2-(4-Fluorophenyl)-6-hydroxy-4,5,6,7-tetrahydropyrazolo[1,5-a]pyrimidin-3-yl]-2-(2-methylphenyl)-3(2H)-pyridazinone;
6-[2-(2,4-Difluorophenyl)-6-(hydroxymethyl)-4,5,6,7-tetrahydropyrazolo[1,5-a]pyrimidin-3-yl]-2-(2-methylphenyl)pyridazin-3(2H)-one;
6-[2'-(4-Fluorophenyl)-2,3,4',5,5',6-hexahydrospiro[pyran-4,6'-pyrazolo[1,5-a]pyrimidin]-3'-yl]-2-(2-methylphenyl)pyridazin-3(2H)-one;
6-[2'-(4-Fluorophenyl)-4',5'-dihydrospiro[1,3-dioxolane-2,6'-pyrazolo[1,5-a]pyrimidin]-3'-yl]-2-(2-methylphenyl)pyridazin-3(2H)-one;
6-[(6R)-2-(4-Fluorophenyl)-6-hydroxy-4,5,6,7-tetrahydropyrazolo[1,5-a]pyrimidin-3-yl]-2-(2-methylphenyl)pyridazin-3(2H)-one;
6-[(5S)-2-(4-fluorophenyl)-5-(hydroxymethyl)-4,5,6,7-tetrahydropyrazolo[1,5-a]pyrimidin-3-yl)-2-(2-methylphenyl)pyridazin-3(2H)-one;
6-[(5S)-2-(4-fluorophenyl)-5-(hydroxymethyl)-4,5,6,7-tetrahydropyrazolo[1,5-a]pyrimidin-3-yl]-2-(2-methylphenyl)pyridazin-3(2H)-one;
6-[2-(4-Fluorophenyl)-6,6-dimethyl-4,5,6,7-teterahydropyrazolo[1,5-a]pyrimidin-3-yl]-2-(2-methylphenyl)pyridazin-3(2H)-one;
(+)-6-[2-(4-Fluorophenyl)-6-(hydroxymethyl)-4,5,6,7-tetrahydropyrazolo[1,5-a]pyrimidin-3-yl]-2-(2-methylphenyl)pyridazin-3(2H)-one;
(−)-6-[2-(4-Fluorophenyl)-6-(hydroxymethyl)-4,5,6,7-tetrahydropyrazolo[1,5-a]pyrimidin-3-yl]-2-(2-methylphenyl)pyridazin-3(2H)-one;
(+)-6-{2-(4-Fluorophenyl)-6-[(dimethylamino)methyl]-4,5,6,7-tetrahydropyrazolo[1,5-a]pyrimidin-3-yl}-2-(2-methylphenyl)pyridazin-3(2H)-one;
(−)-6-{2-(4-Fluorophenyl)-6-[(dimethylamino)methyl]-4,5,6,7-tetrahydropyrazolo[1,5-a]pyrimidin-3-yl}-2-(2-methylphenyl)pyridazin-3(2H)-one;
(+)-6-{2-(3-Methylphenyl)-6-[(dimethylamino)methyl]-4,5,6,7-tetrahydropyrazolo[1,5-a]pyrimidin-3-yl}-2-(2-methylphenyl)pyridazin-3(2H)-one;

(−)-6-(2-(3-Methylphenyl)-6-[(dimethylamino)methyl)-4,5,6,7-tetrahydropyrazolo[1,5-a]pyrimidin-3-yl)-2-(2-methylphenyl)pyridazin-3(2H)-one;

(+)-6-{2-(2-Chloro-4-fluorophenyl)-6-[(dimethylamino)methyl]-4,5,6,7-tetrahydropyrazolo[1,5-a]pyrimidin-3-yl}-2-(2-methylphenyl)pyridazin-3(2H)-one;

(−)-6-{2-(2-Chloro-4-fluorophenyl)-6-[(dimethylamino)methyl]-4,5,6,7-tetrahydropyrazolo[1,5-a]pyrimidin-3-yl}-2-(2-methylphenyl)pyridazin-3(2H)-one;

(+)-6-{2,5-Difluorophenyl)-6-[(dimethylamino)methyl]-4,5,6,7-tetrahydropyrazolo[1,5-a]pyrimidin-3-yl}-2-(2-methylphenyl)pyridazin-3(2H)-one;

(−)-6-(2-(2,5-Difluorophenyl)-6-[(dimethylamino)methyl]-4,5,6,7-tetrahydropyrazolo[1,5-a]pyrimidin-3-yl)-2-(2-methylphenyl)pyridazin-3(2H)-one;

(+)-6-{2-(2,4-Difluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(−)-6-{2-(2,4-Difluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(+)-6-{2-(4-Fluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(−)-6-{2-(4-Fluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(+)-6-{2-(3-Methylphenyl)-6-[(dimethylamino)methyl]-4,5,6,7-tetrahydropyrazolo[1,5-a]pyrimidin-3-yl}-2-(2-methylphenyl)pyridazin-3(2H)-one;

(−)-6-{2-(3-Methylphenyl)-6-[(diethylamino)methyl]-4,5,6,7-tetrahydropyrazolo[1,5-a]pyrimidin-3-yl}-2-(2-methylphenyl)pyridazin-3(2H)-one;

(+)-6-{2-(2-Chloro-4-fluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(−)-6-{2-(2-Chloro-4-fluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(+)-6-{2,5-Difluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(−)-6-{2-(2,5-Difluorophenyl)-6-[(diethylamino)methyl]-4,5,6,7-tetrahydropyrazolo[1,5-a]pyrimidin-3-yl}-2-(2-methylphenyl)pyridazin-3(2H)-one;

(+)-6-(2-(2,4-Difluorophenyl)-6-(hydroxymethyl)-4,5,6,7-tetrahydropyrazolo[1,5-a]pyrimidin-3-yl)-2-(2-methylphenyl)pyridazin-3(2H)-one;

(−)-6-[2-(2,4-Difluorophenyl)-6-(hydroxymethyl)-4,5,6,7-tetrahydropyrazolo[1,5-a]pyrimidin-3-yl]-2-(2-methylphenyl)pyridazin-3(2H)-one;

(+)-6-[2-(3-Methylphenyl)-6-(hydroxymethyl)-4,5,6,7-tetrahydropyrazolo[1,5-a]pyrimidin-3-yl]-2-(2-methylphenyl)pyridazin-3(2H)-one;

(−)-6-[2-(3-Methylphenyl)-6-(hydroxymethyl)-4,5,6,7-tetrahydropyrazolo[1,5-a]pyrimidin-3-yl]-2-(2-methylphenyl)pyridazin-3(2H)-one;

(+)-6-[2-(2,5-Difluorophenyl)-6-(hydroxymethyl)-4,5,6,7-tetrahydropyrazolo[1,5-a]pyrimidin-3-yl]-2-(2-methylphenyl)pyridazin-3(2H)-one;

(−)-6-[2-(2,5-Difluorophenyl)-6-(hydroxymethyl)-4,5,6,7-tetrahydropyrazolol[1,5-a]pyrimidin-3-yl]-2-(2-methylphenyl)pyridazin-3(2H)-one;

(+)-6-[2-(2-Chloro-4-fluorophenyl)-6-(hydroxymethyl)-4,5,6,7-tetrahydropyrazolo[1,5-a]pyrimidin-3-yl]-2-(2-methylphenyl)pyridazin-3(2H)-one;

(−)-6-[2-(2-Chloro-4-fluorophenyl)-6-(hydroxymethyl)-4,5,6,7-tetrahydropyrazolo[1,5-a]pyrimidin-3-yl]-2-(2-methylphenyl)pyridazin-3(2H)-one;

(+)-6-{2-(4-Fluorophenyl)-6-[(methylamino)methyl]-4,5,6,7-tetrahydropyrazolo[1,5-a]pyrimidin-3-yl}-2-(2-methylphenyl)pyridazin-3(2H)-one;

(−)-6-{2-(4-Fluorophenyl)-6-[(methylamino)methyl]-4,5,6,7-tetrahydropyrazolo[1,5-a]pyrimidin-3-yl}-2-(2-methylphenyl)pyridazin-3(2H)-one;

(+)-6-{2-(2,4-Difluorophenyl)-6-[(methylamino)methyl]-4,5,6,7-tetrahydropyrazolo[1,5-a]pyrimidin-3-yl}-2-(2-methylphenyl)pyridazin-3(2H)-one;

(−)-6-{2-(2,4-Difluorophenyl)-6-[(methylamino)methyl]-4,5,6,7-tetrahydropyrazolo[1,5-a]pyrimidin-3-yl}-2-(2-methylphenyl)pyridazin-3(2H)-one;

(+)-6-{2-(2,5-Difluorophenyl)-6-[(methylamino)methyl]-4,5,6,7-tetrahydropyrazolo[1,5-a]pyrimidin-3-yl}-2-(2-methylphenyl)pyridazin-3(2H)-one;

(−)-6-{2-(2,5-Difluorophenyl)-6-[(methylamino)methyl]-4,5,6,7-tetrahydropyrazolo[1,5-a]pyrimidin-3-yl}-2-(2-methylphenyl)pyridazin-3(2H)-one;

(+)-6-{2-(3-Methylphenyl)-6-[(methylamino)methyl]-4,5,6,7-tetrahydropyrazolo[1,5-a]pyrimidin-3-yl}-2-(2-methylphenyl)pyridazin-3(2H)-one;

(−)-6-{2-(3-Methylphenyl)-6-[(methylamino)methyl)-4,5,6,7-tetrahydropyrazolo[1,5-a]pyrimidin-3-yl}-2-(2-methylphenyl)pyridazin-3(2H)-one;

(+)-6-{2-(2-Chloro-4-fluorophenyl)-6-[(methylamino)methyl]-4,5,6,7-tetrahydropyrazolo[1,5-a]pyrimidin-3-yl}-2-(2-methylphenyl)pyridazin-3(2H)-one;

(−)-6-{2-(2-Chloro-4-fluorophenyl)-6-[(methylamino)methyl]-4,5,6,7-tetrahydropyrazolo[1,5-a]pyrimidin-3-yl}-2-(2-methylphenyl)pyridazin-3(2H)-one;

(+)-6-{6-[(tert-Butylamino)methyl]-2-(4-fluorophenyl)-4,5,6,7-tetrahydropyrazolo[1,5-a]pyrimidin-3-yl}-2-(2-methylphenyl)pyridazin-3(2H)-one;

(−)-6-{6-[(tert-Butylamino)methyl]-2-(4-fluorophenyl)-4,5,6,7-tetrahydropyrazolo[1,5-a]pyrimidin-3-yl}-2-(2-methylphenyl)pyridazin-3(2H)-one;

(+)-6-{6-[(tert-Butylamino)methyl]-2-(2,4-difluorophenyl)-4,5,6,7-tetrahydropyrazolo[1,5-a]pyrimidin-3-yl)-2-(2-methylphenyl)pyridazin-3(2H)-one;

(−)-6-{6-[(tert-Butylamino)methyl]-2-(2,4-difluorophenyl)-4,5,6,7-tetrahydropyrazolo[1,5-a]pyrimidin-3-yl}-2-(2-methylphenyl)pyridazin-3(2H)-one;

(+)-6-{6-[(tert-Butylamino)methyl]-2-(2,5-difluorophenyl)-4,5,6,7-tetrahydropyrazolo[1,5-a]pyrimidin-3-yl}-2-(2-methylphenyl)pyridazin-3(2H)-one;

(−)-6-(6-[(tert-Butylamino)methyl]-2-(2,5-difluorophenyl)-4,5,6,7-tetrahydropyrazolo[1,5-a]pyrimidin-3-yl)-2-(2-methylphenyl)pyridazin-3(2H)-one;

(+)-6-{6-[(tert-Butylamino)methyl]-2-(3-methylphenyl)-4,5,6,7-tetrahydropyrazolo[1,5-a]pyrimidin-3-yl}-2-(2-methylphenyl)pyridazin-3(2H)-one;

(−)-6-{6-[(tert-Butylamino)methyl]-2-(3-methylphenyl)-4,5,6,7-tetrahydropyrazolo[1,5-a]pyrimidin-3-yl}-2-(2-methylphenyl)pyridazin-3(2H)-one;

(+)-6-{2-(4-Fluorophenyl)-6-[(4-methylpiperazin-1-yl)methyl]-4,5,6,7-tetrahydropyrazolo[1,5-a]pyrimidin-3-yl}-2-(2-methylphenyl)pyridazin-3(2H)-one;

(−)-6-{2-(4-Fluorophenyl)-6-[(4-methylpiperazin-1-yl)methyl]-4,5,6,7-tetrahydropyrazolo[1,5-a]pyrimidin-3-yl}-2-(2-methylphenyl)pyridazin-3(2H)-one;

(+)-6-{2-(2,4-Difluorophenyl)-6-[(4-methylpiperazin-1-yl)methyl]-4,5,6,7-tetrahydropyrazolo[1,5-a]pyrimidin-3-yl}-2-(2-methylphenyl)pyridazin-3(2H)-one;

(−)-6-{2-(2,4-Difluorophenyl)-6-[(4-methylpiperazin-1-yl) methyl]-4,5,6,7-tetrahydropyrazolo[1,5-a]pyrimidin-3-yl}-2-(2-methylphenyl)pyridazin-3(2H)-one;

(+)-6-{2-(2,5-Difluorophenyl)-6-[(4-methylpiperazin-1-yl) methyl]-4,5,6,7-tetrahydropyrazolo[1,5-a]pyrimidin-3-yl}-2-(2-methylphenyl)pyridazin-3(2H)-one;

(−)-6-{2-(2,5-Difluorophenyl)-6-[(4-methylpiperazin-1-yl) methyl]-4,5,6,7-tetrahydropyrazolo[1,5-a]pyrimidin-3-yl}-2-(2-methylphenyl)pyridazin-3(2H)-one;

(+)-6-{2-(3-Methylphenyl)-6-[(4-methylpiperazin-1-yl) methyl]-4,5,6,7-tetrahydropyrazolo[1,5-a]pyrimidin-3-yl}-2-(2-methylphenyl)pyridazin-3(2H)-one;

(−)-6-{2-(3-Methylphenyl)-6-[(4-methylpiperazin-1-yl) methyl]-4,5,6,7-tetrahydropyrazolo[1,5-a]pyrimidin-3-yl}-2-(2-methylphenyl)pyridazin-3(2H)-one;

(+)-2-(4-Fluorophenyl)-3-[1-(2-methylphenyl)-6-oxo-1,6-dihydropyridazin-3-yl]-4,5,6,7-tetrahydropyrazolo[1,5-a]pyrimidine-6-carbonitrile;

(−)-2-(4-Fluorophenyl)-3-[1-(2-methylphenyl)-6-oxo-1,6-dihydropyridazin-3-yl]-4,5,6,7-tetrahydropyrazolo[1,5-a]pyrimidine-6-carbonitrile;

(+)-2-(2,4-Difluorophenyl)-3-[1-(2-methylphenyl)-6-oxo-1,6-dihydropyridazin-3-yl]-4,5,6,7-tetrahydropyrazolo[1,5-a]pyrimidine-6-carbonitrile;

(−)-2-(2,4-Difluorophenyl)-3-[1-(2-methylphenyl)-6-oxo-1,6-dihydropyridazin-3-yl]-4,5,6,7-tetrahydropyrazolo[1,5-a]pyrimidine-6-carbonitrile;

(+)-2-(2,5-Difluorophenyl)-3-[1-(2-methylphenyl)-6-oxo-1,6-dihydropyridazin-3-yl]-4,5,6,7-tetrahydropyrazolo[1,5-a]pyrimidine-6-carbonitrile (−)-2-(2,5-Difluorophenyl)-3-[1-(2-methylphenyl)-6-oxo-1,6-dihydropyridazin-3-yl]-4,5,6,7-tetrahydropyrazolo[1,5-a]pyrimidine-6-carbonitrile;

(+)-2-(3-Methylphenyl)-3-[1-(2-methylphenyl)-6-oxo-1,6-dihydropyridazin-3-yl]-4,5,6,7-tetrahydropyrazolo[1,5-a]pyrimidine-6-carbonitrile;

(−)-2-(3-Methylphenyl)-3-[1-(2-methylphenyl)-6-oxo-1,6-dihydropyridazin-3-yl]-4,5,6,7-tetrahydropyrazolo[1,5-a]pyrimidine-6-carbonitrile; and (R)-6-(2-(4-fluorophenyl)-6-(hydroxymethyl)-4,5,6,7-tetrahydropyrazolo[1,5-a]pyrimidin-3-yl)-2-(o-tolyl) pyridazin-3(2H)-one ("AS1940477"), Formula IV'.

In one embodiment, the p38 kinase inhibitor is (R)-6-(2-(4-fluorophenyl)-6-(hydroxymethyl)-4,5,6,7-tetrahydropyrazolo[1,5-a]pyrimidin-3-yl)-2-(o-tolyl)pyridazin-3(2H)-one ("AS1940477"), Formula IV'.

Genus IV Definitions

Hereinafter the symbols of the Formula (IV) are explained in detail. Throughout the specification and claims, the term "lower" is intended to mean 1 to 6 carbon atom(s) unless otherwise indicated.

(Definition of $R^1$)

In the Formula (I), $R^1$ is selected from the group consisting of hydrogen, substituted or unsubstituted lower alkyl and substituted or unsubstituted aryl.

Examples of the "lower alkyl" of the "substituted or unsubstituted lower alkyl" for $R^1$ may include straight or branched $(C_{1-6})$alkyl such as methyl, ethyl, propyl, isopropyl, butyl, isobutyl, tert-butyl, pentyl, hexyl, etc., in which the preferred one may be $(C_{1-4})$alkyl, and more preferable one may be methyl, ethyl, propyl, isopropyl, isobutyl, etc.

Examples of the substituents for the "substituted lower alkyl" for $R^1$ may include hydroxy, hydroxy$(C_{5-8})$cycloalkyl, $(C_{5-8})$cycloalkyl, nitro, nitro $(C_{5-8})$cycloalkyl, amido, amido$(C_{5-8})$cycloalkyl, sulfonamido, sulfonamido$(C_{5-8})$cycloalkyl, ureido, ureido $(C_{5-8})$cycloalkyl etc. The number of the substituent may be one; two or more. Where the number of the substituent is two or more, the substituents may be the same or different.

Examples of the "aryl" of the "substituted or unsubstituted aryl" for $R^1$ may include $(C_{6-14})$aryl such as phenyl, naphthyl, indenyl, anthryl, etc., in which the preferred one may be $(C_{6-10})$aryl, and the more preferred one may be phenyl, etc.

Examples of the substituents for the "substituted aryl" for $R^1$ may include lower alkyl [e.g., $(C_{1-4})$alkyl (e.g., methyl, ethyl, propyl, butyl, etc.), etc.], (lower)alkylaminosulfonyl [e.g., $(C_{1-4})$alkylaminosulfonyl (e.g., methylaminosulfonyl, ethylaminosulfonyl, propylaminosulfonyl, tert-butylaminosulfonyl, etc.), etc.], aryloxy (e.g., $(C_{6-14})$aryloxy, etc.), halo(lower)alkyl (e.g., chloromethyl, dichloromethyl, fluoromethyl, difluoromethyl, trifluoromethyl, pentachloroethyl, etc.), hydroxy(lower)alkyl (e.g., hydroxy$(C_{1-4})$alkyl, etc.), lower alkanoyl (e.g., $(C_{1-4})$alkyl-carbonyl, etc.), halogen (e.g., fluoro, chloro, bromo, iodo, etc.), lower alkoxy (e.g., $(C_{1-4})$alkoxy, etc.), carboxy, lower alkoxycarbamoyl, carbamoyl, lower alkylcarbamoyl, etc. The number of the substituent may be one or two or more. Where the number of the substituent is two or more, the substituents may be the same or different.

Suitable examples of $R^1$ may include hydrogen, methylphenyl, (tert-butylamino)sulfonylphenyl, ethylphenyl, methoxyphenyl, aminosulfonylphenyl, etc.

(Definition of $R^2$)

In the Formula (I), $R^2$ is selected from the group consisting of substituted or unsubstituted aryl and substituted or unsubstituted heteroaryl.

Examples of the "aryl" of the "substituted or unsubstituted aryl" for $R^2$ may include aryl similar to those exemplified for $R^1$ above, in which the preferred one may be $(C_{6-10})$aryl, and the more preferred one may be phenyl, etc.

Examples of the substituents for the "substituted aryl" for $R^2$ may include halogen (e.g., fluoro, chloro, bromo, iodo, etc.), lower alkyl [e.g., $(C_{1-4})$alkyl (e.g., methyl, ethyl, propyl, butyl, etc.), etc.], lower alkoxy [e.g., $(C_{1-4})$alkoxy (e.g., methoxy, ethoxy, propoxy, butoxy, etc.), etc.], halo (lower)alkyl (e.g., chloromethyl, dichloromethyl, fluoromethyl, difluoromethyl, trifluoromethyl, pentachloroethyl, etc.), hydroxy(lower)alkyl, etc. The number of the substituent may be one, two or more. Where the number of the substituent is two or more, the substituents may be the same or different.

Examples of the "heteroaryl" of the "substituted or unsubstituted heteroaryl" for $R^2$ may include, 5 to 14-membered heteroaryl, such as furyl, pyrrolyl, thienyl, oxazolyl, etc., in which the preferred one may be 5 or 6-membered heteroaryl, and more preferred one may be thienyl, etc.

Examples of the substituents for the "substituted heteroaryl" for R2 may include substituents similar to the substituents exemplified above for the "substituted aryl" for $R^2$. The number of the substituent may be one or two or more. Where the number of the substituent is two or more, the substituents may be the same or different.

Suitable examples of $R^2$ may include phenyl, fluorophenyl, difluorophenyl, chlorofluorophenyl, methylphenyl, dimethylphenyl, methoxyphenyl, methyl(fluoro)phenyl, etc.

(Definition of $R^3$)

In the Formula (I), $R^3$ is lower alkyl.

Examples of the "lower alkyl" for $R^3$ may include lower alkyl similar to those exemplified for $R^1$ above, in which the preferred one may be $(C_{1-4})$alkyl.

Suitable examples of $R^3$ may include methyl, ethyl, etc.
(Definition of p)

In the Formula (I), p is 0, 1 or 2.

Suitable example of p is 0.
(Definitions of $R^4$ and $R^5$)

In the Formula (I), $R^4$ and $R^5$ are each hydrogen or taken together to form a bond.
(Definitions of $R^6$ and $R^7$)

In the Formula (I), $R^6$ and $R^7$ are taken together to form a group of the Formula:

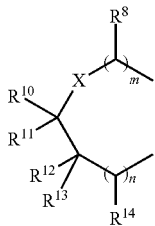

(Definition of $R^8$)

R8 is hydrogen.
(Definition of X)

X is oxygen or N—$R^9$, in which $R^9$ is hydrogen, substituted or unsubstituted lower alkanoyl, or substituted or unsubstituted lower alkyl.

Examples of the "lower alkyl" of the "substituted or unsubstituted lower alkyl" for $R^9$ may include lower alkyl similar to those exemplified for $R^1$ above.

Examples of the substituents for the "substituted lower alkyl for $R^9$ may include those exemplified as the substituents for the "substituted lower alkyl" for $R^{18}$ and $R^{19}$ mentioned below, in which the preferred are carboxy, hydroxy, $(C_{1-6})$alkoxycarbonyl, morpholino, morpholinocarbonyl or $(C_{1-6})$alkylsulfonyloxy.

Examples of the "lower alkanoyl" of the "substituted or unsubstituted lower alkanoyl" for $R^9$ may include $(C_{2-7})$ alkanoyl [e.g, $(C_{1-6})$alkyl-carbonyl (e.g. acetyl, ethylcarbonyl, propylcarbonyl, butylcarbonyl, pentylcarbonyl, hexylcarbonyl, etc.), etc.].

Examples of the substituents for the "substituted lower alkanoyl" for $R^9$ may include those exemplified as the substituents for the "substituted lower alkyl" for $R^{18}$ and $R^{19}$ mentioned below.

Preferred examples of $R^9$ may include hydrogen; $(C_{1-6})$ alkyl optionally substituted by carboxy, hydroxy, $(C_{1-6})$ alkoxycarbonyl, morpholino, morpholinocarbonyl or $(C_{1-6})$ alkylsulfonyloxy; $(C_{2-7})$alkanoyl, etc.

Alternatively, $R^6$ and $R^9$ may be taken together to form a bond.
(Definitions of m and n)

m and n are each 0, 1 or 2.
(Definitions of $R^{10}$ and $R^{11}$)

In the Formula (IV), $R^{10}$ is selected from the group consisting of hydrogen, halogen, hydroxy, formyl, cyano, substituted or unsubstituted lower alkyl, substituted or unsubstituted amino, substituted or unsubstituted lower alkoxy, saturated cyclic amino, substituted or unsubstituted carbamoyl, carboxy and substituted or unsubstituted lower alkoxycarbony.

Specifically, $R^{10}$ is hydrogen or substituted or unsubstituted lower alkyl.

Examples of the "lower alkyl" for the "substituted or unsubstituted lower alkyl" for $R^{10}$ may include lower alkyl similar to those exemplified for $R^1$ above, in which the preferred one may be $(C_{1-6})$alkyl and more preferred one may be methyl, ethyl, isopropyl, etc.

Examples of the substituents for the "substituted lower alkyl" for $R^{10}$ may include:
(1) hydroxy;
(2) arylalkoxy [e.g., $(C_{6-14})$aryl$(C_{1-6})$alkoxy such as benzyloxy, phenethyloxy, etc.];
(3) di$(C_{6-14})$aryl$(C_{1-6})$alkylsilyloxy (e.g., methyldiphenylsilyloxy, tert-butyldiphenylsilyloxy, etc.), etc.

Preferred examples of $R^{10}$ may include hydrogen, $(C_{1-6})$ alkyl optionally substituted by $(C_{6-14})$aryl$(C_{1-6})$alkoxy, di$(C_{6-14})$aryl$(C_{1-6})$alkylsilyloxy or hydroxy, etc.

Examples of the "substituted or unsubstituted amino", "substituted or unsubstituted lower alkoxy", "saturated cyclic amino", "substituted or unsubstituted carbamoyl" and "lower alkoxycarbonyl" for $R^{10}$ may be similar to the "substituted or unsubstituted amino", "substituted or unsubstituted lower alkoxy", "saturated cyclic amino", "substituted or unsubstituted carbamoyl" and "lower alkoxycarbonyl" exemplified above as the substituents for the "substituted lower alkyl" for $R^{12}$ mentioned below.

Alternatively, $R^9$ and $R^{10}$ may be taken together to form lower alkylene (e.g., $(C_{2-6})$alkylene such as ethylene, propylene, butylene, pentylene, hexylene, etc.), in which preferred may be propylene, etc.

$R^{11}$ is selected from the group consisting of hydrogen, halogen, substituted or unsubstituted lower alkyl, carboxy and substituted or unsubstituted lower alkoxycarbonyl.

Examples of the "halogen" for $R^{11}$ may include chloro, fluoro, bromo, iodo, etc.

Examples of the "lower alkyl" for the "substituted or unsubstituted lower alkyl" for $R^{11}$ may include lower alkyl similar to those exemplified for $R^1$ above, and examples of the "lower alkoxycarbonyl" for the "substituted or unsubstituted lower alkoxycarbonyl" for $R^{11}$ may include those exemplified above as the substituent (8) for the "substituted lower alkyl" for $R^{12}$ mentioned below. Examples of the substituents for "substituted lower alkyl" and "substituted lower alkoxycarbonyl" for $R^{11}$ may include those exemplified as the substituents for the "substituted lower alkyl" for $R^1$.

Specifically, $R^{11}$ is hydrogen, or lower alkyl.

Examples of the lower alkyl for $R^{11}$ may include lower alkyl similar to those exemplified for $R^1$ above, in which the preferred may be $(C_{1-4})$alkyl and more preferred may be methyl, ethyl, isopropyl, etc.

Alternatively, $R^{10}$ and $R^{11}$ may be taken together to form
(1) substituted or unsubstituted lower alkylene [e.g., $(C_{2-6})$alkylene (e.g., ethylene, propylene, butylene, pentylene, hexylene, etc., in which the preferred one may be ethylene, propylene, butylene, etc.)];
(2) substituted or unsubstituted lower alkylidene [e.g., $(C_{1-6})$alkylidene such as methylidene, ethylidene, propylidene, butylidene, pentylidene, hexylene, etc., in which the preferred one may be methylidene, ethylidene, propan-2-ylidene, etc.];
(3) oxo, or
(4) hydroxyimino, etc.

As used herein, the term "lower alkylene" in the phrase "substituted lower alkylene" formed by $R^{10}$ and $R^{11}$ may also include alkylene group as defined above in which one or more carbon atom(s) is (are) replaced by one or more heteroatom(s) selected from a nitrogen atom, an oxygen atom and a sulfur atom, and examples of such lower alkylene formed by $R^{10}$ and $R^{11}$ may include following groups such as, but not limited to, —$(CH_2)_2$—O—$(CH_2)_2$—, —$(CH_2)_2$—N—$(CH_2)_2$—, etc.

Examples of the substituents for the above-mentioned "substituted lower alkylene" formed together by $R^{10}$ and $R^{11}$ may include:
(1) arylalkoxycarbonyl [e.g., $(C_{6-14})$aryl$(C_{1-6})$alkoxycarbonyl such as benzyloxycarbonyl, phenetyloxycarbonyl, etc.];
(2) acyl [e.g., $(C_{1-7})$alkanoyl such as formyl, acetyl, propionyl, butyryl, etc., $(C_{6-14})$acyl such as benzoyl, etc.], etc.

Preferred examples of the "substituted or unsubstituted lower alkylene" formed by $R^{10}$ and $R^{11}$ may include $(C_{2-6})$alkylene in which one or more carbon atom(s) may be replaced with heteroatom(s) selected from an oxygen atom and a nitrogen atom, which is optionally substituted by $(C_{6-14})$aryl$(C_{1-6})$alkoxycarbonyl or $(C_{1-7})$alkanoyl.

Alternatively, $R^9$ and $R^{10}$ may be taken together to form lower alkylene or a bond.

Examples of the "lower alkylene" formed by $R^9$ and $R''$ may include $(C_{2-6})$alkylene, in which preferred are propylene, etc.

(Definitions of $R^{12}$, $R^{13}$ and $R^{14}$)

In the above-mentioned Formula (I), $R^{12}$ is selected from the group consisting of hydrogen, halogen, hydroxy, formyl, cyano, substituted or unsubstituted lower alkyl, substituted or unsubstituted amino, substituted or unsubstituted lower alkoxy, saturated cyclic amino, substituted or unsubstituted carbamoyl, carboxy and substituted or unsubstituted lower alkoxycarbonyl, substituted or unsubstituted acyloxy.

Examples of the "halogen" for $R^{12}$ may include chloro, fluoro, bromo, iodo, etc., in which the preferred one may be fluoro, etc.

Examples of the "lower alkyl" of the "substituted or unsubstituted lower alkyl" for $R^{12}$ may include lower alkyl similar to those exemplified above for $R^1$, in which the preferred one may be $(C_{1-4})$alkyl and more preferred one may be methyl, ethyl, isopropyl, etc.

Examples of the substituents for the "substituted lower alkyl" for $R^{12}$ may include:
(1) hydroxy, hydroxyimino or tri(lower)alkylsilyloxy;
(2) halogen (e.g., chloro, fluoro, bromo, iodo, etc.);
(3) substituted or unsubstituted amino [e.g., amino, mono- or di-(substituted or unsubstituted lower alkyl)amino (e.g., mono-$(C_{1-6})$alkylamino in which said $(C_{1-6})$alkyl may be substituted by $(C_{6-14})$aryl, $(C_{3-8})$cycloalkylcarbonyl or hydroxy (e.g., methylamino, ethylamino, propylamino, isopropylamino, butylamino, tert-butylamino, neopentylamino, hydroxymethylamino, hydroxyethylamino, cyclopropanecarbonylamino, etc.), di-$(C_{1-4})$alkylamino in which one or both of said $(C_{1-4})$alkyl may be substituted by $(C_{6-14})$aryl (e.g., dimethylamino, diethylamino, ethylmethylamino, etc.), 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, benzylmethylamino, tert-butylbenzylamino, dibenzylamino etc.), mono-$(C_{2-7})$ alkanoylamino (e.g., acetylamino, ethylcarbonylamino, propylcarbonylamino, isopropylcarbonylamino, butylcarbonylamino, pentylcarbonylamino, hexylcarbonylamino, etc.), $(C_{3-8})$cycloalkylamino (e.g., cyclopropylamino, cyclobutylamino, cyclopentylamino, cyclohexylamino, etc.), etc.];
(4) substituted or unsubstituted lower alkoxy (e.g., $(C_{1-6})$alkoxy (e.g., methoxy, ethoxy, propoxy, isopropoxy, butoxy, neopentyloxy, etc.), $(C_{6-14})$aryl$(C_{1-6})$ alkoxy (e.g., benzyloxy, etc.), 2-hydroxyethyloxy, 2-hydroxy-1,1-dimethylethyloxy, 2-methoxyethyloxy, 2-(dimethylamino)ethyloxy, etc.);
(5) saturated cyclic amino [e.g., 4-, 5- or 6-membered saturated cyclic amino which may further have heteroatom(s) selected from a nitrogen atom, an oxygen atom and a sulfur atom and/or oxo besides the amino nitrogen and may have substituent(s), such as azetidinyl (e.g., 3-hydroxy-1-azetidinyl, 3-amino-1-azetidinyl, 3-methylamino-1-azetidinyl, etc.), pyrrolidinyl (e.g., 1-pyrrolidinyl, 3-hydroxy-1-pyrrolidinyl, 3-amino-1-pyrrolidinyl, 3-methylamino-1-pyrrolidinyl, etc.), morpholinyl (e.g., morpholino, etc.), 4-(lower)alkyl-1-piperazinyl (e.g., 4-methyl-1-piperazinyl, 4-isopropyl-1-piperazinyl, etc.), 4-(mono- or di-(lower)alkylamino)-1-piperidinyl (e.g., 4-(dimethylamino)-1-piperidinyl, etc.), oxopyrrolidinyl (e.g., 2-oxo-1-pyrrolidinyl, etc.), etc.];
(6) substituted or unsubstituted carbamoyl [e.g., carbamoyl, (lower)alkylcarbamoyl (e.g., $(C_{1-4})$alkylcarbamoyl such as methylcarbamoyl, ethylcarbamoyl, propylcarbamoyl, isopropylcarbamoyl, butylcarbamoyl, etc.), $(C_{3-8})$cycloalkylcarbamoyl (e.g., cyclopropylcarbamoyl, etc.), etc.];
(7) carboxy;
(8) lower alkoxycarbonyl [e.g., $(C_{1-6})$alkoxycarbonyl (e.g., methoxycarbonyl, ethoxycarbonyl, propyloxycarbonyl, tert-butoxycarbonyl, pentyloxycarbamoyl, hexyloxycarbamoyl, etc.), etc.];
(9) lower alkylureido [e.g., $(C_{1-6})$alkylureido (e.g., methylureido, ethylureido, etc.)]
(10) lower acyloxy [e.g., $(C_{1-7})$alkanoyloxy (e.g., formyloxy, acetyloxy, ethylcarbonyloxy, propylcarbonyloxy, butylcarbonyloxy, pentylcarbonyloxy, hexylcarbonyloxy, etc.], etc.

The number of the substituent may be one, two or more. Where the number of the substituent is two or more, the substituents may be the same or different.

Examples of the "substituted or unsubstituted amino", "saturated cyclic amino", "substituted or unsubstituted lower alkoxy", "substituted or unsubstituted carbamoyl" and "lower alkoxycarbonyl" for $R^{12}$ may be similar to the "substituted or unsubstituted amino", "saturated cyclic amino", "substituted or unsubstituted lower alkoxy", "substituted or unsubstituted carbamoyl" and "substituted or unsubstituted lower alkoxycarbonyl" exemplified above as the substituents of the "substituted lower alkyl" for $R^{12}$.

Examples of the "acyloxy" for the "substituted or unsubstituted acyloxy" for $R^{12}$ may include lower acyloxy similar to those exemplified above as the substituent (10) for the "substituted lower alkyl" for $R^{12}$ mentioned above.

Examples of the substituents for the "substituted acyloxy" for $R^{12}$ may be similar to those exemplified as the substituents for the "substituted lower alkyl" for $R^{12}$.

Preferable examples for $R^{12}$ may include hydrogen; halogen; hydroxy; carboxy; formyl; cyano; hydroxycyano; $(C_{1-6})$alkyl optionally substituted by hydroxy, hydroxyimino, halogen, $(C_{1-6})$alkoxy, $(C_{1-7})$alkanoyloxy, amino, mono- or di-$(C_{1-6})$alkylamino (in which one or both of said $(C_{1-6})$alkyl is (are) optionally substituted by hydroxy, $(C_{1-6})$alkoxy, $(C_{6-14})$aryl or $(C_{3-6})$cycloalkyl-carbonyl), $(C_{1-6})$ alkylureido, morpholino, $(C_{1-7})$alkanoyloxy, or 4- to 6-membered cyclic amino optionally substituted by hydroxy, $(C_{1-6})$alkyl or di$(C_{1-6})$alkylamino; mono- or di-$(C_{1-7})$alkylamino; 4- to 6-membered cyclic amino; $(C_{1-6})$ alkoxy optionally substituted by $(C_{6-14})$aryl; carbamoyl optionally substituted by $(C_{3-6})$cycloalkyl or hydroxy$(C_{1-6})$ alkyl; $(C_{1-6})$alkoxycarbonyl; $(C_{1-6})$alkoxycarbonyloxy, etc.

Among the above-mentioned substituents, suitable examples of $R^{12}$ may include hydrogen, fluoro, hydroxy, formyl, cyano, methyl, aminomethyl, tert-butylaminomethyl, dimethylaminomethyl, diethylaminomethyl, dibenzylaminomethyl, benzylmethylaminomethyl, benzyl(tert-butyl)aminomethyl, methoxycarbonylmethyl, 3-hydroxyazetinylmethyl, 4-methylpiperazinylmethyl, pyrrolidinylmethyl, hydroxymethyl, hydroxyethylaminomethyl, methoxyethylaminomethyl, iodomethyl, methylaminomethyl, morpholinomethyl, (2-hydroxyethyl)methylaminomethyl, acetyloxymethyl, 4-(dimethylamino)-1-piperidinylmethyl, ethoxycarbonylmethyl, cyclopropylcarbamoylmethyl, ethylureidomethyl, hydroxyiminomethyl, dimethylamino, isopropylamino, 3-hydroxy-1-azetidinyl, piperidino, morpholino, benzyloxy, neopentyloxy, carboxy, methoxycarbonyl, ethoxycarbonyl, tert-butoxycarbonyl, carbamoyl, cyclopropylcarbamoyl, etc.

$R^{13}$ is selected from the group consisting of hydrogen, halogen, substituted or unsubstituted lower alkyl, carboxy and substituted or unsubstituted lower alkoxycarbonyl.

Examples of the "halogen" and "substituted or unsubstituted lower alkoxycarbonyl" for $R^{13}$ may be similar to those exemplified for $R^{11}$.

Examples of the "lower alkyl" of the "substituted or unsubstituted lower alkyl" for $R^{13}$ may include lower alkyl similar to those exemplified above for $R^1$, in which the preferred one may be $(C_{1-4})$alkyl, and more preferred one may be methyl, ethyl, isopropyl, etc.

Examples of the substituents for the "substituted lower alkyl" for $R^{13}$ may include (1) hydroxy;

(2) halogen (e.g., chloro, fluoro, bromo, iodo, etc.);

(3) substituted or unsubstituted amino [e.g., amino, mono- or di-(substituted or unsubstituted lower alkyl)amino (e.g., mono-$(C_{1-6})$alkylamino (e.g., methylamino, ethylamino, propylamino, isopropylamino, butylamino, tert-butylamino, neopentylamino, etc.), di-$(C_{1-4})$alkylamino (e.g., dimethylamino, diethylamino, ethylmethylamino, etc.), 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, etc.), mono-(C2-7)alkanoylamino (e.g., acetylamino, ethylcarbonylamino, propylcarbonylamino, isopropylcarbonylamino, butylcarbonylamino, pentylcarbonylamino, hexylcarbonylamino, etc.), $(C_{3-8})$cycloalkylamino (e.g., cyclopropylamino, cyclobutylamino, cyclopentylamino, cyclohexylamino, etc.), etc.];

(4) substituted or unsubstituted lower alkoxy [e.g., $(C_{1-4})$alkoxy (e.g., methoxy, ethoxy, propoxy, isopropoxy, butoxy, etc.), 2-hydroxyethyloxy, 2-hydroxy-1,1-dimethylethyloxy, 2-methoxyethyloxy, 2-(dimethylamino)ethyloxy, etc.];

(5) lower alkanoyloxy [e.g., $(C_{1-7})$alkanoyloxy [e.g., formyloxy, acetyloxy, ethylcarbonyloxy, propylcarbonyloxy, butylcarbonyloxy, pentylcarbonyloxy, hexylcarbonyloxy, etc.]; etc.

The number of the substituent may be one, two or more. Where the number of the substituent is two or more, the substituents may be the same or different.

Suitable examples of $R^{13}$ may include hydrogen, halogen (e.g., fluoro, etc.), $(C_{1-6})$alkyl optionally substituted by hydroxy, fluoro, halogen, $(C_{1-6})$alkoxy or $(C_{1-7})$alkanoyl (e.g., methyl, hydroxymethyl, fluoromethyl, methoxymethyl, acetyloxymethyl, etc.), in which preferred are hydrogen, halogen or $(C_{1-6})$alkyl optionally substituted by hydroxy or $(C_{1-7})$alkanoyloxy (e.g., hydroxymethyl, acetyloxymethyl, etc.), etc.

$R^{14}$ is selected from the group consisting of hydrogen, halogen, substituted or unsubstituted lower alkyl, carboxy and substituted or unsubstituted lower alkoxycarbonyl.

The "halogen", "substituted or unsubstituted lower alkyl" and "substituted or unsubstituted lower alkoxycarbonyl" for $R^{14}$ may be similar to those exemplified for $R^{11}$.

Preferably, $R^{14}$ is hydrogen.

Alternatively, $R^{12}$ and $R^{13}$ may be taken together to form (1) substituted or unsubstituted lower alkylene [e.g., $(C_{2-6})$alkylene (e.g., ethylene, propylene, butylene, pentylene, hexylene, etc., in which the preferred one may be ethylene, propylene, butylene, etc.)];

(2) substituted or unsubstituted lower alkylidene (e.g., $(C_{1-6})$alkylidene such as methylidene, ethylidene, propylidene, butylidene, pentylidene, hexylidene, etc., in which the preferred one may be methylidene, ethylidene, propan-2-ylidene, etc.];

(3) oxo, or (4) hydroxyimino.

The term "lower alkylene" in the phrase "substituted or unsubstituted lower alkylene" for $R^{12}$ and $R^{13}$ refers to alkylene group as defined above in which one or more carbon atom(s) is (are) replaced by one or more heteroatom(s) selected from a nitrogen atom, an oxygen atom and a sulfur atom Examples of the substituents for the above-mentioned "substituted lower alkylene" formed by $R^{12}$ and $R^{13}$ may include (1) substituents for "substituted or unsubstituted lower alkyl" for $R^{12}$; and (2) substituted or unsubstituted lower alkyl [e.g., substituted or unsubstituted $(C_{1-6})$alkyl (e.g., methyl, ethyl, propyl, isopropyl, n-butyl, tert-butyl, pentyl, hexyl, etc.), examples of the substituent may include the substituents for the "substituted or unsubstituted lower alkyl" for $R^{12}$]

Suitable examples of the "substituted or unsubstituted lower alkylene" formed by $R^{12}$ and $R^{13}$ may include following groups such as, but not limited to:

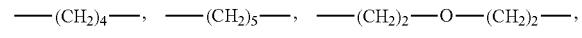
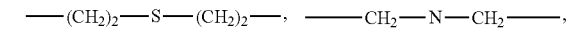
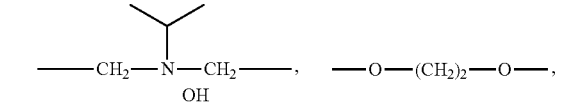
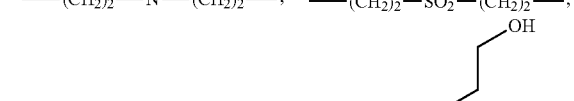
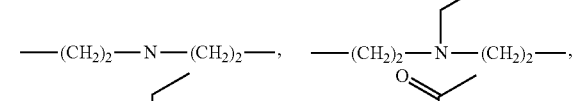
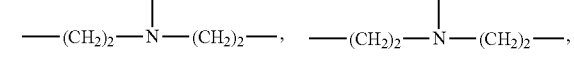

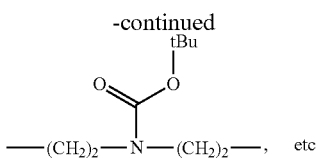

Examples of the substituents for the above-mentioned "substituted lower alkylidene" formed by $R^{12}$ and $R^{13}$ may be similar to those exemplified for the "substituted or unsubstituted alkylene" formed by $R^{12}$ and $R^{13}$.

Suitable examples of the "substituted or unsubstituted lower alkylidene" formed by $R^{12}$ and $R^{13}$ may include ($C_{1-6}$)alkylidene optionally substituted by hydroxy, such as the following groups, but not limited to, —$CH_2$=CH—$CH_3$=CH—$CH_2$—OH, etc.

Alternatively, $R^{11}$ and $R^{12}$ or $R^{13}$ and $R^{14}$ may be taken together to form a bond.

In an embodiment of the present invention, $R^6$ and $R^7$ are taken together to form the following structure (A), (B1) or (B2).

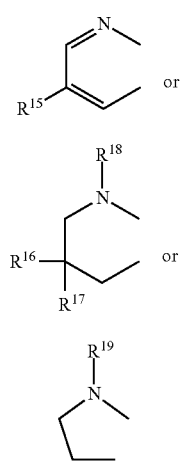

(Definition of $R^{15}$)

In the above-mentioned Formula (A), $R^{15}$ is selected from the group consisting of hydroxy, substituted or unsubstituted lower alkyl, substituted or unsubstituted amino, substituted or unsubstituted lower alkoxy, saturated cyclic amino, lower substituted or unsubstituted carbamoyl, carboxy and substituted or unsubstituted lower alkoxycarbonyl.

Examples of the "lower alkyl" of the "substituted or unsubstituted lower alkyl" for $R^{15}$ may include lower alkyl similar to those exemplified for $R^1$ above, in which the preferred one may be ($C_{1-4}$)alkyl and more preferred one may be methyl, ethyl, isopropyl, etc.

Examples of the substituents for the "substituted lower alkyl" for $R^{15}$ may include:

(1) hydroxy;
(2) substituted or unsubstituted amino [e.g., amino, mono or di-(substituted or unsubstituted lower alkyl)amino (e.g., mono-($C_{1-6}$)alkylamino such as methylamino, ethylamino, propylamino, isopropylamino, butylamino, tert-butylamino, neopentylamino, etc.; di-($C_{1-4}$)alkylamino such as dimethylamino, diethylamino, ethylmethylamino, etc.; 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, etc.), mono-($C_{2-5}$)alkanoylamino (e.g., acetylamino, ethylcarbonylamino, propylcarbonylamino, isopropylcarbonylamino, butylcarbonylamino, etc.), ($C_{3-6}$)cycloalkylamino (e.g., cyclopropylamino, cyclobutylamino, cyclopentylamino, cyclohexylamino, etc.), etc.);
(3) substituted or unsubstituted lower alkoxy [e.g., ($C_{1-4}$)alkoxy (e.g., methoxy, ethoxy, propoxy, isopropoxy, butoxy, etc.), 2-hydroxyethyloxy, 2-hydroxy-1,1-dimethylethyloxy, 2-methoxyethyloxy, 2-(dimethylamino)ethyloxy, etc.];
(4) saturated cyclic amino [e.g., 4-, 5- or 6-membered saturated cyclic amino which may further have heteroatom(s) selected from a nitrogen atom, an oxygen atom and a sulfur atom and/or oxo besides the amino nitrogen and may have substituent(s), such as azetidinyl (e.g., 3-hydroxy-1-azetidinyl, 3-amino-1-azetidinyl), pyrrolidinyl (e.g., 1-pyrrolidinyl, etc.), morpholinyl (e.g., morpholino, etc.), 4-(lower)alkyl-1-piperazinyl (e.g., 4-methyl-1-piperazinyl, 4-isopropyl-1-piperazinyl, etc.), oxopyrrolidinyl (e.g., 2-oxo-1-pyrrolidinyl, etc.), etc.];
(5) substituted or unsubstituted carbamoyl [e.g., carbamoyl, (lower)alkylcarbamoyl (e.g., ($C_{1-4}$)alkylcarbamoyl such as methylcarbamoyl, ethylcarbamoyl, propylcarbamoyl, isopropylcarbamoyl, butylcarbamoyl, etc.), etc.],
(6) carboxy;
(7) lower alkoxycarbonyl [e.g., ($C_{1-6}$)alkoxycarbonyl (e.g., methoxycarbonyl, ethoxycarbonyl, tert-butoxycarbonyl, pentyloxycarbonyl, hexyloxycarbonyl), etc.], etc. The number of the substituent may be one, two or more. Where the number of the substituent is two or more, the substituents may be the same or different.

Examples of the "substituted or unsubstituted amino", "substituted or unsubstituted lower alkoxy", "saturated cyclic amino", "substituted or unsubstituted carbamoyl" and "lower alkoxycarbonyl" for $R^{15}$ may be similar to the "substituted or unsubstituted amino", "substituted or unsubstituted lower alkoxy", "saturated cyclic amino", "substituted or unsubstituted carbamoyl" and "lower alkoxycarbonyl" exemplified above as the substituents for the "substituted lower alkyl" for $R^{15}$.

Suitable examples of $R^{15}$ may include dimethylaminomethyl, methylaminomethyl, hydroxymethyl, morpholino, 3-hydroxyl-azetidinyl, etc.

(Definitions of $R^{16}$ and $R^{17}$)

In the above-mentioned Formula (B1), $R^{16}$ is selected from the group consisting of hydrogen, halogen, hydroxy, substituted or unsubstituted lower alkyl, substituted or unsubstituted amino, saturated cyclic amino, substituted or unsubstituted lower alkoxy, substituted or unsubstituted carbamoyl, carboxy and lower alkoxycarbonyl.

Examples of the "halogen" for $R^{16}$ may include chloro, fluoro, bromo, iodo, etc., in which the preferred one may be fluoro, etc.

Examples of the "lower alkyl" of the "substituted or unsubstituted lower alkyl" for $R^{16}$ may include lower alkyl similar to those exemplified for $R^1$ above, in which the preferred one may be ($C_{1-4}$)alkyl and more preferred one may be methyl, ethyl, isopropyl, etc.

Examples of the substituents for the "substituted lower alkyl" for $R^{16}$ may include:
(1) hydroxy or tri(lower)alkylsilyloxy;
(2) halogen (e.g., chloro, fluoro, bromo, iodo, etc.);

(3) substituted or unsubstituted amino [e.g., amino, mono- or di-(substituted or unsubstituted lower alkyl)amino (e.g., mono-($C_{1-6}$)alkylamino (e.g., methylamino, ethylamino, propylamino, isopropylamino, butylamino, tert-butylamino, neopentylamino, etc.), di-($C_{1-4}$)alkylamino (e.g., dimethylamino, diethylamino, ethylmethylamino, etc.), 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, etc.), mono-($C_{2-5}$)alkanoylamino (e.g., acetylamino, ethylcarbonylamino, propylcarbonylamino, isopropylcarbonylamino, butylcarbonylamino, etc.), ($C_{3-8}$) cycloalkylamino (e.g., cyclopropylamino, cyclobutylamino, cyclopentylamino, cyclohexylamino, etc.), etc.];

(4) substituted or unsubstituted lower alkoxy (e.g., ($C_{1-4}$) alkoxy (e.g., methoxy, ethoxy, propoxy, isopropoxy, butoxy, etc.), 2-hydroxyethyloxy, 2-hydroxy-1,1-dimethylethyloxy, 2-methoxyethyloxy, 2-(dimethylamino)ethyloxy, etc.);

(5) saturated cyclic amino [e.g., 4-, 5- or 6-membered saturated cyclic amino which may further have heteroatom(s) selected from a nitrogen atom, an oxygen atom and a sulfur atom and/or oxo besides the amino nitrogen and may have substituent(s), such as azetidinyl (e.g., 3-hydroxy-1-azetidinyl, 3-amino-1-azetidinyl, 3-methylamino-1-azetidinyl, etc.), pyrrolidinyl (e.g., 1-pyrrolidinyl, 3-hydroxy-1-pyrrolidinyl, 3-amino-1-pyrrolidinyl, 3-methylamino-1-pyrrolidinyl, etc.), morpholinyl (e.g., morpholino, etc.), 4-(lower)alkyl-1-piperazinyl (e.g., 4-methyl-1-piperazinyl, 4-isopropyl-1-piperazinyl, etc.), 4-(mono- or di-(lower)alkylamino)-1-piperidinyl (e.g., 4-(dimethylamino)-1-piperidinyl, etc.), oxopyrrolidinyl (e.g., 2-oxo-1-pyrrolidinyl, etc.), etc.];

(6) substituted or unsubstituted carbamoyl [e.g., carbamoyl, (lower)alkylcarbamoyl (e.g., ($C_{1-4}$)alkylcarbamoyl such as methylcarbamoyl, ethylcarbamoyl, propylcarbamoyl, isopropylcarbamoyl, butylcarbamoyl, etc.), etc.];

(7) carboxy;

(8) lower alkoxycarbonyl [e.g., ($C_{1-4}$)alkoxycarbonyl (e.g., methoxycarbonyl, ethoxycarbonyl, tert-butoxycarbonyl, etc.), etc.], etc. The number of the substituent may be one or two or more. Where the number of the substituent is two or more, the substituents may be the same or different.

Examples of the "substituted or unsubstituted amino", "saturated cyclic amino", "substituted or unsubstituted lower alkoxy", "substituted or unsubstituted carbamoyl" and "lower alkoxycarbonyl" for $R^{16}$ may be similar to the "substituted or unsubstituted amino", "saturated cyclic amino", "substituted or unsubstituted lower alkoxy", "substituted or unsubstituted carbamoyl" and "lower alkoxycarbonyl" exemplified as the substituents of the "substituted or unsubstituted lower alkyl" for $R^7$.

Suitable examples of $R^{16}$ may include hydrogen, fluoro, hydroxy, dimethylaminomethyl, hydroxymethyl, iodomethyl, 4-(dimethylamino)-1-piperidinylmethyl, dimethylamino, piperidino, isopropylamino, methylaminomethyl, morpholinomethyl, (2-hydroxyethyl)methylaminomethyl, morpholino, carboxy, methoxycarbonyl, tert-butoxycarbonyl, 3-hydroxy-1-azetidinyl, etc.

In the above-mentioned Formula (B1), $R^{17}$ is selected from the group consisting of hydrogen, halogen, substituted or unsubstituted lower alkyl, carboxy and lower alkoxycarbonyl.

Examples of the "halogen" for $R^{17}$ may include chloro, fluoro, bromo, iodo, etc., in which the preferred one may be fluoro, etc.

Examples of the "lower alkyl" of the "substituted or unsubstituted lower alkyl" for $R^{17}$ may include lower alkyl similar to those exemplified for $R^1$ above, in which the preferred one may be ($C_{1-4}$)alkyl, and more preferred one may be methyl, ethyl, isopropyl, etc.

Examples of the substituents for the "lower alkyl" for $R^{17}$ may include (1) hydroxy;

(2) halogen (e.g., chloro, fluoro, bromo, iodo, etc.);

(3) substituted or unsubstituted amino [e.g., amino, mono- or di-(substituted or unsubstituted lower alkyl)amino (e.g., mono-($C_{1-6}$)alkylamino (e.g., methylamino, ethylamino, propylamino, isopropylamino, butylamino, t-butylamino, neopentylamino, etc.), di-($C_{1-4}$)alkylamino (e.g., dimethylamino, diethylamino, ethylmethylamino, etc.), 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, etc.), mono-($C_{2-5}$)alkanoylamino (e.g., acetylamino, ethylcarbonylamino, propylcarbonylamino, isopropylcarbonylamino, butylcarbonylamino, etc.), ($C_{3-8}$) cycloalkylamino (e.g., cyclopropylamino, cyclobutylamino, cyclopentylamino, cyclohexylamino, etc.), etc.];

(4) substituted or unsubstituted lower alkoxy [e.g., ($C_{1-4}$)alkoxy (e.g., methoxy, ethoxy, propoxy, isopropoxy, butoxy, etc.), 2-hydroxyethyloxy, 2-hydroxy-1,1-dimethylethyloxy, 2-methoxyethyloxy, 2-(dimethylamino)ethyloxy, etc.], etc. The number of the substituent may be one or two or more. Where the number of the substituent is two or more, the substituents may be the same or different.

Suitable examples of $R^{17}$ may include hydrogen, methyl, hydroxymethyl, fluoro, fluoromethyl, methoxymethyl, etc.

Alternatively, $R^{16}$ and $R^{17}$ are taken together to form lower alkylene or lower alkylidene.

Examples of the "lower alkylene" for $R^{16}$ and $R^{17}$ may include ($C_{2-6}$)alkylene such as ethylene, propylene, butylene, pentylene, hexylene, etc., in which the preferred one may be ethylene, propylene, butylene, etc.

Examples of the "lower alkylidene" for $R^{16}$ and $R^{17}$ may include ($C_{1-6}$)alkylidene such as methylidene, ethylidene, propylidene, butylidene, pentylidene, hexylene, etc., in which the preferred one may be methylidene, ethylidene, propan-2-ylidene, etc.

(Definition of $R^{18}$)

In the above-mentioned Formula (B1), $R^{18}$ is hydrogen or substituted or unsubstituted lower alkyl; provided that when both $R^{16}$ and $R^{17}$ are simultaneously hydrogen, $R^1$ is substituted or unsubstituted lower alkyl.

Examples of the "lower alkyl" of the "substituted or unsubstituted lower alkyl" for R18 may include lower alkyl similar to those exemplified for $R^1$ above, in which the preferred one may be ($C_{1-4}$)alkyl and more preferred one may be ethyl, propyl, etc.

Examples of the substituents for the "substituted lower alkyl" for $R^{18}$ may include (1) hydroxy;

(2) carboxy;

(3) halogen (chloro, fluoro, bromo, iodo);

(4) (lower)alkoxycarbonyl [e.g., ($C_{1-6}$)alkoxycarbonyl (e.g., methoxycarbonyl, ethoxycarbonyl, propoxycarbonyl, butoxycarbonyl, t-butoxycarbonyl, pentyloxycarbonyl, hexyloxycarbonyl, etc.), etc.];
(5) substituted or unsubstituted amino (e.g., amino, mono- or di-(substituted or unsubstituted lower alkyl)amino (e.g., mono-($C_{1-6}$)alkylamino (e.g., methylamino, ethylamino, propylamino, isopropylamino, butylamino, tert-butylamino, neopentylamino, etc.), di-($C_{1-4}$)alkylamino (e.g., dimethylamino, diethylamino, ethylmethylamino, etc.), 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, etc.), mono-($C_{2-5}$)alkanoylamino (e.g., acetylamino, ethylcarbonylamino, propylcarbonylamino, isopropylcarbonylamino, butylcarbonylamino, etc.), ($C_{3-9}$)cycloalkylamino (e.g., cyclopropylamino, cyclobutylamino, cyclopentylamino, cyclohexylamino, etc.), etc.];
(6) substituted or unsubstituted lower alkoxy [e.g., ($C_{1-4}$)alkoxy (e.g., methoxy, ethoxy, propoxy, isopropoxy, butoxy, etc.), 2-hydroxyethyloxy, 2-hydroxy-1,1-dimethylethyloxy, 2-methoxyethyloxy, 2-(dimethylamino)ethyloxy, etc.];
(7) saturated cyclic amino [e.g., 4, 5- or 6-membered saturated cyclic amino which may further have heteroatom(s) selected from a nitrogen atom, an oxygen atom and a sulfur atom and/or oxo besides the amino nitrogen and may have substituent(s), such as azetidinyl (e.g., 3-hydroxy-1-azetidinyl, 3-amino-1-azetidinyl, 3-methylamino-1-azetidinyl, etc.), pyrrolidinyl (e.g., 1-pyrrolidinyl, 3-hydroxy-1-pyrrolidinyl, 3-amino-1-pyrrolidinyl, 3-methylamino-1-pyrrolidinyl, etc.), morpholinyl (e.g., morpholino, etc.), 4-(lower)alkyl-1-piperazinyl (e.g., 4-methyl-1-piperazinyl, 4-isopropyl-1-piperazinyl, etc.), 4-(mono- or di-(lower)alkylamino)-1-piperidinyl (e.g., 4-(dimethylamino)-1-piperidinyl, etc.), oxopyrrolidinyl (e.g., 2-oxo-1-pyrrolidinyl, etc.), etc.];
(8) lower alkylsulfonyloxy [e.g., ($C_{1-6}$)alkylsulfonyloxy (e.g., methylsulfonyloxy, ethylsulfonyloxy, propylsulfonyloxy, butylsulfonyloxy, pentylsulfonyloxy, hexylsulfonyloxy, etc.), etc.];
(9) substituted or unsubstituted arylsulfonyloxy (e.g., p-toluenesulfonyloxy, benzenesulfonyloxy, mesitylenesulfonyloxy, etc.), etc. The number of the substituent may be one or two or more. Where the number of the substituent is two or more, the substituents may be the same or different.

Suitable examples of $R^{18}$ may include hydrogen, methyl, ethyl, tert-butoxycarbonylethyl, carboxyethyl, hydroxypropyl, methoxyethyl, hydroxyethyl, dimethylaminopropyl, etc.
(Definition of $R^{19}$)

In the above-mentioned Formula (B2), $R^{19}$ is hydrogen or substituted or unsubstituted lower alkyl.

Examples of the "lower alkyl" of the "substituted or unsubstituted lower alkyl" for R19 may include lower alkyl similar to those exemplified for $R^1$ above, in which the preferred one may be ($C_{1-14}$)alkyl and more preferred one may be ethyl, propyl, etc.

Examples of the substituents for the "substituted lower alkyl" for $R^{19}$ may include
(1) hydroxy;
(2) carboxy;
(3) (lower)alkoxycarbonyl [e.g., ($C_{1-6}$)alkoxycarbonyl (e.g., methoxycarbonyl, ethoxycarbonyl, propoxycarbonyl, butoxycarbonyl, pentyloxycarbonyl, hexyloxycarbonyl, etc.), etc.];

(4) saturated cyclic amino [e.g., 4-, 5- or 6-membered saturated cyclic amino which may further have heteroatom(s) selected from a nitrogen atom, an oxygen atom and a sulfur atom and/or oxo besides the amino nitrogen and may have substituent(s), such as azetidinyl (e.g., 3-hydroxy-1-azetidinyl, 3-amino-1-azetidinyl, etc.), morpholinyl (e.g., morpholino, etc.), etc.];
(5) (saturated cyclic amino)carbonyl [e.g., a group in which the saturated cyclic amino as exemplified in (4) above is attached to a carbonyl group (e.g., morpholinocarbonyl, etc.), etc.];
(6) (lower)alkylsulfonyloxy [e.g., ($C_{1-6}$)alkylsulfonyloxy (e.g., methylsulfonyloxy, ethylsulfonyloxy, propylsulfonyloxy, butylsulfonyloxy, pentylcarbonyloxy, hexylcarbonyloxy, etc.), etc.];
(7) substituted or unsubstituted amino [e.g., amino, mono- or di-(substituted or unsubstituted lower alkyl)amino (e.g., mono-($C_{1-6}$)alkylamino (e.g., methylamino, ethylamino, propylamino, isopropylamino, butylamino, tert-butylamino, neopentylamino, etc.), di-($C_{1-4}$)alkylamino (e.g., dimethylamino, diethylamino, ethylmethylamino, etc.), 2-hydroxyethylamino, 2-methoxyethylamino, 2-(dimethylamino)ethylamino, 2-hydroxy-1,1-dimethylethylamino, 2-hydroxy-1-(hydroxymethyl)ethylamino, (2-hydroxyethyl)methylamino, (2-methoxyethyl)methylamino, etc.), mono-($C_{2-5}$)alkanoylamino (e.g., acetylamino, ethylcarbonylamino, propylcarbonylamino, isopropylcarbonylamino, butylcarbonylamino, etc.), ($C_{3-8}$) cycloalkylamino (e.g., cyclopropylamino, cyclobutylamino, cyclopentylamino, cyclohexylamino, etc.), etc.),
(8) substituted or unsubstituted arylsulfonyloxy (e.g., p-toluenesulfonyloxy, benzenesulfonyloxy, mesitylenesulfonyloxy, etc.);
(9) halogen (e.g., chloro, fluoro, bromo, iodo, etc.), etc. The number of the substituent may be one or two or more. Where the number of the substituent is two or more, the substituents may be the same or different.

Suitable examples of $R^{19}$ may include methyl, ethyl, propyl, methoxyethyl, methoxypropyl, hydroxyethyl, ethoxycarbonylethyl, carboxyethyl, hydroxypropyl, morpholinocarbonylethyl, methylsulfonyloxypropyl, morpholinopropyl, methylaminopropyl, dimethylaminopropyl, etc.

Genus V Description

Compounds of Genus V can be prepared according to the disclosure of U.S. Pat. No. 7,125,898, which is herein incorporated herein by reference in its entirety.

Genus V is characterized by compounds of Formula V:

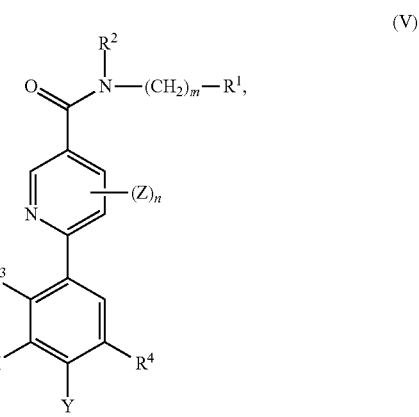

(V)

or stereoisomers thereof, isotopically-enriched compounds thereof, prodrugs thereof, solvates thereof, and pharmaceutically acceptable salts thereof;
wherein:
$R^1$ is selected from hydrogen, $C_{1-6}$alkyl optionally substituted by up to three groups selected from $C_{1-6}$alkoxy, halogen and hydroxy, $C_{2-6}$alkenyl, $C_{3-7}$cycloalkyl optionally substituted by one or more $C_{1-6}$alkyl groups, phenyl optionally substituted by up to three groups selected from $R^5$ and $R^6$, and heteroaryl optionally substituted by up to three groups selected from $R^5$ and $R^6$,
$R^2$ is selected from hydrogen, $C_{1-6}$alkyl and —$(CH_2)_q$—$C_{3-7}$cycloalkyl optionally substituted by one or more $C_{1-6}$alkyl groups, or
—$(CH_2)_m R^1$ and $R^2$ taken together with the nitrogen atom to which they are bound, form a 4-6-membered heterocyclic ring optionally substituted by up to three $C_{1-6}$alkyl groups;
$R^3$ is chloro or methyl;
$R^4$ is —NH—CO—$R^7$ or —CO—NH—$(CH_2)_q$—$R^1$;
$R^5$ is selected from $C_{1-6}$alkyl, $C_{1-6}$alkoxy, —$(CH_2)_q$—$C_{3-7}$cycloalkyl optionally substituted by one or more $C_{1-6}$alkyl groups, —$CONR^9R^{10}$, —$NHCOR^{10}$, —$SO_2NHR^9$, $(CH_2)_s NHSO_2R^{10}$, halogen, —CN, —OH, —$(CH_2)_s NR^{11}R^{12}$, and trifluoromethyl;
$R^6$ is selected from $C_{1-6}$alkyl, $C_{1-6}$alkoxy, halogen, trifluoromethyl, and —$(CH_2)_s NR^{11}R^{12}$;
$R^7$ is selected from hydrogen, $C_{1-6}$alkyl, —$(CH_2)_q$—$C_{3-7}$cycloalkyl optionally substituted by one or more $C_{1-6}$alkyl groups, trifluoromethyl, —$(CH_2)_r$-heteroaryl optionally substituted by $R^{13}$ and/or $R^{14}$, and —$(CH_2)_r$-phenyl optionally substituted by $R^{13}$ and/or $R^{14}$;
$R^8$ is selected from hydrogen, $C_{1-6}$alkyl, $C_{3-7}$cycloalkyl optionally substituted by one or more $C_{1-6}$alkyl groups, —$CONHR^9$, phenyl optionally substituted by $R^{13}$ and/or $R^{14}$, and heteroaryl optionally substituted by $R^{13}$ and/or $R^{14}$;
$R^9$ and $R^{10}$ are each independently selected from hydrogen and $C_{1-6}$alkyl, or
$R^9$ and $R^{10}$ taken together with the nitrogen atom to which they are bound, form a 5- or 6-membered heterocyclic ring optionally containing one additional heteroatom selected from oxygen, sulfur and N—$R^{15}$, wherein the ring may be substituted by up to two $C_{1-6}$ alkyl groups;
$R^{11}$ is selected from hydrogen, $C_{1-6}$alkyl and —$(CH_2)_q$—$C_{3-7}$cycloalkyl optionally substituted by one or more $C_{1-6}$alkyl groups,
$R_{12}$ is selected from hydrogen and $C_{1-6}$alkyl, or
$R^{11}$ and $R^{12}$ taken together with the nitrogen atom to which they are bound, form a 5- or 6-membered heterocyclic ring optionally containing one additional heteroatom selected from oxygen, sulfur and N—$R^{15}$;
$R^{13}$ is selected from $C_{1-6}$alkyl, $C_{1-6}$alkoxy, —$(CH_2)_q$—$C_{3-7}$cycloalkyl optionally substituted by one or more $C_{1-6}$alkyl groups, —$CONR^9R^{10}$, —$NHCOR^{10}$, halogen, —CN, —$(CH_2)_s NR^{11}R^{12}$, trifluoromethyl, phenyl optionally substituted by one or more $R^{14}$ groups and heteroaryl optionally substituted by one or more $R^{14}$ groups;
$R^{14}$ is selected from $C_{1-6}$alkyl, $C_{1-6}$alkoxy, halogen, trifluoromethyl and —$NR^{11}R^{12}$;
$R^{15}$ is selected from hydrogen and methyl;
X and Y are each independently selected from hydrogen, methyl and halogen;
Z is halogen;
m is selected from 0, 1, 2, 3 and 4, wherein each carbon atom of the resulting carbon chain may be optionally substituted with up to two groups selected independently from $C_{1-6}$alkyl and halogen;
n is selected from 0, 1 and 2;
q is selected from 0, 1 and 2;
r is selected from 0 and 1; and
s is selected from 0, 1, 2 and 3.

In one embodiment, the p38 kinase inhibitor from Genus V is selected from the following:
6-(5-cyclopropylcarbamoyl-3-fluoro-2-methyl-phenyl)-N-cyclopropylmethyl-nicotinamide;
6-(5-cyclopropylcarbamoyl-3-fluoro-2-methyl-phenyl)-N-(1-cyclopropylethyl)nicotinamide;
6-(5-cyclopropylcarbamoyl-3-fluoro-2-methyl-phenyl)-N-(2,2-dimethylpropyl)nicotinamide;
6-(5-cyclopropylcarbamoyl-3-fluoro-2-methyl-phenyl)-N-(2-methylpropyl)nicotinamide; and
6-(5-cyclopropylcarbamoyl-3-fluoro-2-methyl-phenyl)-N-(1-methylpropyl)nicotinamide.
6-(5-cyclopropylcarbamoyl-3-fluoro-2-methyl-phenyl)-N-cyclobutylmethyl-nicotinamide;
6-(5-cyclopropylcarbamoyl-3-fluoro-2-methyl-phenyl)-N-cyclobutyl-nicotinamide,
6-{5-[(cyclopropylamino)carbonyl]-3-fluoro-2-methylphenyl}-N-(2,4,5-trifluorobenzyl)nicotinamide;
6-{5-[(cyclopropylamino)carbonyl]-3-fluoro-2-methylphenyl}-N-(2,5-difluorobenzyl)nicotinamide;
6-{5-[(cyclopropylamino)carbonyl]-3-fluoro-2-methylphenyl}-N-(3,4-difluorobenzyl)nicotinamide;
N-(3-chlorobenzyl)-6-{5-[(cyclopropylamino)carbonyl]-3-fluoro-2-methylphenyl}nicotinamide;
N-(4-chlorobenzyl)-6-{5-[(cyclopropylamino)carbonyl]-3-fluoro-2-methylphenyl}nicotinamide;
N-(3-chloro-2-fluorobenzyl)-6-{5-[(cyclopropylamino)carbonyl]-3-fluoro-2-methylphenyl}nicotinamide;
N-(2-chloro-3,6-difluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(2,3-difluoro-4-methylbenzyl)nicotinamide;
6-{5-[(cyclopropylamino)carbonyl]-3-fluoro-2-methylphenyl}-N-(2,3,5-trifluorobenzyl)nicotinamide;
6-{5-[(cyclopropylamino)carbonyl]-3-fluoro-2-methylphenyl}-N-(3-fluoro-4-methylbenzyl)nicotinamide;
N-(5-chloro-2-fluorobenzyl)-6-{5-[(cyclopropylamino)carbonyl]-3-fluoro-2-methylphenyl}nicotinamide;
N-(2-chlorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(4-fluorobenzyl)nicotinamide;
6-{5-[(cyclopropylamino)carbonyl]-3-fluoro-2-methylphenyl}-N-(2,3,4-trifluorobenzyl)nicotinamide;
N-benzyl-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-[3-(trifluoromethyl)benzyl]nicotinamide;
6-{5-[(cyclopropylamino)carbonyl]-3-fluoro-2-methylphenyl}-N-(1,1-dimethylbutyl)nicotinamide;
N-(4-chloro-2-fluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-[4-(trifluoromethyl)benzyl]nicotinamide;
6-{5-[(cyclopropylamino)carbonyl]-3-fluoro-2-methylphenyl}-N-[(5-methyl-2-furyl)methyl]nicotinamide;
6-{5-[(cyclopropylamino)carbonyl]-3-fluoro-2-methylphenyl}-N-(2,3-difluorobenzyl)nicotinamide;

N-(3-chloro-4-fluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(4-methylbenzyl)nicotinamide;
6-{5-[(cyclopropylamino)carbonyl]-3-fluoro-2-methylphenyl}-N-[(3-methylthien-2-yl)methyl]nicotinamide;
N-(3-chloro-2,6-difluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(1-ethyl-1-methylpropyl)nicotinamide;
6-{5-[(cyclopropylamino)carbonyl]-3-fluoro-2-methylphenyl}-N-(2-fluorobenzyl)nicotinamide;
6-{5-[(cyclopropylamino)carbonyl]-3-fluoro-2-methylphenyl}-N-(tert-pentyl)nicotinamide;
6-{5-[(cyclopropylamino)carbonyl]-3-fluoro-2-methylphenyl}-N-(3-methylbenzyl)nicotinamide; and
6-(5-(cyclopropylcarbamoyl)-3-fluoro-2-methylphenyl)-N-neopentylnicotinamide ("Losmapimod"), Formula V'.

In one embodiment, the p38 kinase inhibitor is 6-(5-(cyclopropylcarbamoyl)-3-fluoro-2-methylphenyl)-N-neopentylnicotinamide ("Losmapimod"), Formula V'.

Genus V Definitions

As used herein, the term "alkyl" refers to straight or branched hydrocarbon chains containing the specified number of carbon atoms. For example, C1-6alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A C1-4alkyl group is preferred, for example methyl, ethyl, isopropyl or t-butyl. The said alkyl groups may be optionally substituted with one or more fluorine atoms for example, trifluoromethyl.

As used herein, the term "alkenyl" refers to straight or branched hydrocarbon chains containing the specified number of carbon atoms and containing at least one double bond. For example, C2-6alkenyl means a straight or branched alkenyl containing at least 2, and at most 6, carbon atoms and containing at least one double bond. Examples of "alkenyl" as used herein include, but are not limited to ethenyl, propenyl, 3-methylbut-2-enyl and 1,1-dimethylbut-2-enyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methylprop-2-oxy, pentoxy, or hexyloxy. A C1-4alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, C3-7cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A C3-6cycloalkyl group is preferred, for example, cyclopropyl, cyclopentyl or cyclohexyl. The said cycloalkyl groups may be optionally substituted with one or more C1-6alkyl groups, for example one or two methyl groups. In one embodiment, the cycloalkyl groups may be optionally substituted by up to four C1-6alkyl groups, for example one or two C1-6alkyl groups, in particular one or two C1-4alkyl groups such as methyl or ethyl.

As used herein, the terms "heteroaryl ring" and "heteroaryl" refer to a monocyclic five- to seven-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from C1-6alkyl and oxy.

As used herein, the terms "heterocyclic ring" or "heterocyclyl" refer to a monocyclic three- to seven-membered saturated hydrocarbon ring containing at least one heteroatom independently selected from oxygen, nitrogen and sulfur. Preferably, the heterocyclyl ring has five or six ring atoms. Examples of heterocyclyl groups include, but are not limited to, pyrrolidinyl, imidazolidinyl, pyrazolidinyl, piperidyl, piperazinyl, morpholino, tetrahydropyranyl, tetrahydrofuranyl, and thiomorpholino. The said ring may be optionally substituted by one or more substituents independently selected from C1-6alkyl and oxy.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

Genus VI Description

Compounds of Genus VI can be prepared according to the disclosure of U.S. Pat. No. 7,582,652, which is herein incorporated by reference in its entirety.

Genus VI is characterized by compounds of Formula VI:

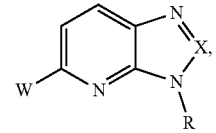

(VI)

or stereoisomers thereof, isotopically-enriched compounds thereof, prodrugs thereof, solvates thereof, and pharmaceutically acceptable salts thereof;
wherein:
W is selected from:

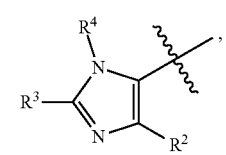

(i)

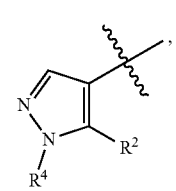

(ii)

-continued

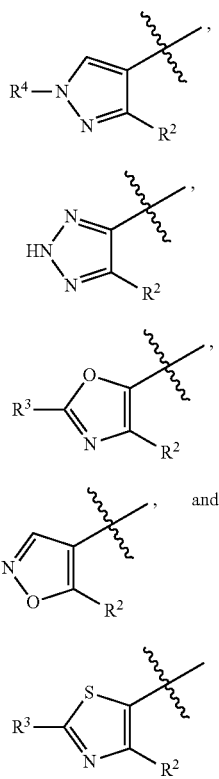

(iii), (iv), (v), (vi), and (vii)

X is N, or C—R$^1$;
R is C$_1$-C$_7$ alkyl, C$_3$-C$_7$ cycloalkyl, (C1-C$_7$ alkylene)-(C$_3$-C$_7$ cycloalkyl), —SO$_2$—(C$_1$-C$_7$ alkyl), or —SO$_2$—NR$^5$R$^6$;
R$^1$ is hydrogen, amino, methyl, or —N=CH(NMe)$_2$;
R$^2$ is phenyl optionally substituted with one or two substituents independently selected from halo;
R$^3$ is hydrogen, C$_1$-C$_7$ alkyl, C$_3$-C$_7$ cycloalkyl, or phenyl optionally substituted with one or two substituents independently selected from halo and trifluoromethyl;
R$^4$ is hydrogen or C$_1$-C$_7$ alkyl; and
R$^5$ and R$^6$ are independently selected from the group consisting of C$_1$-C$_7$ alkyl.

In one embodiment, the p38 kinase inhibitor from Genus VI is selected from the following:

5-(2-tert-Butyl-5-phenyl-3H-imidazol-4-yl)-3-(2,2-dimethylpropyl)-3H-imidazo[4,5-b]pyridin-2-ylamine methanesulfonate;

5-[2-(2,6-Difluorophenyl)-5-phenyl-3H-imidazol-4-yl]-3-(2,2-dimethylpropyl)-3H-imidazo[4,5-b]pyridin-2-ylamine methanesulfonate;

5-(2-tert-Butyl-5-phenyl-3H-imidazol-4-yl)-3-cyclopropylmethyl-3H-imidazo[4,5-b]pyridin-2-ylamine methanesulfonate;

5-(2-Cyclopropyl-5-phenyl-3H-imidazol-4-yl)-3-(2,2-dimethylpropyl)-3H-imidazo[4,5-b]pyridin-2-ylamine methanesulfonate;

3-(2,2-Dimethylpropyl)-5-[5-(4-fluorophenyl)-2-(2-fluoro-6-trifluoromethylphenyl)-3H-imidazol-4-yl]-3H-imidazo[4,5-b]pyridin-2-ylamine methanesulfonate;

3-(2,2-Dimethylpropyl)-5-[2-(2-fluoro-6-trifluoromethylphenyl)-5-phenyl-3H-imidazol-4-yl]-3H-imidazo[4,5-b]pyridin-2-ylamine methanesulfonate;

5-[2-Cyclopropyl-5-(4-fluorophenyl)-3H-imidazol-4-yl]-3-(2,2-dimethylpropyl)-3H-imidazo[4,5-b]pyridin-2-ylamine methanesulfonate;

5-[2-(2,6-Difluorophenyl)-5-(4-fluorophenyl)-3H-imidazol-4-yl]-3-(2,2-dimethylpropyl)-3H-imidazo[4,5-b]pyridin-2-ylamine methanesulfonate;

5-[2-tert-Butyl-5-(4-fluorophenyl)-3H-imidazol-4-yl]-3-(2,2-dimethylpropyl)-3H-imidazo[4,5-b]pyridin-2-ylamine methanesulfonate;

5-[2-tert-Butyl-5-(4-fluorophenyl)-3H-imidazol-4-yl]-3-cyclopropylmethyl-3H-imidazo[4,5-b]pyridin-2-ylamine methanesulfonate;

5-[2-tert-Butyl-5-(2,4-difluorophenyl)-3H-imidazol-4-yl]-3-(2,2-dimethylpropyl)-3H-imidazo[4,5-b]pyridin-2-ylamine methanesulfonate;

R-5-[2-tert-Butyl-5-(4-fluorophenyl)-3H-imidazol-4-yl]-3-(1,2,2-trimethylpropyl)-3H-imidazo[4,5-b]pyridin-2-ylamine methanesulfonate;

R-5-[2-(2,6-Difluorophenyl)-5-(4-fluorophenyl)-3H-imidazol-4-yl]-3-(1,2,2-trimethylpropyl)-3H-imidazo[4,5-b]pyridin-2-ylamine methanesulfonate;

R-5-[5-(4-Fluorophenyl)-2-(2-fluoro-6-trifluoromethylphenyl)-3H-imidazol-4-yl]-3-(1,2,2-trimethylpropyl)-3H-imidazo[4,5-b]pyridin-2-ylamine methanesulfonate;

3-Cyclopropylmethyl-5-[2-(2,6-dichlorophenyl)-5-(4-fluorophenyl)-3H-imidazol-4-yl]-3H-imidazo[4,5-b]pyridin-2-ylamine methanesulfonate;

3-Cyclopropylmethyl-5-[2-(2,6-difluorophenyl)-5-(4-fluorophenyl)-3H-imidazol-4-yl]-3H-imidazo[4,5-b]pyridin-2-ylamine methanesulfonate;

5-[2-(2,6-Dichlorophenyl)-5-(4-fluorophenyl)-3H-imidazol-4-yl]-3-(2,2-dimethylpropyl)-3H-imidazo[4,5-b]pyridin-2-ylamine methanesulfonate;

5-[2-(2-Chloro-6-fluorophenyl)-5-phenyl-3H-imidazol-4-yl]-3-(2,2-dimethylpropyl)-3H-imidazo[4,5-b]pyridin-2-ylamine methanesulfonate;

3-Cyclopropylmethyl-5-[2-(2,6-difluorophenyl)-5-phenyl-3H-imidazol-4-yl]-3H-imidazo[4,5-b]pyridin-2-ylamine methanesulfonate;

3-Cyclopropylmethyl-5-[2-(2,6-dichlorophenyl)-5-phenyl-3H-imidazol-4-yl]-3H-imidazo[4,5-b]pyridin-2-ylamine methanesulfonate;

5-[5-(2,4-Difluorophenyl)-2-(2,6-difluorophenyl)-3H-imidazol-4-yl]-3-(2,2-dimethylpropyl)-3H-imidazo[4,5-b]pyridin-2-ylamine methanesulfonate;

5-[3-(4-Fluorophenyl)-1-methylpyrazol-4-yl]-3H-3-isobutyl-imidazo[4,5-b]pyridin-2-ylamine methanesulfonate;

5-[5-(4-Fluorophenyl)-1-methylpyrazol-4-yl]-3H-3-isobutyl-imidazo[4,5-b]pyridin-2-ylamine methanesulfonate;

5-[3-(4-Fluorophenyl)-1-morpholinoethylpyrazol-4-yl]-3H-3-isobutyl-imidazo[4,5-b]pyridin-2-ylamine-methanesulfonate;

5-[3-(4-Fluorophenyl)-pyrazol-4-yl]-3H-3-isobutyl-imidazo[4,5-b]pyridin-2-ylamine di-methanesulfonate;

3H-3-isobutyl-5-(3-phenyl-1-isopropylpyrazol-4-yl)-imidazo[4,5-b]pyridin-2-ylamine di-methanesulfonate;

3H-3-isobutyl-5-(3-phenyl-1-methylpyrazol-4-yl)-imidazo[4,5-b]pyridin-2-ylamine di-methanesulfonate;

3H-3-isobutyl-5-(3-phenyl-pyrazol-4-yl)-imidazo[4,5-b]pyridin-2-ylamine di-methanesulfonate 5-[3-(2,4-Difluorophenyl)pyrazol-4-yl]-3H-3-isobutyl-imidazo[4,5-b]pyridin-2-ylamine di-methanesulfonate;

5-[2-(2,6-Difluorophenyl)-5-phenyl-3H-imidazol-4-yl]-3-isobutyl-3H-imidazo[4,5-b]pyridin-2-ylamine methanesulfonate;

5-[2-(2,6-Dichlorophenyl)-5-phenyl-3H-imidazol-4-yl]-3-(2,2-dimethylpropyl)-3H-imidazo[4,5-b]pyridin-2-ylamine methanesulfonate;

5-[2-(2,6-Dichlorophenyl)-5-phenyl-1H-imidazol-4-yl]-3-isobutyl-3H-imidazo[4,5-b]pyridin-2-ylamine methanesulfonate;

5-[2-(2,6-Dichlorophenyl)-5-(4-fluorophenyl)-1H-imidazol-4-yl]-3-isobutyl-3H-imidazo[4,5-b]pyridin-2-ylamine methanesulfonate;

5-[2-(2,6-Dichlorophenyl)-5-(2,4-difluorophenyl)-1H-imidazol-4-yl]-3-isobutyl-3H-imidazo[4,5-b]pyridin-2-ylamine methanesulfonate;

R-5-[2-(2-Chloro-6-fluorophenyl)-5-(4-fluorophenyl)-3H-imidazol-4-yl]-3-(1,2,2-trimethylpropyl)-3H-imidazo[4,5-b]pyridin-2-ylamine methanesulfonate;

5-[2-tert-Butyl-5-(4-fluorophenyl)-3H-imidazol-4-yl]-3-(2,2-dimethylpropyl)-2-methyl-3H-imidazo[4,5-b]pyridine methanesulfonate;

5-(2-tert-Butyl-5-phenyl-3H-imidazol-4-yl)-3-(2,2-dimethyl-propyl)-2-methyl-3H-imidazo[4,5-b]pyridine methanesulfonate;

5-[2-(2-Chloro-6-fluorophenyl)-5-phenyl-3H-imidazol-4-yl]-3-(2,2-dimethyl-propyl)-2-methyl-3H-imidazo[4,5-b]pyridine methanesulfonate;

5-[2-(2,6-Difluorophenyl)-5-phenyl-3H-imidazol-4-yl]-3-(2,2-dimethylpropyl)-2-methyl-3H-imidazo[4,5-b]pyridine methanesulfonate;

5-[2-(2,6-Difluorophenyl)-5-(4-fluorophenyl)-3H-imidazol-4-yl]-3-(2,2-dimethylpropyl)-2-methyl-3H-imidazo[4,5-b]pyridine methanesulfonate;

5-[2-(2,6-Dichlorophenyl)-5-(4-fluorophenyl)-3H-imidazol-4-yl]-3-(2,2-dimethylpropyl)-2-methyl-3H-imidazo[4,5-b]pyridine methanesulfonate;

3-Cyclopropylmethyl-5-[2-(2,6-difluorophenyl)-5-phenyl-3H-imidazol-4-yl]-2-methyl-3H-imidazo[4,5-b]pyridine methanesulfonate;

3-Cyclopropylmethyl-5-[2-(2,6-dichlorophenyl)-5-phenyl-3H-imidazol-4-yl]-2-methyl-3H-imidazo[4,5-b]pyridine methanesulfonate;

5-(2-Cyclopropyl-5-phenyl-3H-imidazol-4-yl)-3-(2,2-dimethylpropyl)-2-methyl-3H-imidazo[4,5-b]pyridine methanesulfonate;

5-[2-(2,6-Dichlorophenyl)-5-phenyl-3H-imidazol-4-yl]-3-(2,2-dimethylpropyl)-2-methyl-3H-imidazo[4,5-b]pyridine methanesulfonate;

5-[2-(2-Chloro-6-fluorophenyl)-5-phenyl-3H-imidazol-4-yl]-3-(2,2-dimethylpropyl)-3H-imidazo[4,5-b]pyridine methanesulfonate;

5-(2-Cyclopropyl-5-phenyl-3H-imidazol-4-yl)-3-(2,2-dimethylpropyl)-3H-imidazo [4,5-b]pyridine methanesulfonate;

5-[2-(2,6-Difluorophenyl)-5-phenyl-3H-imidazol-4-yl]-3-isobutyl-3H-imidazo[4,5-b]pyridine methanesulfonate;

5-[3-(4-Fluorophenyl)-1-isopropylpyrazol-4-yl]-3H-3-isobutylimidazo[4,5-b]pyridin-2-ylamine di-methanesulfonate;

5-[2-tert-Butyl-5-phenyl-1H-imidazol-4-yl]-isobutyl-3H-imidazo[4,5-b]pyridin-2-ylamine di-methanesulfonate;

5-[2-(2-Fluoro-6-chlorophenyl)-5-phenyl-1H-imidazol-4-yl]-3-isobutyl-3H-imidazo[4,5-b]pyridin-2-ylamine methanesulfonate;

5-[2-Cyclopropyl-5-phenyl-1H-imidazol-4-yl]-3-isobutyl-3H-imidazo[4,5-b]pyridin-2-ylamine methanesulfonate;

5-[2-(2-Fluoro-6-trifluoromethylphenyl)-5-phenyl-1H-imidazol-4-yl]-3-isobutyl-3H-imidazo[4,5-b]pyridin-2-ylamine methanesulfonate;

5-[2-(2-Fluoro-6-chlorophenyl)-5-(4-fluorophenyl)-1H-imidazol-4-yl]-3-isobutyl-3H-imidazo[4,5-b]pyridin-2-ylamine methanesulfonate;

5-[2-isopropyl-5-phenyl-1H-imidazol-4-yl]-3-isobutyl-3H-imidazo[4,5-b]pyridin-2-ylamine di-methanesulfonate;

5-[2-(2-Fluoro-6-trifluoromethylphenyl)-5-(2,4-difluorophenyl-1H-imidazol-4-yl]-3-isobutyl-3H-imidazo[4,5-b]pyridin-2-ylamine methanesulfonate;

5-[2-tert-Butyl)-5-(2,4-difluorophenyl-1H-imidazol-4-yl]-3-isobutyl-3H-imidazo[4,5-b]pyridin-2-ylamine methanesulfonate;

5-[2-Isopropyl)-5-(2,4-difluorophenyl-1H-imidazol-4-yl]-3-isobutyl-3H-imidazo[4,5-b]pyridin-2-ylamine methanesulfonate;

5-[2-(2-Fluoro-6-chlorophenyl)-5-(2,4-difluorophenyl-1H-imidazol-4-yl]-3-isobutyl-3H-imidazo[4,5-b]pyridin-2-ylamine methanesulfonate;

5-[2-Cyclopropyl-5-(2,4-difluorophenyl)-1H-imidazol-4-yl]-3-isobutyl-3H-imidazo[4,5-b]pyridin-2-ylamine methanesulfonate;

5-[2-Cyclopropyl-5-(4-fluorophenyl)-1H-imidazol-4-yl]-3-isobutyl-3H-imidazo[4,5-b]pyridin-2-ylamine di-methanesulfonate;

5-[2-tert-Butyl-5-(4-fluorophenyl)-1H-imidazol-4-yl]-3-isobutyl-3H-imidazo[4,5-b]pyridin-2-ylamine di-methanesulfonate;

N'-{5-[2-(2,6-Difluorophenyl)-5-phenyl-3H-imidazol-4-yl]-3-isobutyl-3H-imidazo[4,5-b]pyridin-2-yl}-N,N-dimethylformamidine;

5-[2-(2,6-Difluorophenyl)-3-methyl-5-phenyl-3H-imidazol-4-yl]-3-isobutyl-3H-imidazo[4,5-b]pyridin-2-ylamine;

5-[2-(2,6-Dichlorophenyl)-3-methyl-5-phenyl-3H-imidazol-4-yl]-3-isobutyl-3H-imidazo[4,5-b]pyridin-2-ylamine;

3-(2,2-Dimethylpropyl)-5-(5-phenyl-3H-[1,2,3]triazol-4-yl)-3H-imidazo[4,5-b]pyridin-2-ylamine methanesulfonate;

3-(2,2-Dimethylpropyl)-5-[5-(4-fluoro-phenyl)-3H-[1,2,3]triazol-4-yl]-3H-imidazo[4,5-b]pyridin-2-ylamine methanesulfonate;

3-Cyclopropylmethyl-5-[5-(4-fluoro-phenyl)-3H-[1,2,3]triazol-4-yl]-3H-imidazo[4,5-b]pyridin-2-ylamine methanesulfonate;

3-Cyclopropylmethyl-5-(5-phenyl-3H-[1,2,3]triazol-4-yl)-3H-imidazo[4,5-b]pyridin-2-ylamine methanesulfonate;

5-[2-(2-Chloro-6-fluorophenyl)-5-phenyl-1H-imidazol-4-yl]-3-isobutyl-3H-[1,2,3]triazolo[4,5-b]pyridine methanesulfonate;

5-[2-(2,6-Dichlorophenyl)-5-phenyl-1H-imidazol-4-yl]-3-isobutyl-3H-[1,2,3]triazolo[4,5-b]pyridine methanesulfonate;

5-[2-(2,6-Dichlorophenyl)-5-(2,4-difluoro-phenyl)-1H-imidazol-4-yl]-3-isobutyl-3H-[1,2,3]triazolo[4,5-b]pyridine methanesulfonate 5-[2-tert-Butyl-5-(4-fluorophenyl)-1H-imidazol-4-yl]-3-isobutyl-3H-[1,2,3]triazolo[4,5-b]pyridine methanesulfonate;

2-Amino-5-(2-tert-butyl-5-phenyl-3H-imidazol-4-yl)imidazo[4,5-b]pyridine-3-sulfonic acid dimethylamide methanesulfonate;

2-Amino-5-[(2-fluoro-6-chlorophenyl)-5-phenyl-3H-imidazol-4-yl)]imidazo[4,5-b]pyridine-3-sulfonic acid dimethyl-amide methanesulfonate;

2-Amino-5-[(2,6-dichlorophenyl)-5-phenyl-3H-imidazol-4-yl)]imidazo[4,5-b]pyridine-3-sulfonic acid dimethyl-amide methanesulfonate;

2-Amino-5-(2-tert-butyl-5-(2,4-difluoro-phenyl)-3H-imidazol-4-yl)imidazo[4,5-b]pyridine-3-sulfonic acid dimethyl-amide methanesulfonate;

5-[2-(2,6-Difluorophenyl)-5-phenyl-3H-imidazol-4-yl]-3-(propane-2-sulfonyl)-3H-imidazo[4,5-b]pyridin-2-ylamine methanesulfonate;
3-Butyl-5-[2-(2,6-difluorophenyl)-5-phenyl-3H-imidazol-4-yl]-3H-imidazo[4,5-b]pyridin-2-ylamine methanesulfonate;
3-Butyl-5-[2-(2-fluorophenyl)-5-phenyl-3H-imidazol-4-yl]-3H-imidazo[4,5-b]pyridin-2-ylamine, di-methanesulfonate;
3-Butyl-5-[2-(2-chloro-6-fluorophenyl)-5-phenyl-3H-imidazol-4-yl]-3H-imidazo[4,5-b]pyridin-2-ylamine methanesulfonate;
3-Butyl-5-(2-tert-butyl-5-phenyl-3H-imidazol-4-yl)-3H-imidazo[4,5-b]pyridin-2-ylamine methanesulfonate;
3-Butyl-5-[2-(2-fluoro-6-trifluoromethylphenyl)-5-phenyl-3H-imidazol-4-yl]-3H-imidazo[4,5-b]pyridin-2-ylamine methanesulfonate;
2-Amino-5-(5-(phenyl-2H-[1,2,3]triazol-4-yl)imidazo[4,5-b]pyridine-3-sulfonic acid dimethylamide;
5-[2-(2-Fluoro-6-trifluoromethylphenyl)-5-phenyl-3H-imidazol-4-yl]-3-(propane-2-sulfonyl)-3H-imidazo[4,5-b]pyridin-2-ylamine methanesulfonate;
5-(2-tert-Butyl-5-phenyl-3H-imidazol-4-yl)-3-(propane-2-sulfonyl)-3H-imidazo[4,5-b]pyridin-2-ylamine methanesulfonate;
5-[2-(2,6-Dichlorophenyl)-5-phenyl-3H-imidazol-4-yl]-3-(propane-2-sulfonyl)-3H-imidazo[4,5-b]pyridin-2-ylamine methanesulfonate;
5-[2-(2-Chloro-6-fluorophenyl)-5-phenyl-3H-imidazol-4-yl]-3-(propane-2-sulfonyl)-3H-imidazo[4,5-b]pyridin-2-ylamine methanesulfonate;
3-Butyl-5-[2-tert-butyl-5-(2,4-difluorophenyl)-3H-imidazol-4-yl]-3H-imidazo[4,5-b]pyridin-2-ylamine methanesulfonate;
5-[2-tert-Butyl-4-(4-fluorophenyl)oxazol-5-yl]-3-isobutyl-3H-imidazo[4,5-b]pyridin-2-ylamine;
5-[2-tert-Butyl-4-(2,4-difluorophenyl)oxazol-5-yl]-3-isobutyl-3H-imidazo[4,5-b]pyridin-2-ylamine methanesulfonate;
5-[4-(4-Fluorophenyl)-2-isopropyloxazol-5-yl]-3-isobutyl-3H-imidazo[4,5-b]pyridin-2-ylamine methanesulfonate;
3-Isobutyl-5-(2-methyl-4-phenylthiazol-5-yl)-3H-imidazo[4,5-b]pyridin-2-ylamine methanesulfonate;
5-[4-(4-Fluorophenyl)-2-methylthiazol-5-yl]-3-isobutyl-3H-imidazo[4,5-b]pyridin-2-ylamine methanesulfonate;
2-Amino-5-(2-tert-butyl-5-(4-fluorophenyl)oxazol-5-yl)imidazo[4,5-b]pyridine-3-sulfonic acid dimethylamide;
2-Amino-5-(2-ispropyl-5-(4-fluorophenyl) oxazol-5-yl)imidazo[4,5-b]pyridine-3-sulfonic acid dimethylamide methane-sulfonate;
5-[2-(2,6-Dichloro-phenyl)-5-(4-fluoro-phenyl)-1H-imidazol-4-yl]-3-(2,2-dimethyl-propyl)-3H-imidazo[4,5-b]pyridin-2-ylamine methanesulfonate;
3-(2,2-Dimethyl-propyl)-5-[5-(4-fluoro-phenyl)-2-(2-fluoro-6-trifluoromethyl-phenyl)-1H-imidazol-4-yl]-3H-imidazo[4,5-b]pyridin-2-ylamine methanesulfonate;
5-[2-tert-Butyl-5-(2,4-difluoro-phenyl)-1H-imidazol-4-yl]-3-(2,2-dimethyl-propyl)-3H-imidazo[4,5-b]pyridin-2-ylamine methanesulfonate;
5-[2-tert-Butyl-5-(4-fluoro-phenyl)-1H-imidazol-4-yl]-3-(2,2-dimethyl-propyl)-3H-imidazo[4,5-b]pyridin-2-ylamine methanesulfonate;
5-[2-tert-Butyl-5-(4-fluoro-phenyl)-1H-imidazol-4-yl]-3-(2,2-dimethyl-propyl)-3H-imidazo[4,5-b]pyridin-2-ylamine fumarate;
5-[2-tert-Butyl-5-(4-fluoro-phenyl)-1H-imidazol-4-yl]-3-(2,2-dimethyl-propyl)-3H-imidazo[4,5-b]pyridin-2-ylamine dimethanesulfonate;
5-[2-tert-Butyl-5-(4-fluoro-phenyl)-1H-imidazol-4-yl]-3-(2,2-dimethyl-propyl)-3H-imidazo[4,5-b]pyridin-2-ylamine succinate;
5-[2-tert-Butyl-5-(4-fluoro-phenyl)-1H-imidazol-4-yl]-3-(2,2-dimethyl-propyl)-3H-imidazo[4,5-b]pyridin-2-ylamine dimaleate;
5-[2-tert-Butyl-5-(4-fluoro-phenyl)-1H-imidazol-4-yl]-3-(2,2-dimethyl-propyl)-3H-imidazo[4,5-b]pyridin-2-ylamine dihydrochloride;
5-[2-(2-Chloro-6-fluoro-phenyl)-5-phenyl-3H-imidazol-4-yl]-3-(2,2-dimethylpropyl)-3H-imidazo[4,5-b]pyridin-2-ylamine methanesulfonate;
5-[2-tert-Butyl-5-(4-fluoro-phenyl)-3H-imidazol-4-yl]-3-(1(R),2,2-trimethyl-propyl)-3H-imidazo[4,5-b]pyridin-2-ylamine methanesulfonate;
5-[2-(2,6-Difluoro-phenyl)-5-(4-fluoro-phenyl)-3H-imidazol-4-yl]-3-(1(R), 2,2-trimethyl-propyl)-3H-imidazo[4,5-b]pyridin-2-ylamine methanesulfonate;
5-[2-tert-butyl-5-(4-fluoro-phenyl)-1H-imidazol-4-yl]-3-(2,2-dimethyl-propyl)-3H-imidazo[4,5-b]pyridin-2-ylamine dimethanesulfonate 5-Bromo-3-(2,2-dimethyl-propyl)-3H-imidazo[4,5-b]pyridin-2-yl-ammonium bromide;
5-[2-tert-butyl-5-(4-fluoro-phenyl)-1H-imidazol-4-yl]-3-(2,2-dimethyl-propyl)-3H-imidazo[4,5-b]pyridin-2-ylamine dimethanesulfonate 2-Amino-3-(2,2-dimethyl-propyl)-5-[2-(4-fluorophenyl)-2-oxo-acetyl]-3H-imidazo[4,5-b]pyridin-1-ium methanesulfonate;
5-(2-(tert-butyl)-4-(4-fluorophenyl)-1H-imidazol-5-yl)-3-neopentyl-3H-imidazo[4,5-b]pyridin-2-amine methansulfonate ("LY2228820 salt"); and
5-(2-(tert-butyl)-4-(4-fluorophenyl)-1H-imidazol-5-yl)-3-neopentyl-3H-imidazo[4,5-b]pyridin-2-amine ("LY2228820"), Formula VI'.

In one embodiment, the p38 kinase inhibitor is 5-(2-(tert-butyl)-4-(4-fluorophenyl)-1H-imidazol-5-yl)-3-neopentyl-3H-imidazo[4,5-b]pyridin-2-amine ("LY2228820"), Formula VI'.

In one embodiment, the p38 kinase inhibitor is 5-(2-(tert-butyl)-4-(4-fluorophenyl)-1H-imidazol-5-yl)-3-neopentyl-3H-imidazo[4,5-b]pyridin-2-amine methansulfonate ("LY2228820 salt").

In one embodiment, the p38 kinase inhibitor is a dimesylate salt ("[$CH_3S(O)_2OH$]$_2$") of LY2228820.

Genus VI Definitions

The general chemical terms used in the Formulae above have their usual meanings. For example, the term "C1-C7 alkyl" includes methyl, ethyl, propyl, isopropyl, butyl, isobutyl, sec-butyl, tert-butyl, pentyl, hexyl and heptyl moieties. The term "C1-C7 alkylene" includes methylene, ethylene, propylene, isopropylene, butylene, isobutylene, sec-butylene, tert-butylene, pentylene, hexylene and heptylene moieties. The term "C3-C7 cycloalkyl" includes cyclopropyl, cyclobutyl, cyclopentyl, cyclohexyl and cycloheptyl moieties. The term "(C1-C7 alkylene)-(C3-C7 cycloalkyl)" is taken to mean a C3-C7 cycloalkyl attached through a C1-C7alkylene linker. The term "halo" includes fluoro, chloro, bromo, and iodo.

The skilled artisan will also appreciate that when variable "W" is imidazole (i), and R4 is hydrogen, the imidazole ring exists in the following two tautomeric forms:

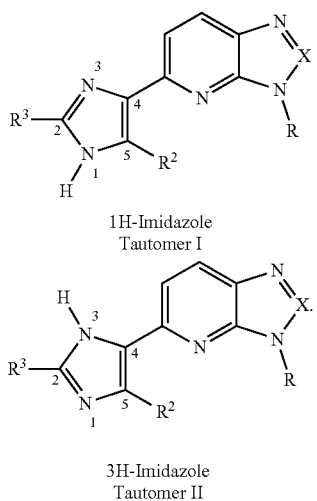

1H-Imidazole
Tautomer I

3H-Imidazole
Tautomer II

Although Tautomers I and II are structurally distinct, the skilled artisan will appreciate that they exist in equilibrium and are easily and rapidly interconvertible under ordinary conditions. (See: March, Advanced Organic Chemistry, Third Edition, Wiley Interscience, New York, N.Y. (1985), pages 66-70; and Allinger, Organic Chemistry, Second Edition, Worth Publishers, New York, N.Y., (1976), page 173) As such, the representation of a compound of Formula I, where variable "W" is imidazole (i) and R4 is hydrogen, in one tautomeric form contemplates both tautomeric forms of the imidazole ring. Likewise, the naming of a compound of Formula I where "W" is imidazole (i) and R4 is hydrogen as either a 1H-imidazole or a 3H-imidazole contemplates both tautomeric forms of the imidazole ring. Specifically, the name 5-[2-tert-butyl-5-(4-fluoro-phenyl)-1H-imidazol-4-yl]-3-(2,2-dimethyl-propyl)-3H-imidazo[4,5-b]pyridin-2-ylamine contemplates the molecule in either the 1H-imidazol-4-yl or 3H-imidazol-4-yl form. Similarly, when variable "W" is triazole (iv), the triazole moiety exists in three tautomeric forms, and the representation or naming of one tautomeric form contemplates all three tautomeric forms of the triazole ring.

Especially preferred are di-methanesulfonic acid salts of the compounds of Formula VI.

Genus VII Description

Compounds of Genus VII can be prepared according to the disclosure of U.S. Pat. No. 6,867,209, which is herein incorporated herein by reference in its entirety.

Genus VII is characterized by compounds of Formula VII:

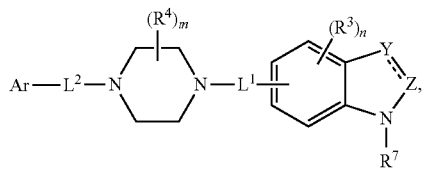

(VII)

or stereoisomers thereof, isotopically-enriched compounds thereof, prodrugs thereof, solvates thereof, and pharmaceutically acceptable salts thereof;

wherein:
═══ represents a single or double bond;
one of Y and Z is CA or $CR^8A$ and the other is $CR^1$, $CR^1_2$, $NR^6$ or N;
wherein:
each $R^1$ is independently hydrogen or is alkyl, alkenyl, alkynyl, aryl, arylalkyl, acyl, aroyl, heteroaryl, —NH-aroyl, halo, —OR, —$NR_2$, —SR, —S(O)R, —$S(O)_2R$, —OC(O)R, —NRC(O)R, —$NRC(O)NR_2$, —NRC(O)OR, —$OC(O)NR_2$, —C(O)R, —C(O)OR, alkyl-OC(O)R, —$SO_3R$, —$C(O)NR_2$, —$S(O)_2NR_2$, —$NRS(O)_2NR_2$, —CN, —$CF_3$, —$SiR_3$, and —$NO_2$,
wherein:
each R is independently —H, alkyl, alkenyl or aryl;
$R^6$ is H, alkyl, alkenyl, alkynyl, aryl, arylalkyl, acyl, aroyl, or heteroaryl, or is —S(O)R, —$S(O)_2R$, —C(O)R, —C(O)OR, -alkyl-C(O)R, —$S(O)_2OR$, —$C(O)NR_2$, —$S(O)_2NR_2$, —CN, —$CF_3$, or —$SiR_3$,
wherein:
each R is independently —H, alkyl, alkenyl or aryl;
$R^8$ is H, halo, alkyl or alkenyl;
A is —$W_1$—$C(O)X_jY$,
wherein:
Y is $C(O)R^2$, and
wherein:
$R^2$ is hydrogen or is straight or branched chain alkyl, alkenyl, alkynyl, aryl, arylalkyl, heteroaryl, or heteroarylalkyl, each optionally substituted with halo, alkyl, —SR, —OR, —$NR_2$, —OC(O)R, —NRC(O)R, —$NRC(O)NR_2$, —$NRS(O)_2R$, —$NRS(O)_2NR_2$, —$OC(O)NR_2$, —CN, —C(O)OR, —$C(O)NR_2$, —C(O)R, or —$SiR_3$, wherein each R is independently —H, alkyl, alkenyl or aryl, or
$R^2$ is —OR, —$NR_2$, —$NRCONR_2$, —$OC(O)NR_2$, —$NRS(O)_2NR_2$, heteroarylalkyl, —C(O)OR, —$NRNR_2$, heteroaryl, heteroaryloxy, heteroaryl-NR, or —NROR,
wherein:
each R is independently —H, alkyl, alkenyl or aryl, or
two R attached to the same N atom may form a 3-8 member ring selected from the group consisting of a piperazine ring, a morpholine ring, a thiazolidine ring, an oxazolidine ring, a pyrrolidine ring, a piperidine ring, an azacyclopropane ring, an azacyclobutane ring and an azacyclooctane ring; and
wherein said ring is optionally substituted with alkyl, alkenyl, alkynyl, aryl, arylalkyl, heteroaryl, heteroarylalkyl, each optionally substituted with halo, —SR, —OR, —$NR_2$, —OC(O)R, —NRC(O)R, —$NRC(O)NR_2$, —$NRS(O)_2R$, —$NRS(O)_2NR_2$, —$OC(O)NR_2$, or —$SiR_3$,
wherein:
each R is independently —H, alkyl, alkenyl, or aryl, or
two R attached to the same N atom may form a 3-8 member ring, optionally substituted as above defined, and
each of W and X is substituted or unsubstituted alkylene, alkenylene or alkynylene, each of 2-6 Å or
Y is tetrazole; 1,2,3-triazole; 1,2,4-triazole; or imidazole, and
each of i and j is independently 0 or 1;
$R^7$ is —H or is alkyl, alkenyl, alkynyl, aryl, arylalkyl, acyl, aroyl, heteroaryl, —S(O)R, —$S(O)_2R$, —C(O)R, —C(O)

OR, -alkyl-COR, —S(O)$_2$OR, —C(O)NR$_2$, —S(O)$_2$NR$_2$, —CN, —CF$_3$, —NR$_2$, —OR, -alkyl-SR, -alkyl-S(O)R, -alkyl-S(O)$_2$R, -alkyl-OC(O)R, -alkyl-C(O)OR, alkyl-CN, -alkyl-C(O)NR$_2$, or —SiR$_3$,
  wherein each R is independently —H, alkyl, alkenyl or aryl or R$^7$ is methoxymethyl, methoxyethyl, ethoxymethyl, benzyloxymethyl, or 2-methoxyethyloxy methyl;
each R$^3$ is independently halo, alkyl, —OC(O)R, —OR, —NRC(O)R, —SR, or —NR$_2$, wherein R is H, alkyl or aryl;
n is 0-3;
L$^1$ is —C(O)—, —S(O)$_2$—, or alkylene (1-4C);
L$^2$ is alkylene (1-4C) or alkenylene (2-4C) optionally substituted with one or two moieties selected from the group consisting of alkyl, alkenyl, alkynyl, aryl, arylalkyl, acyl, aroyl, heteroaryl, —NH-aroyl, halo, —OR, —NR$_2$, —SR, —S(O)R, —S(O)$_2$R, —OC(O)R, —NRC(O)R, —NRC(O)NR$_2$, —NRC(O)OR, —OC(O)NR$_2$, —C(O)R, —C(O)OR, -alkyl-OC(O)R, —S(O)$_2$OR, —C(O)NR$_2$, —S(O)$_2$NR$_2$, —NRS(O)$_2$NR$_2$CN, —CF$_3$, and —SiR$_3$,
  wherein each R is independently H, alkyl, alkenyl or aryl, and wherein two substituents on L2 can be joined to form a non-aromatic saturated or unsaturated ring that includes 0-3 heteroatoms which are O, S and/or N and which contains 3 to 8 members or said two substituents can be joined to form a carbonyl moiety or an oxime, oximeether, oximeester or ketal of said carbonyl moiety;
each R$^4$ is independently selected from the group consisting of alkyl, alkenyl, alkynyl, aryl arylalkyl, acyl, aroyl, heteroaryl, —NH-aroyl, halo, —OR, —NR$_2$, —SR, —SOR, —SO$_2$R, —OCOR, —NRCOR, —NRCONR$_2$, —NRCOOR, —OCONR$_2$, —RCO, —COOR, -alkyl-OOCR, —SO$_3$R, —CONR$_2$, —SO$_2$NR$_2$, —NRSO$_2$NR$_2$, —CN, —CF$_3$, —SiR$_3$, and —NO$_2$, or
two R$^4$ on adjacent positions can be joined to form a fused, optionally substituted aromatic or nonaromatic, saturated or unsaturated ring which contains 3-8 members, or R$^4$ is =O or an oxime, oximeether, oximeester or ketal thereof wherein each R is independently H, alkyl, alkenyl or aryl;
m is 0-4;
Ar is an aryl group substituted with 0-5 substituents selected from the group consisting of alkyl, alkenyl, alkynyl, aryl, arylalkyl, acyl, aroyl, heteroaryl, —NH-aroyl, halo, —OR, —NR$_2$, —SR, —S(O)R, —S(O)$_2$R, —OC(O)R, —NRC(O)R, —NRC(O)NR$_2$, —NRC(O)OR, —OC(O)NR$_2$, —C(O)R, —C(O)OR, -alkyl-OC(O)R, —S(O)$_2$OR, —C(O)NR$_2$, —S(O)$_2$NR$_2$, —NRS(O)$_2$NR$_2$, —CN, —CF$_3$, —SiR$_3$, and —NO$_2$, wherein each R is independently —H, alkyl, alkenyl or aryl, and wherein two of said optional substituents on adjacent positions can be joined to form a fused, optionally substituted aromatic or non-aromatic, saturated or unsaturated ring which contains 3-8 members.

In one embodiment, the p38 kinase inhibitor from Genus VII is selected from the following:
1-methyl-6-methoxy-[4'-fluoro-(4-benzyl-2,5-dimethyl piperazinyl)]-indole-5-carboxamide-3-N,N-dimethyl glyoxalicamide;
1-methyl-6-chloro-[4'-fluoro-(4-benzyl-2,5-dimethyl piperazinyl)]-indole-5-carboxamide-3-N,N-dimethyl glyoxalicamide;
1-methyl-6-chloro-[4'-fluoro-(4-benzyl-2R,5S-dimethyl piperazinyl)]-indole-5-carboxamide-3-N,N-dimethyl glyoxalicamide;
1-methyl-6-chloro-[4'-fluoro-(4-benzyl-2R,5S-dimethyl piperazinyl)]-indole-5-carboxamide-3-glyoxalicamide;
1-methyl-6-chloro-[4'-fluoro-(4-benzyl-2R,5S-dimethyl piperazinyl)]-indole-5-carboxamide-3-N-methyl-glyoxalicamide;
1-methyl-6-methoxy-[4'-fluoro-(4-benzyl-2R,5S-dimethyl piperazinyl)]-indole-5-carboxamide-3-N,N-dimethyl glyoxalicamide;
1-methyl-6-chloro-[4'-fluoro-(4-benzyl-2R,5S-dimethyl piperazinyl)]-indole-5-carboxamide-3-glyoxalic acid-morpholinamide; and
1-methyl-6-methoxy-[4'-fluoro-(4-benzyl-2R,5S-dimethyl piperazinyl)]-indole-5-carboxamide-3-glyoxalic acid-morpholinamide.

In one embodiment, the p38 kinase inhibitor is selected from the following Compounds 1-182:

| Compd. # | STRUCTURE |
|---|---|
| 1 | (structure) |
| 2 | (structure) |

-continued
3 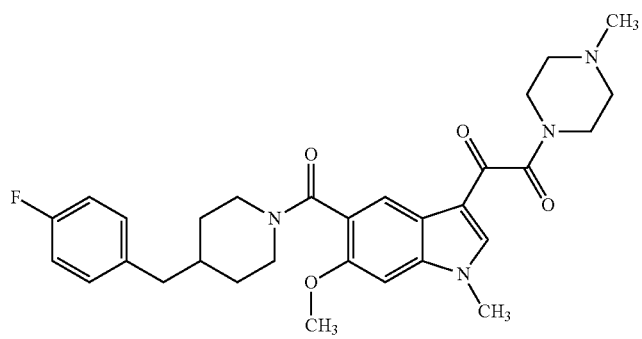 [SMILES: COc1cc2c(cc1C(=O)N1CCC(Cc3ccc(F)cc3)CC1)c(C(=O)C(=O)N1CCN(C)CC1)cn2C]
4 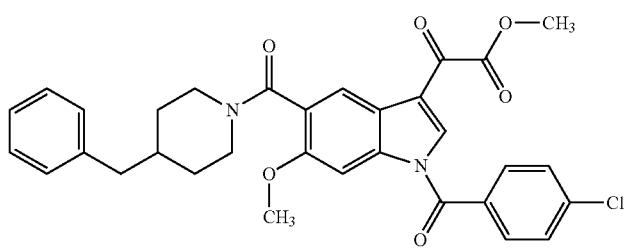 [SMILES: COC(=O)C(=O)c1cn(C(=O)c2ccc(Cl)cc2)c2cc(OC)c(C(=O)N3CCC(Cc4ccccc4)CC3)cc12]
5 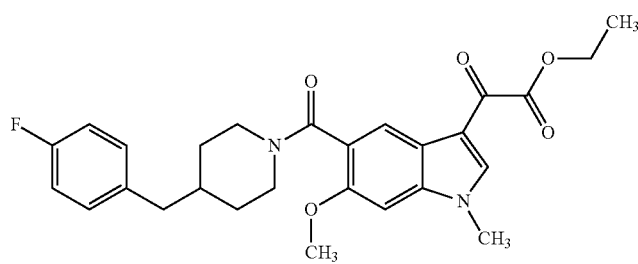 [SMILES: CCOC(=O)C(=O)c1cn(C)c2cc(OC)c(C(=O)N3CCC(Cc4ccc(F)cc4)CC3)cc12]
6 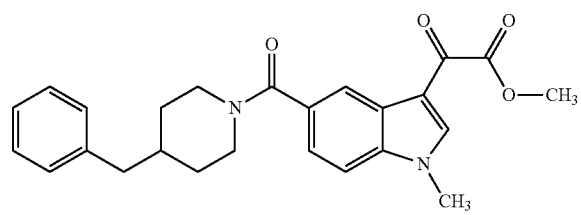 [SMILES: COC(=O)C(=O)c1cn(C)c2ccc(C(=O)N3CCC(Cc4ccccc4)CC3)cc12]
7 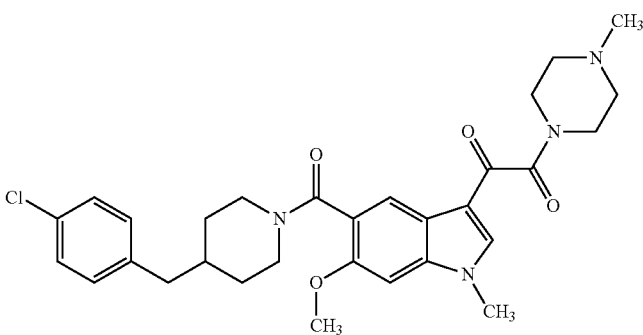 [SMILES: COc1cc2c(cc1C(=O)N1CCC(Cc3ccc(Cl)cc3)CC1)c(C(=O)C(=O)N1CCN(C)CC1)cn2C]

8 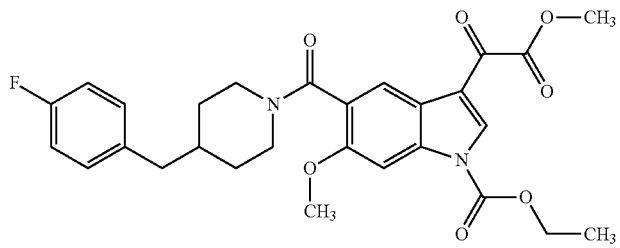 [SMILES: CCOC(=O)n1cc(C(=O)C(=O)OC)c2cc(C(=O)N3CCC(Cc4ccc(F)cc4)CC3)c(OC)cc21]
9 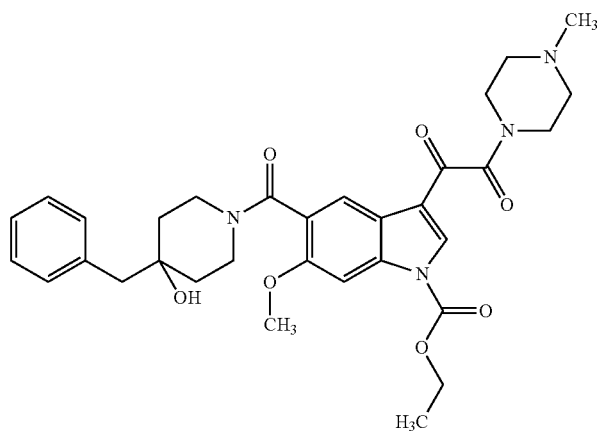 [SMILES: CCOC(=O)n1cc(C(=O)C(=O)N2CCN(C)CC2)c2cc(C(=O)N3CCC(O)(Cc4ccccc4)CC3)c(OC)cc21]
10 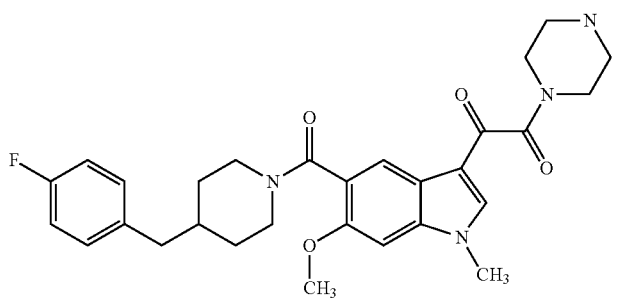 [SMILES: COc1cc2c(cc1C(=O)N1CCC(Cc3ccc(F)cc3)CC1)c(C(=O)C(=O)N1CCNCC1)cn2C]
11 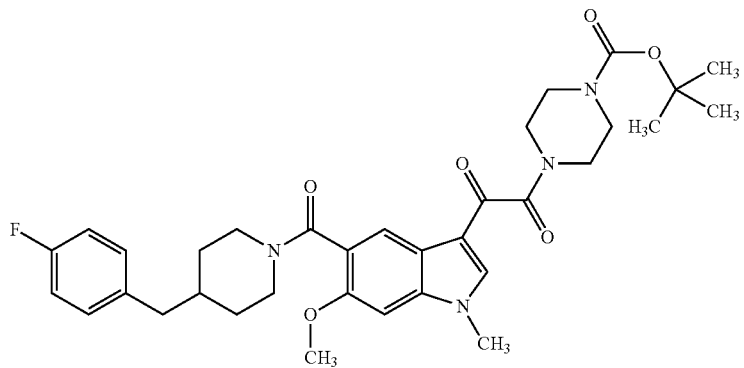 [SMILES: COc1cc2c(cc1C(=O)N1CCC(Cc3ccc(F)cc3)CC1)c(C(=O)C(=O)N1CCN(C(=O)OC(C)(C)C)CC1)cn2C]

12
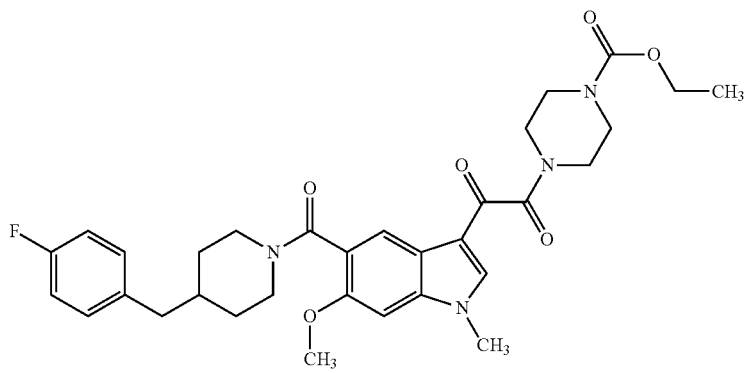 [SMILES: CCOC(=O)N1CCN(C(=O)C(=O)c2cn(C)c3cc(OC)c(C(=O)N4CCC(Cc5ccc(F)cc5)CC4)cc23)CC1]
13
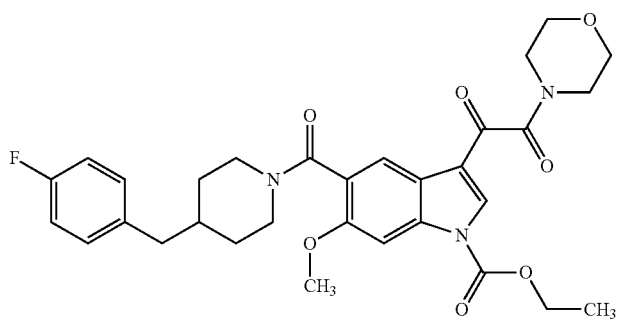 [SMILES: CCOC(=O)n1cc(C(=O)C(=O)N2CCOCC2)c2cc(C(=O)N3CCC(Cc4ccc(F)cc4)CC3)c(OC)cc21]
14
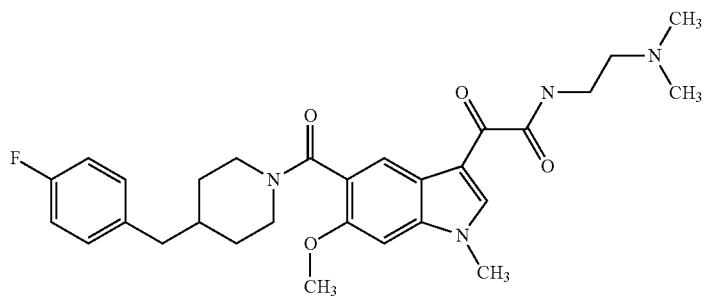 [SMILES: COc1cc2c(cc1C(=O)N1CCC(Cc3ccc(F)cc3)CC1)c(C(=O)C(=O)NCCN(C)C)cn2C]
15
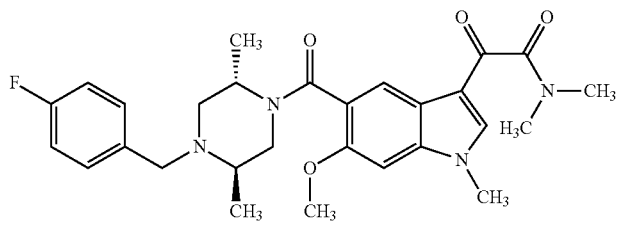 [SMILES: COc1cc2c(cc1C(=O)N1C[C@@H](C)N(Cc3ccc(F)cc3)C[C@@H]1C)c(C(=O)C(=O)N(C)C)cn2C]
16
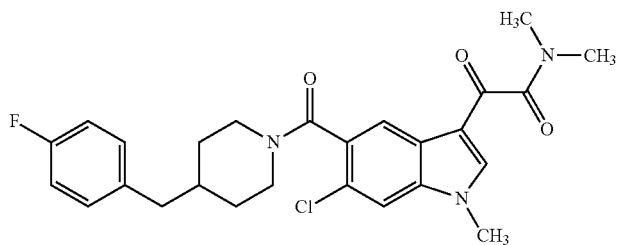 [SMILES: CN(C)C(=O)C(=O)c1cn(C)c2cc(Cl)c(C(=O)N3CCC(Cc4ccc(F)cc4)CC3)cc12]

17 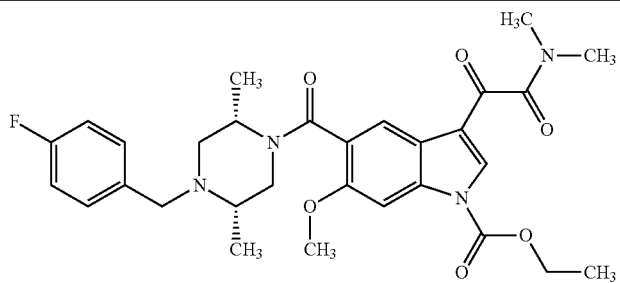
18 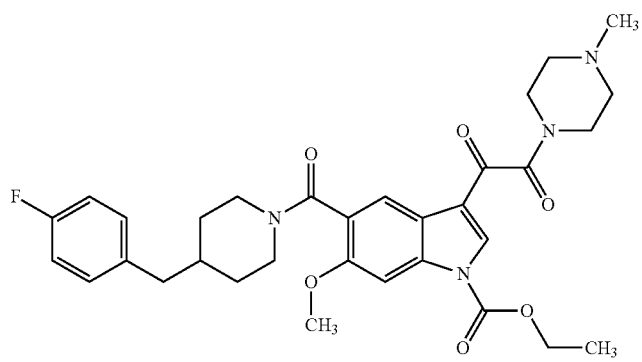 [SMILES: CCOC(=O)n1cc(C(=O)C(=O)N2CCN(C)CC2)c2cc(C(=O)N3CCC(Cc4ccc(F)cc4)CC3)c(OC)cc21]
19 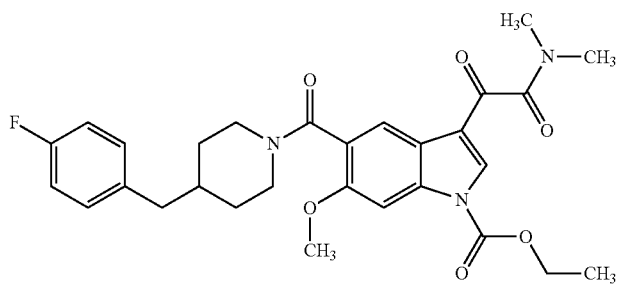 [SMILES: CCOC(=O)n1cc(C(=O)C(=O)N(C)C)c2cc(C(=O)N3CCC(Cc4ccc(F)cc4)CC3)c(OC)cc21]
20 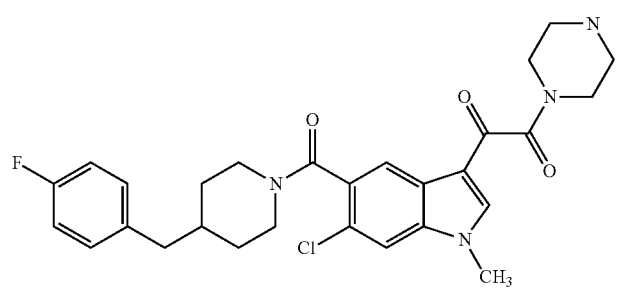 [SMILES: Cn1cc(C(=O)C(=O)N2CCNCC2)c2cc(C(=O)N3CCC(Cc4ccc(F)cc4)CC3)c(Cl)cc21]
21 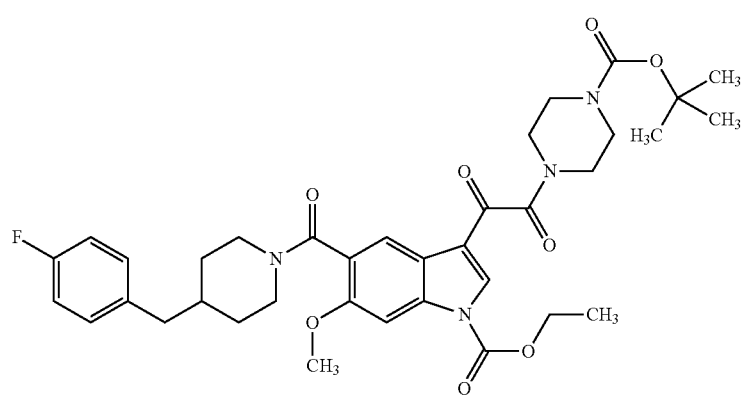 [SMILES: CCOC(=O)n1cc(C(=O)C(=O)N2CCN(C(=O)OC(C)(C)C)CC2)c2cc(C(=O)N3CCC(Cc4ccc(F)cc4)CC3)c(OC)cc21]

-continued
22
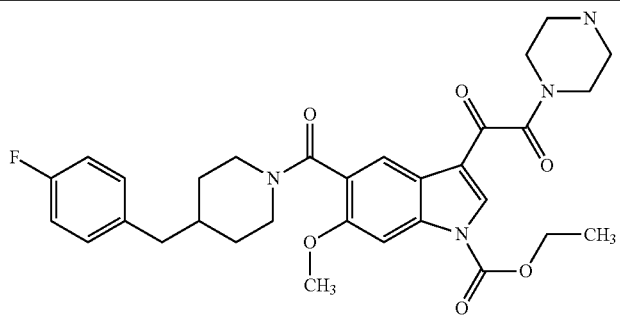
23
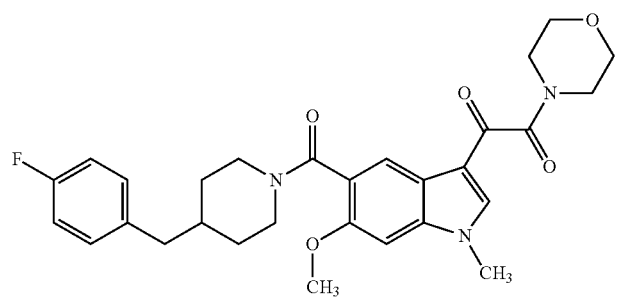 [SMILES: COc1cc2c(cc1C(=O)N1CCC(Cc3ccc(F)cc3)CC1)c(C(=O)C(=O)N1CCOCC1)cn2C]
24
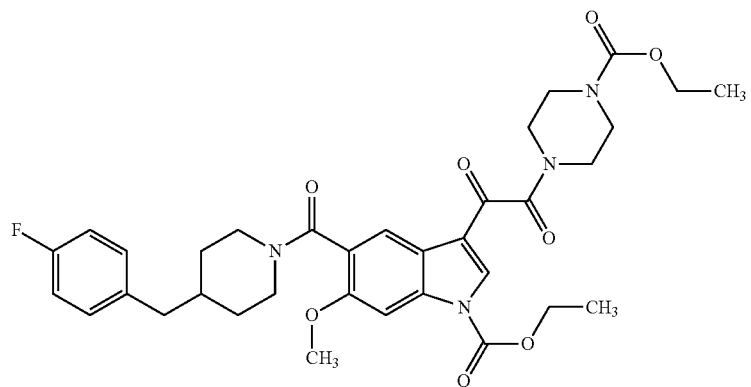 [SMILES: CCOC(=O)N1CCN(C(=O)C(=O)c2cn(C(=O)OCC)c3cc(OC)c(C(=O)N4CCC(Cc5ccc(F)cc5)CC4)cc23)CC1]
25
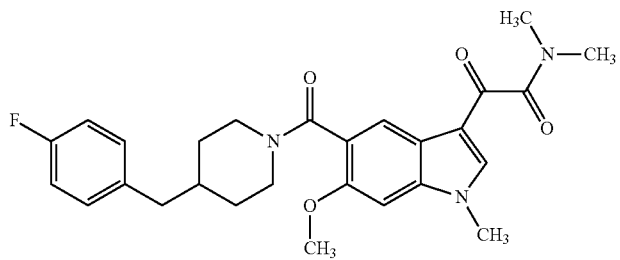 [SMILES: COc1cc2c(cc1C(=O)N1CCC(Cc3ccc(F)cc3)CC1)c(C(=O)C(=O)N(C)C)cn2C]
26
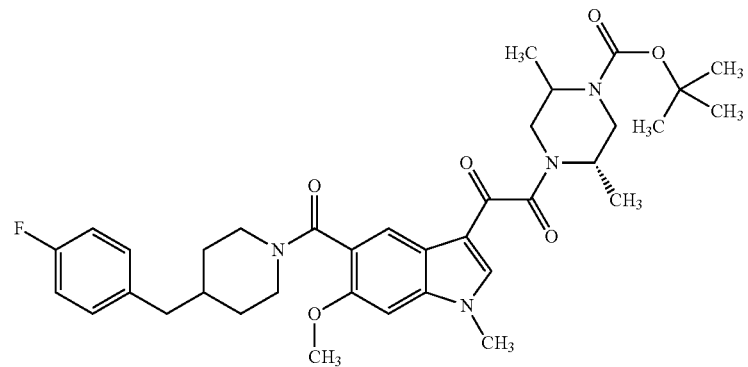 [SMILES: COc1cc2c(cc1C(=O)N1CCC(Cc3ccc(F)cc3)CC1)c(C(=O)C(=O)N1CC(C)N(C(=O)OC(C)(C)C)C[C@@H]1C)cn2C]

27
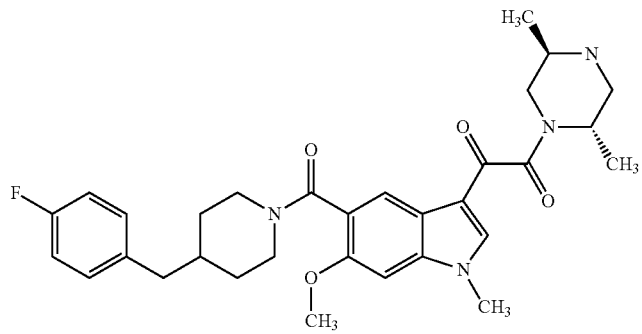 [SMILES: COc1cc2c(cc1C(=O)N1CCC(Cc3ccc(F)cc3)CC1)c(C(=O)C(=O)N1C[C@@H](C)NC[C@@H]1C)cn2C]
28
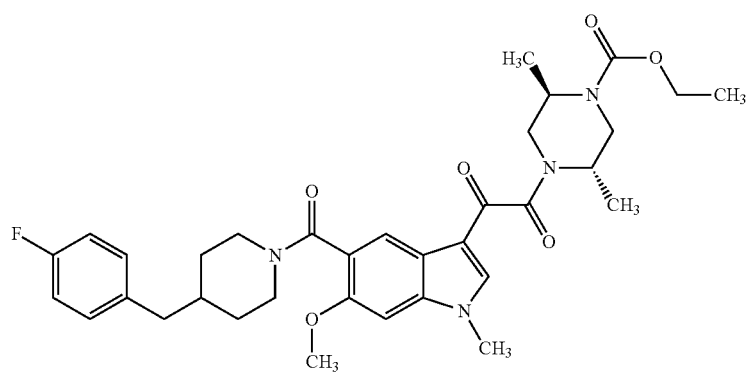 [SMILES: CCOC(=O)N1C[C@H](C)N(C(=O)C(=O)c2cn(C)c3cc(OC)c(C(=O)N4CCC(Cc5ccc(F)cc5)CC4)cc23)C[C@H]1C]
29
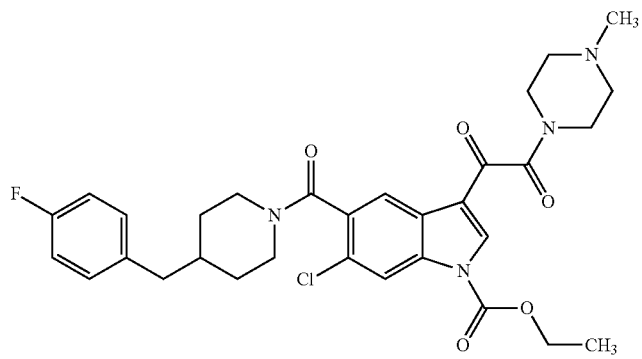 [SMILES: CCOC(=O)n1cc(C(=O)C(=O)N2CCN(C)CC2)c2cc(C(=O)N3CCC(Cc4ccc(F)cc4)CC3)c(Cl)cc21]
30
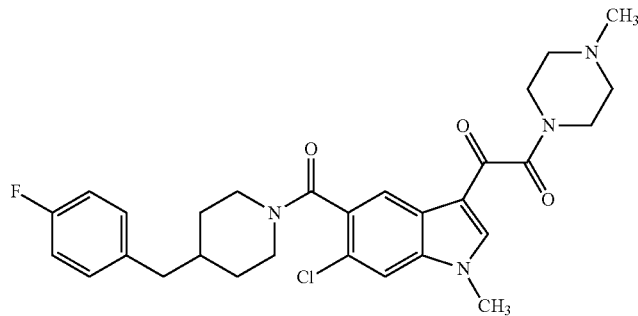 [SMILES: CN1CCN(C(=O)C(=O)c2cn(C)c3cc(Cl)c(C(=O)N4CCC(Cc5ccc(F)cc5)CC4)cc23)CC1]

-continued
31
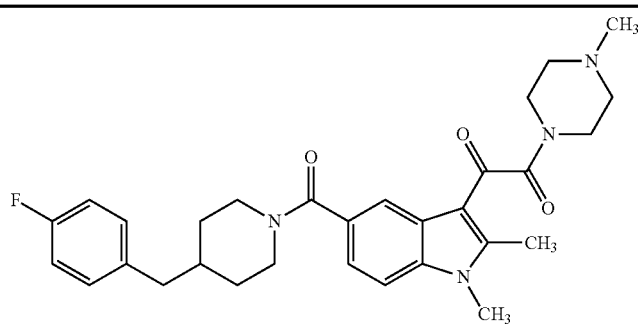
32
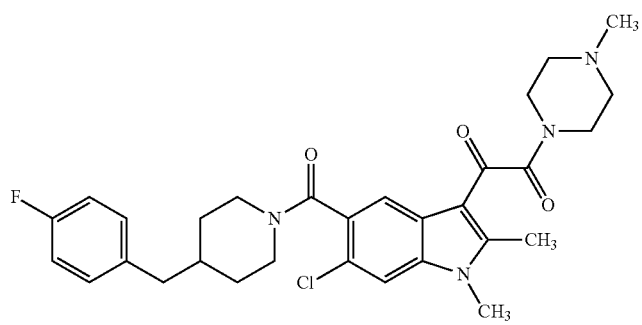 [SMILES: Cc1c(C(=O)C(=O)N2CCN(C)CC2)c2cc(C(=O)N3CCC(Cc4ccc(F)cc4)CC3)c(Cl)cc2n1C]
33
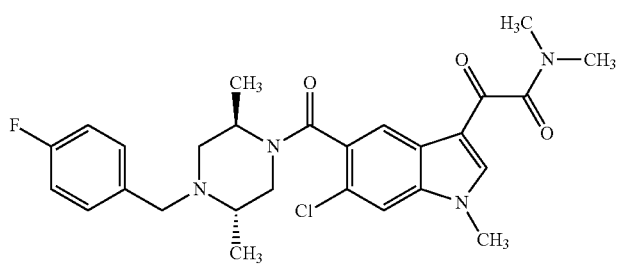 [SMILES: C[C@@H]1CN(Cc2ccc(F)cc2)[C@@H](C)CN1C(=O)c1cc2c(C(=O)C(=O)N(C)C)cn(C)c2cc1Cl]
34
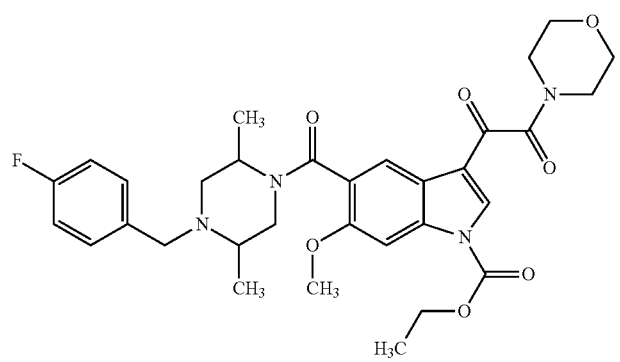 [SMILES: CCOC(=O)n1cc(C(=O)C(=O)N2CCOCC2)c2cc(C(=O)N3CC(C)N(Cc4ccc(F)cc4)CC3C)c(OC)cc21]
35
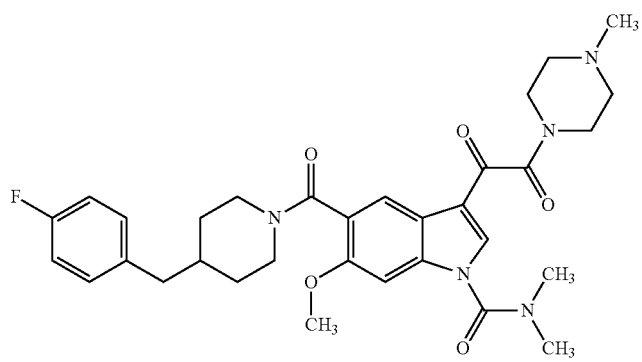 [SMILES: COc1cc2c(cc1C(=O)N1CCC(Cc3ccc(F)cc3)CC1)c(C(=O)C(=O)N1CCN(C)CC1)cn2C(=O)N(C)C]

36
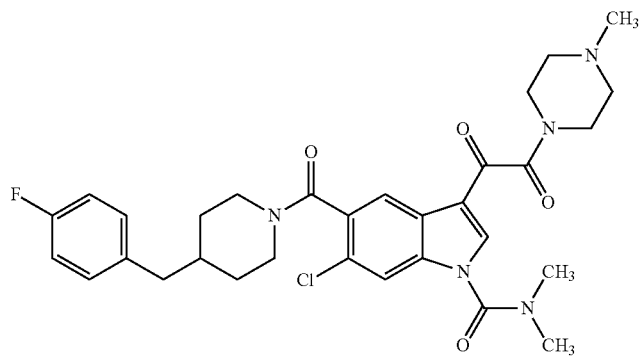 [SMILES: CN1CCN(C(=O)C(=O)c2cn(C(=O)N(C)C)c3cc(Cl)c(C(=O)N4CCC(Cc5ccc(F)cc5)CC4)cc23)CC1]
37
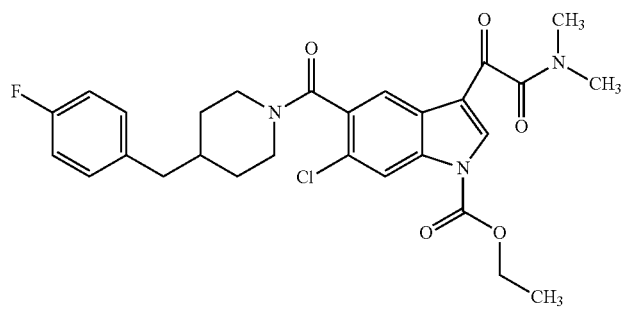 [SMILES: CCOC(=O)n1cc(C(=O)C(=O)N(C)C)c2cc(C(=O)N3CCC(Cc4ccc(F)cc4)CC3)c(Cl)cc21]
38
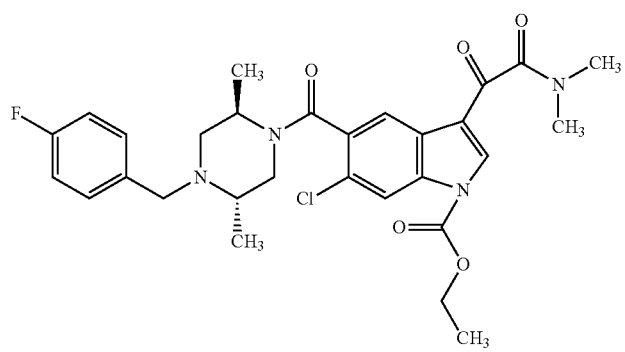 [SMILES: CCOC(=O)n1cc(C(=O)C(=O)N(C)C)c2cc(C(=O)N3C[C@H](C)N(Cc4ccc(F)cc4)C[C@H]3C)c(Cl)cc21]
39
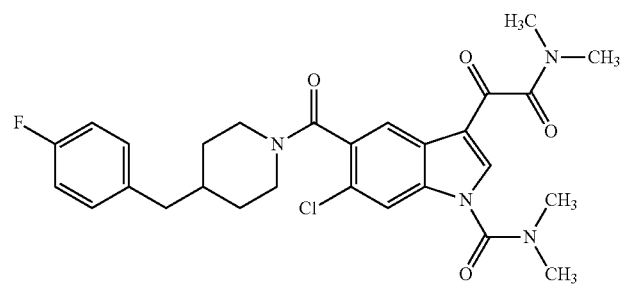 [SMILES: CN(C)C(=O)C(=O)c1cn(C(=O)N(C)C)c2cc(Cl)c(C(=O)N3CCC(Cc4ccc(F)cc4)CC3)cc12]
40
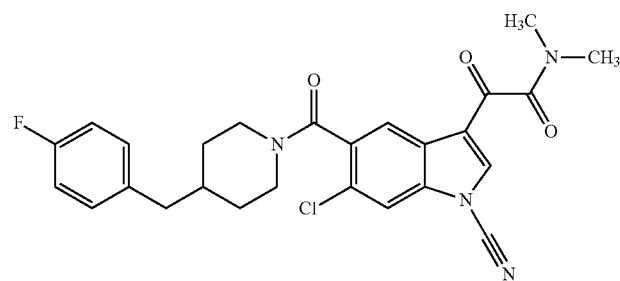 [SMILES: CN(C)C(=O)C(=O)c1cn(C#N)c2cc(Cl)c(C(=O)N3CCC(Cc4ccc(F)cc4)CC3)cc12]

41
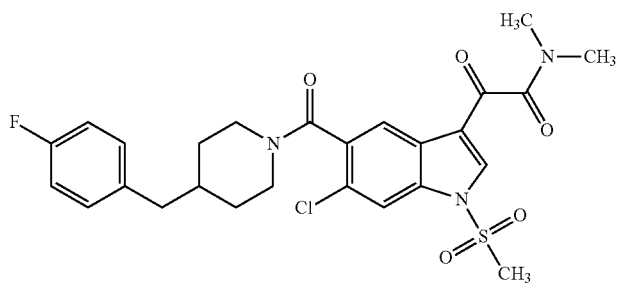 [SMILES: CN(C)C(=O)C(=O)c1cn(S(C)(=O)=O)c2cc(Cl)c(C(=O)N3CCC(Cc4ccc(F)cc4)CC3)cc12]
42
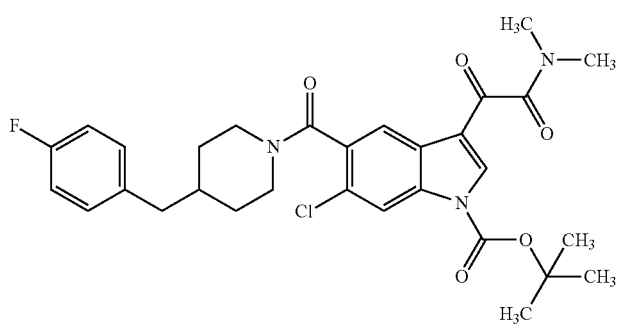 [SMILES: CN(C)C(=O)C(=O)c1cn(C(=O)OC(C)(C)C)c2cc(Cl)c(C(=O)N3CCC(Cc4ccc(F)cc4)CC3)cc12]
43
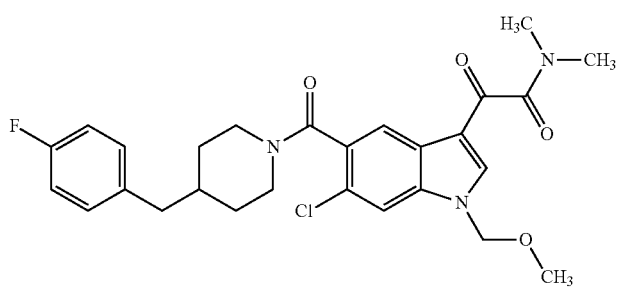 [SMILES: COCn1cc(C(=O)C(=O)N(C)C)c2cc(C(=O)N3CCC(Cc4ccc(F)cc4)CC3)c(Cl)cc21]
44
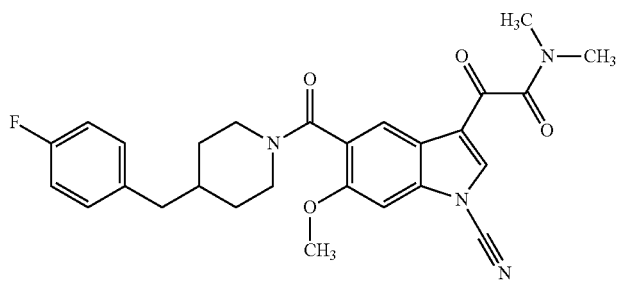 [SMILES: COc1cc2c(cc1C(=O)N1CCC(Cc3ccc(F)cc3)CC1)c(C(=O)C(=O)N(C)C)cn2C#N]
45
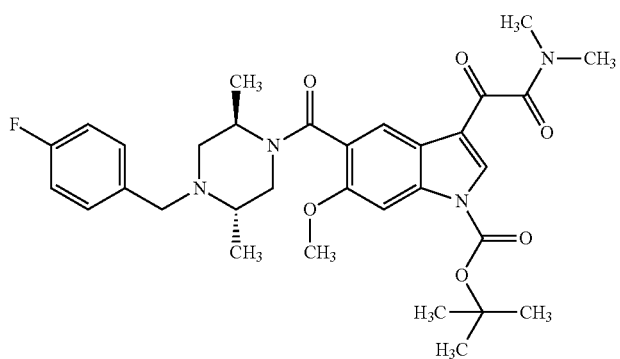 [SMILES: COc1cc2c(cc1C(=O)N1C[C@H](C)N(Cc3ccc(F)cc3)C[C@H]1C)c(C(=O)C(=O)N(C)C)cn2C(=O)OC(C)(C)C]

46
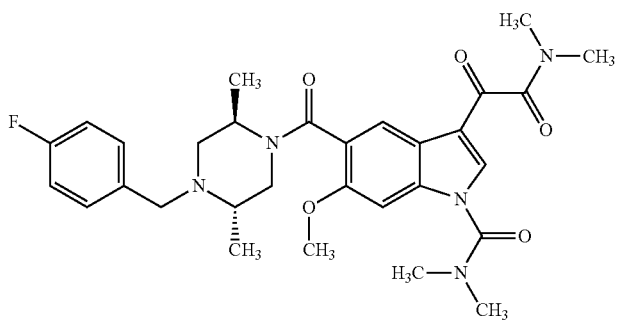 [SMILES: COc1cc2c(cc1C(=O)N1C[C@H](C)N(Cc3ccc(F)cc3)C[C@H]1C)c(C(=O)C(=O)N(C)C)cn2C(=O)N(C)C]
47
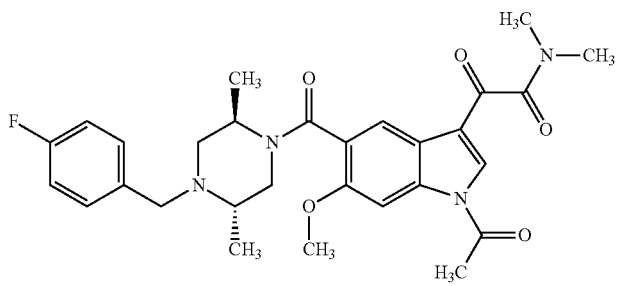 [SMILES: COc1cc2c(cc1C(=O)N1C[C@H](C)N(Cc3ccc(F)cc3)C[C@H]1C)c(C(=O)C(=O)N(C)C)cn2C(C)=O]
48
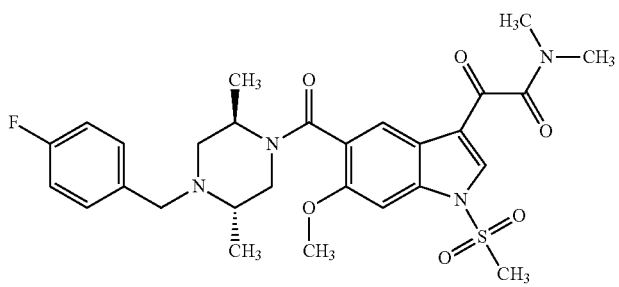 [SMILES: COc1cc2c(cc1C(=O)N1C[C@H](C)N(Cc3ccc(F)cc3)C[C@H]1C)c(C(=O)C(=O)N(C)C)cn2S(C)(=O)=O]
49
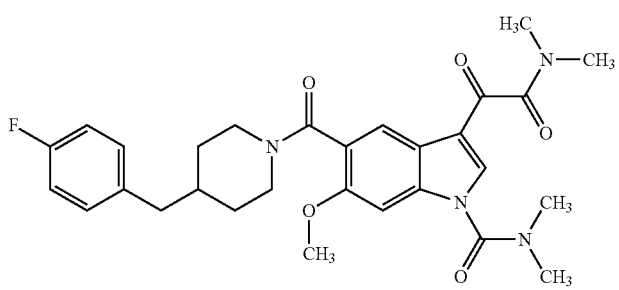 [SMILES: COc1cc2c(cc1C(=O)N1CCC(Cc3ccc(F)cc3)CC1)c(C(=O)C(=O)N(C)C)cn2C(=O)N(C)C]
50
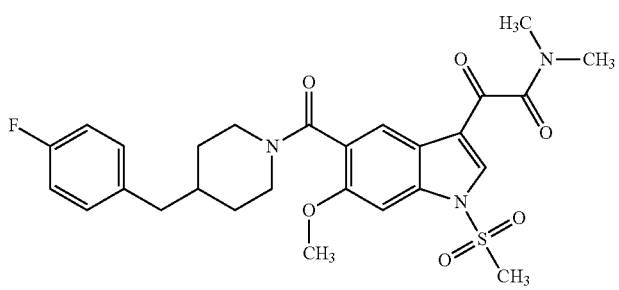 [SMILES: COc1cc2c(cc1C(=O)N1CCC(Cc3ccc(F)cc3)CC1)c(C(=O)C(=O)N(C)C)cn2S(C)(=O)=O]

51 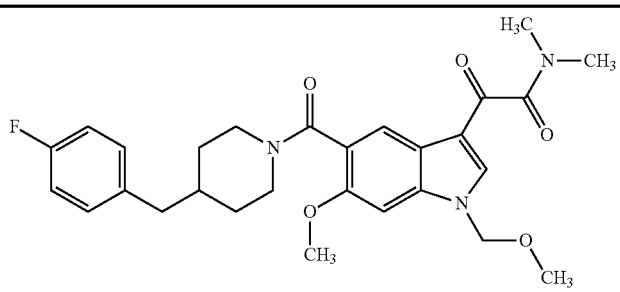
52 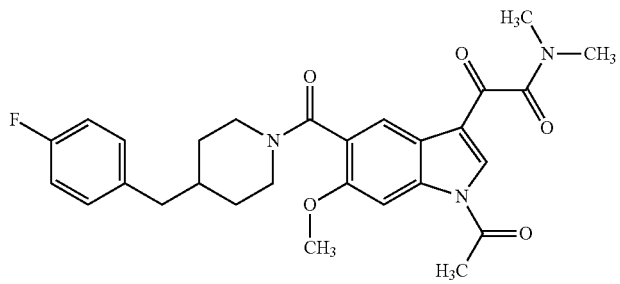 [SMILES: COc1cc2c(cc1C(=O)N1CCC(Cc3ccc(F)cc3)CC1)c(C(=O)C(=O)N(C)C)cn2C(C)=O]
53 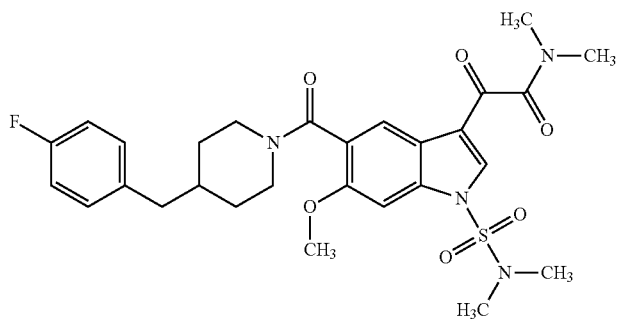 [SMILES: COc1cc2c(cc1C(=O)N1CCC(Cc3ccc(F)cc3)CC1)c(C(=O)C(=O)N(C)C)cn2S(=O)(=O)N(C)C]
54 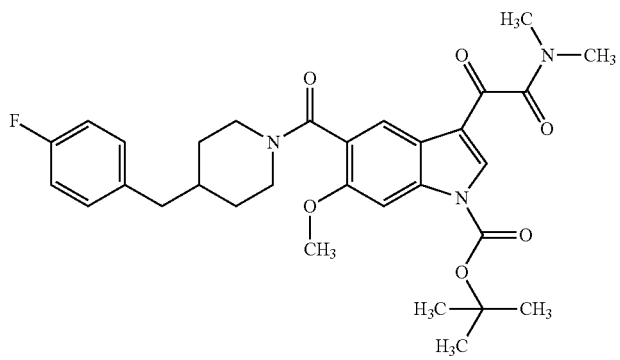 [SMILES: COc1cc2c(cc1C(=O)N1CCC(Cc3ccc(F)cc3)CC1)c(C(=O)C(=O)N(C)C)cn2C(=O)OC(C)(C)C]
55 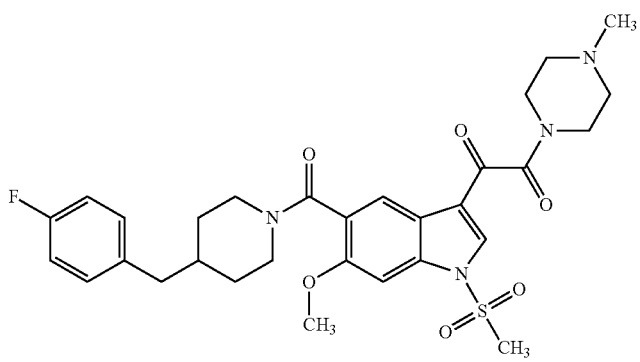 [SMILES: COc1cc2c(cc1C(=O)N1CCC(Cc3ccc(F)cc3)CC1)c(C(=O)C(=O)N1CCN(C)CC1)cn2S(C)(=O)=O]

-continued
| 56 | 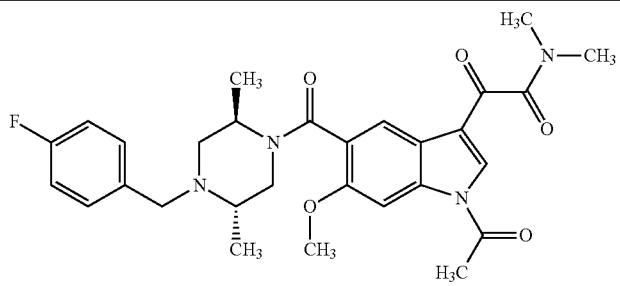 |
| 57 | 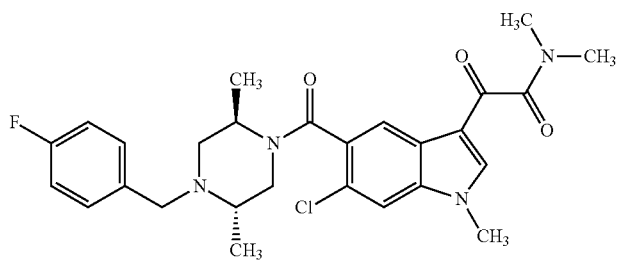 [SMILES: C[C@@H]1CN(Cc2ccc(F)cc2)[C@@H](C)CN1C(=O)c1cc2c(C(=O)C(=O)N(C)C)cn(C)c2cc1Cl] |
| 58 | 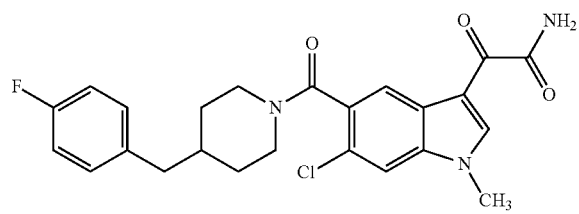 [SMILES: Cn1cc(C(=O)C(N)=O)c2cc(C(=O)N3CCC(Cc4ccc(F)cc4)CC3)c(Cl)cc21] |
| 59 | 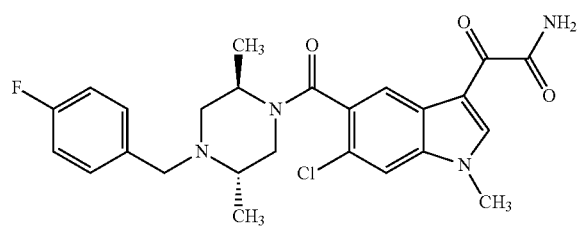 [SMILES: C[C@@H]1CN(Cc2ccc(F)cc2)[C@@H](C)CN1C(=O)c1cc2c(C(=O)C(N)=O)cn(C)c2cc1Cl] |
| 60 | 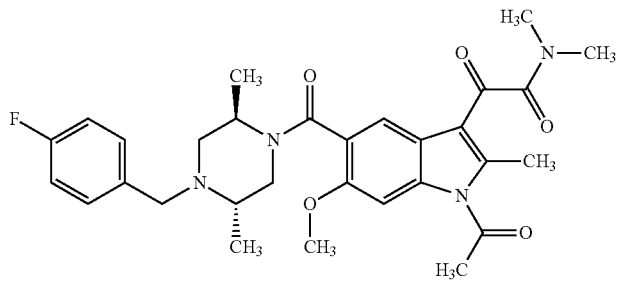 [SMILES: COc1cc2c(cc1C(=O)N1C[C@H](C)N(Cc3ccc(F)cc3)C[C@H]1C)c(C(=O)C(=O)N(C)C)c(C)n2C(C)=O] |
| 61 | 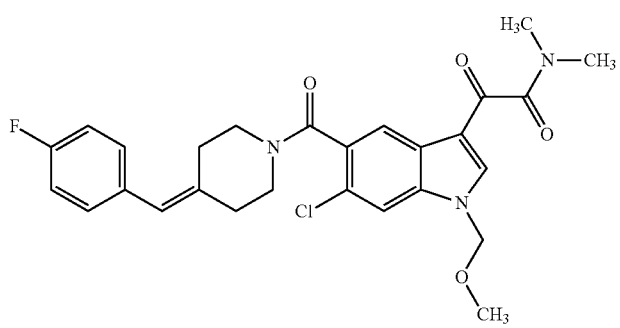 [SMILES: COCn1cc(C(=O)C(=O)N(C)C)c2cc(C(=O)N3CCC(=Cc4ccc(F)cc4)CC3)c(Cl)cc21] |

62 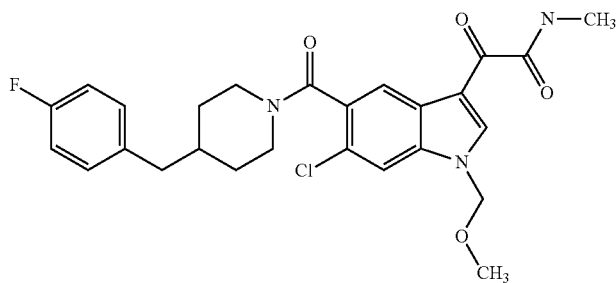 [SMILES: CNC(=O)C(=O)c1cn(COC)c2cc(Cl)c(C(=O)N3CCC(Cc4ccc(F)cc4)CC3)cc12]
63 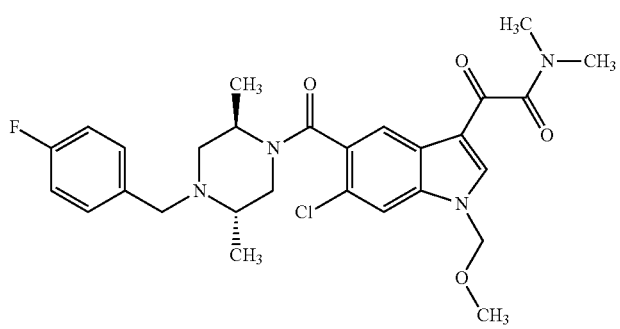 [SMILES: COCn1cc(C(=O)C(=O)N(C)C)c2cc(C(=O)N3C[C@H](C)N(Cc4ccc(F)cc4)C[C@H]3C)c(Cl)cc21]
64 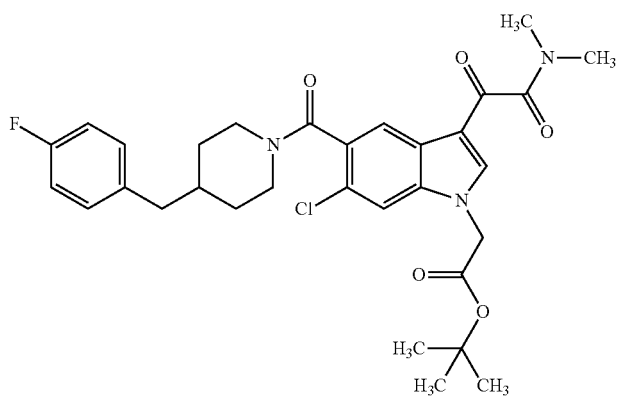 [SMILES: CN(C)C(=O)C(=O)c1cn(CC(=O)OC(C)(C)C)c2cc(Cl)c(C(=O)N3CCC(Cc4ccc(F)cc4)CC3)cc12]
65 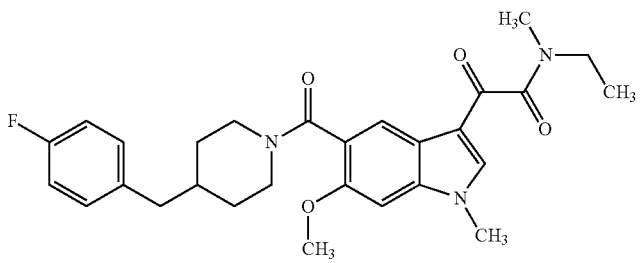 [SMILES: CCN(C)C(=O)C(=O)c1cn(C)c2cc(OC)c(C(=O)N3CCC(Cc4ccc(F)cc4)CC3)cc12]
66 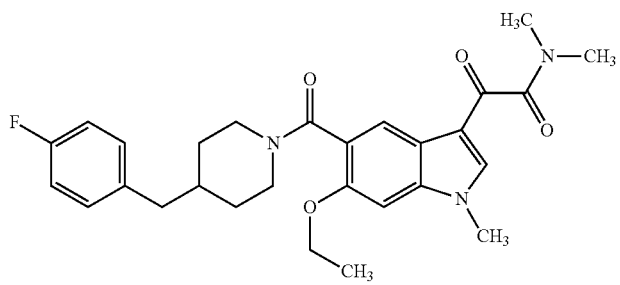 [SMILES: CCOc1cc2c(cc1C(=O)N1CCC(Cc3ccc(F)cc3)CC1)c(C(=O)C(=O)N(C)C)cn2C]

67 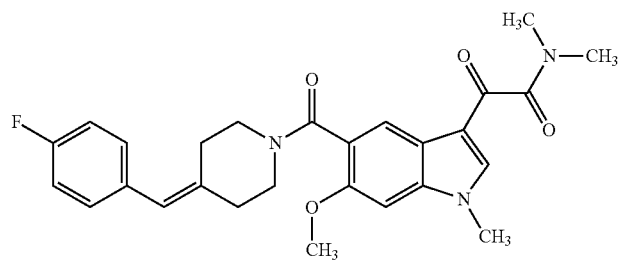 [SMILES: COc1cc2c(cc1C(=O)N1CCC(=Cc3ccc(F)cc3)CC1)c(C(=O)C(=O)N(C)C)cn2C]
68 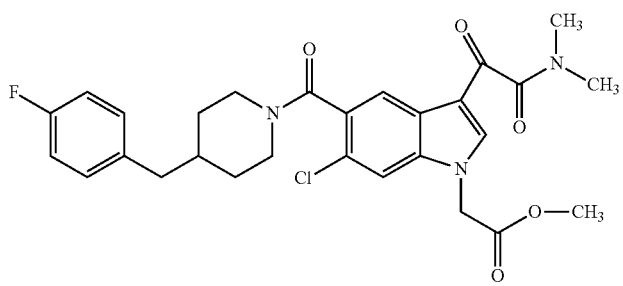 [SMILES: COC(=O)Cn1cc(C(=O)C(=O)N(C)C)c2cc(C(=O)N3CCC(Cc4ccc(F)cc4)CC3)c(Cl)cc21]
69 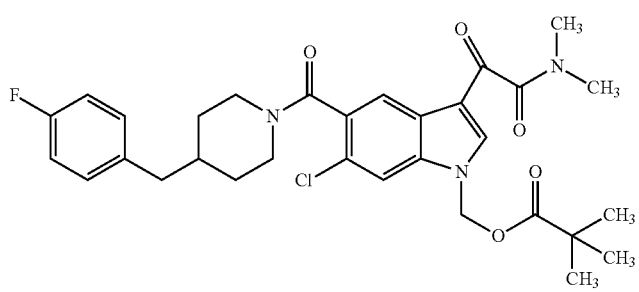 [SMILES: CN(C)C(=O)C(=O)c1cn(COC(=O)C(C)(C)C)c2cc(Cl)c(C(=O)N3CCC(Cc4ccc(F)cc4)CC3)cc12]
70 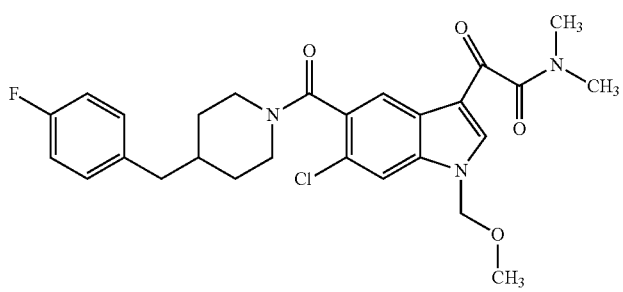 [SMILES: COCn1cc(C(=O)C(=O)N(C)C)c2cc(C(=O)N3CCC(Cc4ccc(F)cc4)CC3)c(Cl)cc21]
71 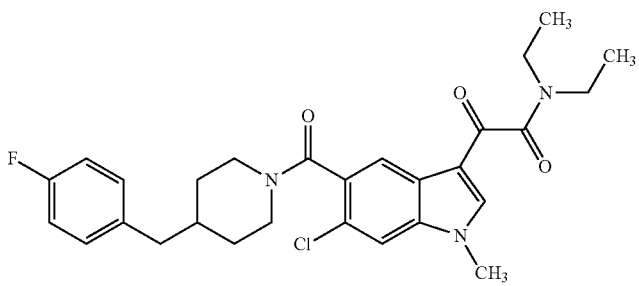 [SMILES: CCN(CC)C(=O)C(=O)c1cn(C)c2cc(Cl)c(C(=O)N3CCC(Cc4ccc(F)cc4)CC3)cc12]

-continued
72
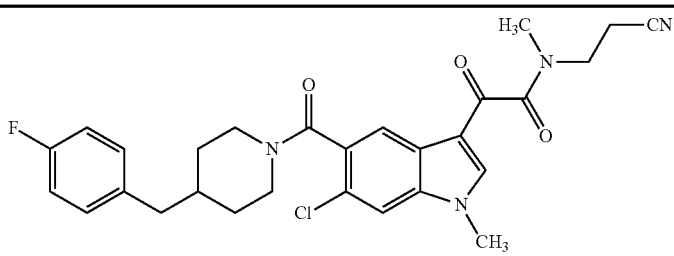
73
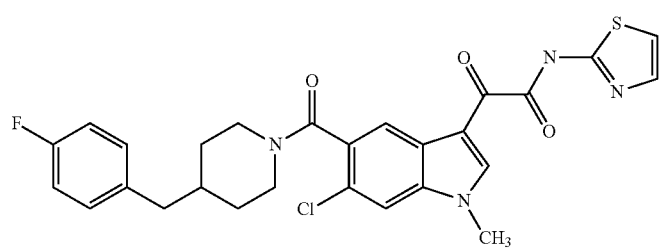 [SMILES: Cn1cc(C(=O)C(=O)Nc2nccs2)c2cc(C(=O)N3CCC(Cc4ccc(F)cc4)CC3)c(Cl)cc21]
74
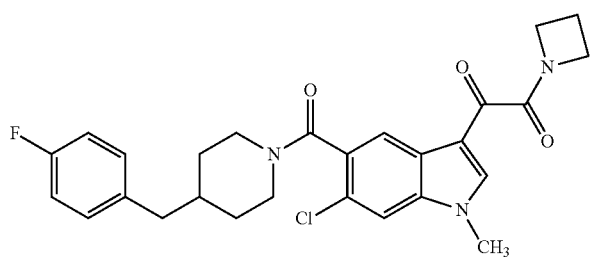 [SMILES: Cn1cc(C(=O)C(=O)N2CCC2)c2cc(C(=O)N3CCC(Cc4ccc(F)cc4)CC3)c(Cl)cc21]
75
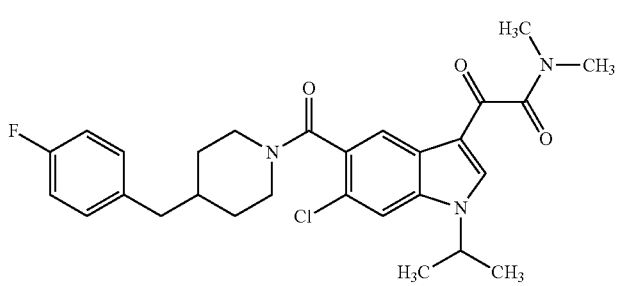 [SMILES: CC(C)n1cc(C(=O)C(=O)N(C)C)c2cc(C(=O)N3CCC(Cc4ccc(F)cc4)CC3)c(Cl)cc21]
76
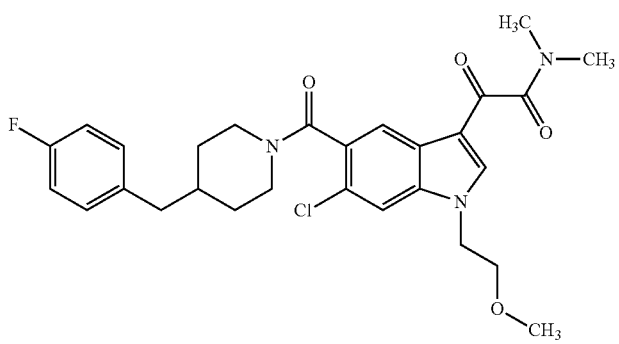 [SMILES: COCCn1cc(C(=O)C(=O)N(C)C)c2cc(C(=O)N3CCC(Cc4ccc(F)cc4)CC3)c(Cl)cc21]
77
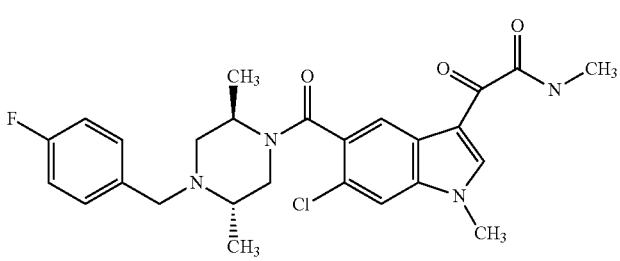 [SMILES: CNC(=O)C(=O)c1cn(C)c2cc(Cl)c(C(=O)N3C[C@H](C)N(Cc4ccc(F)cc4)C[C@H]3C)cc12]

78 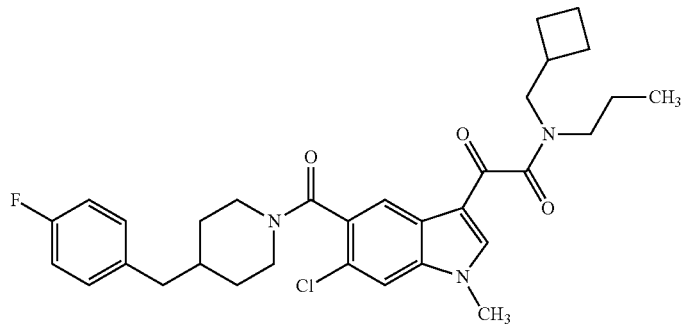 [SMILES: CCCN(CC1CCC1)C(=O)C(=O)c1cn(C)c2cc(Cl)c(C(=O)N3CCC(Cc4ccc(F)cc4)CC3)cc12]
79 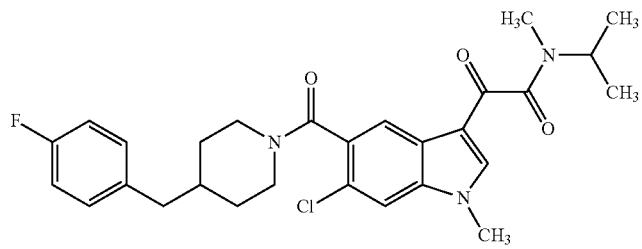 [SMILES: CC(C)N(C)C(=O)C(=O)c1cn(C)c2cc(Cl)c(C(=O)N3CCC(Cc4ccc(F)cc4)CC3)cc12]
80 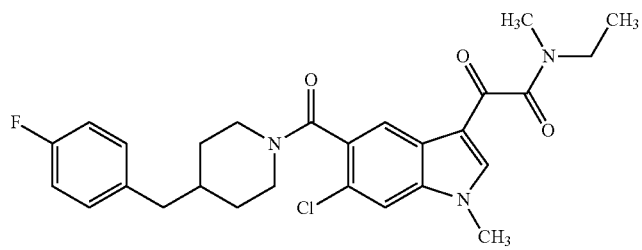 [SMILES: CCN(C)C(=O)C(=O)c1cn(C)c2cc(Cl)c(C(=O)N3CCC(Cc4ccc(F)cc4)CC3)cc12]
81 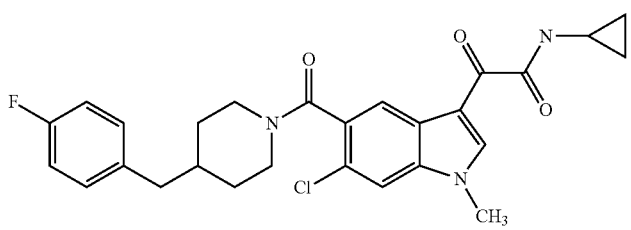 [SMILES: Cn1cc(C(=O)C(=O)NC2CC2)c2cc(C(=O)N3CCC(Cc4ccc(F)cc4)CC3)c(Cl)cc21]
82 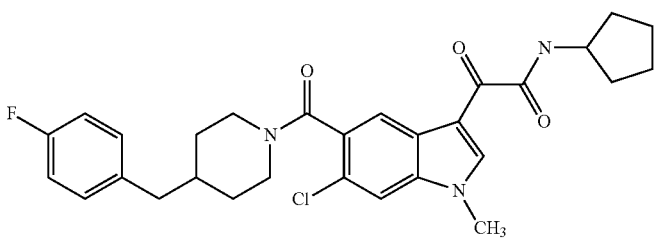 [SMILES: Cn1cc(C(=O)C(=O)NC2CCCC2)c2cc(C(=O)N3CCC(Cc4ccc(F)cc4)CC3)c(Cl)cc21]
83 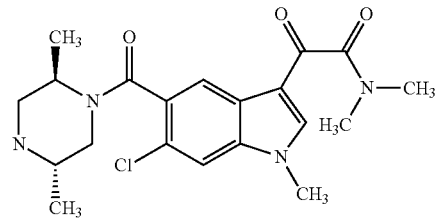 [SMILES: C[C@@H]1CN[C@@H](C)CN1C(=O)c1cc2c(C(=O)C(=O)N(C)C)cn(C)c2cc1Cl]

| | |
|---|---|
| 84 | 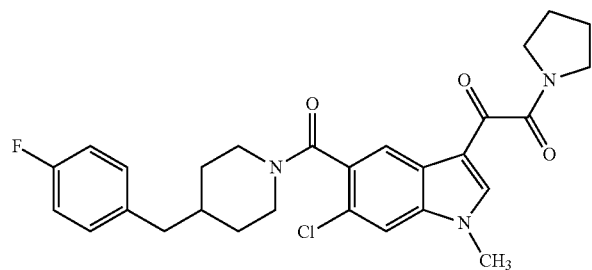 [SMILES: Cn1cc(C(=O)C(=O)N2CCCC2)c2cc(C(=O)N3CCC(Cc4ccc(F)cc4)CC3)c(Cl)cc21] |
| 85 | 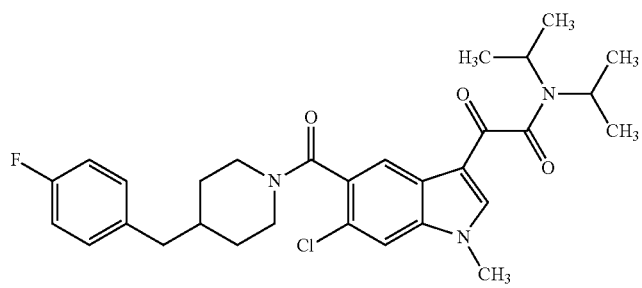 [SMILES: CC(C)N(C(=O)C(=O)c1cn(C)c2cc(Cl)c(C(=O)N3CCC(Cc4ccc(F)cc4)CC3)cc12)C(C)C] |
| 86 | 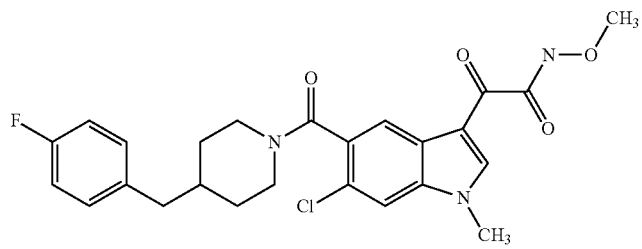 [SMILES: CONC(=O)C(=O)c1cn(C)c2cc(Cl)c(C(=O)N3CCC(Cc4ccc(F)cc4)CC3)cc12] |
| 87 | 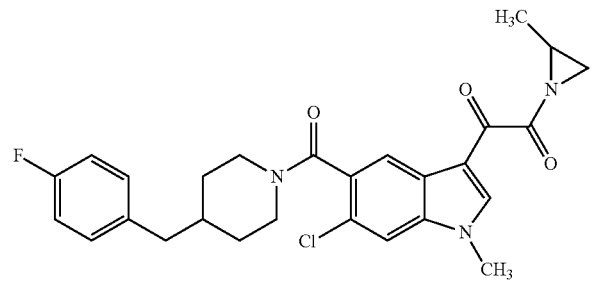 [SMILES: CC1CN1C(=O)C(=O)c1cn(C)c2cc(Cl)c(C(=O)N3CCC(Cc4ccc(F)cc4)CC3)cc12] |
| 88 | 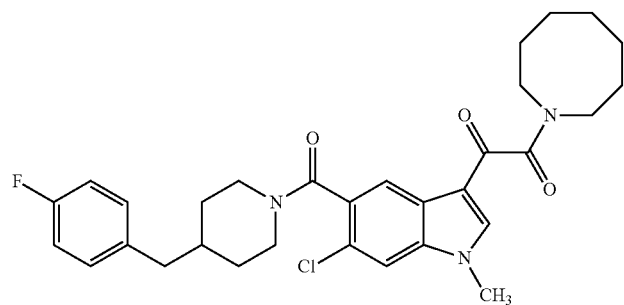 [SMILES: Cn1cc(C(=O)C(=O)N2CCCCCCC2)c2cc(C(=O)N3CCC(Cc4ccc(F)cc4)CC3)c(Cl)cc21] |

-continued
| 89 | 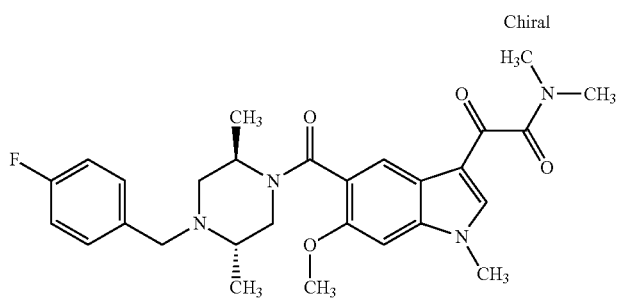 [SMILES: COc1cc2c(cc1C(=O)N1C[C@H](C)N(Cc3ccc(F)cc3)C[C@H]1C)c(C(=O)C(=O)N(C)C)cn2C] |
| 90 | 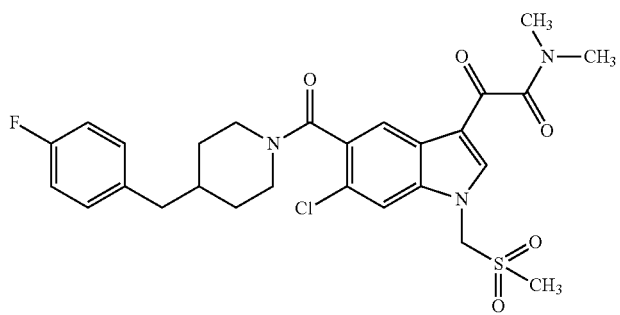 [SMILES: CN(C)C(=O)C(=O)c1cn(CS(C)(=O)=O)c2cc(Cl)c(C(=O)N3CCC(Cc4ccc(F)cc4)CC3)cc12] |
| 91 | 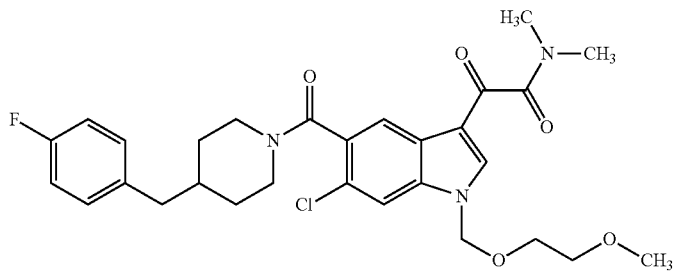 [SMILES: COCCOCn1cc(C(=O)C(=O)N(C)C)c2cc(C(=O)N3CCC(Cc4ccc(F)cc4)CC3)c(Cl)cc21] |
| 92 | 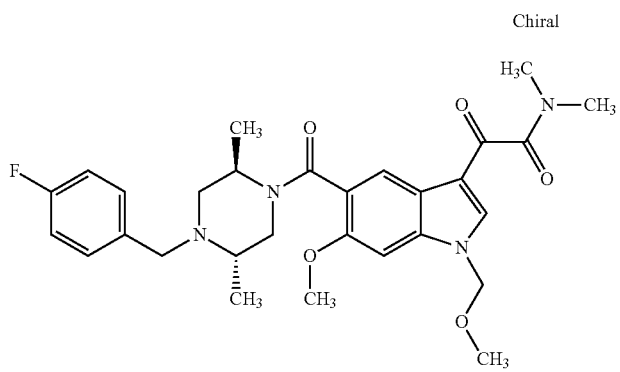 [SMILES: COCn1cc(C(=O)C(=O)N(C)C)c2cc(C(=O)N3C[C@H](C)N(Cc4ccc(F)cc4)C[C@H]3C)c(OC)cc21] |
| 93 | 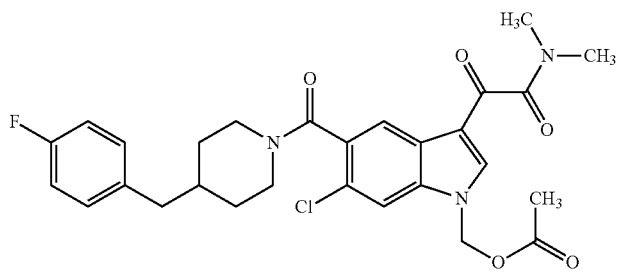 [SMILES: CC(=O)OCn1cc(C(=O)C(=O)N(C)C)c2cc(C(=O)N3CCC(Cc4ccc(F)cc4)CC3)c(Cl)cc21] |

-continued
94
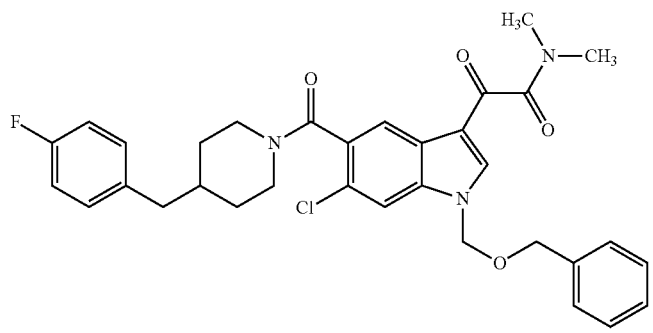 [SMILES: CN(C)C(=O)C(=O)c1cn(COCc2ccccc2)c2cc(Cl)c(C(=O)N3CCC(Cc4ccc(F)cc4)CC3)cc12]
95
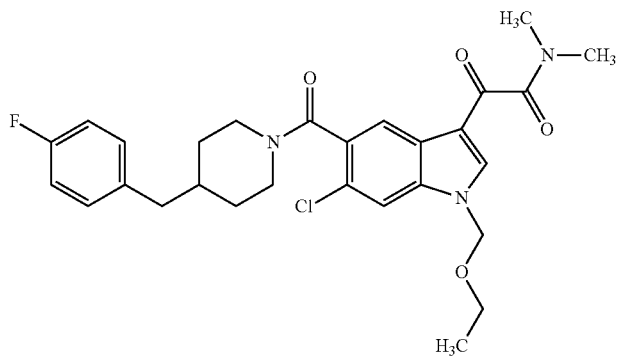 [SMILES: CCOCn1cc(C(=O)C(=O)N(C)C)c2cc(C(=O)N3CCC(Cc4ccc(F)cc4)CC3)c(Cl)cc21]
96
Chiral
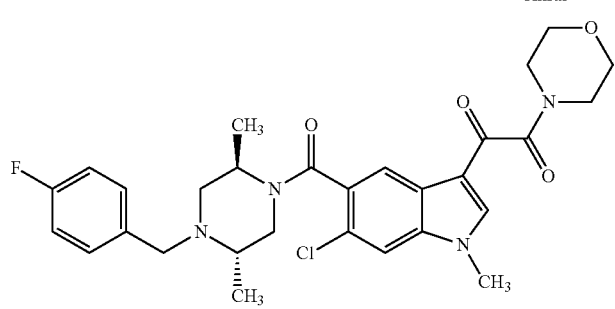
97
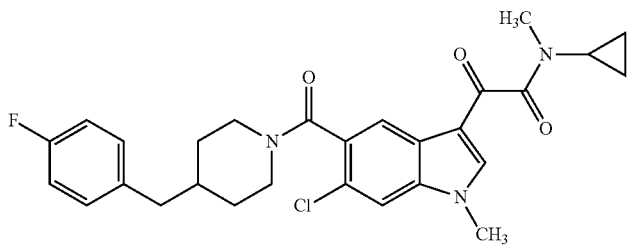 [SMILES: CN(C(=O)C(=O)c1cn(C)c2cc(Cl)c(C(=O)N3CCC(Cc4ccc(F)cc4)CC3)cc12)C1CC1]
98
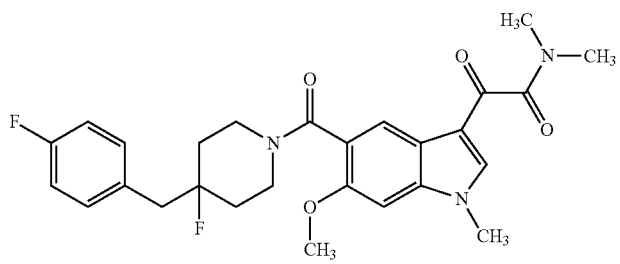

-continued
99
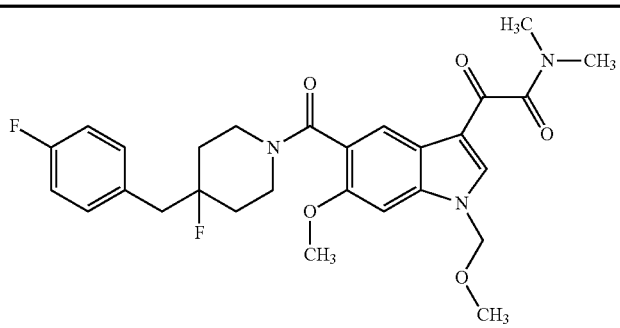
100
Chiral
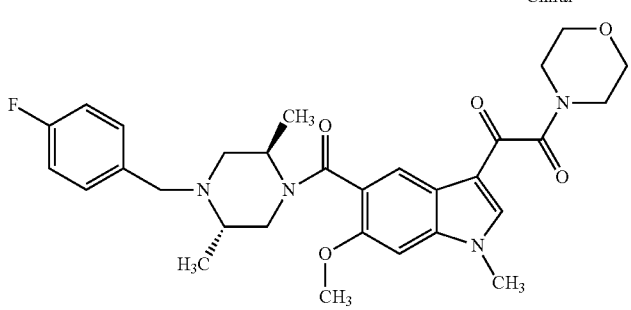
101
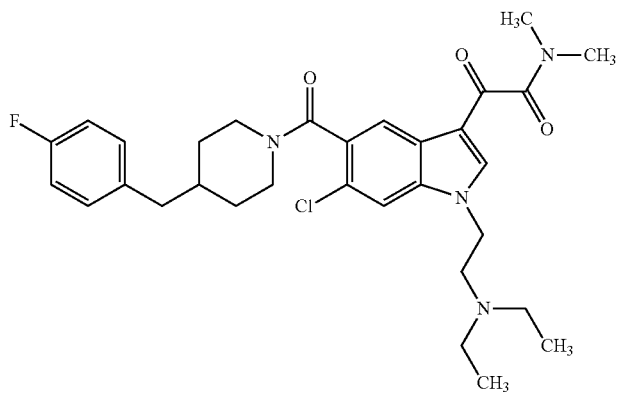 [SMILES: CCN(CC)CCn1cc(C(=O)C(=O)N(C)C)c2cc(C(=O)N3CCC(Cc4ccc(F)cc4)CC3)c(Cl)cc21]
102
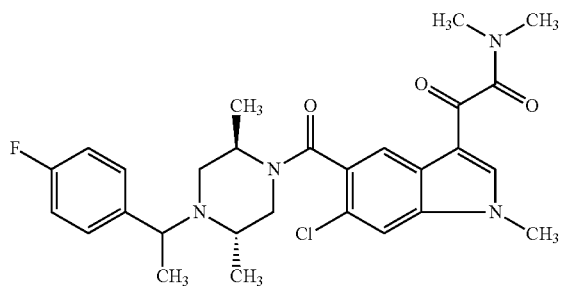 [SMILES: CC(c1ccc(F)cc1)N1C[C@@H](C)N(C(=O)c2cc3c(C(=O)C(=O)N(C)C)cn(C)c3cc2Cl)C[C@@H]1C]
103
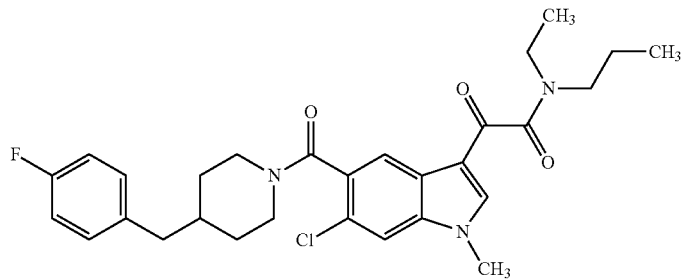 [SMILES: CCCN(CC)C(=O)C(=O)c1cn(C)c2cc(Cl)c(C(=O)N3CCC(Cc4ccc(F)cc4)CC3)cc12]

104
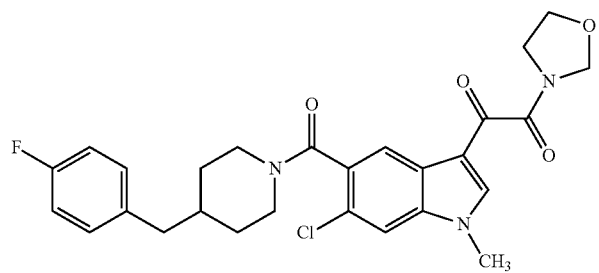 [SMILES: Cn1cc(C(=O)C(=O)N2CCOC2)c2cc(C(=O)N3CCC(Cc4ccc(F)cc4)CC3)c(Cl)cc21]
105
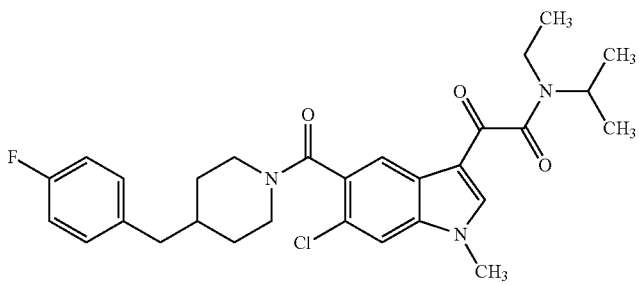 [SMILES: CCN(C(=O)C(=O)c1cn(C)c2cc(Cl)c(C(=O)N3CCC(Cc4ccc(F)cc4)CC3)cc12)C(C)C]
106
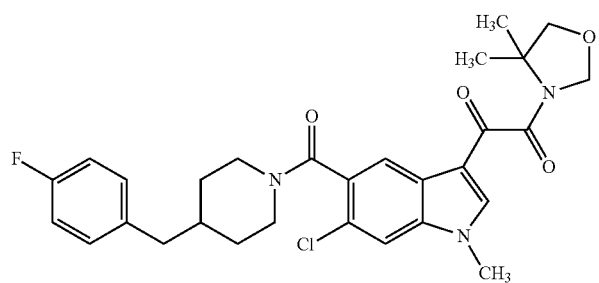 [SMILES: Cn1cc(C(=O)C(=O)N2COCC2(C)C)c2cc(C(=O)N3CCC(Cc4ccc(F)cc4)CC3)c(Cl)cc21]
107
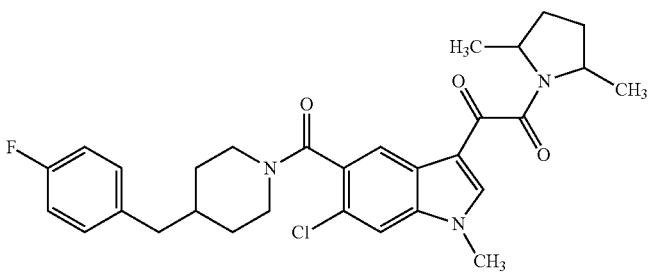 [SMILES: CC1CCC(C)N1C(=O)C(=O)c1cn(C)c2cc(Cl)c(C(=O)N3CCC(Cc4ccc(F)cc4)CC3)cc12]
108
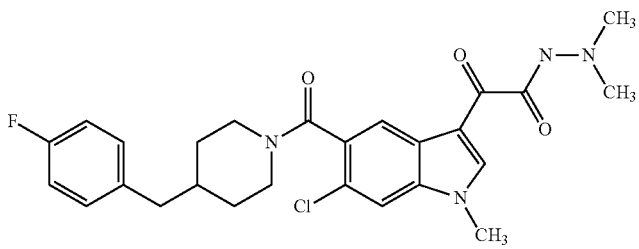 [SMILES: CN(C)NC(=O)C(=O)c1cn(C)c2cc(Cl)c(C(=O)N3CCC(Cc4ccc(F)cc4)CC3)cc12]

-continued
109
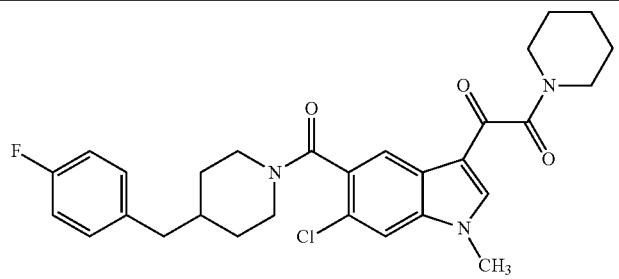
110
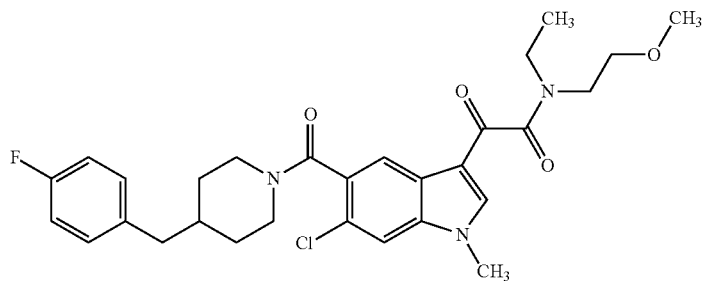 [SMILES: CCN(CCOC)C(=O)C(=O)c1cn(C)c2cc(Cl)c(C(=O)N3CCC(Cc4ccc(F)cc4)CC3)cc12]
111
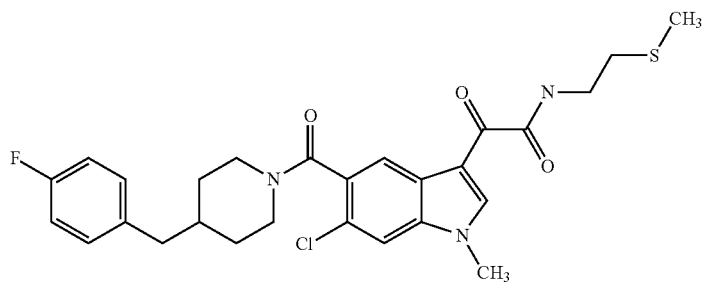 [SMILES: CSCCNC(=O)C(=O)c1cn(C)c2cc(Cl)c(C(=O)N3CCC(Cc4ccc(F)cc4)CC3)cc12]
112
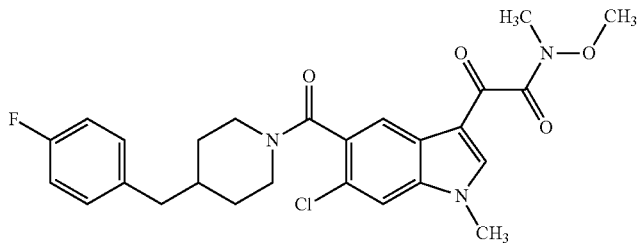 [SMILES: CON(C)C(=O)C(=O)c1cn(C)c2cc(Cl)c(C(=O)N3CCC(Cc4ccc(F)cc4)CC3)cc12]
113
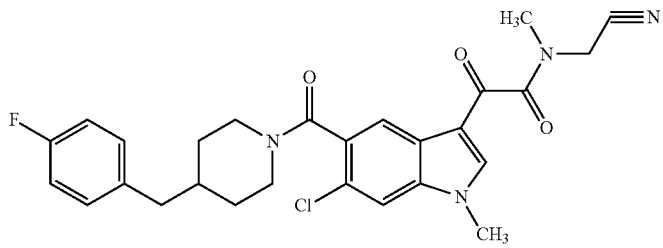 [SMILES: CN(CC#N)C(=O)C(=O)c1cn(C)c2cc(Cl)c(C(=O)N3CCC(Cc4ccc(F)cc4)CC3)cc12]
114
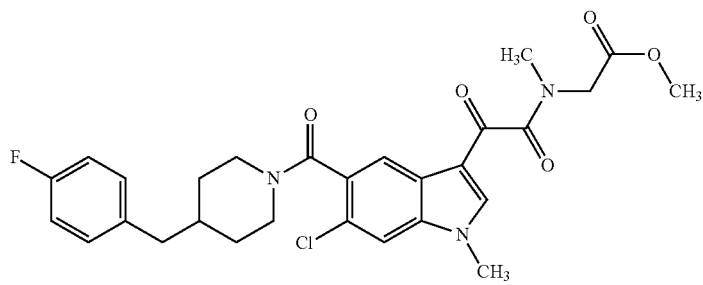 [SMILES: COC(=O)CN(C)C(=O)C(=O)c1cn(C)c2cc(Cl)c(C(=O)N3CCC(Cc4ccc(F)cc4)CC3)cc12]

| 115 | 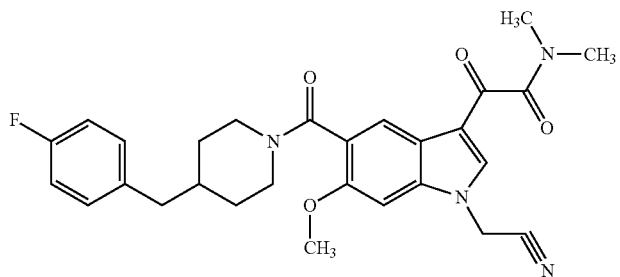 [SMILES: COc1cc2c(cc1C(=O)N1CCC(Cc3ccc(F)cc3)CC1)c(C(=O)C(=O)N(C)C)cn2CC#N] |
| Compd. # | MOLSTRUCTURE |
| --- | --- |
| 117 | 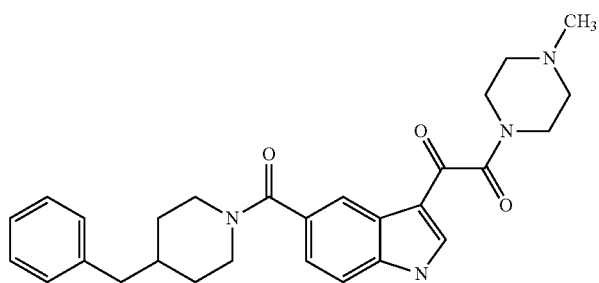 [SMILES: CN1CCN(C(=O)C(=O)c2c[nH]c3ccc(C(=O)N4CCC(Cc5ccccc5)CC4)cc23)CC1] |
| 118 | 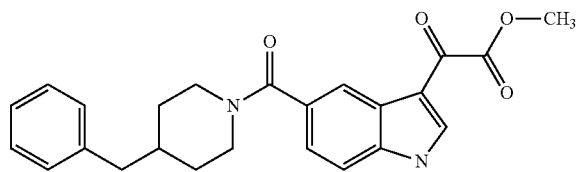 [SMILES: COC(=O)C(=O)c1c[nH]c2ccc(C(=O)N3CCC(Cc4ccccc4)CC3)cc12] |
| 119 | 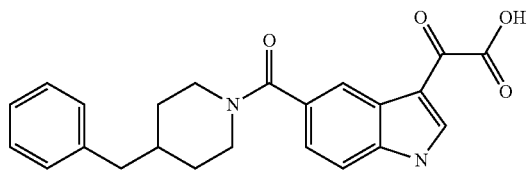 [SMILES: O=C(O)C(=O)c1c[nH]c2ccc(C(=O)N3CCC(Cc4ccccc4)CC3)cc12] |
| 120 | 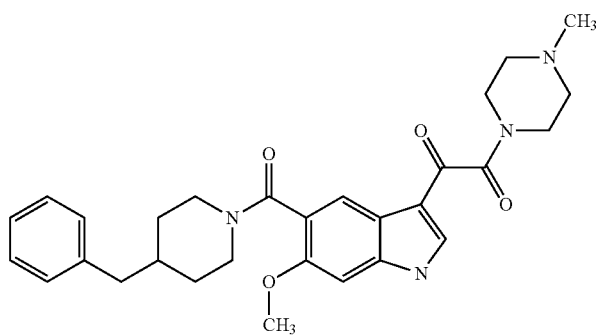 [SMILES: COc1cc2[nH]cc(C(=O)C(=O)N3CCN(C)CC3)c2cc1C(=O)N1CCC(Cc2ccccc2)CC1] |

| | |
|---|---|
| 121 | 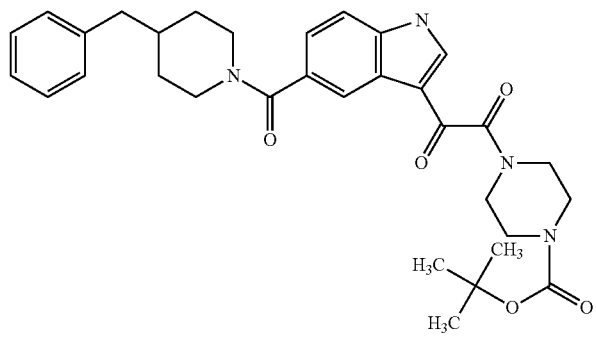 [SMILES: CC(C)(C)OC(=O)N1CCN(C(=O)C(=O)c2c[nH]c3ccc(C(=O)N4CCC(Cc5ccccc5)CC4)cc23)CC1] |
| 122 | 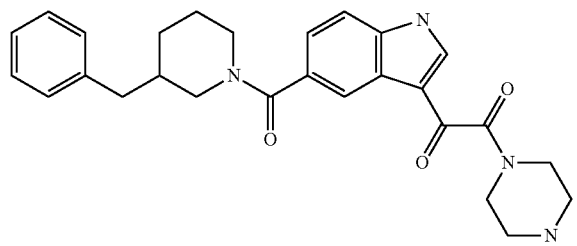 [SMILES: O=C(C(=O)N1CCNCC1)c1c[nH]c2ccc(C(=O)N3CCCC(Cc4ccccc4)C3)cc12] |
| 123 | 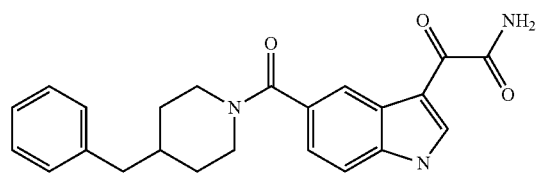 [SMILES: NC(=O)C(=O)c1c[nH]c2ccc(C(=O)N3CCC(Cc4ccccc4)CC3)cc12] |
| 124 | 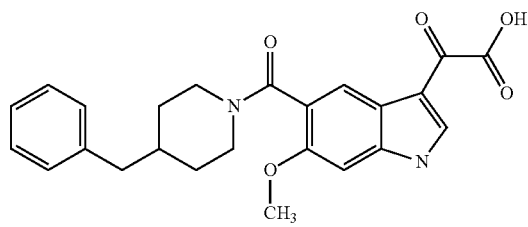 [SMILES: COc1cc2[nH]cc(C(=O)C(=O)O)c2cc1C(=O)N1CCC(Cc2ccccc2)CC1] |
| 125 | 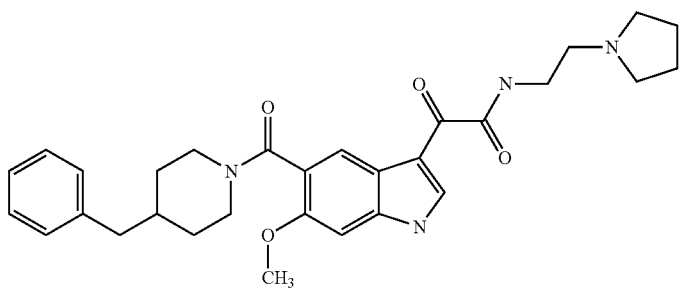 [SMILES: COc1cc2[nH]cc(C(=O)C(=O)NCCN3CCCC3)c2cc1C(=O)N1CCC(Cc2ccccc2)CC1] |
| 126 | 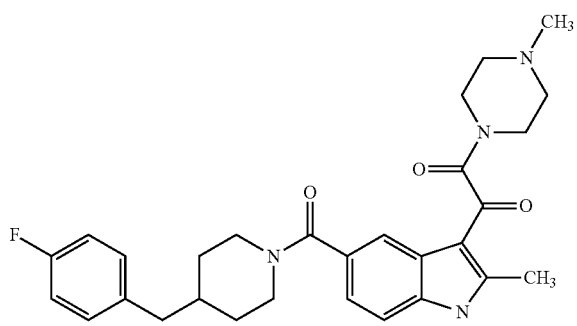 [SMILES: Cc1[nH]c2ccc(C(=O)N3CCC(Cc4ccc(F)cc4)CC3)cc2c1C(=O)C(=O)N1CCN(C)CC1] |

| 127 | 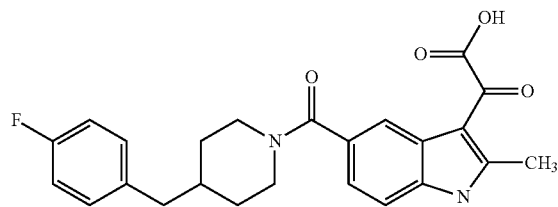 [SMILES: Cc1[nH]c2ccc(C(=O)N3CCC(Cc4ccc(F)cc4)CC3)cc2c1C(=O)C(=O)O] |
| 128 | 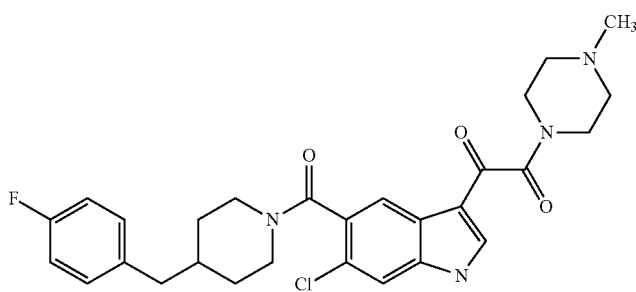 [SMILES: CN1CCN(C(=O)C(=O)c2c[nH]c3cc(Cl)c(C(=O)N4CCC(Cc5ccc(F)cc5)CC4)cc23)CC1] |
| 129 | 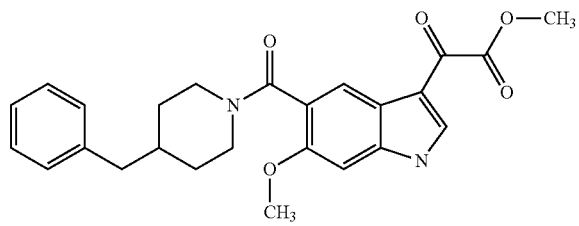 [SMILES: COC(=O)C(=O)c1c[nH]c2cc(OC)c(C(=O)N3CCC(Cc4ccccc4)CC3)cc12] |
| 130 | 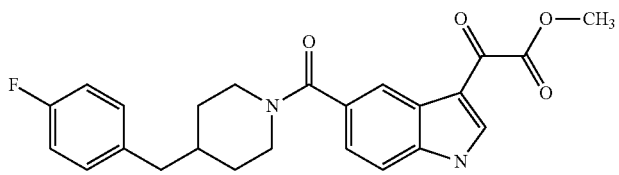 [SMILES: COC(=O)C(=O)c1c[nH]c2ccc(C(=O)N3CCC(Cc4ccc(F)cc4)CC3)cc12] |
| 131 | 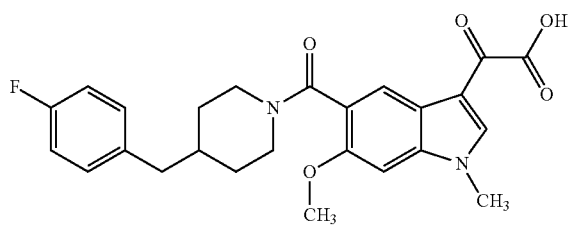 [SMILES: COc1cc2c(cc1C(=O)N1CCC(Cc3ccc(F)cc3)CC1)c(C(=O)C(=O)O)cn2C] |
| 132 | 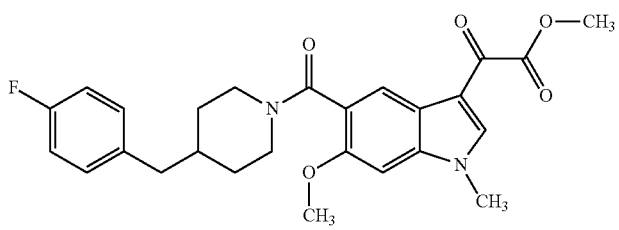 [SMILES: COC(=O)C(=O)c1cn(C)c2cc(OC)c(C(=O)N3CCC(Cc4ccc(F)cc4)CC3)cc12] |
| 133 | 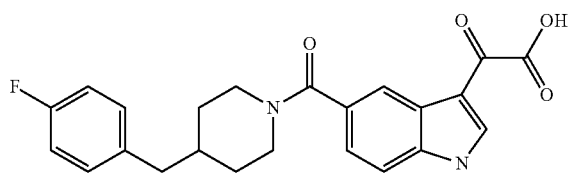 [SMILES: O=C(O)C(=O)c1c[nH]c2ccc(C(=O)N3CCC(Cc4ccc(F)cc4)CC3)cc12] |

-continued
| | |
|---|---|
| 134 | 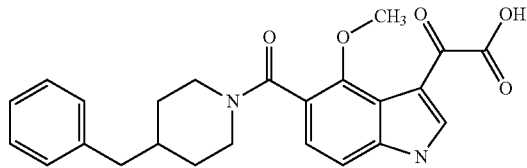 [SMILES: COc1c(C(=O)N2CCC(Cc3ccccc3)CC2)ccc2[nH]cc(C(=O)C(=O)O)c12] |
| 135 | 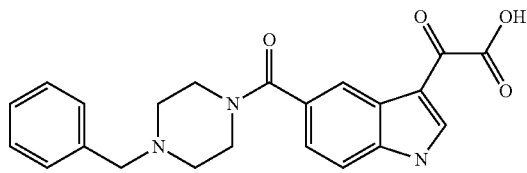 |
| 136 | 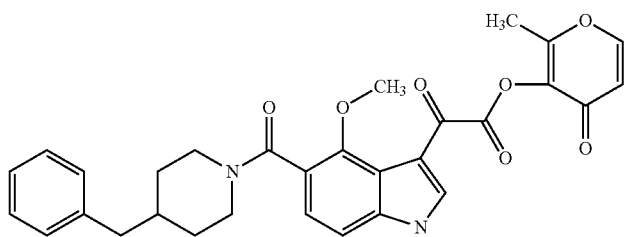 [SMILES: COc1c(C(=O)N2CCC(Cc3ccccc3)CC2)ccc2[nH]cc(C(=O)C(=O)Oc3c(C)occc3=O)c12] |
| 137 | 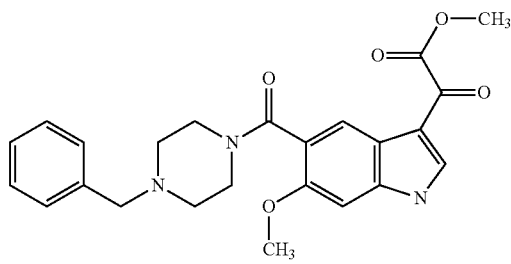 [SMILES: COC(=O)C(=O)c1c[nH]c2cc(OC)c(C(=O)N3CCN(Cc4ccccc4)CC3)cc12] |
| 138 | 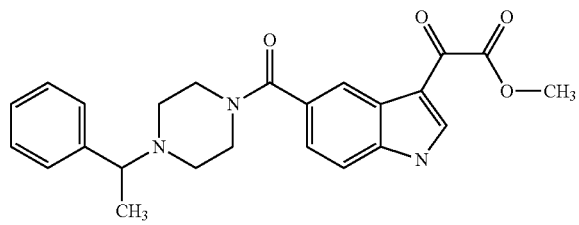 [SMILES: COC(=O)C(=O)c1c[nH]c2ccc(C(=O)N3CCN(C(C)c4ccccc4)CC3)cc12] |
| 139 | 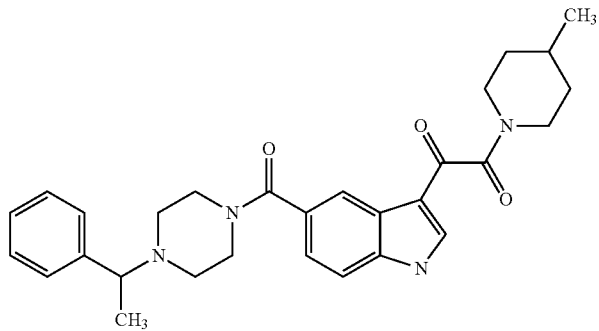 [SMILES: CC1CCN(C(=O)C(=O)c2c[nH]c3ccc(C(=O)N4CCN(C(C)c5ccccc5)CC4)cc23)CC1] |

140
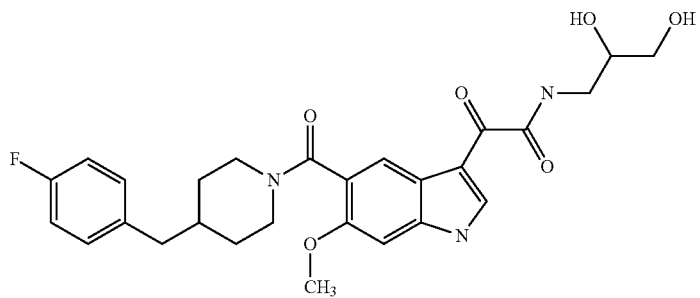 [SMILES: COc1cc2[nH]cc(C(=O)C(=O)NCC(O)CO)c2cc1C(=O)N1CCC(Cc2ccc(F)cc2)CC1]
141
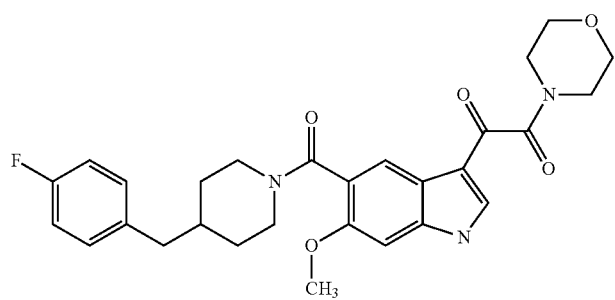 [SMILES: COc1cc2[nH]cc(C(=O)C(=O)N3CCOCC3)c2cc1C(=O)N1CCC(Cc2ccc(F)cc2)CC1]
142
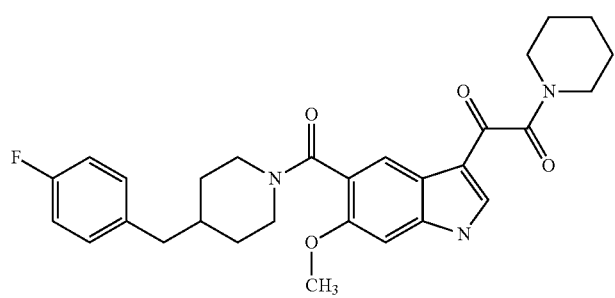 [SMILES: COc1cc2[nH]cc(C(=O)C(=O)N3CCCCC3)c2cc1C(=O)N1CCC(Cc2ccc(F)cc2)CC1]
143
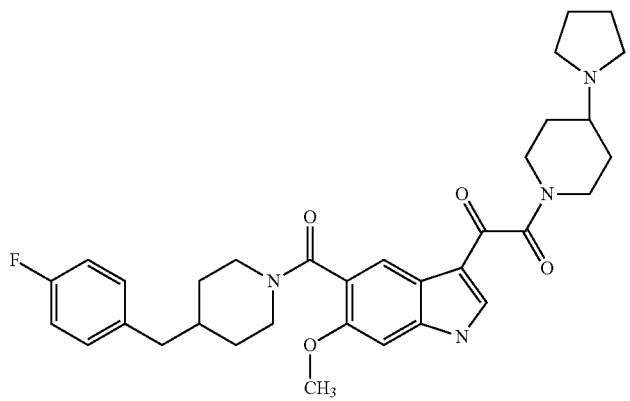 [SMILES: COc1cc2[nH]cc(C(=O)C(=O)N3CCC(N4CCCC4)CC3)c2cc1C(=O)N1CCC(Cc2ccc(F)cc2)CC1]
144
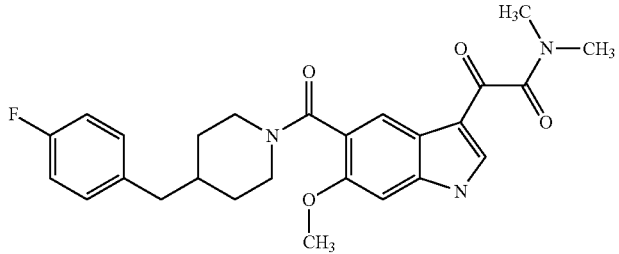 [SMILES: COc1cc2[nH]cc(C(=O)C(=O)N(C)C)c2cc1C(=O)N1CCC(Cc2ccc(F)cc2)CC1]

145 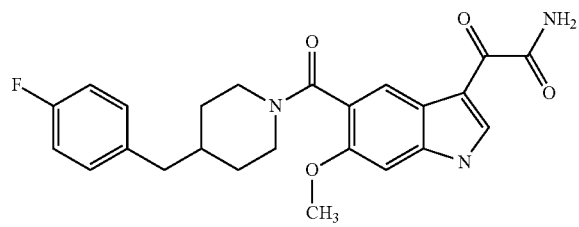 [SMILES: COc1cc2[nH]cc(C(=O)C(N)=O)c2cc1C(=O)N1CCC(Cc2ccc(F)cc2)CC1]
146 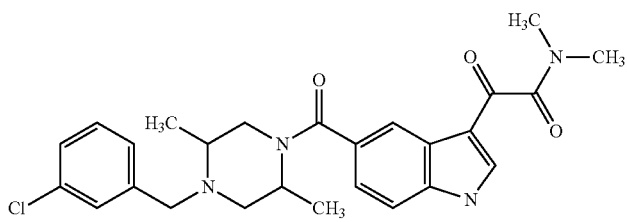 [SMILES: CC1CN(C(=O)c2ccc3[nH]cc(C(=O)C(=O)N(C)C)c3c2)C(C)CN1Cc1cccc(Cl)c1]
147 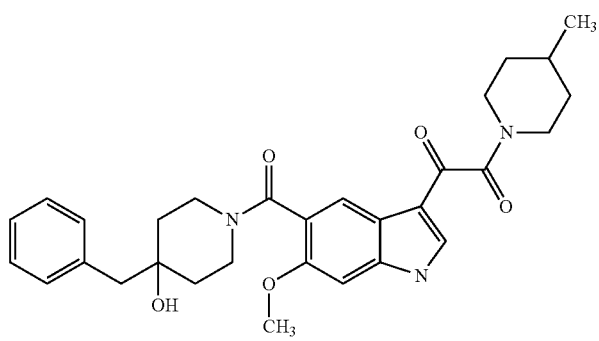 [SMILES: COc1cc2[nH]cc(C(=O)C(=O)N3CCC(C)CC3)c2cc1C(=O)N1CCC(O)(Cc2ccccc2)CC1]
148 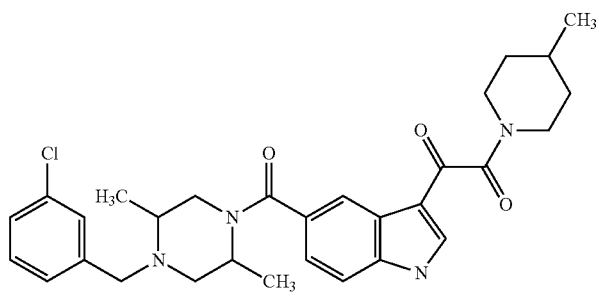 [SMILES: CC1CCN(C(=O)C(=O)c2c[nH]c3ccc(C(=O)N4CC(C)N(Cc5cccc(Cl)c5)CC4C)cc23)CC1]
149 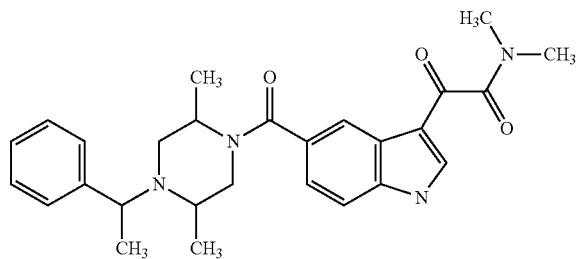 [SMILES: CC1CN(C(C)c2ccccc2)C(C)CN1C(=O)c1ccc2[nH]cc(C(=O)C(=O)N(C)C)c2c1]

150 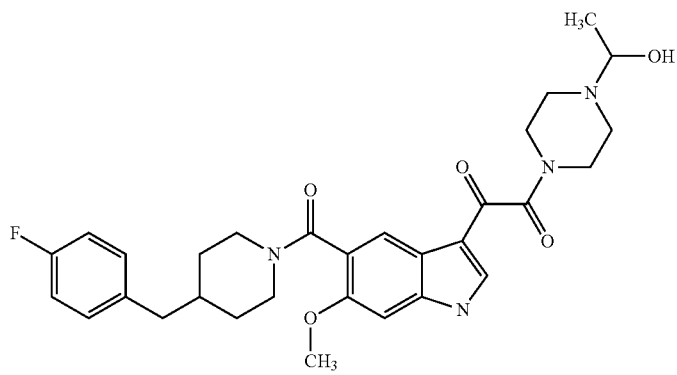 [SMILES: COc1cc2[nH]cc(C(=O)C(=O)N3CCN(C(C)O)CC3)c2cc1C(=O)N1CCC(Cc2ccc(F)cc2)CC1]
151 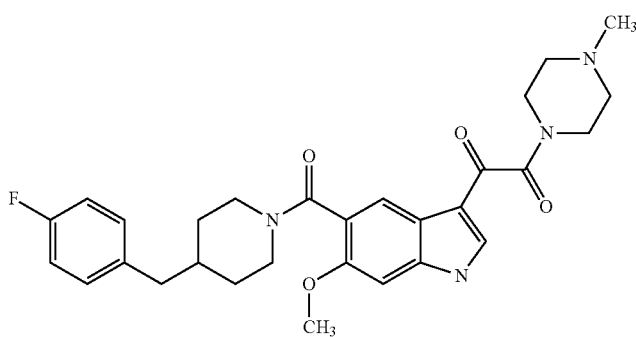 [SMILES: COc1cc2[nH]cc(C(=O)C(=O)N3CCN(C)CC3)c2cc1C(=O)N1CCC(Cc2ccc(F)cc2)CC1]
152 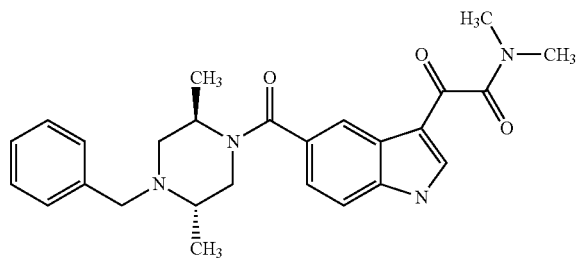 [SMILES: C[C@@H]1CN(Cc2ccccc2)[C@@H](C)CN1C(=O)c1ccc2[nH]cc(C(=O)C(=O)N(C)C)c2c1]
153 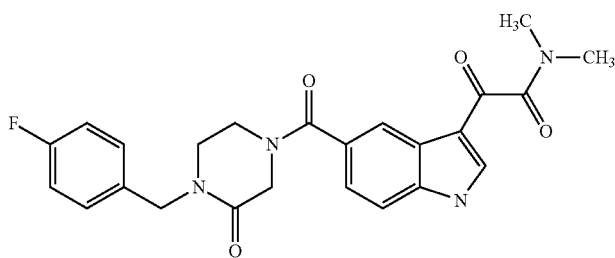 [SMILES: CN(C)C(=O)C(=O)c1c[nH]c2ccc(C(=O)N3CCN(Cc4ccc(F)cc4)C(=O)C3)cc12]
154 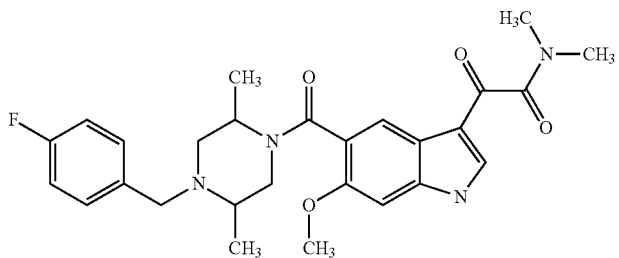 [SMILES: COc1cc2[nH]cc(C(=O)C(=O)N(C)C)c2cc1C(=O)N1CC(C)N(Cc2ccc(F)cc2)CC1C]

155 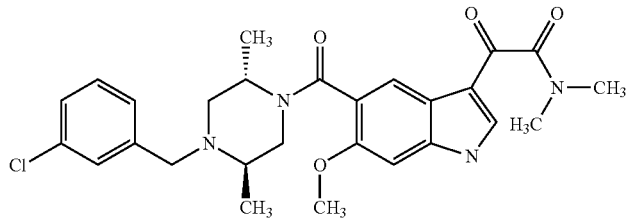 [SMILES: COc1cc2[nH]cc(C(=O)C(=O)N(C)C)c2cc1C(=O)N1C[C@@H](C)N(Cc2cccc(Cl)c2)C[C@@H]1C]
156 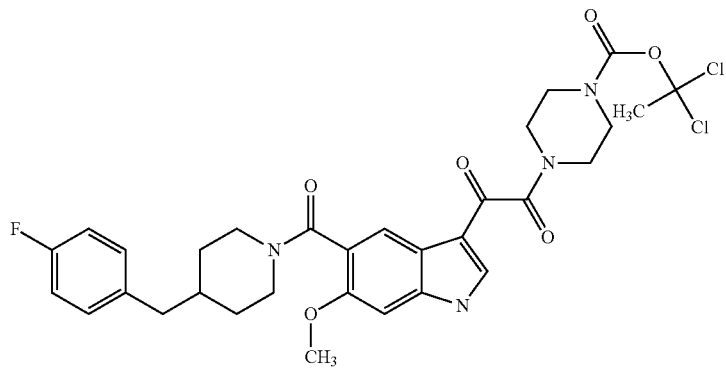 [SMILES: COc1cc2[nH]cc(C(=O)C(=O)N3CCN(C(=O)OC(C)(Cl)Cl)CC3)c2cc1C(=O)N1CCC(Cc2ccc(F)cc2)CC1]
157 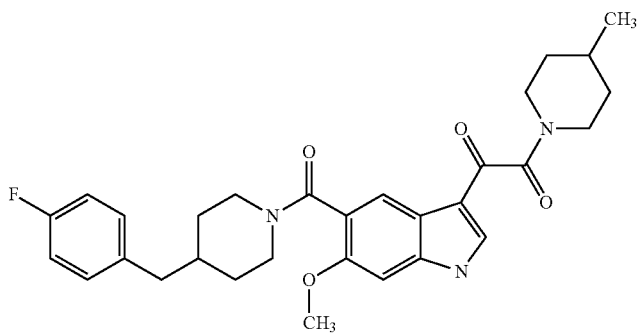 [SMILES: COc1cc2[nH]cc(C(=O)C(=O)N3CCC(C)CC3)c2cc1C(=O)N1CCC(Cc2ccc(F)cc2)CC1]
158 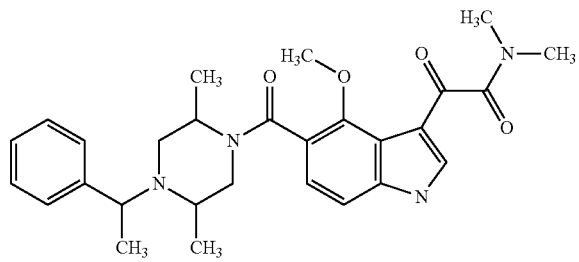 [SMILES: COc1c(C(=O)N2CC(C)N(C(C)c3ccccc3)CC2C)ccc2[nH]cc(C(=O)C(=O)N(C)C)c12]
159 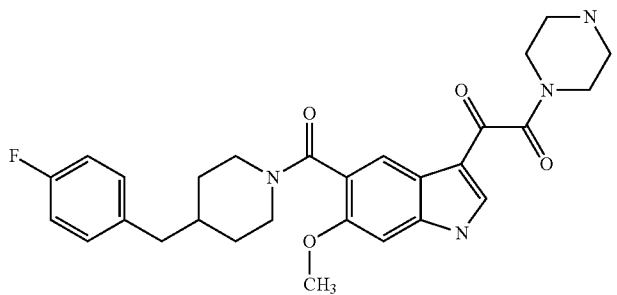 [SMILES: COc1cc2[nH]cc(C(=O)C(=O)N3CCNCC3)c2cc1C(=O)N1CCC(Cc2ccc(F)cc2)CC1]

160 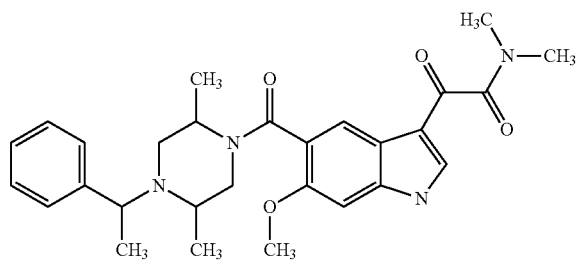 [SMILES: COc1cc2[nH]cc(C(=O)C(=O)N(C)C)c2cc1C(=O)N1CC(C)N(C(C)c2ccccc2)CC1C]
161 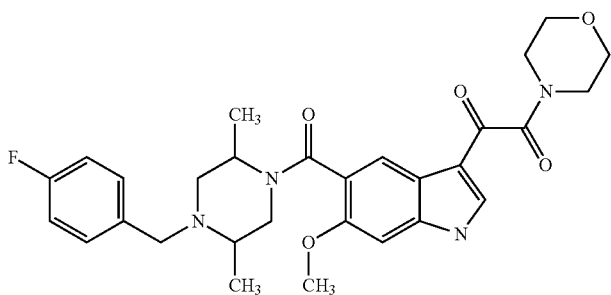 [SMILES: COc1cc2[nH]cc(C(=O)C(=O)N3CCOCC3)c2cc1C(=O)N1CC(C)N(Cc2ccc(F)cc2)CC1C]
162 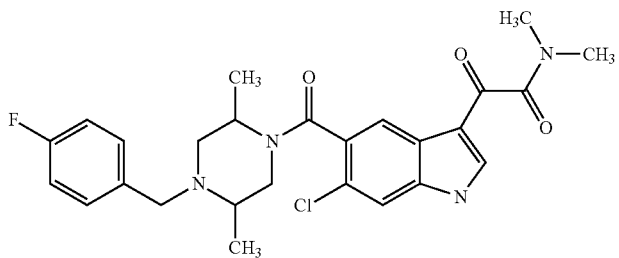 [SMILES: CC1CN(C(=O)c2cc3c(C(=O)C(=O)N(C)C)c[nH]c3cc2Cl)C(C)CN1Cc1ccc(F)cc1]
163 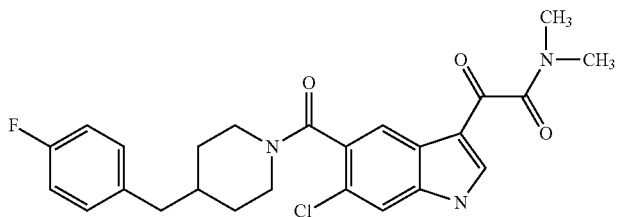 [SMILES: CN(C)C(=O)C(=O)c1c[nH]c2cc(Cl)c(C(=O)N3CCC(Cc4ccc(F)cc4)CC3)cc12]
164 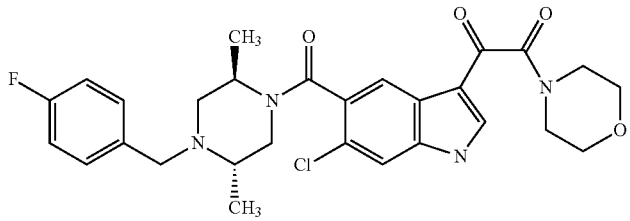 [SMILES: C[C@@H]1CN(Cc2ccc(F)cc2)[C@@H](C)CN1C(=O)c1cc2c(C(=O)C(=O)N3CCOCC3)c[nH]c2cc1Cl]
165 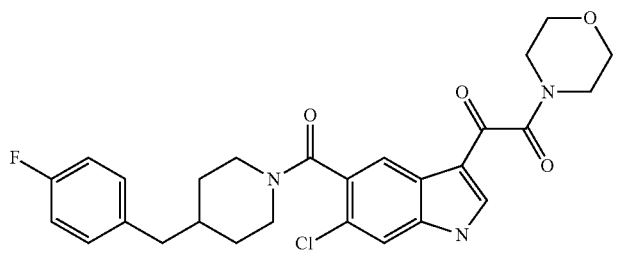 [SMILES: O=C(C(=O)N1CCOCC1)c1c[nH]c2cc(Cl)c(C(=O)N3CCC(Cc4ccc(F)cc4)CC3)cc12]

166 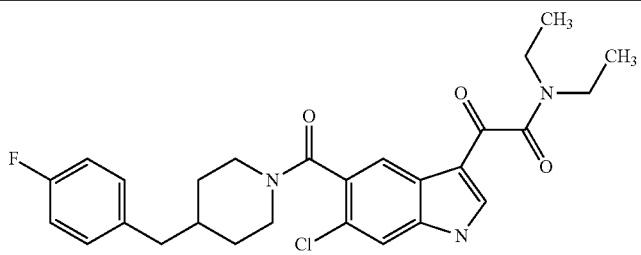
167 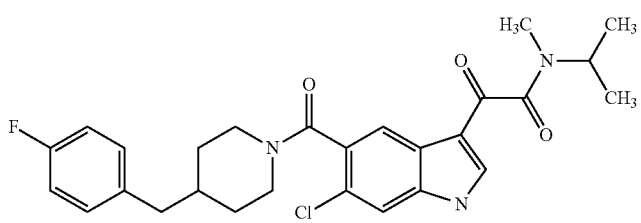 [SMILES: CC(C)N(C)C(=O)C(=O)c1c[nH]c2cc(Cl)c(C(=O)N3CCC(Cc4ccc(F)cc4)CC3)cc12]
168 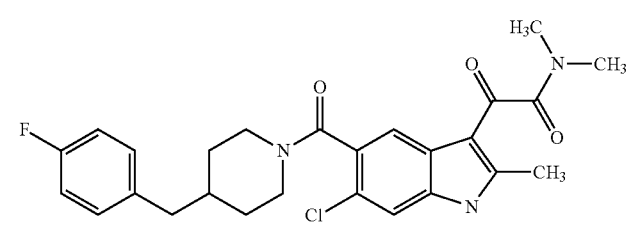 [SMILES: Cc1[nH]c2cc(Cl)c(C(=O)N3CCC(Cc4ccc(F)cc4)CC3)cc2c1C(=O)C(=O)N(C)C]
169 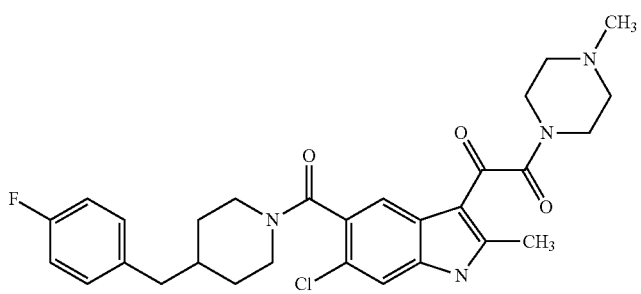 [SMILES: Cc1[nH]c2cc(Cl)c(C(=O)N3CCC(Cc4ccc(F)cc4)CC3)cc2c1C(=O)C(=O)N1CCN(C)CC1]
170 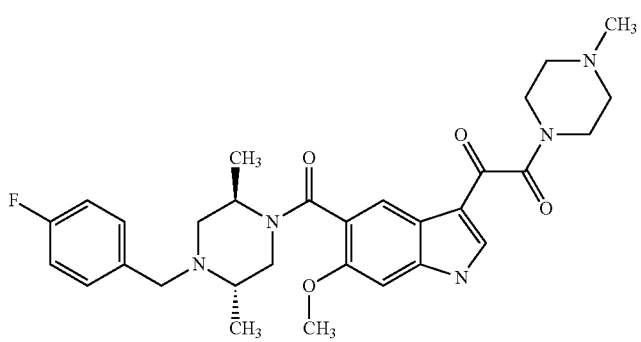 [SMILES: COc1cc2[nH]cc(C(=O)C(=O)N3CCN(C)CC3)c2cc1C(=O)N1C[C@H](C)N(Cc2ccc(F)cc2)C[C@H]1C]
171 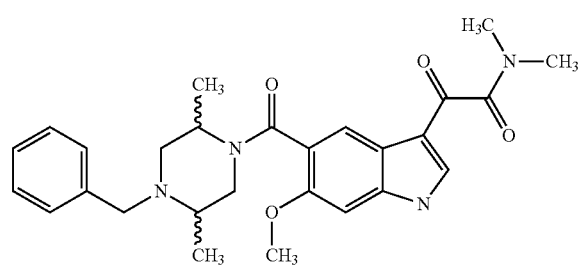

172
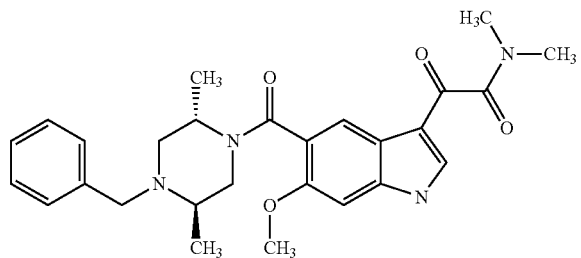 [SMILES: COc1cc2[nH]cc(C(=O)C(=O)N(C)C)c2cc1C(=O)N1C[C@@H](C)N(Cc2ccccc2)C[C@@H]1C]
173
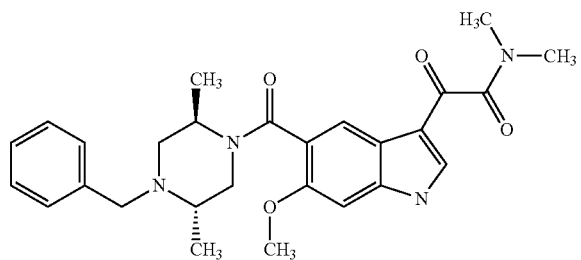 [SMILES: COc1cc2[nH]cc(C(=O)C(=O)N(C)C)c2cc1C(=O)N1C[C@H](C)N(Cc2ccccc2)C[C@H]1C]
174
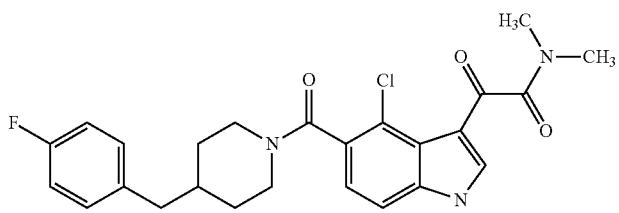 [SMILES: CN(C)C(=O)C(=O)c1c[nH]c2ccc(C(=O)N3CCC(Cc4ccc(F)cc4)CC3)c(Cl)c12]
175
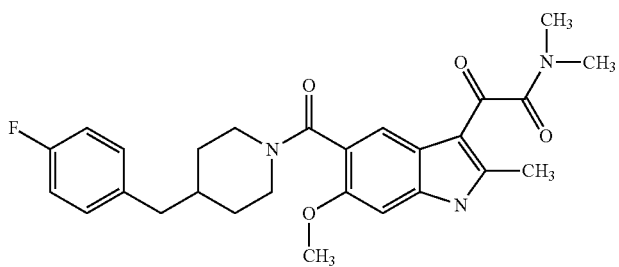 [SMILES: COc1cc2[nH]c(C)c(C(=O)C(=O)N(C)C)c2cc1C(=O)N1CCC(Cc2ccc(F)cc2)CC1]
176
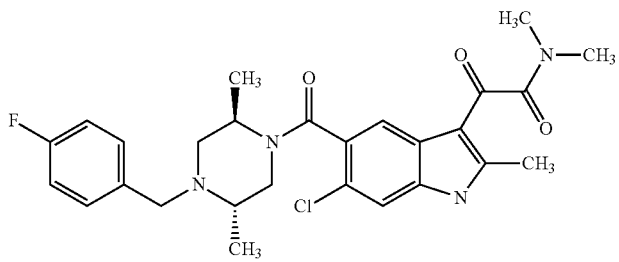 [SMILES: Cc1[nH]c2cc(Cl)c(C(=O)N3C[C@H](C)N(Cc4ccc(F)cc4)C[C@H]3C)cc2c1C(=O)C(=O)N(C)C]
177
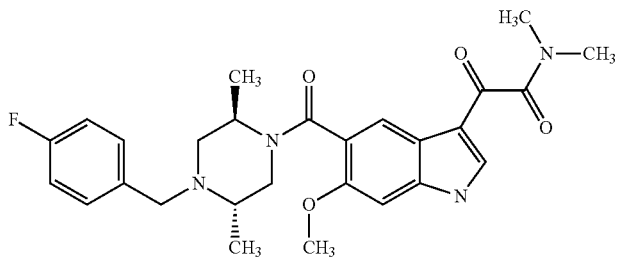 [SMILES: COc1cc2[nH]cc(C(=O)C(=O)N(C)C)c2cc1C(=O)N1C[C@H](C)N(Cc2ccc(F)cc2)C[C@H]1C]

178

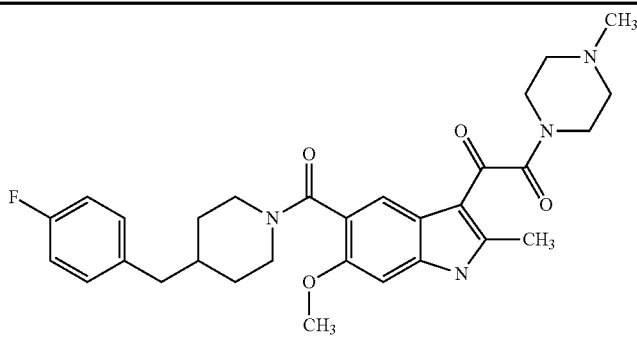

179

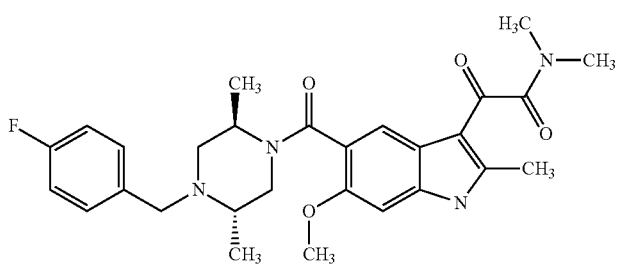 [SMILES: COc1cc2[nH]c(C)c(C(=O)C(=O)N(C)C)c2cc1C(=O)N1C[C@H](C)N(Cc2ccc(F)cc2)C[C@H]1C]

180

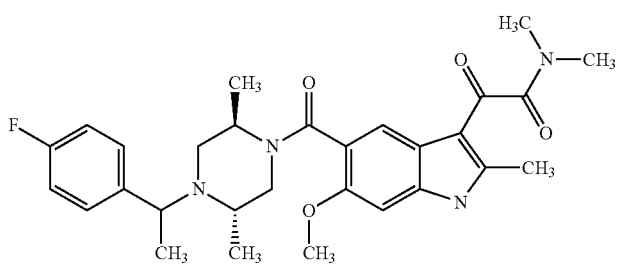 [SMILES: COc1cc2[nH]c(C)c(C(=O)C(=O)N(C)C)c2cc1C(=O)N1C[C@H](C)N(C(C)c2ccc(F)cc2)C[C@H]1C]

181

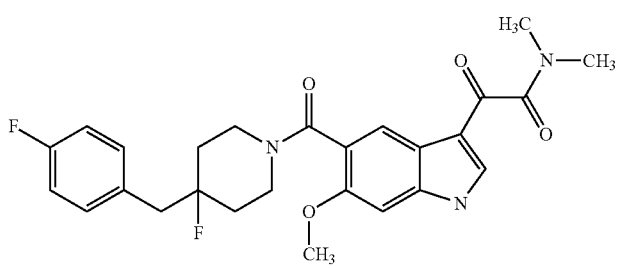 [SMILES: COc1cc2[nH]cc(C(=O)C(=O)N(C)C)c2cc1C(=O)N1CCC(F)(Cc2ccc(F)cc2)CC1]

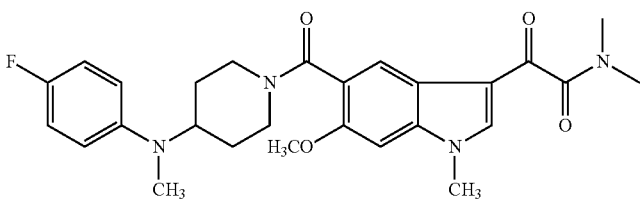 [SMILES: COc1cc2c(cc1C(=O)N1CCC(N(C)c3ccc(F)cc3)CC1)c(C(=O)C(=O)N(C)C)cn2C]

In one embodiment, 2-(6-chloro-5-((2R,5S)-4-(4-fluorobenzyl)-2,5-dimethylpiperazine-1-carbonyl)-1-methyl-1H-indol-3-yl)-N,N-dimethyl-2-oxoacetamide ("SCIO-469"), Formula VI'.

Genus VII Definitions

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1-2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety.

Genus VIII Description

Compounds of Genus VIII can be prepared according to the disclosure of U.S. Pat. No. 6,319,921, which is herein incorporated herein by reference in its entirety.

Genus VIII is characterized by compounds of Formula VIII:

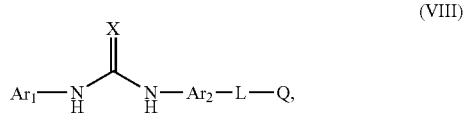

(VIII)

or a stereoisomer thereof, an isotopically-enriched compound thereof, a prodrug thereof, a solvate thereof, or a pharmaceutically acceptable salt thereof,
wherein
$Ar_1$ is pyrazole optionally substituted by one or more $R_1$, $R_2$ or $R_3$;
$Ar_2$ is phenyl, naphthyl quinoline, isoquinoline, tetahydronaphthyl, tetahydroquinoline, tetrahydroisoquinoline, benzimidazole, benzofuran, indanyl, indenyl or indole each being optionally substituted with one to three $R_2$ groups;
L is a $C_{1-10}$ saturated or unsaturated branched or unbranched carbon chain;
  wherein one or more methylene groups are optionally independently replaced by O, N or S; and
  wherein said linking group is optionally substituted with 0-2 oxo groups and one or more $C_{1-4}$ branched or unbranched alkyl which may be substituted by one or more halogen atoms;
Q is selected from the group consisting of:
  a) pyridine, pyrimidine, pyridzine, imidazole, benzimidazole, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups selected from the group consisting of halogen, $C_{1-6}$ alkyl and $C_{1-6}$ alkoxy;
  b) morpholine, thiomophorline, thiomorpholine sulfoxide, thiomorpholine sulfone, piperidine, piperidinone and tetrahydropyrrimidone which are optionally substituted with one to three groups selected from the group consisting of $C_{1-6}$alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;

$R_1$ is selected from the group consisting of:
  a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, $NH_2C(O)$ and di($C_{1-3}$)alkylaminocarbonyl;
  b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to the ring methylene groups are replaced by groups independently selected from O, S, CHOH, >C=O, >C=S and NH;
  c) $C_{3-10}$ branched alkenyl which may optionally be partially or fully halogenated, and which is optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$alkyloxy which is optionally partially or fully halogenated, $NH_2C(O)$, mono- or di($C_{1-3}$)alkylaminocarbonyl;
  d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;
  e) cyano; and,
  f) methoxycarbonyl, ethoxycarbonyl and propoxycarbonyl;

$R^2$ is selected from the group consisting of:
  a) $C_{1-6}$ branched or unbrenched alkyl which may optionally be partially or fully halogenated, acetyl, aroyl, $C_{1-4}$ branched or unbranched alkoxy, which may optionally be partially or fully halogenated, halogen, methoxycarbonyl and phenylsulfonyl;

$R_3$ is selected from the group consisting of:
  a) a phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl; wherein such phenyl, naphthyl or heterocyclic group is optionally substituted with one to five groups selected from the group consisting of a $C_{1-6}$ branched or unbranched alkyl, phenyl naphthyl, heterocycle selected from the group hereinabove described, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$alkyl, naphthyl $C_{1-5}$ alkyl, halo, hydroxy, cyano, $C_{1-3}$ alkyloxy which may optionally be partially or fully halogenated, phenyloxy, naphthyloxy, heteroaryl wherein the heterocyclic moiety is selected from the group hereinabove described, nitro, amino, mono- or di-($C_{1-3}$)alkylamino, phenylamino, naphthylamino, heterocyclylamino, wherein the heterocyclyl moiety is selected from the group hereinabove described, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl($R_8$)N;

b) a fused aryl selected from the group consisting of benzocyclobutanyl, indanyl, indanyl, dihydronaphthyl, tetahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene, wherein the fused aryl or fused heterocyclyl ring is substituted with 0 to 3 groups independently selected from phenyl naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthylamino, heterocyclylamino, wherein the heterocyclyl moiety is selected from the group hereinabove described, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or or di-($C_{1-3}$)alkylamino-$C_{1-5}$ alkyl, $R_9$—$C_{1-5}$alkyl, $R_{10}$—$C_{1-5}$ alkoxy, $R_{11}$—C(O)—$C_{1-5}$ alkyl and $R_{12}$—$C_{1-5}$ alkyl($R_{13}$)N;

c) cycloalkyl selected from the group consisting of cyclopentanyl, cyclohexanyl, cycloheptanyl, bicyclopentanyl, bicyclohexanyl and bicycloheptanyl, wherein the cycloalkyl is optionally partially or fully halogenated and which may optionally be substituted with one to three $C_{1-3}$ alkyl groups;

d) $C_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with 1-3 $C_{1-3}$ alkyl groups;

e) acetyl, aroyl, alkoxycarbonylalkyl or phenylsulfonyl; and f) $C_{1-6}$ branched or unbranched alkyl is optionally be partially or fully halogenated; or $R_1$ and $R_2$ are taken together to form a fused phenyl or pyridinyl ring;

each of $R_8$ and $R_{13}$ are independently selected from the group consisting of hydrogen and $C_{1-4}$ branch or unbranched alkyl which may optionally be partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m=0, 1 or 2; and

X=O or S.

In one embodiment, the p38 kinase inhibitor from Genus VIII is selected from the following:

1-[5-tert-Butyl-2-p-tolyl-2H-pyrazol-3-yl]-3-[4-(2-morpholin-4-yl-ethoxy)naphthalen-1-yl]-urea;

1-[5-tert-Butyl-2-p-tolyl-2H-pyrazol-3-yl]-3-[4-(2-(cis-2,6-dimethylmorpholin-4-yl)ethoxy)naphthalen-1-yl]-urea;

1-[5-tert-Butyl-2-p-tolyl-2H-pyrazol-3-yl]-3-[4-(2-(trans-2,6-dimethylmorpholin-4-yl)ethoxy)naphthalen-1-yl]-urea;

1-[5-tert-Butyl-2-p-tolyl-2H-pyrazol-3-yl]-3-[4-(2-(2-(methoxymethylemorpholin-4-yl)ethoxy)naphthalen-1-yl]-urea;

1-[5-tert-Butyl-2-p-tolyl-2H-pyrazol-3-yl]-3-[4-(2-(morpholin-4-yl)-2-oxoethoxy)naphthalen-1-yl]-urea;

1-[5-tert-Butyl-2-p-tolyl-2H-pyrazol-3-yl]-3-[4-(2-(morpholin-4-yl)-2-methylethoxy)naphthalen-1-yl]-urea;

1-[5-tert-Butyl-2-p-tolyl-2H-pyrazol-3-yl]-3-[4-(2-(morpholin-4-yl)-1-methylethoxy)naphthalen-1-yl]-urea;

1-[5-tert-Butyl-2-p-tolyl-2H-pyrazol-3-yl]-3-[4-(2-thiomorpholin-4-yl-ethoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalen-1-yl]-urea;

1-[5-tert-Butyl-2-p-tolyl-2H-pyrazol-3-yl]-3-[4-(2-morpholin-4-yl-ethoxy)-3-methylnaphthalen-1-yl]-urea;

1-[5-tert-Butyl-2-p-tolyl-2H-pyrazol-3-yl]-3-[4-(2-piperidin-4-yl-ethoxy)naphthalen-1-yl]-urea;

1-[5-tert-Butyl-2-p-tolyl-2H-pyrazol-3-yl]-3-[4-(2-(1-acetylpiperidin-4-yl)ethoxy)naphthalen-1-yl]-urea;

1-[5-tert-Butyl-2-p-tolyl-2H-pyrazol-3-yl]-3-[4-(2-thiazolidin-3-yl-ethoxy)naphthalen-1-yl]-urea;

1-[5-tert-Butyl-2-p-tolyl-2H-pyrazol-3-yl]-3-[4-(2-(morpholin-4-yl-carbonyloxo)ethoxy)naphthalen-1-yl]-urea;

1-[5-tert-Butyl-2-p-tolyl-2H-pyrazol-3-yl]-3-[4-(2-(tetrahydropyran-4-yl)ethoxy)naphthalen-1-yl]-urea;

1-[5-tert-Butyl-2-p-tolyl-2H-pyrazol-3-yl]-3-[4-(2-(N-methyl-2-methoxyethylamino)ethoxy)naphthalen-1-yl]-urea;

1-[5-tert-Butyl-2-p-tolyl-2H-pyrazol-3-yl]-3-[4-(2-(1-oxotetrahydrothiophen-3-yl)ethoxy)naphthalen-1-yl]-urea;

1-[5-tert-Butyl-2-p-tolyl-2H-pyrazol-3-yl]-3-[4-(3-morpholin-4-yl-propyl)naphthalen-1-yl]-urea;

1-[5-tert-Butyl-2-p-tolyl-2H-pyrazol-3-yl]-3-[4-(morpholin-4-yl-methyl)naphthalen-1-yl]-urea;

1-[5-tert-Butyl-2-p-tolyl-2H-pyrazol-3-yl]-3-[4-(3-thiazolidin-3-yl-propyl)naphthalen-1-yl]-urea;

1-[5-tert-Butyl-2-p-tolyl-2H-pyrazol-3-yl]-3-[4-(3-(tetrahydopyran-2-yl-oxy)propyl)naphthalen-1-yl]-urea;

1-[5-tert-Butyl-2-p-tolyl-2H-pyrazol-3-yl]-3-[4-(2-pyridin-4-yl-ethyl)naphthalen-1-yl]-urea;
1-[5-tert-Butyl-2-p-tolyl-2H-pyrazol-3-yl]-3-[4-(2-pyridin-4-yl-ethenyl)naphthalen-1-yl]-urea;
1-[5-tert-Butyl-2-p-tolyl-2H-pyrazol-3-yl]-3-[4-(3-(morpholin-4-yl)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(methoxymethyloxy)propyn-1-yl)naphthalen-1-yl]-urea;
1-[5-tert-Butyl-2-p-tolyl-2H-pyrazol-3-yl]-3-[4-(3-(morpholin-4-yl)-3-methylpropyn-1-yl)naphthalen-1-yl]-urea;
1-[5-tert-Butyl-2-p-tolyl-2H-pyrazol-3-yl]-3-[4-(3-(morpholin-4-yl)-3,3-dimethylpropyn-1-yl)naphthalen-1-yl]-urea;
1-[5-tert-Butyl-2-p-tolyl-2H-pyrazol-3-yl]-3-[4-(3-(tetrahydropyran-2-yl-oxy)butyn-1-yl)naphthalen-1-yl]-urea;
1-[5-tert-Butyl-2-p-tolyl-2H-pyrazol-3-yl]-3-[4-(3-(furan-2-ylcarbonyloxy)propyn-1-yl)naphthalen-1-yl]-urea;
1-[5-tert-Butyl-2-p-tolyl-2H-pyrazol-3-yl]-3-[4-(3-(piperdin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(2-pyridin-4-yl-ethoxy)naphthalen-1-yl]-urea;
1-[5-tert-Butyl-2-p-tolyl-2H-pyrazol-3-yl]-3-[4-(3-pyridin-4-yl-propoxy)naphthalen-1-yl]-urea;
1-[5-tert-Butyl-2-p-tolyl-2H-pyrazol-3-yl]-3-[4-(2-imidazol-1-yl-ethoxy)naphthalen-1-yl]-urea;
1-[5-tert-Butyl-2-p-tolyl-2H-pyrazol-3-yl]-3-[4-(2-benzimidazol-1-yl-ethoxy)naphthalen-1-yl]-urea;
1-[5-tert-Butyl-2-p-tolyl-2H-pyrazol-3-yl]-3-[4-(2-(3,4-dimethoxyphenyl)ethoxy)naphthalen-1-yl)-urea;
1-[5-tert-Butyl-2-p-tolyl-2H-pyrazol-3-yl]-3-[4-(pyridin-4-yl-methylamino)naphthalen-1-yl]-urea;
1-[5-tert-Butyl-2-p-tolyl-2H-pyrazol-3-yl]-3-[4-(pyridin-4-yl-carbonylamino)napthalen-1-yl]-urea;
1-[5-tert-Butyl-2-p-tolyl-2H-pyrazol-3-yl]-3-[4-(morpholin-4-yl-acetamido)naphthalen-1-yl]-urea;
1-[5-tert-Butyl-2-p-tolyl-2H-pyrazol-3-yl]-3-[4-(pyridin-3-yl-methylamino)naphthalen-1-yl]-urea;
1-[5-tert-Butyl-2-p-tolyl-2H-pyrazol-3-yl]-3-[4-(pyridin-3-yl-carbonylamino)naphthalen-1-yl]-urea;
1-[5-iso-Propyl-2-phenyl-2H-pyrazol-3-yl]-3-[4-(2-morpholin-4-yl-ethoxy)naphthalen-1-yl]-urea;
1-[5-(Tetrahydropyran-3-yl)-2-phenyl-2H-pyrazol-3-yl]-3-[4-(2-morpholin-4-yl-ethoxy)naphthalen-1-yl]-urea;
1-[5-cyclohexyl-2-phenyl-2H-pyrazol-3-yl]-3-[4-(2-morpholin-4-yl-ethoxy)naphthalen-1-yl]-urea;
1-[5-(2,2,2-trifluoroethyl)-2-phenyl-2H-pyrazol-3-yl]-3-[4-(2-morpholin-4-yl-ethoxy)naphthalen-1-yl]-urea;
1-[5-(1-methylcycloprop-1-yl)-2-phenyl-2H-pyrazol-3-yl]-3-[4-(2-morpholin-4-ethoxy)naphthalen-1-yl]-urea;
1-[5-ethoxycarbonyl-2-phenyl-2H-pyrazol-3-yl]-3-[4-(2-morpholin-4-yl-ethoxy)naphthalen-1-yl]-urea;
1-[5-(1-methylcyclohex-1-yl)-2-phenyl-2H-pyrazol-3-yl]-3-[4-(2-morpholin-4-ethoxy)naphthalen-1-yl]-urea;
1-[5-tert-butyl-2-methyl-2H-pyrazol-3-yl]-3-[4-(2-morpholin-4-yl-ethoxy)naphthalen-1-yl]-urea;
1-[5-tert-butyl-2-benzyl-2H-pyrazol-3-yl]-3-[4-(2-morpholin-4-yl-ethoxy)napthalen-1-yl]-urea;
1-[5-tert-butyl-2-(4-chlorophenyl)-2H-pyrazol-3-yl]-3-[4-(2-morpholin-4-yl-ethoxy)naphthalen-1-yl]-urea;
1-[5-tert-butyl-2-butyl-2H-pyrazol-3-yl]-3-[4-(2-morpholin-4-yl-ethoxy)naphthalen-1-yl]-urea;
1-[5-tert-butyl-2-(ethoxycarbonylmethyl)-2H-pyrazol-3-yl]-3-[4-(2-morpholin-4-yl-ethoxy)naphthalen-1-yl]-urea;
1-[5-tert-butyl-2-(4-methyl-3-carbamylphenyl)-2H-pyrazol-3-yl]-3-[4-(2-morpholin-4-yl-ethoxy)naphthalen-1-yl]-urea;
1-[5-tert-butyl-2-(4-methyl-3-(2-ethoxycarbonylvinyl)phenyl)-2H-pyrazol-3-yl]-3-[4-(2-morpholin-4-yl-ethoxy)naphthalen-1-yl]-urea;
1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;
1-[5-tert-butyl-2-(4-methyl-3-dimethylaminomethylphenyl)-2H-pyrazol-3-yl]-3-4-(2-morpholin-4-yl-ethoxy)naphthalen-1-yl]-urea;
1-[5-tert-butyl-2-(3-(2-morpholin-4-yl-ethyl)phenyl)-2H-pyrazol-3-yl]-3-[4-(2-morpholin-4-yl-ethoxy)naphthalen-1-yl]-urea;
1-[5-tert-butyl-2-(3-(tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(3-dimethylaminomethylphenyl)-2H-pyrazol-3-yl]-3-[4-(2-morpholin-4-yl-ethoxy)naphthalen-1-yl]-urea;
1-[5-tert-butyl-2-(4-tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(4-(3-benzylureido)phenyl)-2H-pyrazol-3-yl]-3-[4-(2-morpholin-4-yl-ethoxy)naphthalen-1-yl]-urea;
1-[5-tert-butyl-2-(2-chloropyridin-5-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-morpholin-4-yl-ethoxy)naphtlalen-1-yl]-urea;
1-[5-tert-butyl-2-(2-methoxypyridin-5-yl)-2H-pyrazol-3-yl]-3-[4-(2-morpholin-4-yl-ethoxy)naphthalen-1-yl]-urea;
1-[5-tert-butyl-2-(pyridin-3-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-pyridin-4-ethoxy)naphthalen-1-yl]-urea;
1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;
1-[5-tert-butyl-2-(2-methylpyridin-5-yl)-2H-pyrazol-3-yl]-3-[4-(3-morpholin-4-yl-propyn-1-yl)naphthalen-1-yl]-urea;
1-[5-tert-Butyl-2-p-tolyl-2H-pyrazol-3-yl]-3-[4-(2-(2-dimethylaminomethylmorpholin-4-yl)ethoxy)naphthalen-1-yl]-urea;
1-[5-tert-butyl-2-iso-propyl-2H-pyrazol-3-yl]-3-[4-(2-morpholin-4-yl-ethoxy)naphthalen-1-yl]-urea;
1-[5-tert-butyl-2-cyclopropyl-2H-pyrazol-3-yl]-3-[4-(2-morpholin-4-yl-ethoxy)naphthalen-1-yl]-urea;
1-[5-tert-butyl-2-(thiophen-3-yl)-2H-pyrazol-3-yl]-3-[4-(2-morpholin-4-yl-ethoxy)naphthalen-1-yl]-urea;
1-[5-tert-butyl-2-cyclopentyl-2H-pyrazol-3-yl]-3-[4-(2-morpholin-4-yl-ethoxy)naphthalen-1-yl]-urea;
1-[5-tert-butyl-2-iso-propyl-2H-pyrazol-3-yl]-3-[4-(tetrahydropyran-4-yl-ethoxy)naphthalen-1-yl]-urea;
1-[5-tert-butyl-2-cyclopropyl-2H-pyrazol-3-yl]-3-[4-(1-oxo-tetrahydrothiophen-3-yl-ethoxy)naphthalen-1-yl]-urea;
1-[5-tert-butyl-2-(thiophen-3-yl)-2H-pyrazol-3-yl]-3-[4-(2-pyridinyl-4-yl-ethoxy)naphthalen-1-yl]-urea;

1-[5-tert-butyl-2-cyclopentyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(3-(pyridin-4-yl)propyn-1-yl)naphthalen-1-yl]-urea;
1-[5-tert-Butyl-2-p-tolyl-2H-pyrazol-3-yl]-3-[4-(3-(2-methylaminopyridin-4-yl)propyn-1-yl)naphthalen-1-yl]-urea;
1-[5-tert-Butyl-2-p-tolyl-2H-pyrazol-3-yl]-3-[4-(3-(1-oxotetrahydrothiophen-3-yl)propyn-1-yl)naphthalen-1-yl]-urea;
1-[5-tert-Butyl-2-p-tolyl-2H-pyrazol-3-yl]-3-[4-(3-(thiazolidin-3-yl)propyn-1-yl)naphthalen-1-yl]-urea;
1-[5-tert-Butyl-2-p-tolyl-2H-pyrazol-3-yl]-3-[4-(3-(tetrahydropyran-4-yl)propyn-1-yl)naphthalen-1-yl]-urea;
1-[5-tert-Butyl-2-p-tolyl-2H-pyrazol-3-yl]-3-[4-(2-methylaminopyrimidin-4-yl-methoxy)naphthalen-1-yl]-urea;
1-[5-tert-Butyl-2-p-tolyl-2H-pyrazol-3-yl]-3-[4-(2-(2-methylaminopyrimidin-4-yl)ethoxy)naphthalen-1-yl]-urea;
1-[5-tert-Butyl-2-p-tolyl-2H-pyrazol-3-yl]-3-[4-(2-(4-methoxybenzimidazol-1-yl)ethoxy)naphthalen-1-yl]-urea;
1-[5-tert-Butyl-2-p-tolyl-2H-pyrazol-3-yl]-3-[4-(2-(4-methylaminobenzimidazol-1-yl)ethoxy)naphthalen-1-yl]-urea;
1-[5-tert-Butyl-2-p-tolyl-2H-pyrazol-3-yl]-3-[4-(2-(2-imidazo[4,5-b]pyridin-1-yl)ethoxy)naphthalen-1-yl]-urea;
1-[5-tert-Butyl-2-p-tolyl-2H-pyrazol-3-yl]-3-[4-(2-[1,8]naphthyridin-4-yl)ethoxy)naphthalen-1-yl]-urea;
1-[5-tert-Butyl-2-p-tolyl-2H-pyrazol-3-yl]-3-[4-(2-(3,4-dihydro-2H-pyrano[2,3-b]pyridin-5-yl)ethoxy)naphthalen-1-yl]-urea;
1-[5-tert-Butyl-2-pyridin-3-yl-2H-pyrazol-3-yl]-3-[4-(2-methylaminopyrimidin-4-methoxy)naphthalen-1-yl]-urea;
1-[5-tert-Butyl-2-(2-methylpyridin-5-yl)-2H-pyrazol-3-yl]-3-[4-(2-(2-methylaminopyrimidin-4-yl)ethoxy)naphthalen-1-yl]-urea;
1-[5-tert-Buty-2-(2-methylpyridin-5-yl)-2H-pyrazol-3-yl]-3-[4-(2-(4-methoxybenzimidazol-1-yl)ethoxy)naphthalen-1-yl]-urea;
1-[5-tert-Butyl-2-(2-methylpyridin-5-yl)-2H-pyrazol-3-yl]-3-[4-(2-(4-methylaminobenzimidazol-1-yl)ethoxy)naphthalen-1-yl]-urea;
1-[5-tert-Butyl-2-(2-methylpyridin-5-yl)-2H-pyrazol-3-yl]-3-[4-(2-(2-imidazo[4,5b]pyridin-1-yl)ethoxy)naphthalen-1-yl]-urea;
1-[5-tert-Butyl-2-(2-methylpyridin-5-yl)-2H-pyrazol-3-yl]-3-[4-(2-[1,8]naphthyridin-4-yl)ethoxy)naphthalen-1-yl]-urea;
1-[5-tert-Butyl-2-(2-methylpyridin-5-yl)-2H-pyrazol-3-yl]-3-[4-(2-(3,4-dihydro-2H-pyrano[2,3-b]pyridin-5-yl)ethoxy)naphthalen-1-yl]-urea;
1-[5-tert-Butyl-2-cyclopropyl-2H-pyrazol-3-yl]-3-[4-(2-methylaminopyrimidin-4-yl-methoxy)naphthalen-1-yl]-urea;
1-[5-tert-Butyl-2-cyclopropyl-2H-pyrazol-3-yl]-3-[4-(2-(2-methylaminopyrimidin-4-yl)ethoxy)naphthalen-1-yl]-urea;
1-[5-tert-Butyl-2-cyclopropyl-2H-pyrazol-3-yl]-3-[4-(2-(4-methoxybenzimidazol-1-yl)ethoxy)naphthalen-1-yl]-urea;
1-[5-tert-Butyl-2-cyclopropyl-2H-pyrazol-3-yl]-3-[4-(2-(4-methylaminobenzimidazol-1-yl)ethoxy)naphthalen-1-yl]-urea;
1-[5-tert-Butyl-2-methyl-2H-pyrazol-3-yl]-3-[4-(2-(2-imidazo[4,5-b]pyridin-1-yl)ethoxy)naphthalen-1-yl]-urea;
1-[5-tert-Butyl-2-methyl-2H-pyrazol-3-yl]-3-[4-(2-[1,8]naphthyridin-4-yl)ethoxy)naphthalen-1-yl]-urea;
1-[5-tert-Butyl-2-methyl-2H-pyrazol-3-yl]-3-[4-(2-(3,4-dihydro-2H-pyrano[2,3-b]pyridin-5-yl)ethoxy)naphthalen-1-yl]-urea
1-[5-tert-Butyl-2-p-tolyl-2H-pyrazol-3-yl]-3-[4-(2-morpholin-4-yl-ethoxy)naphthalen-1-yl]-urea;
1-[5-tert-Butyl-2-p-tolyl-2H-pyrazol-3-yl]-3-[4-(2-(cis-2,6-dimethylmorpholin-4-yl)ethoxy)naphthalen-1-yl]-urea;
1-[5-tert-Butyl-2-p-tolyl-2H-pyrazol-3-yl]-3-[4-(2-(trans-2,6-dimethylmorpholin-4-yl)ethoxy)naphthalen-1-yl]-urea;
1-[5-tert-Butyl-2-p-tolyl-2H-pyrazol-3-yl]-3-[4-(2-(2-(methoxymethyl)morpholin-4-yl)ethoxy)naphthalen-1-yl]-urea;
1-[5-tert-Butyl-2-p-tolyl-2H-pyrazol-3-yl]-3-[4-(2-(morpholin-4-yl)-2-oxoethoxy)naphthalen-1-yl]-urea;
1-[5-tert-Butyl-2-p-tolyl-2H-pyrazol-3-yl]-3-[4-(2-(morpholin-4-yl)-2-methylethoxy)naphthalen-1-yl]-urea;
1-[5-tert-Butyl-2-p-tolyl-2H-pyrazol-3-yl]-3-[4-(2-(morpholin-4-yl)-1-methylethoxy)naphthalen-1-yl]-urea;
1-[5-tert-Butyl-2-p-tolyl-2H-pyrazol-3-yl]-3-[4-(2-thiomorpholin-4-yl-ethoxy)naphthalen-1-yl]-urea;
1-[5-tert-Butyl-2-p-tolyl-2H-pyrazol-3-yl]-3-[4-(2-(1-oxothiomorpholin-4-yl)ethoxy)naphthalen-1-yl]-urea;
1-[5-tert-Butyl-2-p-tolyl-2H-pyrazol-3-yl]-3-[4-(2-morpholin-4-yl-ethoxy)-3-methylnaphthalen-1-yl]-urea;
1-[5-tert-Butyl-2-p-tolyl-2H-pyrazol-3-yl]-3-[4-(2-(morpholin-4-yl-carbonyloxo)ethoxy)naphthalen-1-yl]-urea;
1-[5-tert-Butyl-2-p-tolyl-2H-pyrazol-3-yl]-3-[4-(2-(tetrahydropyran-4-yl)ethoxy)naphthalen-1-yl]-urea;
1-[5-tert-Butyl-2-p-tolyl-2H-pyrazol-3-yl]-3-[4-(2-(1-oxotetrahydrothiophen-3-yl)ethoxy)naphthalen-1-yl]-urea;
1-[5-tert-Butyl-2-p-tolyl-2H-pyrazol-3-yl]-3-[4-(3-morpholin-4-yl-propyl)naphthalen-1-yl]-urea;
1-[5-tert-Butyl-2-p-tolyl-2H-pyrazol-3-yl]-3-[4-(morpholin-4-yl-methyl)naphthalen-1-yl]-urea;
1-[5-tert-Butyl-2-p-tolyl-2H-pyrazol-3-yl]-3-[4-(2-pyridin-4-yl-ethyl)naphthalen-1-yl]-urea;
1-[5-tert-Butyl-2-p-tolyl-2H-pyrazol-3-yl]-3-[4-(3-(morpholin-4-yl)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)butyn-1-yl)naphthalen-1-yl]-urea;
1-[5-tert-Butyl-2-p-tolyl-2H-pyrazol-3-yl]-3-[4-(3-(piperdin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(2-pyridin-4-yl-ethoxy)naphthalen-1-yl]-urea;
1-[5-tert-Butyl-2-p-tolyl-2H-pyrazol-3-yl]-3-[4-(3-pyridin-4-yl-propoxy)naphthalen-1-yl]-urea;
1-[5-tert-Butyl-2-p-tolyl-2H-pyrazol-3-yl]-3-[4-(2-imidazol-1-yl-ethoxy)naphthalen-1-yl]-urea;
1-[5-tert-Butyl-2-p-tolyl-2H-pyrazol-3-yl]-3-[4-(2-(3,4-dimethoxyphenyl)ethoxy)naphthalen-1-yl]-urea;
1-[5-tert-Butyl-2-p-tolyl-2H-pyrazol-3-yl]-3-[4-(pyridin-4-yl-methylamino)naphthalen-1-yl]-urea;
1-[5-iso-Propyl-2-phenyl-2H-pyrazol-3-yl]-3-[4-(2-morpholin-4-yl-ethoxy)naphthalen-1-yl]-urea;
1-[5-cyclohexyl-2-phenyl-2H-pyrazol-3-yl]-3-[4-(2-morpholin-4-yl-ethoxy)naphthalen-1-yl]-urea;
1-[5-(2,2,2-trifluoroethyl)-2-phenyl-2H-pyrazol-3-yl]-3-[4-(2-morpholin-4-yl-ethoxy)naphthalen-1-yl]-urea;
1-[5-(1-methylcycloprop-1-yl)-2-phenyl-2H-pyrazol-3-yl]-3-[4-(2-morpholin-4-yl-ethoxy)naphthalen-1-yl]-urea;

1-[5-(1-methylcyclohex-1-yl)-2-phenyl-2H-pyrazol-3-yl]-3-[4-(2-morpholin-4-yl-ethoxy)naphthalen-1-yl]-urea;

1-[5-tert-butyl-2-methyl-2H-pyrazol-3-yl]-3-[4-(2-morpholin-4-yl-ethoxy)naphthalen-1-yl]-urea;

1-[5-tert-butyl-2-(4-chlorophenyl)-2H-pyrazol-3-yl]-3-[4-(2-morpholin-4-yl-ethoxy)naphthalen-1-yl]-urea;

1-[5-tert-butyl-2-butyl-2H-pyrazol-3-yl]-3-[4-(2-morpholin-4-yl-ethoxy)naphthalen-1-yl]-urea;

1-[5-tert-butyl-2-(4-methyl-3-carbamylphenyl)-2H-pyrazol-3-yl]-3-[4-(2-morpholin-4-yl-ethoxy)naphthalen-1-yl]-urea;

1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;

1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;

1-[5-tert-butyl-2-(3-dimethylaminomethylphenyl)-2H-pyrazol-3-yl]-3-[4-(2-morpholin-4-yl-ethoxy)naphthalen-1-yl]-urea;

1-[5-tert-butyl-2-(2-chloropyridin-5-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-morpholin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea;

1-[5-tert-butyl-2-(pyridin-3-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;

1-[5-tert-butyl-2-(2-methylpyridin-5-yl)-2H-pyrazol-3-yl]-3-[4-(3-morpholin-4-yl-propyn-1-yl)naphthalen-1-yl]-urea.

1-[5-tert-Butyl-2-p-tolyl-2H-pyrazol-3-yl]-3-[4-(2-morpholin-4-yl-ethoxy)naphthalen-1-yl]-urea;

1-[5-tert-Butyl-2-p-tolyl-2H-pyrazol-3-yl]-3-[4-(2-(1-oxo-thiomorpholin-4-yl)ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea;

1-[5-tert-butyl-2-methyl-2H-pyrazol-3-yl]-3-[4-(2-morpholin-4-yl-ethoxy)naphthalen-1-yl]-urea; and 1-(3-(tert-butyl)-1-(p-tolyl)-1H-pyrazol-5-yl)-3-(4-(2-morpholinoethoxy)naphthalen-1-yl)urea ("Doramapimod"), Formula VIII'.

In one embodiment, the p38 kinase inhibitor is 1-(3-(tert-butyl)-1-(p-tolyl)-1H-pyrazol-5-yl)-3-(4-(2-morpholinoethoxy)naphthalen-1-yl)urea ("Doramapimod"), Formula VIII'.

Genus VIII Definitions

The term "aroyl" as used in the present specification shall be understood to mean "benzoyl" or "naphthoyl".

Genus IX Description

Compounds of Genus IX can be prepared according to the disclosures of U.S. Pat. Nos. 7,160,883, 7,462,616, and 7,759,343 which are herein incorporated herein by reference in their entireties.

Genus IX is characterized by compounds of Formula IX:

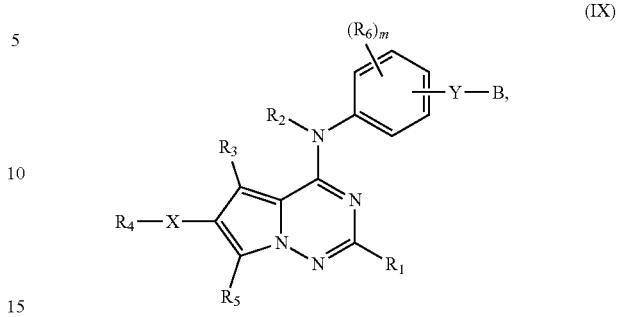

(IX)

or stereoisomers thereof, isotopically-enriched compounds thereof, prodrugs thereof, solvates thereof, and pharmaceutically acceptable salts thereof;

wherein:

X is selected from —O—; —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Y is —C(=O)NH—, —NR$_{10a}$CO—B$^a$, —NR$_{10}$CO$_2$—B$^{aa}$, —NR$_{10}$SO$_2$ or —SO$_2$NR$_{10}$;

B$^a$ and B$^{aa}$ are each independently selected from the group consisting of a C$_{3-7}$ cycloalkyl, a 5-membered heteroaryl, and a 5-6 membered heterocyclo, wherein the C$_{3-7}$ cycloalkyl, 5-membered heteroaryl, or 5-6 membered heterocyclo is optionally substituted with 1-2 R$_7$;

wherein:

(a) R$_7$ is attached to any available carbon or nitrogen atom of B$^a$ or B$^{aa}$ when B$^a$ or B$^{aa}$ is a substituted cycloalkyl, a substituted heterocyclo or a substituted heteroaryl, and (b) at each occurrence R$_7$ is independently selected from the group consisting of keto (=O), alkyl, substituted alkyl, halogen, haloalkoxy, ureido, cyano, —SR$_{20}$, —OR$_{20}$, —NR$_{20}$R$_{21}$, —NR$_{20}$SO$_2$R$_{21}$, —SO$_2$R$_{19}$, —SO$_2$NR$_{20}$R$_{21}$, —CO$_2$R$_{20}$, —C(=O)R$_{20}$, —C(=O)NR$_{20}$R$_{21}$, —OC(=O)R$_{20}$, —OC(=O)NR$_{20}$R$_{21}$, —NR$_{20}$C(=O)R$_{21}$, —NR$_{20}$CO$_2$R$_{21}$, aryl, cycloalkyl, heterocycle, and heteroaryl; and/or (c) when B$^a$ or B$^{aa}$ is cycloalkyl, two R$_7$ groups may join to form an optionally-substituted carbon-carbon bridge of three to four carbon atoms, or two R$_7$ groups may join to form a fused carbocyclic, heterocyclic or heteroaryl ring, said fused ring being in turn optionally substituted with one to three of R$_{22}$;

B is optionally-substituted cycloalkyl, optionally-substituted heterocyclo, or optionally-substituted heteroaryl; or aryl substituted with one R$_{11}$ and 0-2 R$_{12}$, or B is selected from —C(=O)R$_{13}$, —CO$_2$R$_{13}$, and —C(=O)NR$_{13}$R$_{13a}$;

R$_1$ and R$_5$ are independently selected from hydrogen, alkyl, substituted alkyl, —OR$_{14}$, —SR$_{14}$, —OC(=O)R$_{14}$, —CO$_2$R$_{14}$, —C(=O)NR$_{14}$R$_{14a}$, —NR$_{14}$R$_{14a}$, —S(=O)R$_{14}$, —SO$_2$R$_{14}$, —SO$_2$NR$_{14}$R$_{14a}$, —NR$_{14}$SO$_2$NR$_{14a}$R$_{14b}$, —NR$_{14a}$SO$_2$R$_{14}$, —NR$_{14}$C (=O)R$_{14a}$, —NR$_{14}$CO$_2$R$_{14a}$, —NR$_{14}$C(=O)NR$_{14a}$R$_{14b}$, halogen, nitro, and cyano;

R$_2$ is hydrogen or C$_{1-4}$alkyl;

R$_3$ is hydrogen, methyl, perfluoromethyl, methoxy, halogen, cyano, —NH$_2$, or —NH(CH$_3$);

R$_4$ is selected from:
a) hydrogen, provided that R$_4$ is not hydrogen if X is —S(=O)—, —SO$_2$—, —NR$_8$CO$_2$—, or —NR$_8$SO$_2$—;
b) alkyl, alkenyl, and alkynyl, any of which may be optionally substituted with keto and/or one to four R$_{17}$;
c) aryl and heteroaryl, either of which may be optionally substituted with one to three R$_{16}$; and
d) heterocyclo and cycloalkyl, either of which may be optionally substituted with keto and/or one to three R$_{16}$; or R$_4$ is absent if X is halogen, nitro, or cyano;

R$_6$ is attached to any available carbon atom of phenyl ring and at each occurrence is independently selected from alkyl, halogen, —OCF$_3$, —CF$_3$, —OH, —OR$^e$, —C(=O)R$^e$, —OC(=O)R$^e$, —SH, —SR$^e$, —NHC(=O)NH$_2$, —NO$_2$, —CN, —CO$_2$H, —R$^f$CO$_2$H, —C(=O)NH$_2$, —C(=O)OR$^e$, —S(=O)R$^e$, —S(=O)(aryl), —NHSO$_2$(aryl), —NHSO$_3$(aryl), —NHSO$_2$R$^e$, —SO$_3$H, —SO$_2$(R$^e$), —SO$_3$(R$^e$), —SO$_2$NH$_2$, phenyl, benzyl, —O(aryl), and —O(benzyl),
wherein:
R$^e$ is alkyl, and
R$^f$ is alkylene, and each alkyl, alkylene, aryl or benzyl group of R$_6$ in turn may be further substituted by one to two Ris;

R$_8$ and R$_9$ are independently selected from hydrogen, alkyl, substituted alkyl, aryl, cycloalkyl, heterocyclo, and heteroaryl;

R$_{10}$ and R$_{10a}$ are each independently selected from the group consisting of hydrogen, alkyl, substituted alkyl, alkoxy, and aryl;

R$_{11}$ is selected from optionally-substituted cycloalkyl, optionally-substituted heterocyclo, and optionally-substituted heteroaryl;

R$_{12}$ is selected from alkyl, R$_{17}$, and C$_{1-4}$alkyl substituted with keto (=O) and/or one to three R$_{17}$;

R$_{13}$ and R$_{13a}$ are independently selected from hydrogen, alkyl, and substituted alkyl;

R$_{14}$, R$_{14a}$ and R$_{14b}$ are independently selected from hydrogen, alkyl, substituted alkyl, aryl, cycloalkyl, heterocyclo, and heteroaryl, except when R$_{14}$ is joined to a sulphonyl group as in —S(=O)R$_{14}$, —SO$_2$R$_{14}$, and —NR$_{14a}$SO$_2$R$_{14}$, then R$_{14}$ is not hydrogen;

R$_{16}$ is selected from alkyl, R$_{17}$, and C$_{1-4}$alkyl substituted with keto (=O) and/or one to three R$_{17}$;

R$_{17}$ is selected from (a) halogen, haloalkyl, haloalkoxy, nitro, cyano, —SR$_{23}$, —OR$_{23}$, —NR$_{23}$R$_{24}$, —NR$_{23}$SO$_2$R$_{25}$, —SO$_2$R$_{25}$, —SO$_2$NR$_{23}$R$_{24}$, —CO$_2$R$_{23}$, —C(=O)R$_{23}$, —C(=O)NR$_{23}$R$_{24}$, —OC(=O)R$_{23}$, —OC(=O)NR$_{23}$R$_{24}$, —NR$_{23}$C(=O)R$_{24}$, —NR$_{23}$CO$_2$R$_{24}$; (b) aryl or heteroaryl either of which may be optionally substituted with one to three R$_{26}$; or (c) cycloalkyl or heterocyclo, either of which may be optionally substituted with one or more of keto(=O) and 1-3 R$_{26}$;

R$_{18}$ and R$_{26}$ are independently selected from C$_{1-6}$alkyl, C$_{2-6}$alkenyl, halogen, haloalkyl, haloalkoxy, cyano, nitro, amino, C$_{1-4}$alkylamino, aminoC$_{1-4}$alkyl, hydroxy, hydroxyC$_{1-4}$alkyl, alkoxy, C$_{1-4}$alkylthio, phenyl, benzyl, phenyloxy, and benzyloxy;

R$_{19}$ is C$_{1-4}$alkyl, phenyl, C$_{3-7}$cycloalkyl, or 5-6 membered heterocyclo or heteroaryl;

R$_{20}$ and R$_{21}$ are each independently selected from the group consisting of hydrogen, alkyl, alkenyl, substituted alkyl, substituted alkenyl, phenyl, aryl, C$_{3-7}$cycloalkyl, and five-to-six membered heterocyclo and heteroaryl;

R$_{22}$ is selected from the group consisting of C$_{1-6}$alkyl, C$_{2-6}$alkenyl, halogen haloalkyl, haloalkoxy, cyano, nitro, amino, C$_{1-4}$alkylamino, aminoC$_{1-4}$alkyl, hydroxy, hydroxyC$_{1-4}$alkyl, alkoxy, alkylthio, phenyl, benzyl, phenyloxy, and benzyloxy;

R$_{23}$ and R$_{24}$ are each independently selected from hydrogen, alkyl, alkenyl, substituted alkyl, substituted alkenyl, aryl, cycloalkyl, heteroaryl, and heterocyclo;

R$_{25}$ is selected from alkyl, substituted alkyl, aryl, heteroaryl, cyclo alkyl and heterocyclo; and m is 0, 1, 2 or 3.

In one embodiment, the p38 kinase inhibitor from Genus IX is selected from compounds 1-131 of U.S. Pat. No. 7,160,883.

In one embodiment, the p38 kinase inhibitor from Genus IX is selected from the following:

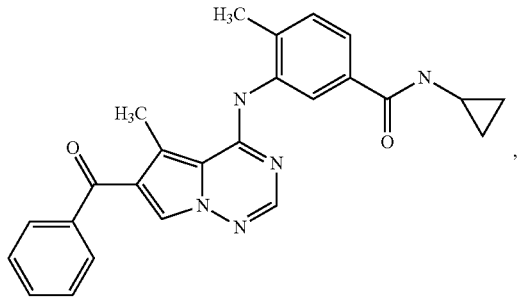

,

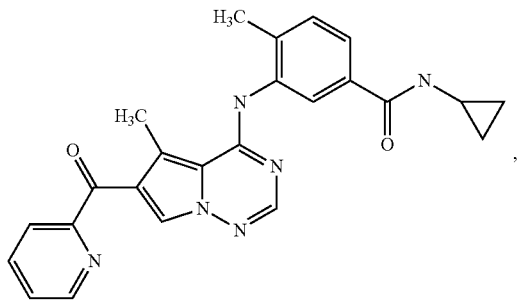

,

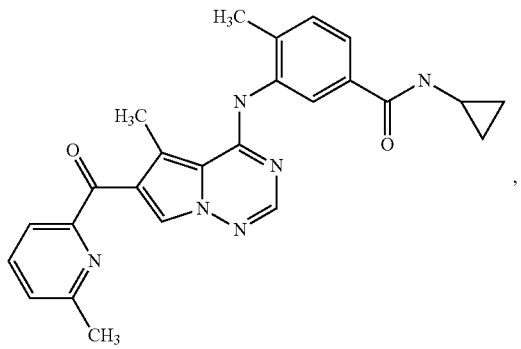

,

-continued
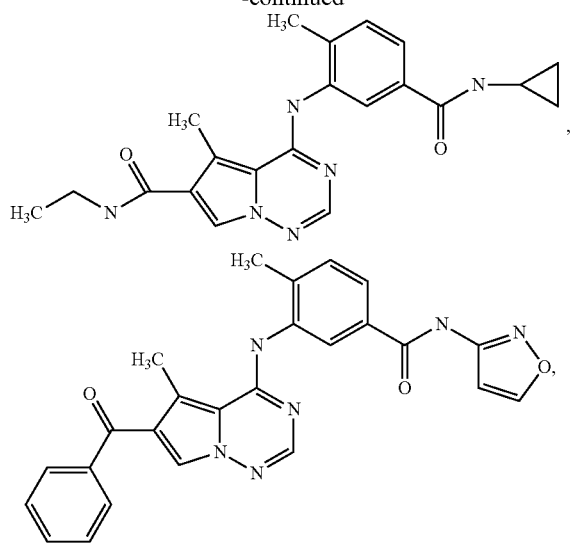
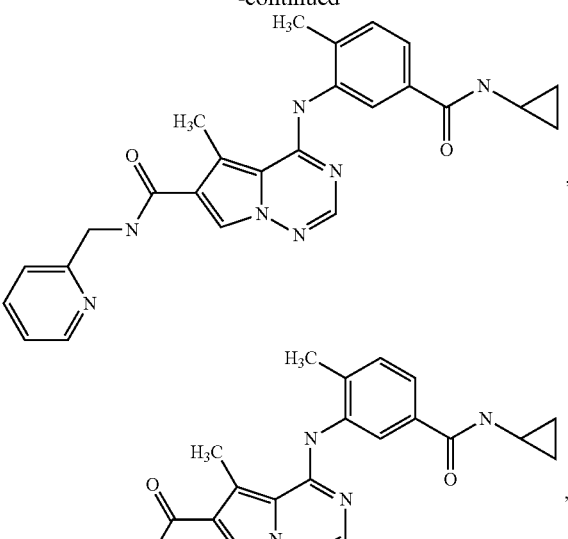
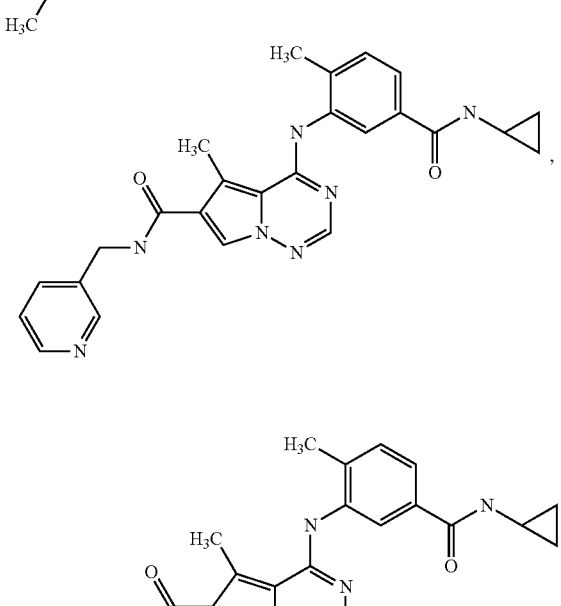
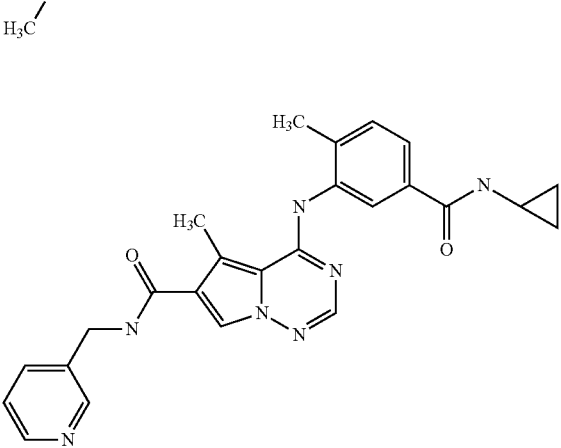

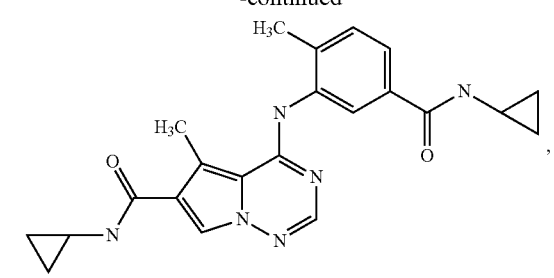,
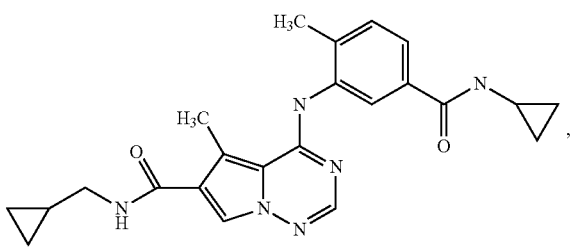,
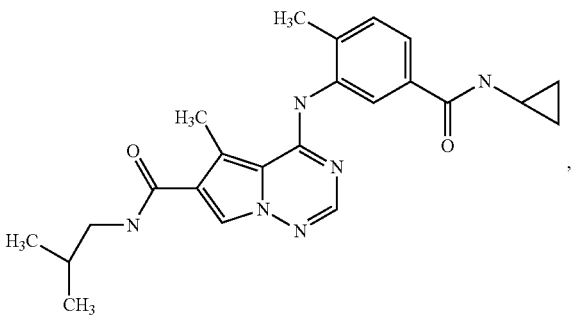,
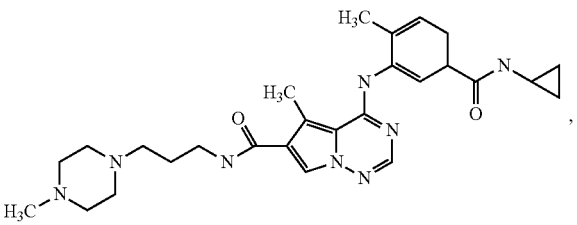,
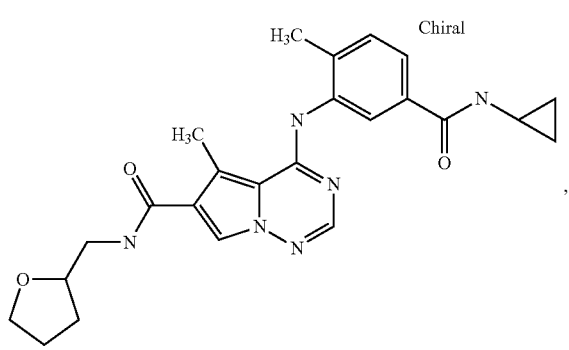,
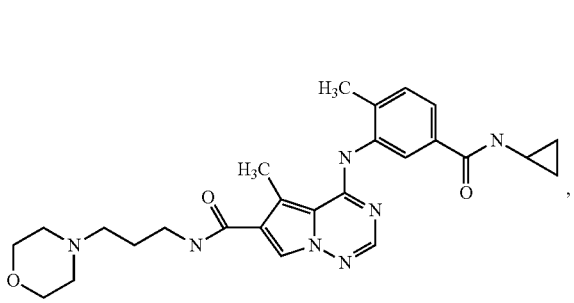,
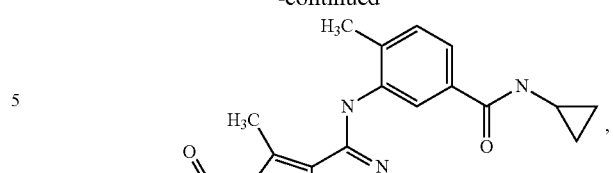,
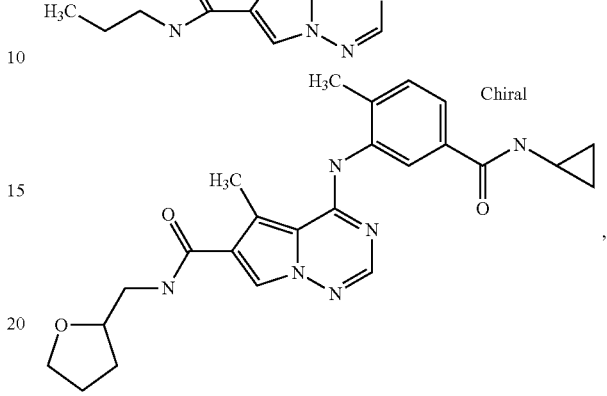,
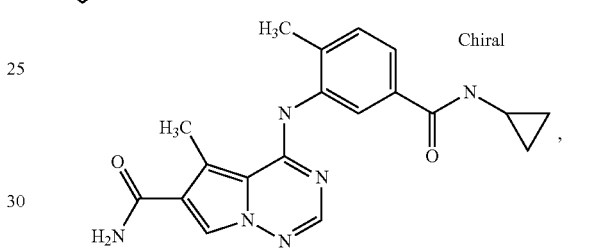,
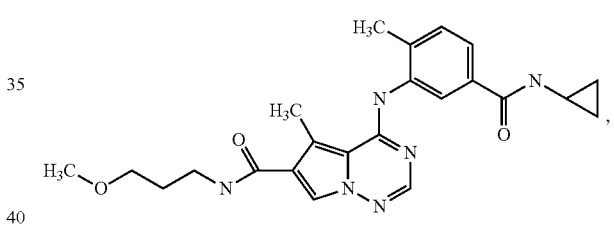,
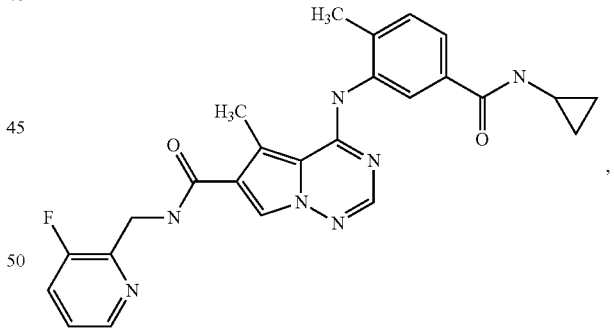,
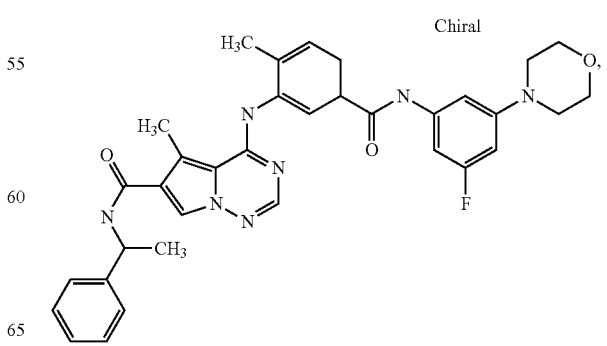,

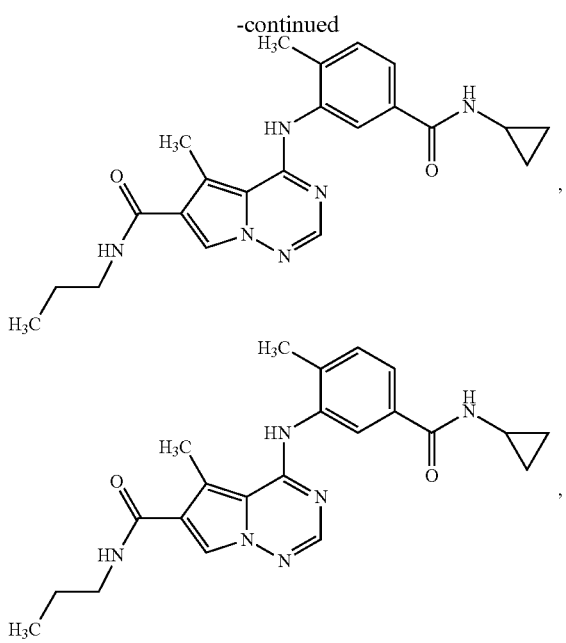

In one embodiment, the p38 inhibitor is 4-((5-(cyclopropylcarbamoyl)-2-methylphenyl)amino)-5-methyl-N-propylpyrrolo[2,1-f][1,2,4]triazine-6-carboxamide ("MBS-582949"), Formula IX'.

Genus IX Definitions

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms.

The term "substituted alkyl" refers to an alkyl group substituted by one to four substituents selected from halogen, hydroxy, alkoxy, keto (=O), alkanoyl, aryloxy, alkanoyloxy, $NR_aR_b$, alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —$SO_2NR_aR_b$, nitro, cyano, —$CO_2H$, —$CONR_aR_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocycle, and heterocyclealkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The term "substituted alkenyl" refers to an alkenyl group substituted by one to two substituents selected from those recited above for alkyl groups.

The term "alkynyl" refers to straight or branched chain hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The term "substituted alkynyl" refers to an alkynyl group substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropylC1-4alkyl means a cyclopropyl group bonded through a straight or branched chain alkyl group having one to four carbon atoms). In the case of substituents, as in "substituted cycloalkylalkyl," the alkyl portion of the group, besides being branched or straight chain, may be substituted as recited above for substituted alkyl groups and/or the first named group (e.g., cycloalkyl) may be substituted as recited herein for that group.

The term "halogen" or "halo" refers to fluorine, chlorine, bromine and iodine.

The term "aryl" refers to monocyclic or bicyclic aromatic substituted or unsubstituted hydrocarbon groups having 6 to 12 carbon atoms in the ring portion, such as phenyl, naphthyl, and biphenyl groups.) Aryl groups may optionally include one to three additional rings (either cycloalkyl, heterocyclo or heteroaryl) fused thereto. Examples include:

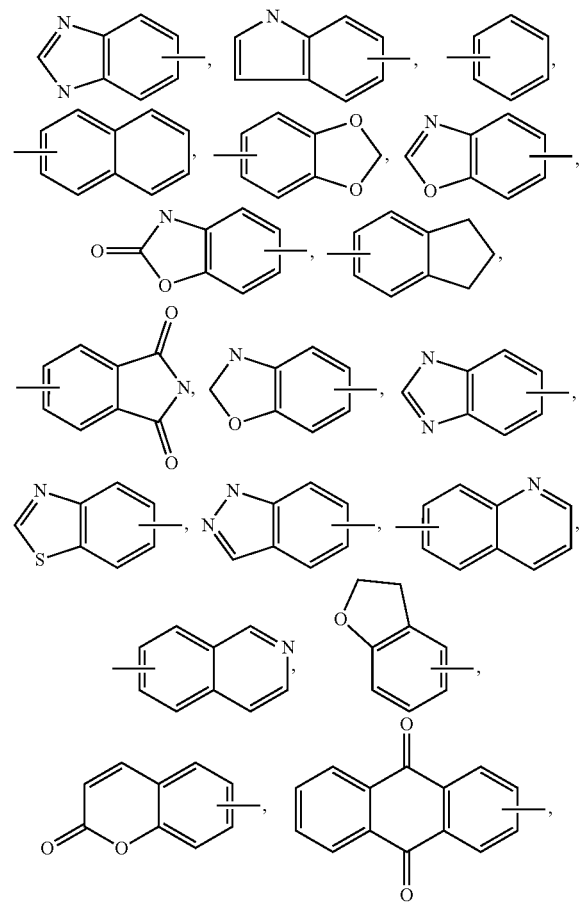

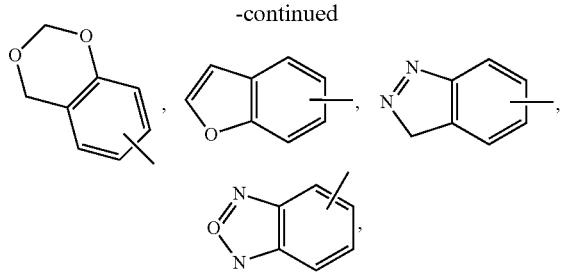

and the like. Each ring of the aryl may be optically substituted with one to three Rc groups wherein Rc at each occurrence is selected from alkyl, substituted alkyl, halogen, trifluoromethoxy, trifluoromethyl, —SR, —OR, —NRR', —NRSO2R', —SO2R, —SO2NRR', —CO2R', —C(=O)R', —C(=O)NRR', —OC(=O)R', —OC(=O)NRR', —NRC(=O)R', —NRCO2R', phenyl, C3-7 cycloalkyl, and five-to-six membered heterocyclo or heteroaryl, wherein each R and R' is selected from hydrogen, alkyl, substituted alkyl, alkenyl, substituted alkenyl, phenyl, C3-7cycloalkyl, and five-to-six membered heterocyclo or heteroaryl, except in the case of a sulfonyl group, then R is not going to be hydrogen. Each substituent Rc optionally in turn may be further substituted by one or more (preferably 0 to 2) Rd groups, wherein Rd is selected from C1-6alkyl, C2-6alkenyl, halogen, haloalkyl, haloalkoxy, cyano, nitro, amino, C1-4alkylamino, aminoC1-4alkyl, hydroxy, hydroxyC1-4alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a "substituted aralkyl," the alkyl portion of the group besides being branched or straight chain, may be substituted as recited above for substituted alkyl groups and/or the aryl portion may be substituted as recited herein for aryl. Thus, the term "optionally substituted benzyl" refers to the group:

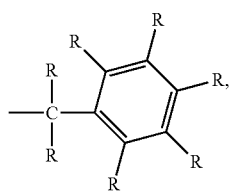

wherein each R group may be hydrogen or may also be selected from Rc as defined above, in turn optionally substituted with one or more Rd. At least two of these "R" groups should be hydrogen and preferably at least five of the "R" groups is hydrogen. A preferred benzyl group involves the alkyl-portion being branched to define:

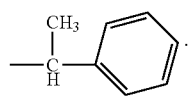

The term "heteroaryl" refers to a substituted or unsubstituted aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. It may optionally be substituted with one to three (preferably 0 to 2) Rc groups, as defined above for aryl, which in turn may be substituted with one or more (preferably 0 to 2) Rd groups, also as recited above.

Exemplary monocyclic heteroaryl groups include pyrrolyl, pyrazolyl, pyrazolinyl, imidazolyl, oxazolyl, isoxazolyl, thiazolyl (i.e., 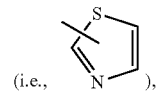 ), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a C3-C7 carbocylic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from Rc groups, as recited above, and/or from keto (where appropriate) which in turn may be substituted with one to three Rd groups, also as recited above. Thus, when it is stated that a carbon-carbon bridge may be optionally substituted, it is meant that the carbon atoms in the bridged ring optionally may be substituted with an Rc group, which preferably is selected from C1-4alkyl, C2-4alkenyl, halogen, haloalkyl, haloalkoxy, cyano, amino, C1-4alkylamino, aminoC1-4alkyl, hydroxy, hydroxyC1-4alkyl, and C1-4alkoxy. Exemplary cycloalkyl groups include cyclopropyl, cyclobutyl, cyclopentyl, cyclohexyl, cycloheptyl, bicycloheptane, cyclooctyl, cyclodecyl, cyclododecyl, and adamantyl.

The terms "heterocycle", "heterocyclic" and "heterocyclo" each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (=O), and/or one or more Rc groups, as recited above, which in turn may be substituted with one to three Rd groups, also as recited above.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxopyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocyclos, such as epoxides and aziridines.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., indolyl), the reference is intended to include rings having 0 to 3, preferably 0-2, substituents selected from those recited above for the the aryl, cycloalkyl, heterocyclo and/or heteroaryl groups, as appropriate. Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds. Thus, for example, in compounds of Formula (IX), when B is a cyclopropyl ring, preferably the ring has no more than two substituents, and preferably said substituents do not comprise nitro ($NO_2$), more than one cyano group, or three halogen groups. Similarly, when m is 3, preferably R6, the substituents on the phenyl ring A, are not all nitro, and so forth.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, aryl, cycloalkyl, and so forth, are as follows: alkoxy is —$OR_e$, alkanoyl is —$C(=O)R_e$, aryloxy is —OAr, alkanoyloxy is —$OC(=O)R_e$, amino is —$NH_2$, alkylamino is —$NHR_e$ or —$N(R_e)_2$, arylamino is —NHAr or —$NR_eAr$, aralkylamino is —NH—$R_f$—Ar, alkanoylamino is —NH—$C(=O)R_e$, aroylamino is —NH—$C(=O)$Ar, aralkanoylamino is —NH—$C(=O)R_f$—Ar, thiol is —SH, alkylthio is —$SR_e$, arylthio is —SAr, aralkylthio is —S—$R_f$—Ar, alkylthiono is —$S(=O)R_e$, arylthiono is —$S(=O)$Ar, aralkylthiono is —$S(=O)R_f$—Ar, alkylsulfonyl is —$SO(q)R_e$, arylsulfonyl is —$SO(q)$Ar, arylsulfonylamine is —NHSO(q)Ar, alkylsulfonylamine is —$NHSO_2Re$, aralkylsulfonyl is —$SO(q)R_f$Ar, sulfonamido is —$SO_2NH_2$, substituted sulfonamide is —$SO_2NHR_e$ or —$SO_2N(R_e)_2$, nitro is —$NO_2$, carboxy is —$CO_2H$, carbamyl is —$CONH_2$, substituted carbamyl is —$C(=O)NHR_g$ or —$C(=O)NR_gR_h$, alkoxycarbonyl is —$C(=O)OR_e$, carboxyalkyl is —$R_f$—$CO_2H$, sulfonic acid is $SO_3H$, guanidino is

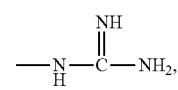

and ureido is

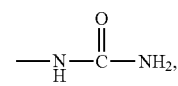

wherein $R_e$ is alkyl or substituted alkyl as defined above, $R_f$ is alkylene or substituted alkylene as defined above, $R_g$ and $R_h$ are selected from alkyl, substituted alkyl, aryl, aralkyl, cycloalkyl, heterocyclo, and heteroaryl; Ar is an aryl as defined above, and q is 2 or 3.

Genus X Description

Compounds of Genus X can be prepared according to the disclosure of US 2005-0176775, which is herein incorporated herein by reference in its entirety.

Genus X is characterized by compounds of Formula X:

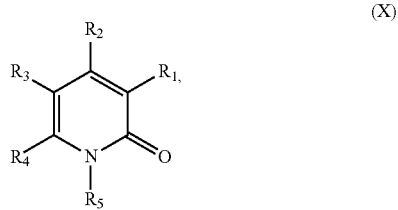

(X)

or stereoisomers thereof, isotopically-enriched compounds thereof, prodrugs thereof, solvates thereof, and pharmaceutically acceptable salts thereof;
wherein:
$R_1$ is halogen substituted with 1, 2, 3, 4, or 5 groups that are independently halogen, —$(C_1$-$C_6)$alkyl-N(R)—$CO_2R_{30}$, haloalkyl, heteroaryl, heteroarylalkyl, —$NR_6R_7$, $R_6R_7N$—$(C_1$-$C_6$ alkyl)-, —C(O)$NR_6R_7$, —$(C_1$-$C_4)$alkyl-C(O)$NR_6R_7$, —$(C_1$-$C_4$ alkyl)-NRC(O)$NR_{16}R_{17}$, haloalkoxy, alkyl, —CN, hydroxyalkyl, dihydroxyalkyl, alkoxy, alkoxycarbonyl, phenyl, —$SO_2$-phenyl wherein the phenyl and —$SO_2$-phenyl groups are optionally substituted with 1, 2, or 3 groups that are independently halogen or —$NO_2$, or —OC(O)$NR_6R_7$,
wherein:
$R_{16}$ and $R_{17}$ are independently —H or $C_1$-$C_6$ alkyl, or $R_{16}$, $R_{17}$ and the nitrogen to which they are attached form a morpholinyl ring;
$R_6$ and $R_7$ are independently at each occurrence —H, alkyl, hydroxyalkyl, dihydroxyalkyl, alkoxy, alkanoyl, arylalkyl, arylalkoxy, alkoxycarbonyl, —$SO_2$-alkyl, —OH, alkoxy, alkoxyalkyl, arylalkoxycarbonyl, —$(C_1$-$C_4)$alkyl-$CO_2$-alkyl, heteroarylalkyl, or arylalkanoyl,
wherein each is unsubstituted or substituted with 1, 2, or 3 groups that are independently, halogen, —OH, —SH, heterocycloalkyl, heterocycloalkylalkyl, $C_3$-$C_7$ cycloalkyl, alkoxy, —$NH_2$, —NH(alkyl), —N(alkyl)(alkyl), —O-alkanoyl, alkyl, haloalkyl, carboxaldehyde, or haloalkoxy, or
$R_6$, $R_7$, and the nitrogen to which they are attached form a morpholinyl, pyrrolidinyl, thiomorpholinyl, thiomorpholinyl-S-oxide, thiomorpholinyl S,S-dioxide, piperidinyl, pyrrolidinyl, or piperazinyl ring which is optionally substituted with 1 or 2 groups that are independently $C_1$-$C_4$ alkyl, alkoxycarbonyl, $C_1$-$C_4$ alkoxy, hydroxyl, hydroxyalkyl, dihydroxyalkyl, or halogen;
$R_{30}$ is $C_1$-$C_6$ alkyl optionally substituted with 1 or 2 groups that are independently —OH, —SH, halogen, amino, monoalkylamino, dialkylamino or $C_3$-$C_6$ cycloalkyl;
$R_3$ is —H, halogen, alkoxycarbonyl, arylalkoxycarbonyl, aryloxycarbonyl, arylalkyl, —OC(O)NH(CH$_2$)$_n$aryl, arylalkoxy, —OC(O)N(alkyl)(CH$_2$)$_n$aryl, aryloxy, arylthio, thioalkoxy, arylthioalkoxy, alkenyl, —$NR_6R_7$, $NR_6R_7$—$(C_1$-$C_6)$alkyl, or alkyl, wherein:
the aryl portion of arylalkoxycarbonyl, aryloxycarbonyl, arylalkyl, —OC(O)NH(CH$_2$)$_n$aryl, arylalkoxy, —OC(O)N(alkyl)(CH$_2$)$_n$aryl, and arylthioalkoxy, is unsubstituted or substituted with 1, 2, 3, 4, or 5 groups that are independently, halogen, alkoxy, alkyl, haloalkyl, or haloalkoxy,
wherein:
n is 0, 1, 2, 3, 4, 5, or 6;
$R_4$ is alkyl unsubstituted or substituted with one or two groups that are independently —$CO_2R$, —$CO_2$—$(C_1$-$C_6)$ alkyl, —C(O)$NR_6R_7$, —C(O)$R_6$, —N($R_{30}$)C(O)$NR_{16}R_{17}$, —N($R_{30}$)C(O)—$(C_1$-$C_6)$alkoxy, or —$NR_6R_7$, arylalkoxy, arylalkyl, heteroaryl, heteroarylalkyl, hydroxyalkyl, dihydroxyalkyl, haloalkyl, $R_6R_7N$—$(C_1$-$C_6$alkyl)-, —$NR_6R_7$, alkoxy, carboxaldehyde, —C(O)$NR_6R_7$, $CO_2R$, alkoxyalkyl, or alkoxyalkoxy, wherein the heteroaryl or aryl portions of is the above are unsubstituted or substituted with 1, 2, 3, 4, or 5 groups that are independently halogen, hydroxy, alkoxy, alkyl, —$CO_2$—$(C_1$-$C_6)$alkyl, —CONR$_6R_7$, —$NR_6R_7$, $R_6R_7N$—$(C_1$-$C_6)$ alkyl-, nitro, haloalkyl, or haloalkoxy; and
$R_5$ is H, aryl, arylalkyl, arylthioalkyl, alkyl optionally substituted with 1, 2, or 3 groups that are independently arylalkoxycarbonyl, —$NR_8R_9$, halogen, —C(O)$NR_8R_9$, alkoxycarbonyl, $C_3$-$C_7$ cycloalkyl, or alkanoyl, alkoxy, alkoxyalkyl optionally substituted with one trimethylsilyl group, amino, alkoxycarbonyl, hydroxyalkyl, dihydroxyalkyl, alkynyl, —$SO_2$-alkyl, alkoxy optionally substituted with one trimethylsilyl group, heterocycloalkylalkyl, cycloalkyl, cycloalkylalkyl, -alkyl-S-aryl, -alkyl-$SO_2$-aryl, heteroarylalkyl, heterocycloalkyl, heteroaryl, or alkenyl optionally substituted with alkoxycarbonyl,
wherein:
each of the above is unsubstituted or substituted with 1, 2, 3, 4, or 5 groups that are independently alkyl, halogen, alkoxy, hydroxyalkyl, dihydroxyalkyl, arylalkoxy, thioalkoxy, alkoxycarbonyl, arylalkoxycarbonyl, $CO_2R$, CN, OH, hydroxyalkyl, dihydroxyalkyl, amidinooxime, —$NR_6R_7$, —$NR_8R_9$, $R_6R_7N$—$(C_1$-$C_6$ alkyl)-, carboxaldehyde, $SO_2$ alkyl, —$SO_2H$, —$SO_2NR_6R_7$, alkanoyl wherein the alkyl portion is optionally substituted with OH, halogen or alkoxy, —C(O)$NR_6R_7$, —$(C_1$-$C_4$ alkyl)-C(O)$NR_6R_7$, amidino, haloalkyl, —$(C_1$-$C_4$ alkyl)-$NR_{15}$C(O)$NR_{16}R_{17}$, —$(C_1$-$C_4$ alkyl)-$NR_{15}$C(O)$R_{18}$, —O—$CH_2$—O, —O—$CH_2CH_2$—O—, or haloalkoxy; wherein:
$R_{15}$ is H or $C_1$-$C_6$ alkyl; and
$R_{18}$ is $C_1$-$C_6$ alkyl optionally substituted with —O—($C_2$-$C_6$ alkanoyl, $C_1$-$C_6$hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In one embodiment, the p38 kinase inhibitor from Genus X is selected from the following:
3-Chloro-4-(2,4-difluorobenzyloxy)-6-methyl-1-(1H-pyrazol-4-ylmethyl-1H-pyridin-2-one;
2-{[3-bromo-4-[(2,4-difluorobenzyl)oxy]-6-methyl-2-oxopyridin-1(2H)-yl]-methyl}benzonitrile;
3-{[3-bromo-4-[(2,4-difluorobenzyl)oxy]-6-methyl-2-oxopyridin-1(2H)-yl]-methyl}benzonitrile;
4-{([3-bromo-4-[(2,4-difluorobenzyl)oxy]-6-methyl-2-oxopyridin-1(2H)-yl]-methyl}benzonitrile;
4-{[3-bromo-4-[(2,4-difluorobenzyl)oxy]-6-methyl-2-oxopyridin-1(2H)-yl]-methyl}benzamide;

Methyl 4-{[3-bromo-4-[(2,4-difluorobenzyl)oxy]-6-methyl-2-oxopyridin-1(2H)-yl]-methyl}benzate;
Methyl 3-{[3-bromo-4-[(2,4-difluorobenzyl)oxy]-6-methyl-2-oxopyridin-1(2H)-yl]-methyl}benzate;
3-{[3-bromo-4-[(2,4-difluorobenzyl)oxy]-6-methyl-2-oxopyridin-1(2H)-yl]-methyl}benzamide;
2-{[3-bromo-4-[(2,4-difluorobenzyl)oxy]-6-methyl-2-oxopyridin-1(2H)-yl]-methyl}benzamide;
1-[2-(aminomethyl)benzyl]-3-bromo-4-[(2,4-difluorobenzyl)oxy]-6-methylpyridin-1(2H)-yl-one;
3-bromo-1-[3-(bromomethyl)benzyl]-4[(2,4-difluorobenzyl)oxy]-6-methylpyridin-2(1H)-one;
3-bromo-1-[4-(bromomethyl)benzyl]-4-[(2,4-difluorobenzyl)oxy]-6-methylpyridin-2(1H)-one;
1-[4-(aminomethyl)benzyl]-3-bromo-4-[(2,4-difluorobenzyl)oxy]-6-methylpyridin-2(1H)-one;
1-[3-(aminomethyl)benzyl]-3-bromo-4-[(2,4-difluorobenzyl)oxy]-6-methylpyridin-2(1H)-one;
1-[3-((morpholin-4-yl)methyl)benzyl]-3-bromo-4-[(2,4-difluorobenzyl)oxy]-6-methylpyridin-2(1H)-one;
1-[3-((dimethylamino)methyl)benzyl]-3-bromo-4-[(2,4-difluorobenzyl)oxy]-6-methylpyridin-2(1H)-one;
1-[3-((isopropylamino)methyl)benzyl]-3-bromo-4-[(2,4-difluorobenzyl)oxy]-6-methylpyridin-2(1H)-one;
1-[3-((piperidin-1-yl)methyl)benzyl]-3-bromo-4-[(2,4-difluorobenzyl)oxy]-6-methylpyridin-2(1H)-one;
1-[3-((2-hydroxyethyl)amino)methyl)benzyl]-3-bromo-4-[(2,4-difluorobenzyl)oxy]-6-methylpyridin-2(1H)-one;
1-[3-((bis(2-hydroxyethyl)amino)methyl)benzyl]-3-bromo-4-[(2,4-difluorobenzyl)oxy]-6-methylpyridin-2(1H)-one;
1-[3-((piperazin-1-yl)methyl)benzyl]-3-bromo-4-[(2,4-difluorobenzyl)oxy]-6-methylpyridin-2(1H)-one;
3-{[3-bromo-4-[(2,4-difluorobenzyl)oxy]-6-methyl-2-oxopyridin-1(2H)-yl]methyl}benzoic acid;
1-[3-((1-oxoethyl)aminomethyl)benzyl]-3-bromo-4-[(2,4-difluorobenzyl)oxy]-6-methylpyridin-2(11H)-one;
1-[3-(carbomethoxyaminomethyl)benzyl]-3-bromo-4-[(2,4-difluorobenzyl)oxy]-6-methylpyridin-2(1H)-one;
1-[3-(methylsulfonylaminomethyl)benzyl]-3-bromo-4-[(2,4-difluorobenzyl)oxy]-6-methylpyridin-2(1H)-one;
1-[3-(glycolylaminomethyl)benzyl]-3-bromo-4-[(2,4-difluorobenzyl)oxy]-6-methylpyridin-2(11H)-one;
1-[3-(aminocarbonylaminomethyl)benzyl]-3-bromo-4-[(2,4-difluorobenzyl)oxy]-6-methylpyridin-2(1H)-one;
1-[4-(isopropylaminomethyl)benzyl]-3-bromo-4-[(2,4-difluorobenzyl)oxy]-6-methylpyridin-2(1H)-one;
1-[4-(morpholin-4-ylmethyl)benzyl]-3-bromo-4-[(2,4-difluorobenzyl)oxy]-6-methylpyridin-2(1H)-one;
1-[4-(dimethylaminomethyl)benzyl]-3-bromo-4-[(2,4-difluorobenzyl)oxy]-6-methylpyridin-2(1H)-one;
1-[4-(piperidin-1-ylmethyl)benzyl]-3-bromo-4-[(2,4-difluorobenzyl)oxy]-6-methylpyridin-2(1H)-one;
1-[4([bis(2-hydroxyethyl)amino]methyl)benzyl]-3-bromo-4-[(2,4-difluorobenzyl)oxy]-6-methylpyridin-2(1H)-one;
1-[4-((2-etholyl)aminomethyl)benzyl]-3-bromo-4-[(2,4-difluorobenzyl)oxy]-6-methylpyridin-2(1H)-one;
1-[4-piperazin-1-ylmethyl)benzyl]-3-bromo-4-[(2,4-difluorobenzyl)oxy]-6-methylpyridin-2(1H)-one;
1-[4-(methoxycarbonylaminomethyl)benzyl]-3-bromo-4-[(2,4-difluorobenzyl)oxy]-6-methylpyridin-2(1H)-one;
1-[4-(acetylaminomethylbenzyl]-3-bromo-4-[(2,4-difluorobenzyl)oxy]-6-methylpyridin-2(1H)-one;
1-[4-(methylsulfonylaminomethyl)benzyl]-3-bromo-4-[(2,4-difluorobenzyl)oxy]-6-methylpyridin-2(11H)-one;
1-[4-(carbamylaminomethyl)benzyl]-3-bromo-4-[(2,4-diflorobenzyl)oxy]-6-methylpyridin-2(1H)-one;
4-(4-{[3-bromo-4-[(2,4-difluorobenzyl)oxy]-6-methyl-2-oxopyridin-1(2H)-yl]methyl}benzoyl)piperazine-1-carboxamide;
N-(4-{[3-bromo-4-[(2,4-difluorobenzyl)oxy]-6-methyl-2-oxopyridin-1(2H)-yl]methyl}benzyl)-2-methoxyacetamide;
methyl 2-(4-((4-(2,4-difluorobenzyloxy)-3-bromo-6-methyl-2-oxopyridin-1(2H)-yl)methyl)benzylcarbamoyl)acetate;
N-(4-((4-(2,4-difluorobenzyloxy)-3-bromo-6-methyl-2-oxopyridin-1(2H)-yl)methyl)benzyl)-2-hydroxy-2-methylpropanamide;
N-(4-((4-(2,4-difluorobenzyloxy)-3-bromo-6-methyl-2-oxopyridin-1(2H)-yl)methyl)benzyl)-1-hydroxycyclopropanecarboxamide;
N-(4-((4-(2,4-difluorobenzyloxy)-3-bromo-6-methyl-2-oxopyridin-1(2H)-yl)methyl)benzyl)-2-aminoacetamide;
N-(4-((4-(2,4-difluorobenzyloxy)-3-bromo-6-methyl-2-oxopyridin-1(2H)-yl)methyl)benzyl)-2-hydroxyacetamide;
N-(4-((4-(2,4-difluorobenzyloxy)-3-bromo-6-methyl-2-oxopyridin-1(2H)-yl)methyl)benzyl)-2-(1-oxoethylamino)acetamide;
1-{4-[(4-acetylpiperazin-1-yl)carbonyl]benzyl}-3-bromo-4-[(2,4-difluorobenzyl)oxy]-6-methylpyridin-2(1H)-one;
3-bromo-4-[(2,4-difluorobenzyl)oxy]-6-methyl-1-(4-{[4-(methylsulfonyl)piperazin-1-yl]carbonyl}benzyl)pyridin-2(1H)-one;
3-Bromo-4-[(2,4-diflurorbenzyl)oxy]-1-[3-(hydroxymethyl)phenyl]-6-methylpyridin-2(11H)-one;
Methyl-4-[3-bromo-4-[(difluorobenzyl)oxy]-6-methyl-2-oxopyridin-1-(2H)-yl]benzoate;
4-[3-bromo-4-[(difluorobenzyl)oxy]-6-methyl-2-oxopyridin-1(2H)-yl]benzoic acid;
4-(Benzyloxy)-1-(3-fluorobenzyl)-3-(trifluoromethyl)pyridin-2(1H)-one;
4-{[3-bromo-4-[(2,4-difluorobenzyloxy]-6-methyl-2-oxopyridin-1(2H)-yl]methyl}benzoic acid;
3-Bromo-4-[(2,4-diflurobenzyl)oxy]-1-[4-(hydroxymethyl)benzyl]-6-methylpyridin-2(1H)-one;
3-Bromo-4-[(2,4-diflurobenzyl)oxy]-1-[4-(1-hydroxy-1-methylethyl)benzyl]-6-methylpyridin-2(11H)-one;
3-bromo-4-[(2,4-difluorobenzyl)oxy]-6-methyl-1-{4-[(methylamino)methyl]benzyl}pyridin-2(1H)-one;
4-[(2,4-diflurobenzyl)oxy]-1-(4-methoxybenzyl)-6-methylpyridin-2(1H)-one;
3-bromo-4-[(2,4-diflurobenzyl)oxy]-1-(4-methoxybenzyl)-6-methylpyridin-2(1H)-one;
3-bromo-4-[(2,4-diflurobenzyl)oxy]-1-(4-hydroxybenzyl)-6-methylpyridin-2(1H)-one;
3-bromo-4-[(2,4-difluorobenzyl)oxy]-1-{4-[(4-hydroxy-4-methylpiperidin-1-yl)carbonyl]benzyl}-6-methylpyridin-2(1H)-one;
4-{[3-bromo-4-[(2,4-difluorobenzyloxy]-6-methyl-2-oxypyridin-1(2H)-yl]methyl}-N-(2-hydroxy-2-methylpropyl)benzamide;
3-bromo-4-[(2,4-difluorobenzyl)oxy]-1-{4-[(4-hydroxypiperidin-1-yl)carbonyl]benzyl}-6-methylpyridin-2(1H)-one;
4-{[3-bromo-4-[(2,4-difluorobenzyl)oxy]-6-methyl-2-oxopyridin-1(2H)-yl]methyl}-N-(2-hydroxyethyl)benzamide;
3-bromo-4-(2,4-difluorophenoxy)-6-methyl-1-[4-((aminoethyl)aminocarbonyl)benzyl]pyridin-2(1H)-one;
3-bromo-4-(2,4-difluorophenoxy)-6-methyl-1-[4-((aminopropyl)aminocarbonyl)benzyl]pyridin-2(1H)-one;

3-bromo-4-(2,4-difluorophenoxy)-6-methyl-1-[4-(hydroxyaminocarbonyl)benzyl]pyridin-2(1H)-one;
3-bromo-4-(2,4-difluorophenoxy)-6-methyl-1-[4-((aminomethyl)aminocarbonyl)benzyl]pyridin-2(1H)-one;
3-bromo-4-(2,4-difluorophenoxy)-6-methyl-1-[4-(dimethylaminocarbonyl)benzyl]pyridin-2(1H)-one;
3-bromo-4-(2,4-difluorophenoxy)-6-methyl-1-[4-(diethanol-2-ylaminocarbonyl)benzyl]pyridin-2(1H)-one;
3-bromo-4-(2,4-difluorophenoxy)-6-methyl-1-[4-(isoyropylaminocarbonyl)benzyl]pyridin-2(1H)-one;
3-bromo-4-(2,4-difluorophenoxy)-6-methyl-1-[4-((dimethylaminoethyl)aminocarbonyl)benzyl]pyridin-2(1H)-one;
3-bromo-4-(2,4-difluorophenoxy)-6-methyl-1-[4-((methoxyethyl)aminocarbonyl)benzyl]pyridin-2(1H)-one;
3-bromo-4-(2,4-difluorophenoxy)-6-methyl-1-[4-((ethanol-2-yl)methylaminocarbonyl)benzyl]pyridin-2(1H)-one;
3-bromo-4-(2,4-difluorophenoxy)-6-methyl-1-[4-((methoxyethyl)methylaminocarbonyl)benzyl]pyridin-2(1H)-one;
4-{[3-bromo-4-[(2,4-difluorobenzyl)oxy]-6-methyl-2-oxopyridin-1(2H)-yl]-N-(2-hydroxyethyl)benzamide;
4-(4-(2,4-difluorobenzyloxy)-3-bromo-6-methyl-2-oxopyridin-1(2H)-yl)-N-(2-aminoethyl)benzamide;
4-(4-(2,4-difluorobenzyloxy)-3-bromo-6-methyl-2-oxopyridin-1(2H)-yl)-N-(3-aminopropyl)benzamide;
4-(4-(2,4-difluorobenzyloxy)-3-bromo-6-methyl-2-oxopyridin-1(2H)-yl)-N-hydroxybenzamide;
4-(4-(2,4-difluorobenzyloxy)-3-bromo-6-methyl-2-oxopyridin-1(2H)-yl)-N-methylbenzamide;
4-(4-(2,4-difluorobenzyloxy)-3-bromo-6-methyl-2-oxopyridin-1(2H)-yl)-N,N-dimethylbenzamide;
4-(4-(2,4-difluorobenzyloxy)-3-bromo-6-methyl-2-oxopyridin-1(2H)-yl)-N,N-bis(2-hydroxyethyl)benzamide;
4-(4-(2,4-difluorobenzyloxy)-3-bromo-6-methyl-2-oxopyridin-1(2H)-yl)-N-isopropylbenzamide;
4-[3-bromo-4-[(2,4-difluorobenzyl)oxy]-6-methyl-2-oxopyridin-1(2H)-yl]benzamide;
Methyl-4-{[3-chloro-4-[(2,4-difluorobenzyl)oxy]-6-methyl-2-oxopyridin-1(2H)-yl]methyl}benzoate;
3-{[3-bromo-4-[(2,4-difluorobenzyl)oxy]-6-methyl-2-oxopyridin-1(2H)-yl]methyl}-N-methylbenzamide;
3-((4-(2,4-difluorobenzyloxy)-3-bromo-6-methyl-2-oxopyridin-1(2H)-yl)methyl)-N-(2-aminoethyl)benzamide;
3-((4-(2,4-difluorobenzyloxy)-3-bromo-6-methyl-2-oxopyridin-1(2H)-yl)methyl)-N-(3-aminopropyl)benzamide;
3-((4-(2,4-difluorobenzyloxy)-3-bromo-6-methyl-2-oxopyridin-1(2H)-yl)methyl)-N-hydroxybenzamide;
3-((4-(2,4-difluorobenzyloxy)-3-bromo-6-methyl-2-oxopyridin-1(2H)-yl)methyl)-N,N-dimethylbenzamide;
3-((4-(2,4-difluorobenzyloxy)-3-bromo-6-methyl-2-oxopyridin-1(2H)-yl)methyl)-N-(2-hydroxyethyl)benzamide;
3-((4-(2,4-difluorobenzyloxy)-3-bromo-6-methyl-2-oxopyridin-1(2H)-yl)methyl)-N,N-bis(2-hydroxyethyl)benzamide;
3-((4-(2,4-difluorobenzyloxy)-3-bromo-6-methyl-2-oxopyridin-1(2H)-yl)methyl)-N-isopropylbenzamide;
N-(3-{[3-bromo-4-[(2,4-difluorobenzyl)oxy]-6-methyl-2-oxopyridin-1(2H)-yl]methyl benzyl]-2-methoxyacetamide;
N-(3-((4-(2,4-difluorobenzyloxy)-3-bromo-6-methyl-2-oxopyridin-1(2H)-yl)methyl)benzyl)-2-aminoacetamide;
N-(3-((4-(2,4-difluorobenzyloxy)-3-bromo-6-methyl-2-oxopyridin-1(2H)-yl)methyl)benzyl)-2-(1-oxoethylamino)acetamide;
N-(3-((4-(2,4-difluorobenzyloxy)-3-bromo-6-methyl-2-oxopyridin-1(2H)-yl)methyl)benzyl)-3-oxobutanamide;
N-(3-{[3-bromo-4-[(2,4-difluorobenzyl)oxy]-6-methyl-2-oxopyridin-1(2H)-yl]methyl}benzyl)-2-hydroxy-2-methylpropanamide;
N-(3-{[3-bromo-4-[(2,4-difluorobenzyl)oxy]-6-methyl-2-oxopyridin-1(2H)-yl]methyl}benzyl)-1-hydroxycyclopropanecarboxamide;
N'-(3-{[3-bromo-4-[(2,4-difluorobenzyl)oxy]-6-methyl-2-oxopyridin-1(2H)-yl]methyl}benzyl)-N,N-dimethylurea;
1-(3-((4-(2,4-difluorobenzyloxy)-3-bromo-6-methyl-2-oxopyridin-1(2H)-yl)methyl)benzyl)-3-methylurea;
3-[3-bromo-4-[(2,4-difluorobenzyl)oxy]-6-methyl-2-oxopyridin-1(2H)-yl]benzoic acid;
Ethyl 3-[3-bromo-4-[(2,4-difluorobenzyl)oxy]-6-methyl-2-oxopyridin-1(2H)-yl]benzoate;
3-[3-bromo-4-[(2,4-difluorobenzyl)oxy]-6-methyl-2-oxopyridin-1(2H)-yl]-N-methylbenzamide;
3-(4-(2,4-difluorobenzyloxy)-3-bromo-6-methyl-2-oxopyridin-1(2H)-yl)-N-(2-aminoethyl)benzamide;
3-(4-(2,4-difluorobenzyloxy)-3-bromo-6-methyl-2-oxopyridin-1(2H)-yl)-N-(3-aminopropyl)benzamide;
3-(4-(2,4-difluorobenzyloxy)-3-bromo-6-methyl-2-oxopyridin-1(2H)-yl)-N-hydroxybenzamide;
3-(4-(2,4-difluorobenzyloxy)-3-bromo-6-methyl-2-oxopyridin-1(2H)-yl)-N,N-dimethylbenzamide;
3-(4-(2,4-difluorobenzyloxy)-3-bromo-6-methyl-2-oxopyridin-1(2H)-yl)-N-(2-hydroxyethyl)benzamide;
3-(4-(2,4-difluorobenzyloxy)-3-bromo-6-methyl-2-oxopyridin-1(2H)-yl)-N-isopropylbenzamide;
3-(4-(2,4-difluorobenzyloxy)-3-bromo-6-methyl-2-oxopyridin-1(2H)-yl)-N-(2-(dimethylamino)ethyl)-benzamide;
3-(4-(2,4-difluorobenzyloxy)-3-bromo-6-methyl-2-oxopyridin-1(2H)-yl)-N-(2-methoxyethyl)benzamide;
3-(4-(2,4-difluorobenzyloxy)-3-bromo-6-methyl-2-oxopyridin-1(2H)-yl)-N-(2-(dimethylamino)ethyl)-N-methylbenzamide;
3-(4-(2,4-difluorobenzyloxy)-3-bromo-6-methyl-2-oxopyridin-1(2H)-yl)-N-(2-hydroxyethyl)-N-methylbenzamide;
3-(4-(2,4-difluorobenzyloxy)-3-bromo-6-methyl-2-oxopyridin-1(2H)-yl)-N-(2-methoxyethyl)-N-methylbenzamide;
3-[3-bromo-4-[(2,4-difluorobenzyl)oxy]-6-methyl-2-oxopyridin-1(2H)-yl]benzamide;
3-[3-chloro-4-[(2,4-difluorobenzyl)oxy]-6-methyl-2-oxopyridin-1(2H)-yl]benzoic acid;
3-chloro-4-[(2,4-difluorobenzyl)oxy]-1-[3-(hydroxymethyl)phenyl]-6-methylpyridin-2(1H)-one;
1-[3-(aminomethyl)phenyl]-3-bromo-4-[(2,4-difluorobenzyl)oxy]-6-methylpyridin-2(1H)-one;
N-{3-[3-bromo-4-[(2,4-difluorobenzyl)oxy]-6-methyl-2-oxopyridin-1(2H)-yl]benzyl}methanesulfonamide;
N-(3-(4-(2,4-difluorobenzyloxy)-3-bromo-6-methyl-2-oxopyridin-1(2H)-yl)benzyl)acetamide;
methyl 3-(4-(2,4-difluorobenzyloxy)-3-bromo-6-methyl-2-oxopyridin-1(2H)-yl)benzylcarbamate;
N-{3-[3-bromo-4-[(2,4-difluorobenzyl)oxy]-6-methyl-2-oxopyridin-1(2H)-yl]benzyl}-2-methoxyacetamide;
N-(3-(4-(2,4-difluorobenzyloxy)-3-bromo-6-methyl-2-oxopyridin-1(2H)-yl)benzyl)-2-aminoacetamide;
N-(3-(4-(2,4-difluorobenzyloxy)-3-bromo-6-methyl-2-oxopyridin-1(2H)-yl)benzyl)-2-hydroxyacetamide;
N'-{3-[3-bromo-4-[(2,4-difluorobenzyl)oxy]-6-methyl-2-oxopyridin-1(2H)-yl]benzyl}-N,N-dimethylurea;

1-(3-(4-(2,4-difluorobenzyloxy)-3-bromo-6-methyl-2-oxopyridin-1(2H)-yl)benzyl)-3-methylurea;
N-{3-[3-bromo-4-[(2,4-difluorobenzyl)oxy]-6-methyl-2-oxopyridin-1(2H)-yl]benzyl}urea;
3-bromo-4-[(2,4-difluorobenzyl)oxy]-1-{3-[(dimethylamino)methyl]phenyl}-6-methylpyridin-2(1H)-one;
3-bromo-4-[(2,4-difluorobenzyloxy]-6-methyl-1-(2-morpholin-4-ylethyl)pyridin-2(11H)-one;
3-bromo-1-(4-bromo-2,6-difluorophenyl)-4-[(2,4-difluorobenzyl)oxy]-6-methylpyridin-2(1H)-one;
3-bromo-4-[(2,4-difluorobenzyl)oxy]-6-methyl-1-(2,4,6-trifluorophenyl)pyridin-2(1H)-one;
3-chloro-4-[(2,4-difluorobenzyl)oxy]-6-methyl-1-(2,4,6-trifluorophenyl)pyridin-2(1H)-one;
3-bromo-4-[(2,4-difluorobenzyl)oxy]-6-(hydroxymethyl)-1-(2,4,6-trifluorophenyl)pyridin-2(1H)-one;
3-chloro-4-[(2,4-difluorobenzyl)oxy]-6-(hydroxymethyl)-1-(2,4,6-trifluorophenyl)pyridin-2(1H)-one;
3-bromo-4-[(2,4-difluorobenzyl)oxy]-1-(2,6-difluoro-4-morpholin-4-ylphenyl)-6-methylpyridin-2(1H)-one;
3-bromo-4-[(2,4-difluorobenzyl)oxy]-1-[2,6-difluoro-4-(4-methylpiperazin-1-yl)phenyl]-6-methylpyridin-2(1H)-one;
3-chloro-4-[(2,4-difluorobenzyl)oxy]-1-[2,6-difluoro-4-(4-methylpiperazin-1-yl)phenyl]-6-methylpyridin-2(1H)-one;
3-bromo-4-[(2,4-difluorobenzyl)oxy]-1-[4-(dimethylamino)-2,6-difluorophenyl]-6-methylpyridin-2(1H)-one;
3-bromo-4-[(2,4-difluorobenzyl)oxy]-1-{2,6-difluoro-4-[(2-hydroxyethyl)(methyl)amino]phenyl}-6-methylpyridin-2(1H)-one;
3-bromo-1-(3,5-dibromo-2,6-difluoro-4-hydroxybenzyl)-4-[(2,4-difluorobenzyl)oxy]-6-methylpyridin-2(1H)-one;
2-{4-[3-bromo-4-[(2,4-difluorobenzyl)oxy]-6-methyl-2-oxopyridin-1(2H)-yl]-3,5-difluorophenoxyl}acetamide;
3-bromo-4-[(2,4-difluorobenzyl)oxy]-1-[2,6-difluoro-4-(2-hydroxyethoxy)phenyl]-6-methylpyridin-2(1H)-one;
3-bromo-1-(2,6-difluorophenyl)-4-{[4-fluoro-2-(hydroxymethyl)benzyl]oxy}-6-methylpyridin-2(1H)-one;
3-chloro-1-(2,6-difluorophenyl)-4-{[4-fluoro-2-(hydroxymethyl)benzyl]oxy}-6-methylpyridin-2(1H)-one;
3-[3-bromo-4-[(2,4-difluorobenzyl)oxy]-6-methyl-2-oxopyridin-1(2H)-yl]-2-methyl)-N-(2-morpholin-4-ylethyl)benzamide;
3-(4-(2,4-difluorobenzyloxy)-3-bromo-6-methyl-2-oxopyridin-1(2H)-yl)-N-(2-methoxyethyl)-2-methylbenzamide;
3-(4-(2,4-difluorobenzyloxy)-3-bromo-6-methyl-2-oxopyridin-1(2H)-yl)-N,N,2-trimethylbenzamide;
3-(4-(2,4-difluorobenzyloxy)-3-bromo-6-methyl-2-oxopyridin-1(2H)-yl)-N-(2-hydroxyethyl)-2-methylbenzamide;
3-(4-(2,4-difluorobenzyloxy)-3-bromo-6-methyl-2-oxopyridin-1(2H)-yl)-N,2-dimethylbenzamide;
3-(4-(2,4-difluorobenzyloxy)-3-bromo-6-methyl-2-oxopyridin-1(2H)-yl)-N-(2-hydroxyethyl)-N,2-dimethylbenzamide;
4-(2,4-difluorobenzyloxy)-1-(3-(4-methylpiperazin-1-yl)carbonyl-2-methylphenyl)-3-bromo-6-methylpyridin-2(1H)-one;
4-(2,4-difluorobenzyloxy)-1-(3-(morpholin-4-yl)carbonyl-2-methylphenyl)-3-bromo-6-methylpyridin-2(1H)-one;
3-(4-(2,4-difluorobenzyloxy)-3-bromo-6-methyl-2-oxopyridin-1(2H)-yl)-N-(2-methoxyethyl)-N,2-dimethylbenzamide;
3-(4-(2,4-difluorobenzyloxy)-3-bromo-6-methyl-2-oxopyridin-1(2H)-yl)-2-methylbenzamide;
3-bromo-4-[(2,4-difluorobenzyl)oxy]-1-[3-(hydroxymethyl)-2-methylphenyl]-6-methylpyridin-2(11H)-one;
3-[3-chloro-4-[(2,4-difluorobenzyhoxy]-6-methyl-2-oxopyridin-1(2H)-yl]-N-(2-methoxyethyl)-2-methylbenzamide;
3-[3-chloro-4-[(2,4-difluorobenzyl)oxy]-6-methyl-2-oxopyridin-1(2H)-yl]-N,2-dimethylbenzamide;
3-[3-chloro-4-[(2,4-difluorobenzyl)oxy]-6-methyl-2-oxopyridin-1(2H)-yl]-N-(2-hydroxyethyl)-2-methylbenzamide;
3-[3-chloro-4-[(2,4-difluorobenzyl)oxy]-6-methyl-2-oxopyridin-1(2H)-yl]-2-methylbenzamide;
3-Bromo-4-[(2,4-difluorobenzyl)oxy]-1-(2,6-dimethylphenyl)-6-methylpyridin-2(1H)-one;
3-Bromo-1-(2,6-dimethylphenyl)-4-[(4-fluorobenzyl)oxy]-6-methylpyridin-2(1H)-one;
3-Bromo-1-(2,6-dimethylphenyl)-6-methyl-4-[(2,4,6-trifluorobenzyl)oxy]pyridin-2(1H)-one;
3-Bromo-4-[(2,6-difluorobenzyl)oxy]-1-(2,6-dimethylphenyl)-6-methylpyridin-2(11H)-one;
3-Bromo-1-(2,6-dichlorophenyl)-4-[(4-fluorobenzyl)oxy]-6-methylpyridin-2(1H)-one;
3-Bromo-1-(2,6-dichlorophenyl)-4-[(2,4-difluorobenzyl)oxy]-6-methylpyridin-2(1H)-one;
3-Bromo-1-(2,6-dichlorophenyl)-4-[(2,6-difluorobenzyl)oxy]-6-methylpyridin-2(1H)-one;
3-Bromo-4-[(2,4-difluorobenzyl)oxy]-1-(2-methoxy-6-methylphenyl)-6-methylpyridin-2(1H)-one;
4-[3-bromo-4-[(2,4-difluorobenzyl)oxy]-6-methyl-2-oxopyridin-1(2H)-yl]-3,5-dichlorobenzenesulfonamide;
3-Bromo-4-[(2,4-difluorobenzyl)oxy]-1-(2,6-difluorophenyl)-6-methylpyridin-2(1H)-one;
3-Bromo-4-[(2,4-difluorobenzyl)oxy]-1-(2,6-difluorophenyl)-5-iodo-6-methylpyridin-2(1H)-one;
3-Bromo-4-[(2,4-difluorobenzyl)oxy]-1-[2-(dimethylamino)-4,6-difluorophenyl]-6-methylpyridin-2(1H)-one;
3-Bromo-4-[(2,4-difluorobenzyl)oxy]-1-{2,4-difluoro-6-[(2-hydroxyethyl)(methyl)amino]phenyl}-6-methylpyridin-2(1H)-one;
2-({[3-Bromo-1-(2,6-difluorophenyl)-6-methyl-2-oxo-1,2-dihydropyridin-4-yl]oxy}methyl)-5-fluorobenzonitrile;
4-{[2-(Aminomethyl)-4-fluorobenzyl]oxy}-3-bromo-1-(2,6-difluorophenyl)-6-methylpyridin-2(1H)-one trifluoroacetate;
N-[2-({[3-bromo-1-(2,6-difluorophenyl)-6-methyl-2-oxo-1,2-dihydropyridin-4-yl]oxy}methyl)-5-fluorobenzyl]urea;
Methyl 2-({[3-bromo-1-(2,6-difluorophenyl)-6-methyl-2-oxo-1,2-dihydropyridin-4-yl]oxy}methyl)-5-fluorobenzylcarbamate;
N-[2-({[3-bromo-1-(2,6-difluorophenyl)-6-methyl-2-oxo-1,2-dihydropyridin-4-yl]oxy}methyl)-5-fluorobenzyl]-2-hydroxyacetamide;
Ethyl 2-({[3-chloro-1-(2,6-difluorophenyl)-6-methyl-2-oxo-1,2-dihydropyridin-4-yl]oxy}methyl)-5-fluorobenzylcarbamate;
Isobutyl 2-({[3-chloro-1-(2,6-difluorophenyl)-6-methyl-2-oxo-1,2-dihydropyridin-4-yl]oxy}methyl)-5-fluorobenzylcarbamate;
Cycloyronylmethyl 2-({[3-chloro-1-(2,6-difluorophenyl)-6-methyl-2-oxo-1,2-dihydropyridin-4-yl]oxy}methyl)-5-fluorobenzylcarbamate;
1-[(4-amino-2-methylpyrimidin-5-yl)methyl]-3-bromo-4-[(2,4-difluorobenzyl)oxy]-6-methylpyridin-2(1H)-one trifluoroacetate;
1-[(4-amino-2-methylpyrimidin-5-yl)methyl]-3-bromo-4-[(2,4-difluorobenzyl)oxy]-6-methylpyridin-2(1H)-one hydrochloride;

1-[(4-amino-2-methylpyrimidin-5-yl)methyl]-3-chloro-4-[(2,4-difluorobenzyl)oxy]-6-methylpyridin-2(1H)-one trifluoroacetate;
1-[(4-amino-2-methylpyrimidin-5-yl)methyl]-3-chloro-4-[(2,4-difluorobenzyl)oxy]-6-methylpyridin-2(1H)-one hydrochloride;
3-Bromo-4-[(2,4-difluorobenzyl)oxy]-1-(1H-indazol-5-ylmethyl)-6-methylpyridin-2(1H)-one trifluoroacetate;
3-bromo-4-[(2,4-difluorobenzyl)oxy]-6-methyl-1-{[2-(methylthio)pyrimidin-4-yl]methyl}pyridin-2(1H)-one;
3-Bromo-4-[(2,4-difluorobenzyl)oxy]-6-methyl-1-{[2-(methylsulfonyl)pyrimidin-4-yl]methyl}pyridin-2(1H)-one;
4-{[3-Bromo-4-[(2,4-difluorobenzyl)oxy]-6-methyl-2-oxopyridin-1(2H)-yl]methyl}pyrimidine-2-carbonitrile trifluoroacetate;
4-{[2-(Aminomethyl)-4-fluorobenzyl]oxy}-3-bromo-1-(2,6-difluorophenyl)-6-methylpyridin-2(1H)-one trifluoroacetate;
3-Bromo-4-[(2,4-difluorobenzyl)oxy]-1-[(2-methoxypyrimidin-4-yl)methyl]-6-methylpyridin-2(1H)-one trifluoroacetate;
Methyl 4-{[3-bromo-4-[(2,4-difluorobenzyl)oxy]-6-methyl-2-oxopyridin-1(2H)-yl]methyl}pyrimidine-2-carboxylate trifluoroacetate;
3-Bromo-4-[(2,4-difluorobenzyl)oxy]-1-[(2-hydroxypyrimidin-4-yl)methyl]-6-methylpyridin-2(1H)-one trifluoroacetate;
4-{[3-bromo-4-[(2,4-difluorobenzyl)oxy]-6-methyl-2-oxopyridin-1(2H)-yl]methyl}pyrimidine-2-carboxamide trifluoroacetate;
Methyl (4-{[3-bromo-4-[(2,4-difluorobenzyl)oxy]-6-methyl-2-oxopyridin-1(2H)-yl]methyl}pyrimidin-2-yl)methylcarbamate;
3-Bromo-4-[(2,4-difluorobenzyl)oxy]-6-methyl-1-[(5-methylpyrazin-2-yl)methyl]pyridin-2(1H)-one;
3-bromo-4-[(2,4-difluorobenzyl)oxy]-6-methyl-1-(pyrazin-2-ylmethyl)pyridin-2(1H)-one;
3-Bromo-4-[(2,4-difluorobenzyl)oxy]-1-{[5-(hydroxymethyl)pyrazin-2-yl]methyl}-6-methylpyridin-2(1H)-one;
3-Bromo-4-[(2,4-difluorobenzyl)oxy]-1-{5-[(dimethylamino)methyl]pyrazin-2-yl}methyl)-6-methylpyridin-2(1H)-one trifluoroacetate;
3-Bromo-4-[(2,4-difluorobenzyl)oxy]-1-[(5-{[(2-hydroxyethyl)-(methyl)amino]methyl}pyrazin-2-yl)methyl]-6-methylpyridin-2(1H)-one trifluoroacetate;
3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one trifluoroacetate;
3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one;
5-{[3-Bromo-4-[(2,4-difluorobenzyl)oxy]-6-methyl-2-oxopyridin-1(2H)-yl]methyl}-N-(2-hydroxyethyl)-N-methylpyrazine-2-carboxamide;
5-{[3-Bromo-4-[(2,4-difluorobenzyl)oxy]-6-methyl-2-oxopyridin-1(2H)-yl]methyl}-N-(2,3-dihydroxypropyl)pyrazine-2-carboxamide;
5-{[3-Bromo-4-[(2,4-difluorobenzyl)oxy]-6-methyl-2-oxopyridin-1(2H)-yl]methyl}-N-(2-hydroxyethyl)pyrazine-2-carboxamide;
3-Bromo-4-[(2,4-difluorobenzyl)oxy]-1-{[5-(methoxymethyl)pyrazin-2-yl]methyl}-6-methylpyridin-2(11H)-one;
3-Bromo-4-[(2,4-difluorobenzyl)oxy]-1-({5-[(2-methoxyethoxy)methyl]pyrazin-2-yl}methyl)-6-methylpyridin-2(1H)-one;
(5-{[3-Bromo-4-[(2,4-difluorobenzyl)oxy]-6-methyl-2-oxopyridin-1(2H)-yl]methyl}pyrazin-2-yl)methyl carbamate;
1-benzyl-3-bromo-4-[(2,4-difluorobenzyl)oxy]-6-methylpyridin-2(1H)-one;
3-chloro-4-[(2,4-difluorobenzyl)oxy]-1-(2,6-difluorophenyl)-6-methylpyridin-2(1H)-one;
3-bromo-1-(4-fluorobenzyl)-4-[(4-fluorobenzyl)amino]-6-methylpyridin-2(1H)-one;
3-bromo-1-(cyclopropylmethyl)-4-[(2,4-difluorobenzyl)oxy]-6-methylpyridin-2(1H)-one;
3-bromo-4-[(2,4-difluorobenzyl)oxy]-6-methyl-1-(pyridin-4-ylmethyl)pyridin-2(1H)-one;
4-(4-fluorobenzyloxy)-3-bromo-6-methyl-1-((pyridin-4-yl)methyl)pyridin-2(1H)-one;
4-(2,4,6-trifluorobenzyloxy)-3-bromo-6-methyl-1-((pyridin-4-yl)methyl)pyridin-2(1H)-one;
4-(2,6-difluorobenzyloxy)-3-bromo-6-methyl-1-((pyridin-4-yl)methyl)pyridin-2(1H)-one;
3-bromo-4-[(2,4-difluorobenzyl)oxy]-6-methyl-1-(pyridin-3-ylmethyl)pyridin-2(1H)-one;
4-(4-fluorobenzyloxy)-3-bromo-6-methyl-1-((pyridin-3-yl)methyl)pyridin-2(1H)-one;
4-(2,4,6-trifluorobenzyloxy)-3-bromo-6-methyl-1-(pyridin-3-yl)methyl)pyridin-2(1H)-one;
4-(2-fluorobenzyloxy)-3-bromo-6-methyl-1-((pyridin-3-yl)methyl)pyridin-2(1H)-one;
4-(2,4,5-trifluorobenzyloxy)-3-bromo-6-methyl-1-((pyridin-3-ylmethyl)pyridin-2(1H)-one;
4-(4-chloro-2-fluorobenzyloxy)-3-bromo-6-methyl-1-((pyridin-3-yl)methyl)pyridin-2(1H)-one;
4-(2-chloro-4-fluorobenzyloxy)-3-bromo-6-methyl-1-((pyridin-3-yl)methyl)pyridin-2(1H)-one;
3-bromo-4-[(2,4-difluorobenzyl)oxy]-6-methyl-1-(pyridin-2-ylmethyl)pyridin-2(1H)-one;
4-(2,6-difluorobenzyloxy)-3-bromo-6-methyl-1-((pyridin-3-yl)methyl)pyridin-2(1H)-one;
4-(4-fluorobenzyloxy)-3-bromo-6-methyl-1-((pyridin-2-yl)methyl)pyridin-2(1H)-one;
4-(2,4,6-trifluorobenzyloxy)-3-bromo-6-methyl-1-((pyridin-2-yl)methyl)pyridin-2(1H)-one;
4-(2,4,5-trifluorobenzyloxy)-3-bromo-6-methyl-1-((pyridin-2-yl)methyl)pyridin-2(1H)-one;
3-bromo-4-[2-(4-fluorophenyl)ethyl]-6-methyl-1-(pyridin-3-ylmethyl)pyridin-2(1H)-one;
3-bromo-4-[2-(4-fluorophenyl)ethyl]-6-methyl-1-(pyridin-4-ylmethyl)pyridin-2(1H)-one;
3-chloro-4-[(2,4-difluorobenzyl)oxy]-6-methyl-1-(pyridin-3-ylmethyl)pyridin-2(1H)-one;
1-[(4-amino-2-methylpyrimidin-5-ylmethyl]-3-bromo-6-methyl-4-[(2,4,6-trifluorobenzyl)oxy]pyridin-2(1H)-one trifluoroacetate;
3-bromo-4-[(2,4-difluorobenzyl)oxy]-6-methyl-1-{[2-methyl-4-(methylamino)pyrimidin-5-yl]methyl}pyridin-2(1H)-one trifluoroacetate;
ethyl N-(5-{[3-bromo-4-[(2,4-difluorobenzyl)oxy]-6-methyl-2-oxopyridin-1(2H)-yl]methyl}-2-methylpyrimidin-4-yl)glycinate trifluoroacetate;
N-(5-{[3-chloro-4-[(2,4-difluorobenzyl)oxy]-6-methyl-2-oxopyridin-1(2H)-yl]methyl}-2-methylpyrimidin-4-yl)-2-hydroxyacetamide trifluoroacetate;
3-chloro-4-[(2,4-difluorobenzyl)oxy]-1-({5-[(4-hydroxypiperidin-1-yl)carbonyl]pyrazin-2-yl}methyl)-6-methylpyridin-2(1H)-one;
5-{[3-chloro-4-[(2,4-difluorobenzyl)oxy]-6-methyl-2-oxopyridin-1(2H)-yl]methyl}-N-(3-hydroxy-2,2-dimethylpropyl)pyrazine-2-carboxamide;

5-{[3-chloro-4-[(2,4-difluorobenzyl)oxy]-6-methyl-2-oxopyridin-1(2H)-yl]methyl}-N-(2,2,2-trifluoroethyl-pyrazine-2-carboxamide;
1-allyl-3-bromo-4-[(2,4-difluorobenzyl)oxy]-6-methylpyridin-2(1H)-one;
1-allyl-3-chloro-4-[(2,4-difluorobenzyl)oxy]-6-methylpyridin-2(1H)-one;
Methyl (2E)-4-[3-bromo-4-[(2,4-difluorobenzyl)oxy]-6-methyl-2-oxopyridin-1(2H)-yl]but-2-enoate;
3-bromo-4-[(2,4-difluorobenzyl)oxy]-6-methyl-1-prop-2-ynylpyridin-2(1H)-one;
3-Bromo-4-[(2,4-difluorobenzyl)oxy]-6-(hydroxymethyl)-1-(pyridin-3-ylmethyl)pyridin-2(1H)-one;
3-bromo-4-[(2,4-difluorobenzyl)oxy]-6-[(dimethylamino)methyl-1-(pyridin-3-ylmethyl)pyridin-2(1H)-one;
3-bromo-4-[(2,4-difluorobenzyl)oxy]-1-(2,6-difluorophenyl)-6-(hydroxymethyl)pyridin-2(1H)-one;
3-chloro-4-[(2,4-difluorobenzyl)oxy]-1-(2,6-difluorophenyl)-6-(hydroxymethyl)pyridin-2(1H)-one;
5-bromo-4-[(2,4-difluorobenzyl)oxy]-1-(2,6-difluorophenyl)-6-oxo-1,6-dihydropyridine-2-carbaldehyde;
3-bromo-4-[(2,4-difluorobenzyl)oxy]-1-(2,6-difluorophenyl)-6-[(dimethylamino)methyl]pyridin-2(1H)-one;
3-bromo-4-[(2,4-difluorobenzyl)oxy]-1-(2,6-difluorophenyl)-6-(morpholin-4-ylmethyl)pyridin-2(1H)-one;
3-bromo-4-[(2,4-difluorobenzyl)oxy]-1-(2,6-difluorophenyl)-6-{[(2-methoxyethyl)amino]methyl}pyridin-2(1H)-one;
5-bromo-4-[(2,4-difluorobenzyl)oxy]-1-(2,6-difluorophenyl)-6-oxo-1,6-dihydropyridine-2-carboxylic acid;
Methyl 4-[3-bromo-4-[(2,4-difluorobenzyl)oxy]-6-methyl-2-oxopyridin-1(2H)-yl]-3-methylbenzoate;
4-(4-(2,4-difluorobenzyloxy)-3-bromo-6-methyl-2-oxopyridin-1(2H)-yl)-3-methylbenzoic acid;
4-(2,4-difluorobenzyloxy)-3-bromo-1-(4-(hydroxymethyl)-2-methylphenyl)-6-methylpyridin-2(1H)-one;
4-(4-(2,4-difluorobenzyloxy)-3-bromo-6-methyl-2-oxopyridin-1(2H)-yl)-N-(2-methoxyethyl)-3-methylbenzamide;
4-(4-(2,4-difluorobenzyloxy)-3-bromo-6-methyl-2-oxopyridin-1(2H)-yl)-N,3-dimethylbenzamide;
3-bromo-4-[(2,4-difluorobenzyl)oxy]-6-methyl-1-(2-methyl-4-vinylphenyl)pyridin-2(1H)-one;
3-bromo-4-[(2,4-difluorobenzyl)oxy]-1-[4-(1,2-dihydroxyethyl)-2-methylphenyl]-6-methylpyridin-2(1H)-one;
methyl 3-[3-bromo-4-[(2,4-difluorobenzyl)oxy]-6-methyl-2-oxopyridin-1(2H)-yl]-4-chlorobenzoate;
3-[3-bromo-4-[(2,4-difluorobenzyl)oxy]-6-methyl-2-oxopyridin-1(2H)-yl]-4-chlorobenzoic acid;
3-bromo-4-[(2,4-difluorobenzyl)oxy]-1-[5-(hydroxymethyl)-2-methylphenyl]-6-methylpyridin-2(1H)-one;
3-chloro-4-[(2,4-difluorobenzyl)oxy]-1-[5-(hydroxymethyl)-2-methylphenyl]-6-methylpyridin-2(1H)-one;
3-bromo-4-[(2,4-difluorobenzyl)oxy]-1-{5-[(dimethylamino)methyl]-2-methylphenyl}-6-methylpyridin-2(1H)-one hydrochloride;
3-bromo-4-[(2,4-difluorobenzyl)oxy]-1-{5-[(isopropylamino)methyl]-2-methylphenyl}-6-methylpyridin-2(1H)-one hydrochloride;
3-[3-bromo-4-[(2,4-difluorobenzyl)oxy]-6-methyl-2-oxopyridin-1(2H)-yl]-N-(2-hydroxyethyl)-4-methylbenzamide;
3-(4-(2,4-difluorobenzyloxy)-3-bromo-6-methyl-2-oxopyridin-1(2H)-yl)-N-(2-methoxyethyl)-4-methylbenzamide;
3-(4-(2,4-difluorobenzyloxy)-3-bromo-6-methyl-2-oxopyridin-1(2H)-yl)-N,4-dimethylbenzamide;
3-(4-(2,4-difluorobenzyloxy)-3-bromo-6-methyl-2-oxopyridin-1(2H)-yl)-N,N,4-trimethylbenzamide;

3-bromo-4-[(2,4-difluorobenzyl)oxy]-1-[5-(1-hydroxy-1-methylethyl)-2-methylphenyl]-6-methylpyridin-2(1H)-one;
methyl 3-[3-chloro-4-[(2,4-difluorobenzyl)oxy]-6-methyl-2-oxopyridin-1(2H)-yl]-4-methylbenzoate;
methyl 4-[3-bromo-4-[(2,4-difluorobenzyl)oxy]-6-methyl-2-oxopyridin-1(2H)-yl]-3-chlorobenzoate;
3-bromo-4-[(2,4-difluorobenzyl)amino]-6-methyl-1-(pyridin-4-ylmethyl)pyridin-2(1H)-one;
3-bromo-4-[(2,4-difluorobenzyl)amino]-6-methyl-1-(pyridin-3-ylmethyl)pyridin-2(1H)-one;
3-bromo-4-[(2,4-difluorobenzyl)amino]-1-(2,6-difluorophenyl)-6-methylpyridin-2(1H)-one;
3-chloro-4-[(2,4-difluorobenzyl)amino]-1-(2,6-difluorophenyl)-6-methylpyridin-2(1H)-one;
3-{[3-chloro-4-[(2,4-difluorobenzyl)amino]-6-methyl-2-oxopyridin-1(2H)-yl]methyl}benzonitrile;
4-{[3-chloro-4-[(2,4-difluorobenzyl)amino]-6-methyl-2-oxopyridin-1(2H)-yl]methyl}benzonitrile;
3-bromo-4-[(2,4-difluorobenzyl)oxy]-1-[2-fluoro-5-(hydroxymethyl)phenyl]-6-methylpyridin-2(1H)-one;
3-[3-chloro-4-[(2,4-difluorobenzyl)oxy]-6-methyl-2-oxopyridin-1(2H)-yl]-4-fluorobenzoic acid;
3-[3-chloro-4-[(2,4-difluorobenzyl)oxy]-6-methyl-2-oxopyridin-1(2H)-yl]-4-fluoro-N-methylbenzamide;
3-(4-(2,4-difluorobenzyloxy)-3-chloro-6-methyl-2-oxopyridin-1(2H)-yl)-4-fluoro-N,N-dimethylbenzamide;
3-(4-(2,4-difluorobenzyloxy)-3-chloro-6-methyl-2-oxopyridin-1(2H)-yl)-4-fluoro-N-(2-hydroxyethyl)benzamide;
3-(4-(2,4-difluorobenzyloxy)-3-chloro-6-methyl-2-oxopyridin-1(2H)-yl)-4-fluoro-N-(2-methoxyethyl)benzamide;
3-(4-(2,4-difluorobenzyloxy)-3-chloro-6-methyl-2-oxopyridin-1(2H)-yl)-4-fluoro-N-(2-hydroxyethyl)-N-methylbenzamide;
3-(4-(2,4-difluorobenzyloxy)-3-chloro-6-methyl-2-oxopyridin-1(2H)-yl)-4-fluoro-N-(3-hydroxypropyl)benzamide;
3-(4-(2,4-difluorobenzyloxy)-3-chloro-6-methyl-2-oxopyridin-1(2H)-yl)-4-fluoro-N-(2,3-dihydroxypropyl)benzamide;
3-[3-bromo-4-[(2,4-difluorobenzyl)oxy]-6-methyl-2-oxopyridin-1(2H)-yl]-4-fluorobenzoic acid;
3-[3-bromo-4-[(2,4-difluorobenzyl)oxy]-6-methyl-2-oxopyridin-1(2H)-yl]-4-methoxybenzoic acid;
3-[3-bromo-4-[(2,4-difluorobenzyl)oxy]-6-methyl-2-oxopyridin-1(2H)-yl]-4-methoxy-N-methylbenzamide;
3-[3-bromo-4-[(2,4-difluorobenzyl)oxy]-6-methyl-2-oxopyridin-1(2H)-yl]-4-methoxy-N,N-dimethylbenzamide;
1-[(5-aminomethyl)-2-fluorophenyl]-3-chloro-4-[(2,4-difluorobenzyl)oxy]-6-methylpyridin-2(1H)-one hydrochloride;
3-[3-chloro-4-[(2,4-difluorobenzyl)oxy]-6-methyl-2-oxopyridin-1(2H)-yl]-4-fluoro-N-[2-hydroxy-1-(hydroxymethyl)ethyl]benzamide;
N-(3-(4-(2,4-difluorobenzyloxy)-3-chloro-6-methyl-2-oxopyridin-1(2H)-yl)-4-fluorobenzyl)acetamide;
N-(3-(4-(2,4-difluorobenzyloxy)-3-chloro-6-methyl-2-oxopyridin-1(2H)-yl)-4-fluorobenzyl)-2-methoxyacetamide;
N-(3-(4-(2,4-difluorobenzyloxy)-3-chloro-6-methyl-2-oxopyridin-1(2H)-yl)-4-fluorobenzyl)-methylsulfonamine;
1-(3-(4-(2,4-difluorobenzyloxy)-3-chloro-6-methyl-2-oxopyridin-1(2H)-yl)-4-fluorobenzyl)urea;
2-({[3-chloro-1-(2,6-difluorophenyl)-6-methyl-2-oxo-1,2-dihydropyridin-4-yl]oxy}methyl)-5-fluorobenzonitrile;

4-{[2-(aminomethyl)-4-fluorobenzyl]oxy}-3-chloro-1-(2,6-difluorophenyl)-6-methylpyridin-2(1H)-one trifluoroacetate;

methyl 2-((3-chloro-1-(2,6-difluorophenyl)-1,2-dihydro-6-methyl-2-oxopyridin-4-yloxy)methyl)-5-fluorobenzylcarbamate;

N-(2-((3-chloro-1-(2,6-difluorophenyl)-1,2-dihydro-6-methyl-2-oxopyridin-4-yloxy)methyl)-5-fluorobenzyl)-2,2,2-trifluoroacetamide;

isopropyl 2-((3-chloro-1-(2,6-difluorophenyl)-1,2-dihydro-6-methyl-2-oxopyridin-4-yloxy)methyl)-5-fluorobenzylcarbamate;

1-(2-((3-chloro-1-(2,6-difluorophenyl)-1,2-dihydro-6-methyl-2-oxopyridin-4-yloxy)methyl)-5-fluorobenzyl)-3-ethylurea;

tetrahydrofuran-3-yl 2-((3-chloro-1-(2,6-difluorophenyl)-1,2-dihydro-6-methyl-2-oxopyridin-4-yloxy)methyl)-5-fluorobenzylcarbamate;

propyl 2-((3-chloro-1-(2,6-difluorophenyl)-1,2-dihydro-6-methyl-2-oxopyridin-4-yloxy)methyl)-5-fluorobenzylcarbamate;

allyl 2-((3-chloro-1-(2,6-difluorophenyl)-1,2-dihydro-6-methyl-2-oxopyridin-4-yloxy)methyl)-5-fluorobenzylcarbamate;

prop-2-ynyl 2-((3-chloro-1-(2,6-difluorophenyl)-1,2-dihydro-6-methyl-2-oxopyridin-4-yloxy)methyl)-5-fluorobenzylcarbamate;

or pharmaceutically acceptable salts thereof.

40. A compound of claim 1 which is t-butyl 2-((3-chloro-1-(2,6-difluorophenyl)-1,2-dihydro-6-methyl-2-oxopyridin-4-yloxy)methyl)-5-fluorobenzylcarbamate;

1-(2-((3-chloro-1-(2,6-difluorophenyl)-1,2-dihydro-6-methyl-2-oxopyridin-4-yloxy)methyl)-5-fluorobenzyl)-3-tert-butylurea;

N-(2-((3-chloro-1-(2,6-difluorophenyl)-1,2-dihydro-6-methyl-2-oxopyridin-4-yloxy)methyl)-5-fluorobenzyl)-2-(propylsulfonyl)acetamide;

N-(2-((3-chloro-1-(2,6-difluorophenyl)-1,2-dihydro-6-methyl-2-oxopyridin-4-yloxy)methyl)-5-fluorobenzyl)-2-(ethylsulfonyl)acetamide;

1-(2-((3-chloro-1-(2,6-difluorophenyl)-1,2-dihydro-6-methyl-2-oxopyridin-4-yloxy)methyl)-5-fluorobenzyl)-3-isopropylurea 1-(2-((3-chloro-1-(2,6-difluorophenyl)-1,2-dihydro-6-methyl-2-oxopyridin-4-yloxy)methyl)-5-fluorobenzyl)-3-methylurea;

3-(2-((3-chloro-1-(2,6-difluorophenyl)-1,2-dihydro-6-methyl-2-oxopyridin-4-yloxy)methyl)-5-fluorobenzyl)-1-tert-butyl-1-methylurea;

1-(2-((3-chloro-1-(2,6-difluorophenyl)-1,2-dihydro-6-methyl-2-oxopyridin-4-yloxy)methyl)-5-fluorobenzyl)-3-cyclopropylurea;

1-(2-((3-chloro-1-(2,6-difluorophenyl)-1,2-dihydro-6-methyl-2-oxopyridin-4-yloxy)methyl)-5-fluorobenzyl)-3-(2,2,2-trifluoroethyl)urea;

1-(2-((3-chloro-1-(2,6-difluorophenyl)-1,2-dihydro-6-methyl-2-oxopyridin-4-yloxy)methyl)-5-fluorobenzyl)-3-(cyclopropylmethyl)urea;

1-(2-((3-chloro-1-(2,6-difluorophenyl)-1,2-dihydro-6-methyl-2-oxopyridin-4-yloxy)methyl)-5-fluorobenzyl)-3-neopentylurea;

3-(2-((3-chloro-1-(2,6-difluorophenyl)-1,2-dihydro-6-methyl-2-oxopyridin-4-yloxy)methyl)-5-fluorobenzyl)-1,1-dimethylurea;

3-bromo-4-[(2,4-difluorobenzyl)oxy]-1-{[5-(1-hydroxy-1-methylethyl)pyridin-2-yl]methyl}-6-methylpyridin-2(1H)-one;

3-bromo-4-[(2,4-difluorobenzyl)oxy]-1-{[5-(hydroxymethyl)pyridin-2-yl]methyl}-6-methylpyridin-2(11H)-one;

6-{[3-bromo-4-[(2,4-difluorobenzyl)oxy]-6-methyl-2-oxopyridin-1(2H)-yl]methyl}-N-(2-hydroxyethyl)-N-methylnicotinamide;

6-{[3-bromo-4-[(2,4-difluorobenzyl)oxy]-6-methyl-2-oxopyridin-1(2H)-yl]methyl}-N-(2-hydroxyethyl)nicotinamide;

6-{[3-bromo-4-[(2,4-difluorobenzyl)oxy]-6-methyl-2-oxopyridin-1(2H)-yl]methyl}-N,N-dimethylnicotinamide;

3-bromo-4-[(2,4-difluorobenzyl)oxy]-6-methyl-1-[2-(trifluoromethyl)phenyl]pyridin-2(1H)-one;

3-bromo-4-[(2,4-difluorobenzyl)oxy]-1-(2,6-difluorophenyl)-6-methyl-5-vinylpyridin-2(11H)-one;

3-bromo-4-[(2,4-difluorobenzyl)oxy]-1-(2,6-difluorophenyl)-5-(1,2-dihydroxyethyl)-6-methylpyridin-2(11H)-one;

3-bromo-4-[(2,4-difluorobenzyl)oxy]-1-(2,6-difluorophenyl)-5-(hydroxymethyl)-6-methylpyridin-2(11H)-one;

4-(benzyloxy)-3-bromo-1-(2,6-difluorophenyl)-6-methylpyridin-2(1H)-one;

5-bromo-4-[(2,4-difluorobenzyl)oxy]-1-(2,6-difluorophenyl)-2-methyl-6-oxo-1,6-dihydropyridin-3-yl]methyl carbamate;

5-bromo-4-[(2,4-difluorobenzyl)oxy]-1-(2,6-difluorophenyl)-2-methyl-6-oxo-1,6-dihydropyridine-3-carbaldehyde;

5-bromo-4-[(2,4-difluorobenzyl)oxy]-1-(2,6-difluorophenyl)-2-methyl-6-oxo-1,6-dihydropyridine-3-carbaldehyde oxime;

5-bromo-4-[(2,4-difluorobenzyl)oxy]-1-(2,6-difluorophenyl)-2-methyl-6-oxo-1,6-dihydropyridine-3-carbonitrile;

4-(benzyloxy)-3-bromo-1-(2,6-difluorophenyl)-5-iodo-6-methylpyridin-2(1H)-one;

3-bromo-4-[(2,4-difluorobenzyloxy]-1-(2,6-difluorophenyl)-6-methyl-5-oxiran-2-ylpyridin-2(1H)-one;

4-(benzylamino)-3-bromo-1-(2,6-difluorophenyl)-5-iodo-6-methylpyridin-2(1H)-one;

3-bromo-4-[(2,4-difluorobenzyl)oxy]-1-(2,6-difluorophenyl)-6-methyl-5-[(E)-2-phenylethenyl]pyridin-2(11H)-one;

ethyl 3-bromo-4-[(2,4-difluorobenzyl)oxy]-6-methyl-2-oxo-2H-1,2'-bipyridine-5'-carboxylate;

3-bromo-4-[(2,4-difluorobenzyl)oxy]-5'-(1-hydroxy-1-methylethyl)-6-methyl-2H-1,2-bipyridin-2-one;

3-bromo-4-[(2,4-difluorobenzyl)oxy]-1-(2-furylmethyl)-6-methylpyridin-2(1H)-one;

3-bromo-4-[(2,4-difluorobenzyl)oxy]-6-methyl-1-(thien-2-ylmethy)pyridin-2(1H)-one;

3-bromo-1-(2,6-difluorophenyl)-4-(2-furylmethoxy)-6-methylpyridin-2(1H)-one;

3-bromo-1-[2-fluoro-6-(3-furylmethoxy)phenyl]-4-(3-furylmethoxy)-6-methylpyridin-2(1H)-one;

3-bromo-1-[2-fluoro-6-(thien-3-ylmethoxy)phenyl]-6-methyl-4-(thien-3-ylmethoxy)pyridin-2(1H)-one;

methyl 2-[3-bromo-4-[(2,4-difluorobenzyl)oxy]-6-methyl-2-oxopyridin-1(2H)-yl]-4-[(methylamino)carbonyl]benzoate;

3-[3-bromo-4-[(2,4-difluorobenzyl)oxy]-6-methyl-2-oxopyridin-1(2H)-yl]-4-(1-hydroxy-1-methylethyl)-N-methylbenzamide;

4-[3-bromo-4-[(2,4-difluorobenzyl)oxy]-6-methyl-2-oxopyridin-1(2H)-yl]-3-chlorobenzamide;

3-[3-chloro-4-[(2,4-difluorobenzyl)oxy]-6-methyl-2-oxopyridin-1(2H)-yl]-4-methylbenzamide;
3-[3-chloro-4-[(2,4-difluorobenzyloxy]-6-methyl-2-oxopyridin-1(2H)-yl]-N,4-dimethylbenzamide;
N-{3-[3-chloro-4-[(2,4-difluorobenzyl)oxy]-6-methyl-2-oxopyridin-1(2H)-yl]-4-fluorobenzyl}propanamide;
N-{3-[3-chloro-4-[(2,4-difluorobenzyl)oxy]-6-methyl-2-oxopyridin-1(2H)-yl]-4-fluorobenzyl}dimethylurea;
N-{3-[3-chloro-4-[(2,4-difluorobenzyl)oxy]-6-methyl-2-oxopyridin-1(2H)-yl]-4-fluorobenzyl}-2-hydroxyacetamide;
N-{3-[3-chloro-4-[(2,4-difluorobenzyl)oxy]-6-methyl-2-oxopyridin-1(2H)-yl]-4-fluorobenzyl}-2-hydroxy-2-methylpropanamide;
N-{3-[3-chloro-4-[(2,4-difluorobenzy)oxy]-6-methyl-2-oxopyridin-1(2H)-yl]-4-fluorobenzyl}glycinamide hydrochloride;
3-[3-bromo-4-[(2,4-difluorobenzyl)oxy]-6-methyl-2-oxopyridin-1(2H)-yl]-4-fluorobenzamide;
3-[3-bromo-4-[(2,4-difluorobenzyl)oxy]-6-methyl-2-oxopyridin-1(2H)-yl]-4-fluoro-N-methylbenzamide;
3-[3-bromo-4-[(2,4-difluorobenzyl)oxy]-6-methyl-2-oxopyridin-1(2H)-yl]-4-fluoro-N,N-dimethylbenzamide;
3-bromo-4-[(2,4-difluorobenzyl)oxy]-1-{2-fluoro-5-[(4-methylpiperazin-1-yl)carbonyl]phenyl}-6-methylpyridin-2(1H)-one;
3-(4-(2,4-difluorobenzyloxy)-3-bromo-6-methyl-2-oxopyridin-1(2H)-yl)-4-fluoro-N-(2-hydroxyethyl)-N-methylbenzamide;
3-(4-(2,4-difluorobenzyloxy)-3-bromo-6-methyl-2-oxopyridin-1(2H)-yl)-4-fluoro-N-(2-hydroxy-2-methylpropyl)benzamide;
methyl 4-[3-bromo-4-[(2,4-difluorobenzyl)oxy]-6-methyl-2-oxopyridin-1(2H)-yl]-3-fluorobenzoate;
4-{[3-chloro-4-[(2,4-difluorobenzyl)oxy]-6-methyl-2-oxopyridin-1(2H)-yl]methyl}benzoic acid;
4-{[3-chloro-4-[(2,4-difluorobenzyl)oxy]-6-methyl-2-oxopyridin-1(2H)-yl]methyl}benzamide;
4-{[3-chloro-4-[(2,4-difluorobenzyl)oxy]-6-methyl-2-oxopyridin-1(2H)-yl]methyl}-N,N-dimethylbenzamide;
4-{[3-chloro-4-[(2,4-difluorobenzyl)oxy]-6-methyl-2-oxopyridin-1(2H)-yl]methyl}-N-(2-hydroxy-2-methylpropyl)benzamide;
N-{4-[3-bromo-4-[(2,4-difluorobenzyl)oxy]-6-methyl-2-oxopyridin-1(2H)-yl]benzyl}-2-hydroxyacetamide;
3-[3-chloro-4-[(2,4-difluorobenzyl)oxy]-6-methyl-2-oxopyridin-1(2H)-yl]benzamide;
1-(4-aminobenzyl)-3-bromo-4-[(2,4-difluorobenzyl)oxy]-6-methylpyridin-2(1H)-one;
1-(3-aminobenzyl)-3-bromo-4-[(2,4-difluorobenzyl)oxy]-6-methylpyridin-2(1H)-one;
N-(4-{[3-bromo-4-[(2,4-difluorobenzyl)oxy]-6-methyl-2-oxopyridin-1(2H)-yl]methyl}phenyl)acetamide;
N-(4-((4-(2,4-difluorobenzyloxy)-3-bromo-6-methyl-2-oxopyridin-1(2H)-yl)methyl)phenyl)-2-hydroxyacetamide;
N-(4-((4-(2,4-difluorobenzyloxy)-3-bromo-6-methyl-2-oxopyridin-1(2H)-yl)methyl)phenyl)-(dimethylaminosulfonylcarbonyl)amine;
N-(3-{[3-bromo-4-[(2,4-difluorobenzyl)oxy]-6-methyl-2-oxopyridin-1(2H)-yl]methyl}phenyl)acetamide;
N-(3-((4-(2,4-difluorobenzyloxy)-3-bromo-6-methyl-2-oxopyridin-1(2H)-yl)methyl)phenyl)-(dimethylaminosulfonylcarbonyl)amine;
N-(3-((4-(2,4-difluorobenzyloxy)-3-bromo-6-methyl-2-oxopyridin-1(2H)-yl)methyl)phenyl)-2-hydroxyacetamide;
N-(4-{[3-bromo-4-[(2,4-difluorobenzyl)oxy]-6-methyl-2-oxopyridin-1(2H)-yl]methyl}benzyl)-N'-methylurea;
N-(4-{[3-bromo-4-[(2,4-difluorobenzyl)oxy]-6-methyl-2-oxopyridin-1(2H)-yl]methyl}benzyl)-N'-(2-hydroxy-2-methylpropyl)urea;
N-(4-{[3-bromo-4-[(2,4-difluorobenzyl)oxy]-6-methyl-2-oxopyridin-1(2H)-yl]methyl}benzyl)piperidine-1-carboxamide;
N-(4-{[3-bromo-4-[(2,4-difluorobenzyl)oxy]-6-methyl-2-oxopyridin-1(2H)-yl]methyl}benzyl)morpholine-4-carboxamide;
N-(4-{[3-bromo-4-[(2,4-difluorobenzyl)oxy]-6-methyl-2-oxopyridin-1(2H)-yl]methyl}benzyl)piperazine-1-carboxamide hydrochloride;
N-(4-{[3-bromo-4-[(2,4-difluorobenzyl)oxy]-6-methyl-2-oxopyridin-1(2H)-yl]methyl}benzyl)-N'-(2-hydroxyethyl)urea;
N'-(4-{[3-bromo-4-[(2,4-difluorobenzyl)oxy]-6-methyl-2-oxopyridin-1(2H)-yl]methyl}benzyl)-N,N-dimethylurea;
N-(4-{[3-bromo-4-[(2,4-difluorobenzyl)oxy]-6-methyl-2-oxopyridin-1(2H)-yl]methyl}benzyl)-4-hydroxypiperidine-1-carboxamide;
4-{[3-bromo-4-[(2,4-difluorobenzyl)oxy]-6-methyl-2-oxopyridin-1(2H)-yl]methyl}-N,N-dimethylbenzenesulfonamide;
4-{[3-bromo-4-[(2,4-difluorobenzyl)oxy]-6-methyl-2-oxopyridin-1(2H)-yl]methyl}-N-(2-hydroxyethyl)benzenesulfonamide;
4-{[3-bromo-4-[(2,4-difluorobenzyl)oxy]-6-methyl-2-oxopyridin-1(2H)-yl]methyl}-N-(2-hydroxy-2-methylpropyl)benzenesulfonamide;
3-Chloro-4-(2,4-difluorobenzyloxy)-6-methyl-1-(1H-pyrazol-3-ylmethyl)-1H-pyridin-2-one;
3-Chloro-4-(2,4-difluorobenzyloxy)-6-methyl-1-(2,3-dihydro-1H-indol-5-ylmethyl)-1H-pyridin-2-one;
5-[3-Chloro-4-(2,4-difluorobenzyloxy)-6-methyl-2-oxo-2H-pyridin-1-ylmethyl]-1,3-dihydro-indol-2-one;
N-[(5-{[3-Bromo-4-[(2,4-difluorobenzyl)oxy]-6-methyl-2-oxopyridin-1(2H)-yl]methyl}pyrazin-2-yl)methyl]-N-methylmethanesulfonamide;
Methyl (5-{[3-Bromo-4-[(2,4-difluorobenzyl)oxy]-6-methyl-2-oxopyridin-1(2H)-yl]methyl}pyrazin-2-yl)methyl(methyl)carbamate;
N-[(5-{[3-Bromo-4-[(2,4-difluorobenzyl)oxy]-6-methyl-2-oxopyridin-1(2H)-yl]methyl}pyrazin-2-yl)methyl]-2-hydroxy-N,2-dimethylpropanamide;
5-{[3-Bromo-4-[(2,4-difluorobenzyhoxy]-6-methyl-2-oxopyridin-1(2H)-yl]methyl}-N-(2-hydroxy-2-methylpropyl)pyrazine-2-carboxamide;
1-[(5-Aminopyrazin-2-yl)methyl]-3-bromo-4-[(2,4-difluorobenzyl)oxy]-6-methylpyridin-2(1H)-one trifluoroacetate;
3-Bromo-4-[(2,4-difluorobenzyl)oxy]-6-methyl-1-[(3-methyl-1,2,4-triazin-6-yl)methyl]pyridin-2(1H)-one trifluoroacetate;
3-Bromo-4-[(2,4-difluorobenzyl)oxy]-1-(1H-indazol-5-yl)-6-methylpyridin-2(1H)-one;
3-bromo-4-[(2,4-difluorobenzyl)oxy]-1-(1H-indazol-6-yl)-6-methylpyridin-2(1H)-one;
methyl 2-{[(3-bromo-6-methyl-1-{2-methyl-5-[(methylamino)carbonyl]phenyl}-2-oxo-1,2-dihydropyridin-4-yl)oxy]methyl}-5-fluorobenzylcarbamate;
methyl 2-({[3-bromo-1-(5-{[(2-hydroxyethyl)amino]carbonyl}-2-methylphenyl)-6-methyl-2-oxo-1,2-dihydropyridin-4-yl]oxy}methyl)-5-fluorobenzylcarbamate;

methyl 2-({[3-bromo-1-(5-{[(2-hydroxy-2-methylpropyl)amino]carbonyl}-2-methylphenyl)-6-methyl-2-oxo-1,2-dihydropyridin-4-yl]oxy}methyl)-5-fluorobenzylcarbamate;
methyl 2-({[3-bromo-1-(5-{[(2-methoxyethyl)amino]carbonyl}-2-methylphenyl)-6-methyl-2-oxo-1,2-dihydropyridin-4-yl]oxy}methyl)-5-fluorobenzylcarbamate;
methyl 2-[({1-[5-(aminocarbonyl)-2-methylphenyl]-3-bromo-6-methyl-2-oxo-1,2-dihydropyridin-4-yl}oxy)methyl]-5-fluorobenzylcarbamate;
N-[2-({[3-chloro-1-(2,6-difluorophenyl)-6-methyl-2-oxo-1,2-dihydropyridin-4-yl]oxy}methyl)-5-fluorobenzyl]-N'-phenylurea;
thien-3-ylmethyl 2-({[3-chloro-1-(2,6-difluorophenyl)-6-methyl-2-oxo-1,2-dihydropyridin-4-yl]oxy}methyl)-5-fluorobenzylcarbamate;
ethyl 2-{[(3-bromo-6-methyl-1-{2-methyl-5-[(methylamino)carbonyl]phenyl}-2-oxo-1,2-dihydropyridin-4-yl)oxy]methyl}-5-fluorobenzylcarbamate;
3-[3-bromo-4-{[2-({[(cyclopropylamino)carbonyl]amino}methyl)-4-fluorobenzyl]oxy}-6-methyl-2-oxopyridin-1(2H)-yl]-N,4-dimethylbenzamide;
3-[3-bromo-4-{[2-({[(cyclopropylamino)carbonyl]amino}methyl)-4-fluorobenzyl]oxy}-6-methyl-2-oxopyridin-1(2H)-yl]-4-methylbenzoic acid;
methyl 3-[6-[(acetyloxy)methyl]-3-bromo-4-[(2,4-difluorobenzyl)oxy]-2-oxopyridin-1(2H)-yl]-4-methylbenzoate;
3-[3-bromo-4-[(2,4-difluorobenzyl)oxy]-6-(hydroxymethyl)-2-oxopyridin-1(2H)-yl]-4-methylbenzoic acid;
3-[3-bromo-4-[(2,4-difluorobenzyl)oxy]-6-(hydroxymethyl)-2-oxopyridin-1(2H)-yl]-4-methylbenzoic acid;
3-[3-bromo-4-[(2,4-difluorobenzyl)oxy]-6-(hydroxymethyl)-2-oxopyridin-1(2H)-yl]-N-(2-hydroxyethyl)-4-methylbenzamide;
3-[3-bromo-4-[(2,4-difluorobenzyl)oxy]-6-(hydroxymethyl)-2-oxopyridin-1(2H)-yl]-N,4-dimethylbenzamide;
3-[3-bromo-4-[(2,4-difluorobenzyl)oxy]-6-(hydroxymethyl)-2-oxopyridin-1(2H)-yl]-4-methylbenzamide;
(5-bromo-4-[(2,4-difluorobenzyl)oxy]-1-{2-methyl-5-[(methylamino)carbonyl]phenyl}-6-oxo-1,6-dihydropyridin-2-yl)methyl acetate;
(2E)-4-[3-bromo-4-[(2,4-difluorobenzyl)oxy]-6-methyl-2-oxopyridin-1(2H)-yl]-N-methylbut-2-enamide;
methyl 5-{[3-bromo-4-[(2,4-difluorobenzyl)oxy]-6-methyl-2-oxopyridin-1(2H)-yl]methyl}-2-furoate;
3-[3-bromo-4-[(2,4-difluorobenzyl)oxy]-6-methyl-2-oxopyridin-1(2H)-yl]-4-(hydroxymethyl)-N-methylbenzamide;
2-[3-bromo-4-[(2,4-difluorobenzyl)oxy]-6-methyl-2-oxopyridin-1(2H)-yl]-N,N'-dimethylterephthalamide;
2-[3-bromo-4-[(2,4-difluorobenzyl)oxy]-6-methyl-2-oxopyridin-1(2H)-yl]-N-(4-methylterephthalamide;
methyl 4-(aminocarbonyl)-2-[3-bromo-4-[(2,4-difluorobenzyl)oxy]-6-methyl-2-oxopyridin-1(2H)-yl]benzoate;
2-[3-bromo-4-[(2,4-difluorobenzyl)oxy]-6-methyl-2-oxopyridin-1(2H)-yl]-N1,N1,N4-trimethylterephthalamide;
2-[3-bromo-4-[(2,4-difluorobenzyl)oxy]-6-methyl-2-oxopyridin-1(2H)-yl]-4-[(methylamino)carbonyl]benzyl carbamate;
3-bromo-4-[(2,4-difluorobenzyl)oxy]-1-(2,6-difluoro-4-vinylphenyl)-6-methylpyridin-2(1H)-one;
3-bromo-4-[(2,4-difluorobenzyl)oxy]-1-[4-(1,2-dihydroxyethyl)-2,6-difluorophenyl]-6-methylpyridin-2(1H)-one;
4-[3-bromo-4-[(2,4-difluorobenzyl)oxy]-6-methyl-2-oxopyridin-1(2H)-yl]-3,5-difluorobenzaldehyde;
4-[3-bromo-4-[(2,4-difluorobenzyl)oxy]-6-methyl-2-oxopyridin-1(2H)-yl]-3,5-difluorobenzyl carbamate;
4-(2,4-difluorobenzyloxy)-3-chloro-6-methyl-1-((5-methylpyrazin-2-yl)methyl)pyridin-2(1H)-one;
4-(2,4-difluorobenzyloxy)-3-chloro-1-((5-(hydroxymethyl)pyrazin-2-yl)methyl)-6-methylpyridin-2(1H)-one;
4-(2,4-difluorobenzyloxy)-3-bromo-1-((1-(2-hydroxyacetyl)indolin-5-yl)methyl)-6-methylpyridin-2(1H)-one;
1-((1H-pyrazol-3-yl)methyl)-4-(2,4-difluorobenzyloxy)-3-bromo-6-methylpyridin-2(1H)-one;
3-(4-(2,4-difluorobenzyloxy)-3-chloro-6-methyl-2-oxopyridin-1(2H)-yl)-N,4-dimethylbenzamide;
3-(4-(2,4-difluorobenzyloxy)-3-chloro-6-methyl-2-oxopyridin-1(2H)-yl)-4-methylbenzamide;
3-(4-(2,4-difluorobenzyloxy)-3-chloro-6-methyl-2-oxopyridin-1(2H)-yl)-4-fluoro-N-methylbenzamide;
3-(4-(2,4-difluorobenzyloxy)-3-chloro-6-methyl-2-oxopyridin-1(2H)-yl)-4-chloro-N-methylbenzamide;
3-(4-(2,4-difluorobenzyloxy)-3-chloro-6-methyl-2-oxopyridin-1(2H)-yl)-4-fluorobenzamide;
3-(4-(2,4-difluorobenzyloxy)-3-chloro-6-methyl-2-oxopyridin-1(2H)-yl)-N,3-dimethylbenzamide;
4-(2,4-difluorobenzyloxy)-3-chloro-1-(4-(1,2-dihydroxyethyl)-2-methylphenyl)-6-methylpyridin-2(11H)-one;
N-(4-((4-(2,4-difluorobenzyloxy)-3-chloro-6-methyl-2-oxopyridin-1(2H)-yl)methyl)phenyl)-2-hydroxyacetamide;
N-(4-((4-(2,4-difluorobenzyloxy)-3-chloro-6-methyl-2-oxopyridin-1(2H)-yl)methyl)benzyl)-1-hydroxycyclopropanecarboxamide;
N-(4-((4-(2,4-difluorobenzyloxy)-3-chloro-6-methyl-2-oxopyridin-1(2H)-yl)methyl)benzyl)-2-hydroxyacetamide;
N-(4-((4-(2,4-difluorobenzyloxy)-3-chloro-6-methyl-2-oxopyridin-1(2H))-ylmethyl)phenyl)acetamide;
ethyl 2-((3-bromo-1-(2,6-difluorophenyl-1,2-dihydro-6-methyl-2-oxopyridin-4-yloxy)methyl)-5-fluorobenzylcarbamate;
3-(4-(2,4-difluorobenzyloxy)-3-bromo-6-(2-hydroxyethyl)-2-oxopyridin-1(2H)-yl)-N,4-dimethylbenzamide;
4-(2,4-difluorobenzyloxy)-3-bromo-1-(5-(2-hydroxyethyl)-2-methylphenyl)-6-methylpyridin-2(1H)-one;
5-(4-(2,4-difluorobenzyloxy)-3-bromo-6-methyl-2-oxopyridin-1(2H)-yl)-2-(2-hydroxyethyl)-N,4-dimethylbenzamide;
4-(2,4-difluorobenzyloxy)-3-bromo-6-methyl-1-(4-methyl-2-(methylsulfonyl)pyrimidin-5-yl)-pyridin-2(1H)-one;
5-(4-(2,4-difluorobenzyloxy)-3-bromo-6-methyl-2-oxopyridin-1(2H)-yl)-4-methylpyrimidine-2-carbonitrile;
4-(2,4-difluorobenzyloxy)-1-(2-(aminomethyl)-4-methylpyrimidin-5-yl)-3-bromo-6-methylpyridin-2(1H)-one;
4-(2,4-difluorobenzyloxy)-3-bromo-1-(2-((dimethylamino)methyl)-4-methylpyrimidin-5-yl)-6-methylpyridin-2(1H)-one;
N-((5-(4-(2,4-difluorobenzyloxy)-3-bromo-6-methyl-2-oxopyridin-1(2H)-yl)-4-methylpyrimidin-2-yl)methyl)-2-hydroxyacetamide;
5-(4-(2,4-difluorobenzyloxy)-3-bromo-6-methyl-2-oxopyridin-1(2H)-yl)-4-methylpyrimidine-2-carboxylic acid;
5-(4-(2,4-difluorobenzyloxy)-3-bromo-6-methyl-2-oxopyridin-1(2H)-yl)-4-methylpyrimidine-2-carboxamide;
5-(4-(2,4-difluorobenzyloxy)-3-bromo-6-methyl-2-oxopyridin-1(2H)-yl)-N,4-dimethylpyrimidine-2-carboxamide;
N-(4-{[3-chloro-4-[(2,4-difluorobenzyl)oxy]-6-methyl-2-oxopyridin-1(2H)-yl]methyl}benzyl)-2-hydroxyacetamide;

N-(4-{[3-chloro-4-[(2,4-difluorobenzyl)oxy]-6-methyl-2-oxopyridin-1(2H)-yl]methyl}benzyl)-1-hydroxycyclopropanecarboxamide;

4-{[3-bromo-4-[(2,4-difluorobenzyl)oxy]-6-methyl-2-oxopyridin-1(2H)-yl]methyl}benzyl carbamate;

2-[4-{[3-bromo-4-[(2,4-difluorobenzyl)oxy]-6-methyl-2-oxopyridin-1(2H)-yl]methyl}phenyl)amino]-1-methyl-2-oxoethyl acetate;

2-[4-{[3-bromo-4-[(2,4-difluorobenzyl)oxy]-6-methyl-2-oxopyridin-1(2H)-yl]methyl}phenyl)amino]-1,1-dimethyl-2-oxoethyl acetate;

{1-[3-(aminocarbonyl)phenyl]-5-chloro-4-[(2,4-difluorobenzyl)oxy]-6-oxo-1,6-dihydropyridin-2-yl}methyl acetate;

or pharmaceutically acceptable salts thereof.

43. A compound of claim 1 which is 3-bromo-4-[(2,4-difluorobenzyl)oxy]-6-methyl-1-{[2-(methylthio)pyrimidin-5-yl]methyl}pyridin-2(1H)-one;

3-bromo-4-[(2,4-difluorobenzyl)oxy]-6-methyl-1-{[2-(methylsulfonyl)pyrimidin-5-yl]methyl}pyridin-2(1H)-one;

Ethyl 2-({[3-bromo-1-(5-{[(2-hydroxyethyl)amino]carbonyl}-2-methylphenyl)-6-methyl-2-oxo-1,2-dihydropyridin-4-yl]oxy}methyl)-5-fluorobenzylcarbamate;

3-bromo-4-[(2,4-difluorobenzyl)oxy]-1-[5-(1H-imidazol-2-yl)-2-methylphenyl]-6-methylpyridin-2(1H)-one trifluoroacetate;

3-bromo-4-[(2,4-difluorobenzyl)oxy]-1-[5-(5-hydroxy-1H-pyrazol-3-yl)-2-methylphenyl]-6-methylpyridin-2(1H)-one;

3-bromo-4-[(2,4-difluorobenzyl)oxy]-1-[5-(5-hydroxylsoxazol-3-yl)-2-methylphenyl]-6-methylpyridin-2(1H)-one;

5-{[3-bromo-4-[(2,4-difluorobenzyl)oxy]-6-methyl-2-oxopyridin-1(2H)-yl]methyl}-2-furamide;

5-[3-bromo-4-[(2,4-difluorobenzyl)oxy]-6-methyl-2-oxopyridin-1(2H)-yl]-2-furamide;

1-[3,5-bis(hydroxymethyl)phenyl]-3-bromo-4-[(2,4-difluorobenzyloxy]-6-methylpyridin-2(1H)-one;

5-[3-bromo-4-[(2,4-difluorobenzyl)oxy]-6-methyl-2-oxopyridin-1(2H)-yl]isophthalamide;

1-[3,5-bis(1-hydroxy-1-methylethyl)phenyl]-3-bromo-4-[(2,4-difluorobenzyl)oxy]-6-methylpyridin-2(1H)-one;

3-bromo-4-[(2,4-difluorobenzyl)oxy]-1-[4-(hydroxymethyl)phenyl]-6-methylpyridin-2(1H)-one;

3-bromo-4-[(2,4-difluorobenzyl)oxy]-1-[4-(1-hydroxy-1-methylethyl)phenyl]-6-methylpyridin-2(1H)-one;

1-(5-amino-2-fluorophenyl)-3-bromo-4-[(2,4-difluorobenzyl)oxy]-6-methylpyridin-2(1H)-one hydrochloride;

N-{3-[3-bromo-4-[(2,4-difluorobenzyl)oxy]-6-methyl-2-oxopyridin-1(2H)-yl]-4-fluorophenyl}-2-hydroxyacetamide;

N-{3-[3-bromo-4-[(2,4-difluorobenzyl)oxy]-6-methyl-2-oxopyridin-1(2H)-yl]-4-fluorophenyl}-2-hydroxy-2-methylpropanamide;

4-[3-bromo-4-[(2,4-difluorobenzyl)oxy]-6-methyl-2-oxopyridin-1(2H)-yl]-3-fluoro-N,N-dimethylbenzamide;

3-chloro-4-[(2,4-difluorobenzyl)oxy]-1-[(1-glycoloyl-2,3-dihydro-1H-indol-5-yl)methyl]-6-methylpyridin-2(1H)-one;

3-chloro-4-[(2,4-difluorobenzyl)oxy]-1-{[1-(2-hydroxy-2-methylpropanoyl)-2,3-dihydro-1H-indol-5-yl]methyl}-6-methylpyridin-2(1H)-one;

3-chloro-4-[(2,4-difluorobenzyl)oxy]-1-{[1-(methoxyacetyl)-2,3-dihydro-1H-indol-5-yl]methyl}-6-methylpyridin-2(1H)-one;

5-{[3-chloro-4-[(2,4-difluorobenzyl)oxy]-6-methyl-2-oxopyridin-1(2H)-yl]methyl}-N,N-dimethylindoline-1-carboxamide; and 3-(3-bromo-4-((2,4-difluorobenzyl)oxy)-6-methyl-2-oxopyridin-1(2H)-yl)-N,4-dimethylbenzamide ("PH-797804"), Formula X'.

In one embodiment, the p38 kinase inhibitor is 3-(3-bromo-4-((2,4-difluorobenzyl)oxy)-6-methyl-2-oxopyridin-1(2H)-yl)-N,4-dimethylbenzamide ("PH-797804"), Formula X'.

Genus X Definitions

As used herein, the term "alkenyl" refers to a straight or branched hydrocarbon of a designed number of carbon atoms containing at least one carbon-carbon double bond. Examples of "alkenyl" include vinyl, allyl, and 2-methyl-3-heptene.

The term "alkoxy" represents an alkyl attached to the parent molecular moiety through an oxygen bridge. Examples of alkoxy groups include, for example, methoxy, ethoxy, propoxy and isopropoxy.

The term "thioalkoxy" represents an alkyl attached to the parent molecular moiety through a sulfur atom. Examples of thioalkoxy groups include, for example, thiomethoxy, thioethoxy, thiopropoxy and thioisopropoxy.

As used herein, the term "alkyl" includes those alkyl groups of a designed number of carbon atoms. Alkyl groups may be straight or branched. Examples of "alkyl" include methyl, ethyl, propyl, isopropyl, butyl, iso-, sec- and tert-butyl, pentyl, hexyl, heptyl, 3-ethylbutyl, and the like. "Cx-Cy alkyl" represents an alkyl group of the specified number of carbons. For example, C1-C4 alkyl includes all alkyl groups that include at least one and no more than four carbon atoms. It also contains subgroups, such as, for example, C2-C3 alkyl or C1-C3 alkyl.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene, indanyl, and biphenyl. Preferred examples of aryl groups include phenyl and naphthyl. The most preferred aryl group is phenyl. The aryl groups herein are unsubstituted or, as specified, substituted in one or more substitutable positions with various groups. Thus, such aryl groups can be optionally substituted with groups such as, for example, C1-C6 alkyl, C1-C6 alkoxy, halogen, hydroxy, cyano, nitro, amino, mono- or di-(C1-C6)alkylamino, C2-C6 alkenyl, C2-C6 alkynyl, C1-C6 haloalkyl, C1-C6 haloalkoxy, amino(C1-C6)alkyl, mono- or di(C1-C6)alkylamino(C1-C6)alkyl.

The term "arylalkyl" refers to an aryl group, as defined above, attached to the parent molecular moiety through an alkyl group, as defined above. Preferred arylalkyl groups include, benzyl, phenethyl, phenpropyl, and phenbutyl. More preferred arylalkyl groups include benzyl and phenethyl. The most preferred arylalkyl group is benzyl. The aryl portions of these groups are unsubstituted or, as specified, substituted in one or more substitutable positions with various groups. Thus, such aryl groups can be optionally substituted with groups such as, for example, C1-C6alkyl, C1-C6 alkoxy, halogen, hydroxy, cyano, nitro, amino, mono- or di-(C1-C6)alkylamino, C2-C6 alkenyl, C2-C6 alkynyl, C1-C6 haloalkyl, C1-C6 haloalkoxy, amino(C1-C6)alkyl, mono- or di(C1-C6)alkylamino(C1-C6)alkyl.

The term "arylalkoxyl" refers to an aryl group, as defined above, attached to the parent molecular moiety through an alkoxy group, as defined above. Preferred arylaloxy groups include, benzyloxy, phenethyloxy, phenpropyloxy, and phenbutyloxy. The most preferred arylalkoxy group is benzyloxy.

The term "cycloalkyl" refers to a C3-C8 cyclic hydrocarbon. Examples of cycloalkyl include cyclopropyl, cyclobutyl, cyclopentyl, cyclohexyl, cycloheptyl and cyclooctyl. More preferred cycloalkyl groups include cyclopropyl.

The term "cycloalkylalkyl," as used herein, refers to a C3-C8 cycloalkyl group attached to the parent molecular moiety through an alkyl group, as defined above. Examples of cycloalkylalkyl groups include cyclopropylmethyl and cyclopentylethyl.

The terms "halogen" or "halo" indicate fluorine, chlorine, bromine, or iodine.

The term "heterocycloalkyl," refers to a non-aromatic ring system containing at least one heteroatom selected from nitrogen, oxygen, and sulfur, wherein the non-aromatic heterocycle is attached to the core. The heterocycloalkyl ring may be optionally fused to or otherwise attached to other heterocycloalkyl rings, aromatic heterocycles, aromatic hydrocarbons and/or non-aromatic hydrocarbon rings. Preferred heterocycloalkyl groups have from 3 to 7 members. Examples of heterocycloalkyl groups include, for example, piperazine, 1,2,3,4-tetrahydroisoquinoline, morpholine, piperidine, tetrahydrofuran, pyrrolidine, and pyrazole. Preferred heterocycloalkyl groups include piperidinyl, piperazinyl, morpholinyl, and pyrolidinyl. The heterocycloalkyl groups herein are unsubstituted or, as specified, substituted in one or more substitutable positions with various groups. Thus, such heterocycloalkyl groups can be optionally substituted with groups such as, for example, C1-C6 alkyl, C1-C6 alkoxy, halogen, hydroxy, cyano, nitro, amino, mono- or di-(C1-C6)alkylamino, C2-C6 alkenyl, C2-C6 alkynyl, C1-C6haloalkyl, C1-C6 haloalkoxy, amino(C1-C6)alkyl, mono- or di(C1-C6)alkylamino(C1-C6)alkyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl. Preferred heteroaryl groups include pyridyl. The heteroaryl groups herein are unsubstituted or, as specified, substituted in one or more substitutable positions with various groups. Thus, such heteroaryl groups can be optionally substituted with groups such as, for example, C1-C6 alkyl, C1-C6alkoxy, halogen, hydroxy, cyano, nitro, amino, mono- or di-(C1-C6)alkylamino, C2-C6alkenyl, C2-C6 alkynyl, C1-C6 haloalkyl, C1-C6 haloalkoxy, amino(C1-C6)alkyl, mono- or di(C1-C6)alkylamino(C1-C6)alkyl.

The term "heteroarylalkyl" refers to a heteroaryl group, as defined above, attached to the parent molecular moiety through an alkyl group, as defined above. Preferred heteroarylalkyl groups include, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, isoxazolemethyl, isoxazoleethyl, pyrazinemethyl and pyrazineethyl. More preferred heteroarylalkyl groups include pyridylmethyl and pyridylethyl. The heteroaryl portions of these groups are unsubstituted or, as specified, substituted in one or more substitutable positions with various groups. Thus, such heteroaryl groups can be optionally substituted with groups such as, for example, C1-C6 alkyl, C1-C6 alkoxy, halogen, hydroxy, cyano, nitro, amino, mono- or di-(C1-C6)alkylamino, C2-C6 alkenyl, C2-C6alkynyl, CL-C6 haloalkyl, C1-C6 haloalkoxy, amino(C1-C6)alkyl, mono- or di(C1-C6) alkylamino(C1-C6)alkyl.

If two or more of the same substituents are on a common atom, e.g., di(C1-C6)alkylamino, it is understood that the nature of each group is independent of the other.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-beta has close structural homology with TNF-alpha (also known as cachectin), and since each induces similar biologic responses and binds to the same cellular receptor, the synthesis of both TNF-alpha and TNF-beta are inhibited by the compounds of the present invention and thus are herein referred to collectively as "TNF" unless specifically delineated otherwise.

The compounds of the invention may exist as atropisomers, i.e., chiral rotational isomers. The invention encompasses the racemic and the resolved atropisomers. The following illustration generically shows a compound (Z) that can exist as atropisomers as well as its two possible atropisomers (A) and (B). This illustration also shows each of atropisomers (A) and (B) in a Fischer projection. In this illustration, R1, R2, and R4 carry the same definitions as set forth for Formula I, Rp' is a substituent within the definition of R5, and Rp is a non-hydrogen substituent within the definition of R5.

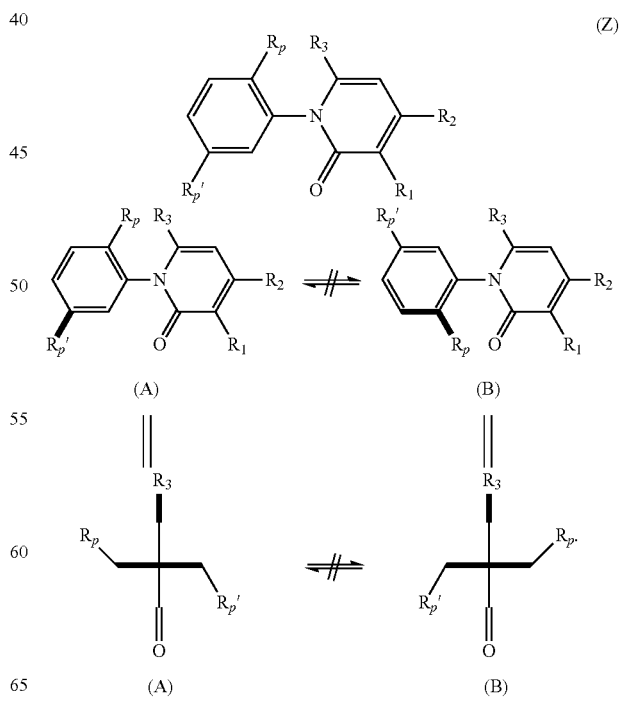

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

Genus XI Description

Compounds of Genus XI can be prepared according to the disclosures of U.S. Pat. Nos. 7,314,881 7,323,472, and 8,058,282, which are herein incorporated herein by reference in their entireties.

Genus XI is characterized by compounds of Formula XI:

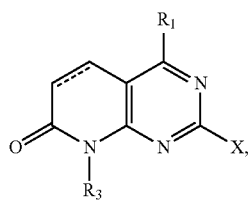

(XI)

or stereoisomers thereof, isotopically-enriched compounds thereof, prodrugs thereof, solvates thereof, and pharmaceutically acceptable salts thereof;
wherein:
==== is a single or double bond;
$R_1$ is an optionally substituted aryl or an optionally substituted heteroaryl ring;
$R_2$ is a moiety selected from hydrogen, $C_{1-10}$ alkyl, $C_{3-7}$ cycloalkyl, $C_{3-7}$cycloalkyl$C_{1-10}$alkyl, aryl, aryl$C_{1-10}$ alkyl, heteroaryl, heteroaryl$C_{1-10}$ alkyl, heterocyclic, and heterocyclyl$C_{1-10}$ alkyl, wherein each moiety, excluding hydrogen, is optionally substituted, or
$R_2$ is $X_1(CR_{10}R_{20})_qC(A_1)(A_2)(A_3)$ or $C(A_1)(A_2)(A_3)$;
$A_1$ is an optionally substituted $C_{1-10}$ alkyl;
$A_2$ is an optionally substituted $C_{1-10}$ alkyl;
$A_3$ is hydrogen or is an optionally substituted $C_{1-10}$ alkyl; and wherein $A_1$, $A_2$, and $A_3$, excluding hydrogen, are optionally substituted 1 to 4 times by $(CR_{10}R_{20})_nOR_6$;
$R_3$ is an $C_{1-10}$ alkyl, $C_{3-7}$ cycloalkyl, $C_{3-7}$ cycloalkyl$C_{1-4}$alkyl, aryl, aryl$C_{1-10}$alkyl, heteroaryl, heteroaryl$C_{1-10}$ alkyl, heterocyclic, or a heterocyclyl$C_{1-10}$alkyl moiety, which moieties are optionally substituted;
$R_6$ is hydrogen, or $C_{1-10}$ alkyl;
$R_{10}$ and $R_{20}$ are independently selected from hydrogen or $C_{1-4}$alkyl;
X is $R_2$, $OR_2$, $S(O)_mR_2$, $(CH_2)_nN(R_{10})S(O)_mR_2$, $(CH_2)_nN(R_{10})C(O)R_2$, $(CH_2)_nNR_4R_{14}$, or $(CH_2)_nN(R_2)_2$;
$X_1$ is $N(R_{10})$, O, $S(O)_m$, or $CR_{10}R_{20}$;
n is 0 or an integer having a value of 1 to 10;
m is 0 or an integer having a value of 1 or 2; and
q is 0 or an integer having a value of 1 to 10.

In one embodiment, the p38 kinase inhibitor from Genus XI is selected from the following:
4-Chloro-2-methylsulfanyl-6-phenylamino-pyrimidine-5-carbaldehyde;
4-Chloro-6-(2,6-difluoro-phenylamino)-2-methylsulfanyl-pyrimidine-5-carbaldehyde;
4-Chloro-6-(2-chloro-phenylamino)-2-methylsulfanyl-pyrimidine-5-carbaldehyde;
4-Chloro-6-(2-fluoro-phenylamino)-2-methylsulfanyl-pyrimidine-5-carbaldehyde;
4-Chloro-6-(1-ethyl-propylamino)-2-methylsulfanyl-pyrimidine-5-carbaldehyde;
4-Chloro-6-isopropylamino-2-methylsulfanyl-pyrimidine-5-carbaldehyde;
4-Chloro-6-cyclopropylamino-2-methylsulfanyl-pyrimidine-5-carbaldehyde;
4-Chloro-6-(cyclopropylmethyl-amino)-2-methylsulfanyl-pyrimidine-5-carbaldehyde;
2-Methylsulfanyl-4-phenyl-6-phenylamino-pyrimidine-5-carbaldehyde;
4-(2-Chlorophenyl)-6-(1-ethyl-propylamino)-2-methylsulfanyl-pyrimidine-5-carbaldehyde;
4-(2-Chlorophenyl)-6-(2-chloro-phenylamino)-2-methylsulfanyl-pyrimidine-5-carbaldehyde;
4-(2-Fluorophenyl)-6-(2-chloro-phenylamino)-2-methylsulfanyl-pyrimidine-5-carbaldehyde;
4-(2-Fluoro-phenyl)-6-isopropyl amino-2-methylsulfanyl-pyrimidine-5-carbaldehyde;
4-Chloro-2-methylsulfanyl-6-cyclohexylaminopyrimidine-5-carboxaldehyde;
2-Methylsulfanyl-4-(2-methyl-4-fluorophenyl)-6-cyclohexylaminopyrimidine-5-carbaldehyde;
4-Amino-6-(2-fluoro-phenyl)-2-methylsulfanyl-pyrimidine-5-carbaldehyde;
4-Cyclopropylamino-6-(2-fluoro-phenyl)-2-methylsulfanyl-pyrimidine-5-carbaldehyde;
4-(Cyclopropylmethyl-amino)-6-(2-fluoro-phenyl)-2-methylsulfanyl-pyrimidine-5-carbaldehyde;
4-(2,6-Difluoro-phenylamino)-6-(2-fluoro-phenyl)-2-methylsulfanyl-pyrimidine-5-carbaldehyde;
4-(2-Fluorophenyl)-6-(2-fluoro-phenylamino)-2-methylsulfanyl-pyrimidine-5-carbaldehyde;
4-sec-Butylamino-6-(2-fluoro-phenyl)-2-methylsulfanyl-pyrimidine-5-carbaldehyde;
4-(4-Fluoro-2-methyl-phenyl)-6-isopropylamino-2-methylsulfanyl-pyrimidine-5-carbaldehyde;
4-Cyclopropylamino-6-(4-fluoro-2-methyl-phenyl)-2-methylsulfanyl-pyrimidine-5-carbaldehyde;
4-(Cyclopropylmethyl-amino)-6-(4-fluoro-2-methyl-phenyl)-2-methylsulfanyl-pyrimidine-5-carbaldehyde;
4-(4-Fluoro-2-methyl-phenyl)-6-(2-fluoro-phenyl amino)-2-methylsulfanyl-pyrimidine-5-carbaldehyde;
4-sec-Butylamino-6-(4-fluoro-2-methyl-phenyl)-2-methylsulfanyl-pyrimidine-5-carbaldehyde;
4-Amino-6-(2-fluoro-phenyl)-2-methylsulfanyl-pyrimidine-5-carbaldehyde;
4-Amino-6-chloro-2-methylsulfanyl-pyrimidine-5-carbaldehyde;
4-sec-Butylamino-6-chloro-2-methylsulfanyl-pyrimidine-5-carbaldehyde;
4-(2,6-Difluoro-phenylamino)-6-(4-fluoro-2-methyl-phenyl)-2-methylsulfanyl-pyrimidine-5-carbaldehyde;
4-(1-Ethylpropylamino)-6-(4-fluoro-2-methyl-phenyl)-2-methylsulfanyl-pyrimidine-5-carbaldehyde;
2-Methylsulfanyl-4-(2-methyl-4-fluorophenyl)-6-cyclohexylaminopyrimidine-5-carbaldehyde;
4-Chloro-2-methylsulfanyl-6-cyclohexylaminopyrimidine-5-carboxaldehyde; and
8-(2,6-difluorophenyl)-2-((1,3-dihydroxypropan-2-yl)amino)-4-(4-fluoro-2-methylphenyl)pyrido[2,3-d]pyrimidin-7(8H)-one ("Dilmapimod"), Formula XI'.

In one embodiment, the p38 kinase inhibitor is 8-(2,6-difluorophenyl)-2-((1,3-dihydroxypropan-2-yl)amino)-4-(4-fluoro-2-methylphenyl)pyrido[2,3-d]pyrimidin-7(8H)-one ("Dilmapimod"), Formula XI'.

Genus XI Definitions

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; —C(O); $NR_4R_{14'}$, wherein $R_{4'}$ and $R_{14'}$ are each independently hydrogen or $C_{1-4}$ alkyl, such as amino or mono or -disubstituted $C_{1-4}$ alkyl or wherein the $R_4R_{14'}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_4R_{14}$ group; $C_{1-4}$ alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formula (XI) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "C1-10alkyl" or "alkyl" or "alkyl1-10" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl.

The term "heteroaryl" (on its own or in any combination, such as "heteroaryloxy", or "heteroaryl alkyl") is used herein to mean a 5-10 membered aromatic ring system in which one or more rings contain one or more heteroatoms selected from the group consisting of N, O or S, such as, but not limited, to pyrrole, pyrazole, furan, pyran, thiophene, quinoline, isoquinoline, quinazolinyl, pyridine, pyrimidine, pyridazine, pyrazine, uracil, oxadiazole, oxazole, isoxazole, oxathiadiazole, thiazole, isothiazole, thiadiazole, tetrazole, triazole, indazole, imidazole, or benzimidazole.

The term "heterocyclic" (on its own or in any combination, such as "heterocyclylalkyl") is used herein to mean a saturated or partially unsaturated 4-10 membered ring system in which one or more rings contain one or more heteroatoms selected from the group consisting of N, O, S, or S(O)m, and m is 0 or an integer having a value of 1 or 2; such as, but not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), pyrrolidine, piperidine, piperazine, morpholine, thiomorpholine (including oxidized versions of the sulfur moiety), or imidazolidine.

The term "aralkyl" or "heteroarylalkyl" or "heterocyclicalkyl" is used herein to mean C1-4 alkyl as defined above attached to an aryl, heteroaryl or heterocyclic moiety as also defined herein unless otherwise indicate.

The term "sulfinyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean C(O)C1-10 alkyl wherein the alkyl is as defined above.

Genus XII Description

Compounds of Genus XII can be prepared according to the disclosure of U.S. Pat. No. 6,147,080, which is herein incorporated herein by reference in its entirety.

Genus XII is characterized by compounds of Formula XII:

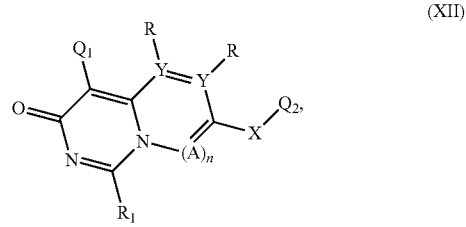

(XII)

or stereoisomers thereof, isotopically-enriched compounds thereof, prodrugs thereof, solvates thereof, and pharmaceutically acceptable salts thereof;

wherein:

each of $Q_1$ and $Q_2$ are independently selected from phenyl and 5-6 membered heteroaryl ring systems having one nitrogen heteroatom;

$Q_1$ is substituted with 1 to 4 substituents, independently selected from halo; $C_1$-$C_3$ alkyl; $C_1$-$C_3$ alkyl substituted with —NR'$_2$, —OR', —CO$_2$R', or —CONR'$_2$; —O—($C_1$-$C_3$)-alkyl; —O—($C_1$-$C_3$)-alkyl substituted with —NR'$_2$, —OR', —CO$_2$R', or —CONR'$_2$; —NR'$_2$; —OCF$_3$; —CF$_3$; —NO$_2$; —CO$_2$R'; —CONR'; —SR'; —S(O$_2$)N(R')$_2$; —SCF$_3$; or —CN; and $Q_2$ is optionally substituted with up to 4 substituents, independently selected from halo; $C_1$-$C_3$ straight or branched alkyl; $C_1$-$C_3$ straight or branched alkyl substituted with —NR', —NR'$_2$, —OR', —CO$_2$R', or —CONR'$_2$; —O—($C_1$-$C_3$)-alkyl; —O— ($C_1$-$C_3$)-alkyl substituted with —NR', —NR'$_2$, —OR', —CO$_2$R', or —CONR'$_2$; —NR'$_2$;

—OCF$_3$; —CF$_3$; —NO$_2$; —CO$_2$R'; —CONR'; —SR'; —S(O$_2$)N(R')$_2$; —SCF$_3$; or —CN;

wherein R' is selected from hydrogen, (C$_1$-C$_3$)-alkyl or (C$_2$-C$_3$)-alkenyl or alkynyl; and X is selected from —S—, —O—, —S(O)$_2$—, —S(O)—, —C(O)—, —N(R)—, or —C(R)$_2$—;

each R is independently selected from hydrogen or (C$_1$-C$_3$) alkyl;

Y is C;

A is CR';

n is 1; and

R$_1$ is selected from hydrogen, (C$_1$-C$_3$)-alkyl, —OH, or —O—(C$_1$-C$_3$)-alkyl.

In one embodiments, the p38 kinase inhibitor from Genus XII is selected from the following:

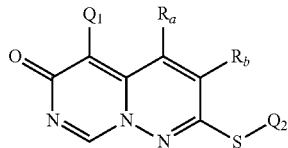

| Cmpd # | Q$_1$ | Q$_2$ | R$_a$ | R$_b$ |
|---|---|---|---|---|
| 2 | 4-fluorophenyl | phenyl | hydrogen | hydrogen |
| 3 | 2,4-dichlorophenyl | phenyl | hydrogen | hydrogen |
| 5 | 2,4-dichlorophenyl | 4-methylphenyl | hydrogen | hydrogen |
| 6 | 2,6-dichlorophenyl | phneyl | hydrogen | hydrogen |
| 7 | 2-chloropehnyl | phenyl | hydrogen | hydrogen |
| 8 | 2-methylphenyl | phenyl | hydrogen | hydrogen |
| 9 | 3,4-dichlorophenyl | phenyl | hydrogen | hydrogen |
| 10 | 4-methoxyphenyl | phenyl | hydrogen | hydrogen |
| 11 | 2-methoxyphenyl | phenyl | hydrogen | hydrogen |
| 12 | 2,6-dichlorophenyl | 4-fluorophenyl | hydrogen | hydrogen |
| 13 | 2,6-dichlorophenyl | phenyl | methyl | methyl |
| 14 | 2,6-dichlorophenyl | 4-methylphenyl | hydrogen | hydrogen |
| 15 | 2,6-dichlorophenyl | 3-methylphenyl | hydrogen | hydrogen |
| 16 | 2,6-dichlorophenyl | 3,4-dichlorophenyl | hydrogen | hydrogen |
| 17 | 2,6-dichlorophenyl | phenyl | hydrogen | hydrogen |
| 18 | 2,6-dichlorophenyl | 2-isopropylphenyl | hydrogen | hydrogen |
| 19 | 2,6-dichlorophenyl | 3,4-dimethylphenyl | hydrogen | hydrogen |
| 20 | 2,6-dichlorophenyl | 2-ethylphenyl | hydrogen | hydrogen |
| 21 | 2,6-dichlorophenyl | 3-fluorophenyl | hydrogen | hydrogen |
| 22 | 2-fluoro-6-trifluoro-methylphenyl | phenyl | hdyrogne | hydrogen |
| 23 | 2,6-dichlorophenyl | 2-methylphenyl | hydrogen | hydrogen |
| 24 | 2,6-dichlorophenyl | 3-chloro-4-fluorophenyl | hydrogen | hydrogen |
| 25 | 2,6-dichlorophenyl | 3-chlorophenyl | hydrogen | hydrogen |
| 26 | 2,6-dichlorophenyl | 2-carbomethoxyphenyl | hydrogen | hydrogen |
| 27 | 2,6-dichlorophenyl | 2-carboxyphenyl | hydrogen | hydrogen |
| 28 | 2,6-dichlorophenyl | 2-methyl-4-chlorophenyl | hydrogen | hydrogen |
| 29 | 2,6-dichlorophenyl | 2-bromophenyl | hydrogen | hydrogen |
| 30 | 2,6-dichlorophenyl | 2-pyridyl | hydrogen | hydrogen |
| 31 | 2,6-dichlorophenyl | 2-methylene-hydroxyphenyl | hydrogen | hydrogen |

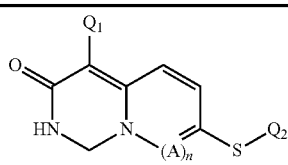

| Cmpd # | Q$_1$ | Q$_2$ | A | n |
|---|---|---|---|---|
| 101 | 2,6-dichlorophenyl | 2-carbomethoxyphenyl | nitrogen | 1 |
| 102 | 2,6-dichlorophenyl | 2-methylphenyl | nitrogen | 1 |
| 103 | 2,6-dichlorophenyl | 4-fluorophenyl | nitrogen | 1 |
| 104 | 2,6-dichlorophenyl | 2-carboxyphenyl | nitrogen | 1 |
| 105 | 2,6-dichlorophenyl | 2-carboxamidophenyl | nitrogen | 1 |
| 106 | 2,6-dichlorophenyl | 2-methyl-4-chlorophenyl | nitrogen | 1 |
| 107 | 2,6-dichlorophenyl | 2-pyridyl | nitrogen | 1 |
| 108 | 2,6-dichlorophenyl | 2-methylenehydroxyphenyl | nitrogen | 1 |
| 109 | 2,6-dichlorophenyl | 2-bromophenyl | nitrogen | 1 |
| 110 | 2,6-dichlorophenyl | phenyl | carbon | 1, |

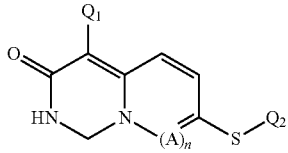

and 5-(2,6-dichlorophenyl)-2-((2,4-difluorophenyl)thio)-6H-pyrimido[1,6-b]pyridazin-6-one ("Neflamapimod"), Formula XII'.

In one embodiment, the p38 kinase inhibitor is 5-(2,6-dichlorophenyl)-2-((2,4-difluorophenyl)thio)-6H-pyrimido[1,6-b]pyridazin-6-one ("Neflamapimod"), Formula XII'.

Genus XIII Description

Compounds of Genus XIII can be prepared according to the disclosure of U.S. Pat. No. 7,521,447, which is herein incorporated herein by reference in its entirety.

Genus XIII is characterized by compounds of Formula XIII:

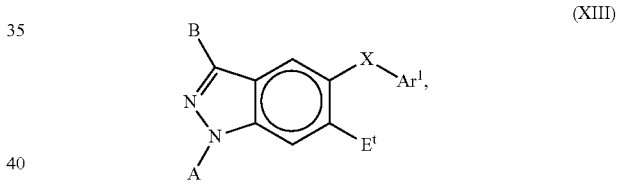

or stereoisomers thereof, isotopically-enriched compounds thereof, prodrugs thereof, solvates thereof, and pharmaceutically acceptable salts thereof;

wherein:

Ar$^1$ is aryl or heteroaryl, each of which may be substituted or unsubstituted;

A is —H, —OH, an amine protecting group, —Z$_n$—NR$^2$R$^3$, —Z$_n$—NR$^2$(C═O)R$^2$, —Z$_n$—SO$_2$R$^2$, —Z$_n$—SOR$^2$, —Z$_n$—SR$^2$, —Z$_n$—OR$^2$, —Z$_n$—(C═O)R$^2$, —Z$_n$—(C═O)OR$^2$, —Z$_n$—O—(C═O)R$^2$, alkyl, allyl, alkenyl, alkynyl, heteroalkyl, heteroallyl, heteroalkenyl, heteroalkynyl, alkoxy, heteroalkoxy, —Z$_n$-cycloalkyl, —Z$_n$-heterocycloalkyl, or —Z$_n$—Ar$^1$, wherein said alkyl, allyl, alkenyl, alkynyl, heteroalkyl, heteroallyl, heteroalkenyl, heteroalkynyl, alkoxy, heteroalkoxy, —Z$_n$-cycloalkyl, —Z$_n$-heterocycloalkyl, or —Z$_n$—Ar$^1$ may be substituted or unsubstituted;

Z is alkylene of from 1 to 4 carbons, or alkenylene or alkynylene each of from 2 to 4 carbons, wherein said alkylene, alkenylene, or alkynylene may be substituted or unsubstituted;

R$^2$ and R$^3$ are independently —H, —OH, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, —$Z_n$-cycloalkyl, —$Z_n$-heterocycloalkyl, or —$Z_n$—$Ar^1$,
wherein said alkyl, allyl, alkenyl, alkynyl, heteroalkyl, heteroallyl, heteroalkenyl, heteroalkynyl, alkoxy, heteroalkoxy, —$Z_n$-cycloalkyl, —$Z_n$-heterocycloalkyl, or $Z_n$—$Ar^1$ may be substituted or unsubstituted, or
$R^2$ together with $R^3$ and N forms a saturated or partially unsaturated heterocycle ring of 1 or more heteroatoms in said ring, wherein said heterocycle may be substituted or unsubstituted and wherein said heterocycle may be fused to an aromatic ring;
B is —H, —$NH_2$, or substituted or unsubstituted methyl;
E is —$Z_n$—$NR^2R^3$, —$Z_n$—(C=O)$R^4$, —$Z_n$—(C=O)$R^5$, —$Z_n$—$NR^5$(C=O)$R^5$, —$Z_n$—O(C=O)$R^5$, —$Z_n$—$OR^5$, —$Z_n$—$SO_2R^5$, —$Z_n$—$SOR^5$, —$Z_n$—$SR^5$, or —$Z_n$—NH(C=O)$NHR^5$;
$R^4$ is —NH(CH$R^6$)(CH$_2$)$_m$$OR^5$, wherein m is an integer from 1 to 4, or —$NR^2R^3$;
$R^5$ is —H, —OH, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, —$Z_n$-cycloalkyl, —$Z_n$-heterocycloalkyl, or —$Z_n$—$Ar^1$,
wherein said alkyl, allyl, alkenyl, alkynyl, heteroalkyl, heteroallyl, heteroalkenyl, heteroalkynyl, alkoxy, heteroalkoxy, —$Z_n$-cycloalkyl, —$Z_n$-heterocycloalkyl, or —$Z_n$—
$Ar^1$ may be substituted or unsubstituted;
$R^6$ is a natural amino acid side chain, —$Z_n$—$NR^2R^3$, $Z_n$—$OR^5$, $Z_n$—$SO_2R^5$, $Z_n$—$SOR^5$, or $Z_n$—$SR^5$; and
n is 0 or 1.

In one embodiment, the p38 kinase inhibitor from Genus XIII is selected from the following:
5-(4-fluorophenoxy)-1-isobutyl-1H-indazole-6-carboxylic acid (2-dimethylaminoethyl)amine;
N-(2-(dimethylamino)ethyl)-N-((5-(4-fluorophenoxy)-1-isobutyl-1H-indazol-6-yl)methyl)methanesulfonamide;
N-(2-(dimethylamino)ethyl)-N-((5-(4-fluorophenoxy)-1-isobutyl-1H-indazol-6-yl)methyl)acetamide
[5-(4-fluorophenoxy)-1-isobutyl-1H-indazol-6-yl]morpholin-4-yl-methanone;
[5-(4-fluorophenoxy)-1-isobutyl-1H-indazol-6-yl]-(4-methylpiperazin-1-yl)methanone;
5-(4-fluorophenoxy)-1-isobutyl-1H-indazole-6-carboxylic acid (1-benzylpiperidin-4-yl)amide;
5-(4-fluorophenoxy)-1-isobutyl-1H-indazole-6-carboxylic acid methyl-(1-methylpiperidin-4-yl)amide;
3-{[5-(4-fluorophenoxy)-1-isobutyl-1H-indazole-6-carbonyl]-amino}-pyrrolidine-1-carboxylic acid tert-butyl ester
(S)-5-(2,4-difluorophenoxy)-1-isobutyl-1H-indazole-6-carboxylic acid (1-carbamoyl-3-dimethylaminopropyl) amide
(S)-methyl 2-(5-(2,4-difluorophenoxy)-1-isobutyl-1H-indazole-6-carboxamido)-4-(dimethylamino)butanoate;
(S)-5-(2,4-difluorophenoxy)-N-(4-(dimethylamino)-1-hydroxybutan-2-yl)-1-isobutyl-1H-indazole-6-carboxamide;
(S)-5-(2,4-difluorophenoxy)-1-isobutyl-1H-indazole-6-carboxylic acid (1-hydroxymethyl-3-isopropylaminopropyl) amide;
(S)-5-(2,4-difluorophenoxy)-1-isobutyl-1H-indazole-6-carboxylic acid (3-dimethylamino-1-dimethylcarbamoylpropyl)amide;
(S)-5-(2,4-difluorophenoxy)-1-isobutyl-1H-indazole-6-carboxylic acid (3-dimethylamino-1-methylcarbamoylpropyl)amide;
5-(2,4-difluorophenoxy)-1-isobutyl-1H-indazole-6-carboxylic acid;
{3-[5-(2,4-difluorophenoxy)-1-isobutyl-1H-indazol-6-yloxy]-propyl}dimethylamine;
5-(2,4-difluorophenoxy)-1-isobutyl-6-(piperidin-4-ylmethoxy)-1H-indazole;
5-(2,4-difluorophenoxy)-1-isobutyl-6-(3-piperazin-1-ylpropoxy)-1H-indazole;
5-(2,4-difluorophenoxy)-1-isobutyl-6-(morpholin-2-ylmethoxy)-1H-indazole;
1-[5-(2,4-difluorophenoxy)-1-isobutyl-1H-indazol-6-yloxy]-3-pyrrolidin-1-yl-propan-2-ol;
{3-[5-(2,4-difluorophenoxy)-1-isobutyl-1H-indazol-6-yloxy]-propyl}dimethylamine;
5-(2,4-difluorophenoxy)-1-isobutyl-6-(piperidin-4-ylmethoxy)-1H-indazole;
5-(2,4-difluorophenoxy)-1-isobutyl-6-(morpholin-2-ylmethoxy)-1H-indazole; N'-[5-(2,4-difluorophenoxy)-1-isobutyl-1H-indazol-6-yl]-N,N-dimethylpropane-1,3-diamine;
[5-(2,4-difluorophenoxy)-1-isobutyl-1H-indazol-6-yl]-piperidin-4-yl-amine;
[5-(2,4-difluorophenoxy)-1-isobutyl-1H-indazol-6-yl]-piperidin-3-ylmethylamine;
(S)-2-{[5-(2,4-difluorophenoxy)-1-isobutyl-1H-indazole-6-carbonyl]-amino}-4-dimethylaminobutyric acid;
(S)-5-(2,4-difluorophenoxy)-1-isobutyl-1H-indazole-6-carboxylic acid (1-hydroxymethyl-3-piperidin-1-ylpropyl) amide;
(S)-5-(2,4-difluorophenoxy)-1-isobutyl-1H-indazole-6-carboxylic acid [1-(2-dimethylaminoethyl)-2-hydroxy-2-methylpropyl]amide;
(S)-5-(2,4-difluorophenoxy)-1-isobutyl-1H-indazole-6-carboxylic acid {1-hydroxymethyl-3-[(2-methoxyethyl) methylamino]propyl}amide;
(S)-5-(2,4-difluorophenoxy)-1-isobutyl-1H-indazole-6-carboxylic acid [3-dimethylamino-1-(2-hydroxyethylcarbamoyl)propyl]amide; and
(5-(2,4-difluorophenoxy)-1-isobutyl-1H-indazol-6-yl)((2-(dimethylamino)ethyl)-12-azaneyl)methanone ("ARRY-797"), Formula XIII'.

In one embodiment, the p38 kinase inhibitor is (5-(2,4-difluorophenoxy)-1-isobutyl-1H-indazol-6-yl)((2-(dimethylamino)ethyl)-12-azaneyl)methanone ("ARRY-797"), Formula XIII'.

Genus XIII Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

"Alkylene" means a linear or branched saturated divalent hydrocarbon radical of one to twelve carbon atoms, e.g., methylene, ethylene, propylene, 2-methylpropylene, pentylene, and the like.

The term "alkenyl" refers to linear or branched-chain monovalent hydrocarbon radical of two to twelve carbon atoms, containing at least one double bond, e.g., ethenyl, propenyl, and the like, wherein the alkenyl radical may be optionally substituted independently with one or more substituents described herein, and includes radicals having "cis" and "trans" orientations, or alternatively, "E" and "Z" orientations.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkynyl" refers to a linear or branched monovalent hydrocarbon radical of two to twelve carbon atoms containing at least one triple bond. Examples include, but are not limited to, ethynyl, propynyl, and the like, wherein the alkynyl radical may be optionally substituted independently with one or more substituents described herein.

The term "alkynylene" to a linear or branched divalent hydrocarbon radical of two to twelve carbons containing at least one triple bond, wherein the alkynylene radical may be optionally substituted independently with one or more substituents described herein.

The term "allyl" refers to a radical having the Formula RC═CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The term "cycloalkyl" refers to saturated or partially unsaturated cyclic hydrocarbon radical having from three to twelve carbon atoms, wherein the cycloalkyl may be optionally substituted independently with one or more substituents described herein. The term "cycloalkyl" further includes bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heterocycloalkyl" refers to a saturated or partially unsaturated cyclic radical of 3 to 8 ring atoms in which at least one ring atom is a heteroatom selected from nitrogen, oxygen and sulfur, the remaining ring atoms being C where one or more ring atoms may be optionally substituted independently with one or more substituent described below and wherein the heterocycloalkyl ring can be saturated or partially unsaturated. The radical may be a carbon radical or heteroatom radical. "Heterocycloalkyl" also includes radicals where heterocycle radicals are fused with aromatic or heteroaromatic rings. Examples of heterocycloalkyl rings include, but are not limited to, pyrrolidine, piperidine, piperazine, tetrahydropyranyl, morpholine, thiomorpholine, homopiperazine, phthalimide, and derivatives thereof.

The term "heteroalkenyl" refers to linear or branched-chain monovalent hydrocarbon radical of two to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" refers to a linear or branched monovalent hydrocarbon radical of two to twelve carbon atoms containing at least one triple bond. Examples include, but are not limited to, ethynyl, propynyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein.

The term "heteroallyl" refers to radicals having the Formula RC═CHCHR, wherein R is alkyl, alkenyl, alkynyl, cycloalkyl, heterocycloalkyl, aryl, heteroaryl, or any substituent as defined herein, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroallyl may be optionally substituted independently with one or more substituents described herein.

"Aryl" means a monovalent aromatic hydrocarbon monocyclic radical of 6 to 10 ring atoms or a polycyclic aromatic hydrocarbon, optionally substituted independently with one or more substituents described herein. More specifically the term aryl includes, but is not limited to, phenyl, 1-naphthyl, 2-naphthyl, and derivatives thereof.

"Heteroaryl" means a monovalent monocyclic aromatic radical of 5 to 10 ring atoms or a polycyclic aromatic radical, containing one or more ring heteroatoms selected from N, O, or S, the remaining ring atoms being C. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof.

The term "halo" represents fluoro, chloro, bromo or iodo.

"Amino protecting groups" refers to those organic groups intended to protect nitrogen atoms against undesirable reactions during synthetic procedures and include, but are not limited to, benzyl, benzyloxycarbonyl (CBZ), tert-butoxycarbonyl (Boc), trifluoroacetyl, and the like.

"Alcohol protecting groups" refers to those organic groups intended to protect alcohol groups or substituents against undesirable reactions during synthetic procedures and include, but are not limited to, (trimethylsilyl)ethoxymethyl (SEM), tert-butyl, methoxymethyl (MOM), and the like.

"Sulfur protecting groups" refers to those organic groups intended to protect sulfur groups or substituents against undesirable reactions during synthetic procedures and include, but are not limited to, benzyl, (trimethylsilyl) ethoxymethyl (SEM), tert-butyl, trityl and the like.

"Acid protecting groups" refers to those organic groups intended to protect acid groups or substituents against undesirable reactions during synthetic procedures and include, but are not limited to, benzyl, (trimethylsilyl)ethoxymethyl (SEM), methylethyl and tert-butyl esters, and the like.

In one embodiment, the p38 kinase inhibitor may be selected from the following: 2-(4-Chlorophenyl)-4-(fluorophenyl)-5-pyridin-4-yl-1,2-dihydropyrazol-3-one, RWJ- 67657, RDP-58, Scios-469 (talmapimod), SB-210313, SB-220025, SB-238039, HEP-689, SB-203580, SB-239063, SB-239065, SB-242235, VX-702 and VX-745, AMG-548, BIRB-796 (Doramapimod), RO 4402257 (Pamapimod), FR-167653, SB-681323 (Dilmapimod), SB-281832, SC-040, SC-XX906, CP-64131, CNI-1493, RPR-200765A, Ro-320-1195, AIK-3, AKP-OO1, LL Z1640-2, ARRY-614, ARRY-797, AS-1940477, AVE-9940, AZD-7624, BCT-197, BIRB-1017BS, BMS-582949, CAY10571, CBS-3595, CCT-196969, CCT-241161, CDP-146, CGH 2466, CHR-3620, Chlormethiazole edisylate, and CM PD-1.

In one embodiment, the p38 kinase inhibitor is selected from the following: Doramapimod, EO 1428, FY-101C, FX-005, GSK-610677 HE-3286, HSB-13, JX 401, KC-706, KC-706 (ITX-5061), LEO-15520, LEO-1606, Losmapimod, LP-590, LY-30007113, LY2228820, M L 3403, OX-27-NO, NP-202, pexmetinib, PF-03715455, PH-797804, PS-540446, ralimetinib, regorafenib, RO-3201195, RWJ 67657, RWJ-67657, SB 202190, SB 203580, SB 203580 hydrochloride, SB202190, SB202190 hydrochloride, SB-681323, SB-856553, SC-80036, SCD-282, SCIO-323, SCIO-469, SD-06, semapimod, SKF 86002, SX Oil, SYD-003, TA-5493, TAK 715, TOP-1210, TOP-1630, UR-13870, UR-13870, VGX-1027.27, 8-(2,6-difluorophenyl)-2-(1,3-dihydroxypropan-2-ylamino)-4-(4-fluoro-2-methylphenyl)pyrido[2,3-d]pyrimidin-7-one (Dilmapimod), and GSK-610677.

In one embodiment, the p38 kinase inhibitor is selected from the following: 6-[5-(cyclopropylcarbamoyl)-3-fluoro-2-methylphenyl]-N-(2,2-dimethylpropyl)pyridine-3-carboxamide (Losmapimod), 5-[(2-chloro-6-fluorophenyl)acetylamino]-3-(4-fluorophenyl)-4-(4-pyrimidinyl)isoxazole (AKP-001), KC-706, (1-[5-tert-butyl-2-(3-chloro-4-hydroxyphenyl)pyrazol-3-yl]-3-[[2-[[3-[2-(2-hydroxyethylsulfanyl)phenyl]-[1,2,4]triazolo[4,3-a]pyridin-6-yl]sulfanyl]phenyl]methyl]urea) (PF-03715455), (3-[3-bromo-4-[(2,4-difluorophenyl)methoxy]-6-methyl-2-oxopyridin-1-yl]-N,4-dimethylbenzamide) (PH-797804), RV-7031.29, 2-methoxy-1-{4-[(4-{3-[5-(tert-butyl)-2-(p-tolyl)-2H-pyrazol-3-yl]ureido}-1, AMG-548, BIRB-796 (Doramapimod), RO 4402257 (Pamapimod), FR-167653 SB-681323 (Dilmapimod), SB-281832, SC-040, and SC-XX906, CP-64131, CNI-1493, RPR-200765A, Ro-320-1195, AIK-3, AKP-OO1, LL Z1640-2, ARRY-614, ARRY-797, AS-1940477, AVE-9940, AZD-7624, BCT-197, BIRB-1017BS, BMS-582949, CAY10571, CBS-3595, CCT-196969, CCT-241161, CDP-146, CGH 2466, CHR-3620, Chlormethiazole edisylate, and CM PD-1.

In one embodiment, the p38 kinase inhibitor is selected from the following: Doramapimod, EO 1428, FY-101C, FX-005, GSK-610677 HE-3286, HSB-13, JX 401, KC-706, KC-706 (ITX-5061), LEO-15520, LEO-1606, Losmapimod, LP-590, LY-30007113, LY2228820, M L 3403, OX-27-NO, NP-202, pexmetinib, PF-03715455, PH-797804, PS-540446, ralimetinib, regorafenib, RO-3201195, RWJ 67657, RWJ-67657, SB 202190, SB 203580, SB 203580 hydrochloride, SB202190, SB202190 hydrochloride, SB-681323, SB-856553, SC-80036, SCD-282, SCIO-323, SCIO-469, SD-06, semapimod, SKF 86002, SX Oil, SYD-003, TA-5493, TAK 715, TOP-1210, TOP-1630, UR-13870, UR-13870, and VGX-1027, SB 203580, SB 203580 hydrochloride, SB681323 (Dilmapimod), and LY2228820 dimesylate.

In one embodiment, the p38 kinase inhibitor is selected from the following: BIRB 796 (Doramapimod), BMS-582949, Pamapimod, GW856553, ARRY-797AL 8697, AMG 548, CMPD-1, EO 1428, JX 401, RWJ 67657, TA 01, TA 02, VX 745, DBM 1285 dihydrochloride, ML 3403, SB 202190, SB 239063, SB 706504, SCIO 469 hydrochloride, SKF 86002 dihydrochloride, SX Oil, TAK 715, VX 702, and PH797804.

In one embodiment, the p38 kinase inhibitor is characterized by a compound of Genus XXX.

In one embodiment, the p38 kinase inhibitor is characterized by a compound of Formula (XXX'):

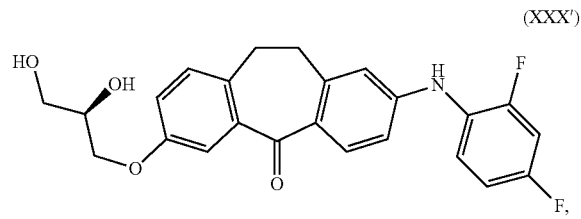 [SMILES: O=C1c2ccc(Nc3ccc(F)cc3F)cc2CCc2ccc(OC[C@H](O)CO)cc21]

(XXX')

or stereoisomers thereof, isotopically-enriched compounds thereof, prodrugs thereof, solvates thereof, and pharmaceutically acceptable salts thereof.

Genus XXX Description

Compounds of Genus XXX can be prepared according to the disclosure of U.S. Pat. No. 8,633,312 which is herein incorporated herein by reference in its entirety.

Genus XXX is characterized by compounds of Formula (XXX'):

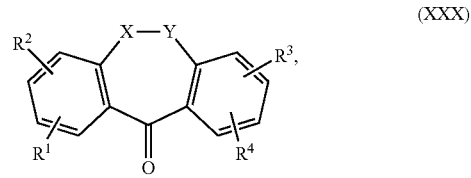

(XXX)

or stereoisomers thereof, isotopically-enriched compounds thereof, prodrugs thereof, solvates thereof, and pharmaceutically acceptable salts thereof;
wherein:
one of the ring atoms X and Y represents $CH_2$ and the other represents O, S, SO, $SO_2$ or $NR_5$, or —X-Y— is —$CH_2$—$CH_2$— or —CH=CH—;
$R^1$ is selected from:
A) RO—, wherein R is chosen from:
  a) $C_1$-$C_6$-alkyl, which is substituted by 1, 2 or 3 hydroxyl or $C_1$-$C_6$-alkoxy groups;
  b) $C_1$-$C_6$-alkyl, which is substituted by a saturated or unsaturated, non-aromatic heterocyclic radical having 5 or 6 ring atoms, which contains 1, 2 or 3 hetero atoms which are chosen independently of each other from O, N and S, wherein the heterocyclic radical can optionally contain 1 or 2 hydroxy, $C_1$-$C_6$-alkoxy or $C_1$-$C_6$-alkyl substituents and can be condensed with a phenyl ring or a saturated or unsaturated carbocyclic radical having 5 or 6 ring atoms;
  c) a non-aromatic heterocyclic radical having 5 or 6 ring atoms, which contains 1 or 2 hetero atoms which are chosen independently of each other from O and N;
  d) $C_1$-$C_6$-alkyl;
  e) H;
  f) $C_1$-$C_6$-alkyl, which is substituted by NR6R7;
  g) $CF_3SO_2$—;

h) $C_1$-$C_6$-alkylcarbonyloxy-$C_1$-$C_6$-alkyl; and
i) ($C_3$-$C_7$-cycloalkyl)-$C_1$-$C_6$-alkyl, which can optionally contain 1 or 2 hydroxy, $C_1$-$C_6$-alkoxy or $C_1$-$C_6$-alkyl substituents on the cycloalkyl radical;

B) $NR_6R_7$;
C) tetrazolo; and
D) $NR_8CONR_{13}R_{14}$;
$R_2$ is H or C1-$C_6$-alkyl;
$R_3$ is selected from:

a)
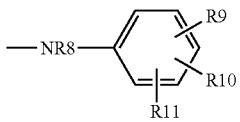

b)
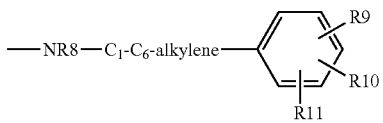

c)
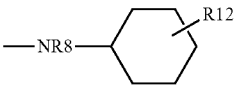

d)
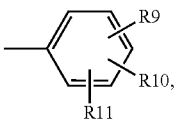

and
e) —NH—$C_1$-$C_6$-alkylene-$NR_6R_7$
$R_4$ is H, halogen or $C_1$-$C_6$-alkyl;
$R_5$ is H or $C_1$-$C_6$-alkyl,
wherein the $C_1$-$C_6$ alkyl is substituted by 1, 2 or 3 hydroxyl or $C_1$-$C_6$-alkoxy groups;
$R_6$ and $R_7$ are each independently H or $C_1$-$C_6$-alkyl, which is substituted by 1, 2 or 3 hydroxyl or $C_1$-$C_6$-alkoxy groups;
$R_8$ is H or $C_1$-$C_6$-alkyl;
$R_9$, $R_{10}$, and $R_{11}$ are each independently selected from H, $NH_2$, mono-$C_1$-$C_6$-alkylamino, di-$C_1$-$C_6$-alkylamino, $C_1$-$C_6$-alkyl, $C_1$-$C_6$-alkoxy, hydroxyl, halogen, $C_1$-$C_6$-alkyl, which is substituted by 1, 2 or 3 halogen atoms; $CONR_6R_7$; and $NO_2$;
$R_{12}$ represents H or $NH_2$;
$R_{13}$ and $R_{14}$, are independently selected from H or $C_1$-$C_6$-alkyl, or
$R_{13}$ and $R_{14}$ are taken together with the nitrogen atom to which they are bonded to form a non-aromatic heterocyclic radical having 5 or 6 ring atoms, which contains 1 or 2 hetero atoms which are chosen independently of each other from O and N.

In one embodiment, the p38 kinase inhibitor from Genus XXX is selected from the following:
(1) 2-(2-aminoanilino)-7-methoxydibenzosuberone;
(2) 2-(2-amino-4-fluoroanilino)-7-methoxydibenzosuberone;
(3) 2-(2,4-difluoroanilino)-7-methoxydibenzosuberone;
(4) 2-(2-chloro-4-fluoroanilino)-7-methoxydibenzosuberone;
(5) 2-(2,4,5-trifluoroanilino)-7-methoxydibenzosuberone;
(6) 2-(2-trifluoromethylanilino)-7-methoxydibenzosuberone;
(7) 2-(anilino)-7-methoxydibenzosuberone;
(8) 2-(2-methoxyanilino)-7-methoxydibenzosuberone;
(9) 2-(3-methyl-4-fluoroanilino)-7-methoxydibenzosuberone;
(10) 2-(2-amino-4-trifluoromethylanilino)-7-methoxydibenzosuberone;
(11) 2-(phenyl)-7-methoxydibenzosuberone;
(12) 2-(2,4-difluoroanilino)-7-methoxydibenzosuberenone;
(13) 2-(2,4-difluoroanilino)-7-(S-1,2-isopropylideneglycer-3-yl)-10,11-dihydrodibenzo[a,d]-cyclohepten-5-one;
(14) 2-(2,4-difluoroanilino)-7-(R-1,2-isopropylideneglycer-3-yl)-10,11-dihydrodibenzo[a,d]-cyclohepten-5-one;
(15) 2-(2-aminoanilino)-7-(S-1,2-isopropylideneglycer-3-yl)-10,11-dihydrodibenzo[a,d]-cyclohepten-5-one;
(16) 2-(2-aminoanilino)-7-(R-1,2-isopropylideneglycer-3-yl)-10,11-dihydrodibenzo[a,d]-cyclohepten-5-one;
(17) 2-(2,4-difluoroanilino)-7-[2R-,3-dihydroxypropoxy]-10,11-dihydrodibenzo[a,d]-cyclohepten-5-one;
(18) 2-(2,4-difluoroanilino)-7-[2S-,3-dihydroxypropoxy]-10,11-dihydrodibenzo[a,d]-cyclohepten-5-one;
(19) 2-(2-aminoanilino-7-[2R-,3-dihydroxypropoxy]-10,11-dihydrodibenzo[a,d]-cyclohepten-5-one;
(20) 2-(2-aminoanilino-7-[2S-,3-dihydroxypropoxy]-10,11-dihydrodibenzo[a,d]-cyclohepten-5-one;
(21) 2-(2,4-difluoroanilino)-7-(2-hydroxy-ethoxy)-10,11-dihydrodibenzo[a,d]-cyclohepten-5-one;
(22) 2-(2,4-difluoroanilino)-7-(3-hydroxy-propoxy)-10,11-dihydrodibenzo[a,d]-cyclohepten-5-one;
(23) 2-(2,4-difluoroanilino)-7-(2-morpholin-4-yl-ethoxy)-10,11-dihydrodibenzo[a,d]-cyclohepten-5-one;
(24) 2-(2-aminoanilino)-7-(2-morpholin-4-yl-ethoxy)-10,11-dihydrodibenzo[a,d]-cyclohepten-5-one;
(25) 2-(2,4-difluoroanilino)-7-(2-tetrahydropyran-4-yloxy)-10,11-dihydrodibenzo[a,d]-cyclohepten-5-one;
(26) (S)-2-(2,4-difluorophenylamino)-8-(2,2-dimethyl-[1,3]dioxolan-4-ylmethoxy)-10,11-dihydrodibenzo[a,d]cyclohepten-5-one;
(27) (R)-2-(2,4-difluorophenylamino)-8-(2,3-dihydroxypropoxy)-10,11-dihydrodibenzo[a,d]cyclohepten-5-one;
(28) (S)-2-(2-aminophenylamino)-8-(2,2-dimethyl-[1,3]dioxolan-4-ylmethoxy)-10,11-dihydrodibenzo[a,d]cyclohepten-5-one;
(29) (R)-2-(2-aminophenylamino)-8-(2,3-dihydroxypropoxy)-10,11-dihydrodibenzo[a,d]cyclohepten-5-one;
(30) 2-(2,4-difluorophenylamino)-8-(2-morpholin-4-yl-ethoxy)-10,11-dihydrodibenzo[a,d]cyclohepten-5-one;
(31) 8-(2,4-difluorophenylamino)-1-hydroxy-10,11-dihydrodibenzo[a,d]cyclohepten-5-one;
(32) 8-(2,4-difluorophenylamino)-1-methoxy-10,11-dihydrodibenzo[a,d]cyclohepten-5-one;
(33) 8-(2-aminophenylamino)-1-methoxy-10,11-dihydrodibenzo[a,d]cyclohepten-5-one;
(34) (S)-8-(2,4-difluorophenylamino)-1-(2,2-dimethyl-[1,3]dioxolan-4-ylmethoxy)-10,11-dihydrodibenzo[a,d]cyclohepten-5-one;
(35) (R)-8-(2,4-difluorophenylamino)-1-(2,3-dihydroxypropoxy)-10,11-dihydrodibenzo-[a,d]cyclohepten-5-one;
(36) (S)-8-(2-aminophenylamino)-1-(2,2-dimethyl-[1,3]dioxolan-4-ylmethoxy)-10,11-dihydrodibenzo[a,d]cyclohepten-5-one;
(37) (R)-8-(2-aminophenylamino)-1-(2,3-dihydroxypropoxy)-10,11-dihydrodibenzo-[a,d]cyclo-hepten-5-one;
(38) 8-(2,4-difluorophenylamino)-1-(tetrahydropyran-4-yloxy)-10,11-dihydrodibenzo[a,d]cyclohepten-5-one;
(39) 8-(2,4-difluorophenylamino)-1-(2-morpholin-4-yl-ethoxy)-10,11-dihydrodibenzo-[a,d]cyclo-hepten-5-one;

(40) 3-(2,4-difluorophenylamino)-8-amino-6H-dibenzo[b,e]oxepin-11-one;
(41) 3-(2-aminophenylamino)-8-amino-6H-dibenzo[b,e]oxepin-11-one;
(42) 8-amino-3-(2-methoxyphenylamino)-6H-dibenzo[b,e]oxepin-11-one;
(43) 8-amino-3-(4-fluoro-2-methoxyphenylamino)-6H-dibenzo[b,e]-oxepin-11-one;
(44) 8-amino-3-(2-amino-4-trifluoromethylphenylamino)-6H-dibenzo[b,e]oxepin-11-one;
(45) 8-amino-3-(tetrazol-1-yl)-6H-dibenzo[b,e]oxepin-11-one;
(46) 3-(2,4-difluorophenylamino)-8-tetrazol-1-yl-6H-dibenzo[b,e]oxepin-11-one;
(47) 2-(2-methyl-4-Fluoroanilino)-7-methoxydibenzosuberone;
(48) 2-(2-chloroanilino)-7-methoxydibenzosuberone;
(49) 2-(2-amino-4-fluoroanilino)-7-hydroxy-10,11-dihydrodibenzo[a,d]-cyclohepten-5-one;
(50) 2-(2,4-difluoroanilino)-7-hydroxy-10,11-dihydrodibenzo[a,d]-cyclohepten-5-one;
(51) 2-(2-chloro-4-fluoroanilino)-7-hydroxy-10,11-dihydrodibenzo[a,d]-cyclohepten-5-one;
(52) 2-(2-chloroanilino)-7-hydroxy-10,11-dihydrodibenzo[a,d]-cyclohepten-5-one;
(53) 2-(anilino)-7-hydroxy-10,11-dihydrodibenzo[a,d]-cyclohepten-5-one;
(54) 2-(2,4-difluoroanilino)-7-hydroxy-dibenzo[a,d]-cyclohepten-5-one;
(55) 2-(2,4-difluoroanilino)-7-[3-(4-Hydroxypiperidin-4-yl-propoxy)]-10,11-dihydrodibenzo[a,d]-cyclohepten-5-one;
(56) 3-(2-amino-4-fluorophenylamino)-8-nitro-6H-dibenzo[b,e]oxepin-11-one;
(57) morpholine-4-carboxylic acid [3-(2,4-difluorophenylamino)-1-oxo-6,11-dihydrodibenzo[b,e]oxepin-8-yl] amide; and
(R)-2-((2,4-difluorophenyl)amino)-7-(2,3-dihydroxypropoxy)-10,11-dihydro-5H-dibenzo[a,d][7]annulen-5-one ("skepinone-L"), Formula XXX'.

In one embodiment, the p38 inhibitor is (R)-2-((2,4-difluorophenyl)amino)-7-(2,3-dihydroxypropoxy)-10,11-dihydro-5H-dibenzo[a,d][7]annulen-5-one ("skepinone-L"), Formula XXX'.

Genus V Definitions

The expression "alkyl" (also in combination with other groups, such as alkoxy, haloalkyl etc.) includes straight-chain and branched alkyl groups having preferably 1 to 6 or 1 to 4 carbon atoms, such as methyl, ethyl, n- and i-propyl, n-, i- and t-butyl, sec-butyl, n-pentyl and n-hexyl.

The expression "halogen" stands for a fluorine, chlorine, bromine or iodine atom, in particular for a fluorine or chlorine atom.

$C_1$-$C_6$-Alkoxy which is substituted by 1, 2 or 3 hydroxyl or $C_1$-$C_6$-alkoxy groups is preferably $C_2$-$C_6$-alkoxy, in particular 2-hydroxyethoxy, 3-hydroxypropoxy, 2-hydroxypropoxy, 1,2-dihydroxyethoxy, 2,3-dihydroxypropoxy or 2,3-dimethoxypropoxy.

A saturated non-aromatic heterocyclic radical is, in particular, pyrrolidinyl, piperidinyl, hydroxypiperidinyl, piperazinyl, tetrahydropyranyl, tetrahydrofuranyl, dioxolanyl, 2,2-dimethyldioxolanyl, dioxanyl, morpholinyl or thiomorpholinyl. The piperidinyl radical can be substituted by 1, 2, 3 or 4 $C_1$-$C_4$-alkyl groups, in particular methyl groups. A preferred piperidinyl radical is 2,2,6,6-tetramethylpiperidinyl. The nitrogen-containing heterocyclic radicals can be bonded via a nitrogen atom or a carbon atom.

An unsaturated non-aromatic heterocyclic radical is, in particular, pyrrolinyl, di- or tetrahydropyridinyl.

An aromatic heterocyclic radical is, in particular, pyridyl, preferably 3- or 4-pyridyl, pyrimidinyl, pyrrolyl, imidazolyl, pyrazolyl, oxazolyl, isoxazolyl, furyl, thienyl, thiazolyl, thiadiazolyl, isothiazolyl or the corresponding benzo derivatives thereof.

In several embodiments, a method for treating a disorder responsive to p38 kinase inhibition is provided. The method may include administering to a subject in need thereof, an effective amount of a p38 agent, or a stereoisomer thereof, an isotopically-enriched compound thereof, a prodrug thereof, a solvate thereof, or a pharmaceutically acceptable salt thereof. The method includes the treatment of disorders associated with DUX4 gene expression, wherein the inhibition of p38 kinase with a p38 agent may reduce DUX4 expression levels and/or the expression of one or more downstream genes in cells of the subject.

In some embodiments, the p38 agent may be selected from any of the p38 kinase inhibitors described herein, and/or selected from the compounds described in any of the following patents and publications, or corresponding U.S. patents and publications that were available at the time that the priority application was filed, i.e., Oct. 5, 2017:

| | | | |
|---|---|---|---|
| WO 2016066687 | WO 2007147103 | WO 2005073232 | WO 2004010995 |
| WO 2015004089 | WO 2007144390 | WO 2005073219 | WO 2003093248 |
| WO 2014014706 | WO 2007147109 | WO 2005073217 | WO 2003088972 |
| WO 2013106643 | WO 2007059500 | WO 2005073189 | WO 2003087394 |
| AR 59008 | WO 2006134382 | WO 2005014550 | WO 2003068747 |
| WO 2009074518 | WO 2006127678 | WO 2004089876 | WO 2003057197 |
| WO 2009074519 | WO 2006110173 | WO 2004089875 | WO 2003033483 |
| WO 2008071665 | WO 2006104889 | WO 2004089874 | WO 2003033482 |
| WO 2008071664 | WO 2006104915 | WO 2004073628 | WO 2003033482 |
| WO 2007147104 | U.S. 20060217401 | WO 2004021979 | WO 2003032987 |
| WO 2003032986 | WO 2002076396 | WO 2001037837 | WO 9857966 |
| WO 2003032980 | WO 2002060869 | U.S. 6,218,537 | WO 9856377 |
| WO 2003032972 | WO 2002059083 | WO 2001019322 | WO 9828292 |
| WO 2003032971 | WO 2002032862 | WO 2000025791 | WO 9807425 |
| WO 2003032970 | U.S. 6,369,068 B1 | WO 2000019824 | U.S. 5,716,955 |
| WO 2002090360 | WO 2002016359 | WO 2000010563 | WO 9735856 |
| WO 2002076985 | WO 2001064679 | WO 9961437 A1 | WO 9735855 |
| WO 2002076984 | WO 2001038314 | WO 9921859 A1 | WO 9734137 |
| WO 2002076954 | WO 2001038313 | WO 9901136 A1 | WO 9733883 |
| WO 2002076463 | WO 2001038312 | WO 9901130 A1 | WO 9732583 |
| WO 9725048 | WO 2000017175 | WO 2008049842 | U.S. 20040033222 |
| WO 9725047 | WO 9964400 | WO 2006067165 | WO 2004004725 |
| WO 9725046 | WO 9958502 | WO 2006067175 | WO 2003087096 |

-continued

| | | | |
|---|---|---|---|
| WO 9640143 | WO 9942592 | WO 2006067168 | WO 2003084539 |
| WO 9621452 | WO 9900357 | WO 2006015775 | WO 2003084503 |
| WO 2004029040 | WO 9900357 | WO 2005018624 | WO 2003064419 |
| WO 2003048340 | WO 9900357 | DE 10255040 | WO 2003064418 |
| WO 2002100405 | WO 2010089391 | WO 2004024699 | WO 2003064417 |
| WO 2002092087 | WO 2009103336 | WO 2004014870 | WO 2003049742 |
| U.S. 6,147,080 | WO 2008098096 | WO 2004014387 | WO 2016142310 |
| WO 2015191996 | WO 2007023114 | U.S. 20040209904 | WO 2001029042 |
| WO 2015191986 | WO 2007023115 | U.S. 20040209903 | WO 2001029041 |
| WO 2015091889 | WO 2007023110 | U.S. 20040097493 | WO 2001021591 |
| WO 2014083026 | WO 2007023105 | WO 2004014907 | WO 9957101 |
| WO 2013174780 | WO 2006063856 | WO 2003082871 | WO 9920624 |
| WO 2012074933 | WO 2006048266 | WO 2003074530 | WO 2008024391 |
| WO 2011050192 | WO 2005085248 | WO 2003020715 | WO 2006055302 |
| U.S. 20080207684 | WO 2005085206 | WO 2002064594 | U.S. 20060079461 |
| U.S. 20080146590 | EP 1538201 | WO 2002018380 | U.S. 20060058296 |
| WO 2007023111 | U.S. 20050107408 | WO 2002018379 | U.S. 20060052390 |
| U.S. 20050288299 | WO 2004019873 | U.S. 6,340,685 | U.S. 8,497,269 |
| WO 2005065691 | WO 2004010929 | WO 2001064676 | WO 2010083246 |
| WO 2005033072 | WO 2003097615 | WO 2000071535 | U.S. 7,759,337 |
| WO 2005032481 | U.S. 6,589,954 | WO 2000059904 | WO 2010042649 |
| WO 2005032551 | U.S. 6,476,031 | WO 2000012497 | WO 2010042646 |
| U.S. 6,867,209 | U.S. 6,448,257 | WO 9961426 | WO 2010025202 |
| WO 2004053107 | U.S. 20020115671 | U.S. 8,772,481 | WO 2010025201 |
| WO 2004032874 | WO 2002046158 | U.S. 8,420,649 | WO 2009117156 |
| WO 2004022712 | WO 2002044168 | U.S. 8,367,671 | WO 2009078992 |
| WO 2004022712 | WO 2002042292 | U.S. 8,314,131 | WO 2009038784 |
| WO 2009011871 | WO 2006044860 | WO 2009034432 | U.S. 20060111416 |
| WO 2009011880 | WO 2006039718 | WO 2008135819 | WO 2006051373 |
| WO 2008136948 | U.S. 20030236193 | WO 2008041095 | WO 2006051375 |
| WO 2008137176 | U.S. 20170073343 | WO 2007107828 | U.S. 20060035922 |
| WO 2008045393 | WO 2014181213 | WO 2007091176 | WO 2005090288 |
| WO 2008011032 | WO 2011083387 | WO 2007091152 | EP 1577292 |
| WO 2007124181 | WO 2010007552 | WO 2007072163 | EP 1577291 |
| WO 2007084391 | WO 2010007561 | WO 2007052124 | EP 1574501 |
| WO 2007024754 | WO 2010004517 | WO 2007045989 | WO 2005060967 |
| WO 2006094187 | WO 2009069032 | WO 2007034325 | WO 2005009966 |
| WO 2005009965 | WO 2004020440 | WO 2007075896 | WO 2004014900 |
| U.S. 20050026952 | WO 2004020438 | WO 2007056016 | WO 2002094833 |
| U.S. 20050020626 | WO 2003032894 | WO 2012074761 | WO 2008001929 |
| U.S. 20050020587 | EP 1247810 | WO 2007053394 | WO 2008001930 |
| WO 2004108675 | WO 2002072579 | WO 2007053346 | WO 2006070927 |
| WO 2004072072 | WO 2002072576 | WO 2006009741 | U.S. 8,202,899 |
| U.S. 20040157877 | WO 2004100946 | EP 1609789 | U.S. 8,044,083 |
| U.S. 20040092547 | WO 2008089034 | WO 2005080380 | WO 2009015000 |
| U.S. 20040087615 | WO 2008021388 | WO 2005075478 | WO 2007126871 |
| U.S. 20040077682 | WO 2007146712 | WO 2004026871 | WO 2007089646 |
| WO 2006122230 | WO 2009015169 | U.S. 20050176965 | U.S. 20040157846 |
| U.S. 20040192653 | U.S. 7,473,784 | WO 2005042537 | U.S. 20040067996 |
| U.S. 20040176325 | U.S. 20080275052 | U.S. 20050043306 | U.S. 20030229081 |
| U.S. 20110166154 | WO 2008079857 | WO 2005012875 | WO 2003099820 |
| WO 2012031057 | WO 2007103839 | U.S. 20040242602 | WO 2003099206 |
| WO 2010120963 | WO 2007016392 | WO 2004099156 | WO 2003091229 |
| WO 2009155389 | U.S. 20060235020 | WO 2004098528 | WO 2003090912 |
| WO 2009155388 | WO 2006084017 | WO 2004098518 | WO 2003082208 |
| WO 2009094556 | U.S. 20060019928 | U.S. 20040209886 | WO 2003002544 |
| U.S. 20090041722 | WO 2005077945 | WO 2004069793 | U.S. 20020137747 |
| WO 2002040486 | WO 2010129208 | WO 2006055404 | WO 2005005380 |
| WO 2001047897 | WO 2009152072 | WO 2006040056 | WO 2004100874 |
| U.S. 8,846,931 | WO 2008103276 | WO 2006026196 | WO 2004041277 |
| U.S. 20120157500 | WO 2008048540 | U.S. 20050277681 | WO 2003103590 |
| U.S. 9,051,318 | WO 2007115670 | WO 2005105091 | WO 2003092588 |
| U.S. 8,003,657 | WO 2007038444 | WO 2005082862 | WO 2003077919 |
| U.S. 8,513,289 | WO 2007021710 | WO 2005075425 | WO 2003059293 |
| WO 2012119690 | WO 2007016358 | WO 2005058308 | WO 2003039534 |
| WO 2012003912 | WO 2006060108 | WO 2005025572 | WO 2003026568 |
| WO 2012000595 | WO 2006058023 | WO 2005005606 | WO 2003000682 |
| WO 2002085405 | U.S. 20140296208 | WO 2017093208 | WO 2013083604 |
| WO 2002058695 | WO 2014140582 | U.S. 8,916,708 | WO 2013083206 |
| U.S. 20160016934 | WO 2014076484 | U.S. 8,450,314 | WO 2013083606 |
| U.S. 20150225373 | WO 2014033449 | U.S. 8,557,797 | WO 2012168359 |
| WO 2016051188 | WO 2014033447 | WO 2016166239 | WO 2011154738 |
| WO 2016051187 | WO 2014033448 | WO 2016128456 | WO 1997025046 |
| WO 2016051186 | WO 2014033446 | WO 2014195402 | WO 1998047892 |
| WO 2015121660 | WO 2014027209 | WO 2014195400 | JP 2009263234 |
| WO 2015121444 | WO 2017134053 | WO 2014194956 | U.S. 2011250197 |
| WO 2015092423 | WO 2017108736 | U.S. 20140069419 | U.S. 2015232449 |
| U.S. 9,427,439 | WO 2000043384 | WO 2005058308 | WO 2016198698 |
| WO 1998027098 | WO 2001004115 | WO 2005063715 | WO 2004072038 |

-continued

| | | | |
|---|---|---|---|
| WO 2005091891 | WO 2002007772 | WO 2005091891 | WO 2007103468 |
| WO 2010038428 | WO 2003005999 | WO 2005110455 | WO 2010038428 |
| WO 2012154814 | WO 2003015828 | WO 2006127678 | WO 2010093889 |
| WO 2016007616 | WO 2003049742 | WO 2013007708 | WO 2010093890 |
| WO 2017075013 | WO 2003068223 | WO 2014155135 | WO 2016159301 |
| U.S. 5,670,527 | WO 2003084503 | WO 2015006752 | WO 2017110093 |
| WO 1996021452 | WO 2005009367 | WO 2015006753 | WO 1999057101 |
| WO 1997035856 | WO 2005018624 | WO 2016159301 | WO 2001021591 |
| WO 2005091891 | WO 2007147104 | WO 2011119863 | WO 2003041644 |
| WO 2006127678 | WO 2013086002 | WO 2000031063 | WO 2004019873 |
| WO 1999001130 | U.S. 6,096,753 | WO 2003068747 | WO 2004021988 |
| WO 2002064594 | WO 2001042189 | WO 2006127678 | WO 2005032551 |
| WO 2005023201 | WO 2002045752 | WO 2007144390 | WO 2006055302 |
| WO 2000071535 | WO 2001026645 | WO 2014014706 | WO 2007005863 |
| U.S. 2016166587 | WO 2002069892 | WO 2015004089 | WO 2008013823 |
| WO 2002059083 | WO 2007016201 | WO 2016066687 | WO 2008024391 |
| WO 2006127678 | WO 2008105808 | U.S. 6,867,209 | WO 2016049677 |
| WO 2007059500 | WO 2011119848 | WO 2000071535 | WO 2005018557 |
| WO 2008072079 | U.S. 20040192653 | WO 2013130573 | WO 2005023761 |
| WO 2014181213 | WO 2006122230 | WO 2014134313 | WO 2007103839 |
| WO 2017110093 | WO 2007126871 | WO 2005009973 | WO 2009158446 |
| WO 2005075478 | WO 2008076265 | WO 2007096151 | WO 2009158450 |
| WO 2013070460 | U.S. 2009312331 | WO 2013139809 | WO 2018148797 |
| WO 2016049677 | U.S. 2012108594 | WO 2004099156 | WO 201800778 |
| WO 2016159301 | WO 2003090912 | WO 2008079857 | WO 2017117182 |
| WO 2006070927 | WO 2006020904 | WO 2004076450 | WO 2010/040843 |
| WO 2008099615 | WO 2012031057 | U.S. 2010093734 | |
| WO 2006089798 | WO 2007089646 | U.S. 2011117055 | |

The above-listed patents and publications are incorporated herein by reference herein in their entireties.

The present disclosure provides methods of reducing the expression a DUX4-fl mRNA, a DUX4 polypeptide, or a polypeptide encoded by a downstream target gene of DUX4, in cells, comprising contacting the cells with a p38 agent that results in a reduction of active p38 protein in the cell, thereby reducing expression the DUX4 polypeptide or the polypeptide encoded by the downstream target gene of DUX4. These methods may be practiced using a variety of different types of p38 agents, and for modulating a variety of different biological processes in the cell, such as inhibiting apoptosis, as well as for treating subjects for diseases associated with aberrant DUX4 expression, such as FSHD. In particular embodiments, the p38 protein is p38-α and/or p38-β. In particular embodiments, the p38 protein is not p38-γ. In certain embodiments, the p38 agent binds a p38 protein, e.g., p38-α or p38-β, or binds a polynucleotide encoding the p38 protein, e.g., p38-α or p38-β, or an antisense polynucleotide thereof.

In certain embodiments of any of the methods disclosed herein, the cell is a muscle cell, optionally a terminally differentiated muscle cell. In some embodiments, the cell has an increased expression level of the DUX4-fl mRNA, the DUX4 polypeptide, or the polypeptide encoded by the downstream target gene, as compared to the expression level of the DUX4-fl mRNA, the DUX4 polypeptide, or the polypeptide encoded by the downstream target gene, in a control cell, e.g., a cell obtained from a healthy subject. In some embodiments, the increased expression level of the DUX4-fl mRNA, the DUX4 polypeptide, or the polypeptide encoded by the downstream target gene, is due to reduced repression at a D4Z4 locus in the cell. In certain embodiments, the cell is associated with facioscapulohumeral muscular dystrophy (FSHD), e.g., it was obtained from a subject diagnosed with FSHD or is present within a subject diagnosed with FSHD. In some embodiments, the cell comprises a deletion of one or more macrosatellite D4Z4 repeats in the subtelomeric region of chromosome 4q35, optionally wherein the cell comprises <7 macrosatellite D4Z4 repeats in the subtelomeric region of chromosome 4q35. In some embodiments, the cell comprises one or more mutations in a Structural Maintenance Of Chromosomes Flexible Hinge Domain Containing 1 (SMCHD1) gene. In some embodiments, the cell comprises at least one non-deleted 4qA allele. In certain embodiments of the methods disclosed herein, the p38 agent inhibits the expression or activity, or reduces the amount, of the p38 protein, wherein the activity is optionally kinase activity.

In some embodiments, the p38 agent inhibits the expression of the p38 protein. In particular embodiments, the p38 agent binds a polynucleotide encoding the p38 protein, or binds an antisense polynucleotide thereof. In particular embodiments, the p38 agent comprises or consists of a nucleic acid, optionally a DNA, RNA, guide RNA (gRNA), short hairpin RNA (shRNA), small interfering RNA (siRNA), or antisense oligonucleotide.

In some embodiments, the p38 agent inhibits the activity of the p38 protein. In particular embodiments, the p38 agent binds the p38 protein. In particular embodiments, the p38 agent comprises or consists of a polypeptide, optionally a protein, a peptide, a protein mimetic, a peptidomimetic, or an antibody or functional fragment thereof. In some embodiments, the p38 agent comprises a small molecule, optionally a small organic molecule or a small inorganic molecule.

In certain embodiments of any of the methods disclosed herein, the downstream target gene is RFPL2, CCNA1, SLC34A2, TPRX1, KHDC1L, ZSCAN4, PRAMEF20, TRIM49, PRAMEF4, PRAME6, PRAMEF15 or ZNF280A.

In particular embodiments of any of the methods disclosed herein, the expression or the activity of the p38 protein, or the amount of the p38 protein, is reduced by at least 10%, at least 20%, at least 30%, at least 40%, at least 50%, at least 60%, at least 70%, at least 80%, at least 90%, at least 95%, at least 98%, at least 99%, or 100%.

In a related embodiment, the present disclosure provides a method of treating or preventing a disease or disorder associated with increased expression of a DUX4-fl mRNA, a DUX4 protein, or a polypeptide encoded by a downstream target gene of DUX4, in a subject in need thereof, comprising providing to the subject a pharmaceutical composition comprising an p38 agent that results in a reduction in the amount of active p38 protein in one or more tissue of the subject, thereby reducing expression of the DUX4-fl mRNA, the DUX4 protein, or the polypeptide encoding the downstream target gene in one or more tissue of the subject.

In many embodiments, the cells are muscle cells. In some embodiments, the cells are terminally-differentiated muscle cells.

In some embodiments, the cells include one or more mutations in a Structural Maintenance Of Chromosomes Flexible Hinge Domain Containing 1 (SMCHD1) gene. In some embodiments, the cells may include at least one non-deleted 4qA allele.

In many embodiments, the cells may include an increased expression level of a DUX4 polypeptide, or a polypeptide encoded by one or more downstream target genes, as compared to the expression level of a DUX4 polypeptide, or a polypeptide encoded by one or more downstream target genes in a control cell.

In many embodiments, the DUX4 is a DUX4 full length (DUX4-fl).

In some embodiments, the cells may be associated with FSHD.

In some embodiments, the disorder is associated with DUX4 gene expression.

In some embodiments, the disorder is associated with DUX4 gene expression and the DUX4 gene expression may result from the subject having less than 10 D4Z4 repeats in the subtelomeric region of chromosome 4q35. In some embodiments, the cells may include a deletion of one or more macrosatellite D4Z4 repeats in the subtelomeric region of chromosome 4q35. In other embodiments, the cells may include less than 7 macrosatellite D4Z4 repeats in the subtelomeric region of chromosome 4q35.

In some embodiments, the cells may include a dysregulated D4Z4 array at chromosome 4q35 prior to administration of the p38 agent. In one embodiment, the cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the cells are muscle cells and the cells may include a dysregulated D4Z4 array at chromosome 4q35 prior to administration of the p38 agent. In one embodiment, the muscles cells may include a dysregulated D4Z4 array including fewer than 11 repeat units. In some embodiments, the dysregulated D4Z4 array may include fewer than 11, 10, 9, 8, 7, 6, 5, 4, 3, or 2 repeat units.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

In one embodiment, the disorder is ICF.
In one embodiment, the disorder is ALS.
In one embodiment, the disorder is IBM.
In one embodiment, the disorder is cancer. The cancer may be selected from Ewing's sarcoma, soft tissue sarcoma, rhabdomyosarcoma, and adult and pediatric B-cell acute lymphoblastic leukemia.

In some embodiments, the disorder may be selected from one or more of: FSHD1, FSHD2, ICF, ALS, IBM, Ewing's sarcoma, soft tissue sarcoma, rhabdomyosarcoma, and adult and pediatric B-cell acute lymphoblastic leukemia.

In one embodiment, the subject is identified as having FSHD based upon the presence of a transcriptionally active DUX4. In another embodiment, the subject is identified as having FSHD based upon the presence of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in muscle. In another embodiment, the subject is identified as having FSHD based upon the presence of increased expression levels of one or more downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A relative to a healthy control. In another embodiment, the subject is identified as having FSHD based upon the presence of a transcriptionally active DUX4 and the presence of downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject prior to the administration of the p38 agent. The method may further include determining that the subject is in need of treatment if the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A is/are elevated relative to a healthy control.

In another embodiment, the method may include measuring the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the cells of the subject before and after the administration of the p38 agent. The method may include comparing the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A in the subject before and after the administration of the p38 agent. The method may include determining the effectiveness of treatment by the comparing of the expression level of one or more of: DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A before and after the administration of the p38 agent, wherein a decrease in the expression level(s) is indicative of effective treatment.

In some embodiments, the p38 agent reduces one or more downstream genes selected from ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In one embodiment, the p38 agent reduces MBD3L2.
In one embodiment, the p38 agent reduces ZSCAN4.
In one embodiment, the p38 agent reduces LEUTX.
In one embodiment, the p38 agent reduces PRAMEF2.
In one embodiment, the p38 agent reduces TRIM43.
In one embodiment, the p38 agent reduces KHDC1L.
In one embodiment, a transcriptional modulator of DUX4 and downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A are inhibited by p38 kinase.

In some embodiments, the administering may be combined with clinical management involving physical therapy, aerobic exercise, respiratory function therapy, orthopedic interventions.

In some embodiments, the administering includes administering of the p38 agent with another pharmaceutical agent.

In some embodiments, the administering includes administering of the p38 agent with another pharmaceutical agent for the treatment of FSHD.

In some embodiments, the administering causes a decrease in muscle degeneration.

In some embodiments, the administering causes a reduction in apoptosis of muscle cells in the subject. In one embodiment, the muscles cells are terminally differentiated.

In several embodiments, a method for treating facioscapulohumeral muscular dystrophy (FSHD) is provided. The method may include administering to a subject in need thereof, an effective amount of a p38 agent described herein, or a stereoisomer thereof, an isotopically-enriched compound thereof, a prodrug thereof, a solvate thereof, or a pharmaceutically acceptable salt thereof.

In some embodiments, the disorder is FSHD. FSHD may include one or more of FSHD1 and FSHD2. In one embodiment, the disorder is FSHD1. In another embodiment, the disorder is FSHD2. In one embodiment, the disorder is FSHD1 and FSHD2.

Modified Compounds of the Invention

A modified compound of any one of such compounds including a modification having an improved, e.g., enhanced, greater, pharmaceutical solubility, stability, bioavailability and/or therapeutic index as compared to the unmodified compound is also contemplated. The examples of modifications include by not limited to the prodrug derivatives, and isotopically-labeled compounds, e.g., deuterium-enriched compounds.

Prodrug derivatives: prodrugs, upon administration to a subject, will converted in vivo into active compounds of the present invention (Nature Reviews of Drug Discovery, 2008, 7:255). It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in Bioorganic and Medicinal Chemistry Letters, 1994, 4:1985.

Certain isotopically-labelled compounds of the various Formulae (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the various Formulae can generally be prepared by following procedures analogous to those disclosed in the Schemes and/or in the Examples herein below, by substituting an appropriate isotopically labelled reagent for a non-isotopically labelled reagent.

Deuterium-enriched compounds: deuterium (D or 2H) is a stable, non-radioactive isotope of hydrogen and has an atomic weight of 2.0144. Hydrogen naturally occurs as a mixture of the isotopes xH (hydrogen or protium), D (2H or deuterium), and T (3H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

The present disclosure is intended to include all isotopes of atoms occurring in the present compounds. Isotopes include those atoms having the same atomic number but different mass numbers. In particular one, some, or all hydrogens may be deuterium. Radioactive isotopes may be used, for instance for structural analysis or to facilitate tracing the fate of the compounds or their metabolic products after administration. By way of general example and without limitation, isotopes of hydrogen include deuterium and tritium and isotopes of carbon include C-13 and C-14.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, bicarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-(C1_4) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs (Mal. Cancer Therapy, 2004 March; 3(3):233-244). Compounds of the present invention that comprise tertiary nitrogen atoms may be oxidized by such agents as hydrogen peroxide (H2O2), Caro's acid or peracids like meta-Chloroperoxybenzoic acid (mCPBA) to from amine oxide.

Pharmaceutical Compositions

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-a-tocopheryl PEG 1000 succinate (20-50%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered topically, orally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, intrathecally, transmucosally, pulmonary, or parenterally, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly. For example, the administering may be combined with myostatin inhibitors, anti-inflammatory agents, and gene therapy to reduce pathogenic DUX4 protein production in FSHD by controlling D4Z4 methylation, suppressing DUX4 mRNA, and inhibiting DUX4 pathways. For example, the administering may be combined with small interfering RNA (siRNA), small hairpin RNA (shRNA), microRNA (miRNA), CRISPR gene editing, and antisense oligonucleotides directed at DUX4 and downstream transcripts.

The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, syrups, emulsions, oils and the like. For parenteral administration, reconstitution of a lyophilized powder is typically used.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms and suitable pharmaceutical excipients can also be well used and adjusted by those skilled in the art. All changes and modifications are envisioned within the scope of the present patent application.

In some embodiments, a compound described herein may be administered at a dosage from about 1 mg/kg to about 60 mg/kg, or more. For example, the compound may be administered to a subject at a dosage of 5, 10, 15, 20, 25, 40, 35, 40, 45, 50, 55, or 60 mg/kg, or within a range between any of the proceeding values, for example, between about 30 mg/kg and about 40 mg/kg, between about 5 mg/kg and about 20 mg/kg, and the like. In another embodiment, a compound described herein may be administered at a dosage from about 1 mg/kg to about 20 mg/kg. For example, the compound may be administered to a subject at a dosage of 1, 2, 3, 4, 5, 6, 7, 8, 9, 10, 11, 12, 13, 14, 15, 16, 17, 18, 19 or 20 mg/kg, or within a range between any of the proceeding values, for example, between about 10 mg/kg and about 15 mg/kg, between about 6 mg/kg and about 12 mg/kg, and the like. In another embodiment, a compound described herein is administered at a dosage of ≤15 mg/kg. For example, a compound may be administered at 15 mg/kg per day for 7 days for a total of 105 mg/kg per week. For example, a compound may be administered at 10 mg/kg twice per day for 7 days for a total of 140 mg/kg per week.

In many embodiments, the dosages described herein may refer to a single dosage, a daily dosage, or a weekly dosage.

In one embodiment, a compound may be administered up to 120 mg/kg per day.

In one embodiment, a compound may be administered up to 840 mg/kg per week

In one embodiment, a compound may be administered once per day. In another embodiment, a compound may be administered twice per day. In some embodiments, a compound may be administered three times per day. In some embodiments, a compound may be four times per day.

In some embodiments, a compound described herein may be administered 1, 2, 3, 4, 5, 6, 7, 8, 9, 10, 11, 12, 13, 14, 15, 16, 17, 18, 19, 20, 21, 22, 23, or 24 times per week. In other embodiments, the compound is administered once biweekly.

In some embodiments, a compound described herein may be administered orally.

In some embodiments, a compound described herein may be administered orally at a dosage of ≤15 mg/kg once per day.

In some embodiments, the compound of Formula (V') may be administered orally at a dosage of ≤15 mg/kg once per day.

In some embodiments, a compound described herein is administered orally at ≤15 mg/kg twice per day.

In some embodiments, the compound of Formula (V') may be administered orally at a dosage of ≤15 mg/kg twice per day.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The amount and frequency of administration of the compounds of the invention and/or the pharmaceutically acceptable salts thereof will be regulated according to the judgment of the attending clinician considering such factors as age, condition and size of the patient as well as severity of the symptoms being treated.

ASO antisense oligonucleotides
DAPI 4',6-diamidino-2-phenylindole (dihydrochloride)
DMSO dimethyl sulfoxide
DUX4 double homeobox 4
DUX4-fl double homeobox 4 full length
FSHD facioscapulohumeral muscular dystrophy
gRNA guide RNA
MBD3L2 methyl CpG binding domain protein 3 like 2
MHC myosin heavy chain MPAK14 mitogen-activated protein kinase 14
mRNA messenger RNA
MYOG myogenin (myogenic factor 4)
p HSP27 phosphorylated heat shock protein 27
PCR polymerase chain reaction
pLAM polyadenylation signal sequence
POLR2A RNA Polymerase II Subunit A
qPCR quantitative polymerase chain reaction
RNA ribonucleic acid
sgRNA single guide RNA
siRNA small interfering RNA

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure.

Materials and Methods

Materials:

Human Skeletal Muscle Myoblasts:

FTCE-00016-01 (immortalized FSDH myoblast line, 6.3 repeats) and isogenic lines A4 control healthy normal and C12 FSHD myoblasts were used for all studies (as described in Mamchaoui et al., 2011; Thorley et al., 2016). Four distinct patient myoblast lines, FTCE-016, -020, -197, -196 were provided by R. Tawil. The FSHD myoblasts were shown to express aberrant DUX4 via demethylation of the D4Z4 on chromosome 4q35.

Media Components and Tissue Culture Materials Included:

Skeletal Muscle Growth Medium (PromoCell, C-23160) supplemented with 15% FBS (Hyclone, SH30071) and Pen/Strep (Gibco, 15140148). Skeletal Muscle Cell Differentiation Medium (PromoCell, C-23061) supplemented with 20% KnockOut Serum Replacement (Gibco, 10828010) and Pen/Strep (Differentiation media). EmbryoMax 0.1% Gelatin Solution (EMDmillipore ES-006-B). PBS (Gibco, 10010023), Tissue culture treated 96-well microplate (Corning, CLS3595), TC-Treated Multiwell Cell Culture Plat (Falcon, 353046).

Real Time PCR Reagents and Kits:

Lysis buffer-Roche Realtime Ready lysis buffer 19.5 µL. (for 20 µL) (Roche, 07248431001), DNAse I (Ambion, AM2222) 0.25 µL, Protector RNase Inhibitor (Roche, 3335402001) 0.25 µL. RNeasy Micro Kit (Qiagen, 74004), Taqman Preamp Master Mix (ThermoFisher Scientific, 4391128), Taqman Multiplex Master Mix (ThermoFisher Scientific, 4484262), ZSCAN4 Taqman Assay (ThermoFisher Scientific, Hs00537549_m1, FAM-MGB), MYOG Taqman Assay (ThermoFisher Scientific, HsO1072232_m1, JUN-QSY), RPLP0 Taqman Assay (ThermoFisher Scientific, Hs99999902_m1), LEUTX Tagman Assay (ThermoFisher Scientific, Hs00418470_m1).

Antisense Oligonucleotides (ASOs)

ASOs were purchased from Exiqon: FTSE-000001 (DUX4 ASO from Exiqon, CAGCGTCGGAAGGTGG (SEQ ID NO: 1), 300610)), Non-targeting ASO (Exiqon, AACACGTCTATACGC (SEQ ID NO: 2), 300610)

Gelatin Coating of Tissue Culture Dishes:

Performed three days prior to treatment, 0.1% gelatin solution was made by combining 1 g gelatin (e.g. Sigma G9391) and 1 L tissue culture grade water; autoclave for 30 minutes to dissolve and sterilize. Sufficient 0.1% gelatin to coat the using a sterile pipette, aspirate the solution until all of the dishes have been coated. Air dried and store in original sleeve at room temperature.

Cell Plating: Performed three days prior to treatment, 10000 cells were plated per well on gelatinized 96-well plates, or 100000 cells on gelatinized 6-well plates.

Antisense Oligonucleotide and Compound Treatment:

For ASO or compound treatments cells were plate into 100 µL of Promocell growth medium containing ASO or compounds at the described concentrations.

Skeletal Muscle Myotube Differentiation:

On day 0, change to differentiation media. Remove plates from the incubator and aspirate the growth medium, Wash once with PBS, 100 µL for 96-wells and 1 mL for a 6-well plate, Add 100 µL or 2 mL of differentiation medium per well, 96- or 6-well respectively. Add antisense oligonucleotides or drug at the desire concentration and put back in the incubator. Fusion should start within day 1-2. Incubate for 3-4 days.

RNA Preparation:

Cells were removed from the incubator and media aspirated. Quickly lysed following one of the following protocols: For lysis in 96-well plates direct lysis and one-step RT-Preamp qPCR protocol described below. For each 96-well prepare a mix containing: 19.5 µL Roche Realtime Ready lysis buffer, 0.25 µL RNAse inhibitor, 0.25 µL DNAseI (from Thermo not the included one in the kit). 20 µL of the mix was added to each well, mix 5 times and incubated 5 minutes at RT or alternatively shaken vigorously for 15 minutes. Lysis was observed under the microscope. Samples were frozen $-80°$ C. at least for 15 minutes, qPCR One Step:

For qPCR, dilute 1:10 and use 2 µL for a 10 µL 1-step RT-qPCR reaction. For detection of GAPDH, RPLP0, TBP, MYOG, FRG1, MYH3, ACTN2, etc.). Per 10 µL reaction: RNA (1:10 dilution lysate) 2 µL, Fast Advanced Taqman Master Mix (2×) 5 µL, RT enzyme mix (40×) 0.25 µL, Taqman probe set (20×) 0.5 µL, $H_2O$ 2.25 µL. The following reaction protocol was run on the QuantStudio 7: 48° C. for 15 min, 50° C. for 2 min, 95° C. for 30 sec, 40×, 95° C. for 5 sec, 60° C. for 30 sec, then plates were read as specified by the manufacturer (Thermo). For 1-step RT-Preamplification used for detection of DUX4 downstream genes, i.e. MBD3L2, ZSCAN4, LEUTX, TRIM43, KHDC1L. POL2RA-VIC was used as Endogenous control). Per 10 µL reaction: RNA (1:10 dilution lysate) 2.25 µL, Taqman PreAmp Master Mix (2×) 5 µL, RT enzyme mix (40×) 0.25 µL, Taqman probe set (0.2×)*2.5 µL, * Pooling the TaqMan Assays: equal volumes of each 20× TaqMan® Gene Expression Assay, up to 100 assays were combined. For example, to pool 50 TaqMan assays, 10 µL of each assay were combined in a microcentrifuge tube. The pooled TaqMan assays were diluted using 1×TE buffer so that each assay is at a final concentration of 0.2×. For the above example, add 500 µL of 1×TE buffer to the pooled TaqMan assays for a total final volume of 1 mL. The QuantStudio7 protocol was used 48° C. 15 min, 95° C. 10 min, 10 cycles: 95° C. 15 sec, 60° C. 4 min, 4° C. infinite. Samples were then diluted to 50 µL and continue with the qPCR step. Per 10 µL reaction: Preamp dilution 2 µL, Fast Advanced Taqman Master Mix (2×) 5 µL, Taqman probe set (20×) 0.5 µL, $H_2O$ 2.5 µL. When multiplexing the volume was adjusted to 10 µL total). The following program was run on the QuantStudio7: 50° C.

for 2 min, 95° C. for 30 sec, 40×, 95° C. for 5 sec, 60° C. for 30 sec, plates were read as per the manufacturers specifications (Thermo).

Methods for Total RNA Extraction from Myotubes Using RNeasy Micro Plus Kit:

In a 6 well plate, 450 μL Buffer RLT Plus was added. Lysate was homogenized by transfer the lysate to a gDNA Eliminator spin column placed in a 2 mL collection tube (supplied), centrifuged for 30 s at ≥8000×g (≥10,000 rpm) and discarded column while saving the flow-through. Then 250 μL of Ethanol (35% final) was added to the flow-through, and mixed well by pipetting, not centrifuged. Then samples were transferred, including any precipitate that may have formed, to an RNeasy MinElute spin column placed in a 2 mL collection tube (supplied). Then centrifuged for 15 s at ≥28000×g. Flow-through was discarded or collected for Protein precipitation. 700 μL Buffer RW1 to the RNeasy MinElute spin column was added then centrifuge for 15 s at ≥8000×g. and discard the flow-through. DNAse treatment was performed by gently mixing 10 μL DNAseI with 70 μL of Buffer RDD and added directly to the column, incubated at room temperature for 20 min. Then, 700 μL Buffer RW1 (per manufactures specification) to the RNeasy MinElute spin column, centrifuged for 15 s at ≥8000×g. and the flow-through discarded. 500 μL Buffer RPE was added to the RNeasy MinElute spin column centrifuged for 15 s at ≥8000×g and discarded the flow-through. 500 μL of 80% ethanol was added to the RNeasy MinElute spin column, centrifuged for 2 min at ≥8000×g to wash the spin column membrane and the collection tube was discarded with the flow-through. The RNeasy MinElute spin column was placed in a new 2 mL collection tube (supplied) centrifuged at full speed for 5 min to dry the membrane and the collection tube was discarded with the flow through. RNeasy MinElute spin column was placed in a new 1.5 mL collection tube (supplied). 14 μL RNase-free water was added directly to the center of the spin column membrane, and centrifuged for 1 min at full speed to elute the RNA. You should end up with about 12 μL of eluted RNA.

Detection of DUX4-Fl Using Method Described by Himeda et al. 2015:

cDNA preparation. Per 10 μL reaction: RNA (1 μg) 1 μL, Oligo dT 0.5 μL, 10 mM dNTPs 0.5 μL, H$_2$O 4.5 μL, Samples were Incubated at 65° C. for 2 min and quickly move to ice and held at least 1 min before adding the enzyme mix, 5× First strand Buffer 2 μL, 0.1M DTT 0.5 μL, RNAse inhibitor 0.5 μL, SSIV RT 0.5 μL, samples were incubated at 55° C. for 20 min and 80° C. for 10 min, with cool down to 4° C. DUX4 pre-amplification was performed: Per 10 μL reaction, RT reaction 1 μL, 5×GC buffer 2 μL, DMSO 0.8 μL, 10 mM dNTPs 0.2 μL, 10 μM TJ38F 0.2 μL, 10 μM TJ40R 0.2 μL, Phusion II DNA pol 0.1 μL, H$_2$O 5.5 μL. The following protocol was run on the QuantStudio 7: 98° C. 2 min, 10 cycles of 98° C., 15 seconds, 64° C., 20 seconds, 72° C., 15 seconds, 4° C. infinite. DUX4 qPCR with nested primers: per 10 μL reaction, DUX4 pre amplification DNA 1 μL, 2× IQ SYBR Mix 5 μL, 10 μM TJ38F 0.4 μL, 10 μM TJ41R 0.4 μL, H$_2$O 3.2 μL. The following protocol was run on the QuantStudio7 95° C. 3 min, 40 cycles of, 95° C. 10 seconds, 64° C. 15 seconds, 72° C. 20 seconds, 86° C. 10 seconds then read plate on QuantStudio7 as per manufactures instruction (Thermo). Ct values were extracted from the QuantStudio Realtime PCR software and Genedata was used to calculate relative levels of expression using POLR2A as a housekeeping gene.

FSHD Myotube Immunocytochemistry

Briefly, cells were fixed in 4% paraformaldehyde and permeabilized in 4% paraformaldehyde (PFA) for 10 min at room temperature. Cells were permeabilized with PBST (1×PBS solution with 0.1% Triton X-100) before blocking with 10% Normal Donkey Serum or 3% BSA (NDS) in PBST. Cells were then incubated with appropriately diluted primary antibodies in PBST with 5% NDS for 1 hours at room temperature or 12 hours at 4° C., washed with PBST for 3 times at room temperature and then incubated with desired secondary antibodies in TBST with 5% NDS and DAPI to counter stain the nuclei. DUX4 was detected by immunocytochemistry using the E5-5 antibody in differentiated FSHD myotubes. Activated Caspase-3 was detected cell signaling antibody that we're using for ICC, Asp175 (https://www.cellsignal.com/products/primary-antibodies/cleaved-caspase-3-asp175-antibody/9661).

RNAseq Methods

The 40 bp single-end reads from Illumina had good quality by checking with FastQC (http://www.bioinformatics.babraham.ac.uk/projects/fastqc/). Reads were mapped to hg19 using TopHat v2.1.1. The gene model for TopHat was created by merging known Gene in gtf format with kgXref table. Both known Gene and kgXref were downloaded from UCSC table browser in hg19 assembly. The read counts were obtained using feature Counts function from Subread package with strandness option as −r 2. Reads were normalized with DESeq2. The biological replicates in the neuron samples, processed at different time periods, have batch effect as suggested by principle component analysis. Consequently, Combat was used for reducing this batch effect. Calculated standard RPKM expression values. Total gene signature is very small and defined at standard statistical cutoffs: 86/19,799 mRNA genes. DUX4-regulated gene signature is majority of total signature: 77/86 mRNA genes=90%. Non-DUX4 regulated genes is minority of total signature with moderate fold changes: 9/86 mRNA genes=10%; 2-2.7×log FC.

Methods for siRNA and Cas9/sgRNA RNP Transduction of FSHD Myotubes:

Synthetic crRNAs were purchased from Thermo Fisher Scientific and annealing to tracrRNAs was performed according to specifications. In short, crRNAs and tracrRNA were resuspended in TE buffer at 100 μM, mixed, and diluted 5-fold in annealing buffer. Annealing was performed in a ProFlex PCR system following manufacturers recommendation. 100 ng of assembled crRNA:tracrRNA were incubated with 500 ng of TrueCut Cas9 (ThermoFisher, #A36497) in the resuspension buffer provided with the Neon transfection system kit (ThermoFisher, #MPK10096). After 15 minute incubation the reaction was used to transfect 50.000 myoblasts according to the methods described. Sequences used for the targeting of MAPK14 (3 sgRNAs) and pLAM region (polyadenylation sequence of DUX4, 4 gRNAs) were:

NT-CTRL, (SEQ ID NO: 3)
GTATTACTGATATTGGTGGG;

MAPK14, (SEQ ID NO: 4)
GCTGAACAAGACAATCTGGG, (SEQ ID NO: 5)
CTGCTTTTGACACAAAAACG,

CTTATCTACCAAATTCTCCG; (SEQ ID NO: 6)

pLAM,
AGAATTTCACGGAAGAACAA, (SEQ ID NO: 7)

CAGGTTTGCCTAGACAGCGT, (SEQ ID NO: 12)

ATTAAAATGCCCCCTCCCTG, (SEQ ID NO: 8)

AATCTTCTATAGGATCCACA. (SEQ ID NO: 9)

siRNA MAPK14, Antisense:
UAGAUUACUAGGUUUUAGGUC, (SEQ ID NO: 10)

CCUAAAACCUAGUAAUCUAUU (SEQ ID NO: 11)

EXPERIMENTAL

Example 1

Repression of DUX4 Using Sequence Directed Antisense Oligonucleotide Reduces Downstream Target Genes Wild type myotubes were treated with DMSO control vehicle, and mature patient-derived FSHD myotubes that express DUX4 protein were treated with DMSO vehicle control or 1 µM of a DUX4 sequence-directed antisense oligonucleotide (ASO; FTX-2) purchased from Exiqon. After treatment, the myotubes were lysed in 19.5 µL of Roche Real Time Ready Lysis Buffer, 0.25 µL of DNAse1 (Ambion, AM2222), 0.25 µL of Protector RNase Inhibitor (Roche, 3335402001), and the RNA was collected in an RNeasy Micro Kit Master Mix. Expression levels of DUX4-regulated downstream genes (ZSCAN4, TRIM43, MBD3L2, LEUTX, and KHDC1L) was determined by real time PCR (ThermoFisher Scientific, 4484262), ZSCAN4 Taqman Assay (ThermoFisher Scientific, Hs00537549_m1, FAM-MGB), MYOG Taqman Assay (ThermoFisher Scientific, Hs01072232_m1, JUN-QSY), RPLP0 Taqman Assay (ThermoFisher Scientific, Hs99999902_m1), and/or LEUTX Taqman Assay (ThermoFisher Scientific, Hs00418470_m1). Ct values were extracted from QuantStudio Realtime PCR software, and Genedata was used to calculate relative levels of expression using POLR2A as a housekeeping gene.

Figure 2:
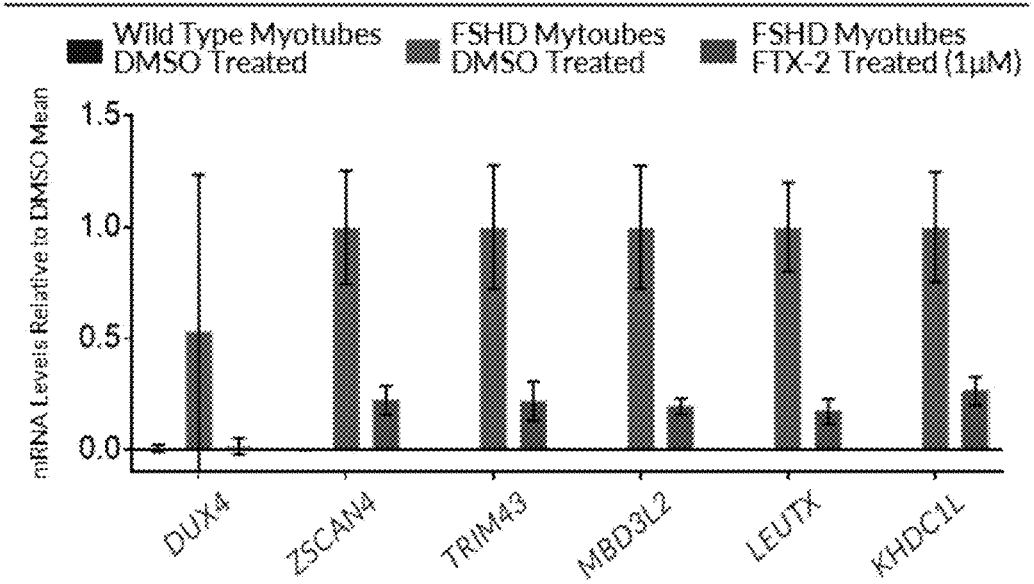
FIG. 2 is a graph showing mRNA expression of the indicated DUX4 regulated genes in wild type myotubes treated with DMSO, or FSHD myotubes treated with FTX-2 or DMSO. For each indicated gene, the bars from left to right correlate to wild type myotubes treated with DMSO, FSHD myotubes treated with DMSO, and FSHD myotubes treated with FTX-2 (DUX4-targeted ASO).

The results showed that FSHD myotubes treated with DUX4 sequence directed ASO express reduced amounts of DUX4 and the DUX4 downstream transcription factor target genes, ZSCAN4, TRIM43, MBD3L2, LEUTX, and KHDC1L, as compared to FSHD myotubes treated with DMSO vehicle control (FIG. 2).

Figure 3A:
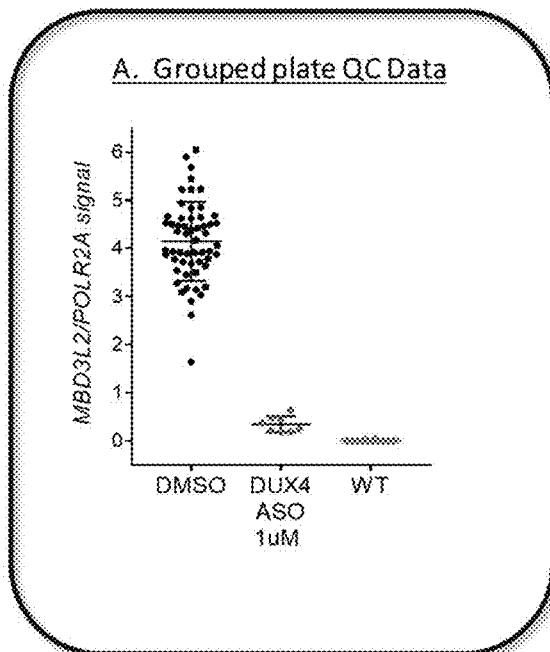
FIGS. 3A-3C show reduction of MBD3L2 mRNA in FSHD myotubes treated with DUX4-targeted ASOs. MBD3L2 was normalized to POLR2A mRNA as measured by qPCR.
Figure 3B:
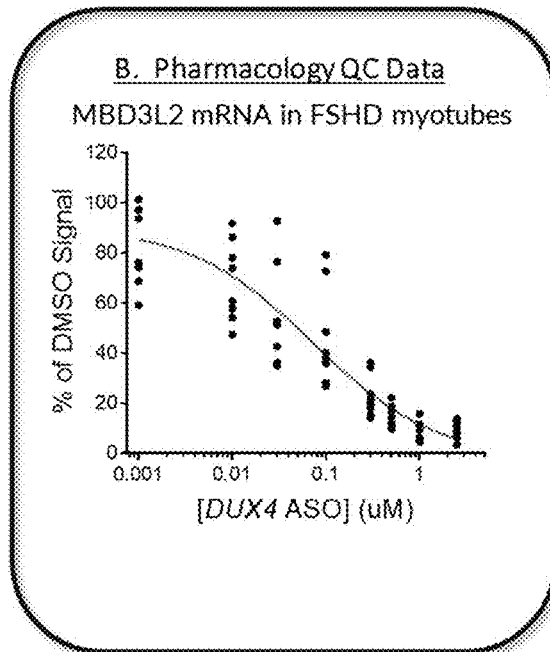
Figure 3C:
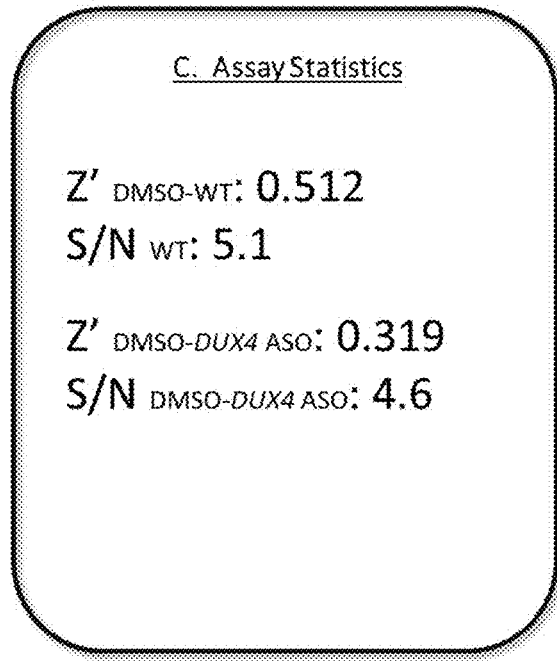

The data in FIG. 3A are grouped plate quality control data comparing expression of MBD3L2 mRNA in FSHD myotubes treated with DMSO control or 1 µM DUX4 ASO, and healthy normal isogenic control myotubes. FIG. 3B shows pharmacologic quality control data and dose dependent reduction of DUX4 and the downstream gene, MBD3L2, using different dilutions of the DUX4 ASO. FIG. 3C shows plate based assay statistics comparing FSHD myotubes treated with DMSO to WT: Z' is 0.512 and Signal to Noise (S/N) is 5.1, and FSHD myotubs treated with DMSO or DUX4 ASO:Z' is 0.319 and Signal to Noise (S/N) is 4.6.

Example 2

P38 Small Molecule Inhibitors Reduce MBD3L2 mRNA Expression

Figure 4A:
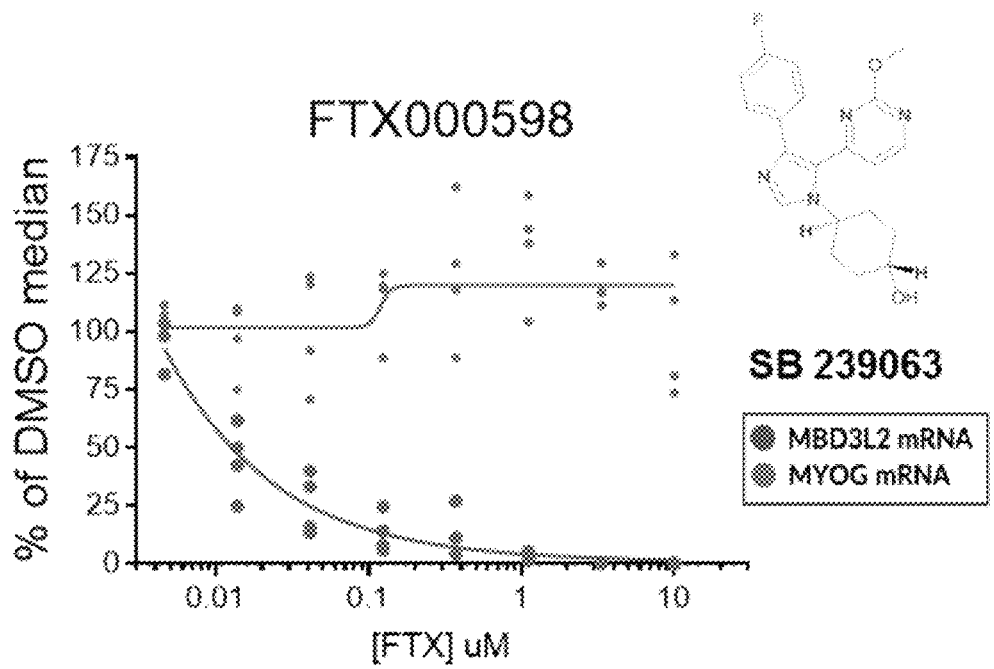
FIGS. 4A-4D are graphs showing expression levels of MBD3L2 mRNA and MYOG mRNA in FSHD myotubes treated with the indicated p38α/β inhibitors relative to treatment with DMSO control. The p38α/β inhibitors included SB 239063 (FIG. 4A), VX-702 (FIG. 4B), Pamapimod (FIG. 4C), and TAK-715 (FIG. 4D). The structures of the inhibitors are also provided.
Figure 4B:
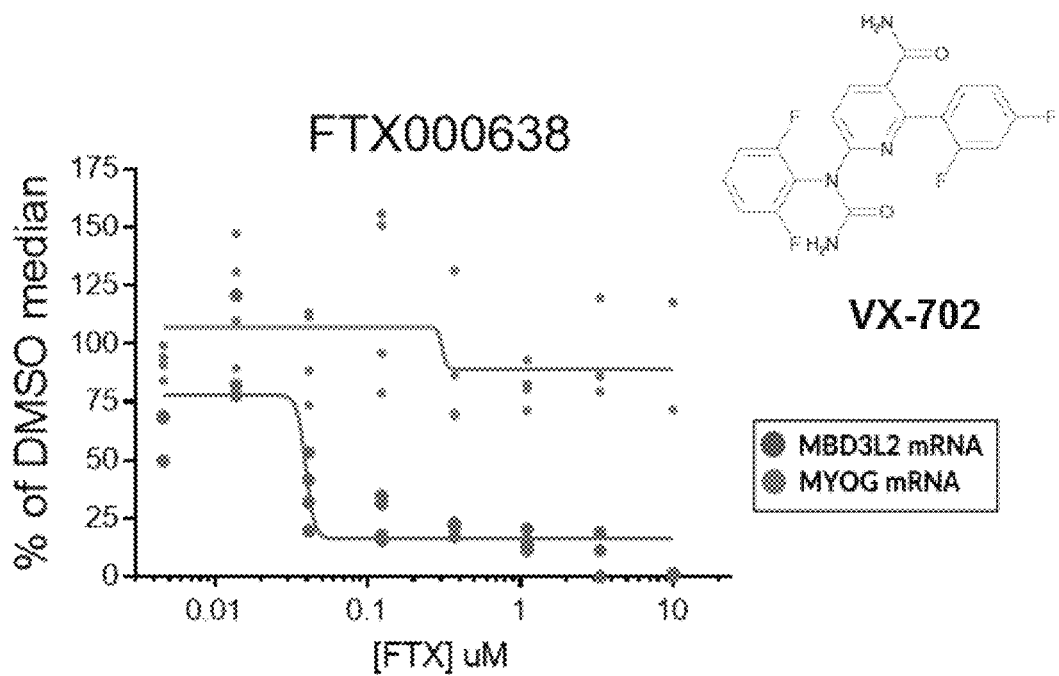
Figure 4C:
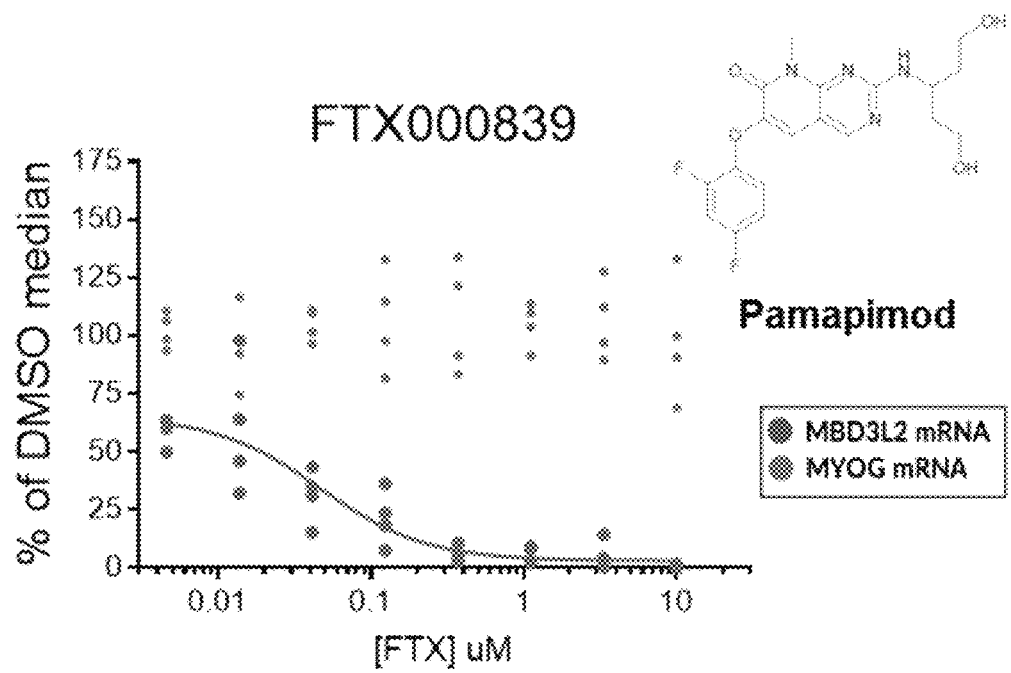
Figure 4D:
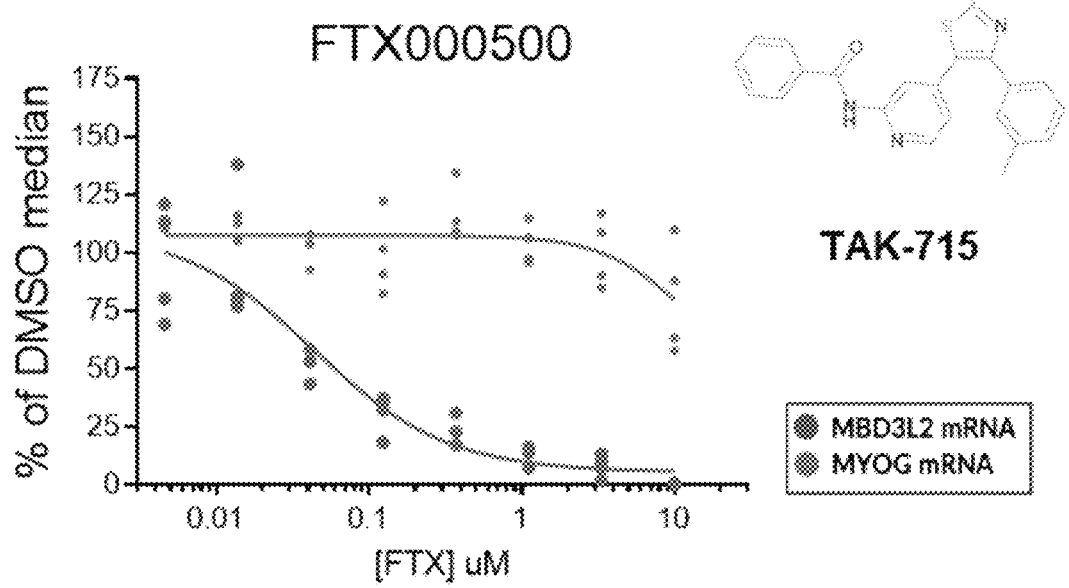

Wild type myotubes and mature patient-derived FSHD myotubes that express DUX4 protein were treated with DMSO vehicle control or multiple concentrations of various p38α/β inhibitors with different ranges of isoform and kinome selectivity, including SB239063 (FIG. 4A; $IC_{50}$=15 nM), VX-702 (FIG. 4B), Pamapimod (FIG. 4C), and TAK-715 (FIG. 4D). After treatment, the control and treated cells were processed for realtime PCR quantification of MBD3L2 mRNA (DUX4 downstream gene) and myogenin (MYOG) mRNA (control) expression. These p38α/β inhibitors showed potent (IC50 approximately <10 nM, FIGS. 4A-D) reduction of MBD3L2 mRNA expression with no impact to MYOG mRNA expression in FSHD myotubes.

Figure 5A:
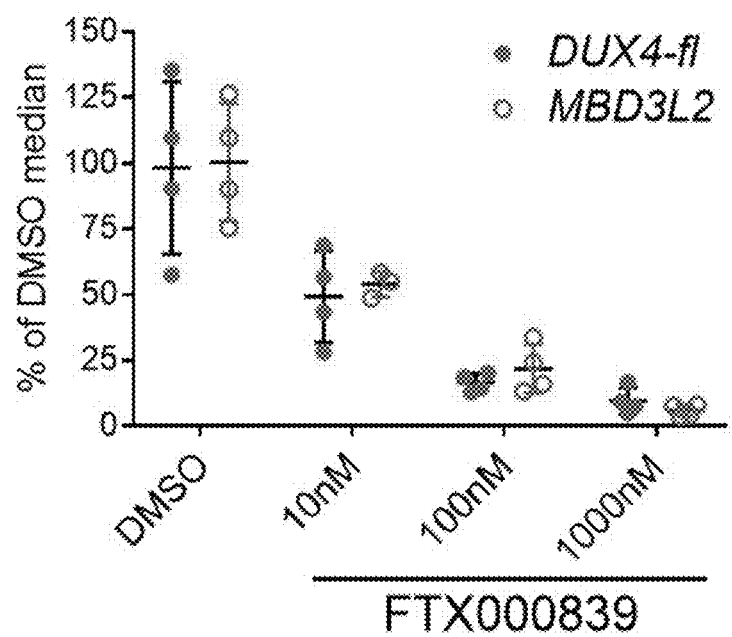
FIGS. 5A and 5B show data from FSHD myotubes treated with Pamapimod.
Figure 5B:
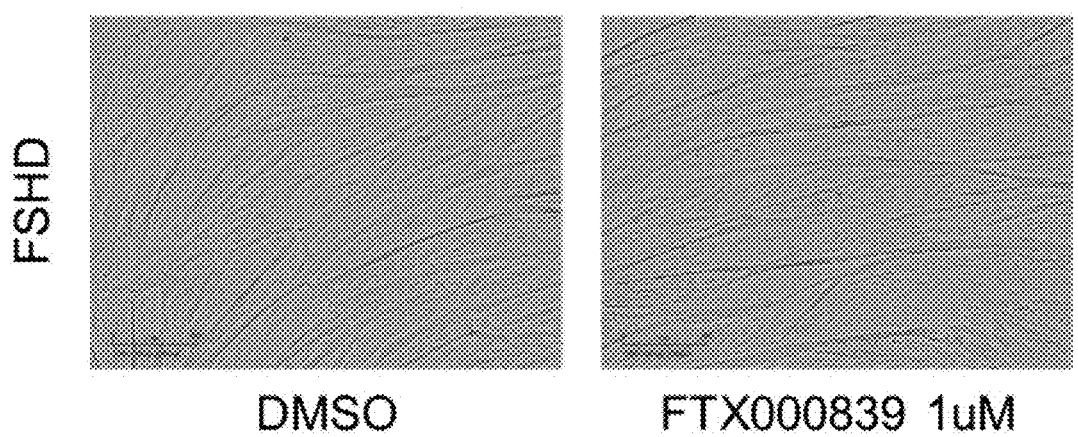

In FSHD myotubes, p38 kinase inhibitors (e.g., Pamapimod) dose-dependently reduced DUX4 mRNA and DUX4 downstream gene MBD3L2 mRNA expression without impacting myotube formation. When compared to DMSO treatment, 10, 100, and 1000 nM FTX000839 (Pamapimod) dose-dependently reduced both DUX4-fl and MBD3L2 downstream gene mRNA levels normalized to POLR2A mRNA, as measured by qPCR and Taqman in FSHD myotubes (FIG. 5A) without impacting differentiation into myotubes (FIG. 5B). The data show that p38 kinase inhibitors dose-dependently reduce MBD3L2 mRNA expression without impacting myogenin mRNA expression.

Example 3

Figure 6A:
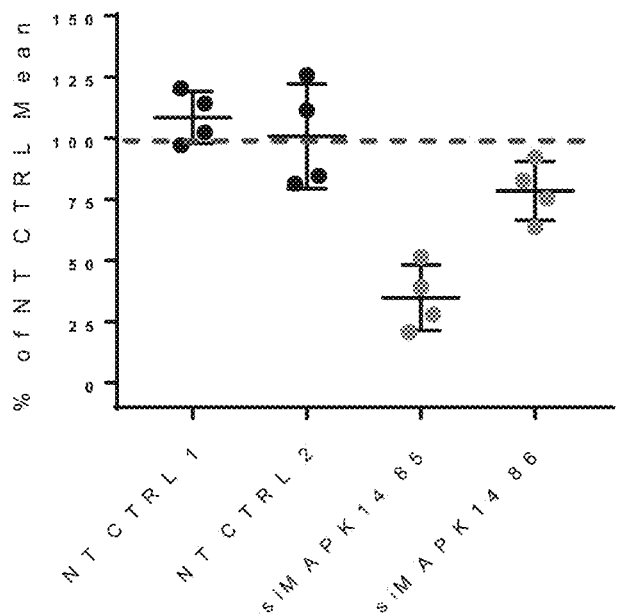
Figure 6B:
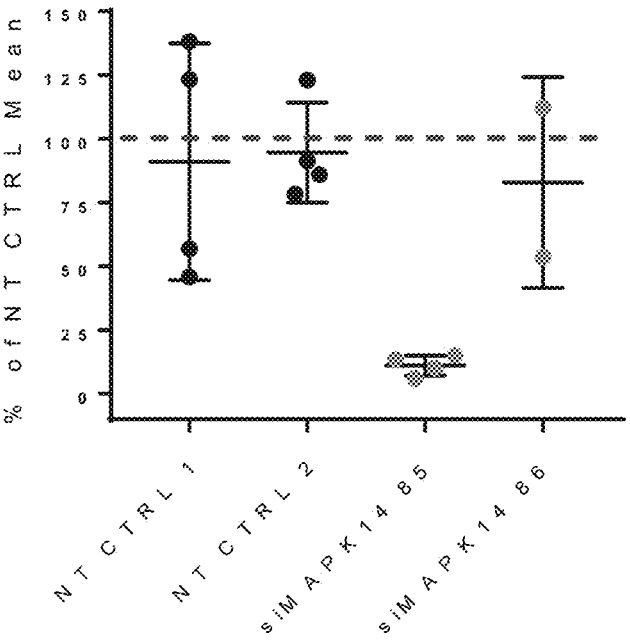

P38 MAPK14 mRNA and MBD3L2 mRNA Reduction Via siRNA Knockdown p38α MAPK14 85 and p38α MAPK14 86 siRNAs were transfected into patient FSHD myotubes as described in Materials and Methods. Each of p38α MAPK14 85 siRNA and p38α MAPK14 86 siRNA (to a lesser extent) reduced p38 MAPK14 expression, as shown in FIG. 6A, and MBD3L2 mRNA (DUX4 target gene) expression, as shown in FIG. 6B, as compared to non-target control siRNAs (NT CTRL 1 and NT CTRL 2). The data shows that genomic reduction of p38α MAPK14>50% specifically reduced DUX4 and downstream target genes, as exemplified by MBD3L2.

Example 4

MBD3L2 mRNA Reduction Via P38α Kinase Cas9/SGRNA RNPs

CRISPR gRNA targeting of MAPK14 or pLAM (polyadenylation signal sequence for DUX4) was conducted as described in Materials and Methods. CRISPR gRNA targeted to MAPK14 or pLAM (polyadenylation signal sequence for DUX4) resulted in a reduction in expression of MBD3L2 but no MYOG. The data indicates that genomic reduction of p38α MAPK14 specifically reduced DUX4 and downstream target genes, as exemplified by MBD3L2.

Example 5

Ftx-1821 Downregulates DUX4 Protein and MBD3L2 mRNA

Patient-derived FSHD myotubes (with 6 repeats of D4Z4 arrays) were treated with DMSO vehicle control and different FTX-1821 concentrations, and DUX4 protein and MBD3L2 mRNA levels were determined as described in Methods and Materials. For DUX4 and MBD3L2, four biological replicates were analyzed. In addition, pHSP27 levels were determined. For pHSP27 quantification, three replicates were obtained in two independent experiments.

Treatment of the FSHD patient derived myotubes with FTX 1821 resulted in a concentration-dependent reduction of DUX4 protein ($IC_{50}$=25 nM) and MBD3L2 mRNA ($IC_{50}$=25 nM) that correlated with the changes observed in phospho HSP27 levels ($IC_{50}$=10 nM) as evidence of target engagement (FIG. 7). The results were indicative of a concentration-dependent reduction of DUX4 protein ($IC_{50}$=25 nM) and MBD3L2 mRNA ($IC_{50}$=10 nM). The reductions in DUX4 protein and MBD3L2 mRNA correlated with the observed changes in p-HSP27 levels ($IC_{50}$=10 nM) as evidence of target engagement. These results indicate that p38α pathway inhibition by FTX-1821 results in potent DUX4 protein and MBD3L2 mRNA downregulation.

Example 6

FTX-1821 does not Affect Myotube Formation

Figure 8A:
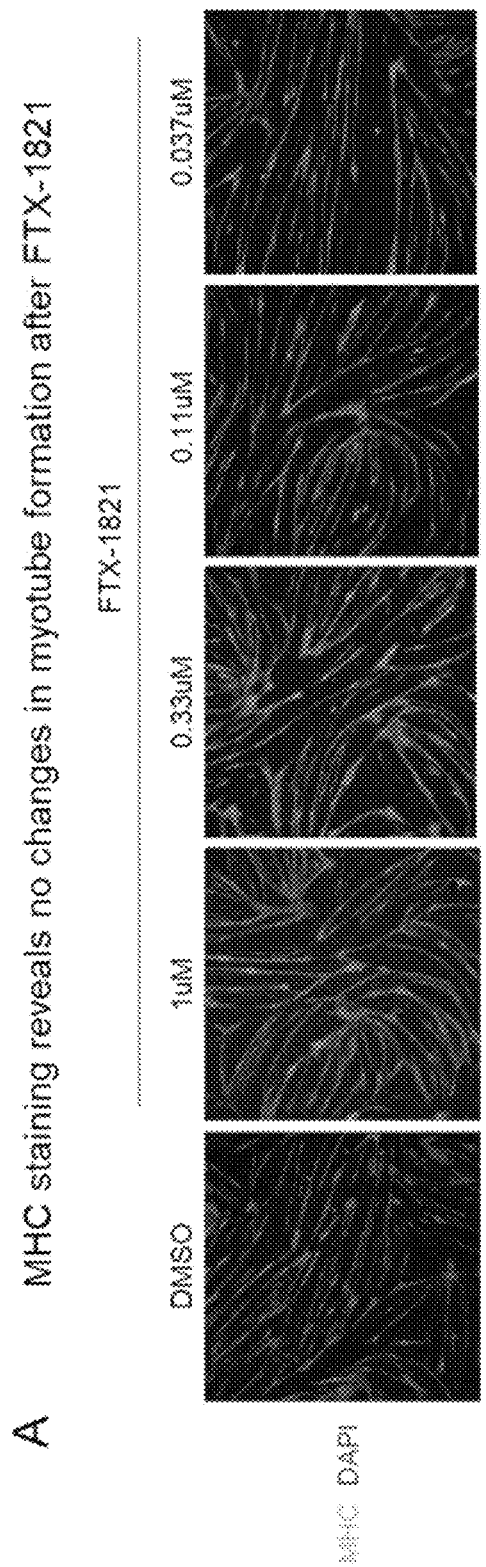

Immortalized FHSD myotubes were differentiated and treated with DMSO vehicle control or FTX-1821 at concentrations of 1 µM, 0.33 µM, 0.11 µM, or 0.037 µM. After 4 days, the cells were fixed and stained with antibodies directed against MHC or DAPI. See FIG. 8A. The nuclei in myotubes were quantified according to MHC staining (FIG. 8B). The results showed no changes in myotube formation or fusion after treatment with FTX-1821 at concentrations tested.

Example 7

FTX-1821 Reduces Apoptosis in FSHD Myotubes

Figure 9A:
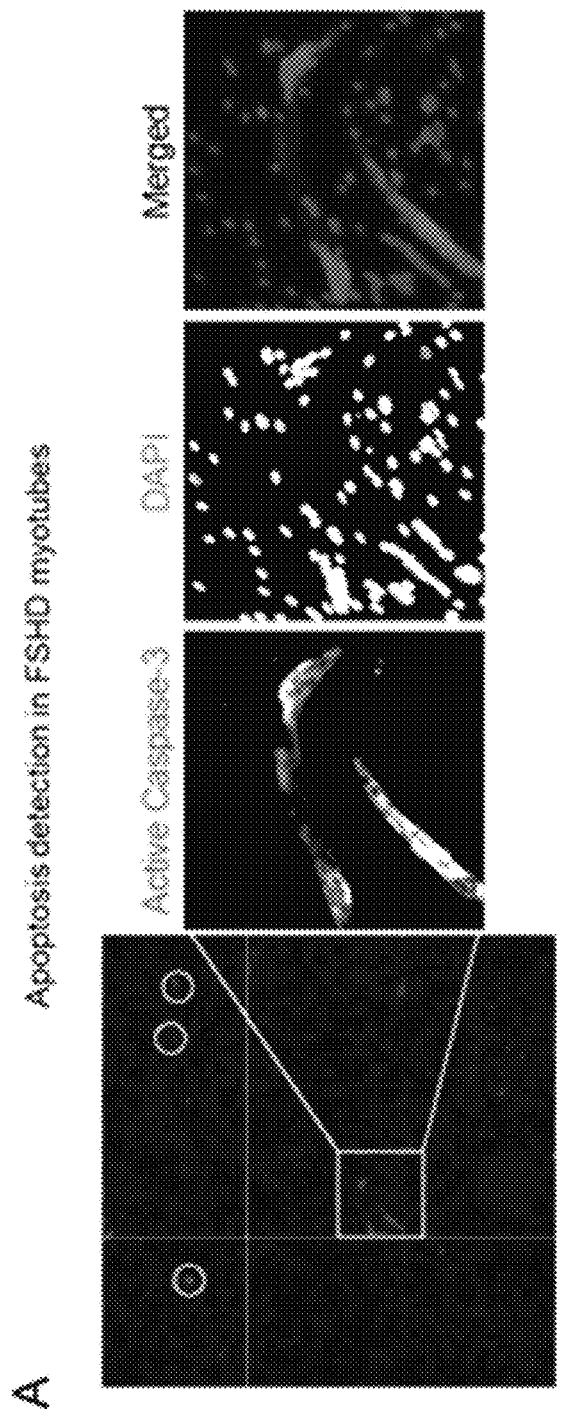
FIGS. 9A and 9B show the results of apoptosis assays in FSHD myotubes in vitro.
Figure 9B:
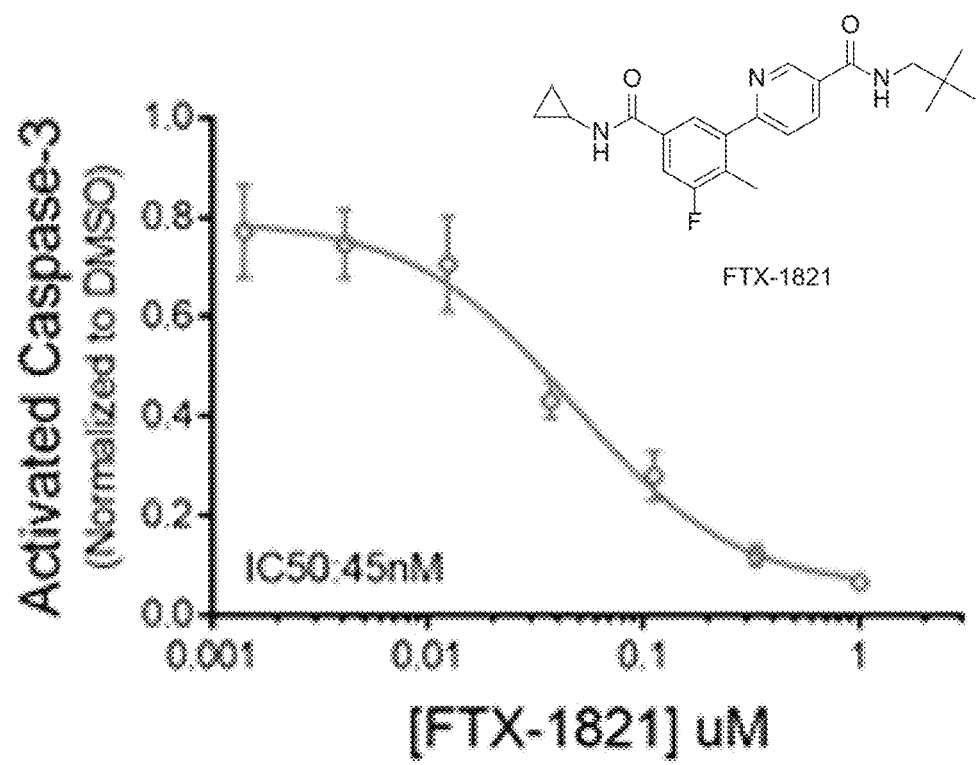

Apoptosis was measured by active Caspase-3 levels in FSHD myotubes in vitro as described in Materials and Methods. Apoptosis was detected in a sporadic manner in a subset of myotubes in culture as shown by the white circles and magnified region in FIG. 9A. Active Caspase-3 signal was quantified in FSHD myotubes that had been treated with FTX-1821 at different concentrations (FIG. 9B). The results showed a dose-dependent reduction of apoptotic signal, as indicated by the reduction in detection of active Caspase 3 ($IC_{50}$=45 nM), and this effect was specific to FSHD myotubes compared to control myotubes. No change in active Caspase-3 signal was observed following DMSO treatment.

Example 8

FTX-1821 Reduces Pathologic DUX4 Transcriptional Program Expression

Studies were conducted as described in Methods and Materials to identify genes in the DUX4 pathway whose expression in down-regulated by in FSHD myotubes treated with FTX-1821 as compared to FSHD myotubes treated with DMSO vehicle control. In addition, gene expression was also determined in wild type myotubes treated with DMSO. Three replicates for each condition were analyzed by RNA-seq and genes were clustered by the direction and intensity of change.

Figure 10B:
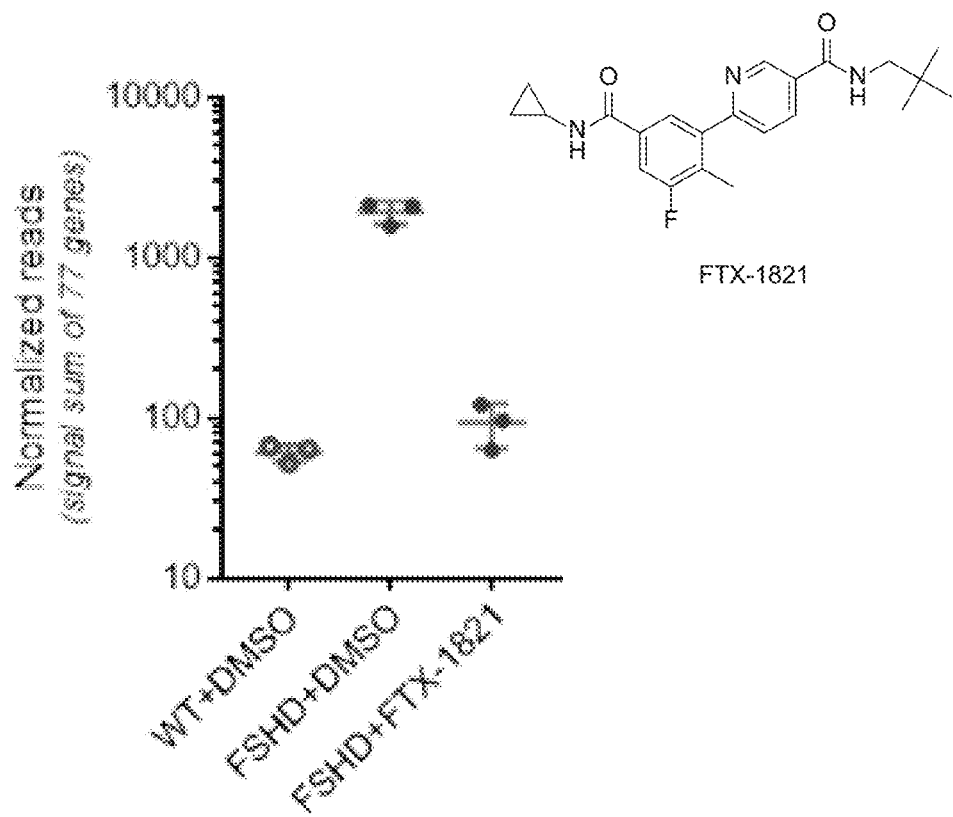
Figure 12B:
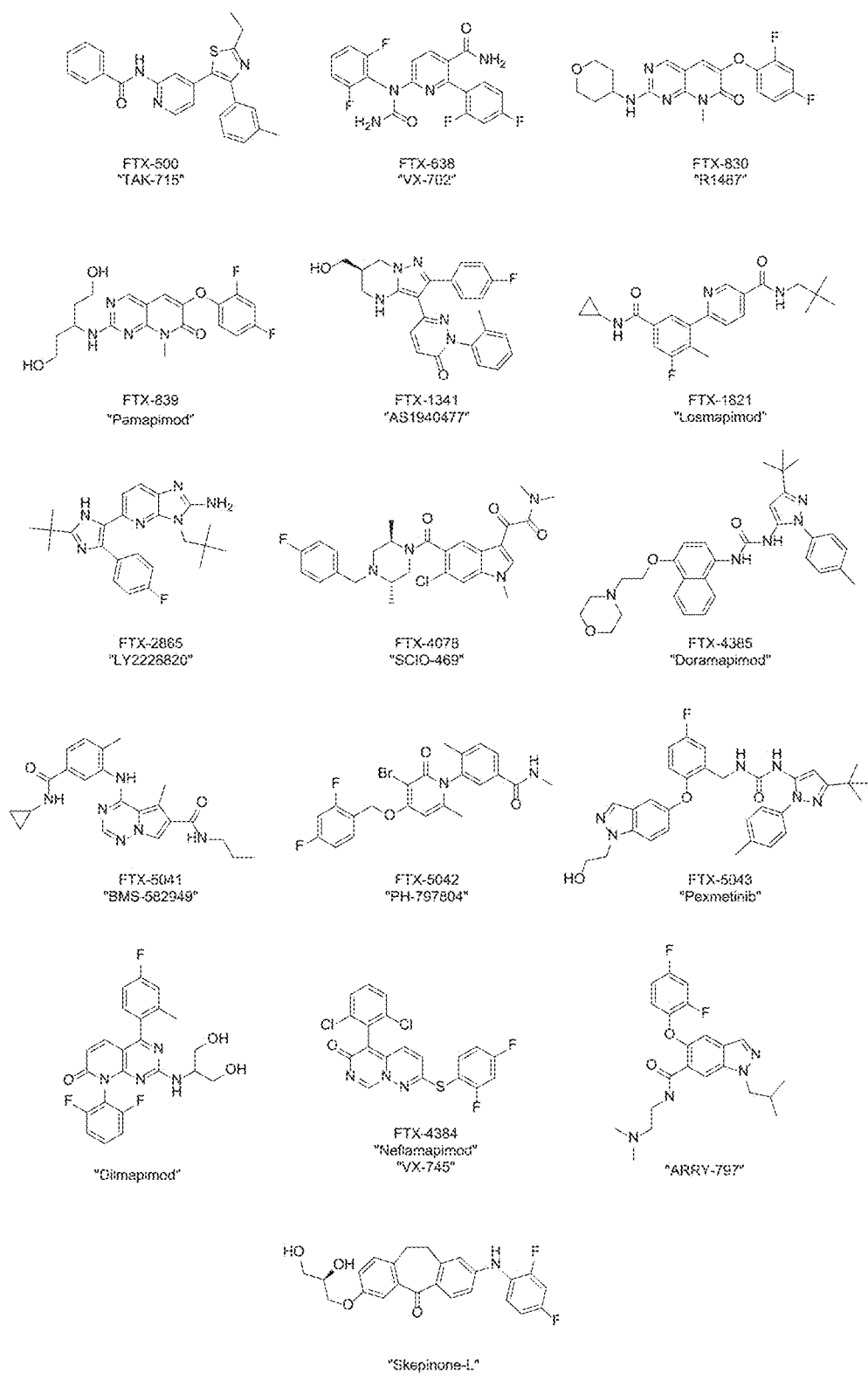

As shown in the heatmap of FIG. 10A, a number of differentially expressed genes were identified by RNA-seq profiling. The bar indicates the normalized changes observed, e.g., genes that were downregulated by FTX-1821 are enriched in samples treated with only DMSO. The expression of these genes was normalized upon treatment with FTX-1821 (1 µM) and closer resembled the observations in wild type cells. Calculated using standard RPKM expression values, the total gene signature was very small and defined at standard statistical cutoffs: 86/19,799 mRNA genes. DUX4-regulated gene signature was a majority of the total signature, and these genes are listed in FIG. 10A. Non-DUX4-regulated genes were minority of the total signature with moderate fold changes: 9/86 mRNA genes=10%; 2-2.7× log FC. FIG. 10B shows the normalized reads, as described in Materials and Methods, of the DUX4 target genes that were downregulated upon treatment with FTX-1821. Three independent replicates per group were analyzed.

Example 9

Reduction of MBD3L2 mRNA in Various FSHD1 Genotypes and Phenotypes

The ability of p38 kinase inhibitors to reduce expression of DUX4 target genes in cells obtained from patients having various different FSHD1 genotypes was conducted as described in Methods and Materials. Four distinct FSHD patient myoblast lines, i.e., FTCE-016,-020, -197, and -196 (kindly provided Rabi Tawil) were treated with FTX-1821 (1 µM) or FTX-839 (1 µM), and mRNA levels of the DUX4 target gene, MBD3L2, were determined following treatment.

MBD3L2 expression levels were reduced in all of the FSHD lines, resulting in levels similar to those measured in healthy controls, FTCE-396 and FTCE-014 (FIG. 11). This is evidence of DUX4 target gene reduction by p38 kinase inhibitors across myotubes derived from diverse FSHD1 genotypes and phenotypes (similar results were observed for FSHD2, data not shown).

Example 10

Reduction of MBD3L2 mRNA from FSHD1 and FSHD2 Genotypes and Phenotypes

To assess the treatment effect of p38 selective inhibition using FTX-1821 in FSHD1 and FSHD2 cells, primary myoblast lines were kindly provided by Rabi Tawil at the University of Rochester. FIG. 13 summarizes the genotypes and phenotypes of 13 FSHD1 and 3 FSHD2 patient myoblasts used in the study. The various FSHD1 and FSHD2 myoblasts were treated with DMSO, FTX-1821 or FTX-839 (1 µM), and following treatment, mRNA expression levels of the DUX4 target gene, MBD3L2, were determined. In addition, apoptosis was determined by measuring active caspase-3 in the FSHD1 and FSHD2 lines.

Figure 14A:
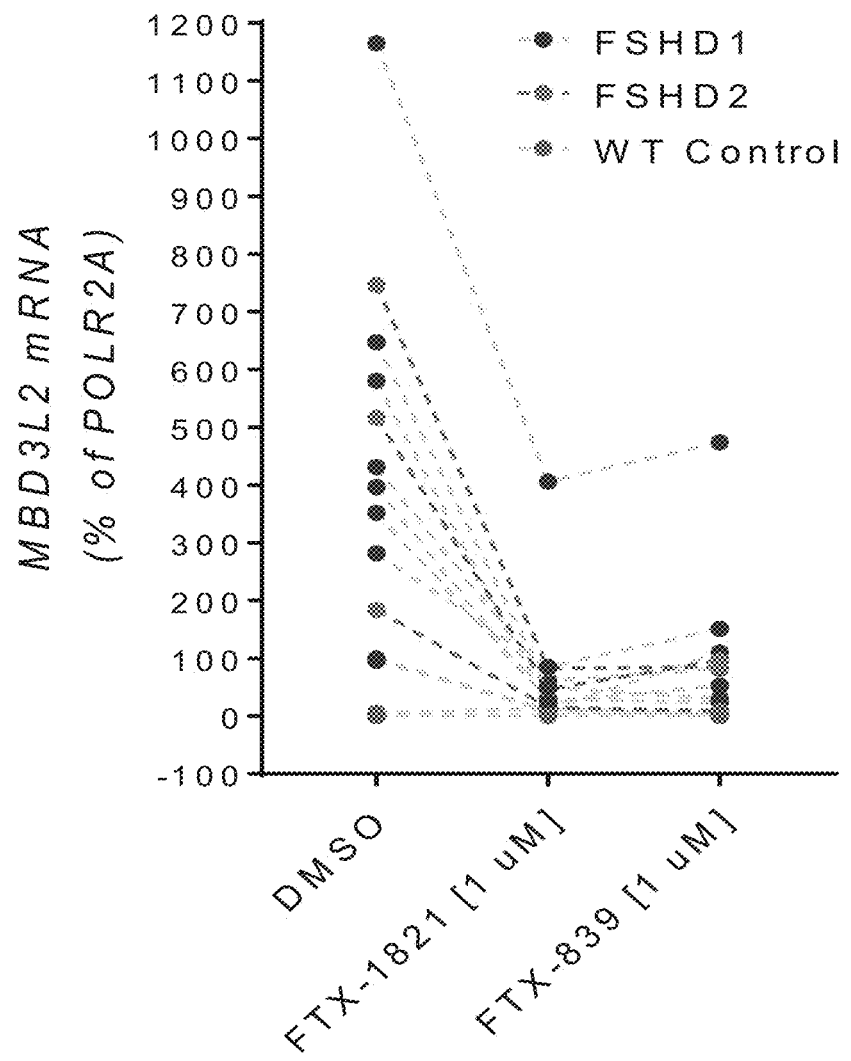
FIGS. 14A and 14B are graphs showing MBD3L2 mRNA expression normalized to POLR2A (by qRT-PCR) (FIG. 14A) and apoptosis as measured by cleaved caspase-3 (FIG. 14B) determined in nine FSHD1 and three FSHD2 patient myotubes (listed in Table 2, FIG. 14B contains only 2 FSHD2 cell lines) following treatment with FTX-1821, FTX-839, or DMSO vehicle control.
Figure 14B:
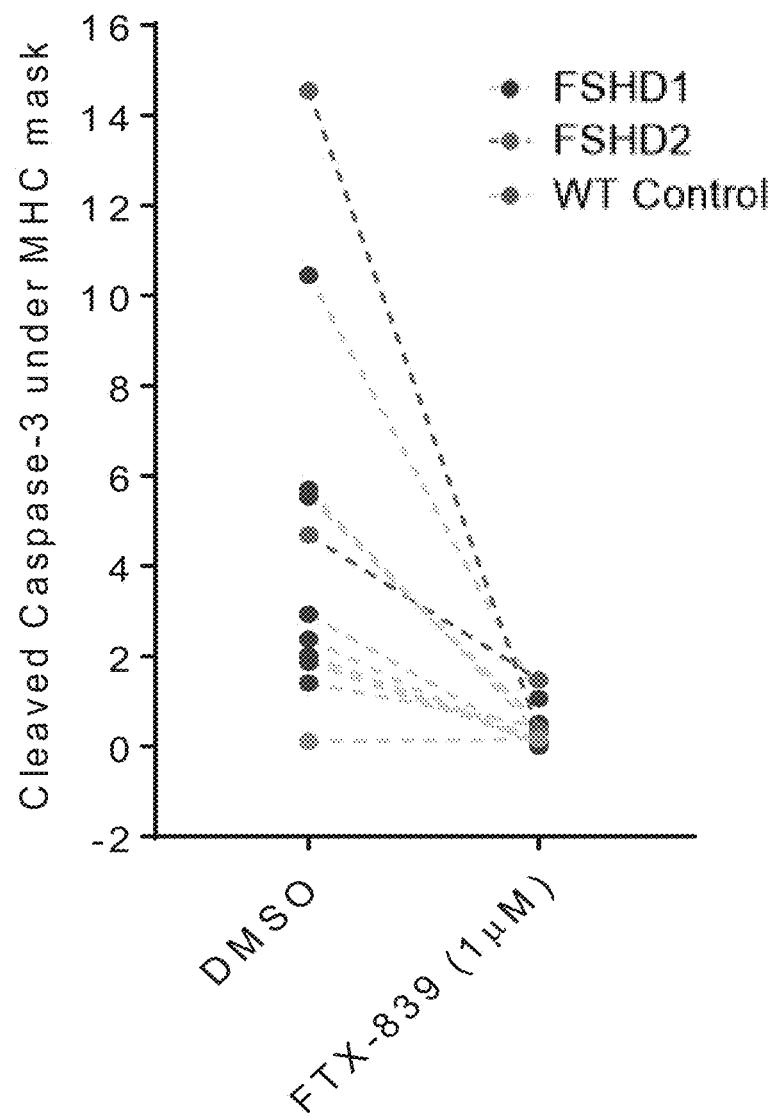

Each of the various FSHD1 and FSHD2 myoblasts showed a reduction of MBD3L2 (FIG. 14A, top 11 lines). The reduction resulted in expression levels similar to those in healthy control lines (CTRL-FTCE-014) (FIG. 14A, bottom 2 lines). In addition, treatment with FTX-839 showed a reduction in apoptosis across both FSHD1 and FSHD2 lines, to a level that was similar to the amount determined in a healthy control line (CTRL-FTCE-014) (FIG. 14B). These results indicate that clinical FSHD biopsy myoblasts, when differentiated into myotubes, show a reduction in both pathologic DUX4 downstream gene expression and resulting cell death across both FSHD1 and FSHD2 genotypes and phenotypes.

Example 11

Target Engagement in Muscle of Wild Type Rats Following Treatment with a Potent and Selective P38 Kinase Inhibitor The pharmacokinetic properties of FTX-1821 were studied in an animal model. FTX-1821 was orally dosed to fasted or unfasted male Sprague-Dawley rats (N=6 animals per time point and treatment group), and phospho p38α: total p38α levels were determined. Pharmacodynamic analysis of p38 system target engagement in muscle tissue was performed by measuring the change in phosphor MAP kinase-activated protein kinase 2 (MK2) to total MK2 ratio before and after drug treatment. All methods used are described in the Materials and Methods section.

FTX-1821 exhibited plasma pharmacokinetic properties similar to those described previously (Aston et al., 2009; data not shown). These studies additionally demonstrated rapid distribution of FTX-1821 to multiple muscles and plasma. Muscle to plasma exposure ratios were equal to or greater than 1 in the rat when clinically relevant plasma exposures were achieved.

Figure 15:
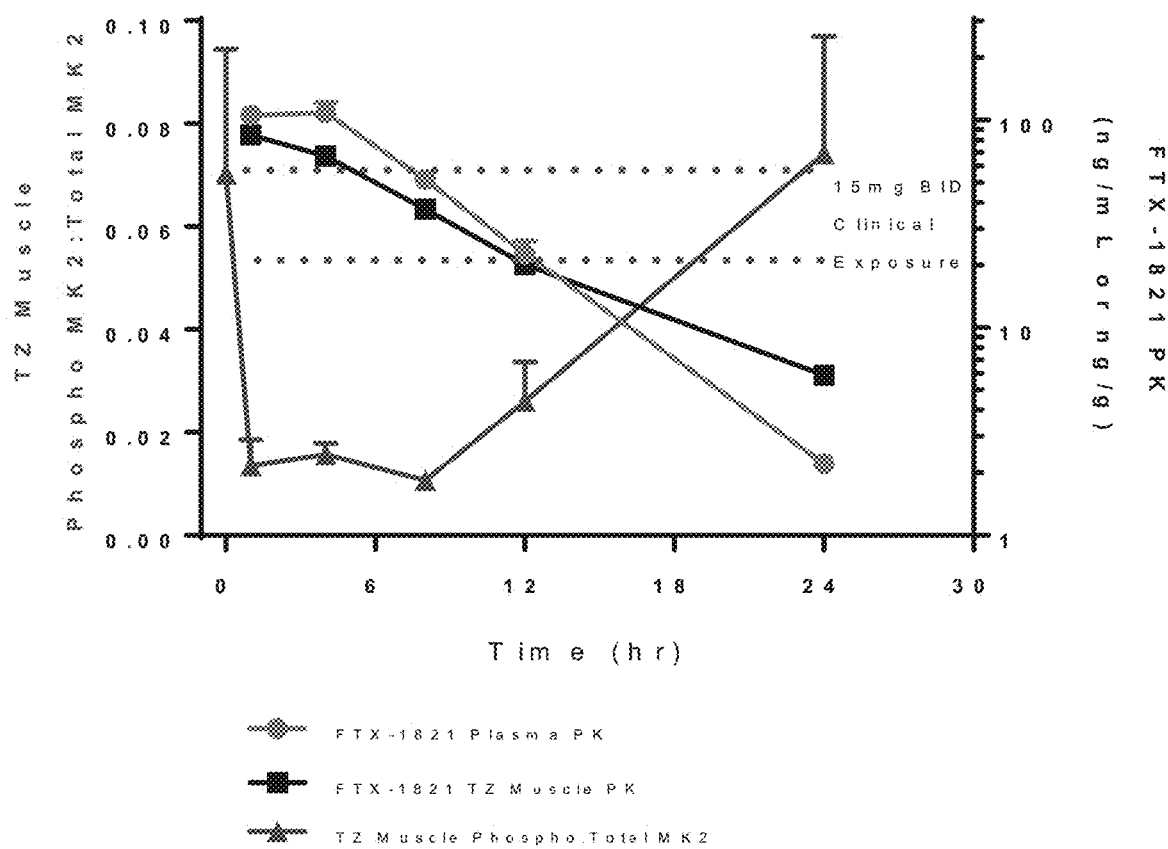
FIG. 15. is a graph showing the time course of plasma exposure, trapezius muscle exposure and p38 target engagement (Phosphorylated-p38α:Total p38α Ratio) in the rat following oral administration of 0.3 mg/kg FTX-1821.

Pharmacodynamic analysis demonstrated that a single, oral dose of FTX-1821 (0.3 mg/kg) resulted in clinically relevant plasma concentrations (Barbour et al., 2012) and significantly decreased the phospho MK2 to total MK2 ratio in rat trapezius muscle within 1-hour of drug treatment (FIG. 15). P38 system target engagement persisted for at least 12 hours following the single dose of FTX-1821 (FIG. 15). P38 system target engagement in trapezius muscle was maximal when plasma and muscle concentrations of FTX-1821 were greater than 20 ng/mL or ng/g and declined at timepoints when exposures decreased. The muscle concentrations of FTX-1821 achieved in the rat study are predicted to result in >70% reduction at Cmax in DUX4 dependent target genes in FSHD patient muscle biopsies based upon in vitro data in FSHD myotubes (above).

This pharmacokinetic and pharmacodynamic analysis indicated that maximal inhibition of the p38 system in muscle was achieved when plasma FTX-1821 concentrations were greater than 20 ng/mL and that significant p38 pathway inhibition would be expected, in human muscle, with clinical doses of 7.5 or 15 mg BID (Barbour et al., 2012).

Example 12

Inhibition of the DUX4 Genomic Program in FSHD Xenografted Mice Following Treatment with a Potent and Selective P38 Kinase Inhibitor FSHD and control muscle xenograft mice were generated by xenografting C6 (FSHD) and A4 (control) IPSC-derived human immortalized isogeneic myoblast cell lines into the bilateral tibialis anterior (TA) muscles of approximately 8-week old male Nod-Rag mice as described by Sakellariou et al., 2016. Following the 4-week long engraftment and INMES procedure, the FSHD xenografted animals were treated with BID injections of either vehicle or FTX-2865 (10 mg/kg) for 8 days (a total of 14 injections) and were sacrificed at approximately the time of maximal plasma concentrations (Tmax) 1-hour after the final morning injection on Day 8. At sacrifice, plasma, trapezius muscle and bilateral tibialis anterior muscles were collected and flash frozen for analysis of pharmacokinetic endpoints, target engagement and DUX4 dependent mRNAs. MBD3L2 was assessed by qPCR using a human specific probe and was normalized to the housekeeping gene CDKN1B. pMK2 and MK2 protein concentrations were assessed by a quantitative MSD assay.

Figure 16:
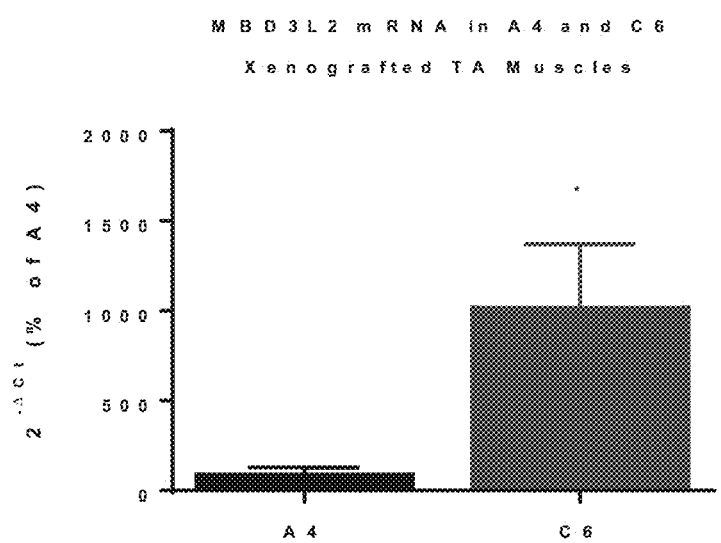
FIG. 16. is a graph showing MBD3L2 mRNA levels in A4 and C6 xenografted TA muscles.

Analysis of TA tissue by qPCR from animals engrafted for 4-6 weeks with A4 or C6 myoblast tissues demonstrated a significant (p<0.05) and >10-fold increase in MBD3L2 and other Dux4 dependent genes (not shown) in the FSHD (C6) vs control (A4) xenografted TA muscles (FIG. 16). N=8 TA samples per group.

Figure 17:
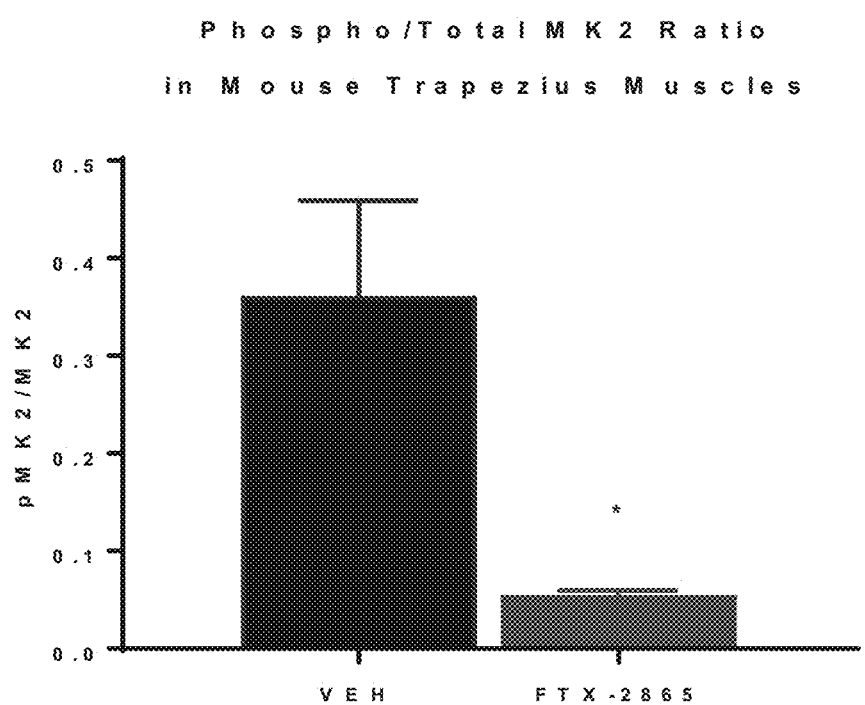
FIG. 17. is a graph showing phosphor/total MC2 ratio in mouse trapezius muscles following treatment with vehicle control or p38 kinase inhibitor, FTX-2865.
Figure 18:
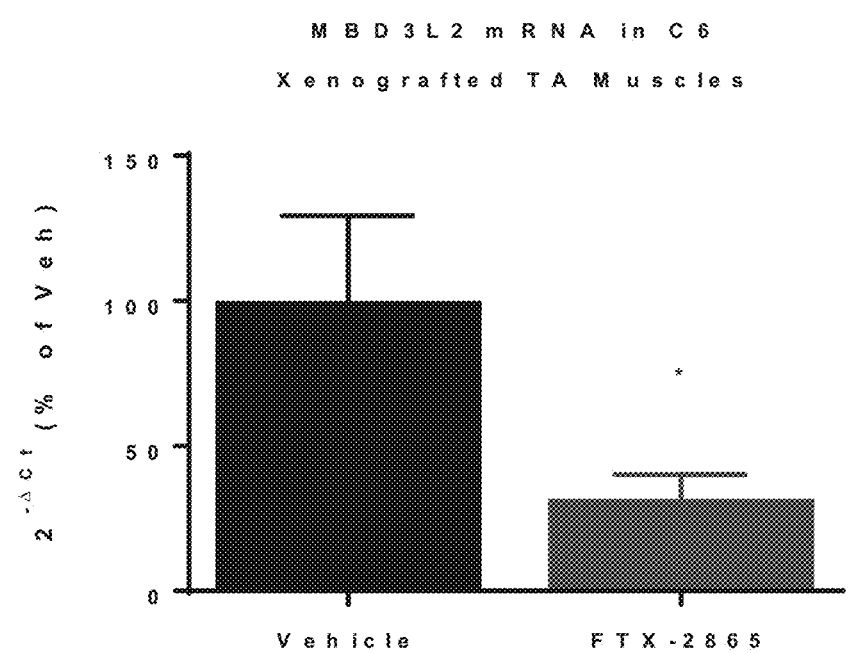
FIG. 18. is a graph showing MBD3L2 mRNA levels in C6 xenografted TA muscles following treatment with vehicle control or p38 inhibitor, FTX-2865.

Treatment of FSHD xenografted animals with the potent and selective p38 kinase inhibitor, FTX-2865, produced p38 system target engagement, as measured by a change in phospho MAP kinase-activated protein kinase 2 (MK2) to total MK2 ratio of >50% in the TA and trapezius muscles of wild-type mice following repeated BID administration of a 10 mg/kg dose given via intraperitoneal (IP) injection (data not shown). FTX-2865 treatment significantly (p<0.05) decreased the ratio of phospho to total MK2 in mouse trapezius muscle, indicating significant p38 system engagement and also indicating sufficient drug concentrations in the skeletal muscles of the animals to inhibit the p38 system by >80% (FIG. 17; N=8 trapezius samples per group). In addition, FTX-286 treatment significantly (p<0.05) decreased the expression of MBD3L2 in the FSHD xenografted TA muscles compared to vehicle treated animals, indicating suppression of the pathologic DUX4 gene program by p38 inhibition (FIG. 18; N=5-7 TA samples per group).

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

Furthermore, it is intended any method described herein may be rewritten into Swiss-type format for the use of any p38 kinase inhibitor or agent described herein, for the manufacture of a medicament, in treating any of the disorders described herein. Likewise, it is intended for any method described herein to be rewritten as a compound for use claim.

For example, use of a p38 kinase inhibitor, for the manufacture of a medicament, for treating a disorder responsive to p38 kinase inhibition, wherein the p38 kinase inhibitor is characterized by Formula (V'):

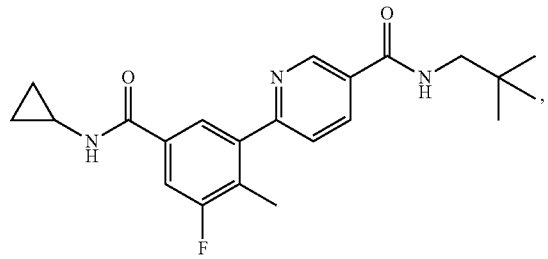

or a stereoisomer thereof, an isotopically-enriched compound thereof, a prodrug thereof, a solvate thereof, or a pharmaceutically acceptable salt thereof; wherein the disorder is associated with DUX4 gene expression, and the p38 kinase inhibitor reduces DUX4 expression levels and/or the expression of one or more downstream genes in cells of the subject.

---

What is claimed is:

1. A method for treating facioscapulohumeral muscular dystrophy (FSHD), the method comprising administering to a subject in need thereof, an effective amount of a p38 kinase inhibitor, wherein the p38 kinase inhibitor is selected from the group consisting of:

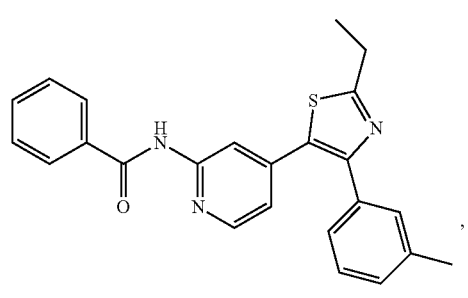

"TAK-715" (I')

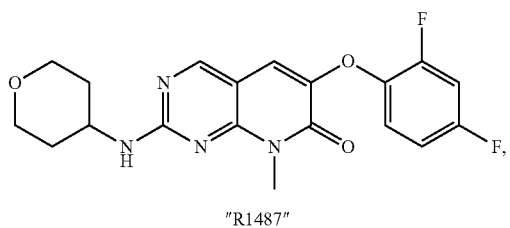

"R1487" (IIIa')

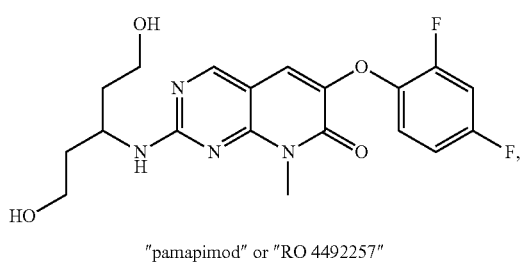

"pamapimod" or "RO 4492257" (IIIb')

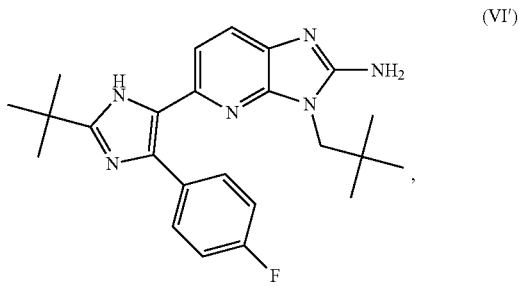

"LY2228820" or "ralimetinib" (VI')

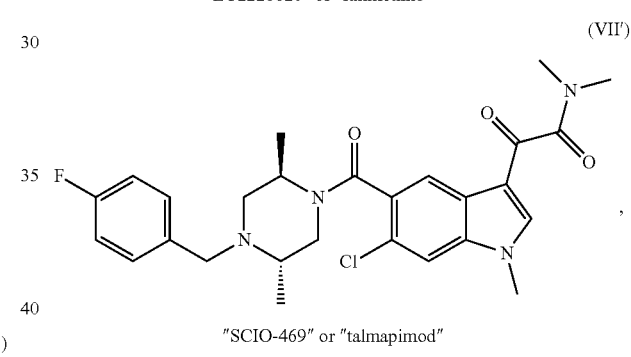

"SCIO-469" or "talmapimod" (VII')

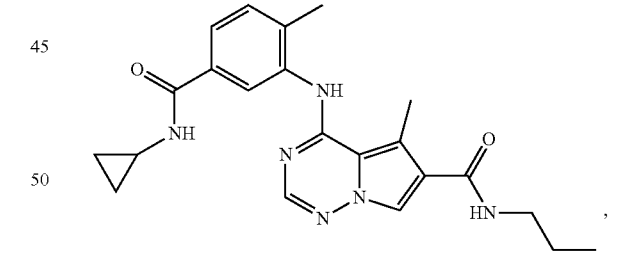

"BMS-582949" or "PS-5404446" (IX")

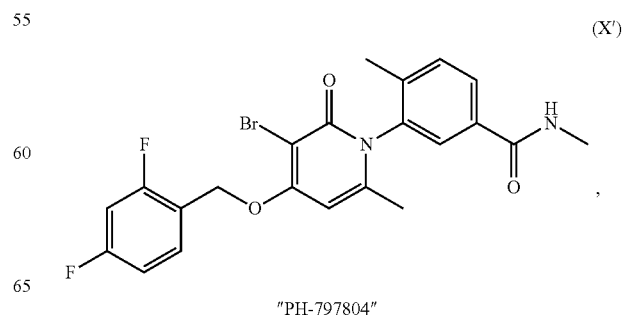

"PH-797804" (X')

(XI')
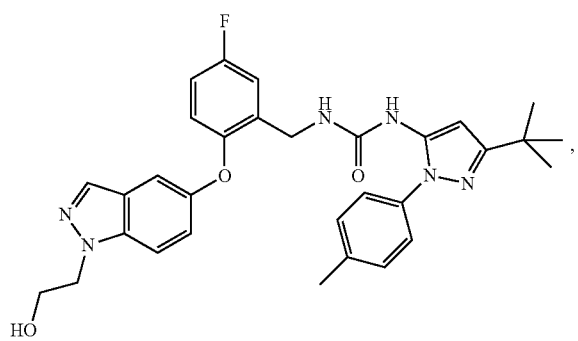
"pexmetinib" or "ARRY-614"
(XII')
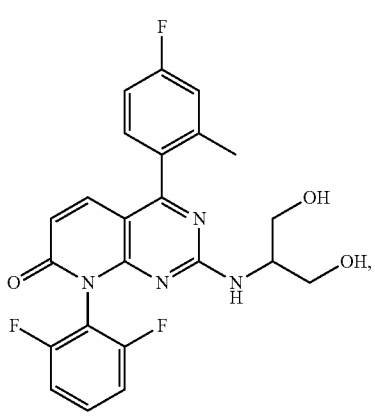
"dilmapimod" or "SB-681323"
(XIV')
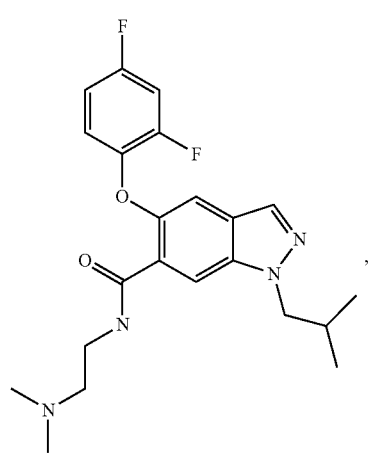
"ARRY-797" or "ARRY-371797"
(XVI')
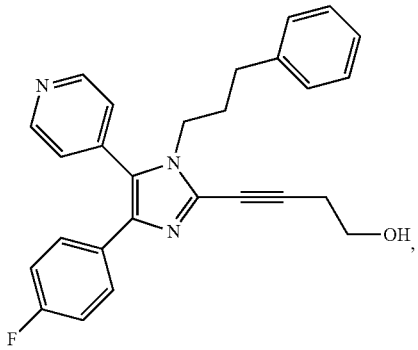
"RWJ-67657"
(XVIII')
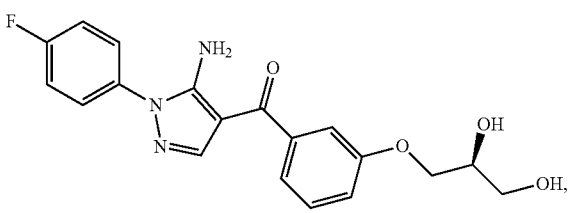
"RO-3201195"
(XX')
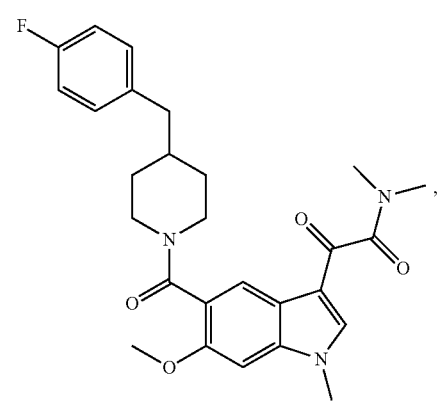
"SCIO-323"
(XXI')
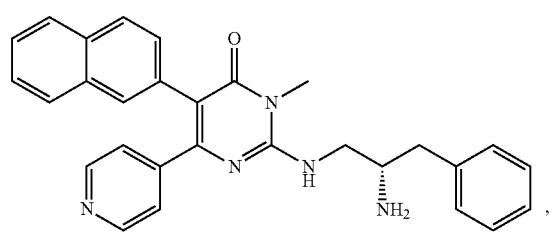
"AMG-548"

-continued

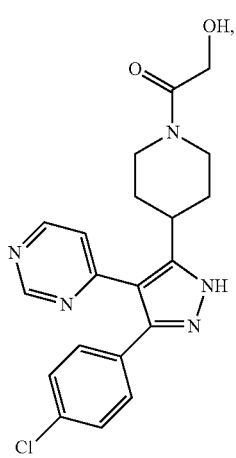

"SD-0006" or "SD-06"

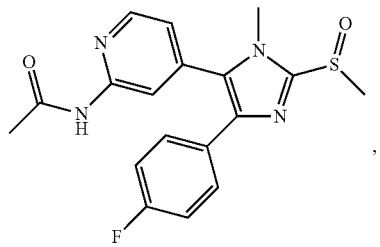

"CBS-3595" or "ML-3595"

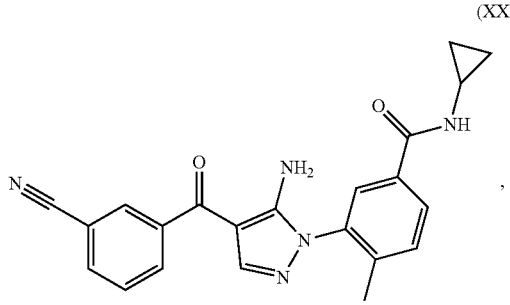

"acumapimod" or "BCT-197"

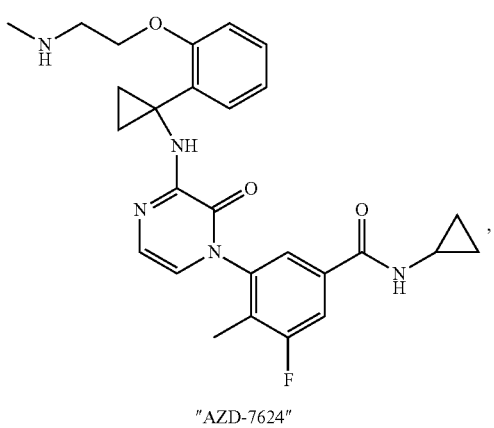

"AZD-7624"

-continued

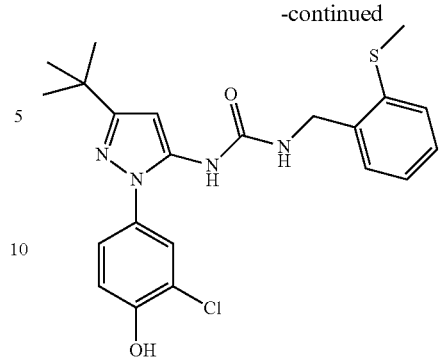

(XXIV')

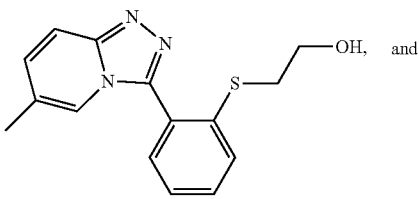

"PF-03715455"

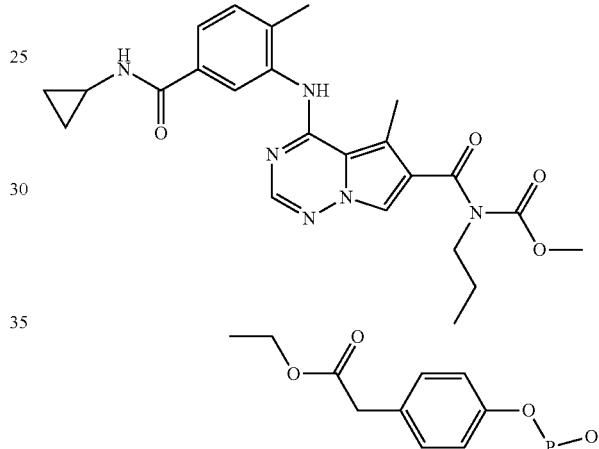

"BMS-751324"

or a pharmaceutically acceptable salt thereof; and
wherein administration of the p38 kinase inhibitor reduces expression levels of a DUX4 polypeptide and/or a polypeptide encoded by a DUX4 downstream gene in muscle cells of the subject.

2. The method of claim 1, wherein the DUX4 downstream gene is selected from the group consisting of: ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

3. The method of claim 1, wherein the muscle cells are terminally differentiated muscle cells.

4. The method of claim 1, wherein the muscle cells comprise a dysregulated D4Z4 array at chromosome 4q35.

5. The method of claim 1, wherein the facioscapulohumeral muscular dystrophy is FSHD type 1 (FSHD1).

6. The method of claim 5, wherein the muscle cells comprise a deletion of one or more macrosatellite D4Z4 repeats in the subtelomeric region of chromosome 4q35.

7. The method of claim 6, wherein the muscle cell comprises less than 11 macrosatellite D4Z4 repeats in the subtelomeric region of chromosome 4q35.

8. The method of claim 1, wherein the facioscapulohumeral muscular dystrophy is FSHD type 2 (FSHD2).

9. The method of claim 8, wherein the muscle cells comprise one or more mutations in a Structural Maintenance Of Chromosomes Flexible Hinge Domain Containing 1 (SMCHD1) gene.

10. The method of claim 1, wherein the muscle cells comprise at least one non-deleted 4qA allele.

11. The method of claim 1, wherein the administering causes a decrease in muscle degeneration in the subject.

12. The method of claim 1, wherein the administering causes a reduction in apoptosis of muscle cells in the subject.

13. The method of claim 1, wherein the compound or the pharmaceutically acceptable salt thereof is administered to the subject parenterally.

14. The method of claim 1, wherein the compound or the pharmaceutically acceptable salt thereof is administered to the subject orally.

15. The method of claim 1, wherein the compound or the pharmaceutically acceptable salt thereof is administered to the subject via inhalation.

* * * * *

SEQUENCE LISTING

<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: DUX4 antisense oligonucleotide

<400> SEQUENCE: 1
cagcgtcgga aggtgg                                              16

<210> SEQ ID NO 2
<211> LENGTH: 15
<212> TYPE: DNA
<213> ORGANISM: Artificial Sequence
<220> FEATURE:
<223> OTHER INFORMATION: Non-targeting antisense oligonucleotide

<400> SEQUENCE: 2
aacacgtcta tacgc                                               15

<210> SEQ ID NO 3
<211> LENGTH: 20
<212> TYPE: DNA
<213> ORGANISM: Artificial Sequence
<220> FEATURE:
<223> OTHER INFORMATION: NT-CRL

<400> SEQUENCE: 3
gtattactga tattggtggg                                          20

<210> SEQ ID NO 4
<211> LENGTH: 20
<212> TYPE: DNA
<213> ORGANISM: Artificial Sequence
<220> FEATURE:
<223> OTHER INFORMATION: MAPK14 sgRNA targeting sequence

<400> SEQUENCE: 4
gctgaacaag acaatctggg                                          20

<210> SEQ ID NO 5
<211> LENGTH: 20

```
<212> TYPE: DNA
<213> ORGANISM: Artificial Sequence
<220> FEATURE:
<223> OTHER INFORMATION: MAPK14 sgRNA targeting sequence

<400> SEQUENCE: 5
ctgcttttga cacaaaaacg                                               20

<210> SEQ ID NO 6
<211> LENGTH: 20
<212> TYPE: DNA
<213> ORGANISM: Artificial Sequence
<220> FEATURE:
<223> OTHER INFORMATION: MAPK14 sgRNA targeting sequence

<400> SEQUENCE: 6
cttatctacc aaattctccg                                               20

<210> SEQ ID NO 7
<211> LENGTH: 20
<212> TYPE: DNA
<213> ORGANISM: Artificial Sequence
<220> FEATURE:
<223> OTHER INFORMATION: pLAM sgRNA targeting sequence

<400> SEQUENCE: 7
agaatttcac ggaagaacaa                                               20

<210> SEQ ID NO 8
<211> LENGTH: 20
<212> TYPE: DNA
<213> ORGANISM: Artificial Sequence
<220> FEATURE:
<223> OTHER INFORMATION: pLAM sgRNA targeting sequence

<400> SEQUENCE: 8
attaaaatgc ccctccctg                                                20

<210> SEQ ID NO 9
<211> LENGTH: 20
<212> TYPE: DNA
<213> ORGANISM: Artificial Sequence
<220> FEATURE:
<223> OTHER INFORMATION: pLAM sgRNA targeting sequence

<400> SEQUENCE: 9
aatcttctat aggatccaca                                               20

<210> SEQ ID NO 10
<211> LENGTH: 21
<212> TYPE: DNA
<213> ORGANISM: Artificial Sequence
<220> FEATURE:
<223> OTHER INFORMATION: MAPK14 siRNA

<400> SEQUENCE: 10
uagauuacua gguuuuaggt c                                             21

<210> SEQ ID NO 11
<211> LENGTH: 21
<212> TYPE: DNA
<213> ORGANISM: Artificial Sequence
<220> FEATURE:
<223> OTHER INFORMATION: MAPK14 siRNA

<400> SEQUENCE: 11
```

```
ccuaaaaccu aguaaucuat t                                              21

<210> SEQ ID NO 12
<211> LENGTH: 20
<212> TYPE: DNA
<213> ORGANISM: Artificial Sequence
<220> FEATURE:
<223> OTHER INFORMATION: pLAM sgRNA targeting sequence

<400> SEQUENCE: 12
caggtttgcc tagacagcgt                                                20
```